US012723023B2

(12) United States Patent
Rajappan et al.

(10) Patent No.: US 12,723,023 B2
(45) Date of Patent: Sep. 1, 2026

(54) IONIZABLE CATIONIC LIPIDS FOR RNA DELIVERY

(71) Applicant: Arcturus Therapeutics, Inc., San Diego, CA (US)

(72) Inventors: Kumar Rajappan, San Diego, CA (US); Steven Tanis, San Diego, CA (US); Amit Sagi, San Diego, CA (US); Priya Prakash Karmali, San Diego, CA (US); Padmanabh Chivukula, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 863 days.

(21) Appl. No.: 17/985,045

(22) Filed: Nov. 10, 2022

(65) Prior Publication Data

US 2023/0295081 A1 Sep. 21, 2023

Related U.S. Application Data

(60) Provisional application No. 63/278,242, filed on Nov. 11, 2021.

(51) Int. Cl.

| | |
|---|---|
| ***C07C 333/04*** | (2006.01) |
| ***A61K 47/54*** | (2017.01) |
| ***A61K 47/69*** | (2017.01) |
| ***C07C 229/04*** | (2006.01) |
| ***C07C 229/16*** | (2006.01) |
| ***C07C 271/20*** | (2006.01) |
| ***C07C 275/16*** | (2006.01) |
| ***C07C 327/06*** | (2006.01) |
| ***C12N 15/113*** | (2010.01) |
| ***C12N 15/88*** | (2006.01) |

(52) U.S. Cl.

CPC .......... *C07C 333/04* (2013.01); *A61K 47/543* (2017.08); *A61K 47/6911* (2017.08); *C07C 229/04* (2013.01); *C07C 229/16* (2013.01); *C07C 271/20* (2013.01); *C07C 275/16* (2013.01); *C07C 327/06* (2013.01); *C12N 15/113* (2013.01); *C12N 15/88* (2013.01); *C07C 2601/14* (2017.05); *C07C 2602/22* (2017.05); *C07C 2602/24* (2017.05); *C07C 2602/28* (2017.05); *C12N 2310/14* (2013.01)

(58) Field of Classification Search

CPC .............. A61K 47/543; A61K 47/6911; A61K 9/0019; A61K 9/19; A61K 9/5123

See application file for complete search history.

(56) References Cited

U.S. PATENT DOCUMENTS

| | | | |
|---|---|---|---|
| 4,511,069 A | 4/1985 | Kalat | |
| 4,778,810 A | 10/1988 | Wenig et al. | |
| 5,849,902 A | 12/1998 | Arrow et al. | |
| 7,982,027 B2 | 7/2011 | Maclachlan et al. | |
| 8,158,601 B2 | 4/2012 | Chen et al. | |
| 9,011,903 B2 | 4/2015 | Niitsu et al. | |
| 9,365,610 B2 | 6/2016 | Payne et al. | |
| 9,567,296 B2 | 2/2017 | Payne et al. | |
| 9,593,077 B2 | 3/2017 | Payne et al. | |
| 9,670,152 B2 | 6/2017 | Payne et al. | |
| 9,834,510 B2 * | 12/2017 | Payne .................. | C07C 271/22 |
| 9,850,202 B2 | 12/2017 | Payne et al. | |
| 9,896,413 B2 | 2/2018 | Payne et al. | |
| 9,951,002 B2 | 4/2018 | Payne et al. | |
| 10,383,952 B2 | 8/2019 | Payne et al. | |
| 10,526,284 B2 | 1/2020 | Payne et al. | |
| 10,961,188 B2 | 3/2021 | Payne et al. | |
| 10,980,895 B2 | 4/2021 | Payne et al. | |
| 11,744,887 B2 | 9/2023 | Sullivan et al. | |

(Continued)

FOREIGN PATENT DOCUMENTS

| | | |
|---|---|---|
| CN | 102215820 A | 10/2011 |
| CN | 102884041 A | 1/2013 |

(Continued)

OTHER PUBLICATIONS

International Search Report and Written Opinion for International Application No. PCT/US2024/028521, mailed on Jul. 31, 2024, 15 pages.

International Search Report and Written Opinion received for International Application No. PCT/US2015/030218, mailed on Aug. 25, 2015, 9 pages.

(Continued)

*Primary Examiner* — Pancham Bakshi

(74) *Attorney, Agent, or Firm* — Greenberg Traurig LLP

(57) ABSTRACT

The present disclosure describes compounds of Formula (I) and pharmaceutically acceptable salts thereof:

(I)

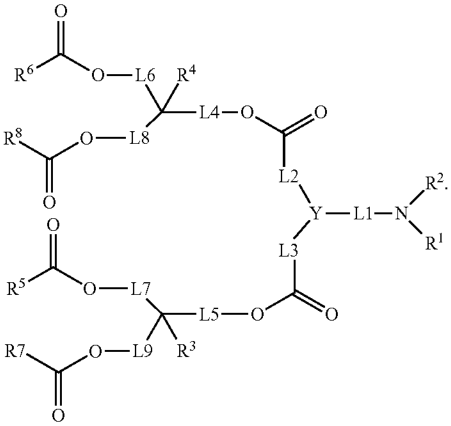

32 Claims, No Drawings

(56) References Cited

U.S. PATENT DOCUMENTS

| | | | |
|---|---|---|---|
| 12,220,455 | B2 | 2/2025 | Sullivan et al. |
| 2010/0160168 | A1 | 6/2010 | Lindner |
| 2012/0027803 | A1 | 2/2012 | Manoharan et al. |
| 2012/0165275 | A1 | 6/2012 | Holmes et al. |
| 2013/0022665 | A1 | 1/2013 | Niitsu et al. |
| 2013/0115274 | A1 | 5/2013 | Knopov et al. |
| 2013/0129811 | A1 | 5/2013 | Kuboyama et al. |
| 2013/0274504 | A1 | 10/2013 | Colletti et al. |
| 2015/0306039 | A1 | 10/2015 | Akinc et al. |
| 2017/0114010 | A1 | 4/2017 | Payne et al. |
| 2017/0190661 | A1 | 7/2017 | Payne et al. |
| 2018/0169268 | A1 | 6/2018 | Payne et al. |
| 2018/0170865 | A1 | 6/2018 | Payne et al. |
| 2018/0170866 | A1 | 6/2018 | Payne et al. |
| 2018/0208555 | A1 | 7/2018 | Payne et al. |
| 2019/0388562 | A1 | 12/2019 | Payne et al. |
| 2020/0109113 | A1 | 4/2020 | Payne et al. |
| 2020/0297634 | A1 | 9/2020 | Karmali et al. |
| 2021/0252163 | A1 | 8/2021 | Payne et al. |
| 2021/0284974 | A1 | 9/2021 | Chivukula et al. |
| 2022/0340886 | A1 | 10/2022 | Tachikawa et al. |
| 2023/0219996 | A1 | 7/2023 | Matsuda et al. |
| 2024/0115692 | A1 | 4/2024 | Sullivan et al. |
| 2025/0136953 | A1 | 5/2025 | Chivukula et al. |
| 2025/0161434 | A1 | 5/2025 | Sullivan et al. |

FOREIGN PATENT DOCUMENTS

| | | | |
|---|---|---|---|
| CN | 104066712 | A | 9/2014 |
| CN | 104640841 | A | 5/2015 |
| CN | 107207428 | A | 9/2017 |
| EP | 1502576 | A2 | 2/2005 |
| EP | 3496243 | A1 | 6/2019 |
| EP | 4122920 | A1 | 1/2023 |
| FR | 1481016 | A | 5/1967 |
| JP | 61089286 | A | 5/1986 |
| JP | 61136584 | A | 6/1986 |
| JP | 2013095755 | A | 5/2013 |
| JP | 2015523990 | A | 8/2015 |
| JP | 2019533351 | A | 11/2019 |
| JP | 2019533410 | A | 11/2019 |
| JP | 2021195408 | A | 12/2021 |
| WO | 9207065 | A1 | 4/1992 |
| WO | 9315187 | A1 | 8/1993 |
| WO | 2010/057160 | A1 | 5/2010 |
| WO | 2010/061880 | A1 | 6/2010 |
| WO | 2011/136368 | A1 | 11/2011 |
| WO | 2012044638 | A1 | 4/2012 |
| WO | 2012/170952 | A2 | 12/2012 |
| WO | 2012/170952 | A9 | 2/2013 |
| WO | 2013/065825 | A1 | 5/2013 |
| WO | 2013/086373 | A1 | 6/2013 |
| WO | 2013/185116 | A1 | 12/2013 |
| WO | 2016/081029 | A1 | 5/2016 |
| WO | 2018119163 | A1 | 6/2018 |
| WO | 2022235935 | A2 | 11/2022 |
| WO | 2023086514 | A1 | 5/2023 |

OTHER PUBLICATIONS

International Preliminary Report on Patentability Patent Application No. PCT/US2017/015886, mailed on May 23, 2019, 48 pages.

International Search Report and Written Opinion for International Application No. PCT/US2022/049607, mailed on Mar. 16, 2023, 10 pages.

International Search Report and Written Opinion received for PCT Application No. PCT/US2017/067756, mailed on Mar. 26, 2018, 7 pages.

International Search Report and Written Opinion received on Patent Application No. PCT/US2017/015886, mailed on Aug. 29, 2017, 8 pages.

SID 439158409, *Pubchem*, Dec. 19, 2020, 7 pages.

Dorwald Florencioz "Side Reactions in Organic Synthesis: A Guide to Successful Synthesis Design", *Wiley-VCH*, 2005, 390 pages.

Healy et al. "Pharmaceutical Solvates, Hydrates and Amorphous Forms: A Special Emphasis on Cocrystals", *Adv. Drug Deliv. Rev.*, 2017, 22 pages.

Merriam-Webster, "Definition of alkylene" *In Merriam-Webster.com dictionary, from https://www.merriam-webster.com/dictionary/alkylene*, retrieved Jan. 16, 2017.

Reeck et al. ""Homology" in proteins and nucleic acids: a terminology muddle and a way out of it", *Cell*, Aug. 28, 1987, 50,667.

Reusch "Heterocyclic Chemistry—Heterocyclic Compounds", *Vir. Textbook of Org. Chem.*, 1999, 14 pages.

Reusch "Virtual Textbook of Organic Chemistry", *available at—https://www2.chemistry.msu.edu/faculty/reusch/VirtTxtJml/intro1.html*, accessed Jul. 13, 2016, 1999, 4 pages.

Wan et al. "Lipid Nanoparticle Delivery Systems for siRNA-Based Therapeutics", *Drug Deliv. Transl. Res.*, 2013, 10 pages.

* cited by examiner

IONIZABLE CATIONIC LIPIDS FOR RNA DELIVERY

CROSS-REFERENCE TO RELATED APPLICATIONS

This application claims priority to U.S. Provisional Application No. 63/278,242, filed Nov. 11, 2021, which is hereby incorporated by reference in its entirety.

TECHNICAL FIELD

Embodiments herein relate generally to lipids. In particular, embodiments herein relate to new lipids and lipid compositions that facilitate the intracellular delivery of biologically active and therapeutic molecules.

BACKGROUND

The variety of nucleic acid-based therapeutics for targeted delivery creates a challenge for lipid-based delivery vehicles. For example, nucleic acids are structurally diverse in size and type. Examples include DNA used in gene therapy, plasmids, small interfering nucleic acids (siNA), and microRNA (miRNA) for use in RNA interference (RNAi), antisense molecules, ribozymes, antagomirs, and aptamers.

The design and use of cationic lipids and ionizable cationic lipids for inclusion in such lipid-based delivery vehicles has shown great advantages. However, use of these lipids can contribute to significant side effects when administered in vivo. One problem that has been observed includes low biodegrability and clearance from target tissues, thus creating an in vivo build up of the lipid. Another problem is that large amounts of the lipid may cause an adverse immunogenic effects, which can result in discomfort in the subject and a decrease in the therapeutic effect of the active ingredient. A third problem associated with many cationic lipids is a low percentage of effective delivery to the target, thus resulting in a relatively low therapeutic effect or low potency. Finally, it is not only important that the cationic lipid in the delivery vehicle have a specially tuned pKa so it can formulate with the nucleic acid-based therapeutic agent and protect it from degradation during administration, but be able to release the therapeutic agent once the vehicle has reached its target. Thus, there is a need in the art for the development of new lipids that can meet the special needs of lipid-nucleic acid delivery systems.

Each of the following references is hereby incorporated by reference in its entirety: international application number PCT/US2014/066242, published as WO2015074085A1, international application number PCT/US2015/030218, published as WO2016081029A1, U.S. Pat. Nos. 10,227,302, 10,383,952, and 10,526,284, each of which discloses ionizable cationic lipids for RNA delivery; international application number PCT/US2016/069493, published as WO2017117530A1, which discloses ionizable cationic lipids; international application number PCT/US2019/025246, published as WO2019191780A1, which discloses lipid particles for nucleic acid delivery; and U.S. application Ser. No. 16/823,212, published as US2020/0297634, which discloses methods of making lipid-encapsulated RNA nanoparticles.

SUMMARY

The present disclosure provides lipids of Formula (I) as described herein useful for lipid-based delivery of nucleic acids and other therapeutic agents for treating diseases. These and other uses will be apparent to those skilled in the art. Additional features and advantages of the subject technology will be set forth in the description below, and in part will be apparent from the description, or may be learned by practice of the subject technology. The advantages of the subject technology will be realized and attained by the structures particularly pointed out in the written description and embodiments hereof as well as the appended drawings.

It is to be understood that both the foregoing general description and the following detailed description are exemplary and explanatory and are intended to provide further explanation of the subject technology.

In some embodiments, the present disclosure provides a compound of Formula I, or a pharmaceutically acceptable salt thereof:

(I)

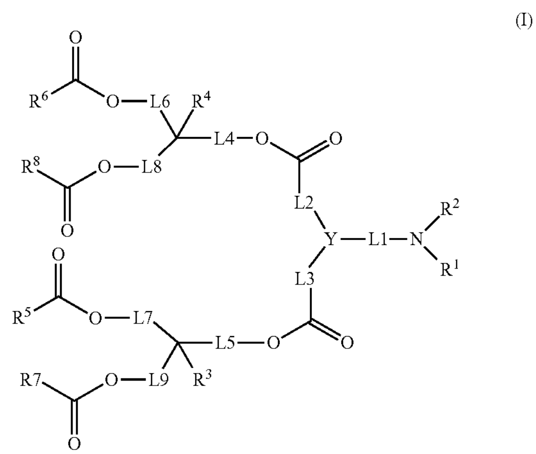

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $-(CH_2)_m(X)_n-$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

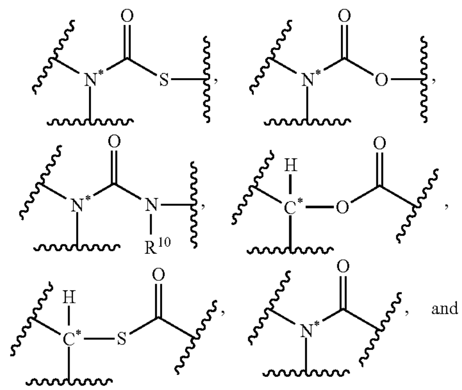

and

-continued

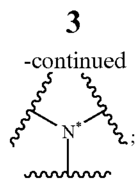

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or —$CH_2$—, provided that:

at least two of L4, L6 and L8 are —$CH_2$—; and at least two of L5, L7 and L9 are —$CH_2$—;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

In some embodiments, the present disclosure provides a lipid nanoparticle, comprising a plurality of ligands, wherein each ligand is independently a compound described herein, wherein the plurality of ligands self-assembles to form the lipid nanoparticle comprising an interior and exterior.

In some embodiments, the present disclosure provides a pharmaceutical composition comprising the compound described herein or the lipid nanoparticle described herein, and a pharmaceutically acceptable excipient.

In some embodiments, the present disclosure provides a method of treating a disease in a subject in need thereof, comprising administering a therapeutically effective amount to the subject the compound described herein, the lipid nanoparticle described herein, or the pharmaceutical composition described herein.

In some embodiments, the present disclosure provides a method of delivering a nucleic acid to a subject in needed thereof, comprising encapsulating a therapeutically effective amount of the nucleic acid in the lipid nanoparticle described herein, and administering the lipid nanoparticle to the subject.

DETAILED DESCRIPTION

I. General

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary and detailed description are to be regarded as illustrative in nature and not as restrictive.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details.

II. Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

The term "alkoxy," as used herein, alone or in combination, refers to an alkyl ether radical, wherein the term alkyl is as defined below. Alkoxy groups may have the general formula: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, and the like. The alkoxy groups can be further optionally substituted as defined herein.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may have 1 carbon, 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, or 20 carbons. The alkyl group may be linear or branched. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The alkyl group may also be a medium size alkyl having 1 to 9 carbon atoms. The alkyl group could also be a lower alkyl having 1 to 6 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $—(CH_2)_n—$ where "n" is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

The term "lower alkyl" means a group having one to six carbons in the chain which chain may be straight or branched. Non-limiting examples of suitable alkyl groups include methyl, ethyl, n-propyl, isopropyl, n-butyl, t-butyl, n-pentyl, and hexyl.

The term "amino," as used herein, represents $—N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkylcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkylheterocyclyl (e.g., alkylheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the disclosure can be an unsubstituted amino (i.e., $—NH_2$) or a substituted amino (i.e., $—N(R')_2$). In a preferred embodiment, amino is $—NH_2$ or $—NHR^{N1}$, wherein $R^{N1}$ is, independently, OH, $NO_2$, $NH_2$, $N(R^{N2})_2$, $SO_2OR^{N2}$, $SO_2R^{N2}$, $SOR^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{1-10}$ aryl.

The term "anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl. A $C_{6-10}$ aryl of the present disclosure includes a $C_6$ aryl, a $C_7$ aryl, a $C_8$ aryl, $C_9$ aryl, or a $C_{10}$ aryl. In embodiments, the $C_{6-10}$ aryl is monocyclic, such as a phenyl group. In embodiments, the $C_{6-10}$ aryl is bicyclic, such as biphenyl, naphthyl group, or an indanyl group.

The phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The terms "include," "have," or the like is used in the description or the claims, such term is intended to be inclusive in a manner similar to the term "comprise" as "comprise" is interpreted when employed as a transitional word in a claim.

The term "cationic lipid" means amphiphilic lipids and salts thereof having a positive, hydrophilic head group; one, two, three, or more hydrophobic fatty acid or fatty alkyl chains; and a connector between these two domains. An ionizable or protonatable cationic lipid is typically protonated (i.e., positively charged) at a pH below its pKa and is substantially neutral at a pH above the pKa. Preferred ionizable cationic lipids are those having a pKa that is less than physiological pH, which is typically about 7.4. The cationic lipids of the disclosure may also be termed titratable cationic lipids. The cationic lipids can be an "amino lipid" having a protonatable tertiary amine (e.g., pH-titratable) head group. Some exemplary amino lipids can include C18 alkyl chains; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA) (also known as 1-Bl 1).

The term "comprising" is intended to be open and permits but does not require the inclusion of additional elements or steps. When the term "comprising" is used herein, the terms "consisting of" and "consisting essentially of" are thus also encompassed and disclosed.

The term "commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Or.), and Wako Chemicals USA, Inc. (Richmond, Va.).

The phrase "compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," 2nd Ed., Academic Press, New York, 1983; H. O. House, "Modern Synthetic Reactions," 2nd Ed., W. A. Benjamin, Inc. Menlo Park, Calif., 1972; T. L. Glichrist, "Heterocyclic Chemistry," 2nd Ed. John Wiley and Sons, New York, 1992; J. March, "Advanced Organic Chemistry: Reactions, Mechanisms and Structure," 5th Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as those listed above) provide custom synthesis services.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

The term "compound," is meant to include all stereoisomers, geometric isomers, tautomers, and isotopes of the structures depicted.

The term "cycloalkyl," or, alternatively, "carbocycle," as used herein, alone or in combination, refers to a saturated or partially saturated monocyclic, or bicyclic alkyl radical wherein each cyclic moiety contains from 3 to 12 carbon atom ring members and which may optionally be a benzo fused ring system which is optionally substituted as defined herein. In some embodiments, a cycloalkyl may comprise from from 3 to 8 carbon atoms, or from 7 to 12 carbon atoms. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane. In embodiments, the cycloalkyl ring is a monocyclic ring from 3- to 8-carbons. In embodiments, the monocyclic ring has 3 carbons, 4 carbons, 5 carbons, 6 carbons, 7 carbons, or 8 carbons. In embodiments, the cycloalkyl ring is a bicyclic ring from 7- to 12-carbons. In embodiments, the bicyclic ring has 7 carbons, 8 carbons, 9 carbons, 10 carbons, 11 carbons, or 12 carbons.

The term "delivery" refers to the act or manner of delivering a compound, substance, entity, moiety, cargo or payload.

The term "fragment," as used herein, refers to a portion. For example, fragments of proteins may comprise polypeptides obtained by digesting full-length protein isolated from cultured cells.

The term "hydrophobic lipids" means compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

The term "lipid delivery vehicle" means a lipid formulation that can be used to deliver a therapeutic nucleic acid (e.g., mRNA) to a target site of interest (e.g., cell, tissue, organ, and the like). The lipid delivery vehicle can be a nucleic acid-lipid particle, which can be formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

The term "lipid encapsulated" means a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

The term "amphipathic lipid" or "amphiphilic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized (i.e. bond to 4 groups). The heteroatom(s) O, N and S may be placed at any interior position of the heteroalkyl group. Up to two heteroatoms may be consecutive, such as, for example, $—CH_2NHOCH_3$.

The term "linker" or "linking moiety" refers to a group of atoms, e.g., 10-100 atoms, and can be comprised of the atoms or groups such as, but not limited to, carbon, amino, alkylamino, oxygen, sulfur, sulfoxide, sulfonyl, carbonyl, and imine. The linker may be of sufficient length as to not interfere with incorporation into an amino acid sequence. Examples of chemical groups that can be incorporated into the linker include, but are not limited to, alkyl, alkenyl, alkynyl, amido, amino, ether, thioether, ester, alkyl, heteroalkyl, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond, which can be cleaved for example by the use of tris(2-carboxyethyl) phosphine (TCEP), or other reducing agents, and/or photolysis, as well as an ester bond, which can be cleaved for example by acidic or basic hydrolysis.

The term "mammal" means a human or other mammal or means a human being.

The term "messenger RNA" (mRNA) refers to any polynucleotide which encodes a protein or polypeptide of interest and which is capable of being translated to produce the encoded protein or polypeptide of interest in vitro, in vivo, in situ or ex vivo.

The term "modified" refers to a changed state or structure of a molecule of the disclosure. Molecules may be modified in many ways including chemically, structurally, and functionally. In one embodiment, nucleic acid active ingredients are modified by the introduction of non-natural nucleosides and/or nucleotides, e.g., as it relates to the natural ribonucleotides A, U, G, and C. Noncanonical nucleotides such as the cap structures are not considered "modified" although they may differ from the chemical structure of the A, C, G, U ribonucleotides.

The term "naturally occurring" means existing in nature without artificial aid.

The term "patient" refers to a subject who may seek or be in need of treatment, requires treatment, is receiving treatment, will receive treatment, or a subject who is under care by a trained professional for a particular disease or condition.

The phrase "optionally substituted X" (e.g., optionally substituted alkyl) is intended to be equivalent to "X, wherein X is optionally substituted" (e.g., "alkyl, wherein said alkyl is optionally substituted.") It is not intended to mean that the feature "X" (e.g. alkyl) per se is optional.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The phrase "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

The term "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

The term "pharmaceutically acceptable solvate," as used herein, means a compound of the disclosure wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "phosphate" is used in its ordinary sense as understood by those skilled in the art and includes its protonated forms, for example

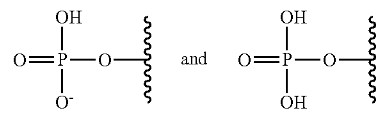

As used herein, the terms "monophosphate," "diphosphate," and "triphosphate" are used in their ordinary sense as understood by those skilled in the art, and include protonated forms.

The term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The term "RNA" means a molecule comprising at least one ribonucleotide residue. By "ribonucleotide" is meant a nucleotide with a hydroxyl group at the 2' position of a β-D-ribo-furanose moiety. The term includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA.

The term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

The terms "significant" or "significantly" are used synonymously with the term "substantially."

The phrase "single unit dose" is a dose of any therapeutic administered in one dose/at one time/single route/single point of contact, i.e., single administration event.

The term "siRNA" or small interfering RNA, sometimes known as short interfering RNA or silencing RNA, refers to a class of double-stranded RNA non-coding RNA molecules, typically 18-27 base pairs in length, similar to miRNA, and operating within the RNA interference (RNAi) pathway. It interferes with the expression of specific genes with complementary nucleotide sequences by degrading mRNA after transcription, thereby preventing translation.

The term "solvate" means a physical association of a compound of this disclosure with one or more solvent molecules. This physical association involves varying degrees of ionic bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "stable" refers to a compound that is sufficiently robust to survive isolation to a useful degree of purity from a reaction mixture, and preferably capable of formulation into an efficacious therapeutic agent.

The terms "stabilize", "stabilized," "stabilized region" means to make or become stable.

The term "substituted" means substitution with specified groups other than hydrogen, or with one or more groups, moieties, or radicals which can be the same or different, with each, for example, being independently selected.

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantially equal" relates to time differences between doses, the term means plus/minus 2%.

The phrase "substantially simultaneously" relates to plurality of doses, the term means within 2 seconds.

The phrase "suffering from" relates to an individual who is "suffering from" a disease, disorder, and/or condition has been diagnosed with or displays one or more symptoms of a disease, disorder, and/or condition.

The phrase "susceptible to" relates to an individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The term "synthetic" means produced, prepared, and/or manufactured by the hand of man. Synthesis of polynucleotides or polypeptides or other molecules of the present disclosure may be chemical or enzymatic.

The term "therapeutic agent" refers to any agent that, when administered to a subject, has a therapeutic, diagnostic, and/or prophylactic effect and/or elicits a desired biological and/or pharmacological effect.

The term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

The term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

The term "total daily dose" is an amount given or prescribed in 24 hour period. It may be administered as a single unit dose.

The term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The term "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by enantio-selective and/or stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

The term "half-life" is the time required for a quantity such as nucleic acid or protein concentration or activity to fall to half of its value as measured at the beginning of a time period.

The term "in vitro" refers to events that occur in an artificial environment, e.g., in a test tube or reaction vessel, in cell culture, in a Petri dish, etc., rather than within an organism (e.g., animal, plant, or microbe).

The term "in vivo" refers to events that occur within an organism (e.g., animal, plant, or microbe or cell or tissue thereof).

The term "monomer" refers to a single unit, e.g., a single nucleic acid, which may be joined with another molecule of the same or different type to form an oligomer. In some embodiments, a monomer may be an unlocked nucleic acid, i.e., a UNA monomer.

The term "neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" means an amphipathic lipid or a neutral lipid or anionic lipid and is described herein.

The terms "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

The term "translatable" may be used interchangeably with the term "expressible" and refers to the ability of polynucleotide, or a portion thereof, to be converted to a polypeptide by a host cell. As is understood in the art, translation is the process in which ribosomes in a cell's cytoplasm create polypeptides. In translation, messenger RNA (mRNA) is decoded by tRNAs in a ribosome complex to produce a specific amino acid chain, or polypeptide. Furthermore, the term "translatable" when used in this specification in reference to an oligomer, means that at least a portion of the oligomer, e.g., the coding region of an oligomer sequence (also known as the coding sequence or CDS), is capable of being converted to a protein or a fragment thereof.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications, and equivalents. In particular, this disclosure includes any combination of the features, terms, or elements of the various illustrative components and examples.

III. Compounds

In some embodiments, the present disclosure provides a compound of Formula I, or a pharmaceutically acceptable salt thereof:

(I)

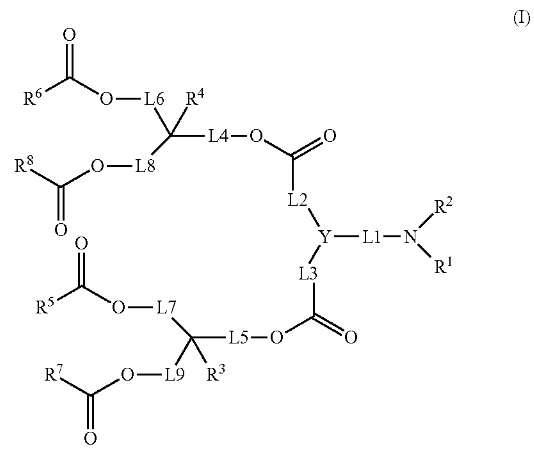

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $-(CH_2)_m(X)_n-$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

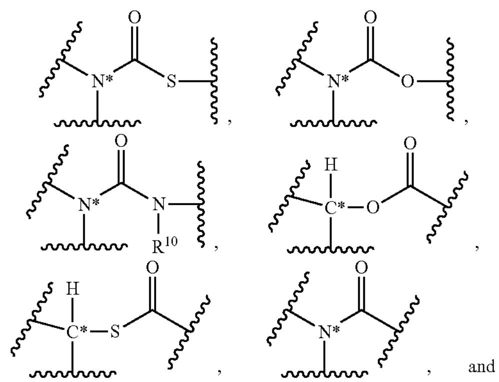

, , , , , and

-continued

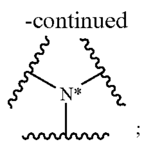

;

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or $—CH_2—$, provided that:

at least two of L4, L6 and L8 are $—CH_2—$; and at least two of L5, L7 and L9 are $—CH_2—$;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

In some embodiments, the present disclosure provides a compound of Formula I, or a pharmaceutically acceptable salt thereof:

(I)

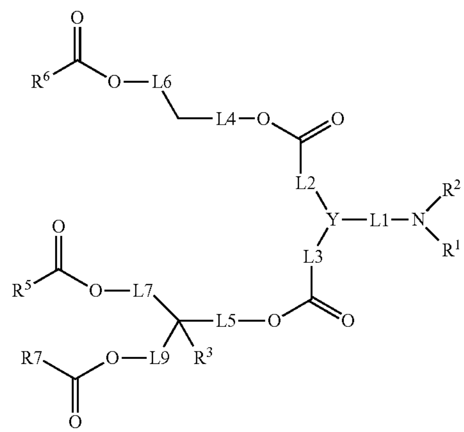

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $—(CH_2)_m(X)_n—$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

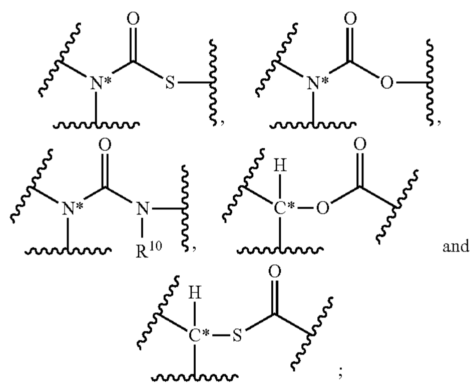

,  ,  ,  and  ;

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or $—CH_2—$, provided that:

at least two of L4, L6 and L8 are $—CH_2—$; and at least two of L5, L7 and L9 are $—CH_2—$;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

In some embodiments, $R^1$ is H or $C_{1-6}$ alkyl, and $R^2$ is $C_{1-6}$ alkyl; or $R^1$ and $R^2$ are joined to form said saturated heterocyclic ring.

In some embodiments, Y is selected from the group consisting of:

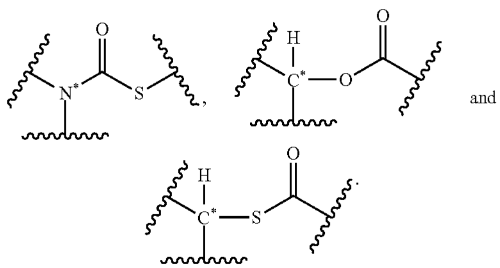

In some embodiments, Y is:

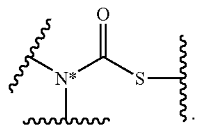

In some embodiments, Y is:

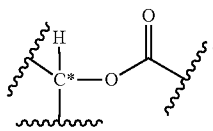

In some embodiments, Y is:

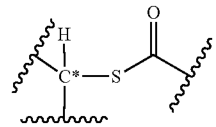

In some embodiments, when Y is

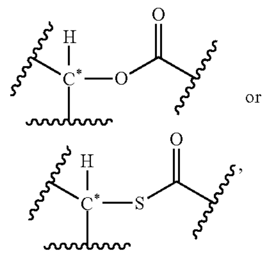

and at least one of $R^1$ and $R^2$ is H; then L1 is $—CH_2—$ or $—CH_2CH_2—$. In some embodiments, at least one of $R^1$ and $R^2$ is H; L1 is $—CH_2—$ or $—CH_2CH_2—$, the identity of Y notwithstanding.

In some embodiments, Y is:

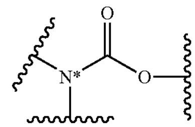

In some embodiments, Y is:

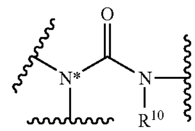

In some embodiments, Y is:

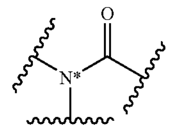

In some embodiments, Y is:

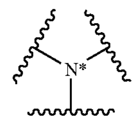

In some embodiments, $R^1$ and $R^2$ are each independently $C_{1-6}$ alkyl. In some embodiments, $R^1$ and $R^2$ are each independently $C_{1-3}$ alkyl. In some embodiments, $R^1$ and $R^2$ are each methyl.

In some embodiments, $R^1$ and $R^2$ are joined to form a heterocyclic ring. In some embodiments, the heterocyclic ring is selected from the group consisting of:

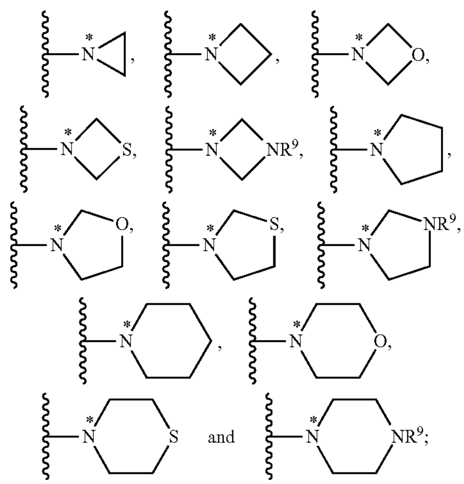

wherein each asterisk (*) indicates the atom attached to L1.

In some embodiments, $R^1$ and $R^2$ are joined to form a heterocyclic ring selected from the group consisting of:

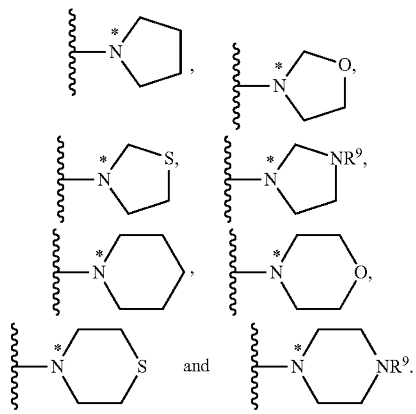

In some embodiments, $R^1$ and $R^2$ are joined to form a heterocyclic ring selected from the group consisting of:

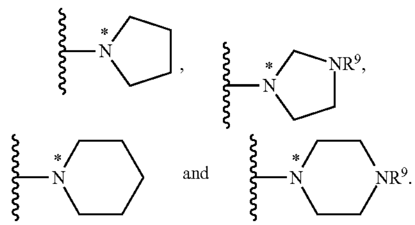

In some embodiments, $R^5$, $R^6$, $R^7$ and $R^8$ are each independently selected from the group consisting of:

linear $C_{1-8}$ alkyl, wherein each said linear $C_{1-8}$ alkyl is optionally substituted with one or more substituents selected from the group consisting of:

$C_{1-3}$ alkyl, $C_{1-3}$ alkoxy and —F, wherein each said $C_{1-3}$ alkyl substituent is optionally substituted with one or more groups selected from the group consisting of $C_{1-3}$ alkoxy and —F;

saturated $C_{3-6}$ monocycloalkyl, wherein each said saturated $C_{3-6}$ monocycloalkyl is optionally substituted with one or more substituents selected from the group consisting of $C_{1-6}$ alkyl, $C_{1-3}$ alkoxy and —F;

saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-3}$ alkoxy and —F;

saturated $C_{3-6}$ monocycloalkyl, wherein each said $C_{3-6}$ monocycloalkyl is optionally substituted with one or more substituents selected from the group consisting of $C_{1-6}$ alkyl, $C_{1-3}$ alkoxy and —F;

saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-3}$ alkoxy and —F.

In some embodiments, $R^5$, $R^6$, $R^7$ and $R^8$ are each independently linear $C_{1-8}$ alkyl, wherein each said linear $C_{1-8}$ alkyl is optionally substituted with one or more substituents selected from the group consisting of $C_{1-3}$ alkyl, $C_{1-3}$ alkoxy and —F, wherein each said $C_{1-3}$ alkyl substituent is optionally substituted with one or more groups selected from the group consisting of $C_{1-3}$ alkoxy and —F. In some embodiments, $R^5$, $R^6$, $R^7$ and $R^8$ are each independently linear $C_{1-8}$ alkyl optionally substituted with one or more $C_{1-3}$ alkyl. In some embodiments, $R^5$, $R^6$, $R^7$ and $R^8$ are each independently linear $C_{6-8}$ alkyl optionally substituted with one to three methyl groups. In some embodiments, $R^5$, $R^6$, $R^7$ and $R^8$ are each independently n-heptyl or n-octyl.

In some embodiments, $R^5$, $R^6$, $R^7$ and $R^8$ are each independently linear $C_{1-8}$ alkyl optionally substituted with saturated $C_{3-6}$ monocycloalkyl, wherein each said saturated $C_{3-6}$ monocycloalkyl is optionally substituted with one or more substituents selected from the group consisting of $C_{1-6}$ alkyl, $C_{1-3}$ alkoxy and —F. In some embodiments, each said saturated $C_{3-6}$ monocycloalkyl is optionally substituted with one or more $C_{1-3}$ alkyl. In some embodiments, each said saturated $C_{3-6}$ monocycloalkyl is optionally substituted with one to three methyl groups.

In some embodiments, $R^5$, $R^6$, $R^7$ and $R^8$ are each independently linear $C_{1-8}$ alkyl optionally substituted with saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F. In some embodiments, each said saturated $C_{7-12}$ bicycloalkyl is optionally substituted with one or more $C_{1-3}$ alkyl. In some embodiments, each said saturated $C_{7-12}$ bicycloalkyl is optionally substituted with one to three methyl groups.

In some embodiments, $R^5$, $R^6$, $R^7$ and $R^8$ are each independently linear $C_{1-8}$ alkyl optionally substituted with $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-3}$ alkoxy and —F. In some embodiments, each said $C_{6-10}$ aryl is a monocyclic or bicyclic aromatic hydrocarbon optionally substituted with one or more $C_{1-3}$ alkyl. In some embodiments, each said $C_{6-10}$ aryl is a monocyclic or bicyclic aromatic hydrocarbon optionally substituted with one to three methyl groups.

In some embodiments, $R^5$, $R^6$, $R^7$ and $R^8$ are each independently saturated $C_{3-6}$ monocycloalkyl, wherein each said $C_{3-6}$ monocycloalkyl is optionally substituted with one or more substituents selected from the group consisting of $C_{1-6}$ alkyl, $C_{1-3}$ alkoxy and —F. In some embodiments, each said $C_{3-6}$ monocycloalkyl is optionally substituted with one or more $C_{1-3}$ alkyl. In some embodiments, each said $C_{3-6}$ monocycloalkyl is optionally substituted with one to three methyl groups. In some embodiments, the optionally substituted $C_{3-6}$ monocycloalkyl is cyclopentyl. In some embodiments, the optionally substituted $C_{3-6}$ monocycloalkyl is cyclohexyl.

In some embodiments, $R^5$, $R^6$, $R^7$ and $R^8$ are each independently saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F. In some embodiments, each said $C_{7-12}$ bicycloalkyl is optionally substituted with one or more $C_{1-3}$ alkyl. In some embodiments, each said $C_{7-12}$ bicycloalkyl is optionally substituted with one to three methyl groups.

In some embodiments, $R^5$, $R^6$, $R^7$ and $R^8$ are each independently $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-3}$ alkoxy and —F. In some embodiments, each said $C_{6-10}$ aryl is a monocyclic or bicyclic aromatic hydrocarbon optionally substituted with one or more $C_{1-3}$ alkyl. In some embodiments, each said $C_{6-10}$ aryl is a monocyclic or bicyclic aromatic hydrocarbon optionally substituted with one to three methyl groups. In some embodiments, each said optionally substituted $C_{6-10}$ aryl is an optionally substituted monocyclic aromatic hydrocarbon. In some embodiments, the optionally substituted monocyclic aromatic hydrocarbon is phenyl. In some embodiments, each said optionally substituted $C_{6-10}$ aryl is an optionally substituted bicyclic aromatic hydrocarbon. In some embodiments, the optionally substituted bicyclic aromatic hydrocarbon is naphthyl.

In some embodiments, $R^5$, $R^6$, $R^7$ and $R^8$ are each independently monocycloalkyl selected from the group consisting of:

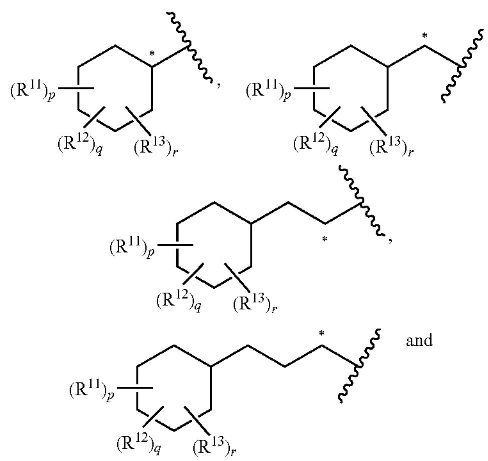

-continued

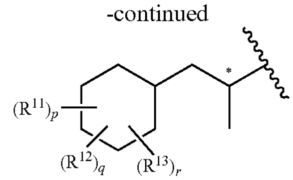

wherein:

each asterisk (*) indicates the atom attached to the carbonyl carbon;

each $R^{11}$ is independently $C_{1-6}$ alkyl;

each $R^{12}$ is independently $C_{1-3}$ alkoxy;

each $R^{13}$ is —F;

each p is independently 0 to 11;

each q is independently 0 to 11; and each r is independently 0 to 11;

wherein the sum of p, q and r is no greater than 11.

In some embodiments, $R^5$, $R^6$, $R^7$ and $R^8$ are each independently bicycloalkyl selected from the group consisting of:

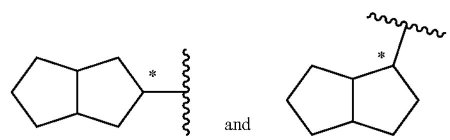

wherein:

each asterisk (*) indicates the atom attached to the carbonyl carbon; and each bicycloalkyl is optionally substituted with one or more substituents selected from the group consisting of:

$(R^{11})_p$, wherein each $R^{11}$ is independently $C_{1-6}$ alkyl and each p is independently 0 to 13;

$(R^{12})_q$, wherein each $R^{12}$ is independently $C_{1-3}$ alkoxy and each q is independently 0 to 13; and $(R^{13})_r$, wherein each $R^{13}$ is —F and each r is independently 0 to 13;

wherein the sum of p, q and r is no greater than 13.

In some embodiments, $R^5$, $R^6$, $R^7$ and $R^8$ are each independently bicycloalkyl selected from the group consisting of:

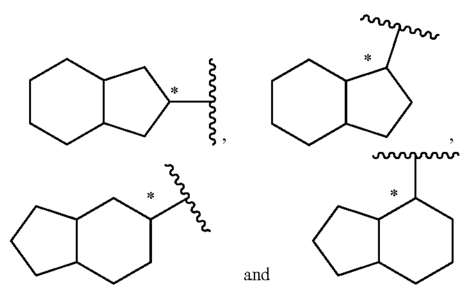

wherein:

each asterisk (*) indicates the atom attached to the carbonyl carbon; and each bicycloalkyl is optionally substituted with one or more substituents selected from the group consisting of:

$(R^{11})_p$, wherein each $R^{11}$ is independently $C_{1-6}$ alkyl and each p is independently 0 to 15;

$(R^{12})_q$, wherein each $R^{12}$ is independently $C_{1-3}$ alkoxy and each q is independently 0 to 15; and $(R^{13})_r$, wherein each $R^{13}$ is —F and each r is independently 0 to 15;

wherein the sum of p, q and r is no greater than 15.

In some embodiments, $R^5$, $R^6$, $R^7$ and $R^8$ are each independently bicycloalkyl selected from the group consisting of:

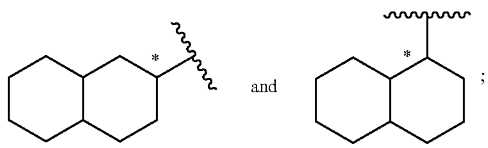 [SMILES: *C1CCC2CCCCC2C1 ; *C1CCCC2CCCCC12]

and ;

wherein:

each asterisk (*) indicates the atom attached to the carbonyl carbon; and each bicycloalkyl is optionally substituted with one or more substituents selected from the group consisting of:

$(R^{11})_p$, wherein each $R^{11}$ is independently $C_{1-6}$ alkyl and each p is independently 0 to 17;

$(R^{12})_q$, wherein each $R^{12}$ is independently $C_{1-3}$ alkoxy and each q is independently 0 to 17; and $(R^{13})_r$, wherein each $R^{13}$ is —F and each r is independently 0 to 17;

wherein the sum of p, q and r is no greater than 17.

In some embodiments, the sum of p, q and r is 0.

In some embodiments, the sum of p, q and r is 1.

In some embodiments, $R^5$, $R^6$, $R^7$ and $R^8$ are each independently selected from the group consisting of:

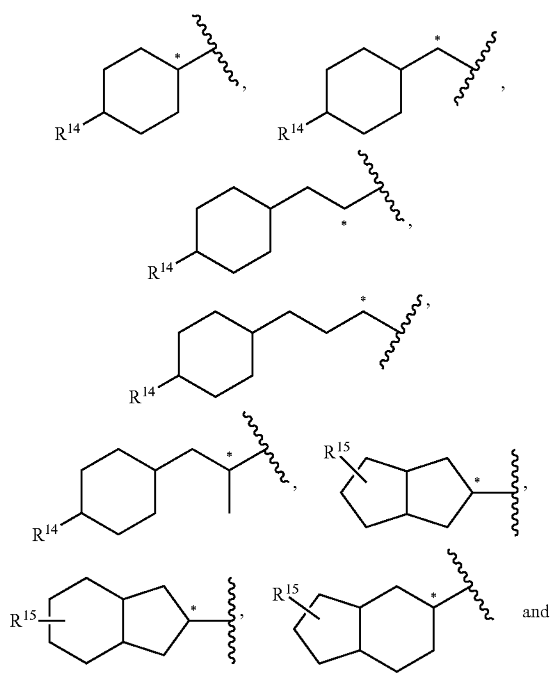

, , , , , , and

-continued

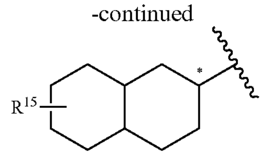

;

wherein:

each asterisk (*) indicates the atom attached to the carbonyl carbon;

each $R^{14}$ is independently H or $C_{1-6}$ alkyl; and each $R^{15}$ is independently H or $C_{1-6}$ alkyl.

In some embodiments, each $R^{14}$ is independently H or methyl, and $R^{15}$ is H.

In some embodiments, $R^5$, $R^6$, $R^7$ and $R^8$ are each independently selected from the group consisting of:

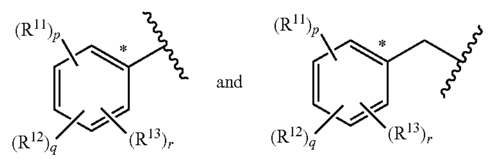

and ;

wherein:

each asterisk (*) indicates the atom attached to the carbonyl carbon;

each $R^{11}$ is independently $C_{1-6}$ alkyl;

each $R^{12}$ is independently $C_{1-3}$ alkoxy;

each $R^{13}$ is —F;

each p is independently 0 to 5;

each q is independently 0 to 5; and each r is independently 0 to 5;

wherein the sum of p, q and r is no greater than 5.

In some embodiments, $R^5$, $R^6$, $R^7$ and $R^8$ are each independently selected from the group consisting of:

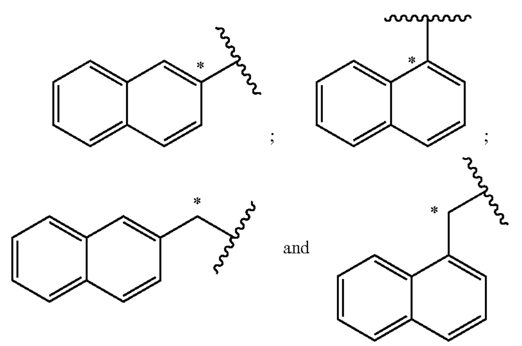

; ; and ;

wherein:

each asterisk (*) indicates the atom attached to the carbonyl carbon; and each bicyclic aromatic hydrocarbon is optionally substituted with one or more substituents selected from the group consisting of:

$(R^{11})_p$, wherein each $R^{11}$ is independently $C_{1-6}$ alkyl and each p is independently 0 to 7;

$(R^{12})_q$, wherein each $R^{12}$ is independently $C_{1-3}$ alkoxy and each q is independently 0 to 7; and $(R^{13})_r$, wherein each $R^{13}$ is-F and each r is independently 0 to 7;

wherein the sum of p, q and r is no greater than 7.

In some embodiments, the sum of p, q and r is 0.

In some embodiments, the sum of p, q and r is 1.

In some embodiments, $R^5$ and $R^6$ are the same. In some embodiments, $R^7$ and $R^8$ are the same. In some embodiments, $R^5$, $R^6$, $R^7$ and $R^8$ are the same.

In some embodiments, L1 is linear unsubstituted alkylene. In some embodiments, L1 is propylene.

In some embodiments, L2 and L3 are each independently linear $C_{1-5}$ alkylene. In some embodiments, L2 and L3 are the same.

In some embodiments, L4 and L5 are the same. In some embodiments, L6 and L7 are the same. In some embodiments, L8 and L9 are the same. In some embodiments, L4, L5, L6, L7, L8 and L9 are each $—CH_2—$. In some embodiments, L6, L7, L8 and L9 are each $—CH_2—$; and L4 and L5 are absent. In some embodiments, L4, L5, L8 and L9 are each $—CH_2—$; and L6 and L7 are absent. In some embodiments, L4, L5, L6 and L7 are each $—CH_2—$; and L8 and L9 are absent.

In some embodiments, L4 and L5 are the same. In some embodiments, L6 and L7 are the same. In some embodiments, L8 and L9 are the same. In some embodiments, L4, L5, L6, L7, L8 and L9 are each $—CH_2—$. In some embodiments, L6, L7, L8 and L9 are each $—CH_2—$; and L4 and L5 are absent. In some embodiments, L4, L5, L8 and L9 are each $—CH_2—$; and L6 and L7 are absent. In some embodiments, L4, L5, L6 and L7 are each $—CH_2—$; and L8 and L9 are absent.

In some embodiments, $R^3$ and $R^4$ are each independently H or methyl. In some embodiments, $R^3$ and $R^4$ are each H. In some embodiments, $R^3$ and $R^4$ are each methyl. In some embodiments, the compound is selected from the group consisting of:

LIPID 1

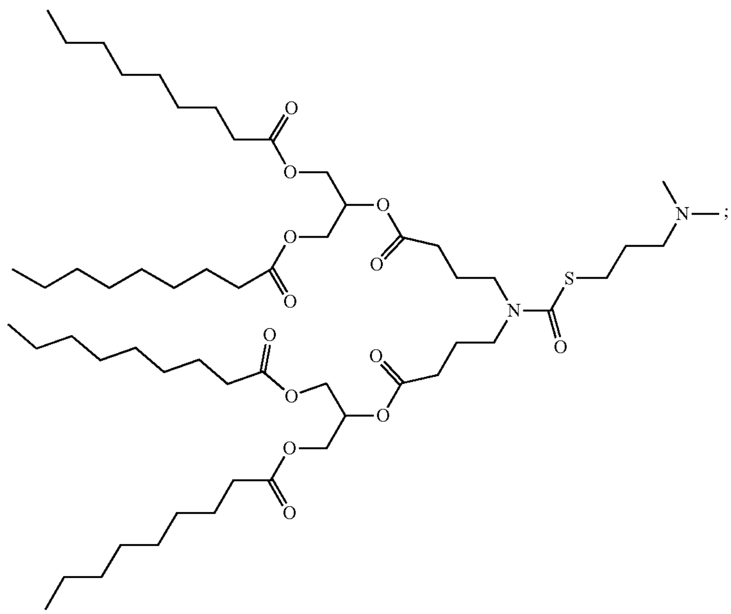

LIPID 2

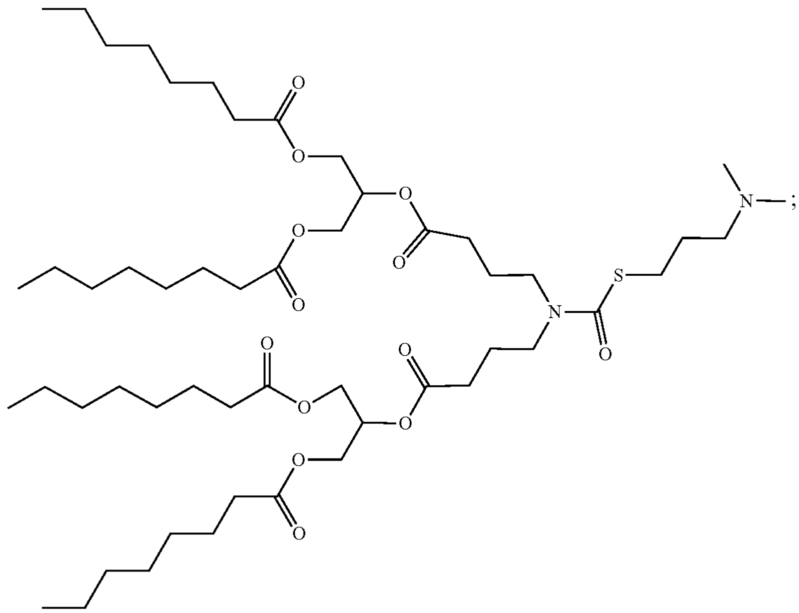

-continued
LIPID 3
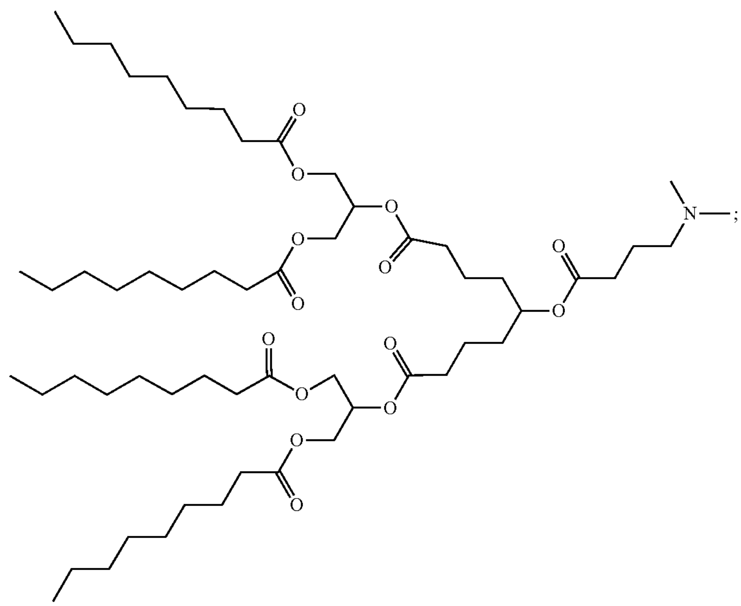
LIPID 4
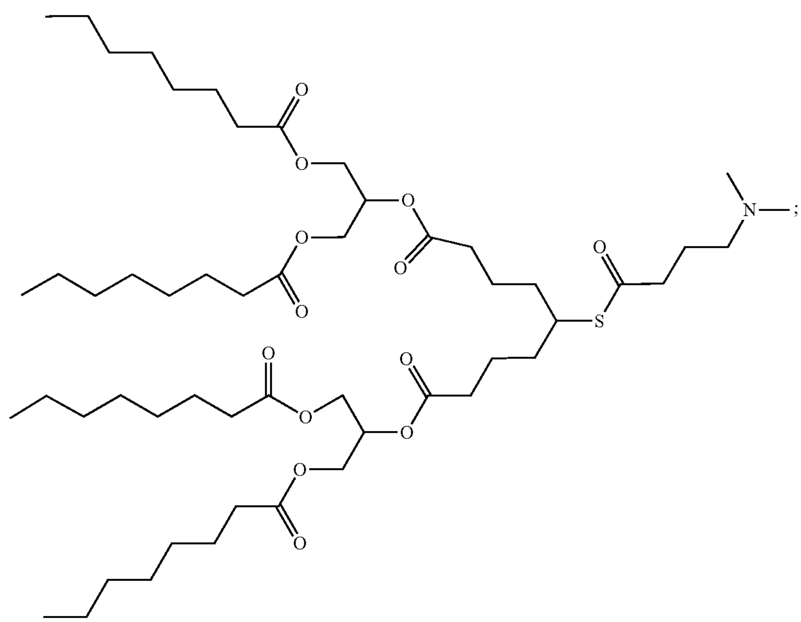

-continued
LIPID 5
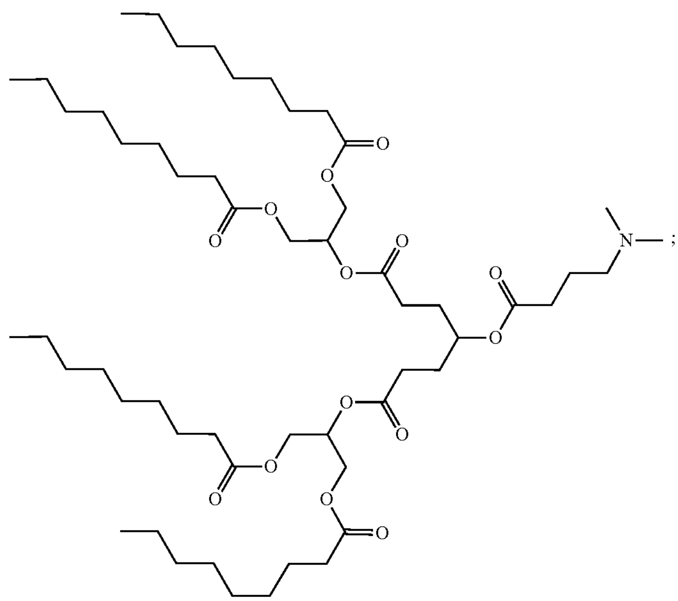
LIPID 6
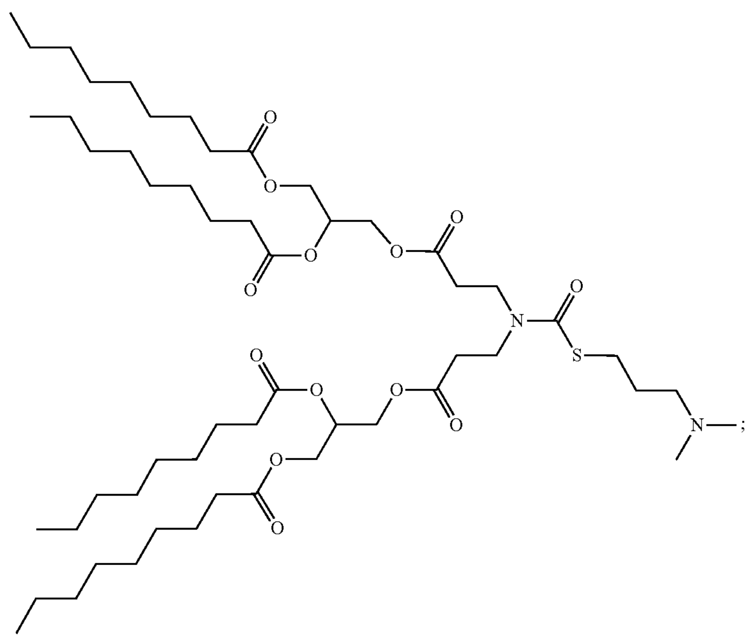

-continued
LIPID 6a
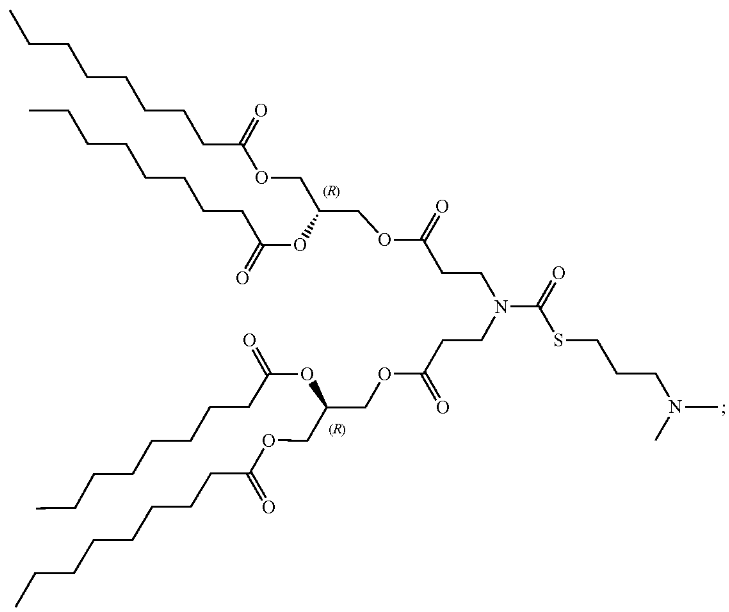
LIPID 7
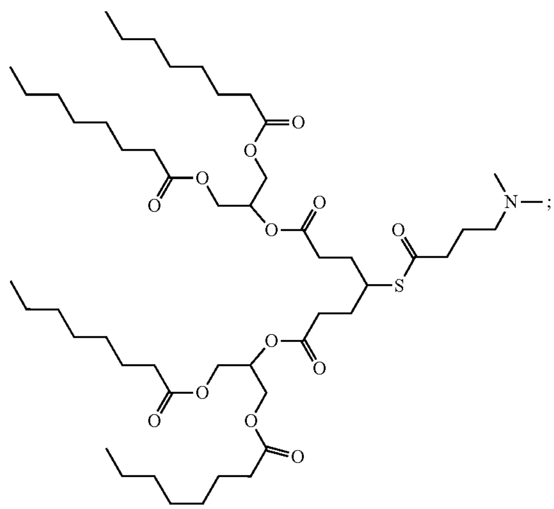
LIPID 8
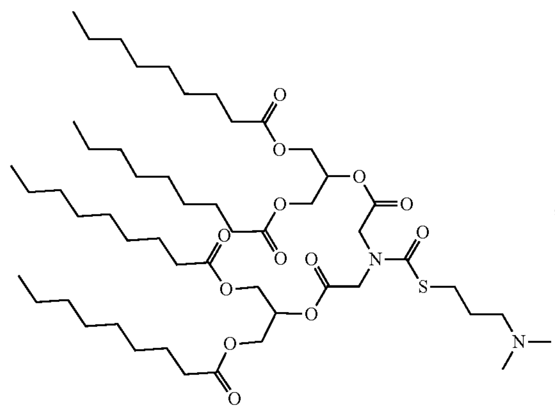
;

-continued
LIPID 9
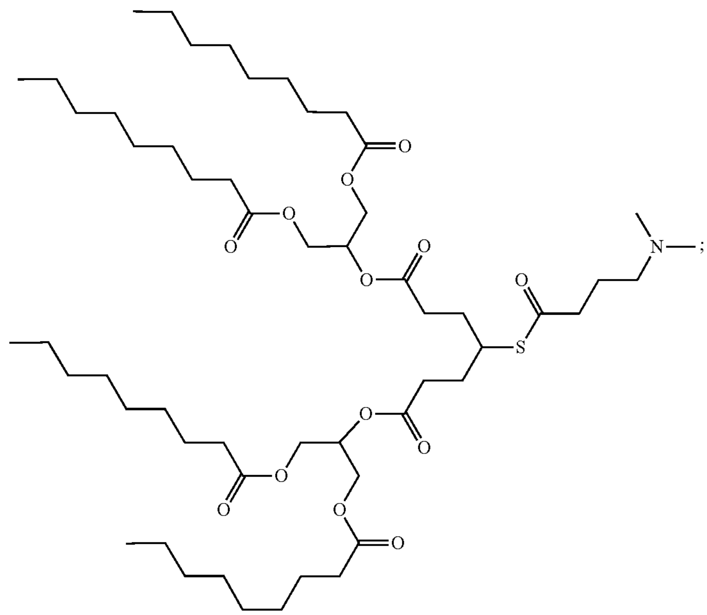
LIPID 10
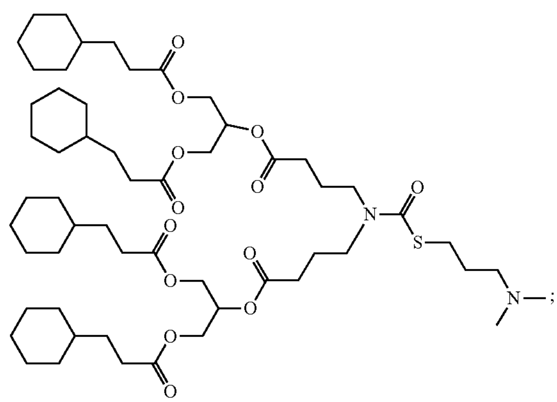
LIPID 11
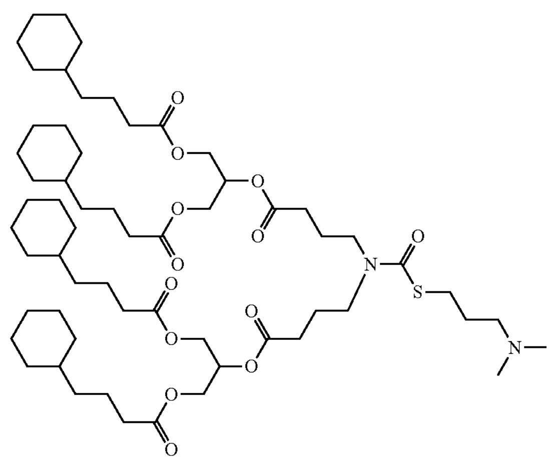
LIPID 12
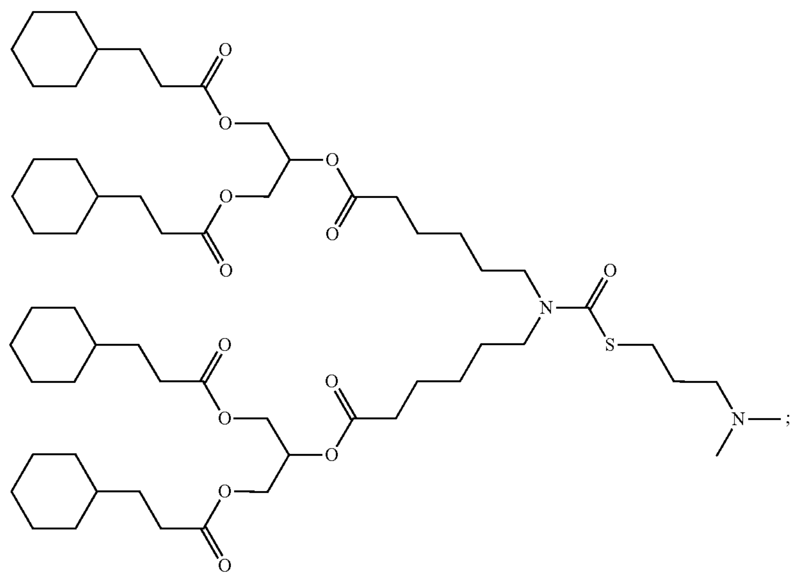

-continued
LIPID 13
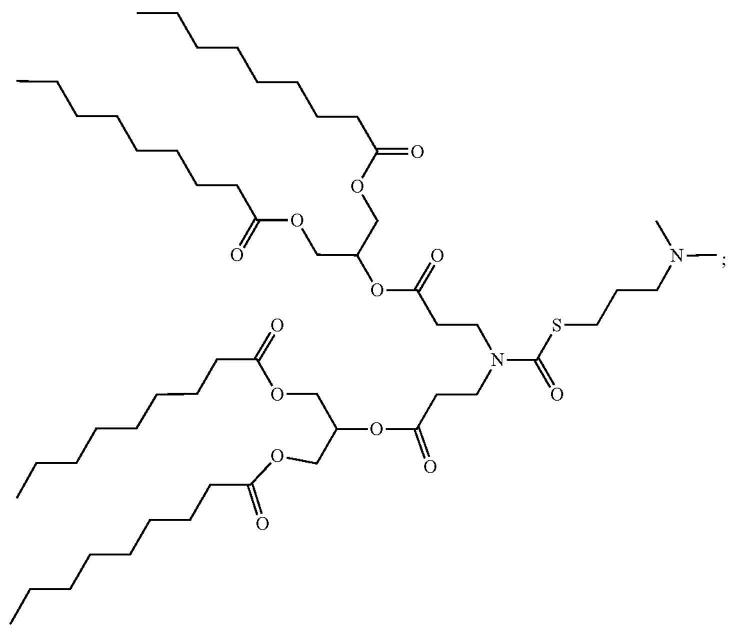
LIPID 14
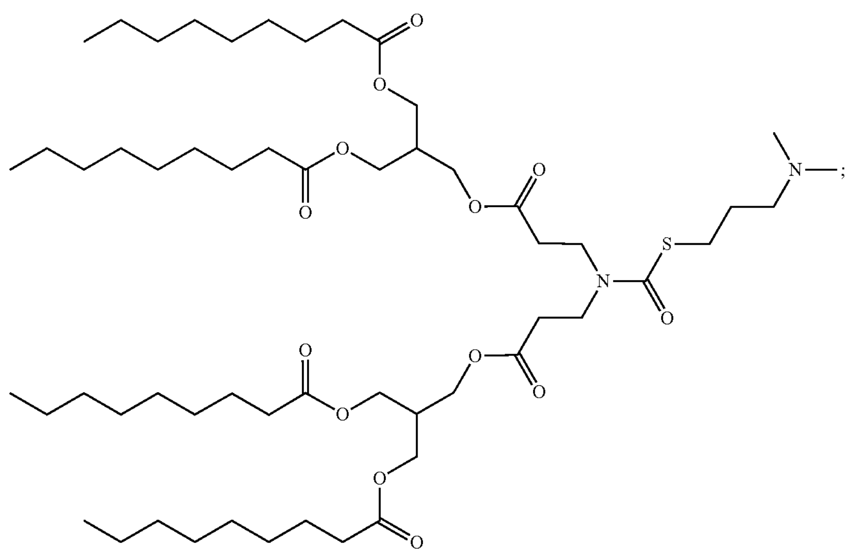

-continued
LIPID 15
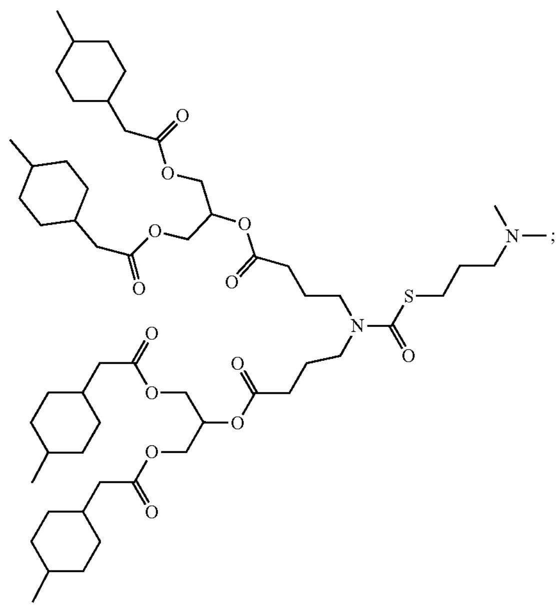
LIPID 16
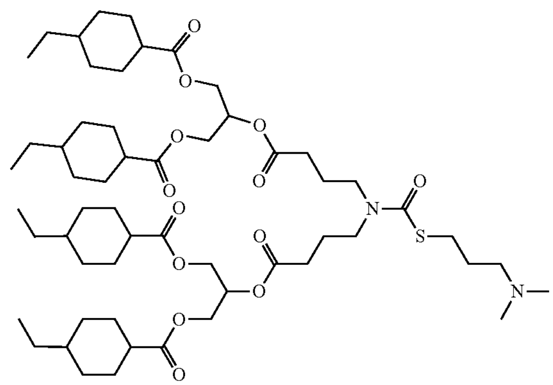
;
LIPID 17
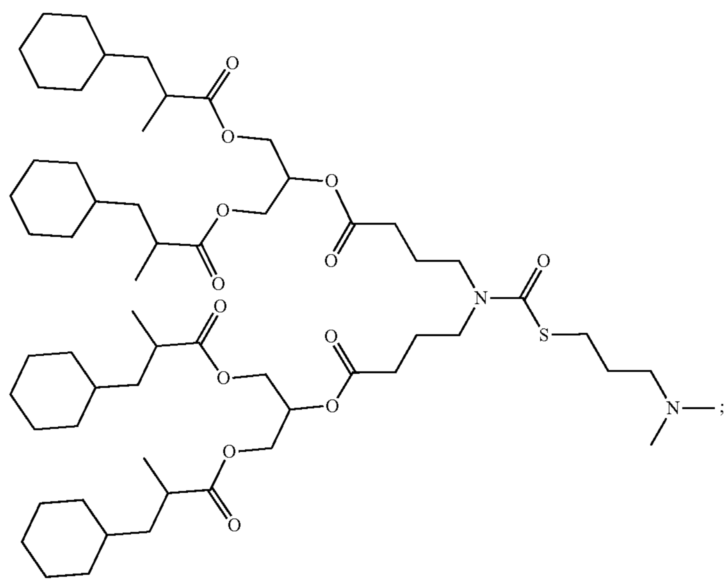

-continued
LIPID 18
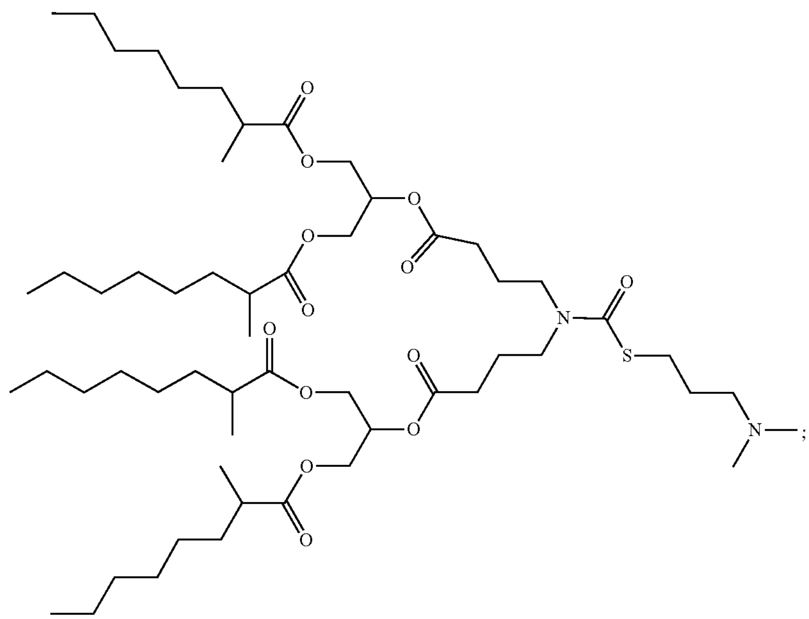
LIPID 19
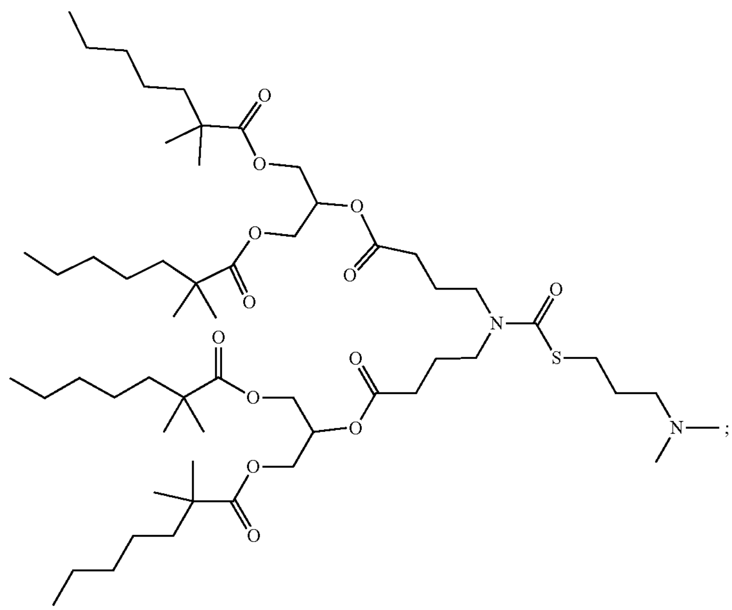

-continued
LIPID 20
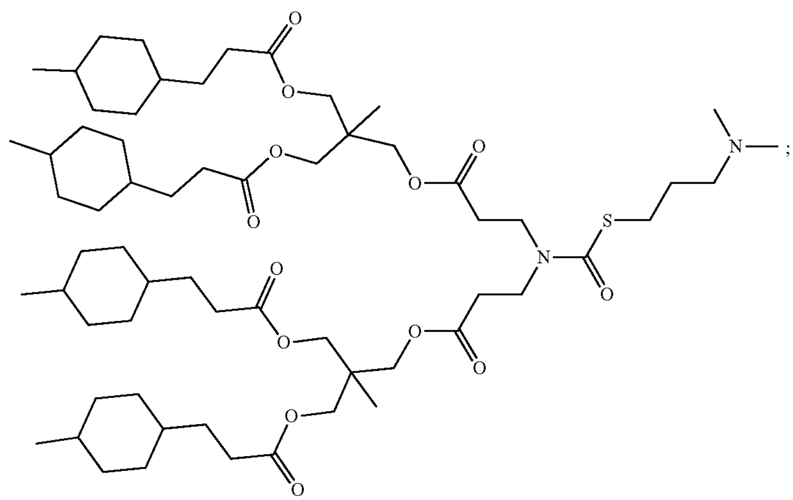
LIPID 21
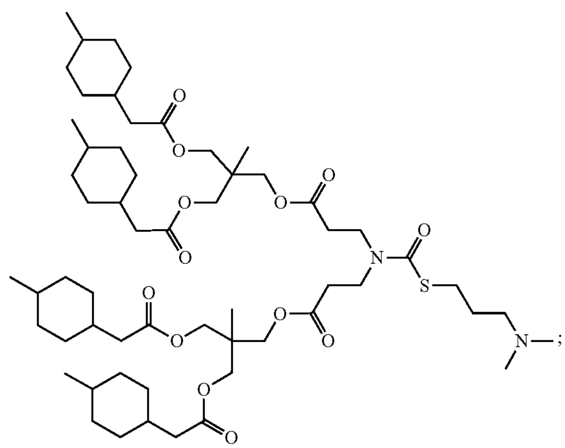
LIPID 22
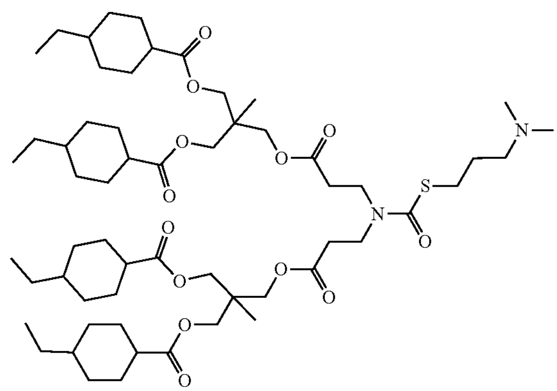
;
LIPID 23
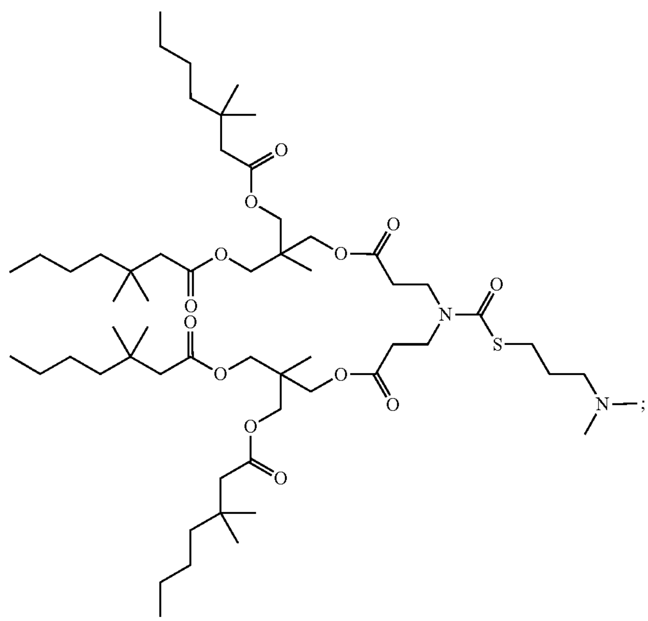

-continued
LIPID 24
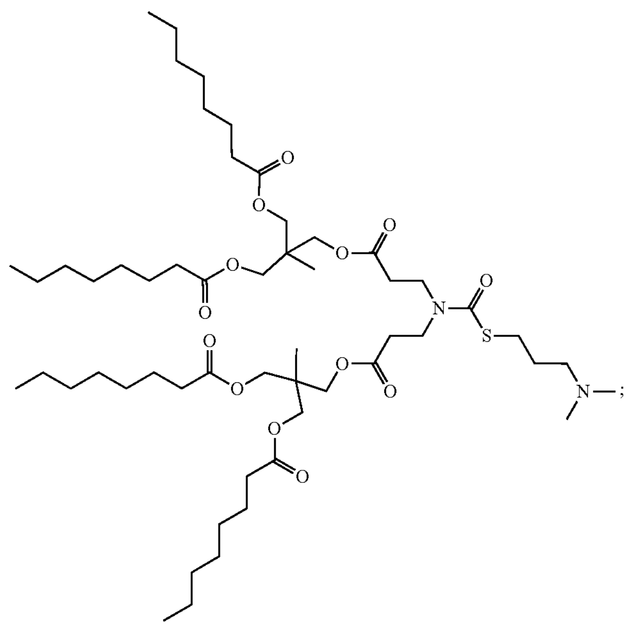
LIPID 25
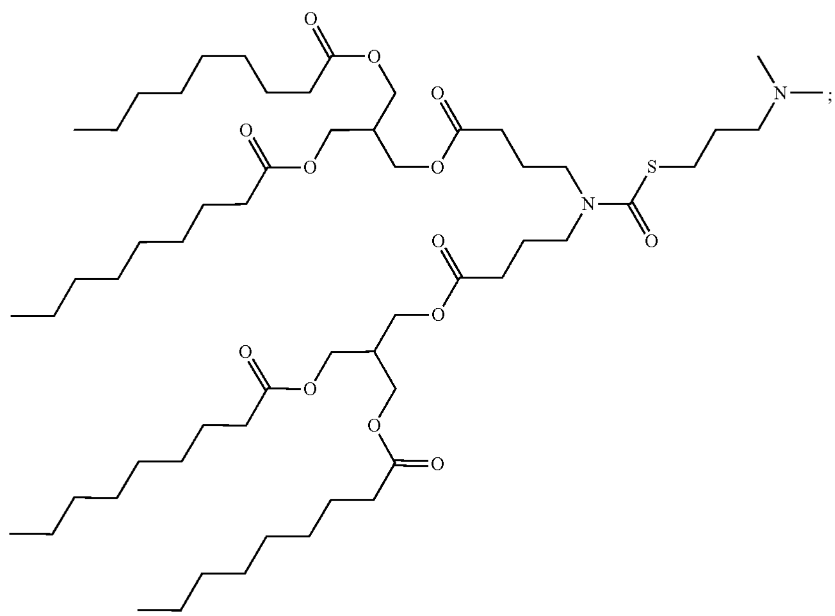

-continued
LIPID 26
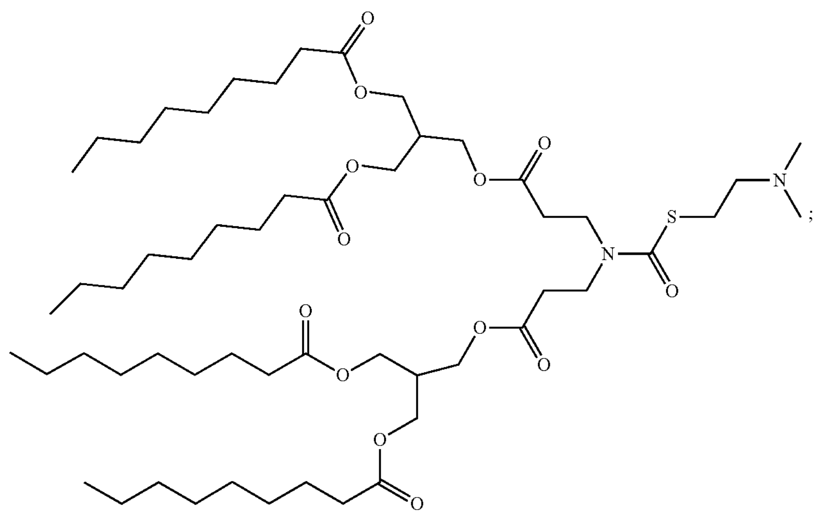
LIPID 27
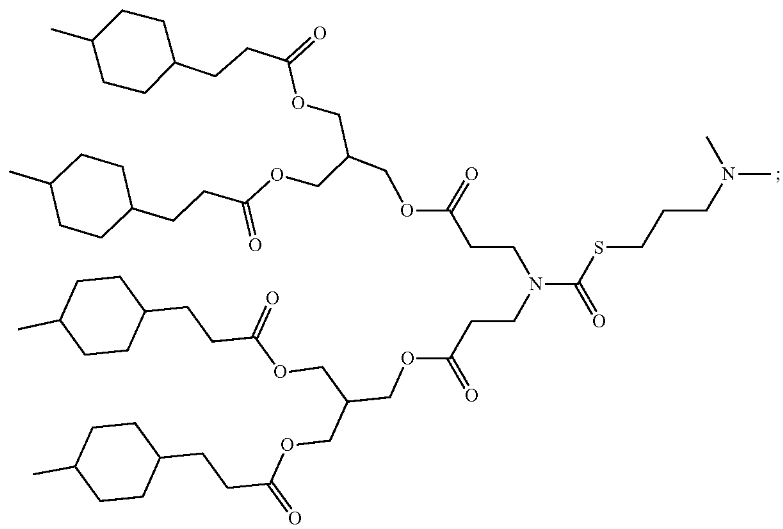
LIPID 28
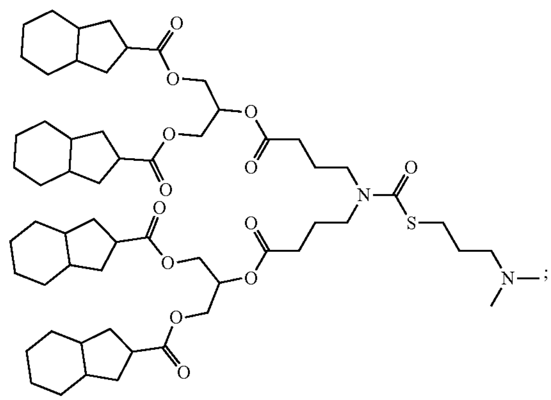
LIPID 29
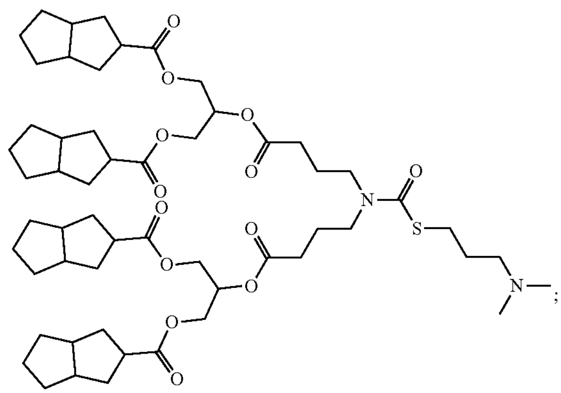

-continued
LIPID 30
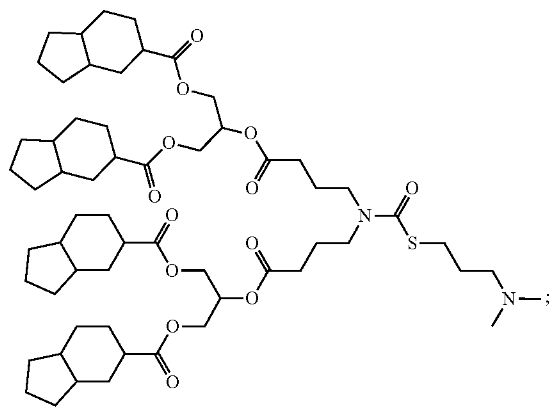
LIPID 31
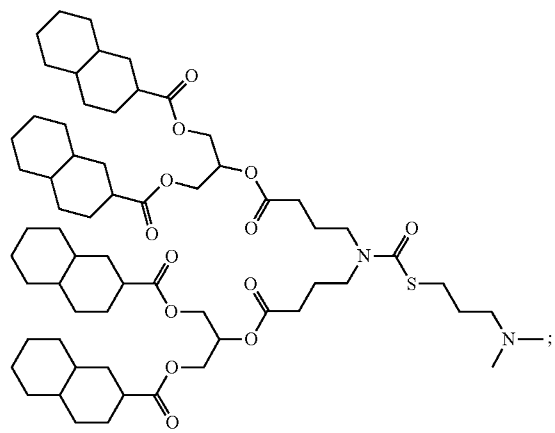
LIPID 32
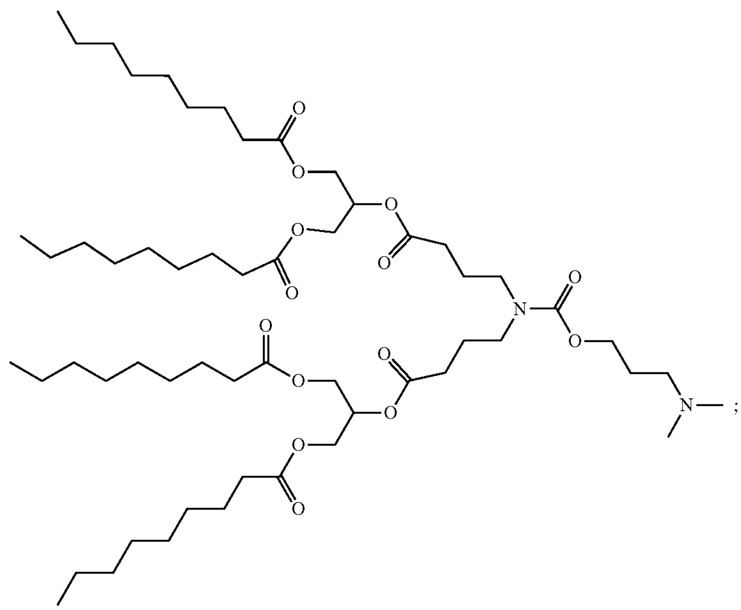

-continued
LIPID 33
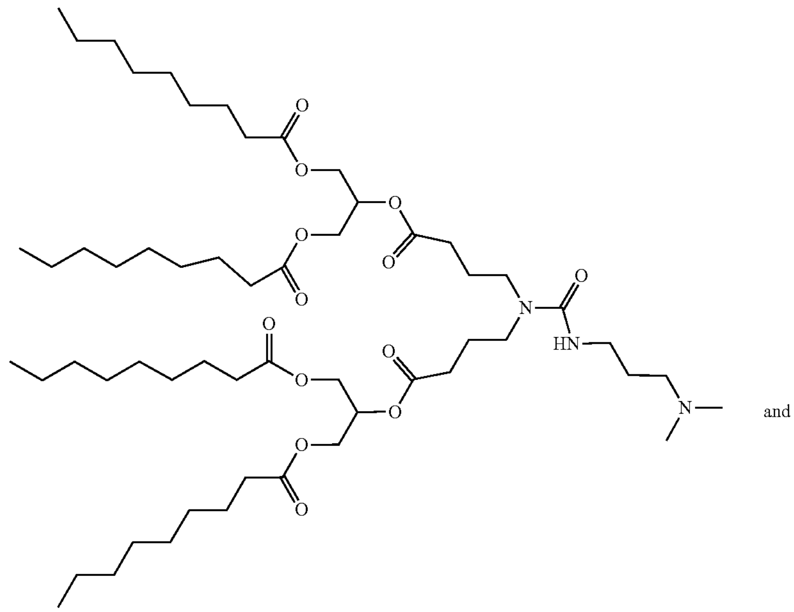
and
LIPID 34
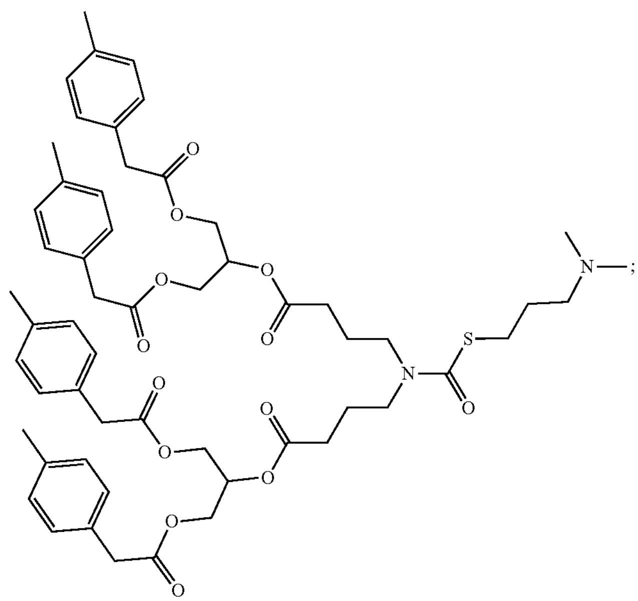
;
and pharmaceutically acceptable salts thereof.

In some embodiments, the compound is LIPID 1:

LIPID 1

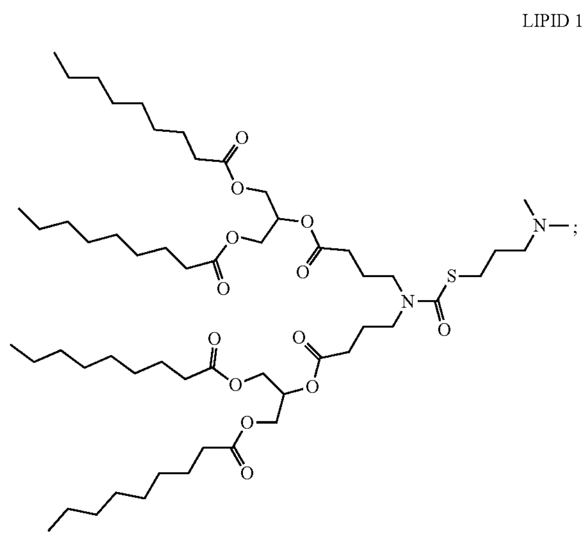 [SMILES: CCCCCCCCC(=O)OCC(COC(=O)CCCCCCCC)OC(=O)CCCN(CCCC(=O)OC(COC(=O)CCCCCCCC)COC(=O)CCCCCCCC)C(=O)SCCCN(C)C]

or a pharmaceutically acceptable salt thereof.

In some embodiments, the compound is LIPID 2:

LIPID 2

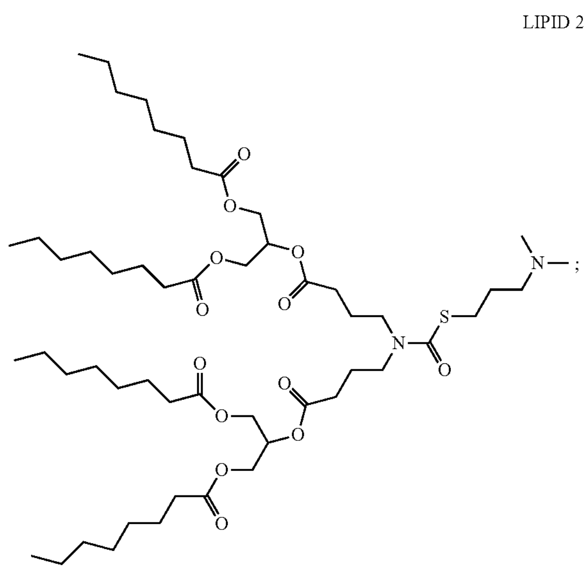 [SMILES: CCCCCCCC(=O)OCC(COC(=O)CCCCCCC)OC(=O)CCCN(CCCC(=O)OC(COC(=O)CCCCCCC)COC(=O)CCCCCCC)C(=O)SCCCN(C)C]

or a pharmaceutically acceptable salt thereof.

In some embodiments, the compound is LIPID 3;

LIPID 3

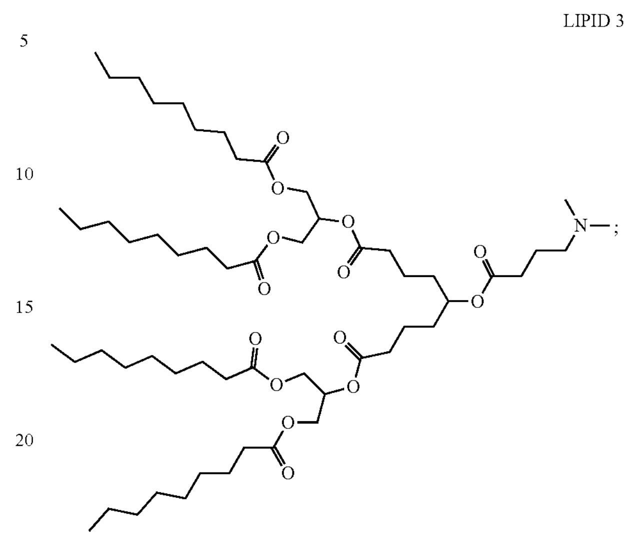

or a pharmaceutically acceptable salt thereof.

In some embodiments, the compound is LIPID 4:

LIPID 4

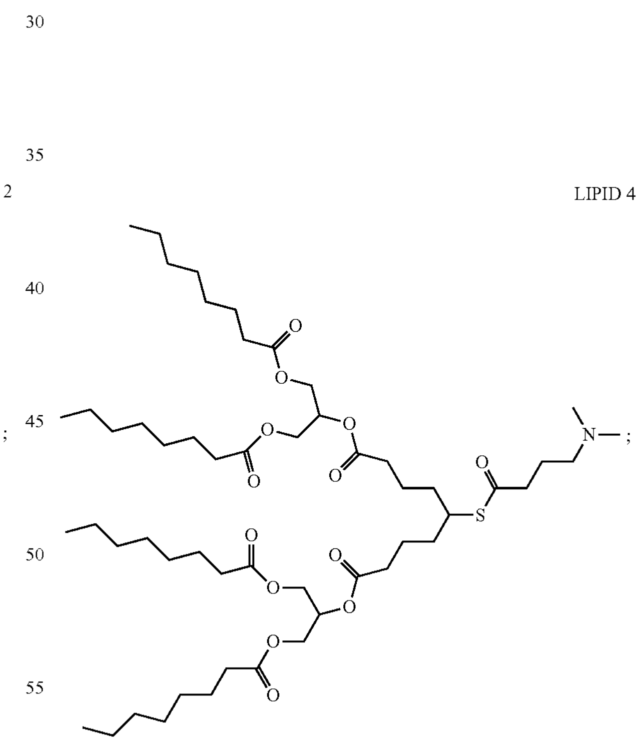

or a pharmaceutically acceptable salt thereof.

In some embodiments, the compound is LIPID 5:
LIPID 5
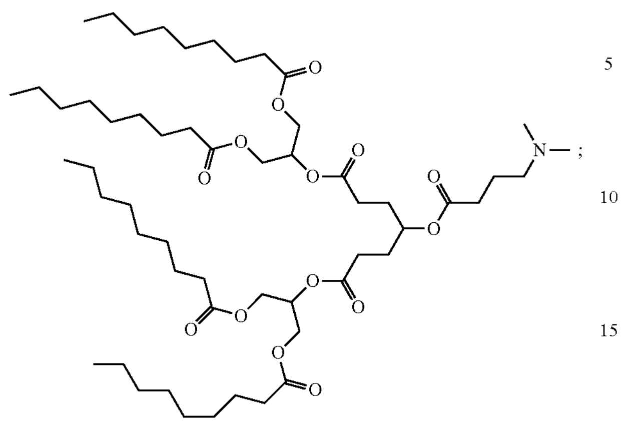
or a pharmaceutically acceptable salt thereof.
In some embodiments, the compound is LIPID 6:
LIPID 6
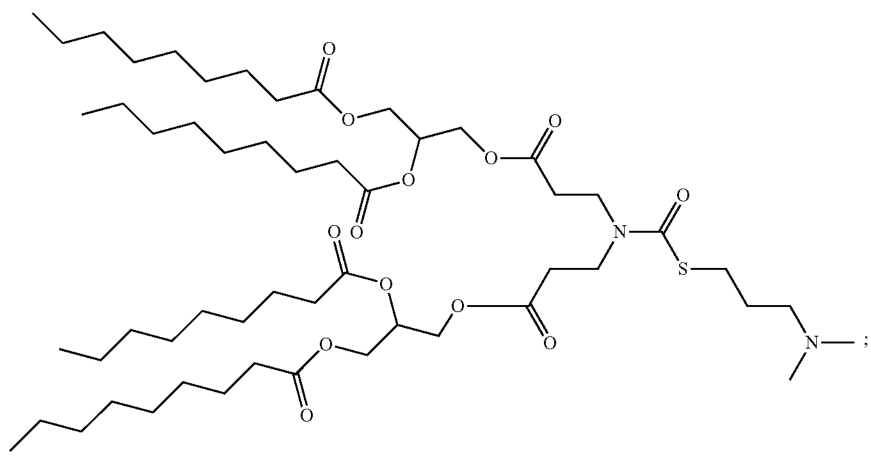
or a pharmaceutically acceptable salt thereof.
In some embodiments, the compound is LIPID 6a:
LIPID 6a
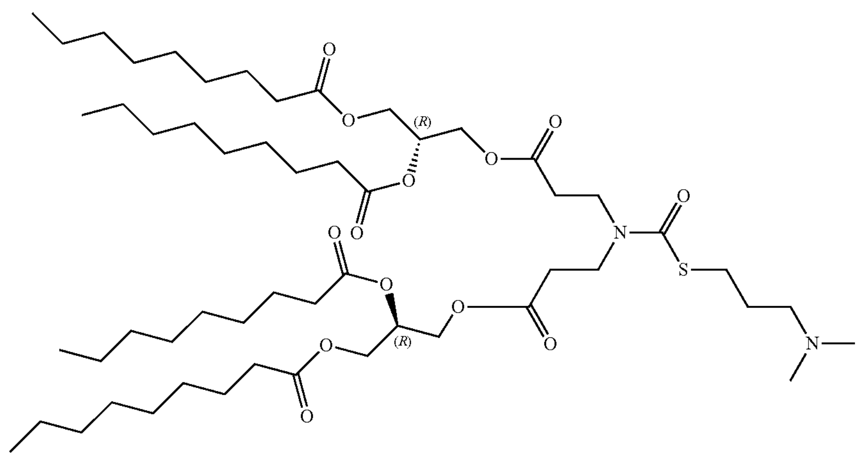
or a pharmaceutically acceptable salt thereof.

In some embodiments, the compound is LIPID 7:

LIPID 7

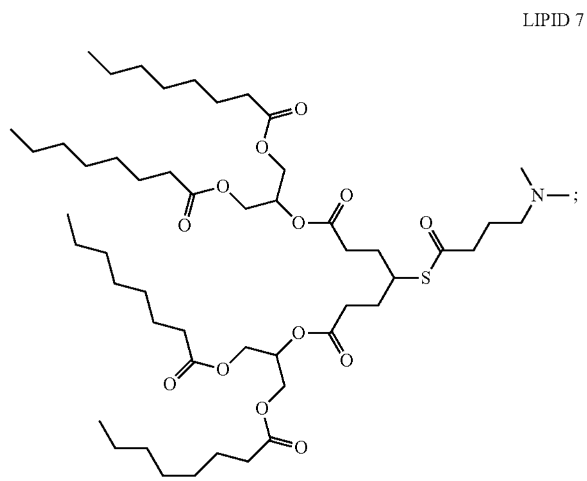 [SMILES: CCCCCCCC(=O)OCC(COC(=O)CCCCCCC)OC(=O)CCC(CCC(=O)OC(COC(=O)CCCCCCC)COC(=O)CCCCCCC)SC(=O)CCCN(C)C]

or a pharmaceutically acceptable salt thereof.

In some embodiments, the compound is LIPID 8:

LIPID 8

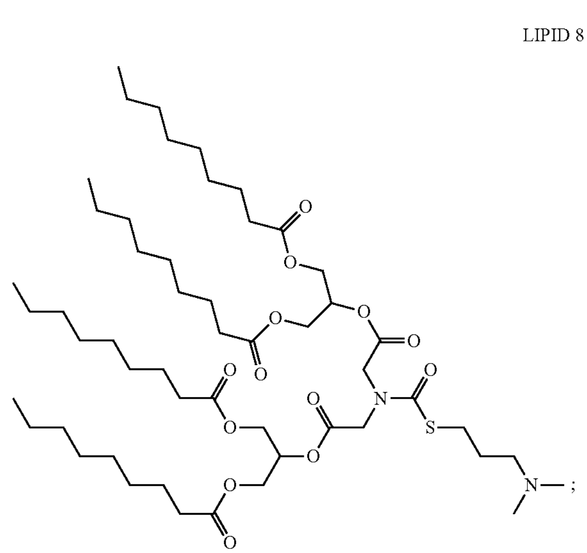 [SMILES: CCCCCCCCC(=O)OCC(COC(=O)CCCCCCCC)OC(=O)CN(CC(=O)OC(COC(=O)CCCCCCCC)COC(=O)CCCCCCCC)C(=O)SCCCN(C)C]

or a pharmaceutically acceptable salt thereof.

In some embodiments, the compound is LIPID 9:

LIPID 9

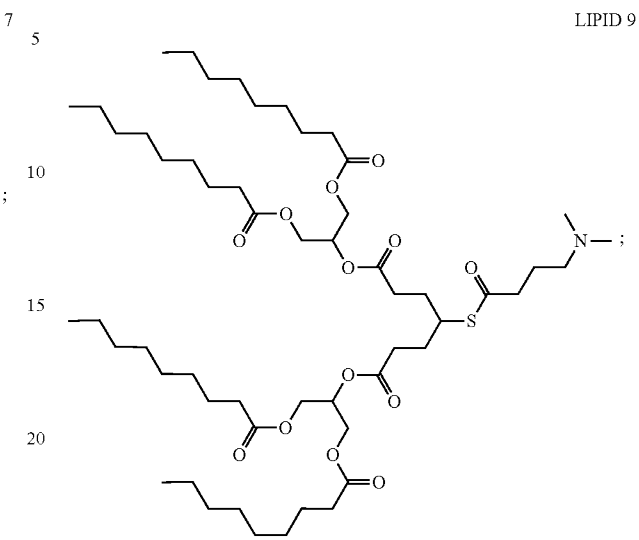

or a pharmaceutically acceptable salt thereof.

In some embodiments, the compound is LIPID 10:

LIPID 10

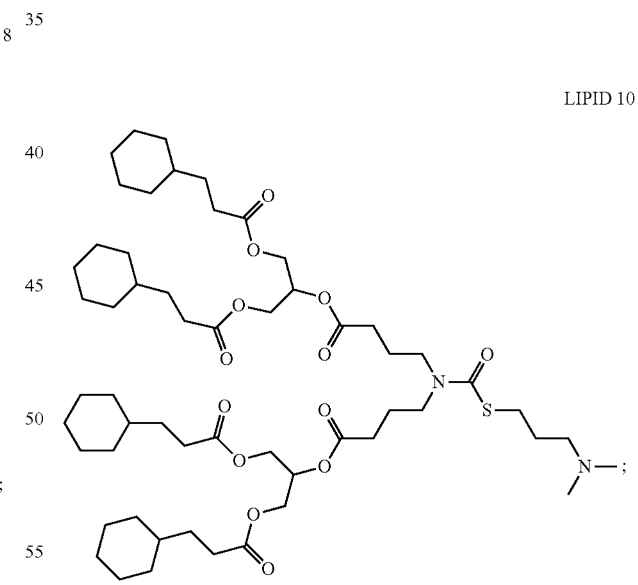

or a pharmaceutically acceptable salt thereof.

In some embodiments, the compound is LIPID 11:
LIPID 11
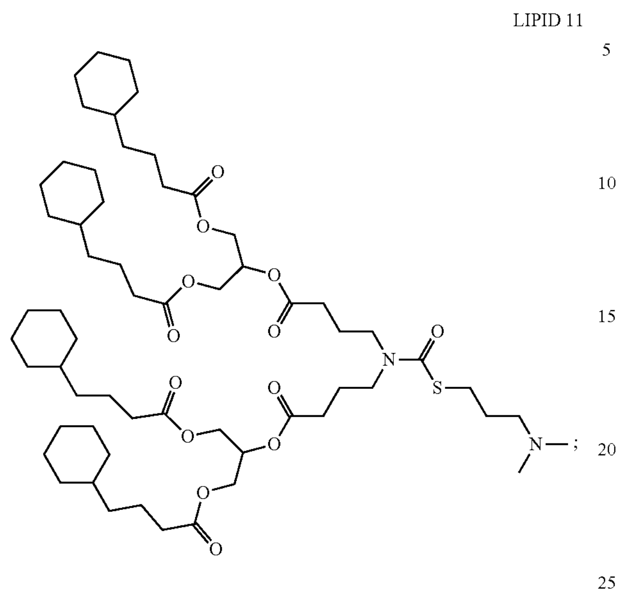
or a pharmaceutically acceptable salt thereof.
In some embodiments, the compound is LIPID 12:
LIPID 12
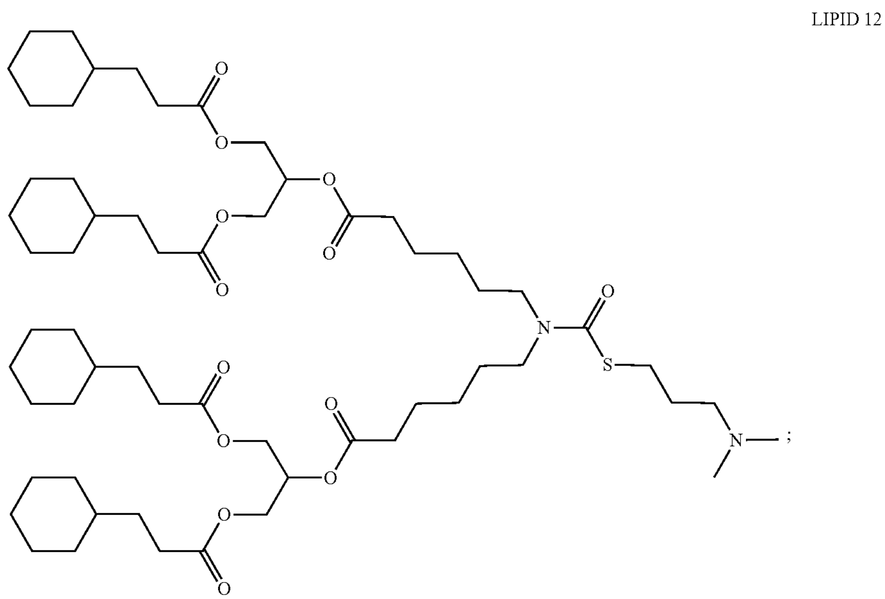 [SMILES: CN(C)CCCSC(=O)N(CCCCCC(=O)OC(COC(=O)CCC1CCCCC1)COC(=O)CCC1CCCCC1)CCCCCC(=O)OC(COC(=O)CCC1CCCCC1)COC(=O)CCC1CCCCC1]
or a pharmaceutically acceptable salt thereof.

In some embodiments, the compound is LIPID 13:
LIPID 13
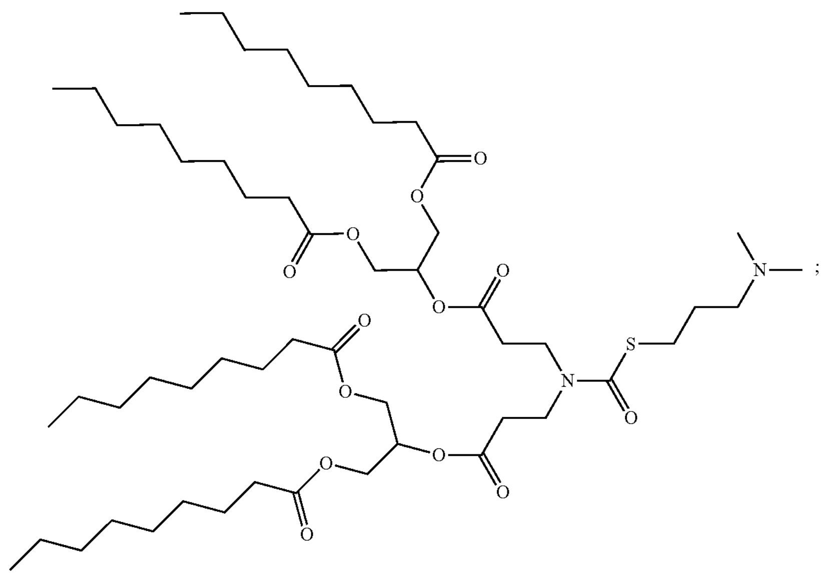
or a pharmaceutically acceptable salt thereof.
In some embodiments, the compound is LIPID 14:
LIPID 14
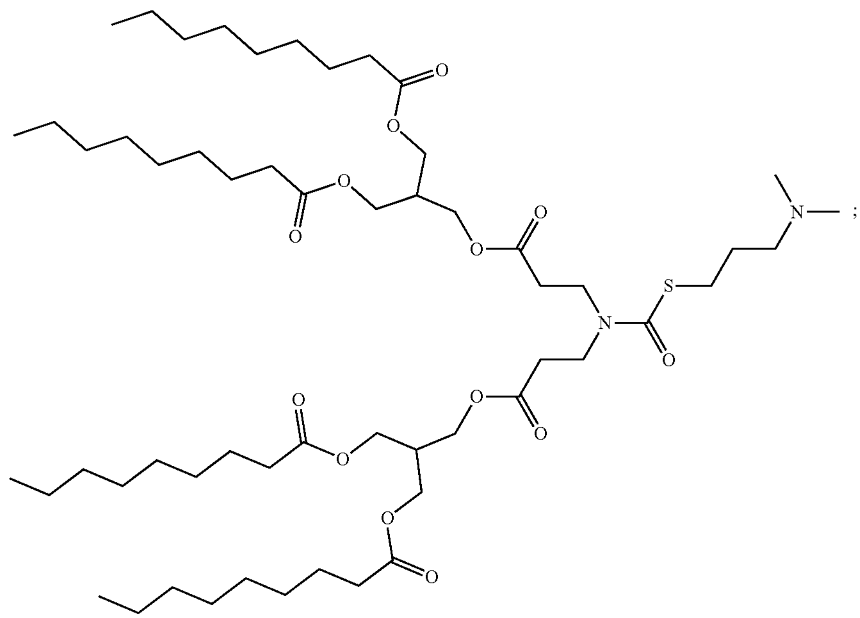
or a pharmaceutically acceptable salt thereof.

In some embodiments, the compound is LIPID 15:

LIPID 15

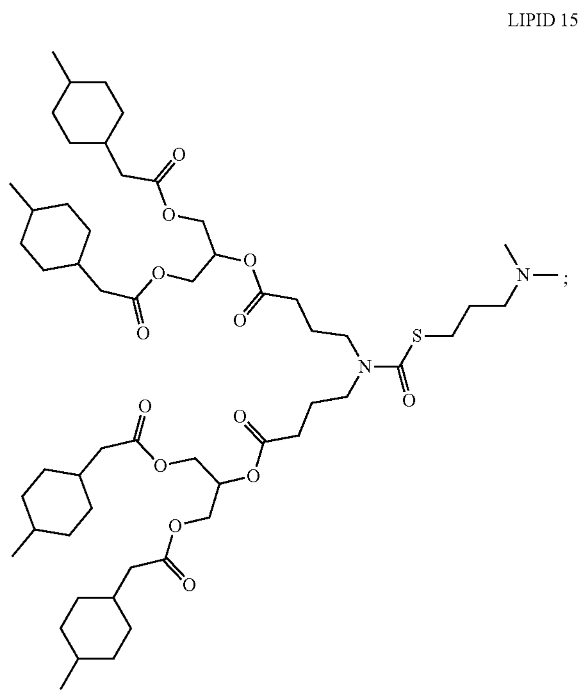

or a pharmaceutically acceptable salt thereof.

In some embodiments, the compound is LIPID 16:

LIPID 16

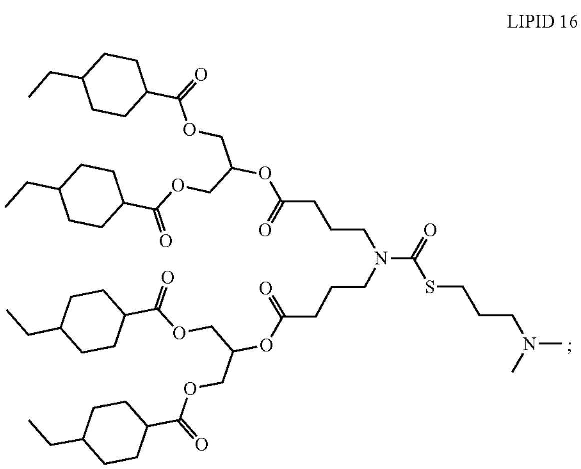 [SMILES: CCC1CCC(C(=O)OCC(COC(=O)C2CCC(CC)CC2)OC(=O)CCCN(CCCC(=O)OC(COC(=O)C2CCC(CC)CC2)COC(=O)C2CCC(CC)CC2)C(=O)SCCCN(C)C)CC1]

or a pharmaceutically acceptable salt thereof.

In some embodiments, the compound is LIPID 17:

LIPID 17

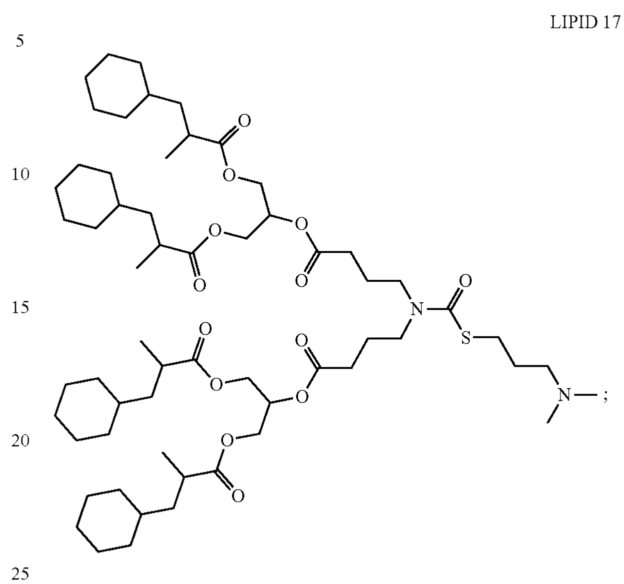

or a pharmaceutically acceptable salt thereof.

In some embodiments, the compound is LIPID 18:

LIPID 18

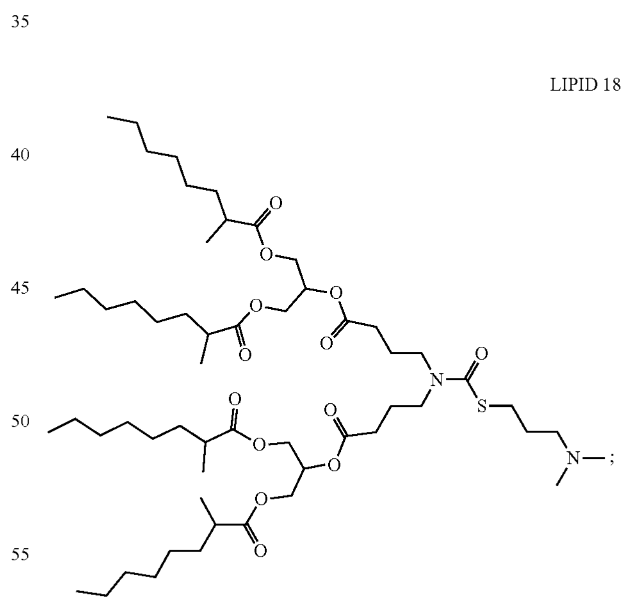

or a pharmaceutically acceptable salt thereof.

In some embodiments, the compound is LIPID 19:
LIPID 19
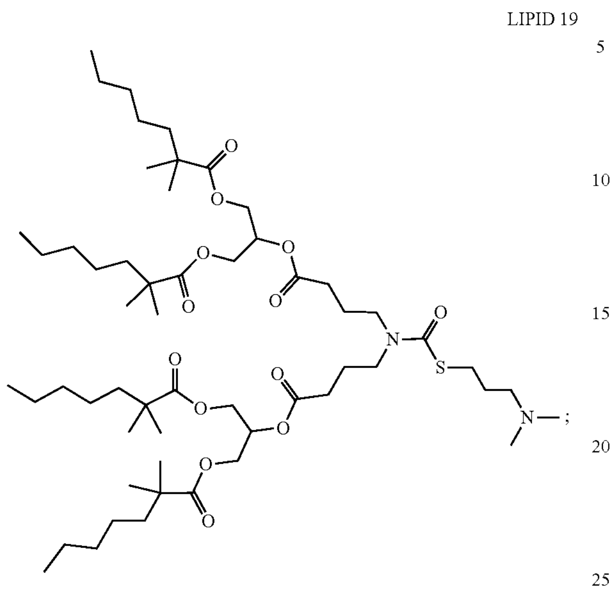
or a pharmaceutically acceptable salt thereof.
In some embodiments, the compound is LIPID 20:
LIPID 20
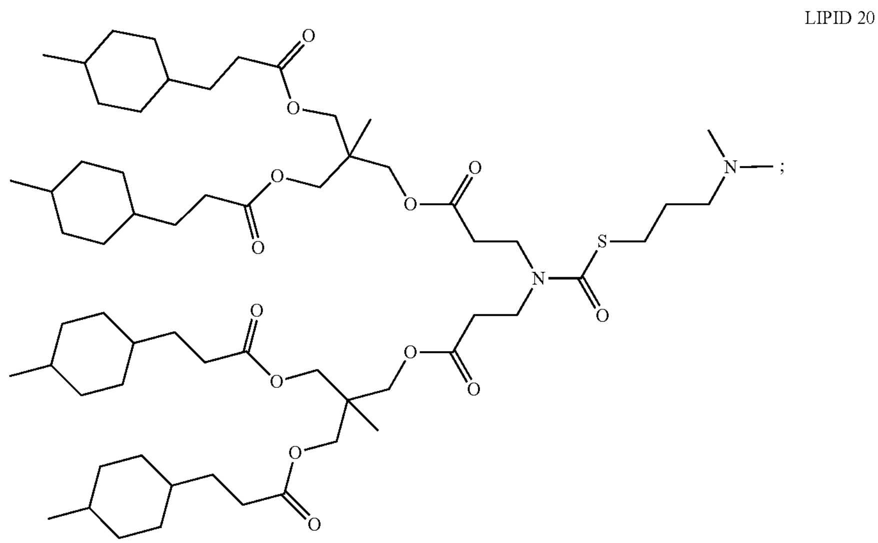
or a pharmaceutically acceptable salt thereof.

In some embodiments, the compound is LIPID 21:
LIPID 21
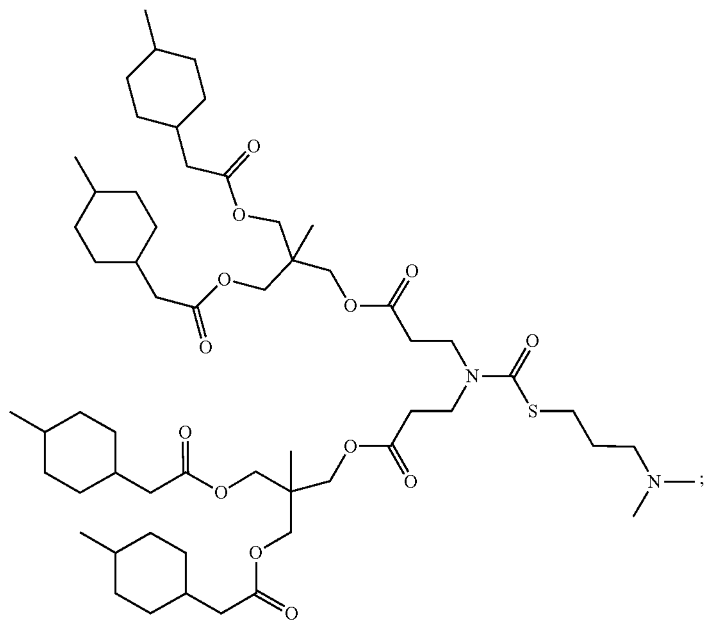
or a pharmaceutically acceptable salt thereof.
In some embodiments, the compound is LIPID 22:
LIPID 22
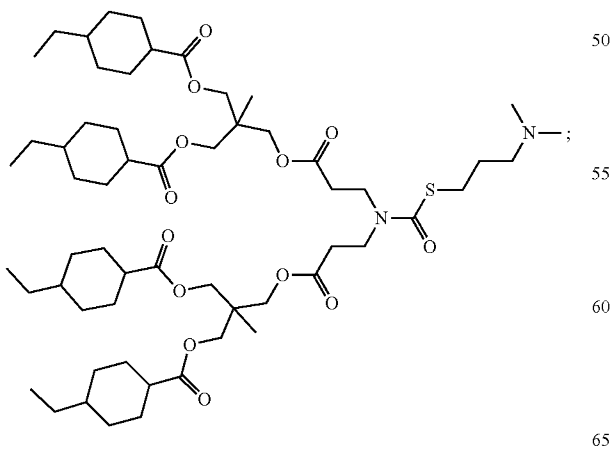
or a pharmaceutically acceptable salt thereof.

In some embodiments, the compound is LIPID 23:
LIPID 23
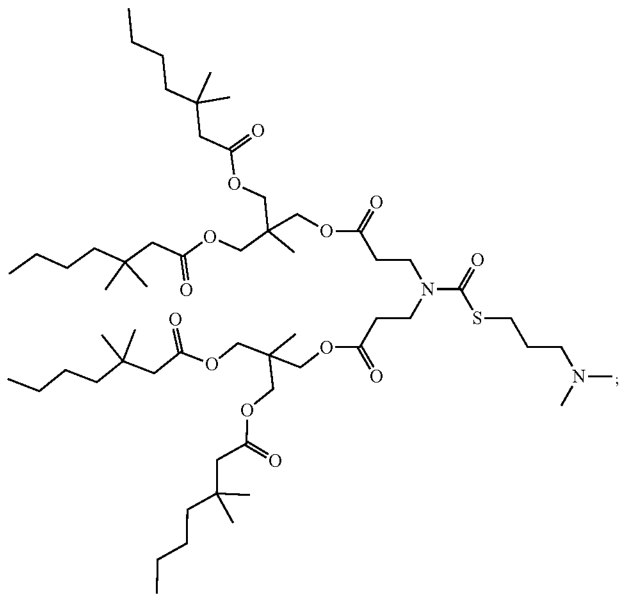
or a pharmaceutically acceptable salt thereof.
In some embodiments, the compound is LIPID 24:
LIPID 24
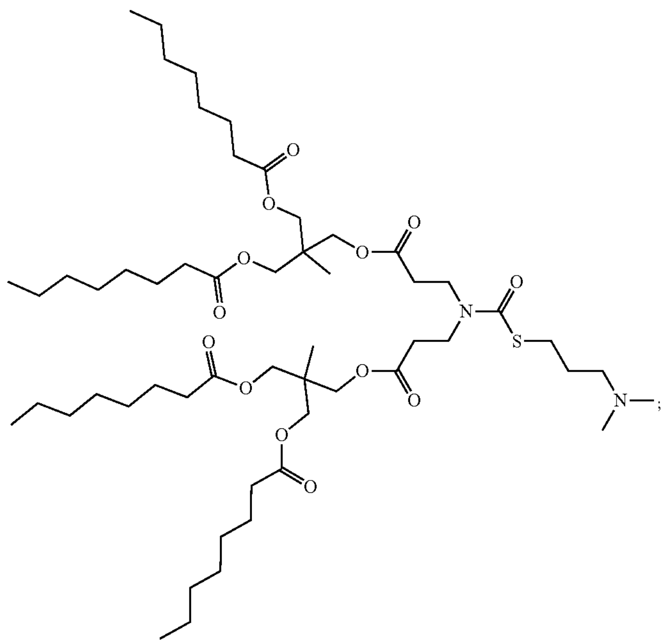
or a pharmaceutically acceptable salt thereof.

In some embodiments, the compound is LIPID 25:
LIPID 25
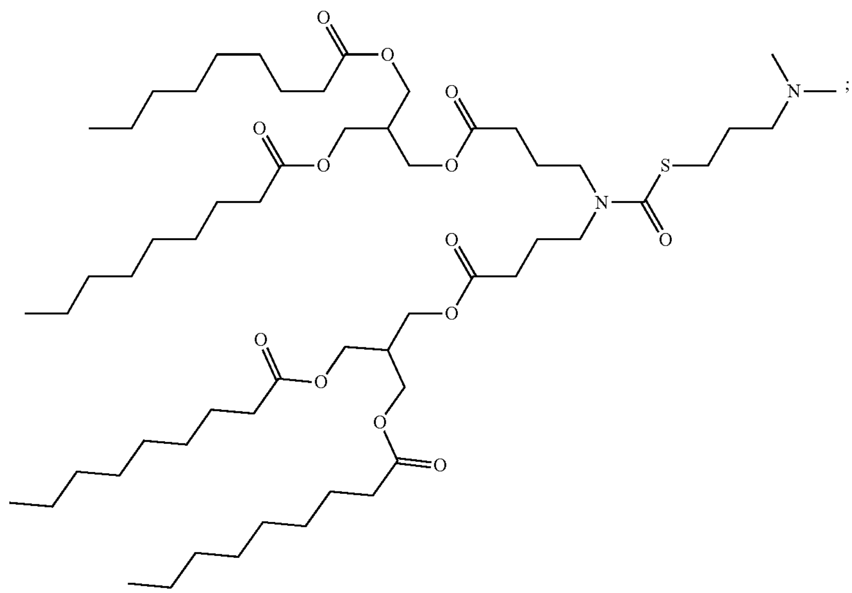
or a pharmaceutically acceptable salt thereof.
In some embodiments, the compound is LIPID 26:
LIPID 26
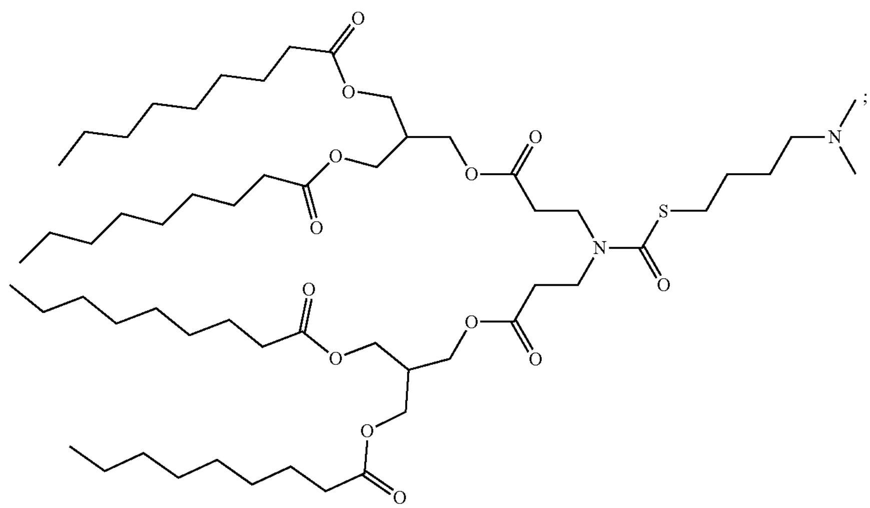
or a pharmaceutically acceptable salt thereof.

In some embodiments, the compound is LIPID 27:
LIPID 27
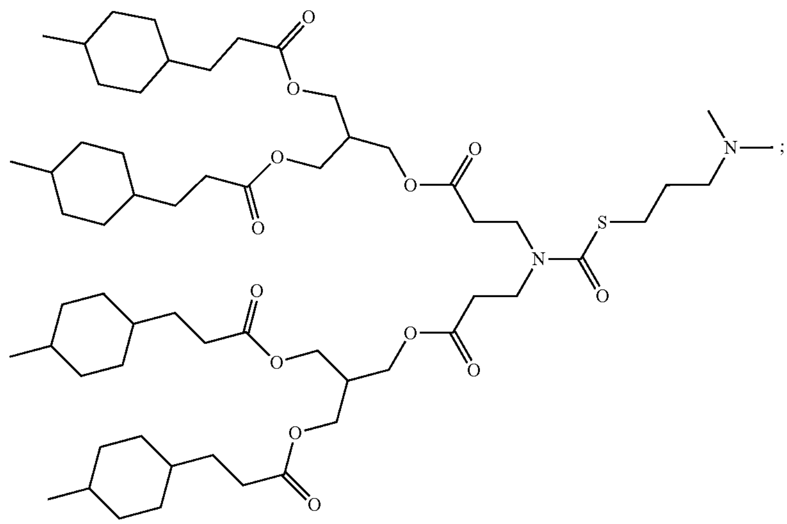
or a pharmaceutically acceptable salt thereof.
In some embodiments, the compound is LIPID 28:
LIPID 28
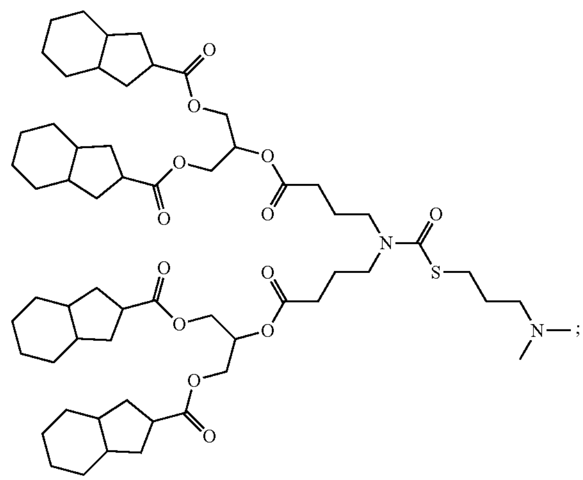
or a pharmaceutically acceptable salt thereof.
In some embodiments, the compound is LIPID 29:
LIPID 29
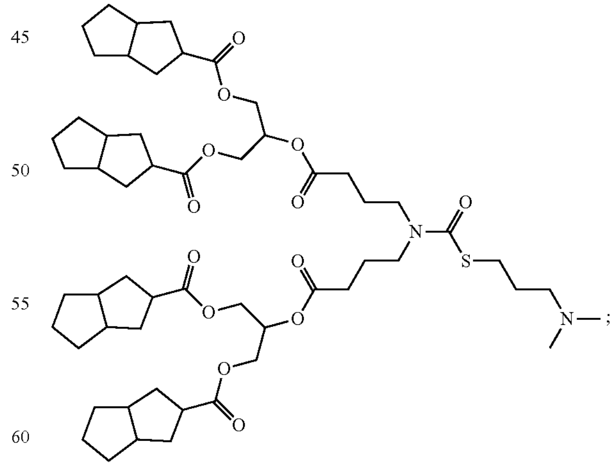
or a pharmaceutically acceptable salt thereof.

In some embodiments, the compound is LIPID 30:

LIPID 30

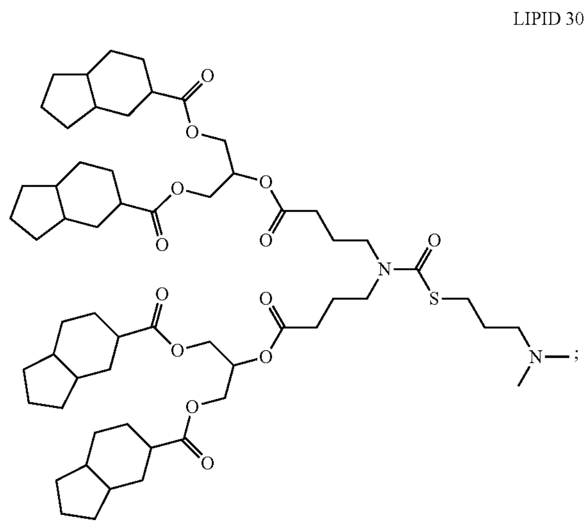 [SMILES: CN(C)CCCSC(=O)N(CCCC(=O)OC(COC(=O)C1CCC2CCCC2C1)COC(=O)C1CCC2CCCC2C1)CCCC(=O)OC(COC(=O)C1CCC2CCCC2C1)COC(=O)C1CCC2CCCC2C1]

or a pharmaceutically acceptable salt thereof.

In some embodiments, the compound is LIPID 31:

LIPID 31

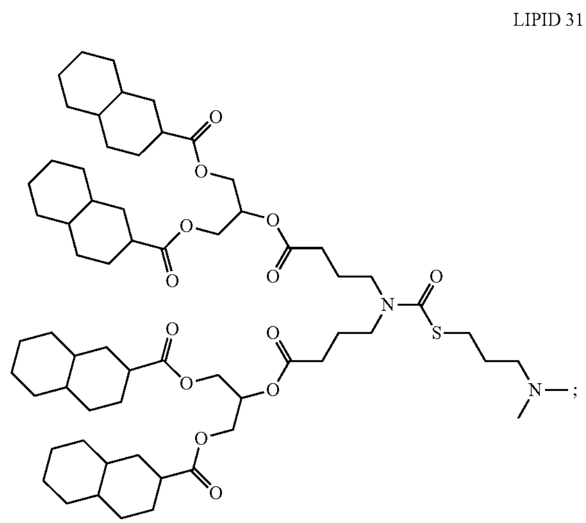 [SMILES: CN(C)CCCSC(=O)N(CCCC(=O)OC(COC(=O)C1CCC2CCCCC2C1)COC(=O)C1CCC2CCCCC2C1)CCCC(=O)OC(COC(=O)C1CCC2CCCCC2C1)COC(=O)C1CCC2CCCCC2C1]

or a pharmaceutically acceptable salt thereof.

In some embodiments, the compound is LIPID 32:

LIPID 32

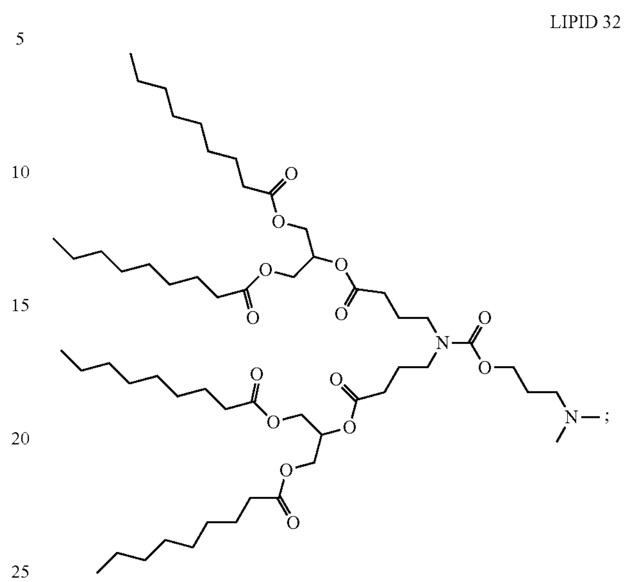

or a pharmaceutically acceptable salt thereof.

In some embodiments, the compound is LIPID 33:

LIPID 33

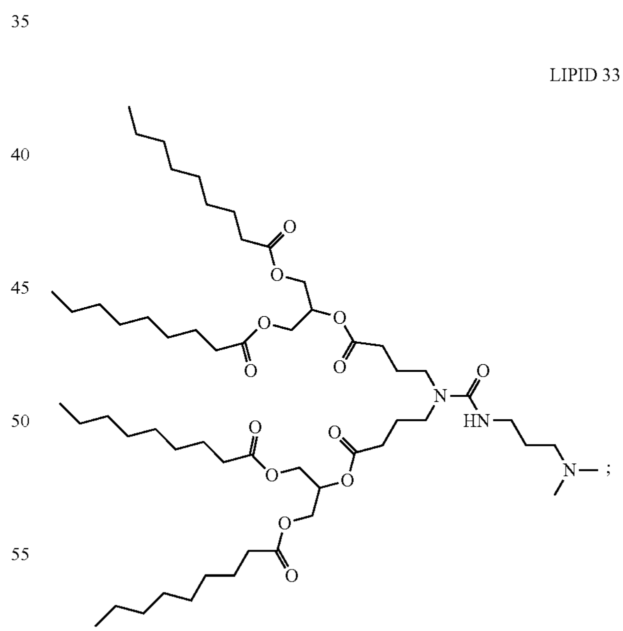

or a pharmaceutically acceptable salt thereof.

In some embodiments, the compound is LIPID 34:

LIPID 34

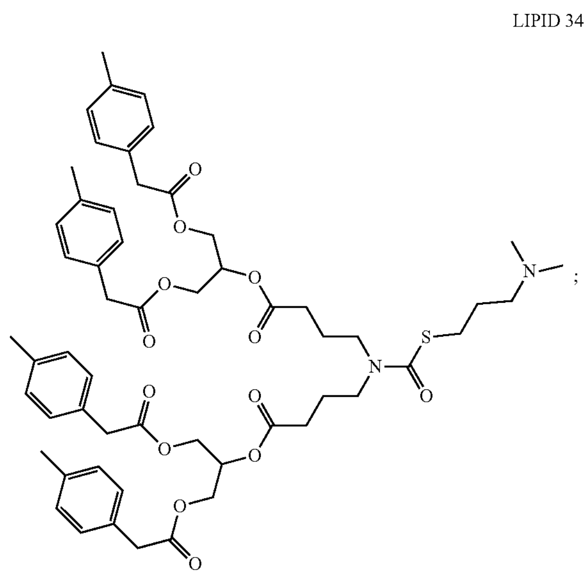

or a pharmaceutically acceptable salt thereof.

In some embodiments, the compound is LIPID 35:

LIPID 35

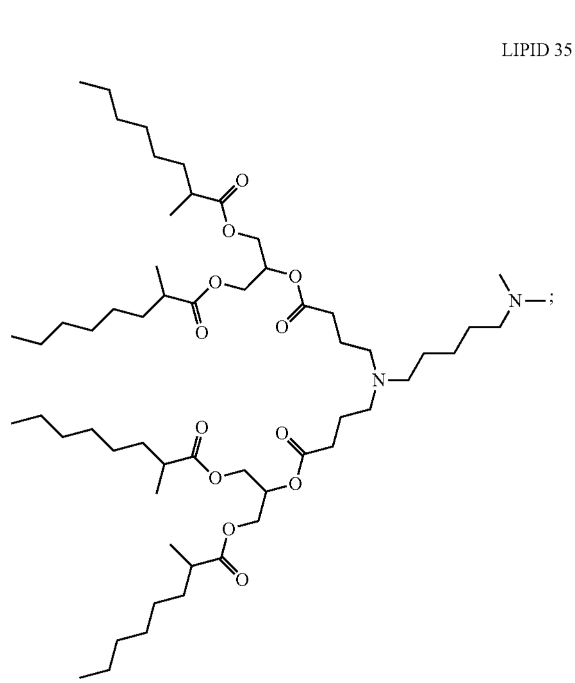 [SMILES: CCCCCCC(C)C(=O)OCC(COC(=O)C(C)CCCCCC)OC(=O)CCCN(CCCCCN(C)C)CCCC(=O)OC(COC(=O)C(C)CCCCCC)COC(=O)C(C)CCCCCC]

or a pharmaceutically acceptable salt thereof.

In some embodiments, the compound is LIPID 36:

LIPID 36

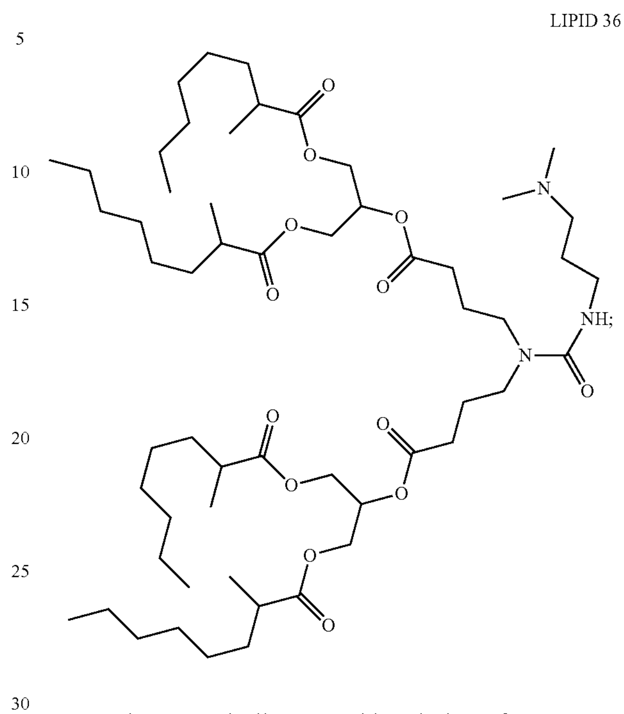

or a pharmaceutically acceptable salt thereof.

In some embodiments, the compound is LIPID 37:

LIPID 37

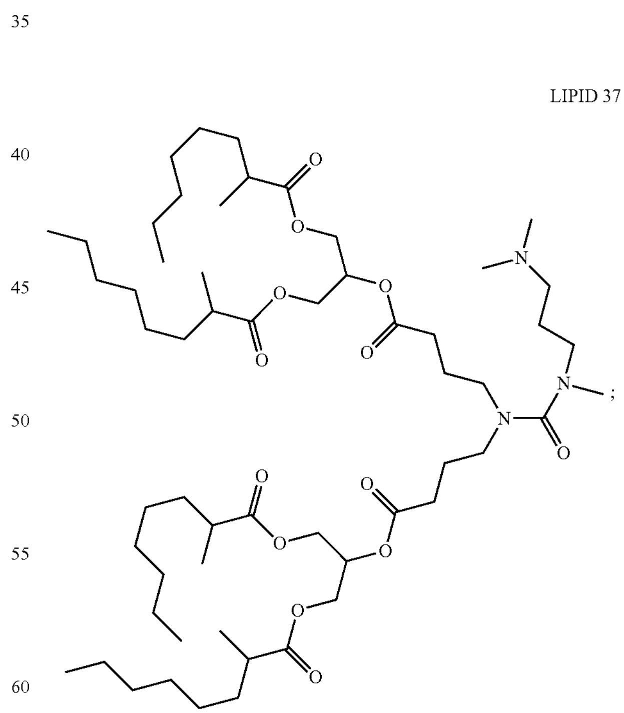

or a pharmaceutically acceptable salt thereof.

In some embodiments, the compound is LIPID 38:

LIPID 38

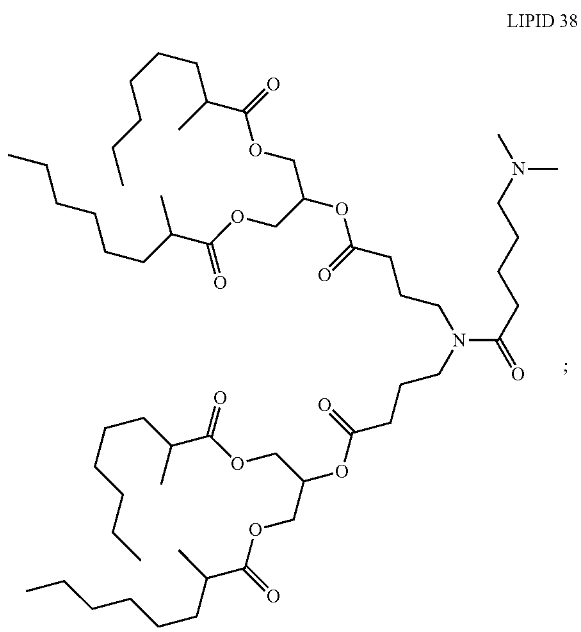 [SMILES: CCCCCCC(C)C(=O)OCC(COC(=O)C(C)CCCCCC)OC(=O)CCCN(CCCC(=O)OC(COC(=O)C(C)CCCCCC)COC(=O)C(C)CCCCCC)C(=O)CCCCN(C)C]

or a pharmaceutically acceptable salt thereof.

In some embodiments, the compound is LIPID 39:

LIPID 39

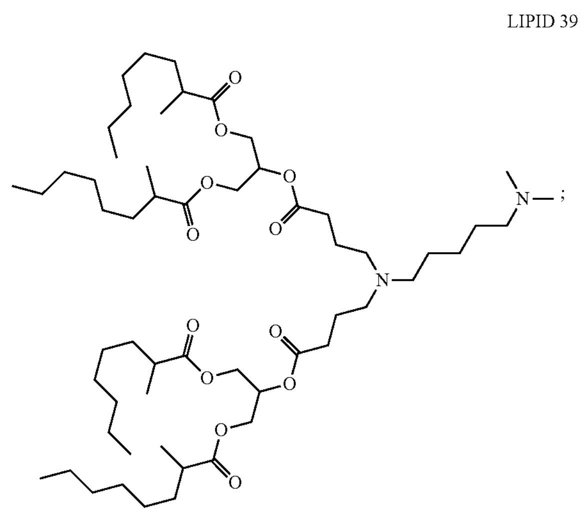 [SMILES: CCCCCCC(C)C(=O)OCC(COC(=O)C(C)CCCCCC)OC(=O)CCCN(CCCCCN(C)C)CCCC(=O)OC(COC(=O)C(C)CCCCCC)COC(=O)C(C)CCCCCC]

or a pharmaceutically acceptable salt thereof.

In some embodiments, the compound is LIPID 40:

LIPID 40

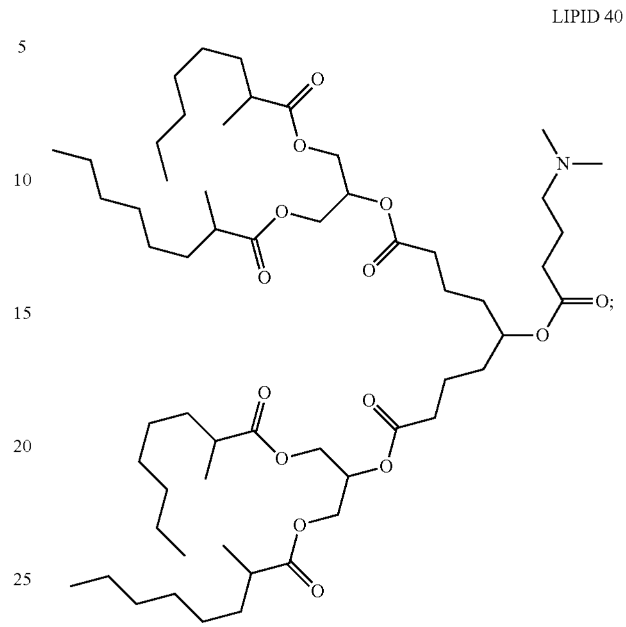

or a pharmaceutically acceptable salt thereof.

In some embodiments, the compound is LIPID 41:

LIPID 41

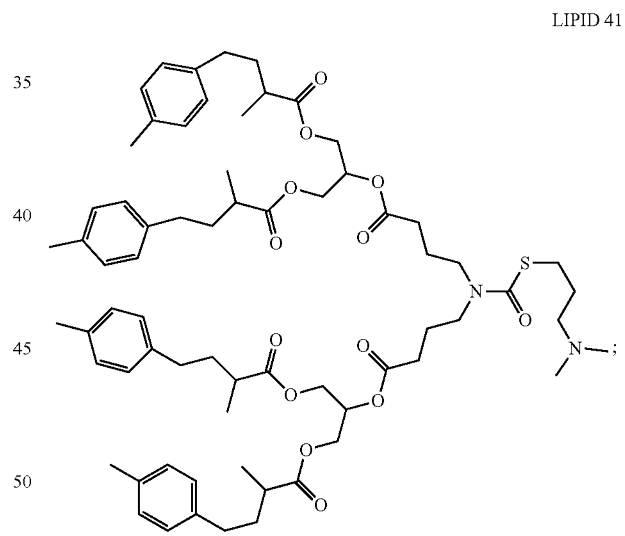

or a pharmaceutically acceptable salt thereof.

In some embodiments, the present disclosure provides a lipid composition comprising a nucleic acid and a compound of the present disclosure. In some embodiments, the nucleic acid is selected from an siRNA, an mRNA, a self-replicating RNA, a DNA plasmid, and an antisense oligonucleotide. In some embodiments, the nucleic acid is a mRNA or a self-replicating RNA comprising a coding region that encodes a therapeutic protein of interest. In some embodiments, the therapeutic protein of interest is an enzyme, and antibody, an antigen, a receptor, or a transporter. In some embodiments, the therapeutic protein of interest is a gene-editing enzyme. In some embodiments, the gene-editing enzyme is selected from a TALEN, a CRISPR, a meganuclease, or a zinc finger nuclease. In some embodiments, the lipid composition comprises liposomes, lipoplexes, or lipid nanoparticles.

IV. Lipid Formulations and Nanoparticles

Lipid-Based Formulations

Therapies based on the intracellular delivery of nucleic acids to target cells face both extracellular and intracellular barriers. Indeed, naked nucleic acid materials cannot be easily systemically administered due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida M Pharm Res. 1995 June; 12 (6): 825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), and release at the cytoplasm (for RNA). Successful nucleic acid-based therapy thus depends upon the ability of the vector to deliver the nucleic acids to the target sites inside of the cells in order to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still undergoing development. The use of mRNA in lipid delivery vehicles quickly rose to prominence as a result of the COVID-19 pandemic with several vaccines delivering mRNA encoding the spike protein of COVID-19 showing strong protective capabilities. Such lipid-based mRNA vaccines include Pfizer and BioNtech's BNT162b2 and Moderna's mRNA-1273, which have received emergency use authorization around the world.

Some art-recognized lipid-formulated delivery vehicles for nucleic acid therapeutics include, according to various embodiments, polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. These lipid formulations can vary in their structure and composition, and as can be expected in a rapidly evolving field, several different terms have been used in the art to describe a single type of delivery vehicle. At the same time, the terms for lipid formulations have varied as to their intended meaning throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16:307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns. Liposomal formulations can be prepared as a colloidal dispersion or they can be lyophilized to reduce stability risks and to improve the shelf-life for liposome-based drugs. Methods of preparing liposomal compositions are known in the art and are within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicles (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several non-concentric lipid bilayers.

Liposomes have long been perceived as drug delivery vehicles because of their superior biocompatibility, given that liposomes are basically analogs of biological membranes, and can be prepared from both natural and synthetic phospholipids (Int. J. Nanomedicine. 2014; 9:1833-1843). In their use as drug delivery vehicles, because a liposome has an aqueous solution core surrounded by a hydrophobic membrane, hydrophilic solutes dissolved in the core cannot readily pass through the bilayer, and hydrophobic compounds will associate with the bilayer. Thus, a liposome can be loaded with hydrophobic and/or hydrophilic molecules. When a liposome is used to carry a nucleic acid such as RNA, the nucleic acid is contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion.

In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed herein below.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell can be formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the LIPOFECTAMINE® reagent, have found considerable utility for in vitro transfection. However, these first-generation lipoplexes have not proven useful in vivo. The large particle size and positive charge (imparted by the cationic lipid) result in rapid plasma clearance, hemolytic and other toxicities, as well as immune system activation.

In some embodiments, the lipid nanoparticle comprises a lipid of Formula I:

(I)

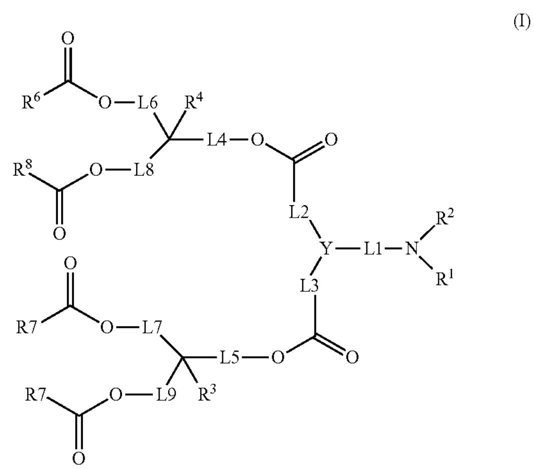

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $—(CH_2)_m(X)_n—$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

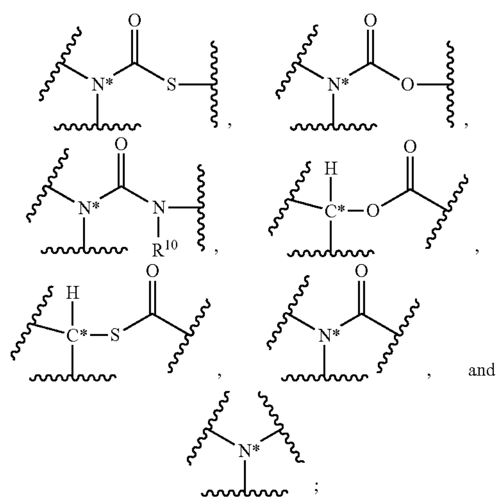

, , , , , and ;

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or $—CH_2—$, provided that:

at least two of L4, L6 and L8 are $—CH_2—$; and at least two of L5, L7 and L9 are $—CH_2—$;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

In some embodiments, the lipid nanoparticle comprises a lipid of Formula I:

(I)

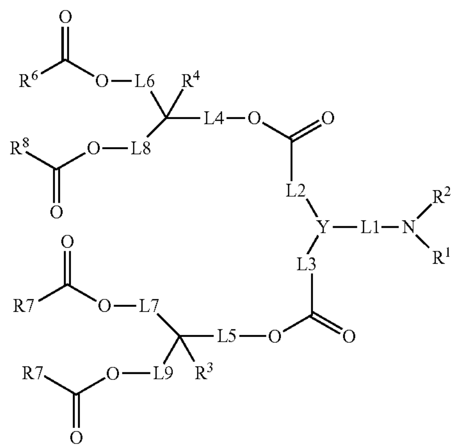

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $—(CH_2)_m(X)_n—$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

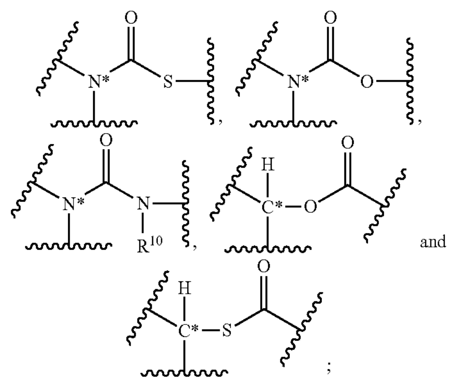

, , , and ;

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or $—CH_2—$, provided that:

at least two of L4, L6 and L8 are $—CH_2—$; and at least two of L5, L7 and L9 are $—CH_2—$;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

In some embodiments, any one or more lipids recited herein may be expressly excluded.

In some embodiments, the present disclosure provides a lipid nanoparticle, comprising a plurality of ligands, wherein each ligand is independently a compound described herein, wherein the plurality of ligands self-assembles to form the lipid nanoparticle comprising an interior and exterior.

In some embodiments, the average size of the lipid nanoparticle is about 100 nm. In some embodiments, the average size of the lipid nanoparticle is less than about 100 nm. In some embodiments, the average particle size of the lipid nanoparticle is about 40 nm to about 100 nm. In some embodiments, the average particle size of the lipid nanoparticle is about 50 nm to about 90 nm. In some embodiments, the average particle size of the lipid nanoparticle is about 55 nm to about 85 nm.

In some embodiments, the lipid nanoparticle further comprises nucleic acids in the interior. In some embodiments, the nucleic acid is selected from an siRNA, an mRNA, a self-replicating RNA, a DNA plasmid, and an antisense oligonucleotide. In some embodiments, the nucleic acid is a mRNA or a self-replicating RNA comprising a coding region that encodes a therapeutic protein of interest. In some embodiments, the therapeutic protein of interest is an enzyme, and antibody, an antigen, a receptor, or a transporter. In some embodiments, the therapeutic protein of interest is a gene-editing enzyme. In some embodiments, the gene-editing enzyme is selected from a TALEN, a CRISPR, a meganuclease, or a zinc finger nuclease.

In some embodiments, the lipid nanoparticle further comprises siRNA or mRNA in the interior. In some embodiments, the lipid nanoparticle further comprises mRNA in the interior.

In some embodiments, the lipid nanoparticle further comprises a helper lipid as described below. In some embodiments, the lipid nanoparticle further comprises PEG-lipid conjugates as described herein.

In some embodiments, the lipid nanoparticle comprises about 45 mol % to 65 mol % of the compound of the present disclosure, about 2 mol % to about 15 mol % of a helper lipid, about 20 mol % to about 42 mol % of cholesterol, and about 0.5 mol % to about 3 mol % of a PEG-lipid conjugate. In some embodiments, the lipid nanoparticle comprises about 50 mol % to about 61 mol % of the compound of the present disclosure, about 5 mol % to about 9 mol % of the helper lipid, about 29 mol % to about 38 mol % of cholesterol, and about 1 mol % to about 2 mol % of the PEG-lipid conjugate. In some embodiments, the lipid nanoparticle comprises about 56 mol % to about 58 mol % of the compound of the present disclosure, about 6 mol % to about 8 mol % of DSPC, about 31 mol % to about 34 mol % of cholesterol, and about 1.25 mol % to about 1.75 mol % of the PEG-lipid conjugate.

In some embodiments, the lipid nanoparticle comprises about 50 mol % to 61 mol % of the compound of the present disclosure, about 2 mol % to about 12 mol % of DSPC, about 25 mol % to about 42 mol % of cholesterol, and about 0.5 mol % toa bout 3 mol % of PEG2000-DMG. In some embodiments, the lipid nanoparticle comprises about 50 mol % to about 61 mol % of the compound of the present disclosure, about 5 mol % to about 9 mol % of DSPC, about 29 mol % to about 38 mol % of cholesterol, and about 1 mol % to about 2 mol % of PEG2000-DMG. In some embodiments, the lipid nanoparticle comprises about 56 mol % to about 58 mol % of the compound of the present disclosure, about 6 mol % to about 8 mol % of DSPC, about 31 mol % to about 34 mol % of cholesterol, and about 1.25 mol % to about 1.75 mol % of PEG2000-DMG.

In some embodiments, the lipid nanoparticle has a total lipid:nucleic acid weight ratio of about 50:1 to about 10:1. In some embodiments, the lipid nanoparticle has a total lipid:nucleic acid weight ratio of about 40:1 to about 20:1. In some embodiments, the lipid nanoparticle has a total lipid:nucleic acid weight ratio of about 35:1 to about 25:1. In some embodiments, the lipid nanoparticle has a total lipid:nucleic acid weight ratio of about 32:1 to about 28:1. In some embodiments, the lipid nanoparticle has a total lipid:nucleic acid weight ratio of about 31:1 to about 29:1.

In some embodiments, the lipid nanoparticle has a total lipid:mRNA weight ratio of about 50:1 to about 10:1. In some embodiments, the lipid nanoparticle has a total lipid: mRNA weight ratio of about 40:1 to about 20:1. In some embodiments, the lipid nanoparticle has a total lipid:mRNA weight ratio of about 35:1 to about 25:1. In some embodiments, the lipid nanoparticle has a total lipid:mRNA weight ratio of about 32:1 to about 28:1. In some embodiments, the lipid nanoparticle has a total lipid:mRNA weight ratio of about 31:1 to about 29:1.

In some embodiments, the lipid nanoparticle nanoparticle comprises a HEPES buffer at a pH of about 7.4. In some embodiments, the HEPES buffer is at a concentration of about 7 mg/mL to about 15 mg/mL. In some embodiments, the lipid nanoparticle further comprises about 2.0 mg/mL to about 4.0 mg/mL of NaCl.

In some embodiments, the lipid nanoparticle further comprises one or more cryoprotectants. In some embodiments, the one or more cryoprotectants are selected from sucrose, glycerol, or a combination of sucrose and glycerol. In some embodiments, the lipid nanoparticle comprises a combination of sucrose at a concentration of about 70 mg/mL to about 110 mg/mL and glycerol at a concentration of about 50 mg/mL to about 70 mg/mL.

Lipid-Nucleic Acid Formulations

A nucleic acid or a pharmaceutically acceptable salt thereof can be incorporated into a lipid formulation (i.e., a lipid-based delivery vehicle).

In the context of the present disclosure, a lipid-based delivery vehicle typically serves to transport a desired nucleic acid (siRNA, plasmid DNA, mRNA, self-replicating RNA, etc.) to a target cell or tissue. The lipid-based delivery vehicle can be any suitable lipid-based delivery vehicle known in the art. In some embodiments, the lipid-based delivery vehicle is a liposome, a cationic liposome, or a lipid nanoparticle containing a nucleic acid. In some embodiments, the lipid-based delivery vehicle comprises a nanoparticle or a bilayer of lipid molecules and a nucleic acid. In some embodiments, the lipid bilayer preferably further comprises a neutral lipid or a polymer. In some embodiments, the lipid formulation preferably comprises a liquid medium. In some embodiments, the formulation preferably further encapsulates a nucleic acid. In some embodiments, the lipid formulation preferably further comprises a nucleic acid and a neutral lipid or a polymer. In some embodiments, the lipid formulation preferably encapsulates the nucleic acid.

The description provides lipid formulations comprising one or more therapeutic nucleic acid molecules encapsulated within the lipid formulation. In some embodiments, the lipid formulation comprises liposomes. In some embodiments, the lipid formulation comprises cationic liposomes. In some embodiments, the lipid formulation comprises lipid nanoparticles.

In some embodiments, the nucleic acid is fully encapsulated within the lipid portion of the lipid formulation such that the nucleic acid in the lipid formulation is resistant in aqueous solution to nuclease degradation. In other embodiments, the lipid formulations described herein are substantially non-toxic to mammals such as humans.

The lipid formulations of the disclosure also typically have a total lipid:nucleic acid ratio (mass/mass ratio) of from about 1:1 to about 100:1, from about 1:1 to about 50:1, from about 2:1 to about 45:1, from about 3:1 to about 40:1, from about 5:1 to about 38:1, or from about 6:1 to about 40:1, or from about 7:1 to about 35:1, or from about 8:1 to about 30:1; or from about 10:1 to about 25:1; or from about 8:1 to about 12:1; or from about 13:1 to about 17:1; or from about 18:1 to about 24:1; or from about 20:1 to about 30:1. In some preferred embodiments, the total lipid:nucleic acid ratio (mass/mass ratio) is from about 10:1 to about 25:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, are resistant in aqueous solution to degradation with a nuclease.

In preferred embodiments, the lipid formulations comprise a nucleic acid, a cationic lipid (e.g., one or more cationic lipids or salts thereof described herein), a phospholipid, and a conjugated lipid that inhibits aggregation of the particles (e.g., one or more PEG-lipid conjugate and/or other lipid conjugate of the disclosure). The lipid formulations can also include cholesterol.

In some embodiments, the lipid nanoparticle further comprises a PEG-lipid conjugate. In some embodiments, the PEG-lipid conjugate is PEG-DMG. In some embodiments, the PEG-DMG is PEG2000-DMG.

In the nucleic acid-lipid formulations, the nucleic acid may be fully encapsulated within the lipid portion of the formulation, thereby protecting the nucleic acid from nuclease degradation. In preferred embodiments, a lipid formulation comprising a nucleic acid is fully encapsulated within the lipid portion of the lipid formulation, thereby protecting the nucleic acid from nuclease degradation. In certain instances, the nucleic acid in the lipid formulation is not substantially degraded after exposure of the particle to a nuclease at 37° C. for at least 20, 30, 45, or 60 minutes. In certain other instances, the nucleic acid in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the formulation.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as E=(I0−I)/I0, where I and I0 refer to the fluorescence intensities before and after the addition of detergent.

In other embodiments, the present disclosure provides a nucleic acid-lipid composition comprising a plurality of nucleic acid-liposomes, nucleic acid-cationic liposomes, or nucleic acid-lipid nanoparticles. In some embodiments, the nucleic acid-lipid composition comprises a plurality of nucleic acid-liposomes. In some embodiments, the nucleic acid-lipid composition comprises a plurality of nucleic acid-cationic liposomes. In some embodiments, the nucleic acid-lipid composition comprises a plurality of nucleic acid-lipid nanoparticles.

In some embodiments, the lipid formulations comprise a nucleic acid that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the nucleic acid encapsulated therein. The amount may be any value or subvalue within the recited ranges, including endpoints.

Depending on the intended use of the lipid formulation, the proportions of the components can be varied, and the delivery efficiency of a particular formulation can be measured using assays known in the art.

According to some embodiments, expressible polynucleotides, nucleic acid active agents, and mRNA constructs can be lipid formulated. The lipid formulation is preferably selected from, but not limited to, liposomes, cationic liposomes, and lipid nanoparticles. In one preferred embodiment, a lipid formulation is a cationic liposome or a lipid nanoparticle (LNP) comprising:

(a) a nucleic acid (mRNA, siRNA, etc.), (b) a lipid of the present disclosure, which may be cationic (c) optionally a non-cationic lipid (such as a neutral lipid), and (d) optionally, a sterol.

Cationic Lipids

The lipid formulation preferably includes a cationic lipid suitable for forming a cationic liposome or lipid nanoparticle. Cationic lipids are widely studied for nucleic acid delivery because they can bind to negatively charged membranes and induce uptake. Generally, cationic lipids are amphiphiles containing a positive hydrophilic head group, two (or more) lipophilic tails, or a steroid portion and a connector between these two domains. Preferably, the cationic lipid carries a net positive charge at about physiological pH. Cationic liposomes have been traditionally the most commonly used non-viral delivery systems for oligonucleotides, including plasmid DNA, antisense oligos, and siRNA/small hairpin RNA-shRNA. Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids by electrostatic interaction, providing high in vitro transfection efficiency.

In the presently disclosed lipid formulations, the cationic lipid may include, for example, N,N-dimethyl-N,N-di-9-cis-octadecenylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino) ethoxypropane (DLin-EG-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl-4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P-(N—(N',N'-dimethylaminoethane)-carbamoyl) cholesterol (DC-Chol), N-(1-(2,3-dioleyloxy)propyl)-N-2-(sperminecarboxamido)ethyl)-N,N-dimethylammonium trifluoracetate (DOSPA), dioctadecylamidoglycyl carboxyspermine (DOGS), 1,2-dioleoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107 (5), 1864-69, 2010, the contents of which are herein incorporated by reference.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated alkyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ may be used. Other scaffolds can also be used to separate the amino group and the fatty acid or fatty alkyl portion of the amino lipid.

In some embodiments, cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises a lipid of Formula I:

(I)

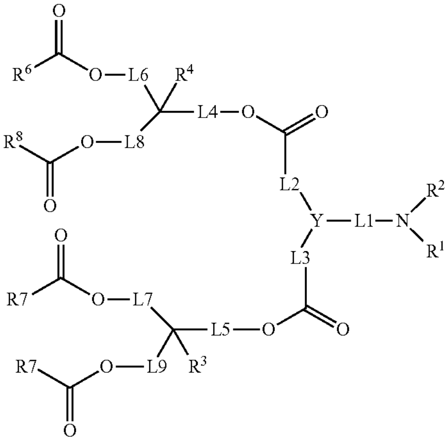

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $-(CH_2)_m(X)_n-$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

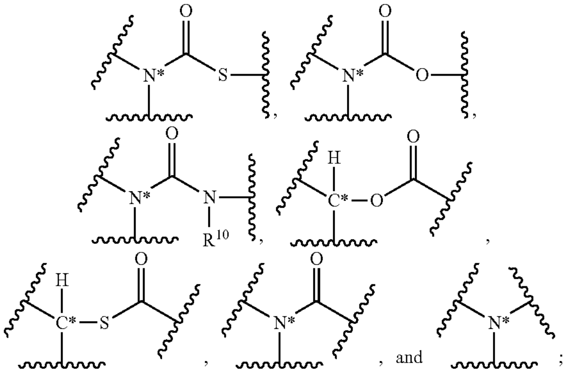

, , , , , and ;

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or $-CH_2-$, provided that:

at least two of L4, L6 and L8 are $-CH_2-$; and at least two of L5, L7 and L9 are $-CH_2-$;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and $-F$, wherein each said $C_{1-6}$ alkyl substituent is optionally substituted with one or more groups selected from the group consisting of $C_{1-3}$ alkoxy and $-F$;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and $-F$;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and $-F$; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and $-F$;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and $-F$;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and $-F$; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and $-F$.

In some embodiments, the lipid formulation comprises a lipid of Formula I:

(I)

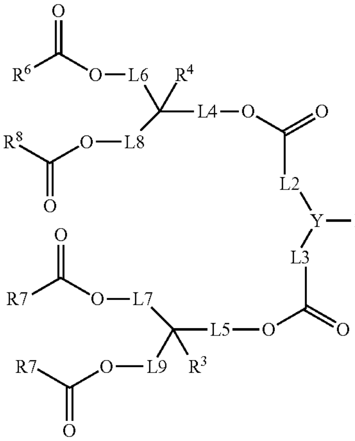

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $-(CH_2)_m(X)_n-$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

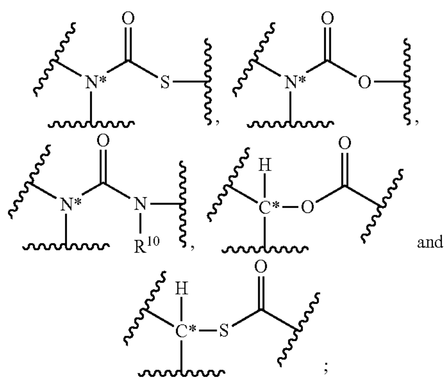

and wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or —$CH_2$—, provided that:

at least two of L4, L6 and L8 are —$CH_2$—; and at least two of L5, L7 and L9 are —$CH_2$—;

$R^3$ and $R^4$ are each independently H, methyl or ethyl; and $R^5$, $R^6$, $R^7$ and $R^8$ are each independently selected from the group consisting of:

linear $C_{1-20}$ alkyl, wherein each said linear $C_{1-20}$ alkyl is optionally substituted with one or more substituents selected from the group consisting of:

$C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

$C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

$C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

In some embodiments, any one or more lipids recited herein may be expressly excluded.

Helper Lipids and Sterols

The mRNA-lipid formulations of the present disclosure can comprise a helper lipid, which can be referred to as a neutral lipid, a neutral helper lipid, non-cationic lipid, non-cationic helper lipid, anionic lipid, anionic helper lipid, or a zwitterionic lipid. It has been found that lipid formulations, particularly cationic liposomes and lipid nanoparticles have increased cellular uptake if helper lipids are present in the formulation. (Curr. Drug Metab. 2014; 15 (9): 882-92). For example, some studies have indicated that neutral and zwitterionic lipids such as 1,2-dioleoyl-sn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9 (1): 105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

In some embodiments, the helper lipid is selected from: dioleoylphosphatidyl ethanolamine (DOPE), dimyristoylphosphatidyl choline (DMPC), distearoylphosphatidylcholine (DSPC), dimyristoylphosphatidyl glycerol (DMPG), dipalmitoyl phosphatidylcholine (DPPC), and phosphatidylcholine (PC). In some embodiments, the helper lipid is distearoylphosphatidylcholine (DSPC).

Additional examples of non-cationic lipids include sterols such as cholesterol and derivatives thereof. One study concluded that as a helper lipid, cholesterol increases the spacing of the charges of the lipid layer interfacing with the nucleic acid making the charge distribution match that of the nucleic acid more closely. (J. R. Soc. Interface. 2012 Mar. 7; 9 (68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the helper lipid present in the lipid formulation comprises or consists of a mixture of one or more phospholipids and cholesterol or a derivative thereof. In other embodiments, the helper lipid present in the lipid formulation comprises or consists of one or more phospholipids, e.g., a cholesterol-free lipid formulation. In yet other embodiments, the helper lipid present in the lipid formulation comprises or consists of cholesterol or a derivative thereof, e.g., a phospholipid-free lipid formulation. In some embodiments, the lipid nanoparticle further comprises cholesterol.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the helper lipid comprises from about 1 mol % to about 50 mol %, from about 5 mol % to about 48 mol %, from about 5 mol % to about 46 mol %, about 25 mol % to about 44 mol %, from about 26 mol % to about 42 mol %, from about 27 mol % to about 41 mol %, from about 28 mol % to about 40 mol %, or about 29 mol %, about 30 mol %, about 31 mol %, about 32 mol %, about 33 mol %, about 34 mol %, about 35 mol %, about 36 mol %, about 37 mol %, about 38 mol %, or about 39 mol % (or any fraction thereof or the range therein) of the total lipid present in the lipid formulation. In some embodiments, the helper lipid comprises from about 1 mol % to about 20 mol %, about 2 mol % to about 12 mol %, about 5 mol % to about 9 mol % or about 6 mol % to about 8 mol %.

In some embodiments, the total of helper lipid in the formulation comprises two or more helper lipids and the total amount of helper lipid comprises from about 20 mol % to about 50 mol %, from about 22 mol % to about 48 mol %, from about 24 mol % to about 46 mol %, about 25 mol % to about 44 mol %, from about 26 mol % to about 42 mol %, from about 27 mol % to about 41 mol %, from about 28 mol % to about 40 mol %, or about 29 mol %, about 30 mol %, about 31 mol %, about 32 mol %, about 33 mol %, about 34 mol %, about 35 mol %, about 36 mol %, about 37 mol %, about 38 mol %, or about 39 mol % (or any fraction thereof or the range therein) of the total lipid present in the lipid formulation. In some embodiments, the helper lipids are a combination of DSPC and DOTAP. In some embodiments, the helper lipids are a combination of DSPC and DOTMA.

The cholesterol or cholesterol derivative in the lipid formulation may comprise up to about 40 mol %, about 45 mol %, about 50 mol %, about 55 mol %, or about 60 mol % of the total lipid present in the lipid formulation. In some embodiments, the cholesterol or cholesterol derivative comprises about 15 mol % to about 45 mol %, about 20 mol % to about 40 mol %, about 30 mol % to about 40 mol %, or about 35 mol %, about 36 mol %, about 37 mol %, about 38 mol %, about 39 mol %, or about 40 mol % of the total lipid present in the lipid formulation.

The percentage of helper lipid present in the lipid formulation is a target amount, and the actual amount of helper lipid present in the formulation may vary, for example, by +5 mol %.

Mechanism of Action for Cellular Uptake of Lipid Formulations

Lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28(3): 146-157, 2018). Specifically, in the case of a nucleic acid-lipid formulations described herein, the lipid formulation enters cells through receptor mediated endocytosis. Prior to endocytosis, functionalized ligands such as a the lipid conjugate of the disclosure at the surface of the lipid delivery vehicle can be shed from the surface, which triggers internalization into the target cell. During endocytosis, some part of the plasma membrane of the cell surrounds the vector and engulfs it into a vesicle that then pinches off from the cell membrane, enters the cytosol and ultimately undergoes the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For mRNA or self-replicating RNA payloads, the cell's own internal translation processes will then translate the RNA into the encoded protein. The encoded protein can further undergo post-translational processing, including transportation to a targeted organelle or location within the cell.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual asymmetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

V. Pharmaceutical Compositions and Delivery Methods

To facilitate nucleic acid activity (e.g., mRNA expression, or knockdown by an ASO or siRNA) in vivo, the lipid formulation delivery vehicles described herein can be combined with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

The lipid formulations and pharmaceutical compositions of the present disclosure may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

The pharmaceutical compositions disclosed herein can be formulated using one or more excipients to: (1) increase stability; (2) increase cell transfection; (3) permit a sustained or delayed release (e.g., from a depot formulation of the nucleic acid); (4) alter the biodistribution (e.g., target the nucleic acid to specific tissues or cell types); (5) increase the activity of the nucleic acid or a protein expressed therefrom in vivo; and/or (6) alter the release profile of the nucleic acid or an encoded protein in vivo.

Preferably, the lipid formulations may be administered in a local rather than systemic manner. Local delivery can be affected in various ways, depending on the tissue to be targeted. For example, aerosols containing compositions of the present disclosure can be inhaled (for nasal, tracheal, or bronchial delivery).

Pharmaceutical compositions may be administered to any desired tissue. In some embodiments, the nucleic acid delivered by a lipid formulation or composition of the present disclosure is active in the tissue in which the lipid formulation and/or composition was administered. In some embodiments, the nucleic acid is active in a tissue different from the tissue in which the lipid formulation and/or composition was administered. Example tissues in which the nucleic acid may be delivered include, but are not limited to the lung, trachea, and/or nasal passages, muscle, liver, eye, or the central nervous system.

The pharmaceutical compositions described herein may be prepared by any method known or hereafter developed in the art of pharmacology. In general, such preparatory methods include the step of associating the active ingredient (i.e., nucleic acid) with an excipient and/or one or more other accessory ingredients. A pharmaceutical composition in accordance with the present disclosure may be prepared, packaged, and/or sold in bulk, as a single unit dose, and/or as a plurality of single unit doses.

Pharmaceutical compositions may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with a primary DNA construct, or mRNA (e.g., for transplantation into a subject), hyaluronidase, nanoparticle mimics and combinations thereof.

Accordingly, the formulations described herein can include one or more excipients, each in an amount that together increases the stability of the nucleic acid in the lipid formulation, increases cell transfection by the nucleic acid (e.g., mRNA or siRNA), increases the expression of an encoded protein, and/or alters the release profile of the encoded protein, or increases knockdown of a target native nucleic acid. Further, a nucleic acid may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

A dosage form of the composition of this disclosure can be solid, which can be reconstituted in a liquid prior to administration. The solid can be administered as a powder. In some embodiments, the pharmaceutical composition comprises a nucleic acid lipid formulation that has been lyophilized.

In a preferred embodiment, the dosage form of the pharmaceutical compositions described herein can be a liquid suspension of nucleic acid-lipid nanoparticles described herein. In some embodiments, the liquid suspension is in a buffered solution. In some embodiments, the buffered solution comprises a buffer selected from the group consisting of HEPES, MOPS, TES, and TRIS. In some embodiments, the buffer has a pH of about 7.4. In some preferred embodiments, the buffer is HEPES. In some further embodiments, the buffered solution further comprises a cryoprotectant. In some embodiments, the cryoprotectant is selected from a sugar and glycerol or a combination of a sugar and glycerol. In some embodiments, the sugar is a dimeric sugar. In some embodiments, the sugar is sucrose. In some preferred embodiments, the buffer comprises HEPES, sucrose, and glycerol at a pH of 7.4. In some embodiments, the suspension is frozen during storage and thawed prior to administration. In some embodiments, the suspension is frozen at a temperature below about −70° C. In some embodiments, the suspension is diluted with sterile water prior to inhalable administration. In some embodiments, an inhalable administration comprises diluting the suspension with about 1 volume to about 4 volumes of sterile water. In some embodiments, a lyophilized nucleic acid-lipid nanoparticle formulation can be resuspended in a buffer as described herein.

A dosage form of the composition of this disclosure can be solid, which can be reconstituted in a liquid prior to administration. The solid can be administered as a powder. The solid can be in the form of a capsule, tablet, or gel.

To formulate compositions for pulmonary delivery within the present disclosure, the nucleic acid-lipid formulation can be combined with various pharmaceutically acceptable additives, as well as a base or carrier for dispersion of the nucleic acid-lipid formulation(s). Examples of additives include pH control agents such as arginine, sodium hydroxide, glycine, hydrochloric acid, citric acid, and mixtures thereof. Other additives include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of ⅓ to 3, more typically ½ to 2, and most often ¾ to 1.7.

The nucleic acid-lipid formulation may be dispersed in a base or vehicle, which may comprise a hydrophilic compound having a capacity to disperse the nucleic acid-lipid formulation and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly(hydroxybutyric acid-glycolic acid) copolymer, and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination and enhanced structural integrity can be imparted to the carrier by partial crystallization, ionic bonding, crosslinking, and the like. The carrier can be provided in a variety of forms, including fluid or viscous solutions, gels, pastes, powders, microspheres, and films for direct application to the nasal mucosa. The use of a selected carrier in this context may result in promotion of absorption of the nucleic acid-lipid formulation.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

According to the present disclosure, a therapeutically effective dose of the provided composition, when administered regularly, results in an increased nucleic acid activity level in a subject as compared to a baseline activity level before treatment. Typically, the activity level is measured in a biological sample obtained from the subject such as blood, plasma or serum, urine, or solid tissue extracts. The baseline level can be measured immediately before treatment. In some embodiments, administering a pharmaceutical composition described herein results in an increased nucleic acid activity level in a biological sample (e.g., plasma/serum or lung epithelial swab) by at least about 10%, 20%, 30%, 40%, 50%, 60%, 70%, 80%, 90%, or 95% as compared to a baseline level before treatment. In some embodiments, administering the provided composition results in an increased nucleic acid activity level in a biological sample (e.g., plasma/serum or lung epithelial swab) by at least about 10%, 20%, 30%, 40%, 50%, 60%, 70%, 80%, 90%, or 95% as compared to a baseline level before treatment for at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days.

In some embodiments, the present disclosure provides a pharmaceutical composition comprising the compounds described herein, or the lipid nanoparticle described herein, and a pharmaceutically acceptable excipient.

In some embodiments, the present disclosure provides a method of delivering a nucleic acid to a subject in needed thereof, comprising encapsulating a therapeutically effective amount of the a nucleic acid in the lipid nanoparticle described herein, and administering the lipid nanoparticle to the subject.

In some embodiments, the present disclosure provides a method of delivering mRNA to a subject in needed thereof, comprising encapsulating a therapeutically effective amount of the mRNA in the lipid nanoparticle described herein, and administering the lipid nanoparticle to the subject.

VI. Method of Treatment

In some embodiments, the present disclosure provides a method of treating a disease in a subject in need thereof, comprising administering a therapeutically effective amount to the subject the compound described herein, the lipid nanoparticle described herein, or the pharmaceutical composition described herein. In some embodiments, the compound or lipid nanoparticle is administered intravenously or intramuscularly. In some embodiments, the compound or lipid nanoparticle is administered intravenously. In some embodiments, the compound or lipid nanoparticle is administered intramuscularly.

In some embodiments, a method of treating a disease in a subject in need thereof is provided comprising administering to the subject a lipid composition described herein. In some embodiments, the lipid composition is administered intravenously or intramuscularly. In some embodiments, the lipid composition is administered intravenously. In some embodiments, the lipid composition is administered intramuscularly.

In some embodiments, there are provided a methods of treating a disease or disorder in a mammalian subject. A therapeutically effective amount of a composition comprising a lipid, as disclosed herein, specifically a cationic lipid, a nucleic, an amphiphile, a phospholipid, cholesterol, and a PEG-linked cholesterol may be administered to a subject having a disease or disorder associated with expression or overexpression of a gene that can be reduced, decreased, downregulated, or silenced by the composition. The compositions described herein can be used in a methods for treating cancer or inflammatory disease. The disease may be one selected from the group consisting of central nervous system disorders, peripheral nervous system disorders, muscle atrophies, muscle dystrophies, immune disorder, cancer, renal disease, fibrotic disease, genetic abnormality, inflammation, and cardiovascular disorder.

In some embodiments, the present disclosure provides a method of expressing a protein or polypeptide in a target cell, comprising contacting the target cell with a lipid nanoparticle described herein, or the pharmaceutical composition described herein. In some embodiments, the protein or polypeptide is an antigen, and expression of the antigen provides an in vivo immunogenic response.

VII. Examples
Example 1. Synthesis of LIPID 1: ((4,4-(((3-(Dimethylamino)propyl)thio)carbonyl) azanediyl)bis(butanoyl))bis(oxy))bis(propane-2,1,3-triyl) tetranonanoate
LIPID 1
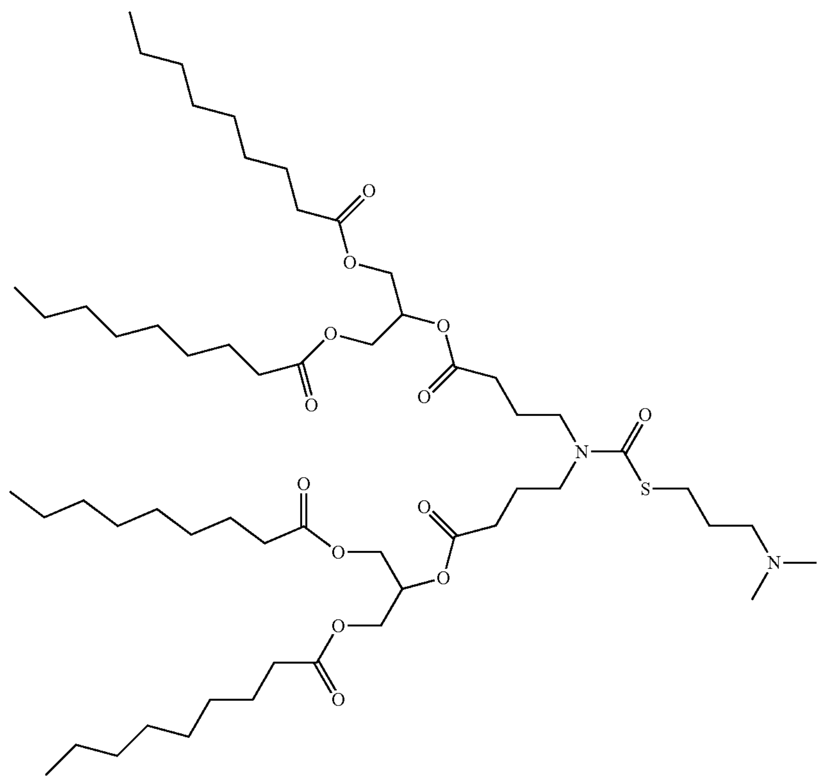
General Scheme
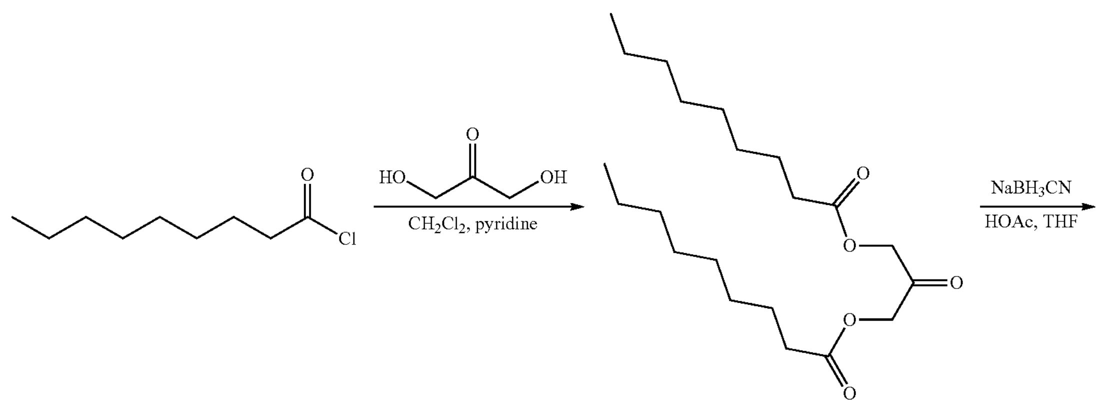
1-1

-continued
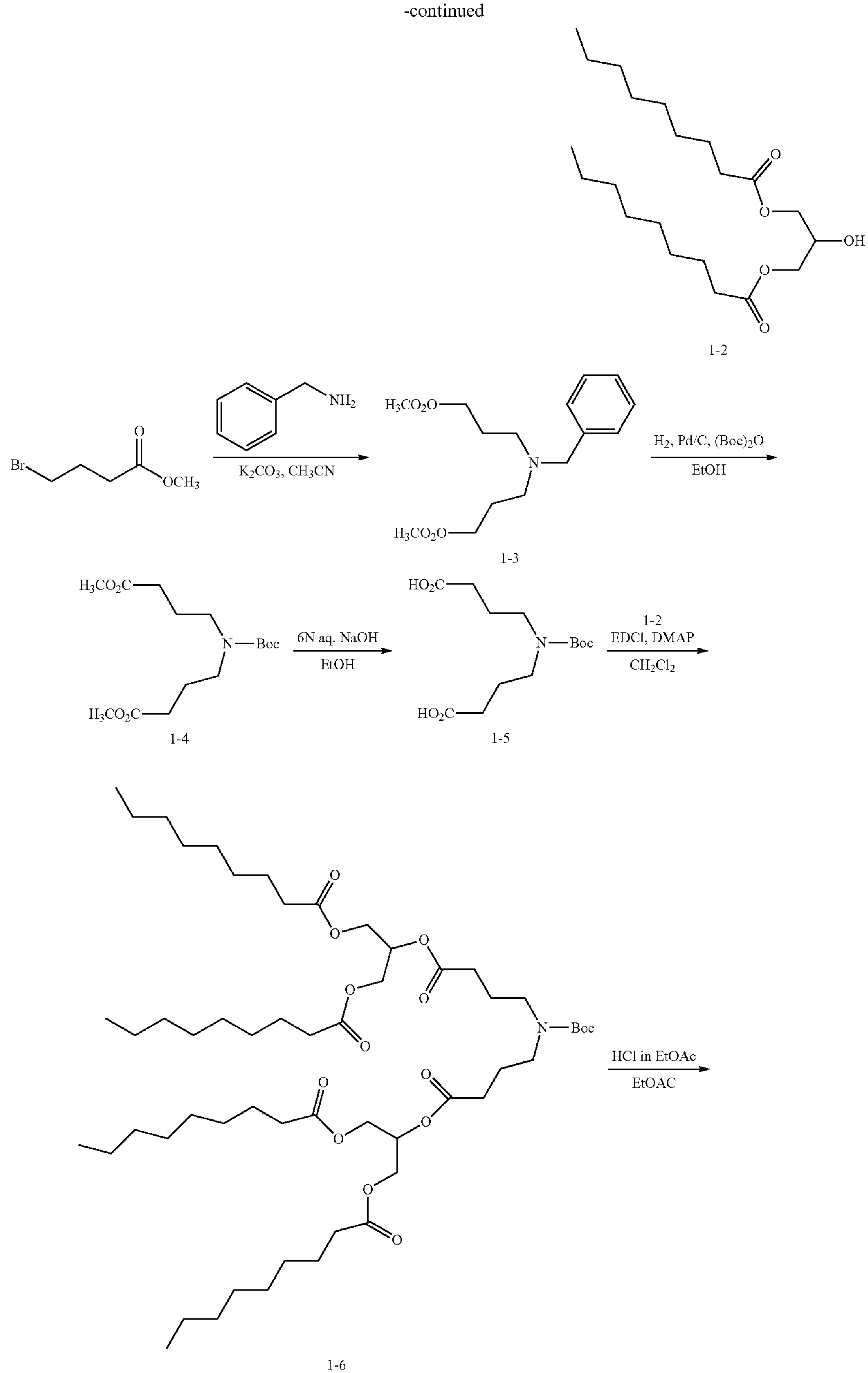
1-2
1-3
1-4
1-5
1-6

-continued
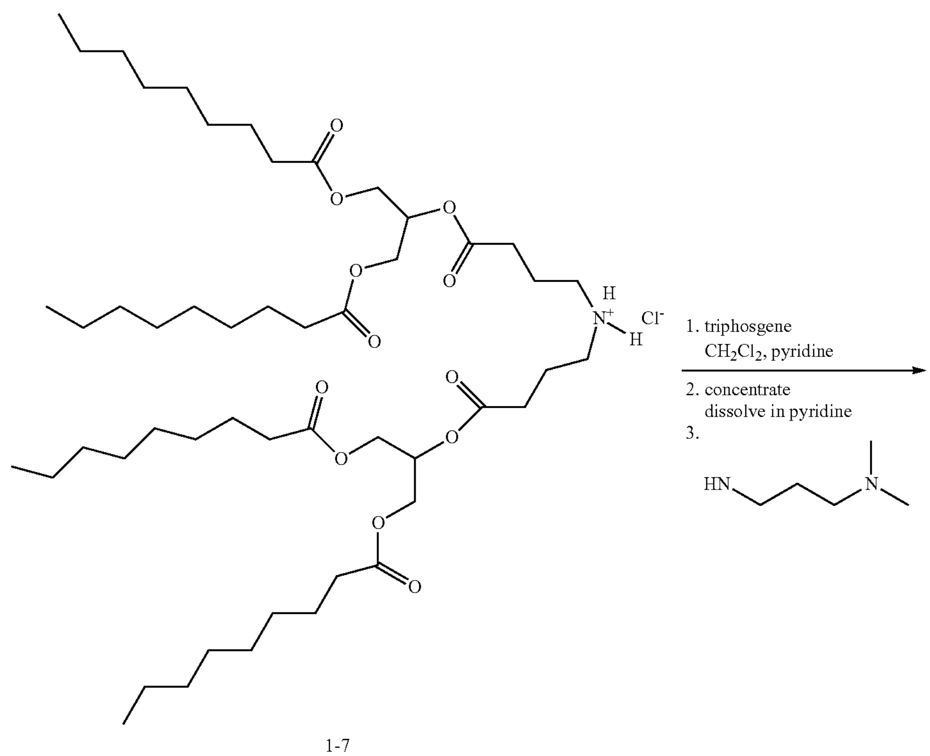
1-7
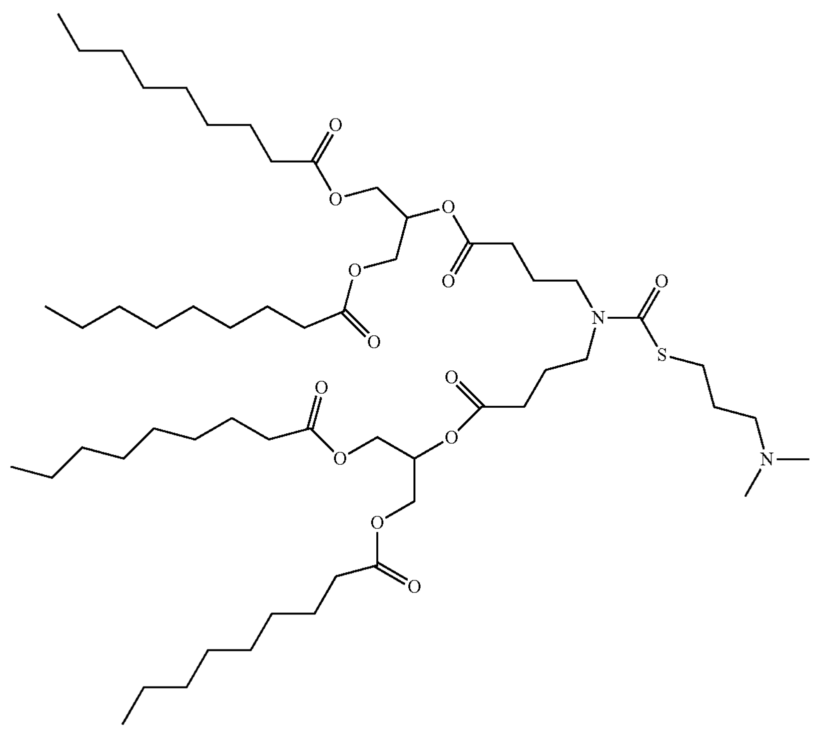
LIPID 1

Synthesis of 1-1: 2-Oxopropane-1,3-diyl dinonanoate

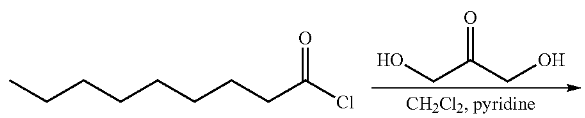

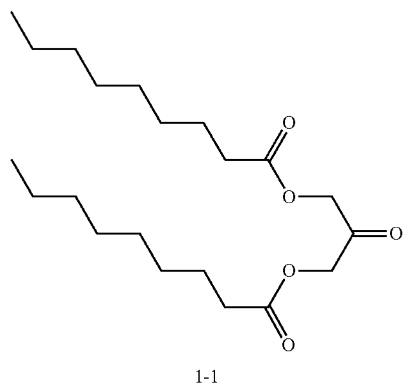

1-1

Into a 500 mL 3-necked round-bottom flask reactor under an atmosphere of $N_2$, was added a solution of 1,3-dihydroxyacetone (6.8 g, 1 eq) in $CH_2Cl_2$. Started agitation and adjusted temp to r.t. Charged pyridine (17.9 g, 3 eq) to the reactor while maintain temperature at 25±5° C. Charged 4-dimethylaminopyridine (DMAP) (0.276 g, 0.03 eq) to the reactor while maintain temperature at 25±5° C. Charged nonanoyl chloride (20 g, 1.5 eq) dropwise to the reactor dropwise at 0°-5° C. After charging kept the temperature at r.t. and stirred for 6 hours. Charged another 6.66 g of nonanoyl chloride (0.5 eq) to the reactor dropwise at 0-5° C. The temperature of the reaction was raised to room temperature and stirred under nitrogen overnight. The pyridine hydrochloride formed was removed by filtration and washed with $CH_2Cl_2$. The combined filtrate and washings were then washed with 200 mL each of 5% aq. $NaHCO_3$, 0.1N HCl and brine. The solution was then dried over $Na_2SO_4$ and concentrated under vacuum. The residue was then crystallized from methanol (50 mL) to give a white solid. This resulted in 16 g (59.7%) of white product. ELSD A: water/0.05% TFA: B: $CH_3CN$/0.05% TFA 95:5 to 5:95 A/B at 3 min., hold 0.7 min): RT 2.26 min, m/z (Calcd.) 370.27, (found) 371.00 ($M+H^+$).

Synthesis of 1-2: 2-Hydroxypropane-1,3-diyl dinonanoate

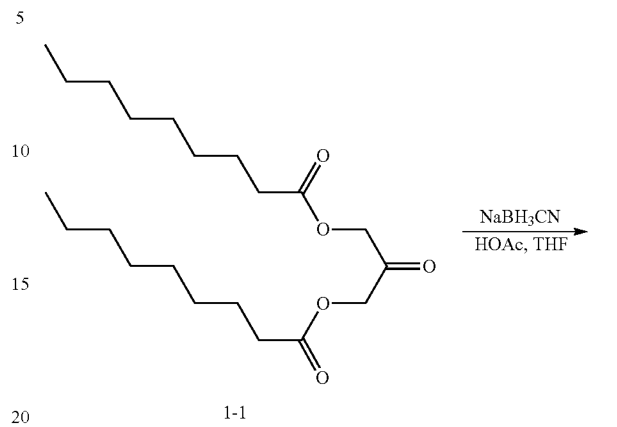

1-1

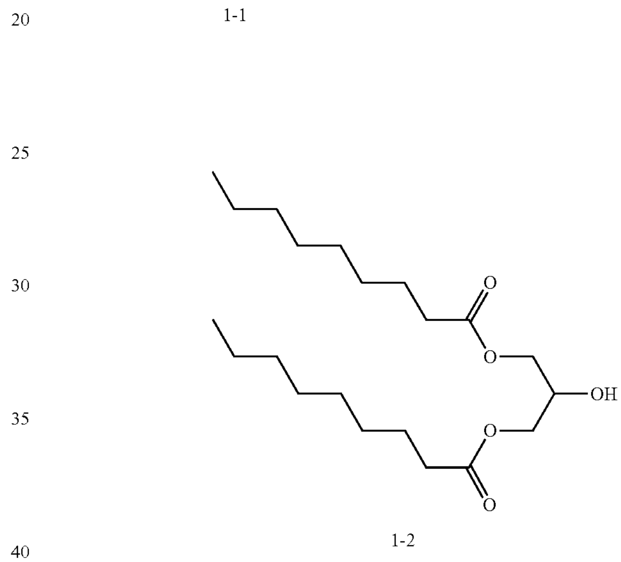

1-2

Into a 250 mL three-necked round-bottom flask was placed a solution of Lipid-1-1 (9.6 g, 1.0 eq) in 100 mL THF. To the solution was added AcOH (2.02 g, 1.3 eq) at 0° C. And then to the mixture was added $NaBH_3CN$ (1.96 g, 1.2 eq) at 0° C. The mixture was Stirred 16 hs at r.t. under an atmosphere of nitrogen. The reaction mixture was quenched with 100 mL water. The mixture was extracted with 100 mL of EtOAc 3 times. The organic layers were combined, washed with brine (300 mL) and concentrated under vacuum. This resulted in 9.5 g (crude) of 1-2 which is used in the next step without purification.

Synthesis of 1-3: Dimethyl 4,4'-(benzylazanediyl)dibutyrate

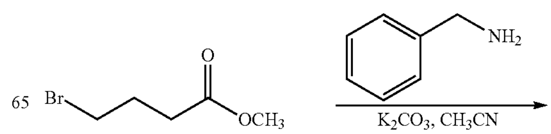

-continued

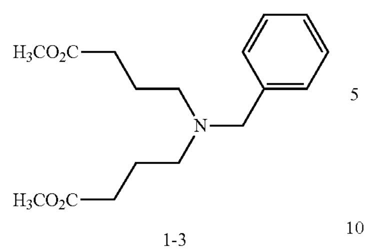

1-3

Into a 1 L 3-necked round-bottom flask purged and maintained with an inert atmosphere of nitrogen, was charged acetonitrile (208 mL), $K_2CO_3$ (31 g, 2.3 eq), benzyl amine (10.3 g, 1.0 eq) and methyl 4-bromobutyrate (40 g, 2.3 eq) at 25° C. The mixture was heated to 80° C. and stirred for 15 h. The reaction was cooled to 25° C. Charged water (200 mL, 20 V) into the flask and extracted with EtOAc (2×200 mL). The organic phase was dried ($Na_2SO_4$) and concentrated at 35° C. under reduced pressure. This resulted in 1-3 (23 g, crude) as a crude product which was carried forward without additional purification. ELSD A: water/0.05% TFA: B: $CH_3CN$/0.05% TFA 95:5 to 5:95 A/B at 3 min., hold 0.7 min): RT 2.26 min, m/z (Calcd.) 370.27, (found) 371.00 (M+H).

Synthesis of 1-4: Dimethyl 4,4'-((tert-butoxycarbonyl)azanediyl)dibutyrate

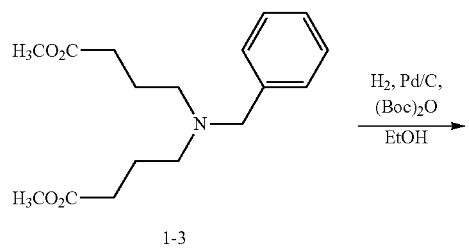

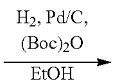

1-3

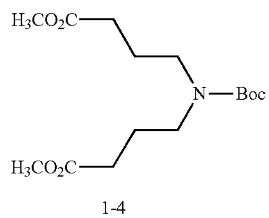

1-4

Charged EtOH (230 mL, 10 V), 1-3 (23.0 g, 1.0 eq), $(Boc)_2O$ (18.0 g, 1.1 eq) and Pd/C (2.3 g, 10% w/w) into a 1 L hydrogenation autoclave at ambient temperature. Stirred for 16 hrs at room temperature under 5 atm hydrogen atmosphere. TLC observation indicated that 1-3 was completely consumed. The reaction mixture was filtered and concentrated under vacuum at 40° C. to get 22 g of crude 1-4.

Synthesis of 1-5: 4,4'-((tert-Butoxycarbonyl)azanediyl)dibutyric Acid

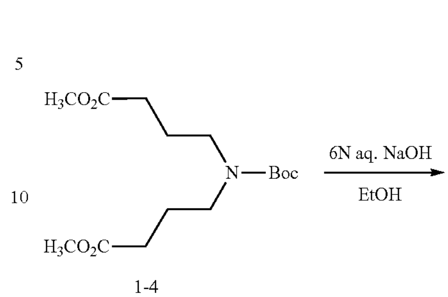

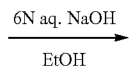

1-4

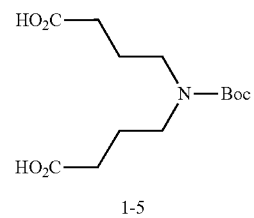

1-5

Into a 500 mL 3-necked round-bottom flask purged and maintained with an inert atmosphere of nitrogen, was charged a solution of 1-4 (22 g, 1.0 eq) in ethanol (110 mL). An aqueous solution of NaOH (6M, 110 mL, 5 V) was added at room temperature. The reaction mixture was stirred at 60° C. for 2 hours. The reaction was then diluted with brine (220 mL, 10 V), and was extracted with t-BuOH/n-heptane (2:1, 220 mL, 2×) to remove organic impurities. The aqueous phase was acidified by the addition of 3M aqueous HCl solution to about pH=3 and then extracted with t-BuOH:n-heptane (2:1) (220 mL). The organic layers were concentrated under reduced pressure. The residue was slurried with diethyl ether (44 mL, 2 V) and filtered. Collected the filter cake to give 1-5 (14 g, 43% yield in three steps) as white solid.

Synthesis of 1-6: ((4,4'-((tert-Butoxycarbonyl)azanediyl)bis(butanoyl))bis(oxy))bis(propane-2,1,3-triyl) tetranonanoate

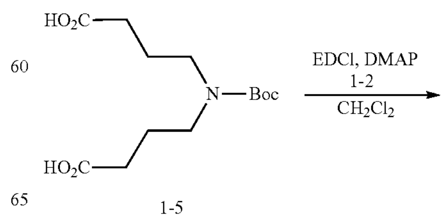

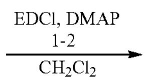

1-5

-continued

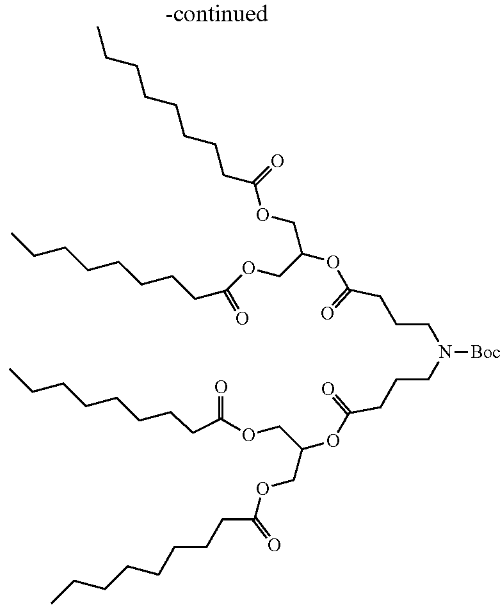

1-6

Into a 250 mL 3-necked round-bottom flask purged and maintained with an inert atmosphere of nitrogen, was placed a solution of 1-5 (3.7 g, 1.00 equiv) in 100 mL of $CH_2Cl_2$. To the solution was added 1-2 (9.5 g, 2.00 equiv), DMAP (4.69 g, 3 equiv) and 1-ethyl-3-(3-dimethylaminopropyl) carbodiimide (EDCI) (7.35 g, 3 equiv) at 0° C. The reaction mixture was stirred overnight at 25° C. The reaction was then quenched with 200 mL of 10% aq. citric acid. The organic layer was washed with 200 mL of brine. The mixture was dried over anhydrous sodium sulfate and concentrated under vacuum. This resulted in 12 g of 1-6 and used to the next step without additional purification. ELSD A: water/0.05% TFA: B: $CH_3CN$/0.05% TFA 95:5 to 5:95 A/B at 3 min., hold 0.7 min): RT 2.46 min, m/z (Calcd.) 997.71, (found) 1020.6 (M+Na).

Synthesis of 1-7: bis(4-((1,3-bis(nonanoyloxy)propan-2-yl)oxy)-4-oxobutyl)ammonium chloride

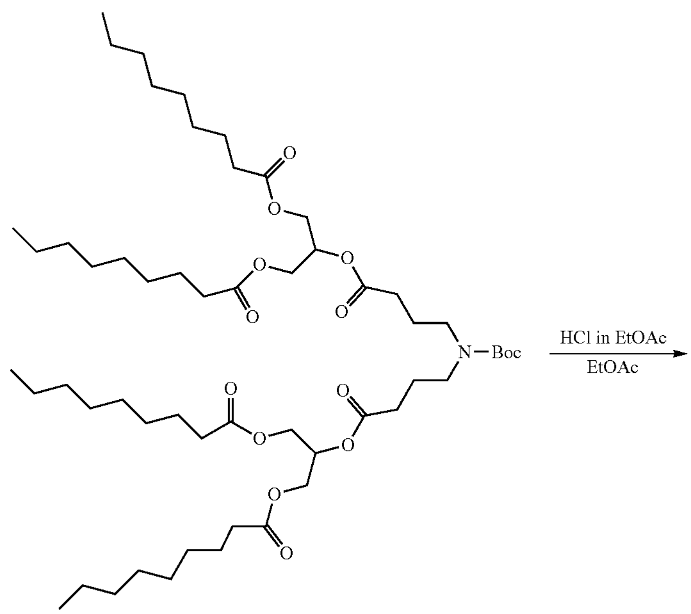

1-6

-continued

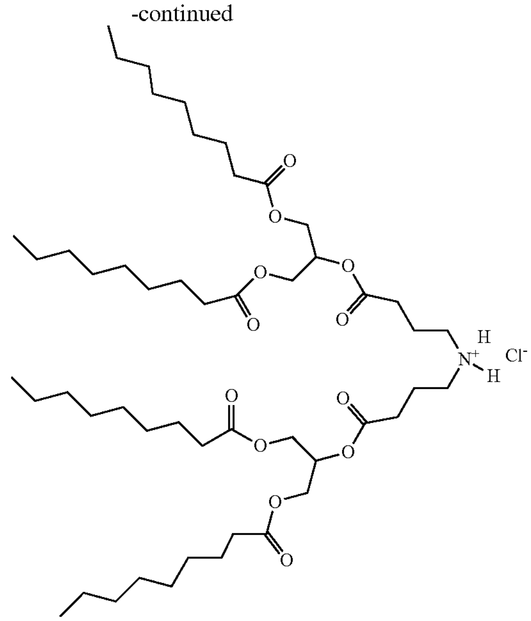

1-7

Into a 500 mL round-bottom flask purged and maintained with an inert atmosphere of nitrogen, was placed a solution of 1-6 (12 g, 1.00 equiv) in EtOAc (68 mL). To the solution was added EtOAc/HCl (15 mL, 5.00 equiv, 4M) dropwise at 0-10° C. The resulting solution was stirred for 5 h at room temperature. The resulting mixture was concentrated under vacuum. The residue was diluted with $CH_2Cl_2$ (100 mL) and 25 g of silica gel (type: ZCX-2, 100-200 mesh) was added. The mixture was concentrated under vacuum and then applied onto atmospheric silica gel column with $CH_2Cl_2$/MeOH gradient from 1:0 to 15:1. The product eluent was collected from 20:1 to 15:1 and concentrated under vacuum. This resulted in 4.2 g of 1-7 as light yellow oil. ELSD A: water/0.05% TFA: B: $CH_3CN$/0.05% TFA 95:5 to 5:95 A/B at 3 min., hold 0.7 min): RT 1.50 min, m/z (Calcd.) 897.65, (found) 898.6 (M+H).

Synthesis of LIPID 1: ((4,4'-((((3-(Dimethylamino)propyl)thio)carbonyl)azanediyl)bis(butanoyl))bis(oxy))bis(propane-2,1,3-triyl) tetranonanoate

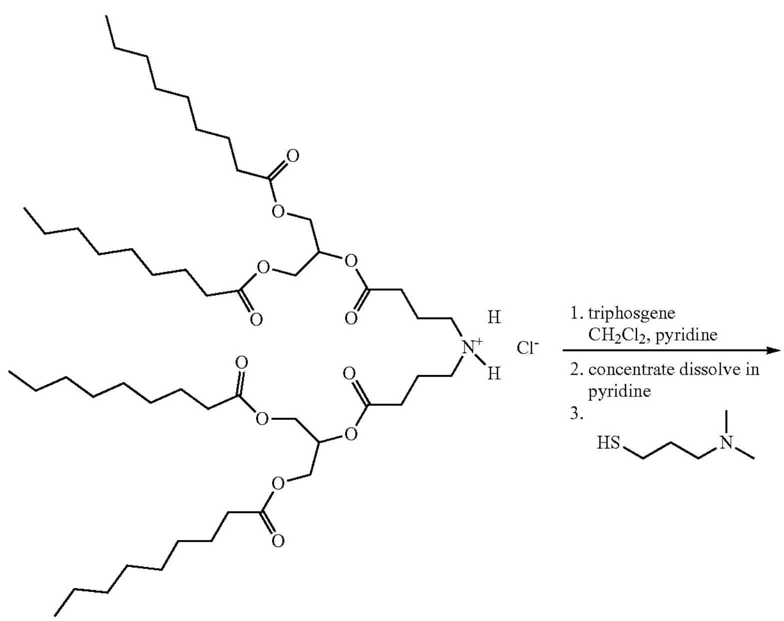

1-7

-continued

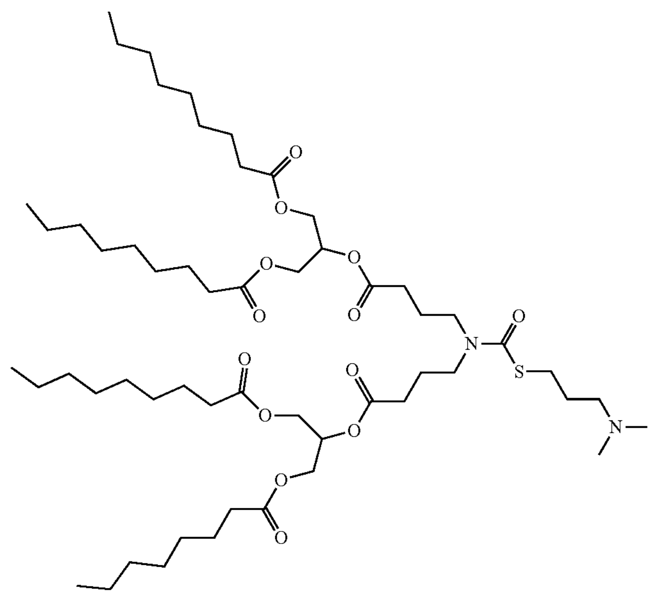

LIPID 1

Into a 250-mL 3-necked round-bottom flask purged and maintained with an inert atmosphere of nitrogen, was placed a solution of 1-7 (4.2 g, 1 eq) in $CH_2Cl_2$ (150 mL). To the mixture was added triphosgene (1.33 g, 1 equiv) at r.t. This was followed by the addition of pyridine (1.78 g, 5.00 equiv) dropwise with stirring at 0° C. The mixture was stirred for 4 h at r.t and then concentrated under vacuum. The residue was dissolved with pyridine (600 mL). To this solution was added 3-(dimethylamino)propane-1-thiol (0.92 g, 1.20 equiv) dropwise with stirring at 0° C. in 10 min. The resulting solution was stirred overnight at room temperature. The resulting mixture was concentrated under vacuum. The residue was diluted with 100 mL of EtOAc. The mixture was washed with 2×100 mL of 10% citric acid and 2×100 mL of $NaHCO_3$. The mixture was washed with 100 mL of brine and dried over anhydrous sodium sulfate and concentrated under vacuum. The residue was dissolved in 100 mL $CH_2Cl_2$ and 12 g of Silica gel (type: ZCX-2, 100-200 mesh) was added. The mixture was concentrated under vacuum and then applied onto atmospheric silica gel column with $CH_2Cl_2$/MeOH gradient from 1:0 to 15:1. The product eluent was collected from 20:1 to 15:1 and concentrated under vacuum. The product was dissolved in 36 mL n-heptane (20V) and 0.09 g activated charcoal powder was added. The mixture was stirred for 4 h at r.t and then filtered. 0.09 g activated charcoal powder was added to the filtrate and the mixture was stirred for another 4 h at r.t. The mixture was filtered. 0.045 g activated charcoal powder was added to the filtrate and the mixture was stirred overnight at r.t. The mixture was filtered. A mixture of methanol (60 mL) and water (20 mL) was charged into the filtrate. The mixture was stirred for 30 min at r.t., kept for phase separation and collected the upper phase. A mixture of methanol (60 mL) and water (20 mL) was charged into the n-heptane phase. The mixture was stirred for 30 min at r.t., kept for phase separation and collected the upper phase that was concentrated to afford 1.5 g (31.9%) of LIPID 1 (HPLC Purity: 96.7%, 205 nm). ELSD A: water/0.05% TFA: B: $CH_3CN$/0.05% TFA 95:5 to 5:95 A/B at 8 min, hold 0.7 min): RT 7.07 min, m/z (Calcd.) 1042.71, (found) 1043.8 (M+H); $^1H$ NMR (300 MHz, $CDCl_3$): δ 5.27 (m, 2H), 4.33 (dd, J=11.9, 4.4 Hz, 4H), 4.17 (dd, J=11.9, 5.7 Hz, 4H), 3.41 (brm, 4H), 2.94 (t, J=7.3 Hz, 2H), 2.10-2.35 (20H), 1.92 (s, 6H), 1.65 (m, 8H), 1.10-1.57 (40H), 0.96-0.85 (12H).

Example 2. Synthesis of LIPID 2: ((4,4'-(((3-(Dimethylamino)propyl)thio)carbonyl)azanediyl)bis(butanoyl)bis(oxy))bis(propane-2,1,3-triyl)tetraoctanoate
LIPID 2
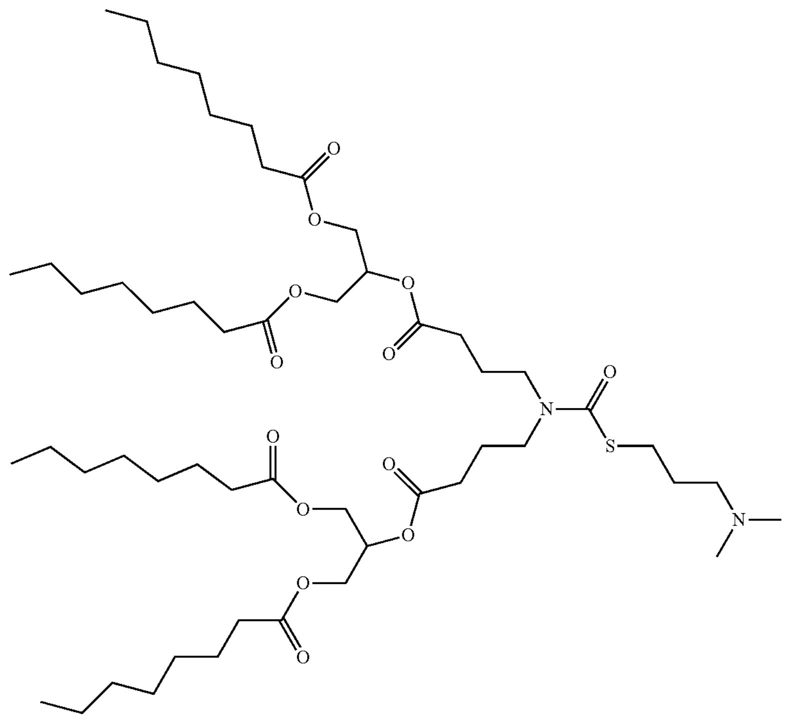
General Scheme
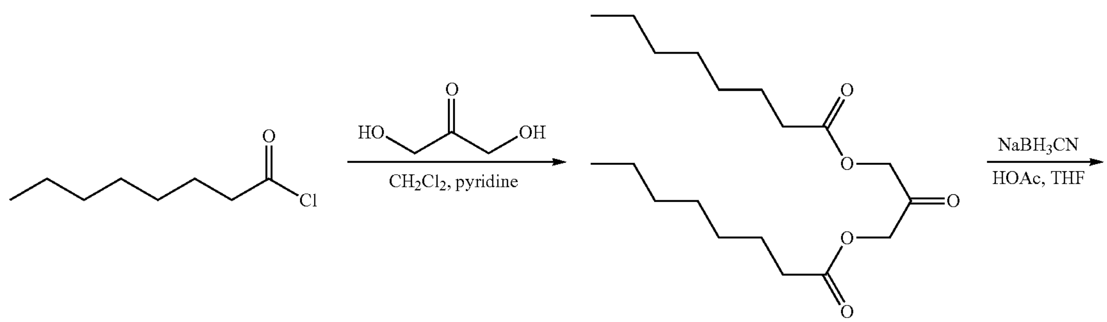
2-1

-continued
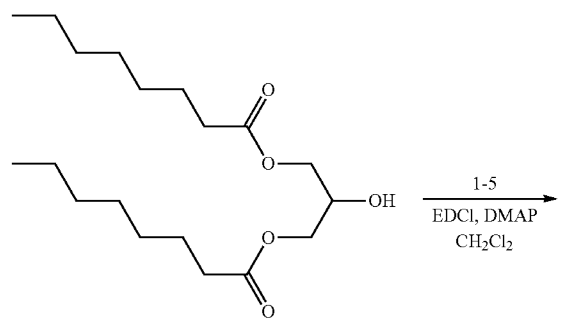
2-2
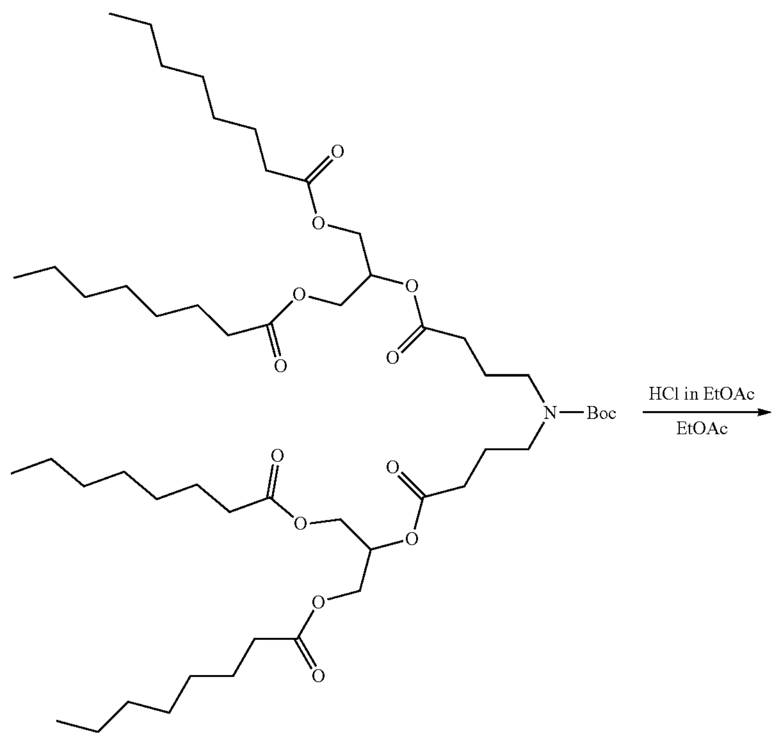
2-3

-continued
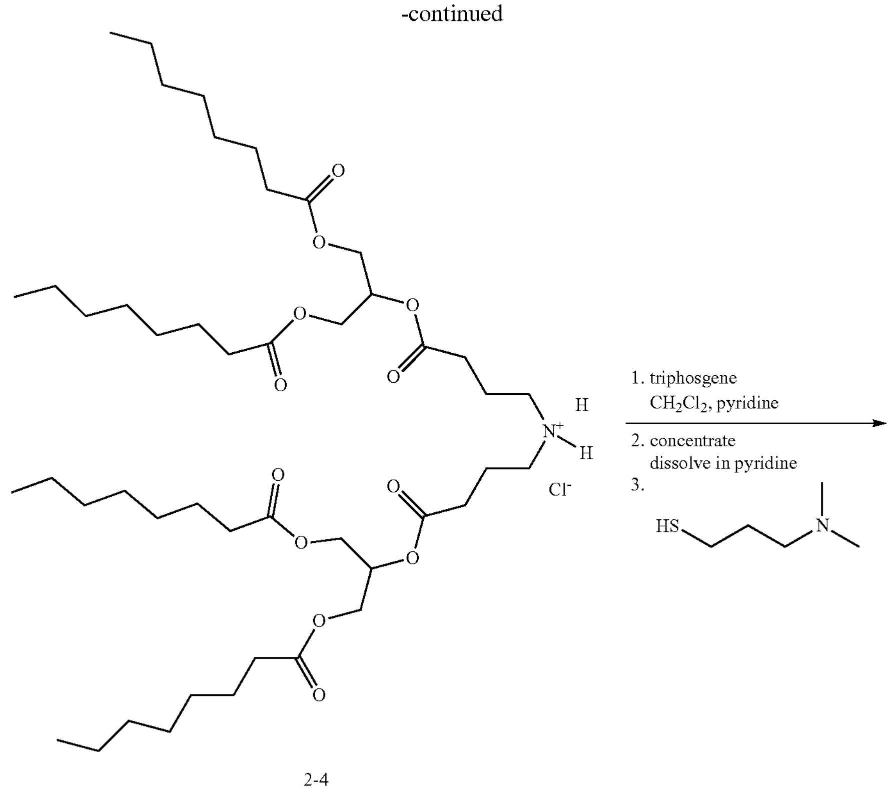
2-4
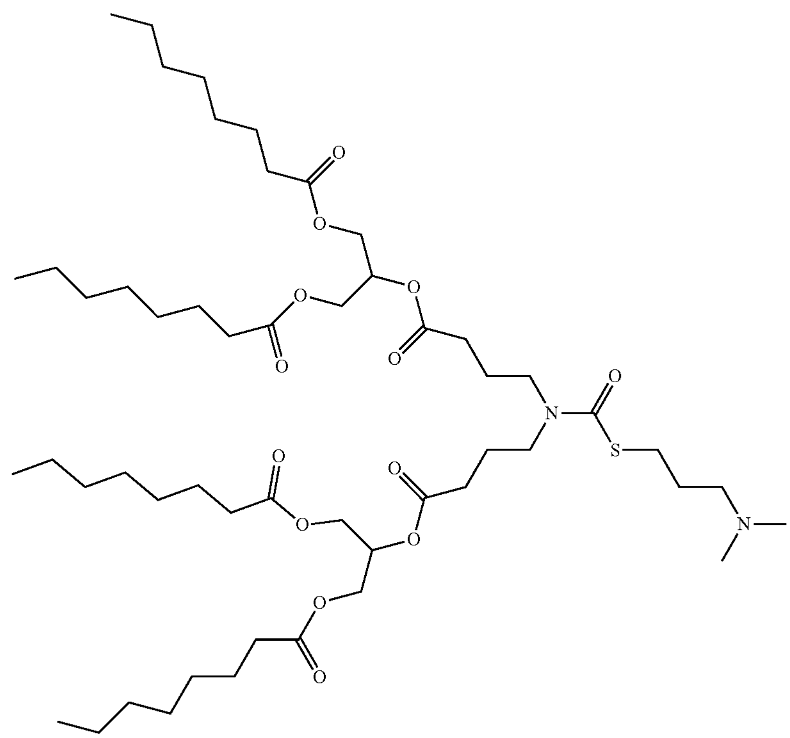
LIPID 2

Synthesis of 2-1: 2-Oxopropane-1,3-diyl dioctanoate

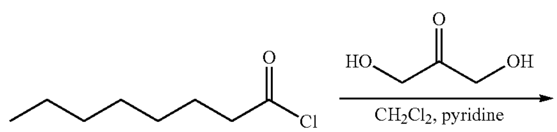

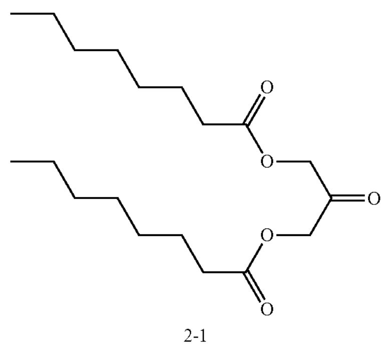

2-1

Into a 2 L 3-necked round-bottom flask purged and maintained with an inert atmosphere of nitrogen, was placed a solution of 1,3-dihydroxyacetone (50 g, 1.0 eq) and octanoyl chloride (225.8 g, 2.5 eq) in $CHCl_3$ (900 mL). Added pyridine (175.8 g, 4.0 eq) to the reactor while maintaining the temperature at 0° C. for 40 minutes. The mixture was stirred at room temperature under nitrogen overnight. The pyridine hydrochloride formed was removed by filtration and washed with $CH_2Cl_2$. The combined filtrate and washings were then washed with 200 mL 5% aqueous $NaHCO_3$ and brine (200 mL). The solution was then dried over $Na_2SO_4$ and concentrated under vacuum. The crude was slurred in n-heptane (125 mL) for 30 minutes and filtered. This resulted in 98 g (52% yield) 2-1 as a colorless oil. ELSD A: water/0.05% TFA: B: $CH_3CN$/0.05% TFA 95:5 to 5:95 A/B at 3 min., hold 0.7 min): RT 2.09 min, m/z (Calcd.) 342.24, (found) 343.45 ($M+H^+$).

Synthesis of 2-2: 2-Hydroxypropane-1,3-diyl dioctanoate

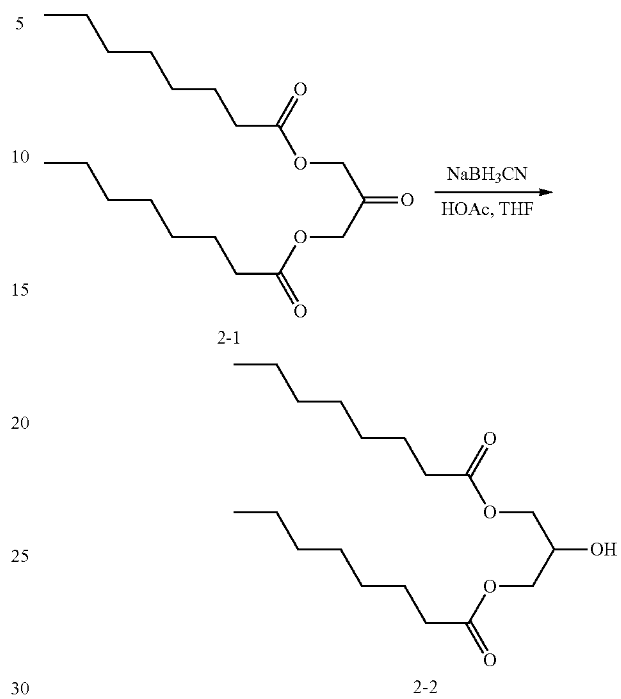

2-1

2-2

Into a 500 mL 3-necked round-bottom flask purged and maintained with an inert atmosphere of nitrogen, was placed a solution of 2-1 (20 g, 1.0 eq) in 200 mL of THF. To the solution was added AcOH (4.56 g, 1.3 eq) at 0° C., and then to the mixture was added $NaBH_3CN$ (4.3 g, 1.2 eq) at 0° C. The mixture was stirred for 4 h at room temperature. The reaction mixture was quenched with 200 mL water. The mixture was extracted with $CH_2Cl_2$ (3×200 mL) and the combined organic phases were washed with 5% aq. $NaHCO_3$ (500 mL), brine (500 mL), then dried with $Na_2SO_4$. Filtration and concentration under vacuum gave crude 2-2 (19.5 g) which was used in the next step without purification.

Synthesis of 2-3: ((4,4'-((tert-Butoxycarbonyl) azanediyl)bis(butanoyl))bis(oxy))bis(propane-2,1,3-triyl)tetraoctanoate

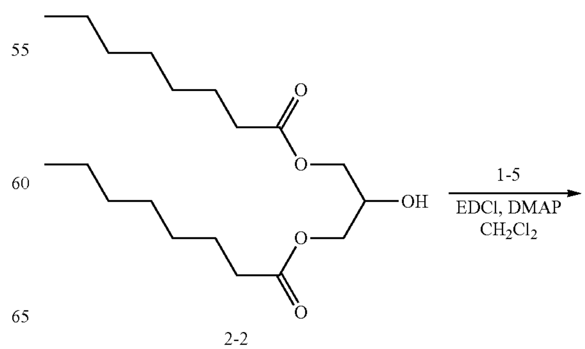

2-2

-continued

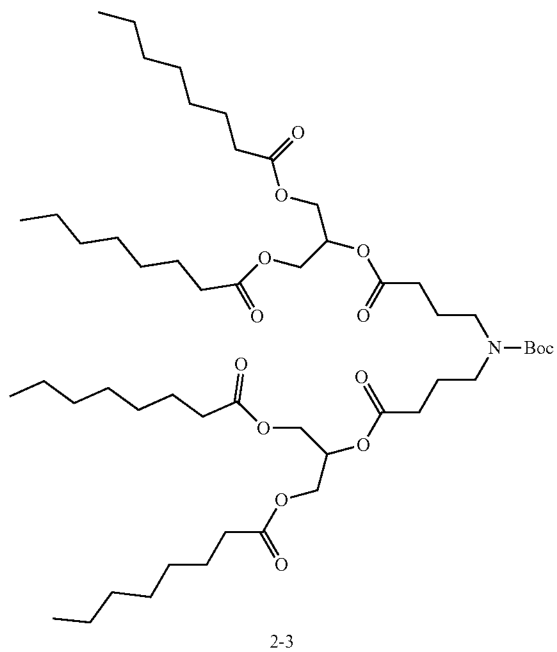

2-3

Into a 500 mL 3-necked round-bottom flask purged and maintained with an inert atmosphere of nitrogen, was added 1-5 (8.4 g, 1.0 eq) flowed by a solution of 2-2 in $CH_2Cl_2$ (175 ml) and the solution was cooled in an ice-water bath. To the solution was added DMAP (3.55 g, 1.0 equiv) and EDCI (22.3 g, 4.0 equiv) at 0° C. The reaction mixture was stirred overnight at 25° C. The reaction was then quenched with 200 mL of 10% aqueous citric acid solution. The organic layer was separated, washed with brine (200 mL), and dried over anhydrous sodium sulfate. Filtration and concentration in vacuum provided crude 2-3 which was dissolved in $CH_2Cl_2$ and the solution adsorbed on 54 g of silica gel (type: ZCX-2, 100-200 mesh, 6.43 w./w.), and purified on a silica gel column (270 g of silica gel, type: ZCX-2, 100-200 mesh, 32.14 w./w.) using a petroleum ether/ethyl acetate gradient from 100:0 to 90:10. Product containing fractions were pooled, combined and concentrated under reduced pressure to obtain 15 g (55% for 2 steps) of 2-3 as light yellow oil.

Synthesis of 2-4: bis(4-((1,3-bis(Octanoyloxy)propan-2-yl)oxy)-4-oxobutyl)ammonium chloride

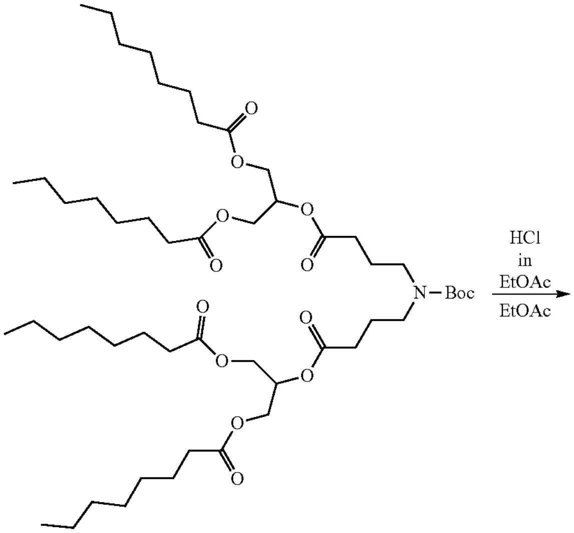

2-3

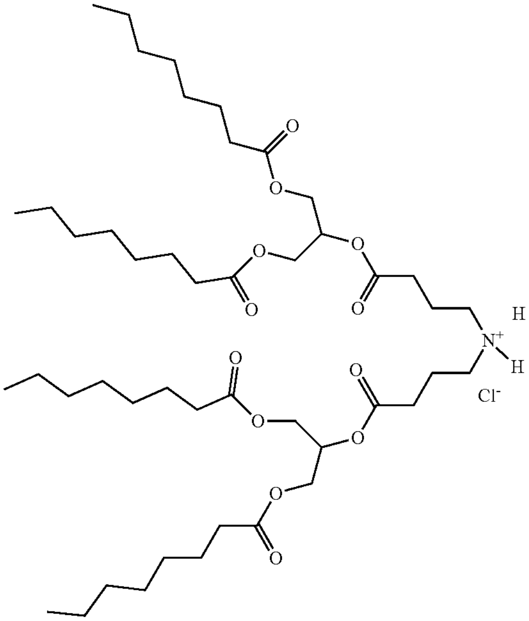

2-4

Into a 500 mL round-bottom flask purged and maintained with an inert atmosphere of nitrogen, was placed a solution of 2-3 (15 g, 1.0 equiv) in EtOAc (85.5 mL), the mixture was cooled in an ice-water bath. To the solution was added HCl in EtOAc (80 mL, 10.0 equiv, 2 mol/L) dropwise at 0-10° C. The resulting solution was stirred overnight at room temperature. The mixture was concentrated under vacuum. This resulted in 13 g (93% yield) of 2-4 as light-yellow oil that was used in the next reaction without further purification.

ELSD A: water/0.05% TFA: B: $CH_3CN$/0.05% TFA 95:5 to 5:95 A/B at 3 min., hold 0.7 min): RT 0.746 min, m/z (Calcd.) 842.60, (found) 842.71 ($M+H^+$).

Synthesis of LIPID 2: ((4,4'-((((3-(Dimethylamino) propyl)thio)carbonyl) azanediyl)bis(butanoyl))bis (oxy))bis(propane-2,1,3-triyl)tetraoctanoate

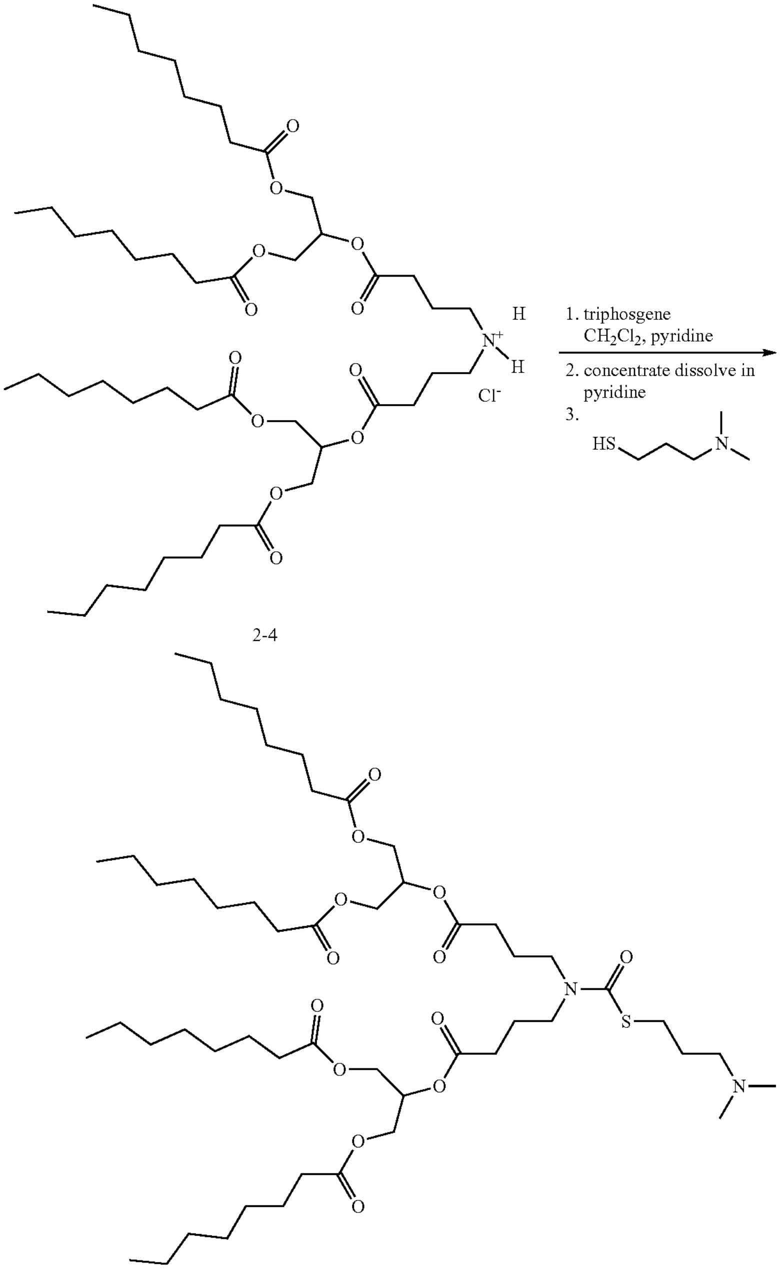

2-4

LIPID 2

Into a 500-mL 3-necked round-bottom flask purged and maintained with an inert atmosphere of nitrogen, was placed 2-4 (8 g, 1 eq) dissolved in $CH_2Cl_2$ (280 mL), and the solution was cooled in an ice-water bath. To the mixture was added triphosgene (2.82 g, 1 equiv) and this was followed by the addition of pyridine (3.76 g, 5.00 equiv) dropwise with stirring at 0° C. The mixture was stirred for 4 h at r.t and then concentrated under vacuum. The residue was dissolved with pyridine (160 mL) and the solution was cooled in an ice-water bath under nitrogen. To this solution was added 3-(dimethylamino)propane-1-thiol (1.356 g, 1.20 equiv) dropwise with stirring at 0° C. over 10 min. The resulting solution was stirred overnight at room temperature. The mixture was concentrated under vacuum and the residue was dissolved in $CH_2Cl_2$ (200 mL). The mixture was washed with 10% aq. citric acid (2×100 mL), 5% aq. $NaHCO_3$ (2×100 mL), and brine (100 mL). The mixture was dried over anhydrous sodium sulfate and concentrated under vacuum. The crude product was dissolved in $CH_2Cl_2$ (25 mL) and adsorbed on 12 g of silica gel (type: ZCX-2, 100-200 mesh, 6.43 w./w.), and purified on a silica gel column (80 g of silica gel, type: ZCX-2, 100-200 mesh, 32.14 w./w.) using $CH_2Cl_2$/MeOH gradient from 100:0 to 97:3. Fractions containing pure products were analyzed, pooled, combined and concentrated under reduced pressure. The product thus obtained was dissolved in 36 mL n-heptane and 0.22 g activated charcoal powder was added. The mixture was stirred for 4 h at r.t and then filtered. The filtrate was concentrated under vacuum. This resulted in 3.8 g (42%) of 2 as a viscous, pale yellow oil. ELSD A: water/0.05% TFA: B: $CH_3CN$/0.05% TFA 95:5 to 5:95 A/B at 2 min., hold 0.7 min): RT 1.48 min, m/z (Calcd.) 986.65, (found) 987.4 (M+H); $^1H$ NMR (300 MHz, $CDCl_3$) δ 5.26 (m, 2H), 4.32 (dd, J=11.9, 4.4 Hz, 4H), 4.16 (dd, J=11.9, 5.7 Hz, 4H), 3.40 (brm, 4H), 2.93 (t, J=7.3 Hz, 2H), 2.39-2.25 (18H), 1.91-1.59 (16H), 1.06-1.45 (32H), 0.913-0.869 (12H).

Example 3. Synthesis LIPID 3; bis(1,3-bis(Nonanoyloxy)propan-2-yl) 5-((4-(dimethylamino)butanoyl)oxy)nonanedioate HCl Salt

LIPID 3

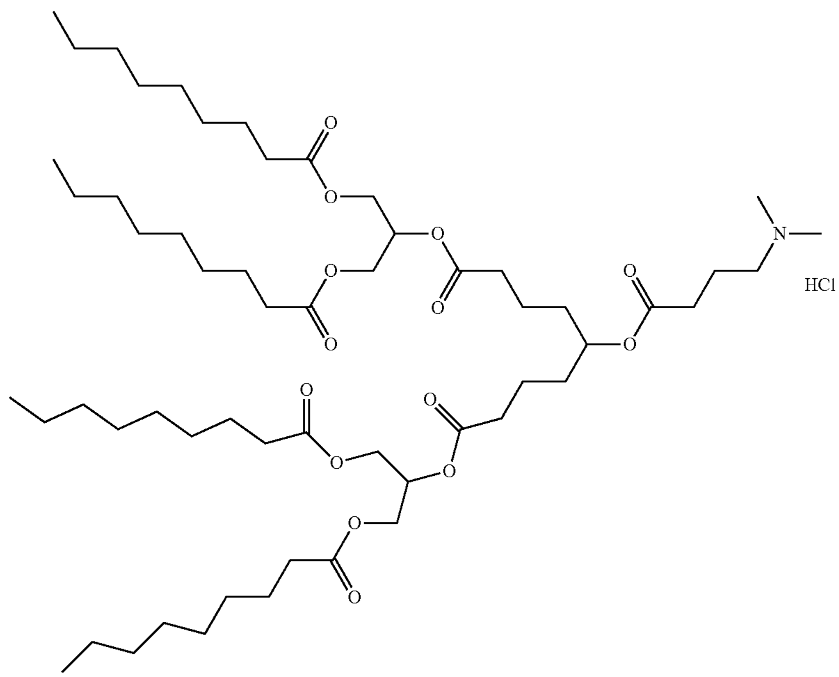

General Scheme

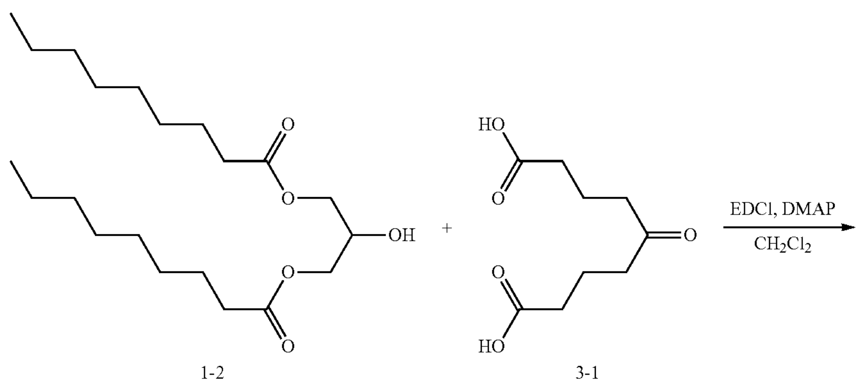

1-2

3-1

-continued
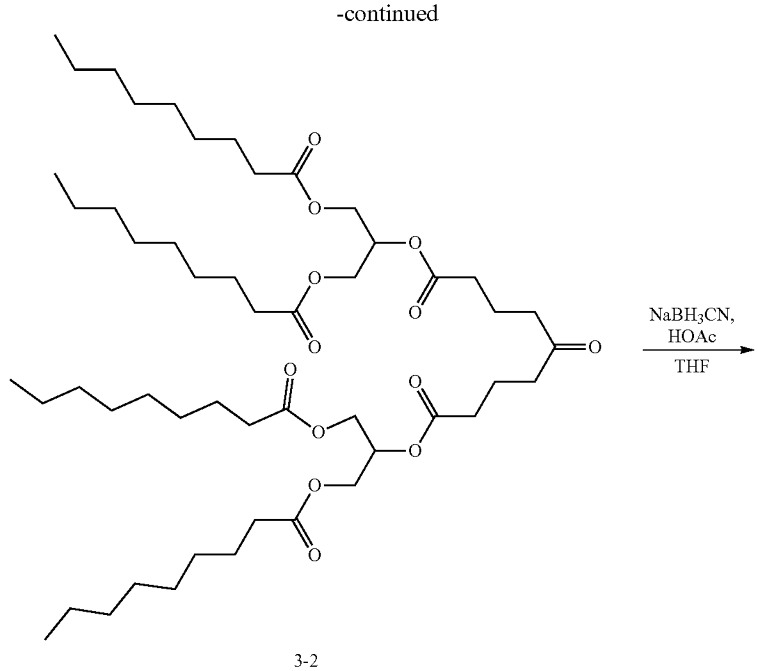
3-2
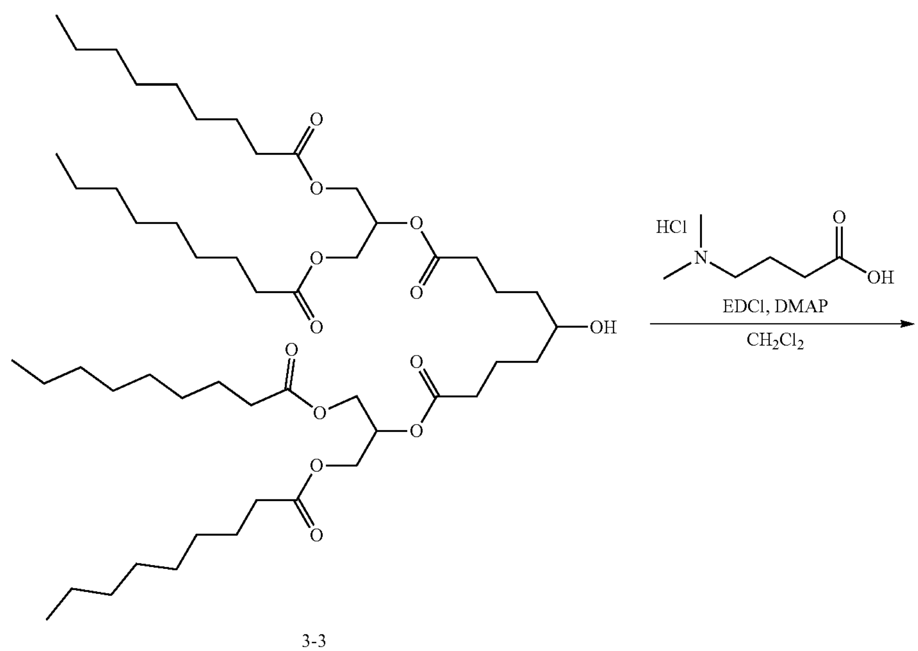
3-3

-continued
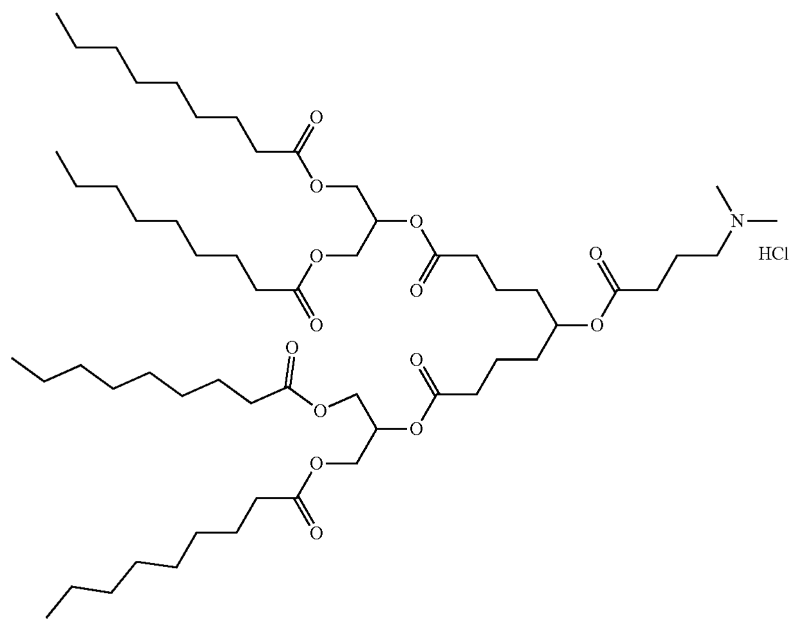
LIPID 3
Synthesis of 3-2: bis(1,3-bis(Nonanoyloxy)propan-2-yl) 5-oxononanedioate
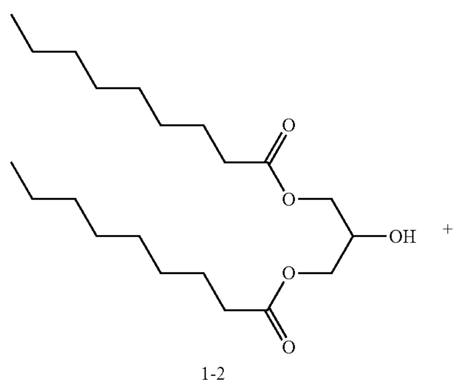
1-2
+
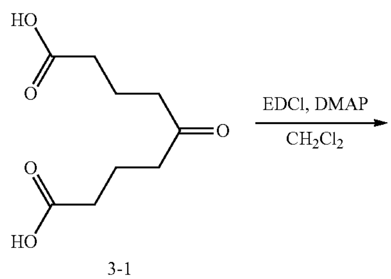
3-1
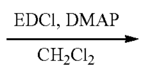
-continued
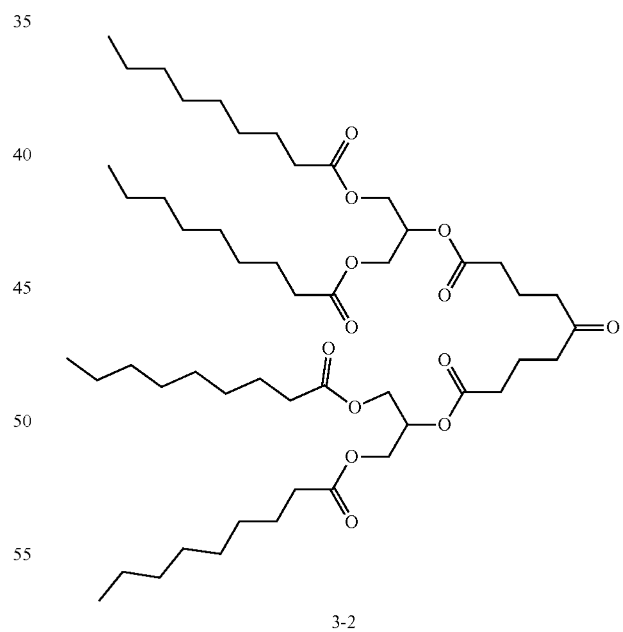
3-2
Into a 250 mL 3-necked round-bottom flask purged and maintained with an inert atmosphere of nitrogen, was placed 3-1 (7.04 g, 1.0 eq, Chemistry-A European Journal 2017, 23, 12744-12748) into $CH_2Cl_2$ (100 mL), cooled in an ice-water bath under nitrogen. This was followed by the addition of 1-2 (25.95 g, 2.0 eq), DMAP (4.26 g, 1.0 eq), and EDCI (20.09 g, 3.0 eq) at 0° C. The resulting solution was stirred for 16 h at room temperature. The reaction mixture was adsorbed on 90 g of silica gel (type: ZCX-2, 100-200 mesh, 6.43 w./w.), and purified on a silica gel column (900 g, type: ZCX-2, 100-200 mesh) with PE/EA, gradient from 100:0 to 90:10. The fractions containing pure product were pooled, concentrated under vacuum and dried over $P_2O_5$ to get 19.7 g (62.2%) of 3-2 as a yellow oil. ELSD A: water/0.05% TFA: B: $CH_3CN$/0.05% TFA 95:5 to 5:95 A/B at 3 min., hold 0.7 min): RT 0.87 min, m/z (Calcd.) 910.63, (found) 933.35 (M+Na).

Synthesis of 3-3: bis(1,3-bis(Nonanoyloxy)propan-2-yl) 5-hydroxynonanedioate

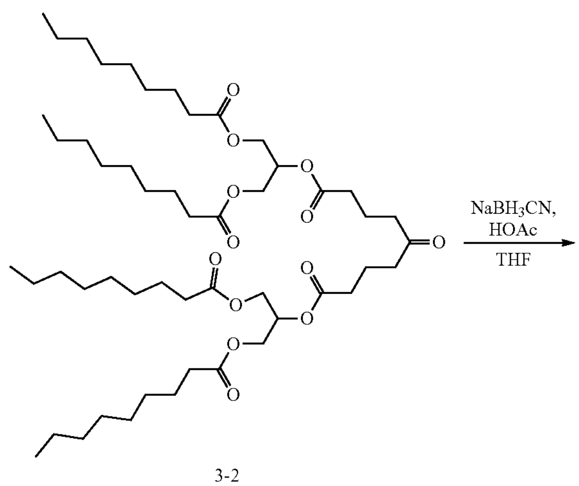

3-2

-continued

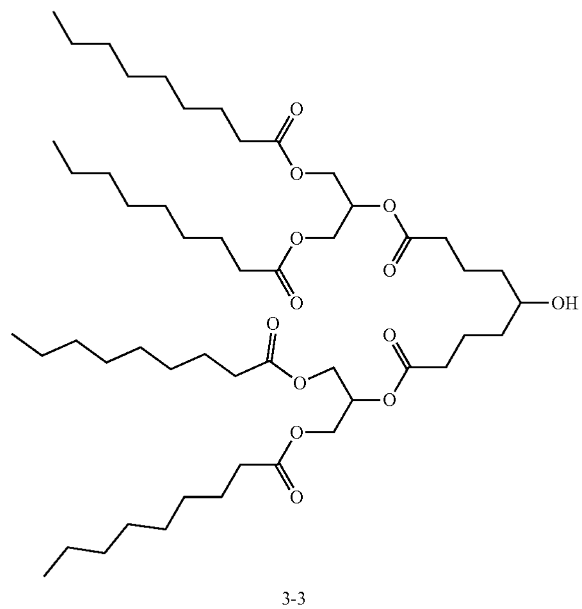

3-3

Into a 250-mL 3-necked round-bottom flask purged and maintained with an inert atmosphere of nitrogen, was placed 3-2 (10.7 g, 1.0 eq) into THF (100 mL, 10 V), cooled in an ice-water bath. This was followed by the addition of HOAc (7.96 g, 11.3 eq), $NaBH_3CN$ (8.88 g, 12.0 eq) at 0° C. The resulting solution was stirred for 16 h at room temperature. The reaction was then quenched by the addition of water (100 mL, 10 V). The resulting solution was extracted with ethyl acetate (3×100 mL) and the organic layers were combined. The resulting mixture was washed with brine (2×100 mL). The mixture was dried over anhydrous sodium sulfate and the organic layers was concentrated under vacuum. The reaction mixture was adsorbed on 40 g of silica gel (type: ZCX-2, 100-200 mesh, 6.43 w./w.), and purified on a silica gel column (400 g, type: ZCX-2, 100-200 mesh) with PE/EA, gradient from 100:0 to 80:20. The fractions containing pure product was pooled, concentrated under vacuum and dried over $P_2O_5$ to get 7.42 g (69.2%) of 3-3 as a yellow oil ELSD A: water/0.05% TFA: B: $CH_3CN$/0.05% TFA 95:5 to 5:95 A/B at 3 min., hold 0.7 min): RT 0.87 min, m/z (Calcd.) 913.27, (found) 935.35 (M+Na).

Synthesis of LIPID 3: bis(1,3-bis(Nonanoyloxy) propan-2-yl) 5-((4-(dimethylamino)butanoyl)oxy) nonanedioate HCl Salt

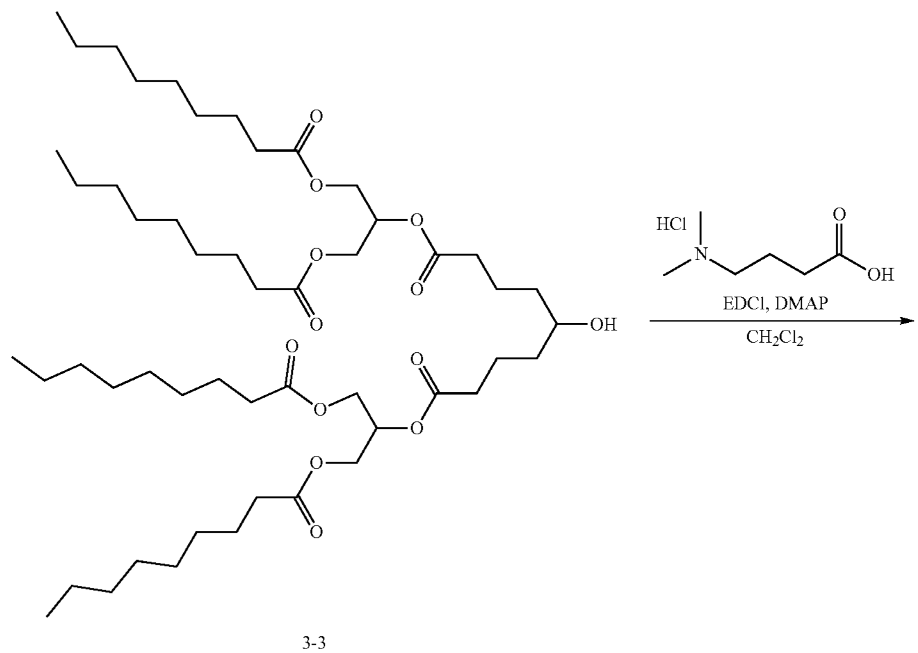

3-3

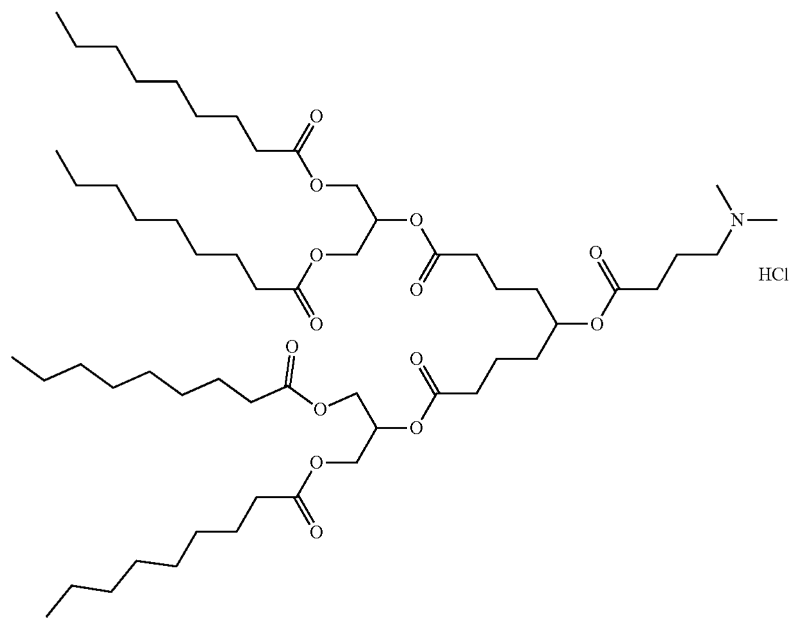

LIPID 3

Into a 250-mL 3-necked round-bottom flask purged and maintained with an inert atmosphere of nitrogen, was placed a solution of 3-3 (7.42 g, 1.0 eq) in $CH_2Cl_2$ (110 mL), cooled in an ice-water bath. 4-(dimethylamino)butanoic acid-HCl salt (1.63 g, 1.2 eq), DMAP (0.4 g, 0.4 eq) were added, followed by the addition of EDCI (3.74 g, 2.4 eq) in portions at 0° C. The resulting solution was stirred for 16 h at room temperature. Silica gel (40 g, type: ZCX-2, 100-200 mesh, 6.43 w./w.) was added to the reaction and adsorbed it on the silica gel. It was purified on a silica gel column (300 g, type: ZCX-2, 100-200 mesh) with EtOAc/THF, gradient from 100:0 to 75:25. The fractions containing pure product were pooled and concentrated under vacuum to get 1.9 g (26.3%) of 3 as a yellow oil. ELSD A: water/0.05% TFA: B: $CH_3CN$/0.05% TFA 95:5 to 5:95 A/B at 3 min, hold 0.7 min): RT 1.89 min, m/z (Calcd.) 1025.74, (found) 1026.55 (M+H); $^1H$ NMR (300 MHz, $CDCl_3$): δ 5.21 (m, 2H), 4.89 (brs, 1H), 4.34 (m, 4H), 4.13 (m, 4H), 2.27-2.37 (16H), 2.22 (s, 6H), 2.04 (brm, 2H), 1.80 (m, 2H), 1.59-1.74 (14H), 1.15-1.28 (40H), 0.85-0.96 (12H).

Example 4. Synthesis of LIPID 4: bis(1,3-bis(Octanoyloxy)propan-2-yl) 5-((4-(dimethylamino)butanoyl)thio)nonanedioate
LIPID 4
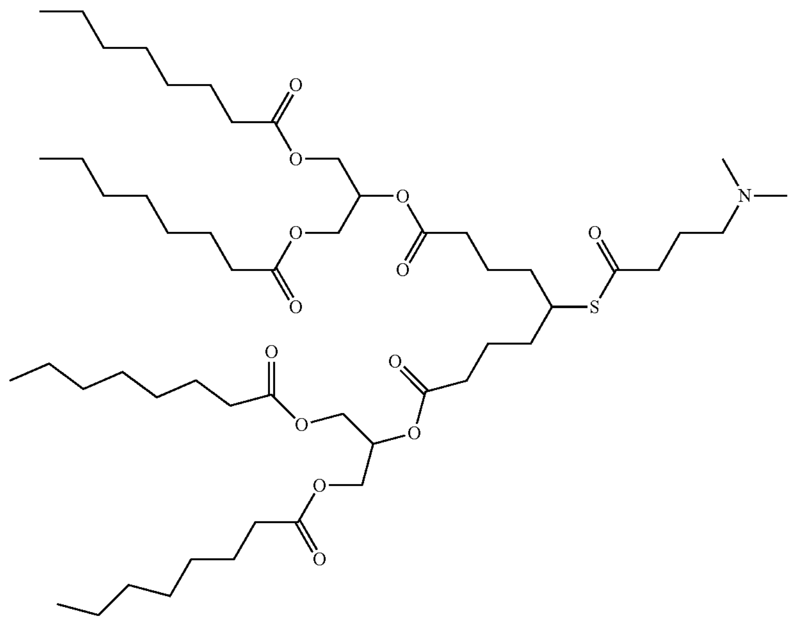
General Scheme
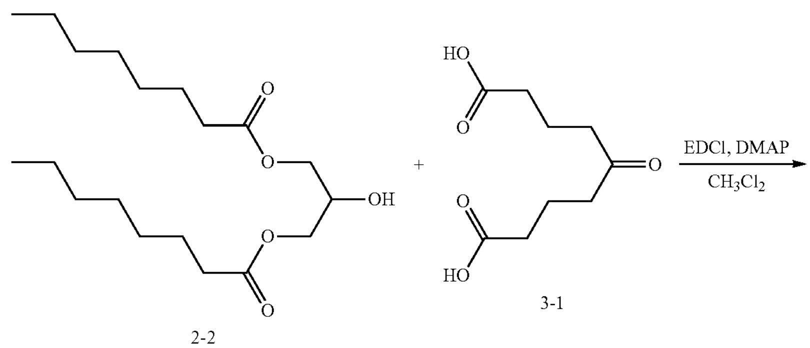
2-2
3-1

-continued
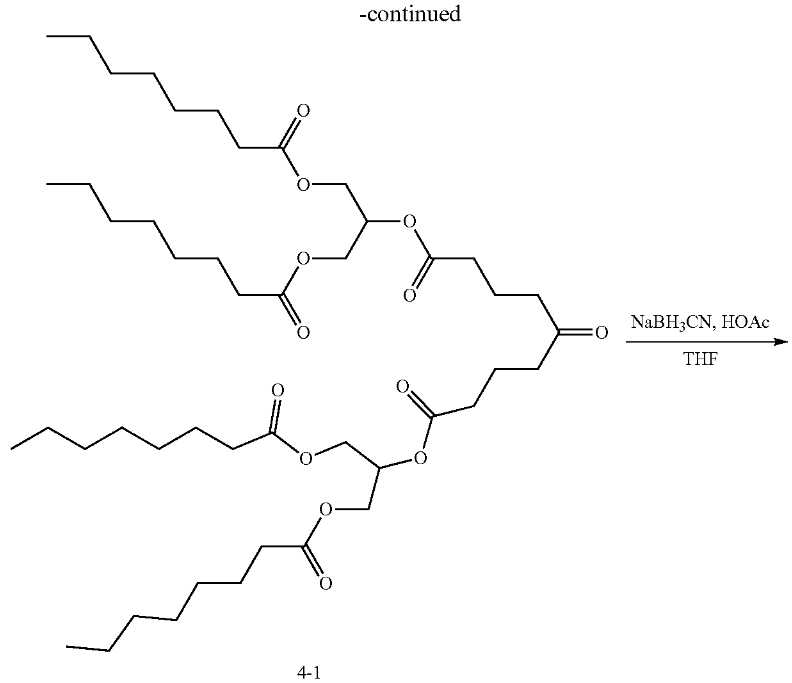
4-1
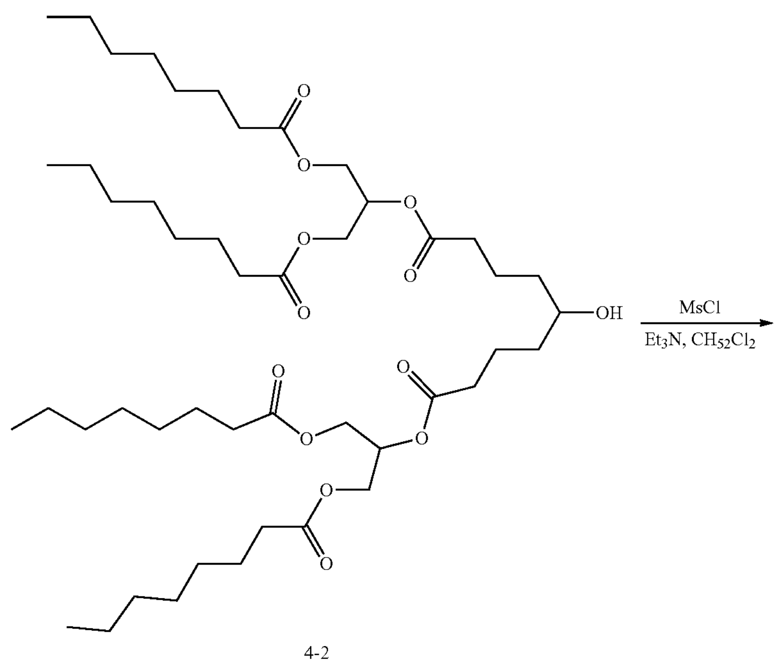
4-2

-continued
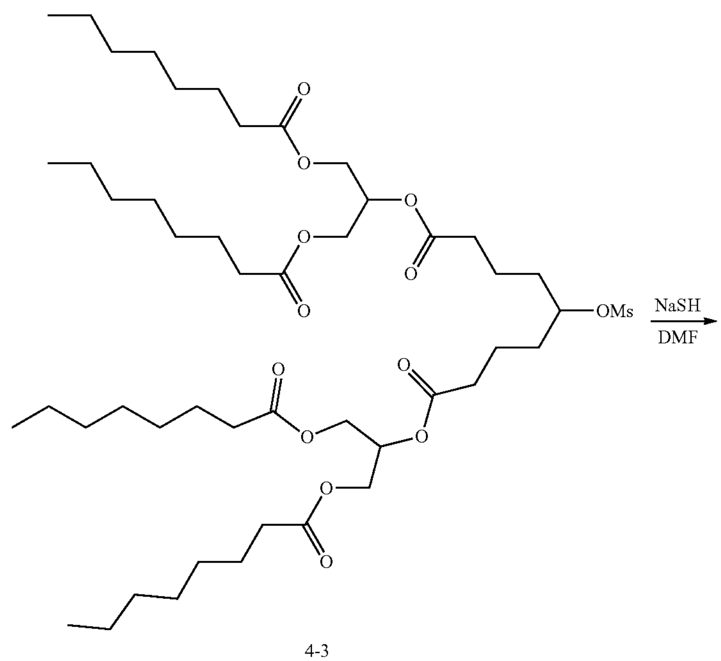
4-3
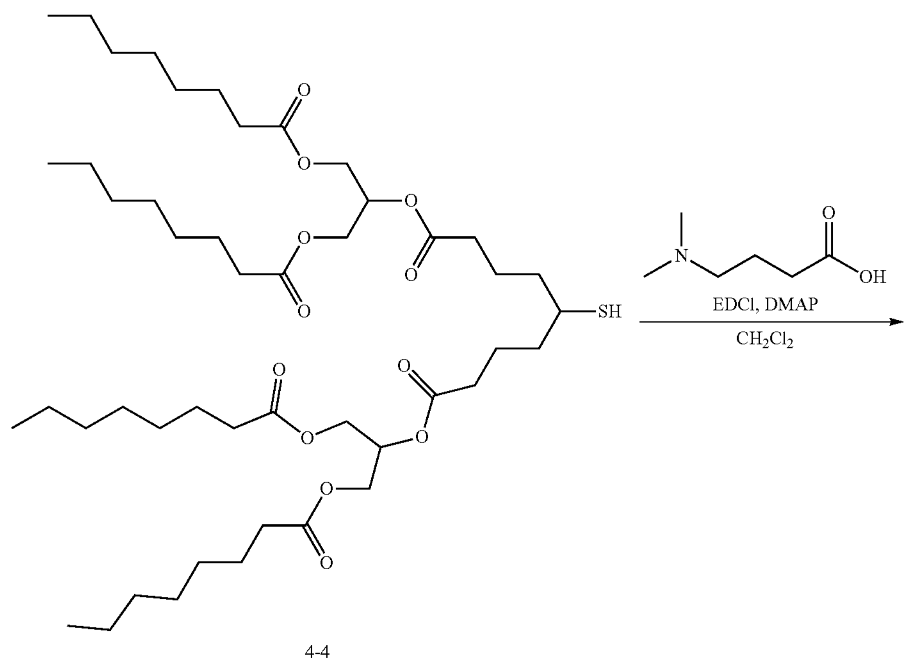
4-4

-continued

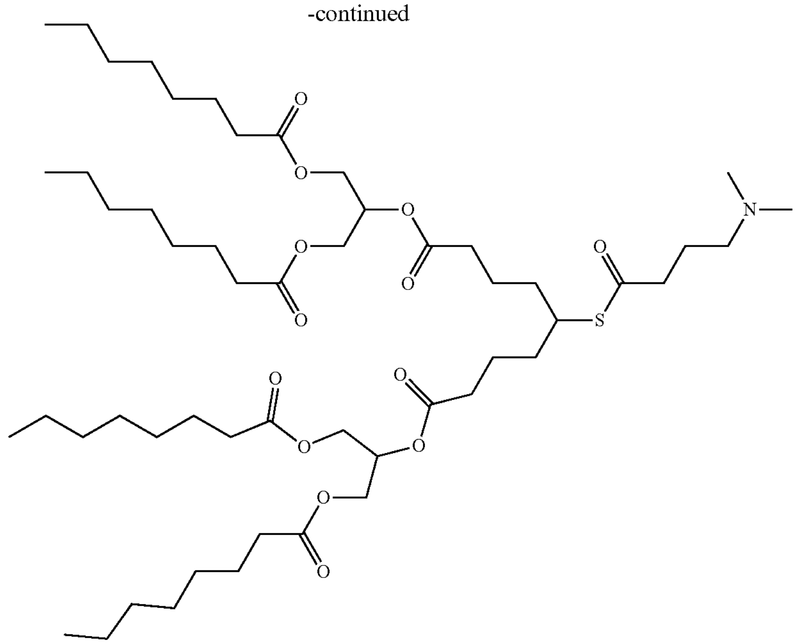

LIPID 4

Synthesis of 4-1: bis(1,3-bis(Octanoyloxy)propan-2-yl) 5-oxononanedioate

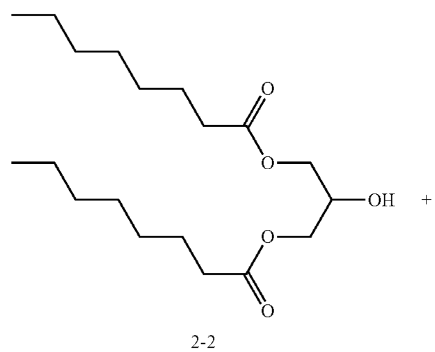

2-2

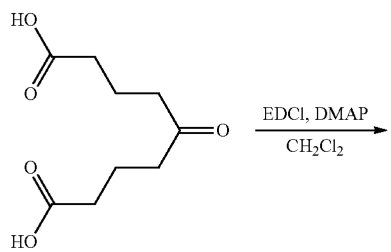

3-1

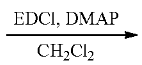

-continued

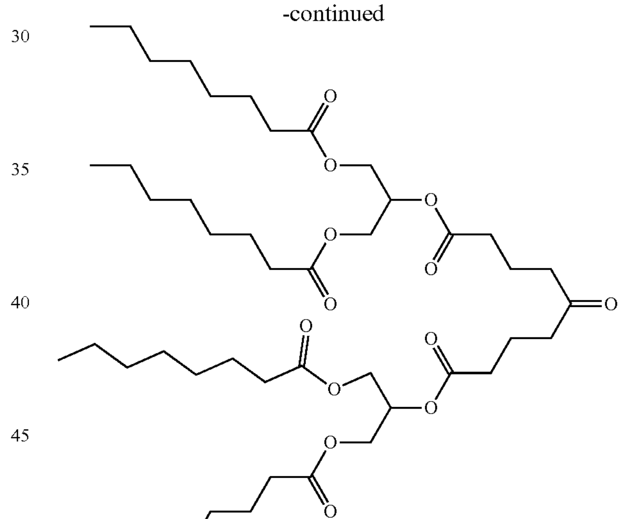

4-1

Into a 1-L 3-necked round-bottom flask, was placed 3-1 (20.0 g, 98.909 mmol, 1.00 equiv), 2-2 (68.2 g, 197.818 mmol, 2 equiv) and DMAP (36.3 g, 296.727 mmol, 3 equiv) in $CH_2Cl_2$ (600 mL), cooled in an ice-water bath under nitrogen. This was followed by the addition of EDCI (56.9 g, 296.727 mmol, 3 equiv) in several batches at 0° C. The resulting solution was stirred for 16 hours at room temperature. The reaction was then quenched by the addition of aqueous HCl (1 mol/L, 75 mL). The resulting solution was extracted with $CH_2Cl_2$ (200 mL). The combined organic phases were washed with brine (2×200 mL). The mixture was dried over anhydrous sodium sulfate and concentrated. The crude material dissolved in $CH_2Cl_2$ (200 mL) and was adsorbed on the silica gel (108 g, type: ZCX-2, 100-200 mesh) and purified on a silica gel column (720 g, type: ZCX-2, 100-200 mesh) with PE/EA gradient from 100:0 to 90:10. The fractions containing pure product was pooled and concentrated under vacuum to get 50 g (53.2%) 4-1 as a yellow oil. ELSD A: water/0.05% TFA: B: $CH_3CN$/0.05% TFA 95:5 to 5:95 A/B at 3 min., hold 0.7 min): RT 1.74 min, m/z 854.58 (Calcd.), (found) 877.75 (M+Na).

Synthesis of 4-2: bis(1,3-bis(Octanoyloxy)propan-2-yl) 5-hydroxynonanedioate

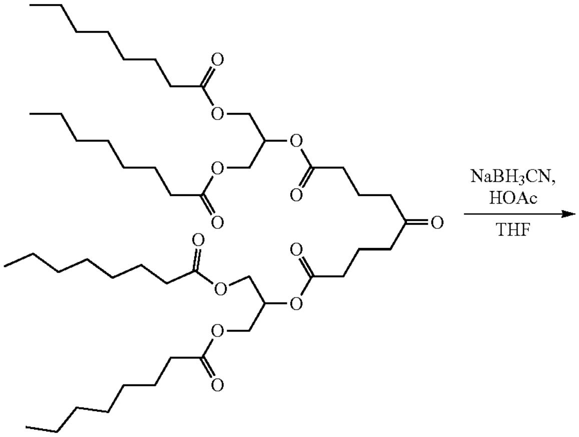

4-1

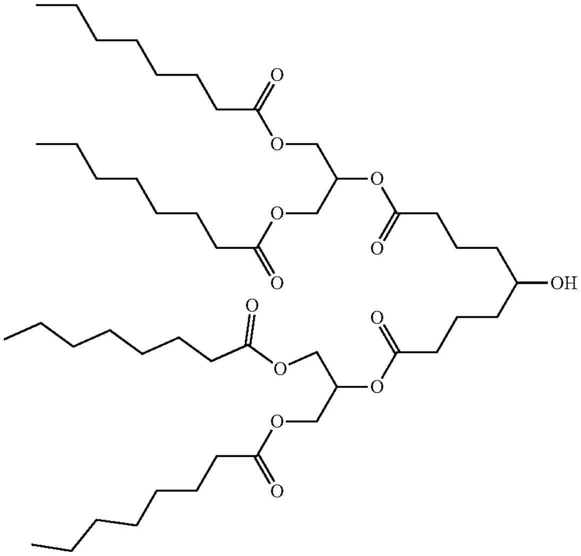

4-2

Into a 1-L 3-necked round-bottom flask, was placed 4-1 (50.0 g, 58.469 mmol, 1.00 equiv) in THF (500 mL). This solution was cooled in an ice-water bath under nitrogen and HOAc (35.1 g, 584.686 mmol, 10 equiv) was added at 0° C. To this was added $NaBH_3CN$ (36.7 g, 584.686 mmol, 10 equiv) in several portions at 0° C. The resulting solution was stirred for 3 hours at room temperature. The reaction was then quenched by the addition of water (200 ml). The resulting solution was extracted with dichloromethane (1000 ml), the organic phase was dried over anhydrous $Na_2SO_4$ and concentrated. The crude material was adsorbed on the silica gel (160 g, type: ZCX-2, 100-200 mesh) and purified on a silica gel column (400 g, type: ZCX-2, 100-200 mesh) with PE/EA gradient from 100:0 to 90:10. The fractions containing pure product was pooled and concentrated under vacuum to get 20 g (40%) 4-2 as a yellow oil. ELSD A: water/0.05% TFA: B: $CH_3CN$/0.05% TFA 95:5 to 5:95 A/B at 3 min., hold 0.7 min): RT 1.00 min, m/z 856.59 (Calcd.), (found) 879.70 (M+Na).

Synthesis of 4-3: bis(1,3-bis(Octanoyloxy)propan-2-yl) 5-((methylsulfonyl)oxy)nonanedioate

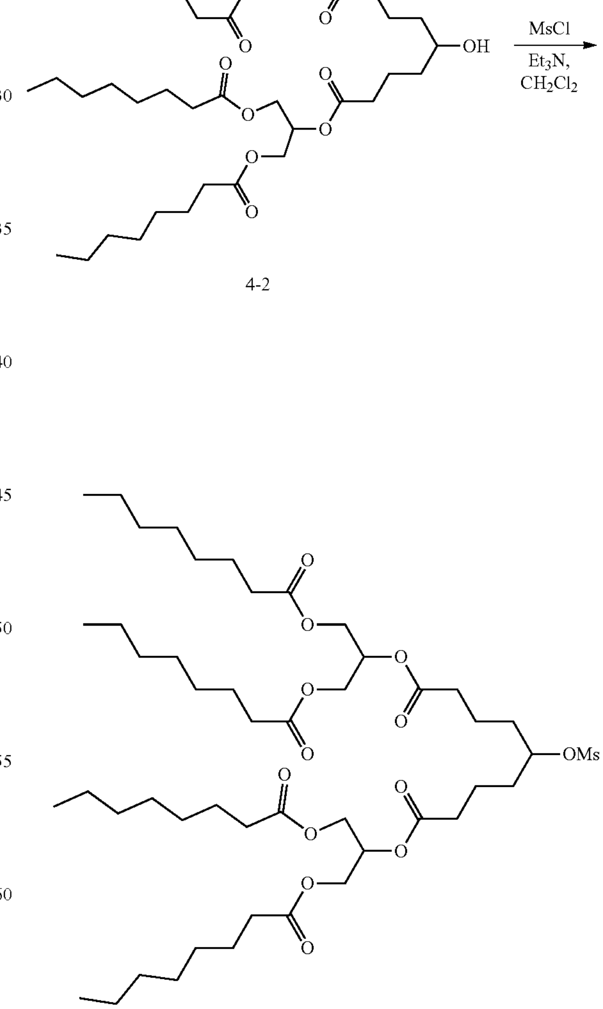

4-2

4-3

Into a 500-mL 3-necked round-bottom flask, was placed 4-2 (25.0 g, 29.166 mmol, 1.00 equiv) and $Et_3N$ (5.9 g, 58.331 mmol, 2 equiv) in $CH_2Cl_2$ (250 mL), cooled in an ice-water bath under nitrogen. This was followed by the addition of MsCl (5.0 g, 43.748 mmol, 1.5 equiv) dropwise with stirring at 0° C. over 20 min. The resulting solution was stirred for 3 hours at room temperature. The reaction was then quenched by the addition of water/ice (100 mL). The resulting solution was extracted with $CH_2Cl_2$ (2×100 mL). The combined organic phases were washed with brine (100 ml) and dried over $Na_2SO_4$. After concentration, this resulted in 24 g (crude) 4-3 as light-yellow oil that was used as such in the next reaction. ELSD A: water/0.05% TFA: B: $CH_3CN$/0.05% TFA 95:5 to 5:95 A/B at 2 min., hold 0.7 min): RT 1.71 min, m/z 934.57 (Calcd.), (found) 957.65 (M+Na).

Synthesis of 4-4: bis(1,3-bis(Octanoyloxy)propan-2-yl) 5-mercaptononanedioate

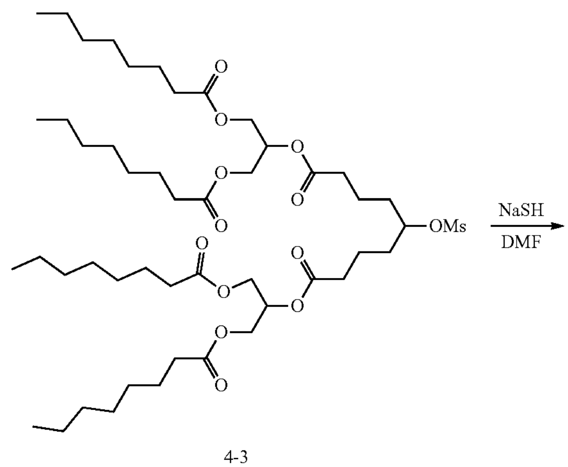

4-3

-continued

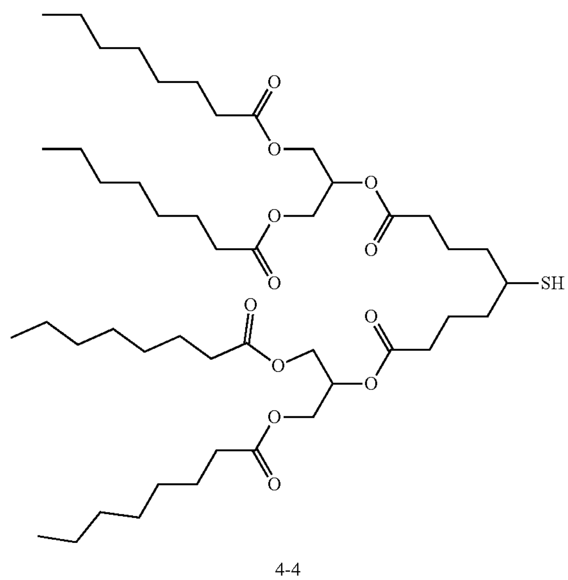

4-4

Into a 500-mL 3-necked round-bottom flask, was placed 4-3 (30.0 g, 32.077 mmol, 1.00 equiv) in DMF (300, 10 V), and the mixture was cooled in an ice-water bath under nitrogen. This was followed by the addition of NaSH (9.0 g, 160.383 mmol, 5.00 equiv) in three portions over 1.5 hours at 0° C. The resulting solution was stirred for 5 hours at room temperature. The reaction was then quenched by the addition of water/ice (100 mL). The mixture was extracted with EtOAc (3×100 mL). The combined organic phases were washed with brine (2×100 mL). The mixture was dried over anhydrous sodium sulfate and concentrated. This resulted in 10 g (crude) 4-4 as light-yellow oil. ELSD A: water/0.05% TFA: B: $CH_3CN$/0.05% TFA 95:5 to 5:95 A/B at 2 min., hold 0.7 min): RT 1.17 min, m/z 872.57 (Calcd.), (found) 895.70 (M+Na).

Synthesis of LIPID 4: bis(1,3-bis(Octanoyloxy) propan-2-yl) 5-((4-(dimethylamino)butanoyl)thio) nonanedioate

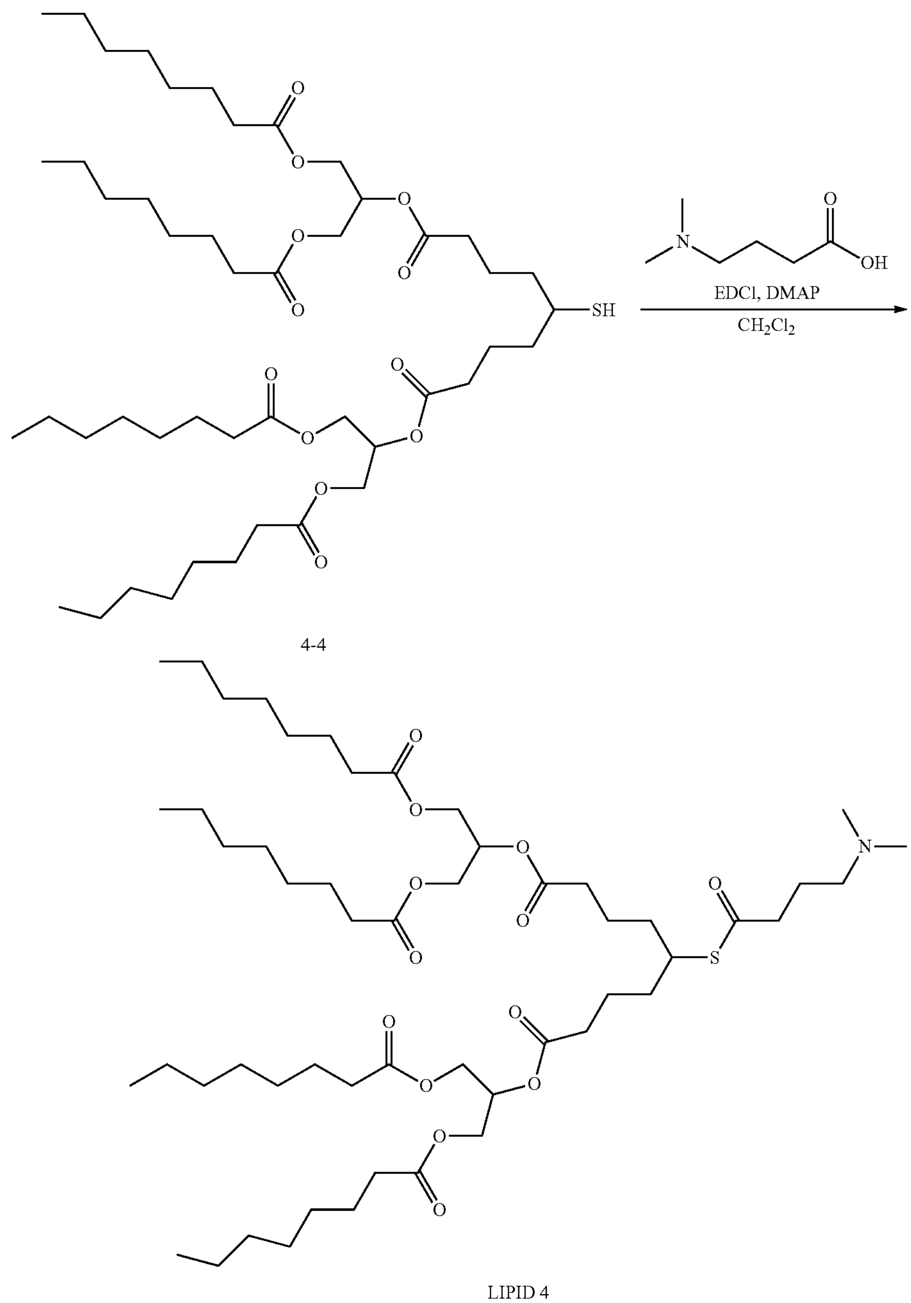

4-4

LIPID 4

Into a 250-mL 3-necked round-bottom flask, was placed 4-4 (12.0 g, 13.742 mmol, 1.00 equiv), 4-(dimethylamino) butanoic acid (2.2 g, 16.490 mmol, 1.2 equiv) and DMAP (2.0 g, 16.490 mmol, 1.2 equiv) in DCM (120 mL), and the solution was cooled in an ice-water bath under nitrogen. This was followed by the addition of EDCI (3.16 g, 16.490 mmol, 1.2 equiv) in several batches at 0° C. The resulting solution was stirred for 16 hours at room temperature. The reaction was then quenched by the addition of aqueous HCl (1 mol/L, 50 mL). The resulting solution was extracted with dichloromethane (2×100 mL). The combined organic phases were washed with brine (2×100 mL) and dried over anhydrous sodium sulfate and then concentrated. The crude material was adsorbed on the silica gel (25 g, type: ZCX-2, 100-200 mesh) and purified on a silica gel column (200 g, type: ZCX-2, 100-200 mesh) with $CH_2Cl_2$/MeOH gradient from 100:0 to 25:1. The fractions containing pure product was pooled and concentrated under vacuum to get 1.5 g (three steps yield of 6.5%) LIPID 4 as light-yellow oil. ELSD A: water/0.05% TFA: B: $CH_3CN$/0.05% TFA 95:5 to 5:95 A/B at 2 min., hold 0.7 min): RT 1.15 min, m/z 985.66 (Calcd.), (found) 986.55 (M+Na); $^1$H-NMR (400 MHZ, $CDCl_3$): δ 5.26 (m, 2H), 4.31 (m, 4H), 4.15 (m, 4H), 3.53 (brs, 1H), 2.61 (t, J=7.5 Hz, 2H), 2.39-2.28 (14H), 2.24 (s, 6H), 1.85 (m, 2H), 1.787-1.512 (16H), 1.34-1.29 (32H), 0.98-0.80 (12H).

Example 5. Synthesis of LIPID 5; bis(1,3-bis (Nonanoyloxy)propan-2-yl) 4-((4-(dimethylamino) butanoyl)oxy)heptanedioate
LIPID 5
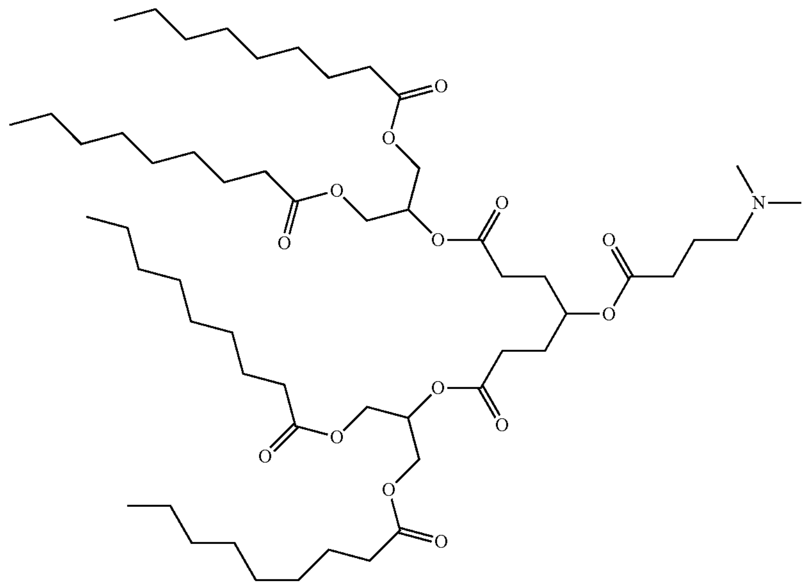
General Scheme
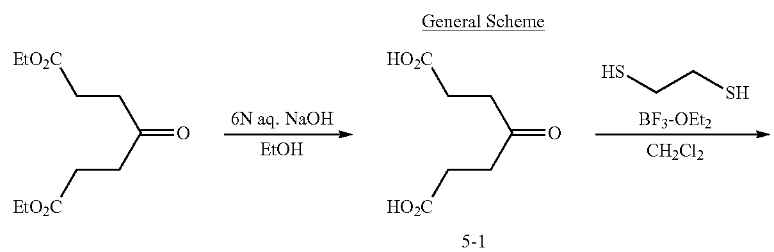
5-1
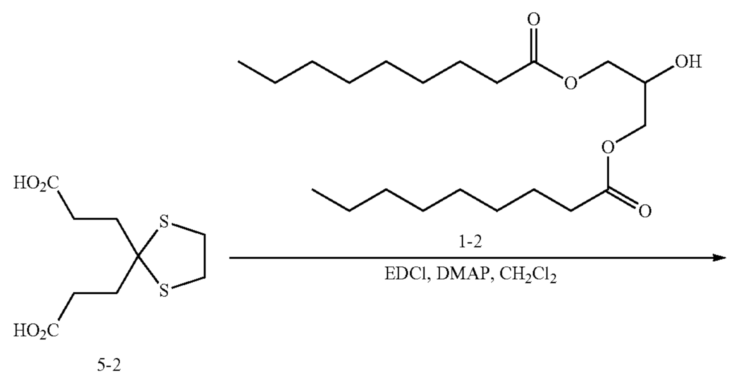
1-2
5-2

-continued
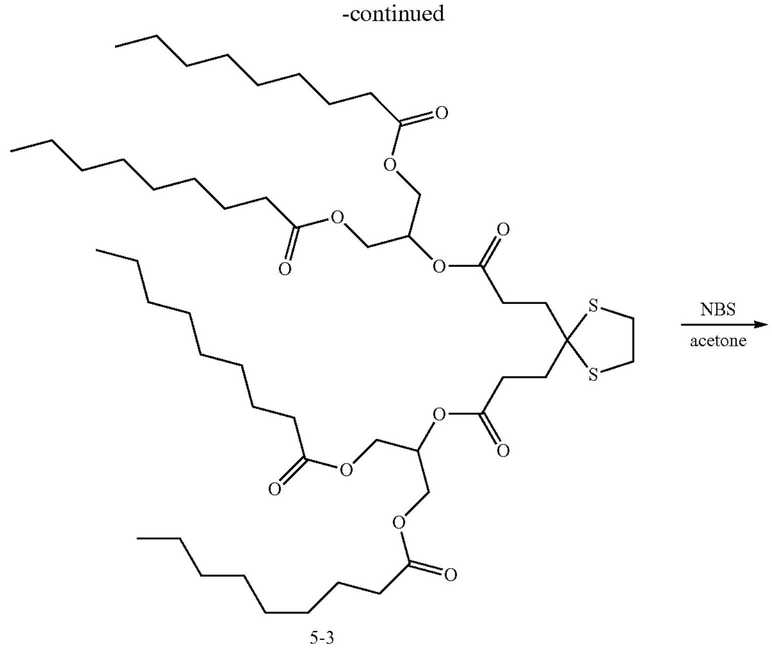
5-3
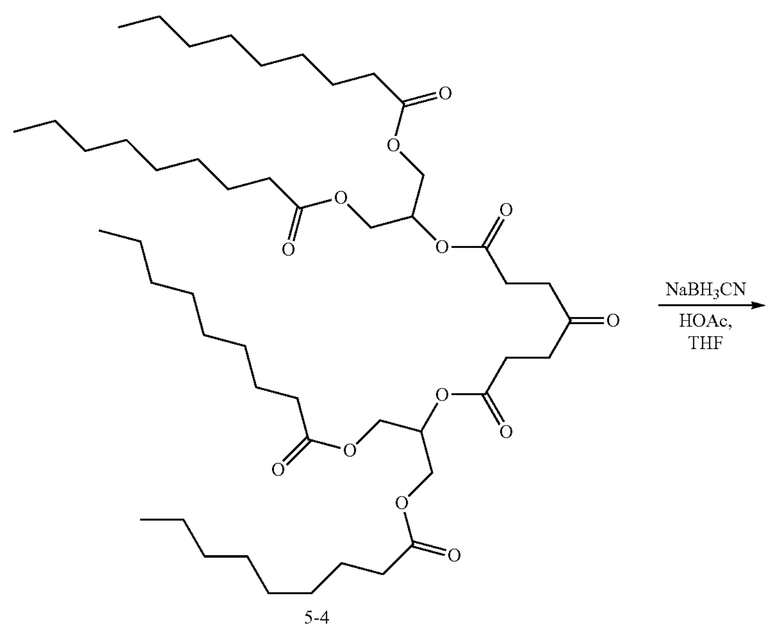
5-4

-continued

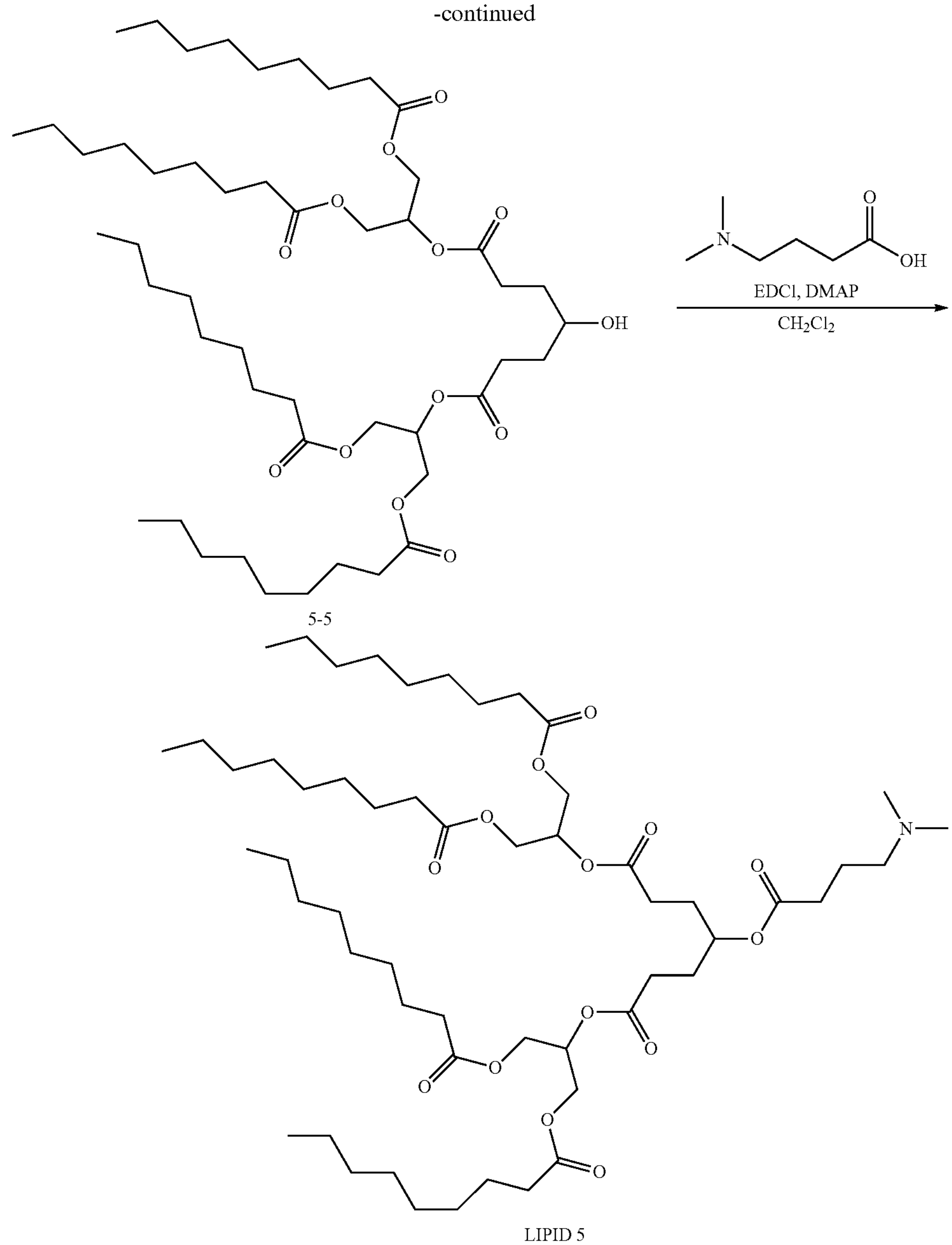

5-5

LIPID 5

Synthesis of 5-1: 4-Oxoheptanedioic Acid

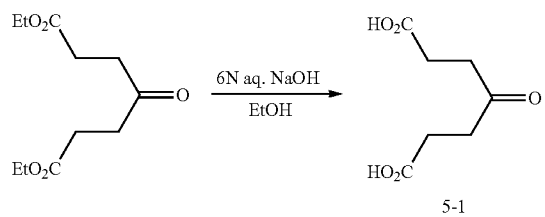 [SMILES: "EtOH" ; CCOC(=O)CCC(=O)CCC(=O)OCC ; O=C(O)CCC(=O)CCC(=O)O]

5-1

To a three-neck round-bottom flask was added EtOH (25 mL, 5 V) and diethyl-4-oxo-heptanesioate (5 g, 1 eq) at room temperature under nitrogen. The mixture was cooled in an ice-water bath, then aqueous sodium hydroxide (6N, 25 mL) was added slowly to the mixture at 0° C. The resulting solution was then warmed and stirred for 2 h at 60° C. After cooling to room temperature, brine (50 mL) and $CH_2Cl_2$ (50 mL) were added to the mixture and stirred for 10 minutes, then the aqueous phase was separated. The pH value of the aqueous phase was adjusted to 3~4 with 3 N HCl. The mixture was extracted with $CH_2Cl_2$ (100 mL). The organic phase was dried with anhydrous $MgSO_4$ and then filtered. Concentration under vacuum afforded 5-1 (3.2 g, 84.6% yield) as a light yellow solid. ELSD A: water/0.05% TFA: B: $CH_3CN$/0.05% TFA 95:5 to 5:95 A/B at 2 min., hold 0.7 min): RT 0.81 min, m/z 174.05 (Calcd.), (found) 197.06 (M+Na).

Synthesis of 5-2: 3,3'-(1,3-dithiolane-2,2-diyl)dipropionic Acid

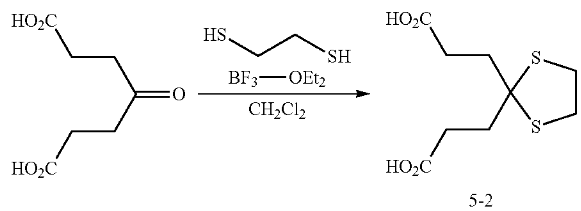

5-2

To a three-neck round-bottom flask was added $CH_2Cl_2$ (32 mL), 5-1 (3.2 g, 1 eq) and ethane-1,2-dithiol (2.1 g, 1.2 eq) one portion at room temperature. The mixture was cooled in an ice-water bath under nitrogen and $BF_3 \cdot Et_2O$ (6.48 g, 2.5 eq) was added slowly to the mixture at 0° C. The resulting solution was stirred for 16 h at 20° C. The solid was collected by filtration. The solid was dried under vacuum to afford the 5-2 (4 g, 88% yield) as light yellow solid. ELSD A: water/0.05% TFA: B: $CH_3CN$/0.05% TFA 95:5 to 5:95 A/B at 2 min., hold 0.7 min): RT 0.20 min, m/z 250.03 (Calcd.), (found) 268.2 (M+Na).

Synthesis of 5-3: ((3,3'-(1,3-Dithiolane-2,2-diyl)bis(propanoyl))bis(oxy))bis(propane-2,1,3-triyl) tetranonanoate

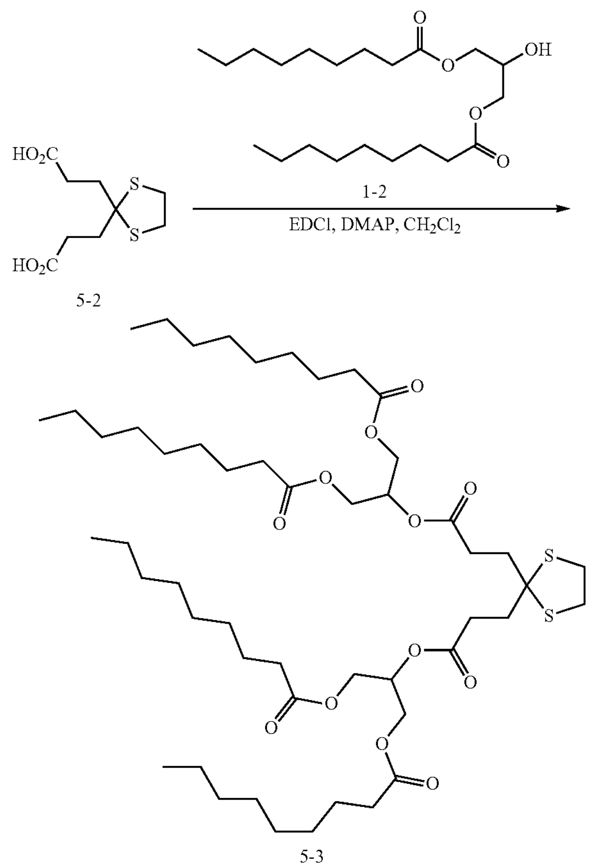

5-2

5-3

To a three-neck round-bottom flask was added $CH_2Cl_2$ (100 mL), 5-2 (5 g, 1.0 eq), 1-2 (16.37 g, 2.2 eq) and DMAP (2.44 g, 1 eq) successively. The mixture was cooled in an ice-water bath under nitrogen, then EDCI (8.42 g, 2.2 eq) was added to the reaction mixture at 0° C. in portions. The resulting solution was stirred for 16 h at 20° C. The reaction system was quenched with 10% aq. citric acid (50 mL). The organic phase was separated, washed with 10% aq. citric acid (50 mL), brine (50 mL), and dried with anhydrous $MgSO_4$ and then filtered. Concentration under vacuum provided crude 5-3 which was dissolved in $CH_2Cl_2$ (50 mL) and the solution was adsorbed on silica gel (50 g, type: ZCX-2, 100-200 mesh) and purified on a silica gel column (200 g, type: ZCX-2, 100-200 mesh) with PE/EA gradient from 100:0 to 98:2. The fractions containing pure product was pooled and concentrated under vacuum to give 5-3 (16.1 g, 84% yield) as a colorless oil. (Due to poor ionization no mass was observed. Hence, without further characterization the molecule was used in the next step).

Synthesis of 5-4: bis(1,3-bis(Nonanoyloxy)propan-2-yl) 4-oxoheptanedioate

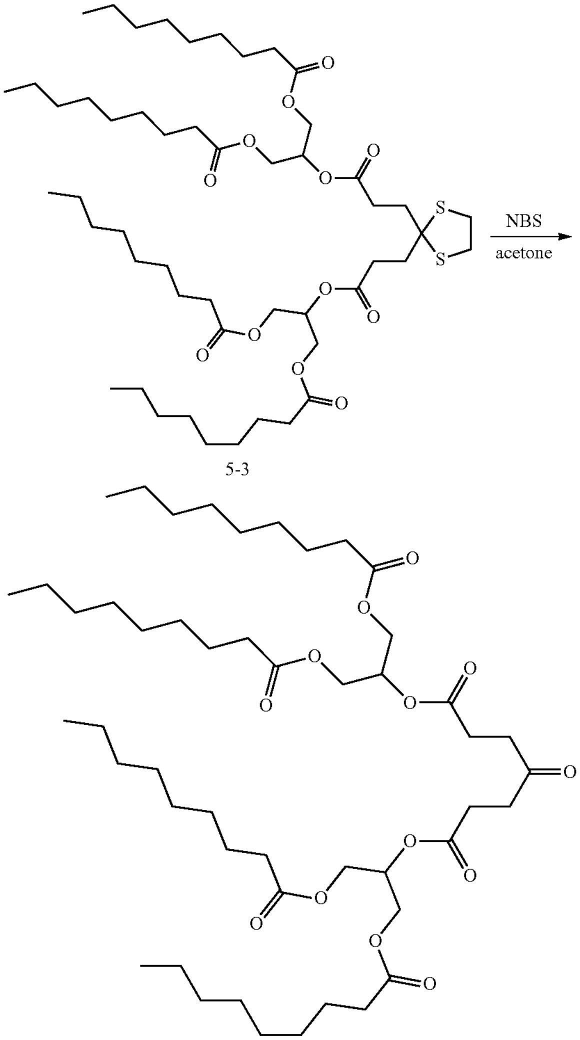

5-3

5-4

To a three-neck round-bottom flask was added acetone (400 mL) and 5-3 (16 g, 1.0 eq) and the solution was cooled to −20° C. under nitrogen. NBS (11.87 g, 4 eq) in acetone (80 mL) was added dropwise to the reaction mixture at −20° C. over a period of 15 mins. The resulting solution was stirred for 1 h at −20° C. The reaction was quenched with $H_2O$ (320 mL) and warmed to room temperature. Acetone was removed by concentration under vacuum and the mixture was extracted with EtOAc (160 mL). The organic phase was dried over $Na_2SO_4$, filtered and the solvent was removed under reduced pressure. The crude material was dissolved in $CH_2Cl_2$ (75 mL), and was adsorbed on silica gel (30 g, type: ZCX-2, 100-200 mesh) and purified on a silica gel column (200 g, type: ZCX-2, 100-200 mesh) with PE/EA gradient from 100:0 to 97:3. The fractions containing pure product was pooled and concentrated under vacuum to get 5-4 (10.3 g, 70% yield) as a colorless oil. $^1H$ NMR (300 MHZ, $CDCl_3$) δ 5.23 (q, J=5.0 Hz, 2H), 4.30 (dd, J=11.9, 4.4 Hz, 4H), 4.16 (dd, J=12.0, 5.7 Hz, 4H), 2.78 (t, J=6.5 Hz, 4H), 2.63 (t, J=6.6 Hz, 4H), 2.33 (t, J=7.5 Hz, 8H), 1.67-1.53 (10H), 1.37-1.24 (38H), 0.94-0.84 (m, 12H).

Synthesis of 5-5: bis(1,3-bis(Nonanoyloxy)propan-2-yl) 4-hydroxyheptanedioate

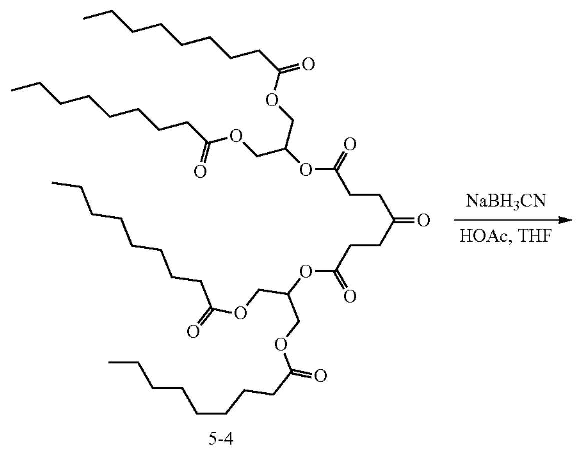

5-4

-continued

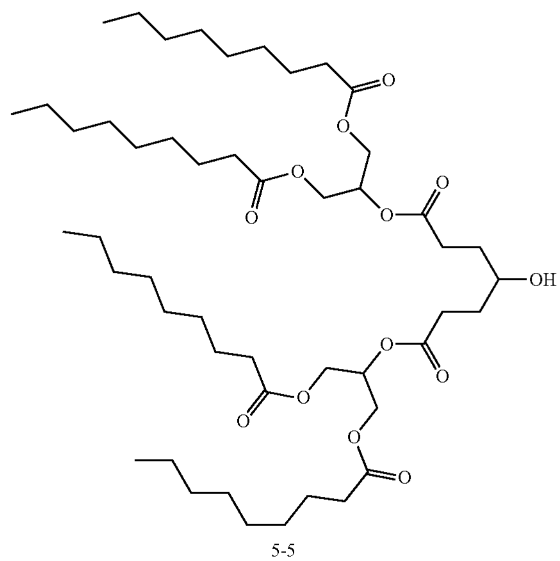

5-5

Into a 500-mL 4-necked round-bottom flask purged and maintained with an inert atmosphere of nitrogen, was placed 5-4 (10.3 g, 1 eq) and THF (100 mL). To this was added AcOH (7.0 g, 10 eq) and the solution was cooled in an ice-water bath. This was followed by the addition of $NaBH_3CN$ (7.32 g, 10 eq) in several batches at 0° C. The resulting solution was stirred for 18 hr at 25° C. The reaction system was quenched with $H_2O$ (400 mL). The mixture was extracted with EtOAc (100 mL), the organic phase ws separated, dried over $Na_2SO_4$, filtered, and concentrated under vacuum. Crude 5-5 was dissolved in $CH_2Cl_2$ and was adsorbed on silica gel (30 g, type: ZCX-2, 100-200 mesh) and purified on a silica gel column (150 g, type: ZCX-2, 100-200 mesh) with PE/EA gradient from 100:0 to 95:5. The fractions containing pure product was pooled and concentrated under vacuum to get 5-5 (6 g, 70% yield) as a colorless oil. ELSD A: water/0.05% TFA: B: $CH_3CN$/0.05% TFA 95:5 to 5:95 A/B at 5 min., hold 0.7 min): RT 3.48 min, m/z 884.62 (Calcd.), (found) 907.35 (M+Na).

Synthesis of LIPID 5: bis(1,3-bis(Nonanoyloxy) propan-2-yl) 4-((4-(dimethylamino)butanoyl)oxy) heptanedioate

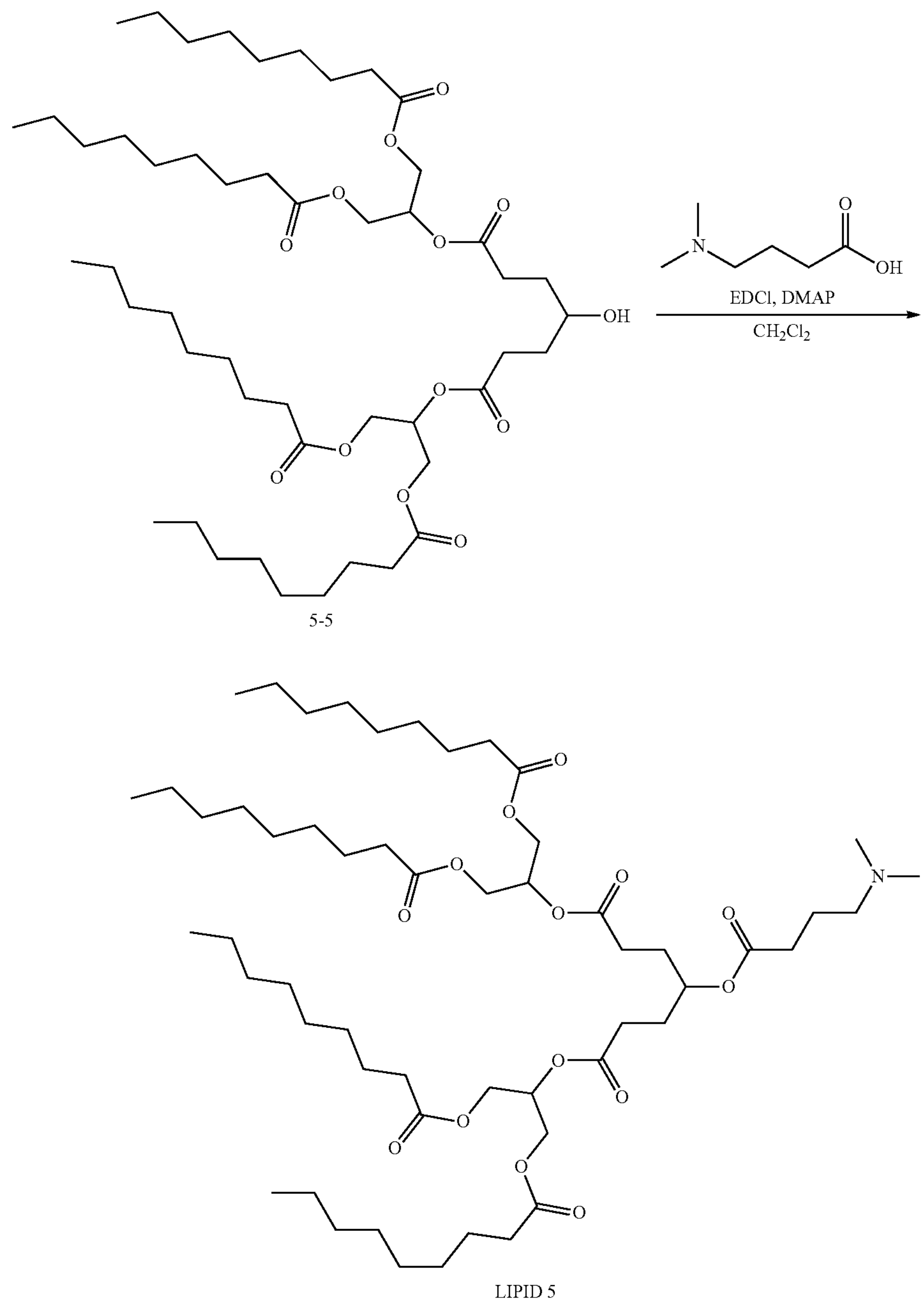

5-5

LIPID 5

To a three-neck round-bottom flask was added 5-5 (4 g, 1 eq), 4-(dimethylamino) butanoic acid (0.99 g, 1.3 eq), DMAP (0.39 g, 0.7 eq), $CH_2Cl_2$ (60 mL) successively. The mixture was cooled in an ice-water bath under nitrogen, then EDCI (1.21 g, 1.4 eq) was added to the reaction mixture at 0° C. with portions. The resulting solution was stirred for 16 h at 20° C. The reaction system was quenched with 10% aq. citric acid solution (40 mL). The organic phase separated, washed with 10% aq. citric acid solution (40 mL), brine (40 mL), dried with anhydrous $MgSO_4$ and then filtered. The solvent was removed under vacuum and the residue ws dissolved in $CH_2Cl_2$ (25 mL), the crude material was adsorbed on silica gel (10 g, type: ZCX-2, 100-200 mesh) and purified on a silica gel column (50 g, type: ZCX-2, 100-200 mesh) with $CH_2Cl_2$/MeOH gradient from 100:0 to 80:1. The fractions containing pure product was pooled and concentrated under vacuum to to afford 5 (1.2 g, 27% yield) as a light-yellow oil. ELSD A: water/0.05% TFA: B: $CH_3CN$/0.05% TFA 95:5 to 5:95 A/B at 2 min, hold 0.7 min): RT 1.82 min, m/z 997.71 (Calcd.), (found) 998.56 (M+H); $^1$H-NMR (300 MHz, $CDCl_3$): δ 5.24 (m, 2H), 4.96 (dd, J=8.1, 4.2 Hz, 1H), 4.30 (m, 4H), 4.15 (m, 4H), 2.41-2.25 (20H), 1.80-1.92 (6H), 1.67-1.54 (10H), 1.02-1.49 (40H), 0.94-0.84 (12H).

Example 6. Synthesis of LIPID 6a
LIPID 6a
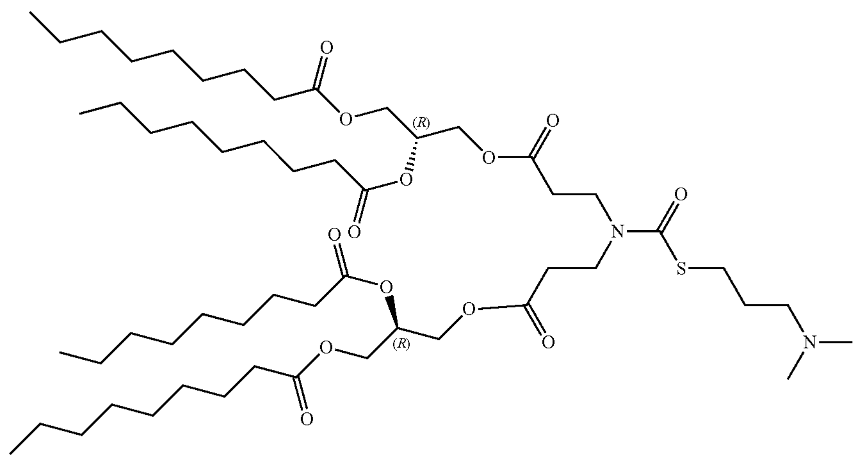
General Scheme:
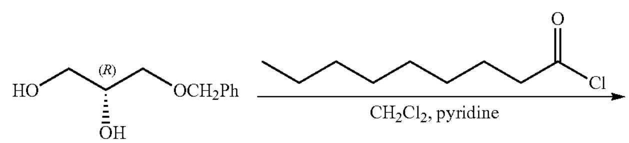
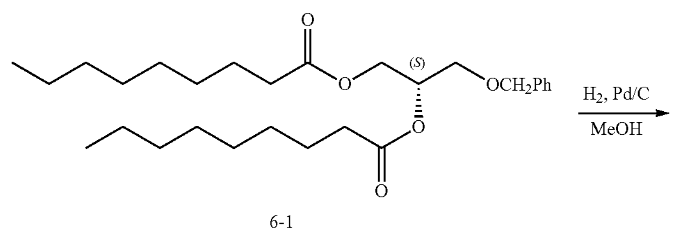
6-1
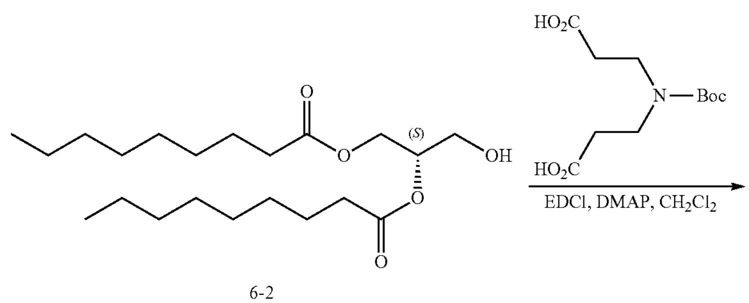
6-2

-continued
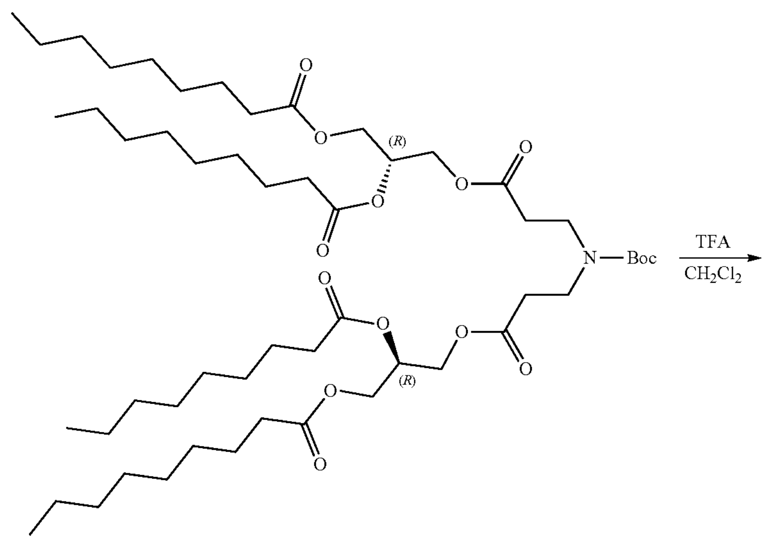
6-3
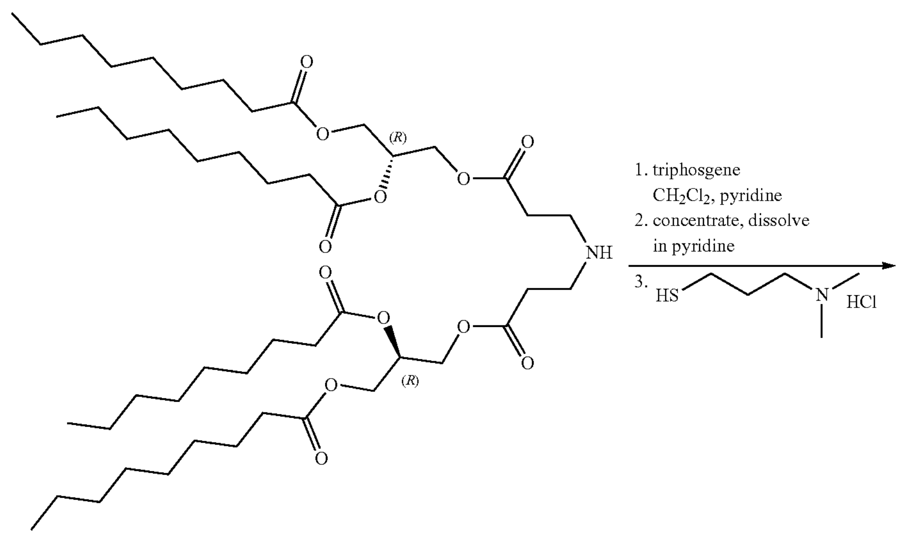
6-4

-continued

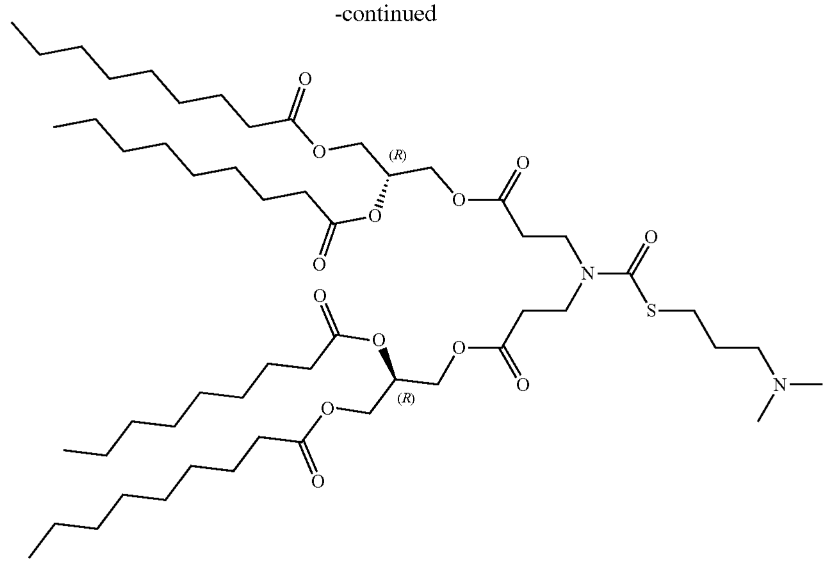

LIPID 6a

Synthesis of 6-1: (S)-3-(benzyloxy)propane-1,2-diyl dinonanoate

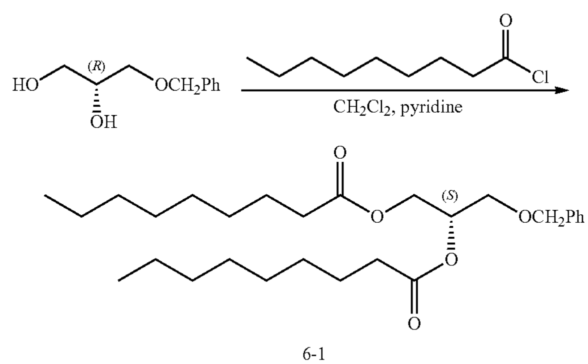

6-1

To a three-neck flask was added $CH_2Cl_2$ (60 mL), (R)-3-(benzyloxy)propane-1,2-diol (3 g, 1 eq), nonanoyl chloride (6.4 g, 2.2 eq) as one portion at room temperature, the mixture was cooled in an ice-water bath under nitrogen. Pyridine (3.90 g, 3 eq) was added to the reaction mixture at 0° C. over a period of 10 minutes. The resulting solution was stirred for 16 h at 20° C. The reaction was then quenched by the addition of 30 mL of water and was stirred 10 min. The organic phase was separated. The aqueous layer was extracted with $CH_2Cl_2$ (75 mL). The combined organic layers were dried over anhydrous sodium sulfate then filtered. Concentration in vacuum provided crude 6-1 which was dissolved in $CH_2Cl_2$ (50 mL) which was adsorbed on 20 g of silica gel (type: ZCX-2, 100-200 mesh, 6.43 w./w.), and purified on a silica gel column (100 g of silica gel, type: ZCX-2, 100-200 mesh, 32.14 w./w.) using petroleum ether/EtOAc gradient from 100:0 to 50:1. Fractions containing pure products were analyzed, pooled, combined and concentrated under reduced pressure to afford the 6-1 (6.0 g, 80% yield) as a colorless oil. ELSD A: water/0.05% TFA: B: $CH_3CN$/0.05% TFA 95:5 to 5:95 A/B at 2 min., hold 0.7 min): RT 1.1 min, m/z (Calcd.) 462.33, (found) 485.2 (M+Na).

Synthesis of 6-2: (S)-3-hydroxypropane-1,2-diyl dinonanoate

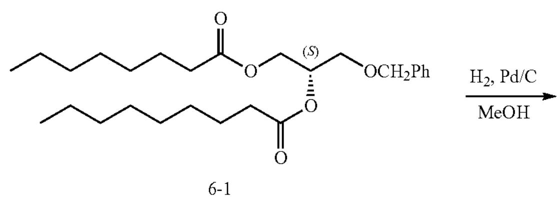

6-1

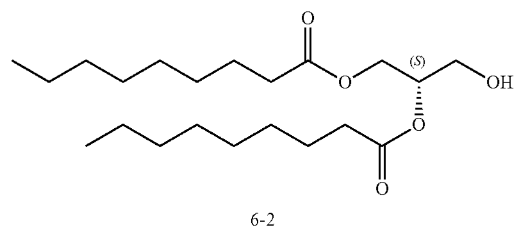

6-2

To a three-neck flask was added MeOH (60 mL), 6-1 (6 g, 1 eq), Pd/C (0.6 g, 10% wt) under nitrogen atmosphere at room temperature. The flask was evacuated and flushed three times with hydrogen. The mixture was stirred 16 h at room temperature under an atmosphere of hydrogen (balloon). Filtered and the filtrate was concentrated to dryness under vacuum to afford 6-2 (3.1 g, 64% yield) as colorless oil. ELSD A: water/0.05% TFA: B: $CH_3CN$/0.05% TFA 95:5 to 5:95 A/B at 2 min., hold 0.7 min): RT 0.89 min, m/z (Calcd.) 3722.29, (found) 395.3 (M+Na).

Synthesis of 6-3: (2R,2'R)-((3,3'-((tert-Butoxycarbonyl)azanediyl)bis(propanoyl))bis(oxy))bis(propane-3,1,2-triyl) tetranonanoate

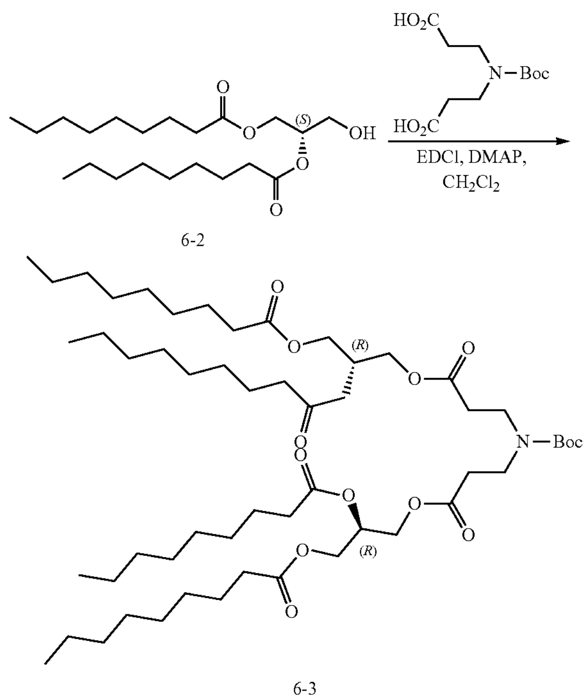

To a three-neck round-bottom flask was added $CH_2Cl_2$ (20 mL), 3,3'-((tert-butoxycarbonyl)azanediyl)dipropionic acid (commercially available, 1 g, 1.0 eq), 6-2 (3.10 g, 2.2 eq) and DMAP (0.47 g, 1 eq) successively, the mixture was cooled in an ice-water bath under nitrogen. EDCI (1.60 g, 2.2 eq) was added to the reaction mixture at 0° C. in portions over 10 minutes. The resulting solution was stirred for 16 h at 20° C. and the reaction was quenched with 10% aq. citric acid solution (10 mL). The organic phase was separated and washed with 10% aq. citric acid solution (10 mL), brine (10 mL), and dried with anhydrous $MgSO_4$ and then filtered. Concentration under vacuum gave crude 6-3 which was dissolved in $CH_2Cl_2$ (10 mL) and adsorbed on 5 g of silica gel (type: ZCX-2, 100-200 mesh, 6.43 w./w.), and purified on a silica gel column (25 g of silica gel, type: ZCX-2, 100-200 mesh, 32.14 w./w.) using petroleum ether/EtOAc gradient from 100:0 to 50:1. Fractions containing pure products were analyzed, pooled, combined and concentrated under reduced pressure to afford the 6-3 (3 g, 81% yield) as a yellow oil. ELSD A: water/0.05% TFA: B: $CH_3CN$/0.05% TFA 95:5 to 5:95 A/B at 3 min., hold 0.7 min): RT 2.35 min, m/z (Calcd.) 969.68, (found) 992.5 (M+Na).

Synthesis of 6-4: (2R,2'R)-((3,3'-Azanediylbis(propanoyl))bis(oxy))bis(propane-3,1,2-triyl) tetranonanoate

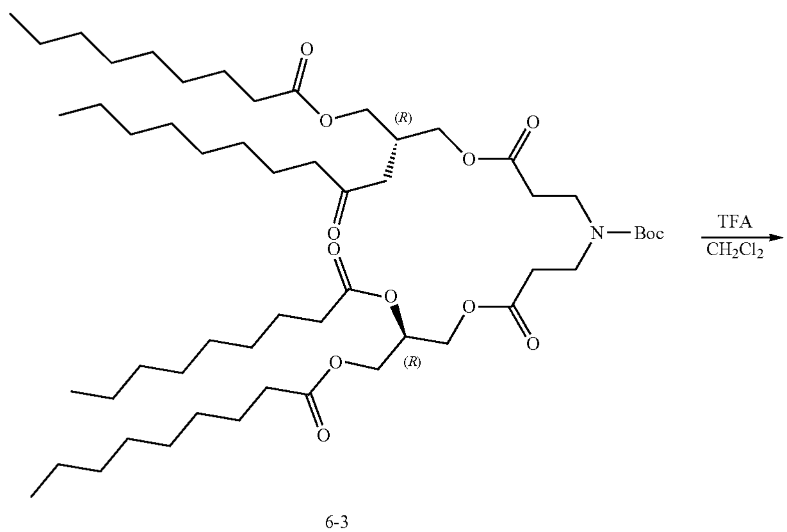

6-3

-continued

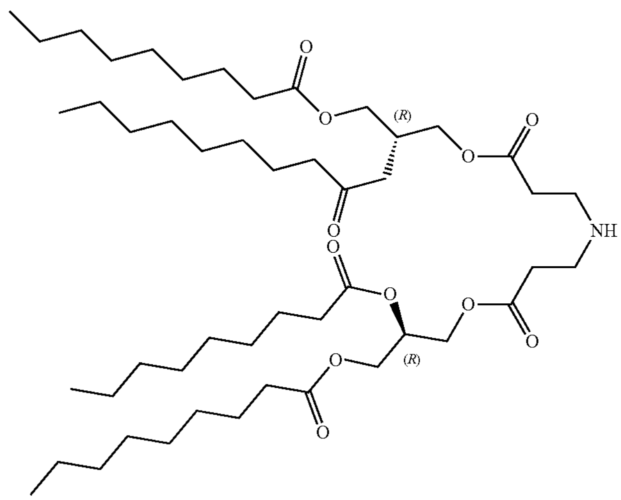

6-4

To a three-neck flask was added $CH_2Cl_2$ (60 mL), 6-3 (3 g, 1 eq) as one portion at room temperature, the mixture was cooled in an ice-water bath under nitrogen, then TFA (4.5 ml) was added slowly the reaction mixture at 0~5° C. The reaction mixture was stirred for 2 h at 25° C. The reaction was then quenched by the addition of 5% aq. sodium carbonate solution (10 wt. %, 30 mL). The organic phase was separated. The organic phase was washed with brine (2×30 mL), dried with anhydrous $MgSO_4$, and then filtered and concentrated to dryness under vacuum to afford the 6-4 (2.5 g, 94% yield) as a yellow oil. ELSD A: water/0.05% TFA: B: $CH_3CN$/0.05% TFA 95:5 to 5:95 A/B at 3 min., hold 0.7 min): RT 0.87 min, m/z (Calcd.) 869.62, (found) 892.40 (M+Na).

Synthesis of LIPID 6a

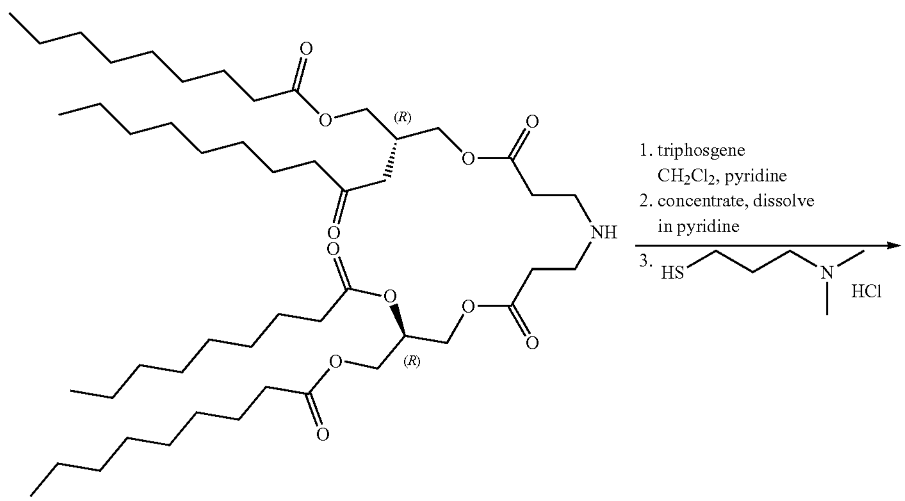

6-4

-continued

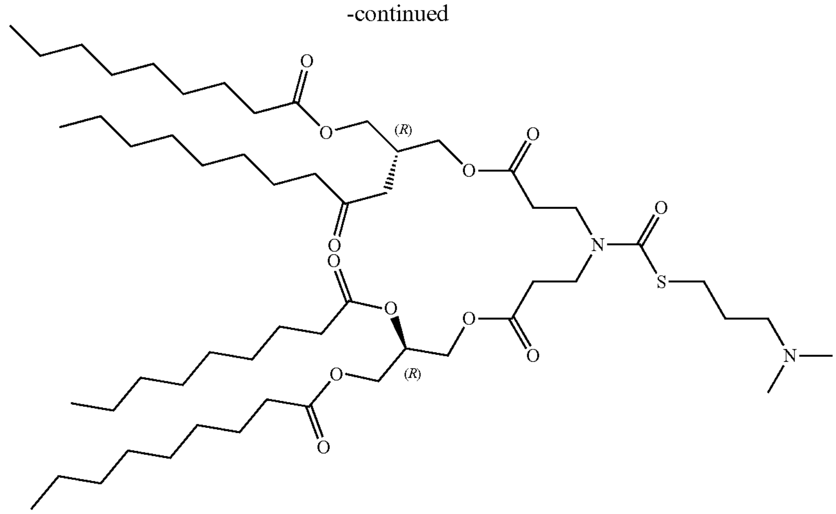

LIPID 6a

To a three-neck flask was added $CH_2Cl_2$ (50 mL, 20 V), 6-4 (2.50 g, 1 eq) as one portion at room temperature, the mixture was then cooled in an ice-water bath under nitrogen and then triphosgene (0.85 g, 1 eq) was added to the reaction mixture at 0~5° C. in portions. Pyridine (1.13 g, 5 eq) was added slowly the reaction mixture over 2±0.5 hours. After addition, the reaction mixture was stirred for 2 h at room temperature. Solvent was evaporated under reduced pressure and the residue was dissolved in anhydrous pyridine (50 ml, 20 V) and cooled in an ice bath under nitrogen. To this was added 3-(dimethylamino)-1-propanethiol hydrochloride (0.41 g, 1.2 eq) at 0° C. After addition, the above mixture was stirred for 18 h at room temperature. The solvent was removed by rotary evaporation under vacuum. The mixture was diluted with $CH_2Cl_2$ (50 mL). The organic phase was washed with 10% aq. citric acid solution (3×25 mL). The organic phase was dried with anhydrous $MgSO_4$ and then filtered. Concentration under vacuum gave crude LIPID 6a which was adsorbed on 10 g of silica gel (type: ZCX-2, 100-200 mesh, 6.43 w./w.), and purified on a silica gel column (50 g of silica gel, type: ZCX-2, 100-200 mesh, 32.14 w./w.) using $CH_2Cl_2$/MeOH gradient from 100:0 to 98:2. Fractions containing pure products were analyzed, pooled, combined and concentrated under reduced pressure to afford 6 (1.2 g, 41% yield) as a yellow oil. ELSD A: water/0.05% TFA: B: $CH_3CN$/0.05% TFA 95:5 to 5:95 A/B at 2 min., hold 0.7 min): RT 1.1 min, m/z (Calcd.) 1014.68, (found) 1015.68 (M+H); $^1$H NMR (300 MHz, $CDCl_3$) δ 5.26 (m, 2H), 4.31 (m, 4H), 4.15 (m, 4H), 3.65 (t, J=7.2 Hz, 4H), 2.93 (t, J=7.3 Hz, 2H), 2.65 (t, J=7.1 Hz, 4H), 2.50-2.19 (16H), 1.52-1.70 (10H), 1.36-1.23 (40H), 0.93-0.83 (12H).

Example 7. Synthesis of LIPID 7: bis(1,3-bis(Octanoyloxy)propan-2-yl) 4-((4-(dimethylamino)butanoyl)thio)heptanedioate

LIPID 7

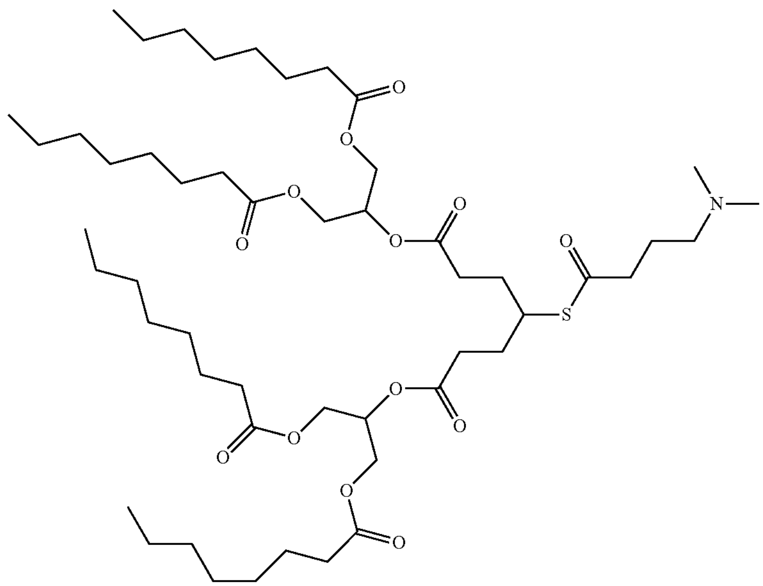

General Scheme:
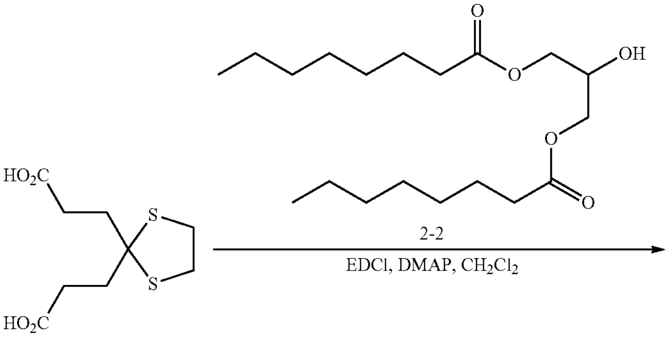
5-2
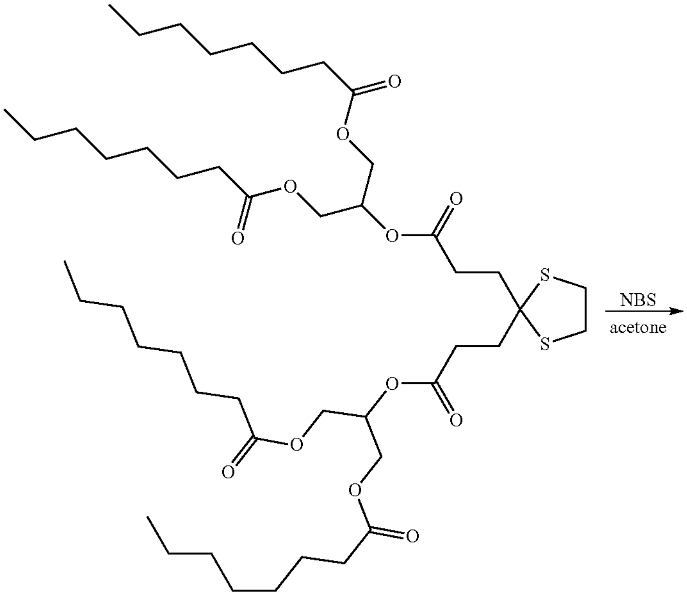
7-1
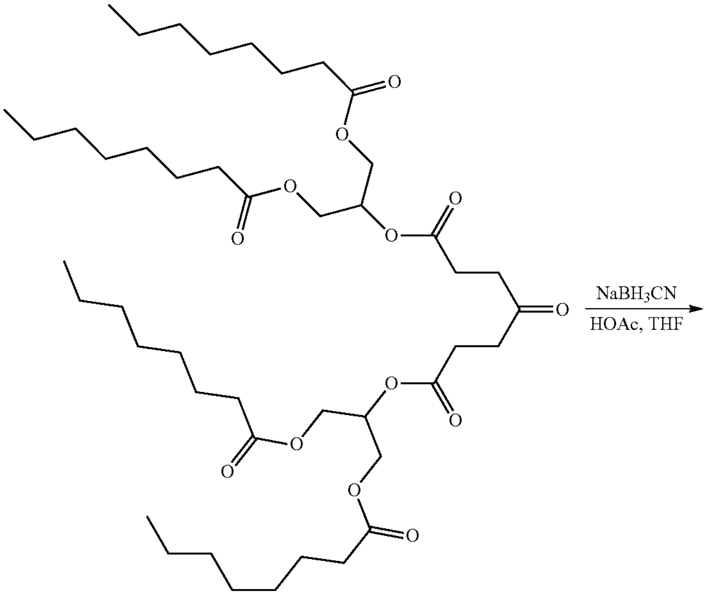
7-2

-continued
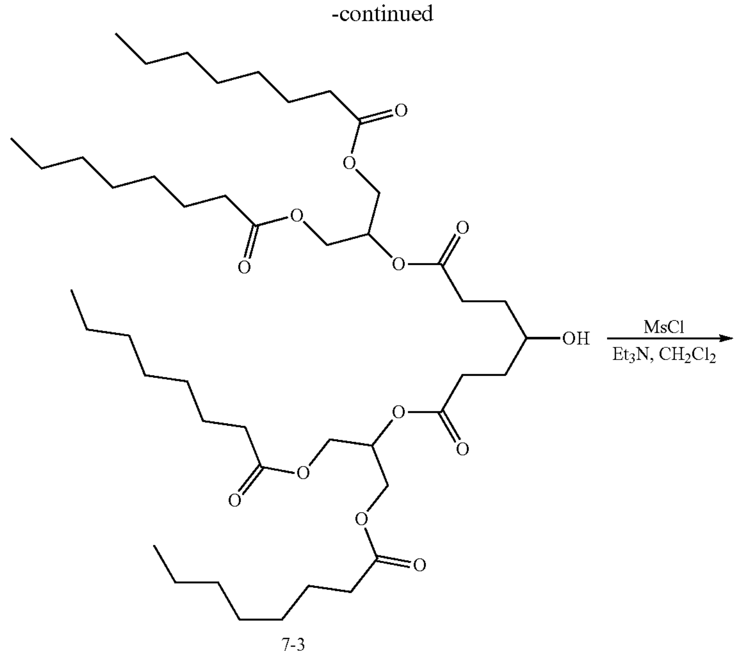
7-3
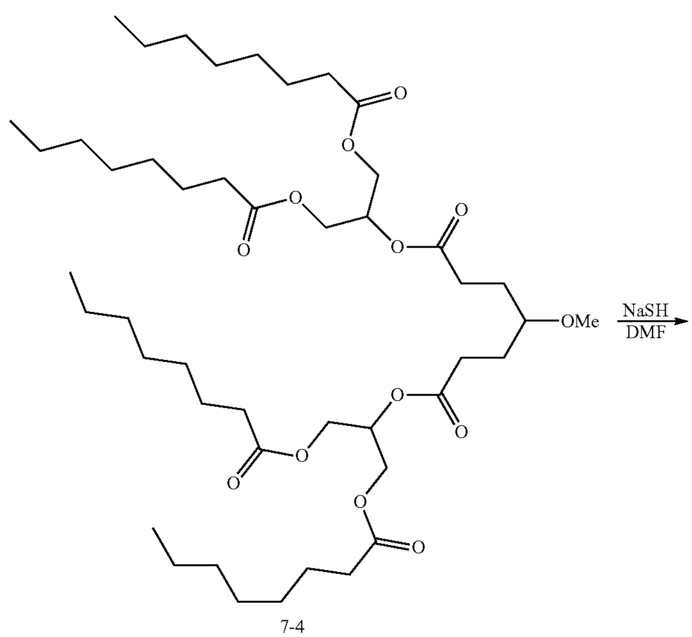
7-4

-continued
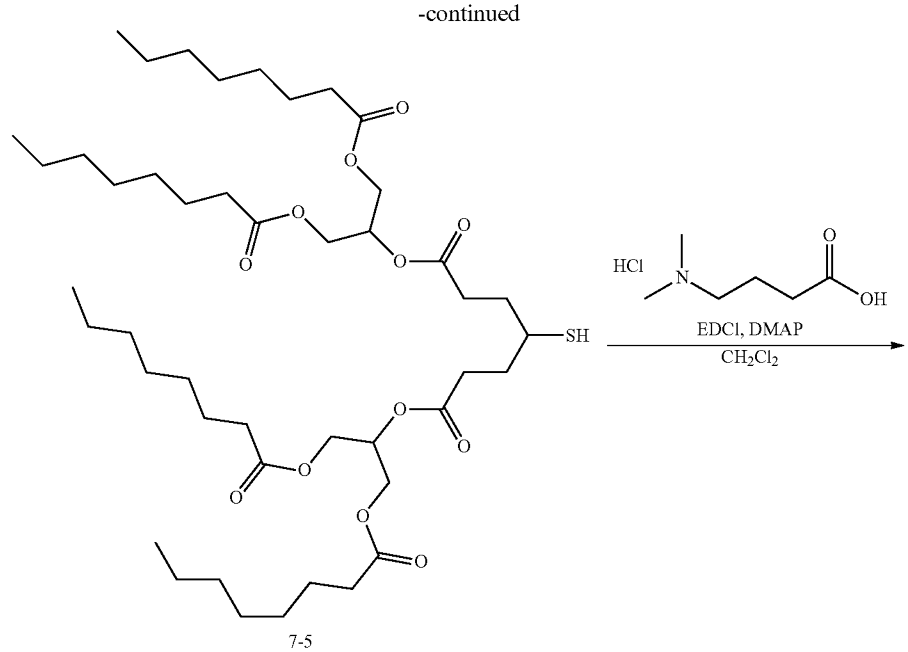
7-5
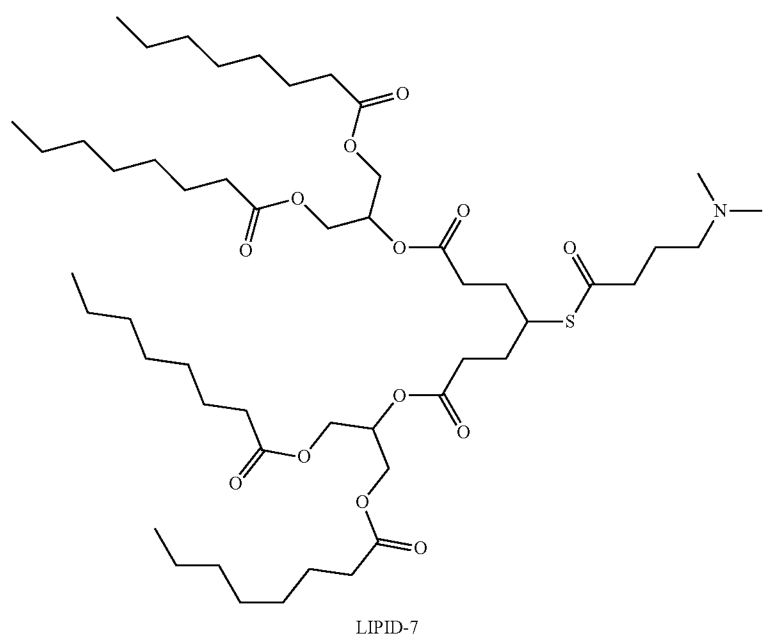 [SMILES: CCCCCCCC(=O)OCC(COC(=O)CCCCCCC)OC(=O)CCC(CCC(=O)OC(COC(=O)CCCCCCC)COC(=O)CCCCCCC)SC(=O)CCCN(C)C]
LIPID-7

Synthesis of 7-1: ((3,3'-(1,3-Dithiolane-2,2-diyl)bis(propanoyl))bis(oxy))bis(propane-2,1,3-triyl)tetraoctanoate

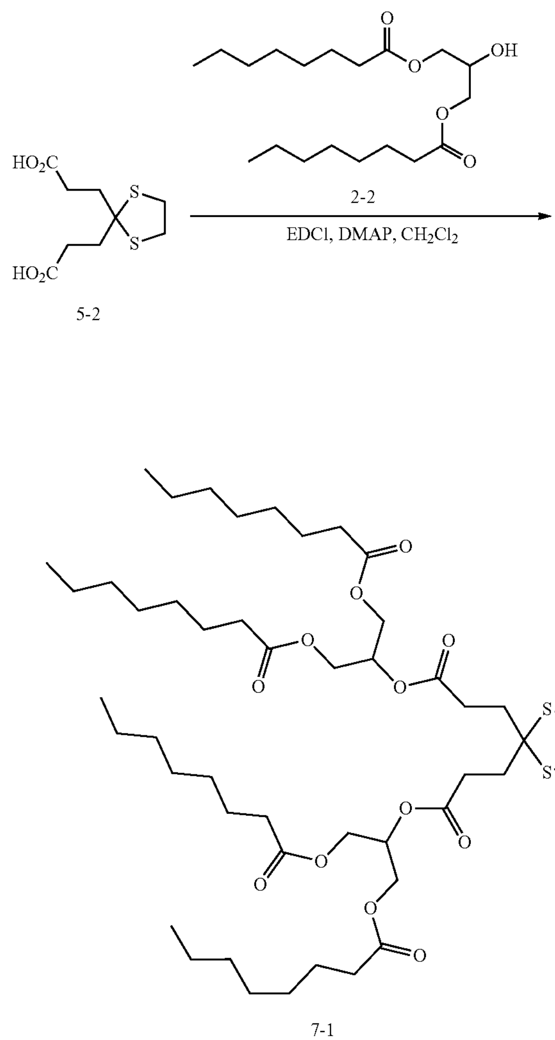

5-2

2-2

7-1

Synthesis of 7-2: bis(1,3-bis(Octanoyloxy)propan-2-yl) 4-oxoheptanedioate

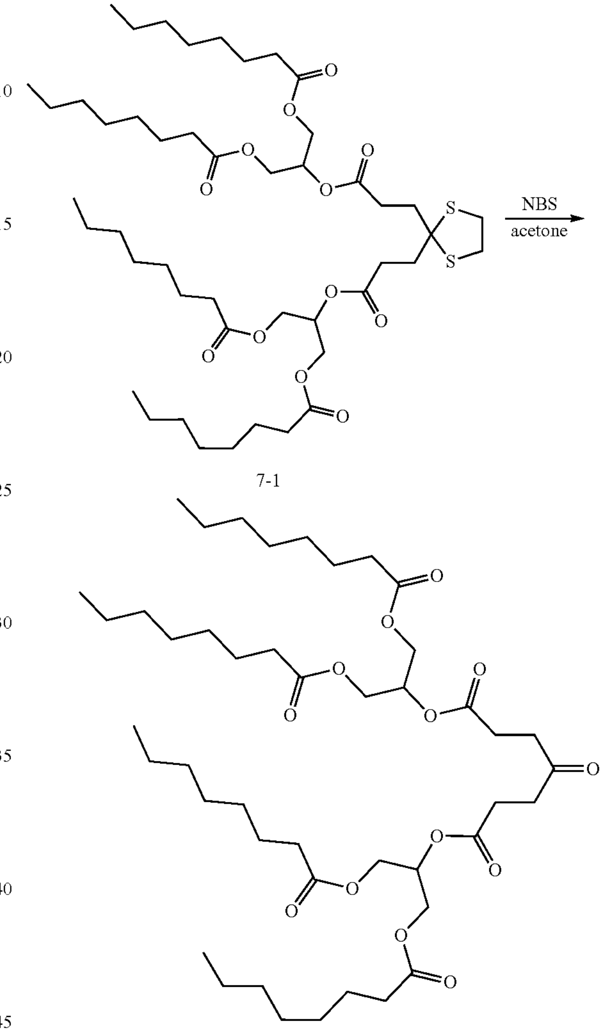

7-1

7-2

Into a 500 mL 3-necked round-bottom flask purged and maintained with an inert atmosphere of nitrogen, was placed 5-2 (16 g, 1.0 equiv) in $CH_2Cl_2$ (240 mL). This was followed by the addition of 2-2 (48 g, 2.0 equiv), DMAP (23 g, 1.0 equiv), and the mixture was cooled in an ice-water bath under nitrogen. To this cooled solution was added EDCI (36.8 g, 3.0 equiv) at 0° C. in portions over 45 minutes. The resulting solution was stirred for 16 h at room temperature. This reaction mixture was adsorbed on silica gel (110 g, type: ZCX-2, 100-200 mesh) and purified on a silica gel column (800 g, type: ZCX-2, 100-200 mesh) with petroleum ether/EtOAc gradient from 100:0 to 90:10. The fractions containing pure product was pooled and concentrated under vacuum to afford the 7-1 (60 g, 95% yield) as a yellow oil. ELSD A: water/0.05% TFA: B: $CH_3CN$/0.05% TFA 95:5 to 5:95 A/B at 2 min., hold 0.7 min): RT 1.60 min, m/z 902.52 (Calcd.), (found) 925.50 (M+Na).

To a 3-L three-neck round-bottom flask was added acetone (1.5 L,) and 7-1 (60 g, 1.0 equiv), the mixture was cooled to −20° C. under nitrogen, then a solution of NBS (47.3 g, 4.0 equiv) in acetone (300 mL) was added dropwise to the reaction mixture over 15 mins. The resulting solution was stirred for 1 h at −20° C. The reaction was quenched with water (300 mL), warmed to room temperature and concentrated under vacuum to remove acetone. The mixture was extracted with EtOAc (600 mL), the organic phase was dried ($Na_2SO_4$), filtered, and concentrated under vacuum to give crude 7-2. The solvent was removed under reduced pressure. Crude 7-2 was dissolved in $CH_2Cl_2$ (200 mL) and was adsorbed on silica gel (120 g, type: ZCX-2, 100-200 mesh) and purified on a silica gel column (800 g, type: ZCX-2, 100-200 mesh) with a petroleum ether/EtOAc gradient from 100:0 to 90:10. The fractions containing pure product was pooled and concentrated under vacuum to afford the 7-2 (44 g, 80% yield) as a colorless oil. ELSD A:

water/0.05% TFA: B: $CH_3CN$/0.05% TFA 95:5 to 5:95 A/B at 2 min., hold 0.7 min): RT 1.36 min, m/z 826.54 (Calcd.), (found) 849.50 (M+Na).

Synthesis of 7-3: bis(1,3-bis(Octanoyloxy)propan-2-yl) 4-hydroxyheptanedioate

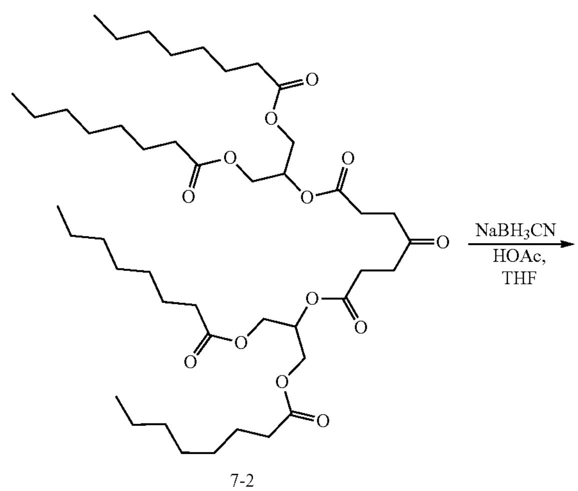

7-2

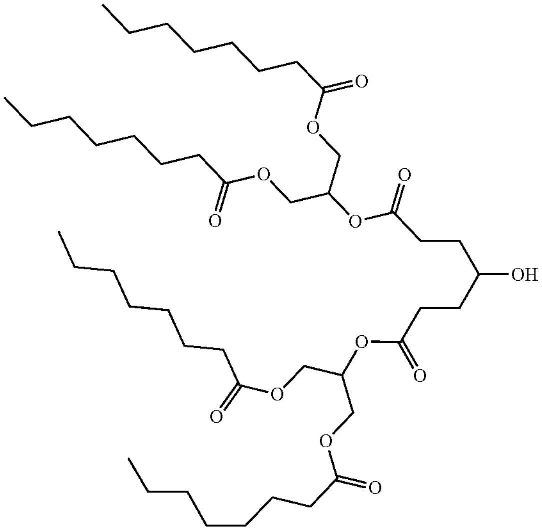

7-3

Into a 1-L 4-necked round-bottom flask purged and maintained with an inert atmosphere of nitrogen, was placed 7-2 (44 g, 1.0 equiv) in THF (400 mL). To this was added HOAc (37 g, 12.0 equiv) at 0° C. This was followed by the addition of $NaBH_3CN$ (39 g, 12.0 equiv) in several batches at 0° C. The resulting solution was stirred for 18 hr at 25° C. The reaction was quenched with water (800 mL,). The mixture was extracted with EA (800 mL). The organic phase was separated, dried over $Na_2SO_4$, filtered and concentrated under vacuum to give crude 7-3. Crude 7-3 was dissolved in $CH_2Cl_2$ (150 mL) and was adsorbed on silica gel (80 g, type: ZCX-2, 100-200 mesh) and purified on a silica gel column (800 g, type: ZCX-2, 100-200 mesh) with a petroleum ether/EtOAc gradient from 100:0 to 80:20. The fractions containing pure product was pooled and concentrated under vacuum to afford 7-3 (16 g, 36% yield) as a colorless oil. ELSD A: water/0.05% TFA: B: $CH_3CN$/0.05% TFA 95:5 to 5:95 A/B at 2 min., hold 0.7 min): RT 1.32 min, m/z 828.56 (Calcd.), (found) 851.50 (M+Na).

Synthesis of 7-4: bis(1,3-bis(Octanoyloxy)propan-2-yl) 4-((methylsulfonyl)oxy)heptanedioate

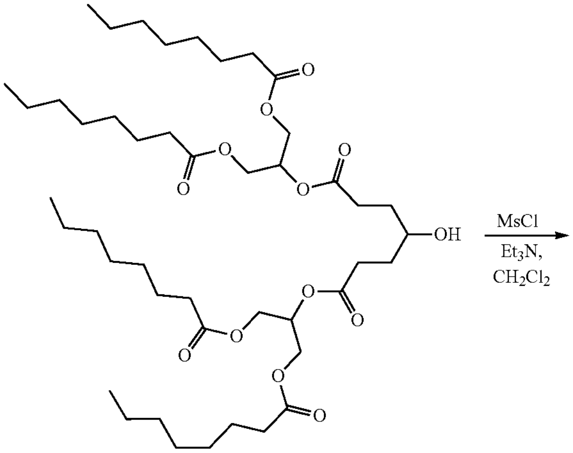

7-3

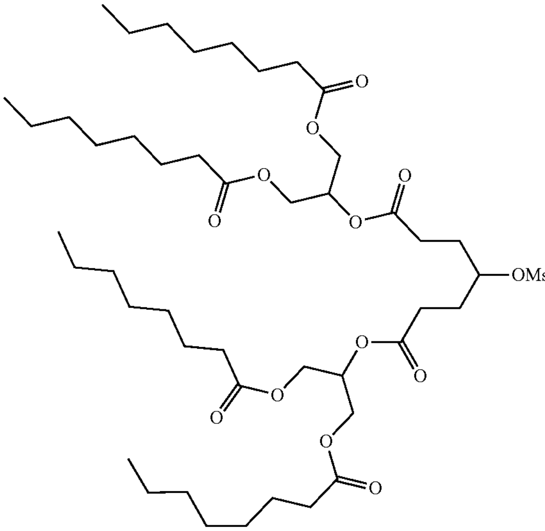

7-4

Into a 500-mL 3-necked round-bottom flask, was placed 7-3 (16 g, 1.0 equiv) and $Et_3N$ (2.4 g, 1.2 equiv) in DCM (160 mL) and the solution was cooled in an ice-water bath under nitrogen. To this cooled solution was added MsCl (2.42 g, 1.1 equiv) dropwise with stirring at 0° C. over 20 min. The resulting solution was stirred for 3 hours at room temperature. The reaction was then quenched by the addition of water/ice (100 mL). The resulting solution was extracted with dichloromethane (2×00 mL). The combined organic phases were washed with brine (100 ml). The organic phase was separated, dried over $Na_2SO_4$, filtered and the solvent was removed under reduced pressure to give crude 7-4. Crude 7-4 was dissolved in $CH_2Cl_2$ (75 mL) and was adsorbed on silica gel (32 g, type: ZCX-2, 100-200 mesh) and purified on a silica gel column (500 g, type: ZCX-2, 100-200 mesh) with a petroleum ether/EtOAc gradient from 100:0 to 80:20. The fractions containing pure product was pooled and concentrated under vacuum to afford 7-4 (10 g, 60% yield) as a colorless oil. ELSD A: water/0.05% TFA: B: $CH_3CN$/0.05% TFA 95:5 to 5:95 A/B at 2 min, hold 0.7 min): RT 1.26 min, m/z 906.54 (Calcd.), (found) 929.50 (M+Na).

Synthesis of 7-5: bis(1,3-bis(Octanoyloxy)propan-2-yl) 4-((methylsulfonyl)oxy)heptanedioate

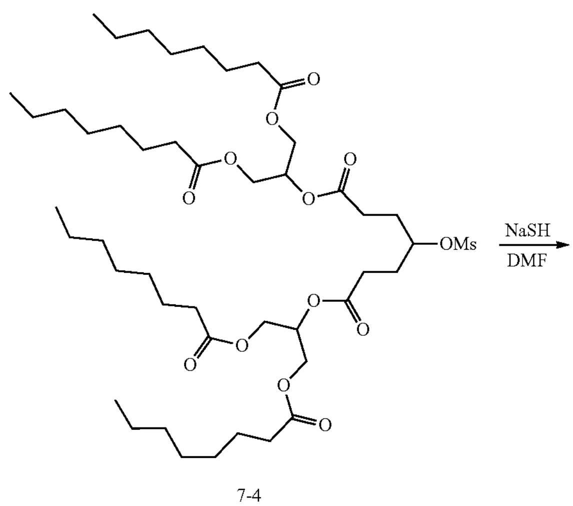

7-4

-continued

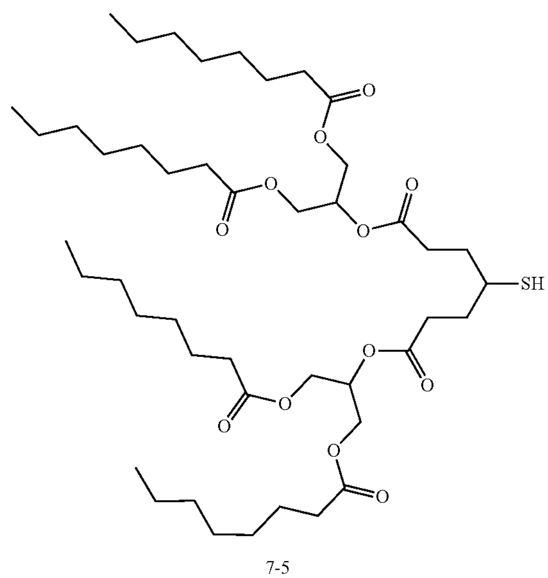

7-5

Into a 500-mL 3-necked round-bottom flask, was placed 7-4 (200 mg, 1.0 equiv) in DMF (4 ml) and the solution was cooled in an ice-water bath under nitrogen. This was followed by the addition of NaSH (37.5 mg, 3.0 equiv) at 0° C. The resulting solution was stirred for 3 hours at 0° C. The reaction was then quenched by the addition of water/ice (20 mL). The resulting solution was extracted with ethyl acetate (40 mL). The organic phase was separated, washed with brine (2×30 mL). The same scale reaction process repeated 50×. The combined mixture (from the repeated reactions) was dried over anhydrous sodium sulfate and concentrated under vacuum to give crude 7-5. Crude 7-5 was dissolved in THF (75 mL) and was adsorbed on silica gel (20 g, type: ZCX-2, 100-200 mesh) and purified on a silica gel column (200 g, type: ZCX-2, 100-200 mesh) with a petroleum ether/EtOAc gradient from 100:0 to 80:20. The fractions containing pure product was pooled and concentrated under vacuum to afford the 7-5 (3 g, 32% yield) as a light-yellow oil. ELSD A: water/0.05% TFA: B: $CH_3CN$/0.05% TFA 95:5 to 5:95 A/B at 2 min., hold 0.7 min): RT 1.26 min, m/z 844.54 (Calcd.), (found) 845.65 (M+H).

Synthesis of LIPID 7: bis(1,3-bis(Octanoyloxy) propan-2-yl) 4-((4-(dimethylamino)butanoyl)thio) heptanedioate

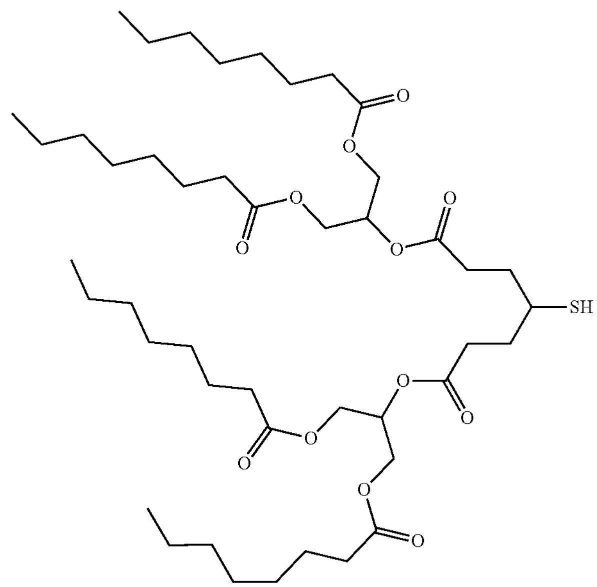

7-5

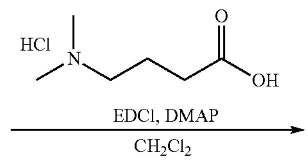

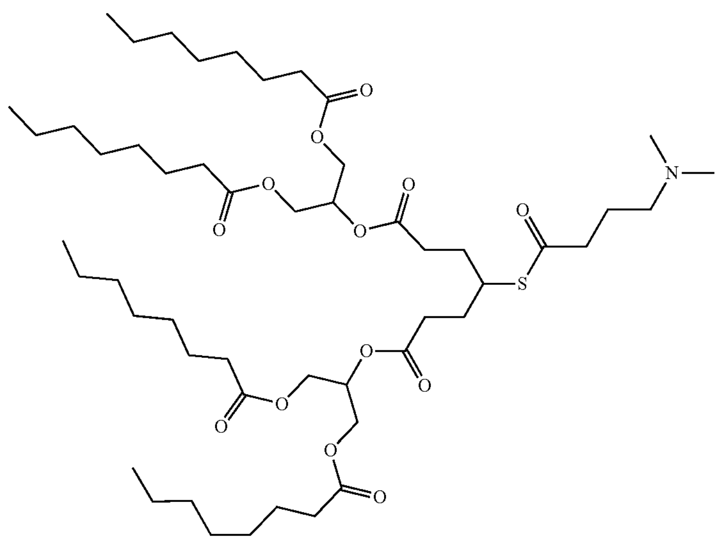

LIPID 7

Into a 100-mL 3-necked round-bottom flask purged and maintained with an inert atmosphere of nitrogen, was placed a solution of 7-5 (3 g, 1.0 equiv) in $CH_2Cl_2$ (30 mL). 4-(dimethylamino)butanoic acid HCl salt (0.71 g, 1.2 equiv), DMAP (0.43 g, 1.0 equiv) were added and the mixture was cooled in an ice water bath. This was followed by the addition of EDCI (1.02 g, 1.5 equiv) in portions at 0° C. The resulting solution was stirred for 16 h at room temperature. The reaction mixture was adsorbed on silica gel (250 g, type: ZCX-2, 100-200 mesh) and purified on a silica gel column (250 g, type: ZCX-2, 100-200 mesh) with an n-heptane/acetone gradient from 100:0 to 50:50. The fractions containing pure product was pooled and concentrated under vacuum to afford LIPID 7 (1.1 g, 32% yield) as a yellow oil. ELSD A: water/0.05% TFA: B: $CH_3CN$/0.05% TFA 95:5 to 5:95 A/B at 2 min., hold 0.7 min): RT 0.75 min, m/z 957.52 (Calcd.), (found) 958.50 (M+H). $^1$H-NMR (300 MHz, $CDCl_3$): δ 5.25 (m, 2H), 4.29 (m, 4H), 4.15 (m, 4H), 3.54 (brm, 1H), 2.62 (t, J=7.4 Hz, 2H), 2.52-2.21 (20H), 2.03 (m, 2H), 1.83 (m, 4H), 1.61 (m, 8H), 1.39-1.17 (28H), 0.97-0.80 (16H).

Example 8. Synthesis of LIPID 8: ((2,2'-((((3-(Dimethylamino)propyl)thio)carbonyl)azanediyl)bis(acetyl)bis(oxy))bis(propane-2,1,3-triyl) tetranonanoate
LIPID 8
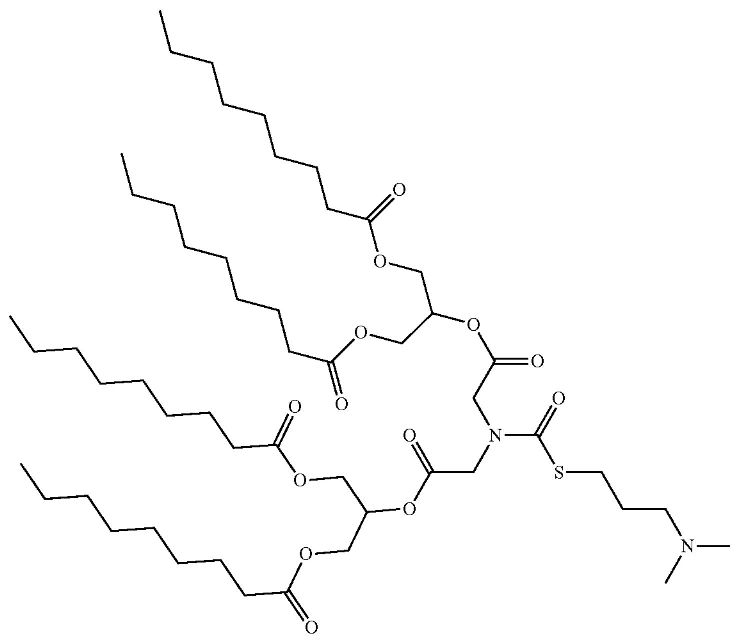
General Scheme
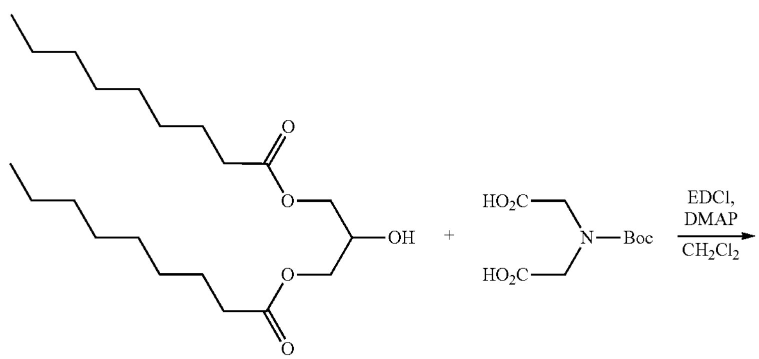
1-2

-continued
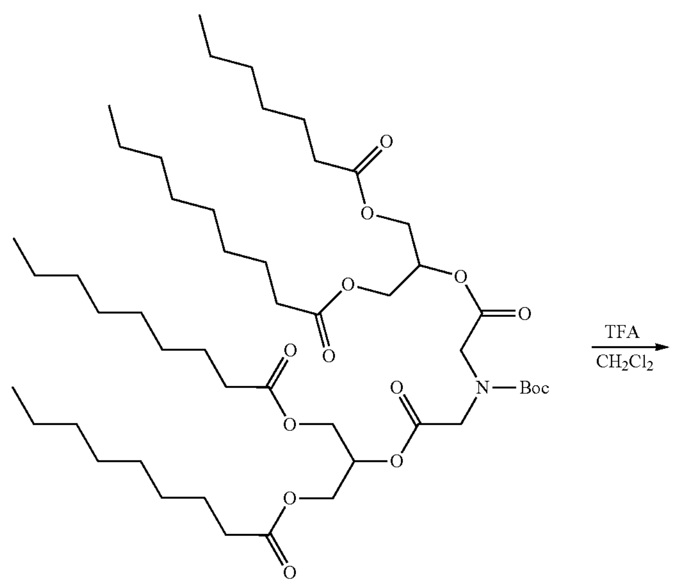
8-1
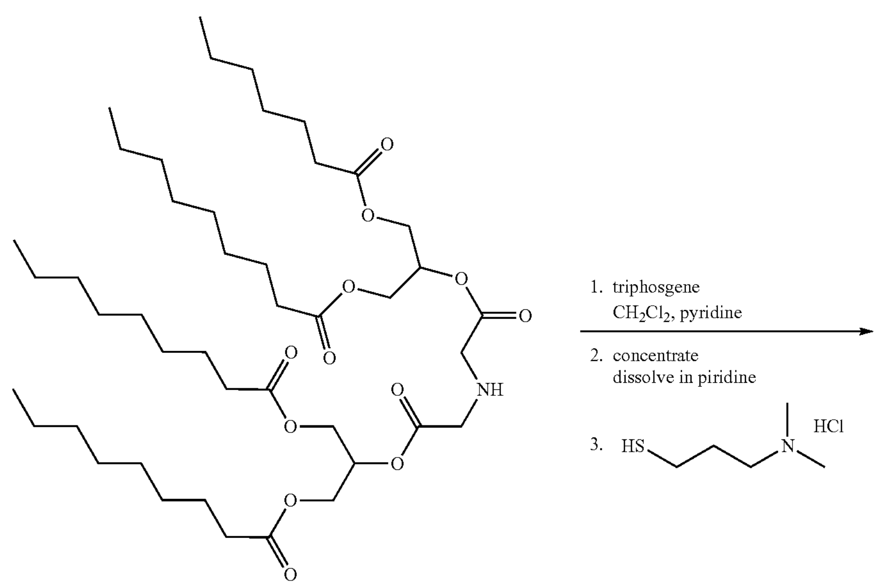
8-2

-continued
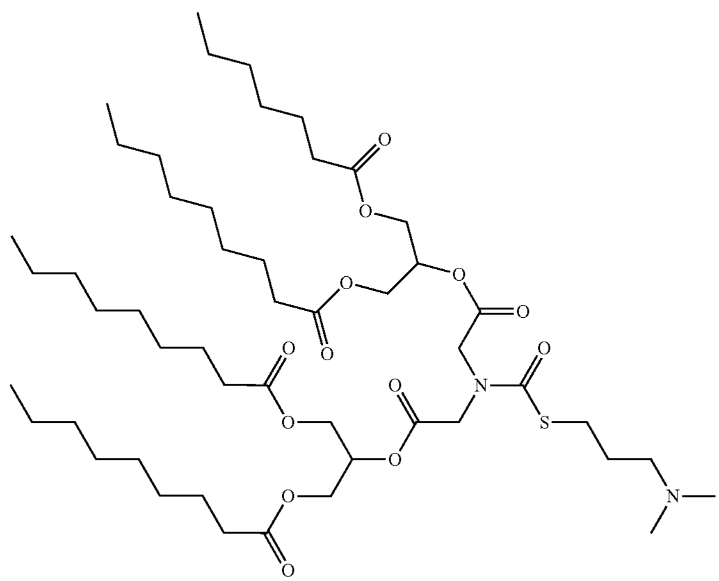
LIPID 8
Synthesis of 8-1: ((2,2'-((tert-butoxycarbonyl) azanediyl)bis(acetyl))bis(oxy))bis(propane-2,1,3-triyl) tetranonanoate
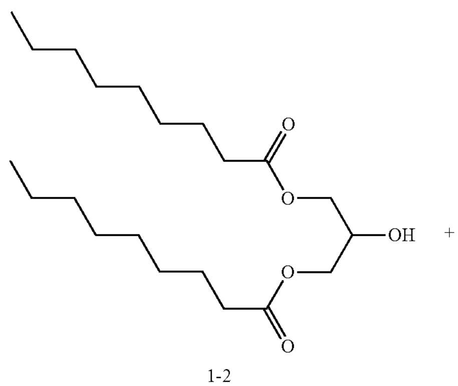
1-2
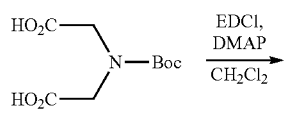
-continued
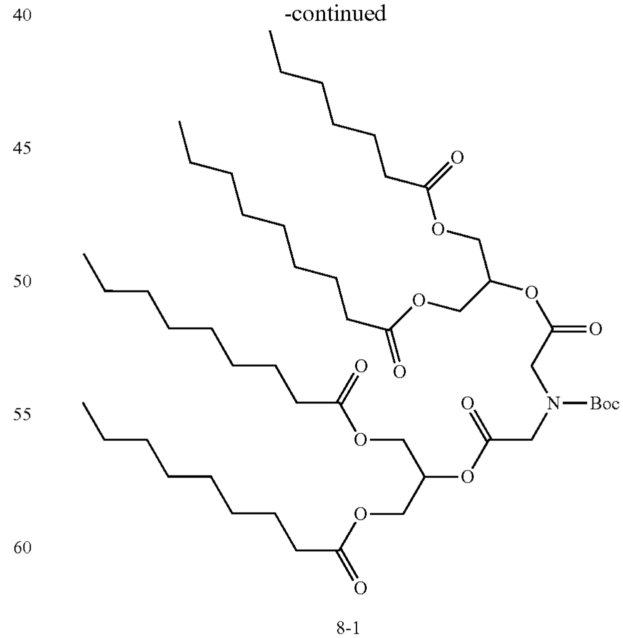
8-1
To a three-necked round-bottom flask was added 2,2'-((tert-butoxycarbonyl)azanediyl)diacetic acid (1 g, 1.0 eq), 1-2 (3.50 g, 2.2 eq) and DMAP (0.52 g, 1 eq) in DCM (20 ml), and the solution was cooled in an ice-water bath under nitrogen. To this cooled solution was added EDCI (1.80 g, 2.2 eq) at 0° C. in several portions. The resulting solution was stirred for 16 h at 20° C. The reaction was quenched with 10% aqueous citric acid solution (10 mL). The organic phase was separated, washed with 10% aqueous citric acid solution (10 mL, 10 V), brine (10 mL, 10 V), and dried with anhydrous $MgSO_4$. Filtration and concentration under vacuum gave crude 8-1 which was dissolved in $CH_2Cl_2$ (15 mL), and adsorbed on 5 g of silica gel (type: ZCX-2, 100-200 mesh, 6.43 w./w.), and purified on a silica gel column (20 g of silica gel, type: ZCX-2, 100-200 mesh, 32.14 w./w.) using petroleum ether/EtOAc (volume ratio). (gradient from 100:0 to 50:1). Fractions containing pure products were analyzed, pooled, combined and concentrated under reduced pressure to afford 8-1 (3.27 g, 81% yield) as yellow oil. ELSD A: water/0.05% TFA: B: $CH_3CN$/0.05% TFA 95:5 to 5:95 A/B at 3 min., hold 0.7 min): RT 2.2 min, m/z (Calcd.) 941.64, (found) 964.60 (M+Na).

Synthesis of 8-2: ((2,2'-Azanediylbis(acetyl))bis (oxy))bis(propane-2,1,3-triyl) tetranonanoate

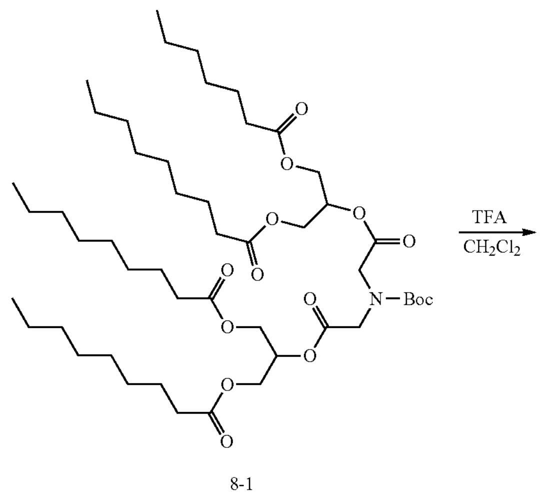

8-1

-continued

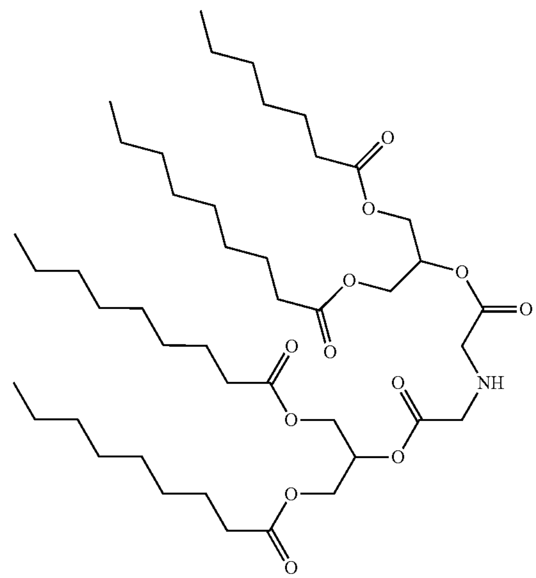

8-2

To a three-necked flask, was added 8-1 (3 g, 1 eq) in $CH_2Cl_2$ (60 mL) and the resulting solution was cooled in an ice-water bath under nitrogen, then, TFA (4.5 ml) was added slowly at 0~5° C. The resulting solution was stirred for 2 h at 20° C. The reaction was then quenched by the careful addition of 10% aqueous sodium carbonate solution (30 mL). The organic phase was separated and washed with brine (2×30 mL), dried with anhydrous $MgSO_4$ and filtered. The solvent was removed under vacuum to afford the 8-2 (2.5 g, 93% yield) as yellow oil. ELSD A: water/0.05% TFA: B: $CH_3CN$/0.05% TFA 95:5 to 5:95 A/B at 3 min., hold 0.7 min): RT 1.15 min, m/z (Calcd.) 841.59, (found) 842.51 (M+H).

Synthesis of LIPID 8: ((2,2'-((((3-(Dimethylamino)propyl)thio)carbonyl) azanediyl)bis(acetyl))bis(oxy))bis(propane-2,1,3-triyl) tetranonanoate

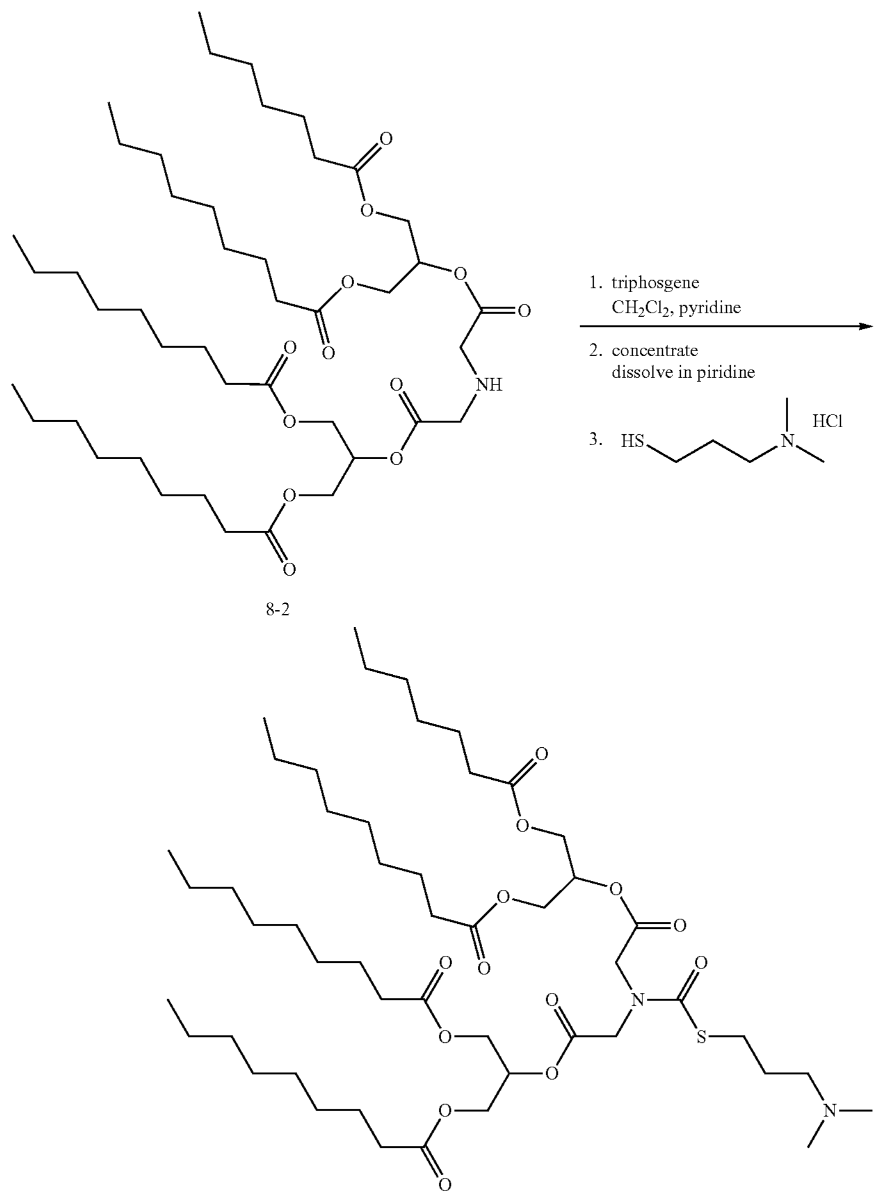

8-2

LIPID 8

To a three-necked flash was added 8-2 (2.50 g, 1 eq) in $CH_2Cl_2$ (50 mL) as one portion at room temperature, the resulting solution was cooled in an ice-water bath under nitrogen, then triphosgene (0.88 g, 1 eq) was added to the reaction mixture at 0~5° C. over 5 minutes. Pyridine (1.17 g, 5 eq) was the added slowly to the reaction mixture over 2±0.5 hours. After addition, the reaction mixture was stirred for 2 h at room temperature. Solvent was evaporated under reduced pressure and the residue was dissolved in anhydrous pyridine (50 mL) and cooled in an ice-water bath. To this was added 3-(dimethylamino)-1-propanethiol hydrochloride (0.42 g, 1.2 eq) and the above mixture was stirred for 18 hours at room temperature. Solvent was removed by under vacuum. The residue was dissolved in $CH_2Cl_2$ (50 mL) and washed with 10% aqueous citric acid solution (3×25 ml). The organic phase was separated, dried with anhydrous $MgSO_4$ and then filtered. Concentration under vacuum afforded crude LIPID 8, the crude product dissolved in $CH_2Cl_2$ (15 mL), and adsorbed on silica gel (5 g, type: ZCX-2, 100-200 mesh, 6.43 w./w.), and purified on a silica gel column (20 g of silica gel, type: ZCX-2, 100-200 mesh, 32.14 w./w.) using a gradient of $CH_2Cl_2$/MeOH (volume ratio, gradient from 100/0 to 98:2). Fractions containing LIPID 8 were analyzed, pooled, combined and concentrated under reduced pressure to afford LIPID 8 (1.2 g, 41% yield) as a yellow oil. ELSD A: water/0.05% TFA: B: $CH_3CN$/0.05% TFA 95:5 to 5:95 A/B at 2 min., hold 0.7 min): RT 0.88 min, m/z (Calcd.) 986.65, (found) 987.95 (M+H); $^1H$ NMR (300 MHz, $CDCl_3$): δ 5.28 (m, 2H), 4.35 (m, 4H), 4.18 (m, 8H), 2.95 (t, J=7.3 Hz, 2H), 2.340-2.212 (16H), 1.78 (m, 2H), 1.71-1.57 (8H), 1.35-1.20 (40H), 0.94-0.80 (12H).
Example 9. Synthesis of LIPID 9: bis(1,3-bis(Nonanoyloxy)propan-2-yl) 4-((4-(dimethylamino)butanoyl)thio)heptanedioate
LIPID 9
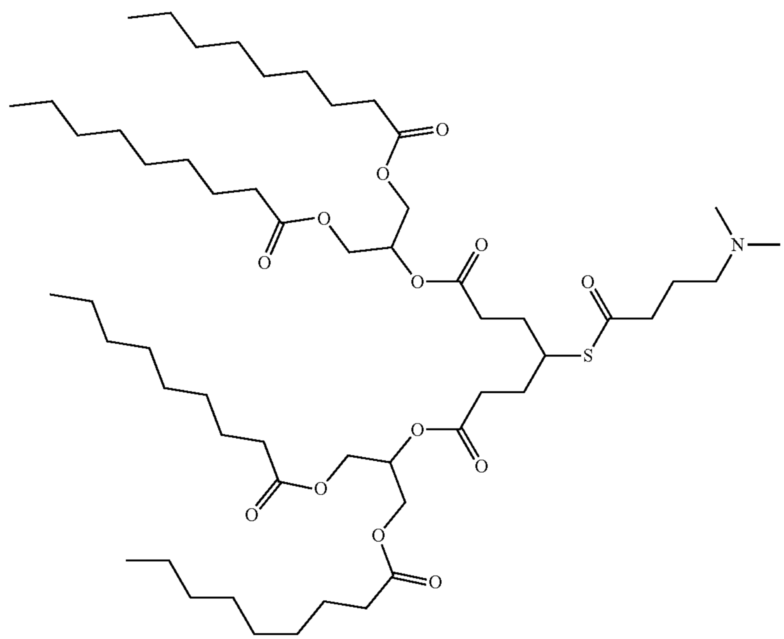
General Scheme
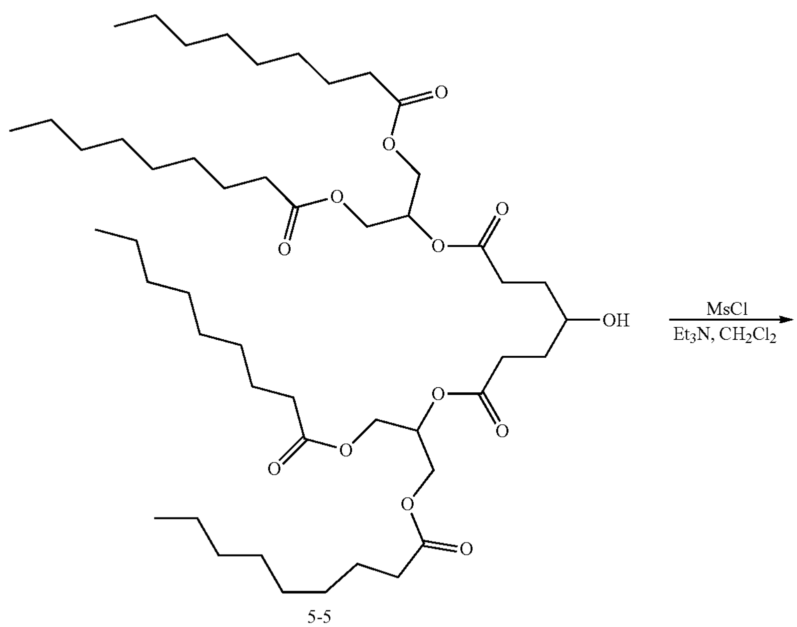
5-5

-continued
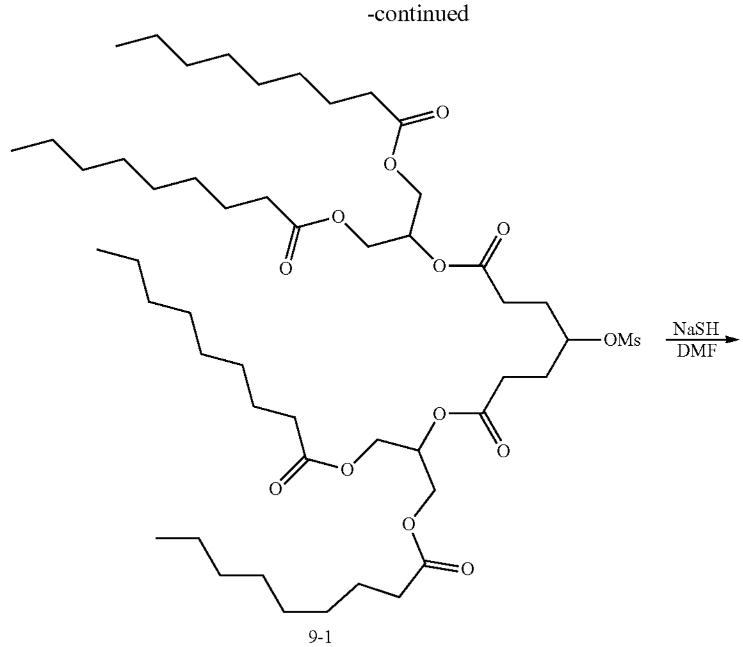
9-1
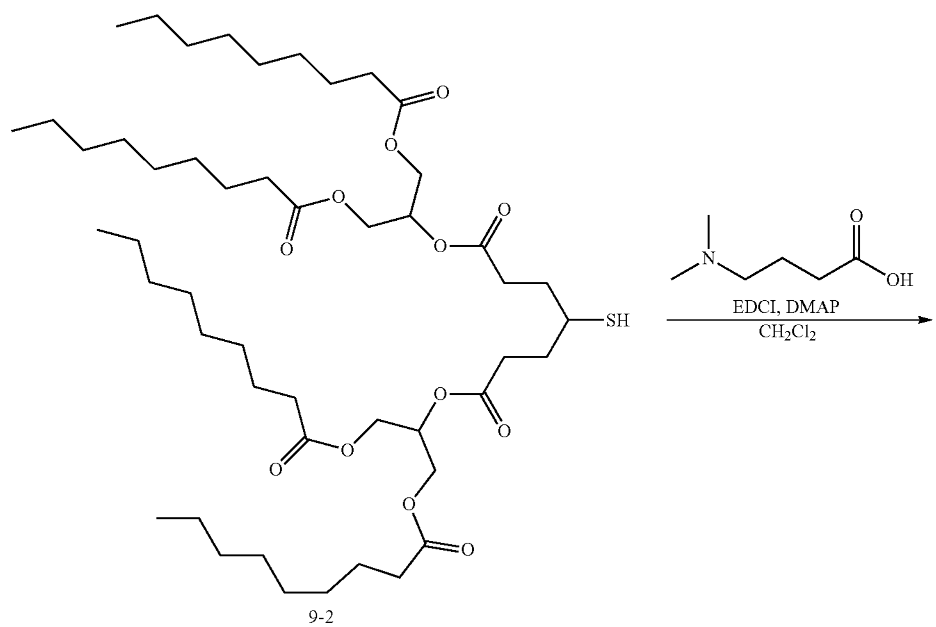
9-2

-continued
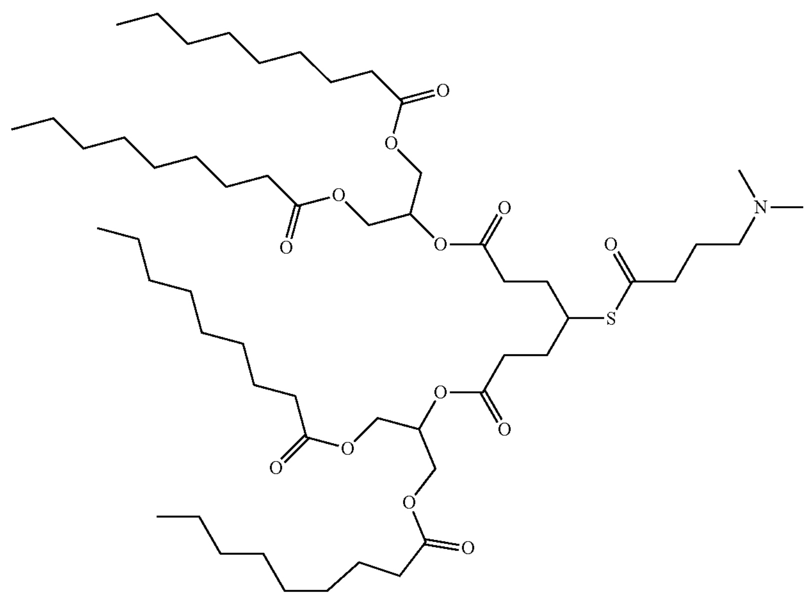
LIPID 9
Synthesis of 9-1: bis(1,3-bis(Nonanoyloxy)propan-2-yl) 4-((methylsulfonyl)oxy)heptanedioate
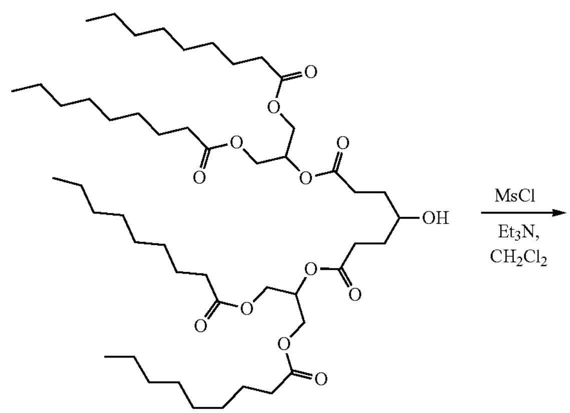
5-5
-continued
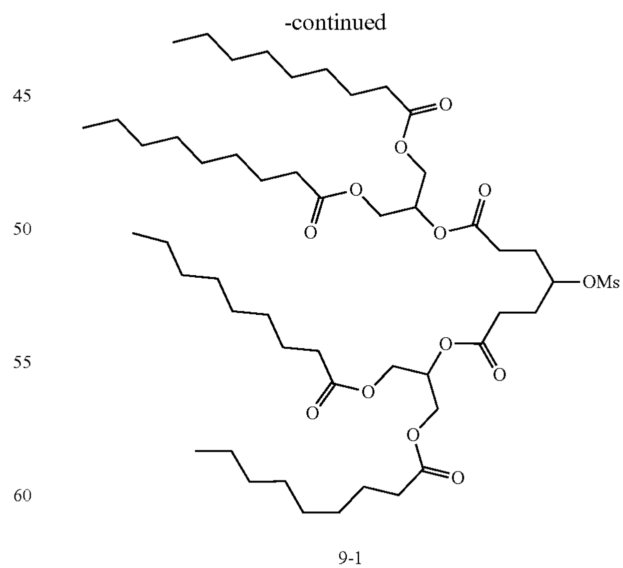
9-1
To a 250-mL four-necked round-bottle flask with mechanical stirring under $N_2$, was added 5-5 (6 g, 1.0 eq) in $CH_2Cl_2$ (90 mL). This was followed by the addition of $Et_3N$ (2.06 g, 3.0 eq) and the resulting solution was cooled in an ice-water bath under nitrogen. To the cooled solution was added MsCl (1.16 g, 1.5 eq) dropwise with stirring at 0° C. The resulting solution was stirred for 12 h at room temperature. The reaction was then quenched by the addition of $H_2O$ (100 ml). The phases were separated, and the aqueous layer was extracted with $CH_2Cl_2$ (100 ml). Then the combined organic phases were dried over anhydrous sodium sulfate, filtered, and concentrated under vacuum. The crude 9-2 was purified by High-Flash-Prep-HPLC with the following conditions: column, XB-C18 silica gel; mobile phase, i-PrOH in 1 mmol $NH_4HCO_3$ in water, 65% to 95% gradient in 30 min; detector, UV ELSD. Concentrated to dryness under vacuum to afford the 9-1 (5 g, 44% overall yield in 2 steps) as a colorless oil. ELSD A: water/0.05% TFA: B: $CH_3CN$/0.05% TFA 95:5 to 5:95 A/B at 2 min., hold 0.7 min): RT 1.66 min, m/z 962.60 (Calcd.), (found) 985.50 (M+Na).

Synthesis of 9-2: bis(1,3-bis(Nonanoyloxy)propan-2-yl) 4-mercaptoheptanedioate

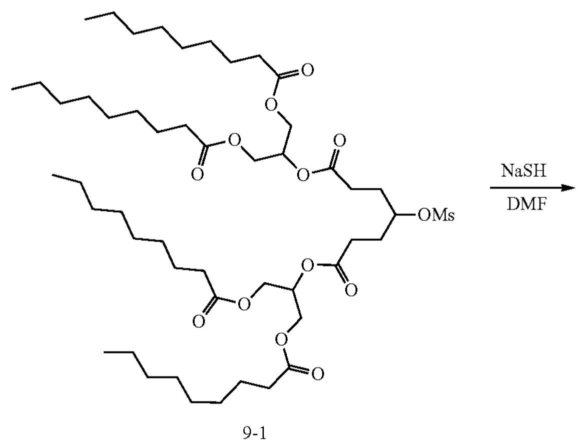

9-1

-continued

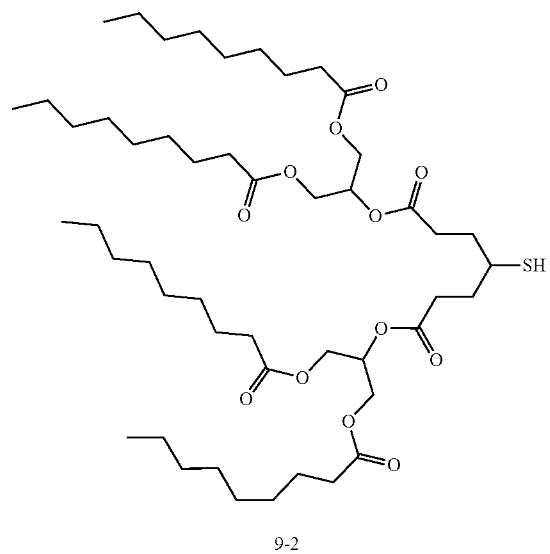

9-2

Into a 100-mL 3-necked round-bottom flask purged and maintained with an inert atmosphere of nitrogen, was placed 9-1 (100 mg, 1.00 equiv) in DMF (0.5 mL), the resulting solution was cooled in an ice-water bath under nitrogen. This was followed by the addition of NaSH (29.1 mg, 5.00 eq) at 0° C. The resulting solution was stirred for 24 h at 0° C. This reaction was repeated for 49× and overall mixture was combined to work up. The reaction was then quenched by the addition of water/ice (200 ml). The resulting solution was extracted with EtOAc (3×100 mL) and the organic phases were combined, dried over anhydrous sodium sulfate, filtered, and concentrated under vacuum to afford 9-2 (4.8 g, crude) as a colorless oil. ELSD A: water/0.05% TFA: B: $CH_3CN$/0.05% TFA 95:5 to 5:95 A/B at 3 min., hold 0.7 min): RT 2.08 min, m/z 900.60 (Calcd.), (found) 923.50 (M+Na).

Synthesis of LIPID 9: bis(1,3-bis(Nonanoyloxy) propan-2-yl) 4-((4-(dimethylamino)butanoyl)thio) heptanedioate

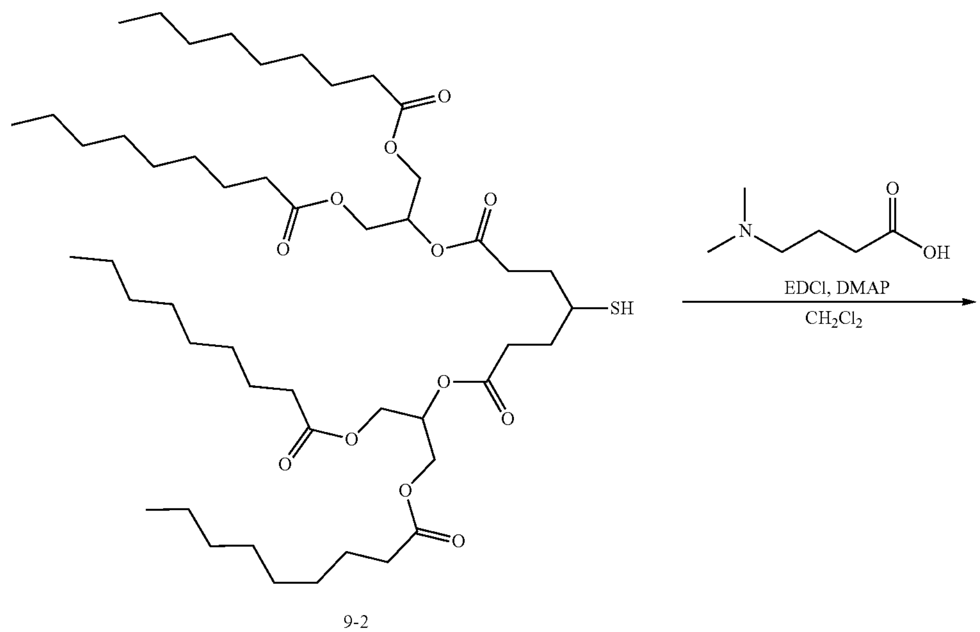

9-2

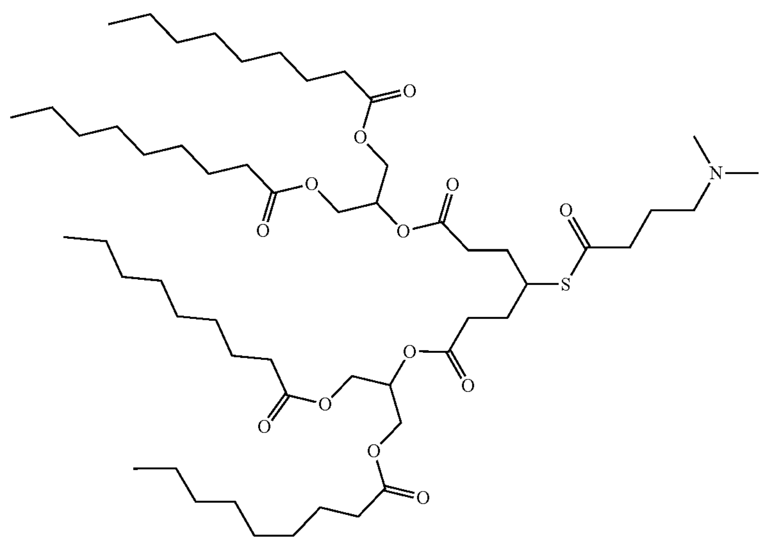

LIPID 9

To a three-necked round-bottom flask was added 9-2 (4.8 g, 1.0 eq), 4-(dimethylamino)butanoic acid (1.16 g, 1.3 eq) and DMAP (0.46 g, 0.7 eq) in $CH_2Cl_2$ (72 mL), the resulting solution was cooled in an ice-water bath under nitrogen. EDCI (1.84 g, 1.4 eq) was added to the reaction mixture at 0° C. in several portions. The resulting solution was stirred for 12 h at room temperature. The reaction system was quenched with 10% aqueous citric acid (48 mL). The organic phase was separated, washed with 10% aqueous citric acid (48 mL), brine (48 mL, 10 V), and dried with anhydrous $MgSO_4$. Filtration and concentration under vacuum gave crude 9 which was dissolved in $CH_2Cl_2$ (25 mL) and this was adsorbed on silica gel column (10 g, type: ZCX-2, 100-200 mesh) and purified on a silica gel column (50 g, type: ZCX-2, 100-200 mesh) with an n-heptane/acetone gradient from 100:0 to 75:50. The fractions containing pure 9 was pooled and concentrated under vacuum to afford the 9 (0.9 g, 18% yield) as a yellow oil. ELSD A: water/0.05% TFA: B: $CH_3CN$/0.05% TFA 95:5 to 5:95 A/B at 3 min., hold 0.7 min): RT 1.24 min, m/z 1013.68 (Calcd.), (found) 1015.40 (M+H); $^1H$ NMR (300 MHz, $CDCl_3$): δ 5.27 (q, J=5.1 Hz, 2H), 4.30 (m, 4H), 4.16 (m, 4H), 3.54 (brm, 1H), 2.64 (t, J=7.3 Hz, 2H), 2.46-2.23 (18H), 2.04 (m, 2H), 1.84 (m, 4H), 1.35-1.76 (13H), 1.00-1.32 (37H), 0.96-0.83 (12H).

Example 10. Synthesis of LIPID 10: ((4,4'-(((3-(Dimethylamino)propyl)thio)carbonyl)azanediyl)bis(butanoyl)bis(oxy)bis(propane-2,1,3-triyl) tetrakis(3-cyclohexylpropanoate)
LIPID 10
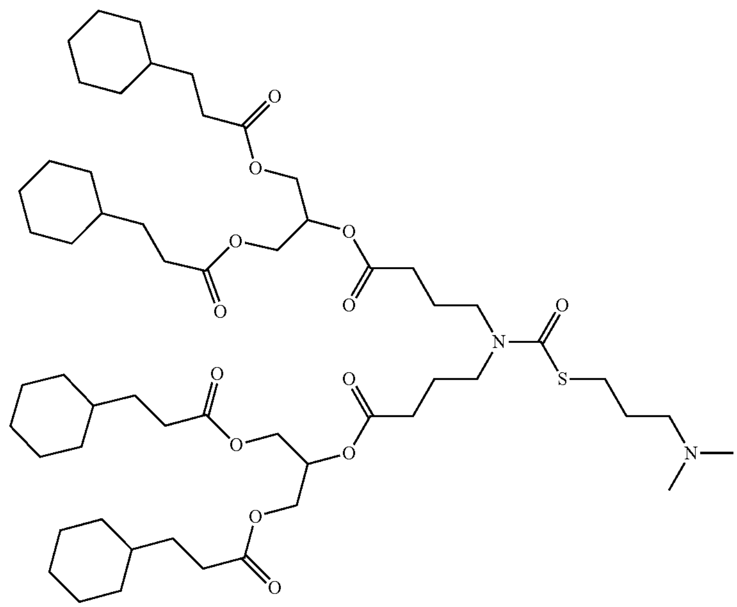
General Scheme
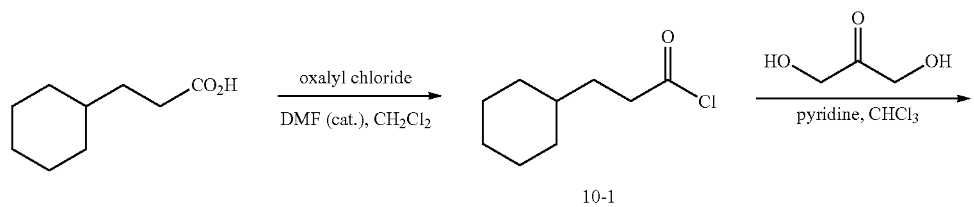
10-1
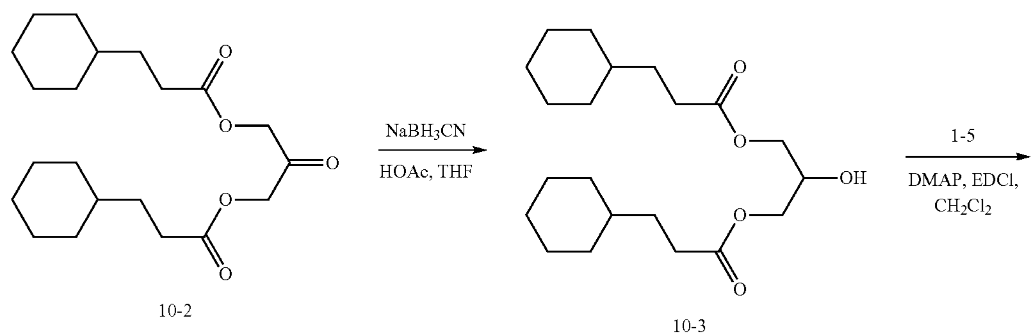
10-2
10-3

-continued
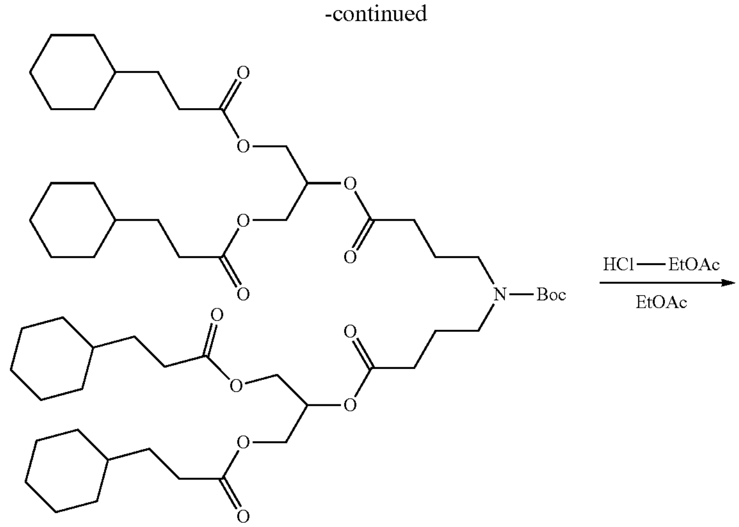
10-4
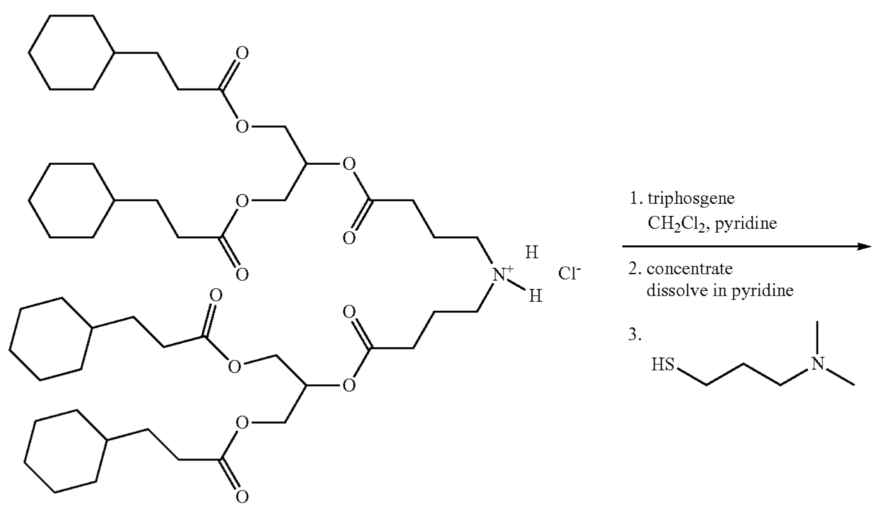
10-5
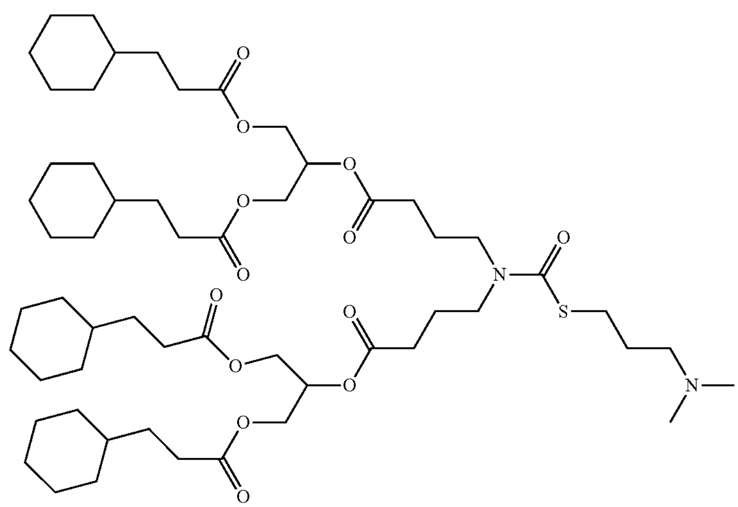
LIPID 10

Synthesis of 10-1: 3-Cyclohexylpropanoyl chloride

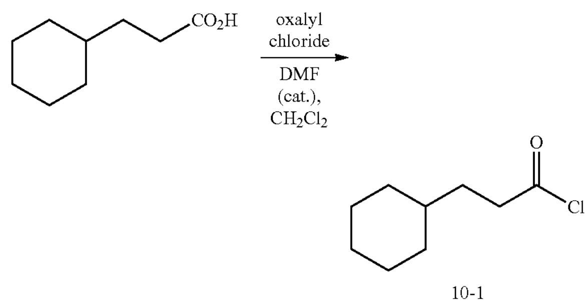

10-1

Into a 2000 mL 3-necked round-bottom flask purged and maintained with an inert atmosphere of nitrogen, was placed a solution of 3-cyclohexylpropanoic acid (100 g, 1.0 eq) in $CH_2Cl_2$ (1 L) and added DMF (0.2 mL). Oxalyl chloride (161.00 g, 2.00 eq) was added in dropwise at r.t. The mixture was stirred at room temperature under nitrogen overnight. The mixture was concentrated under vacuum to give crude 10-1. This was used as such in the next reaction.

Synthesis of 10-2: 2-Oxopropane-1,3-diyl bis(3-cyclohexylpropanoate)

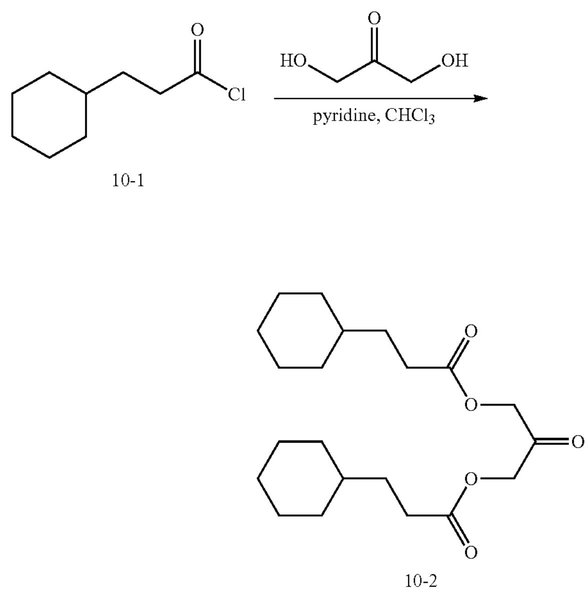

10-1

10-2

Into a 2000 mL 3-necked round-bottom flask purged and maintained with an inert atmosphere of nitrogen, was placed a solution of 10-1 (83.00 g, 2.50 eq) and dihydroxy-acetone (17.20 g, 1.00 eq) in $CHCl_3$ (1600 mL), the solution was cooled in an ice-water bath under nitrogen. To this cooled solution was added pyridine (61.00 g, 4.00 eq) while maintaining temperature at 0° C. over 40 minutes. The mixture was stirred at room temperature under nitrogen overnight. The pyridine hydrochloride formed was removed by filtration and washed with $CH_2Cl_2$ (200 mL). The combined filtrates were then washed with 5% aq. $NaHCO_3$ (2000 mL), 5% aq. HCl (2000 mL), brine (2000 mL), and dried over $Na_2SO_4$. Concentration under vacuum gave 65 g (92.8% yield) of 10-2 as a yellow oil. ELSD A: water/0.05% TFA: B: $CH_3CN$/0.05% TFA 95:5 to 5:95 A/B at 3 min, hold 0.7 min): RT 2.56 min, m/z 366.24 (Calcd.), (found) 367.40 (M+H).

Synthesis of 10-3: 2-Hydroxypropane-1,3-diyl bis(3-cyclohexylpropanoate)

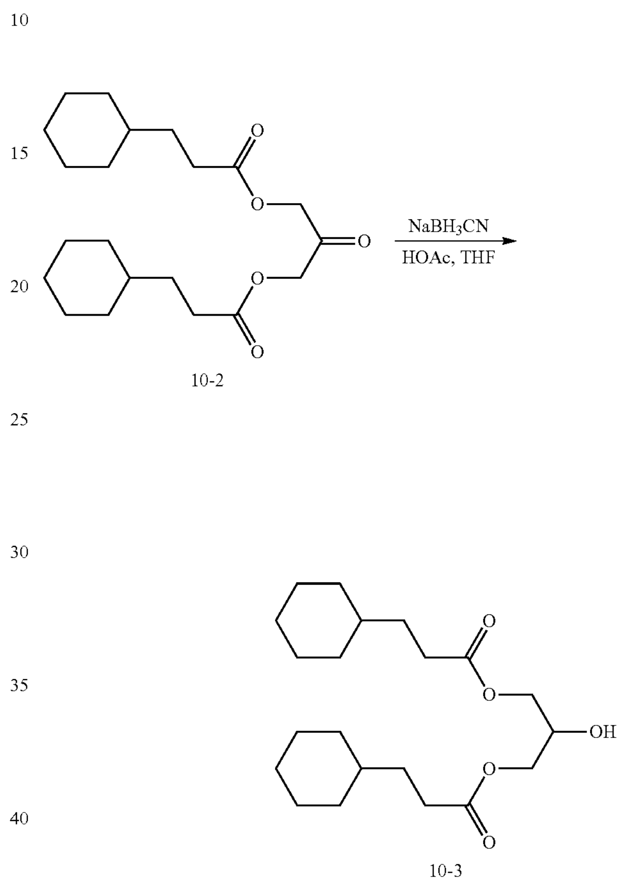

10-2

10-3

Into a 2000 mL 3-necked round-bottom flask purged and maintained with an inert atmosphere of nitrogen, was placed a solution of 10-2 (85.00 g, 1.00 eq) in THF (1 L). To the solution was added HOAc (18.00 g, 1.30 eq) and the solution was cooled in an ice-water bath. To this cooled solution was added $NaBH_3CN$ (18.00 g, 1.20 eq) at 0° C. The mixture was stirred overnight at r.t. The reaction mixture was quenched with brine (1 L). The mixture was extracted with EtOAc (3×400 mL). The combined organic phases were then washed with 5% aq. $NaHCO_3$ (200 mL), 5% aq. HCl (200 mL), brine (200 mL), and dried over $Na_2SO_4$. Filtration and concentration under vacuum gave crude 10-3 which was dissolved in $CH_2Cl_2$ (500 mL) and adsorbed on silica gel (240 g, type: ZCX-2, 100-200 mesh). The crude material was purified on a silica gel column (800 g, type: ZCX-2, 100-200 mesh) with a petroleum ether/EtOAc gradient from 100:0 to 90:10. The fractions containing pure product were pooled and concentrated under vacuum to afford the 10-3 (61 g (70.1% yield)) as a yellow oil. ELSD A: water/0.05% TFA: B: $CH_3CN$/0.05% TFA 95:5 to 5:95 A/B at 3 min., hold 0.7 min): RT 2.50 min, m/z 368.26 (Calcd.), (found) 351.2 ($M-H_2O$).

Synthesis of 10-4: ((4,4'-((tert-Butoxycarbonyl)azanediyl)bis(butanoyl))bis(oxy))bis(propane-2,1,3-triyl) tetrakis(3-cyclohexylpropanoate)

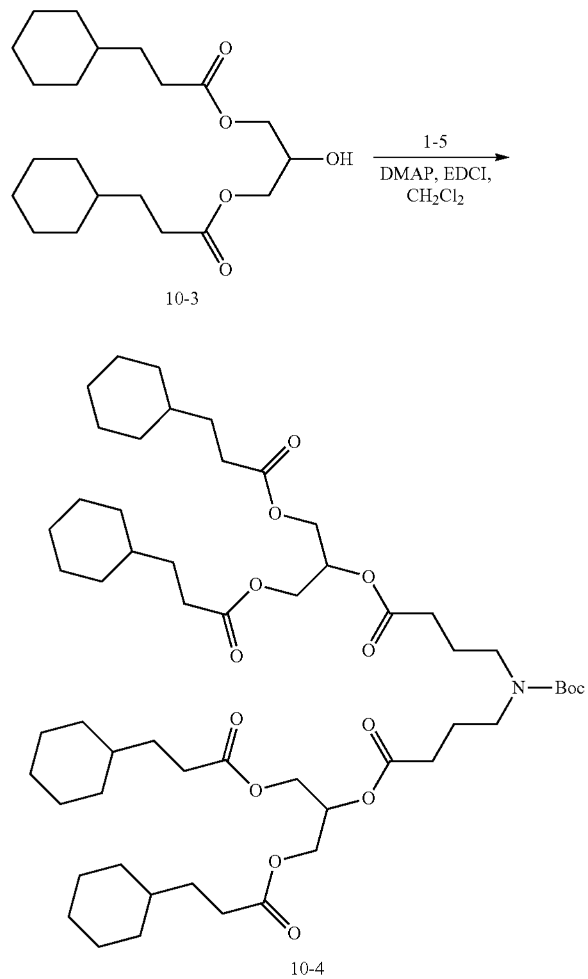

10-3

10-4

Into a 250 mL 3-necked round-bottom flask purged and maintained with an inert atmosphere of nitrogen, was added 1-5 (4.00 g, 1 eq) and 10-3 (10.20 g, 2 equiv), and the mixture was dissolved in $CH_2Cl_2$ (80 mL). The solution was cooled in an ice-water bath and DMAP (1.69 g, 1.00 eq) and EDCI (10.60 g, 4.00 eq) were added in order at 0° C. The reaction mixture was stirred overnight at r.t. The reaction was then quenched with 10% aq. citric acid (200 mL) and the organic phase was separated. The organic phase was washed with 10% aq. $NaHCO_3$ (200 mL), brine (200 mL), and was dried over anhydrous sodium sulfate. Filtration and concentration under vacuum gave crude 10-4 which was dissolved in $CH_2Cl_2$ (100 mL) and adsorbed on silica gel (50 g, type: ZCX-2, 100-200 mesh) and purified on a silica gel column (400 g, type: ZCX-2, 100-200 mesh) with a petroleum ether/EtOAc gradient from 100:0 to 90:10. The fractions containing pure product was pooled and concentrated under vacuum to afford 11 g (77.7% yield) of 10-4 as light yellow oil. ELSD A: water/0.05% TFA: B: $CH_3CN$/0.05% TFA 95:5 to 5:95 A/B at 3 min, hold 0.7 min): RT 1.79 min, m/z 989.64 (Calcd.), (found) 1012.50 (M+Na).

Synthesis of 10-5: bis(4-((1,3-bis((3-cyclohexylpropanoyl)oxy)propan-2-yl)oxy)-4-oxobutyl)ammonium chloride

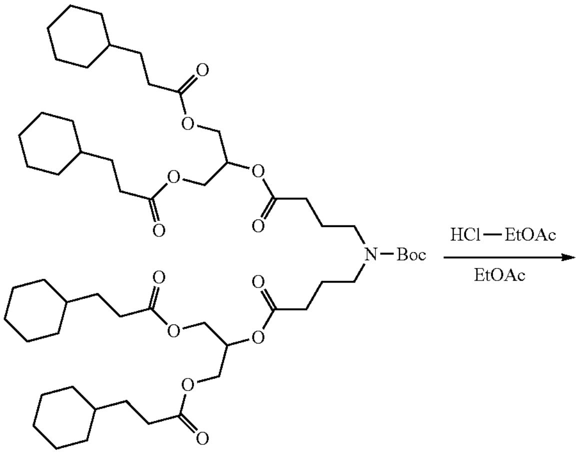

10-4

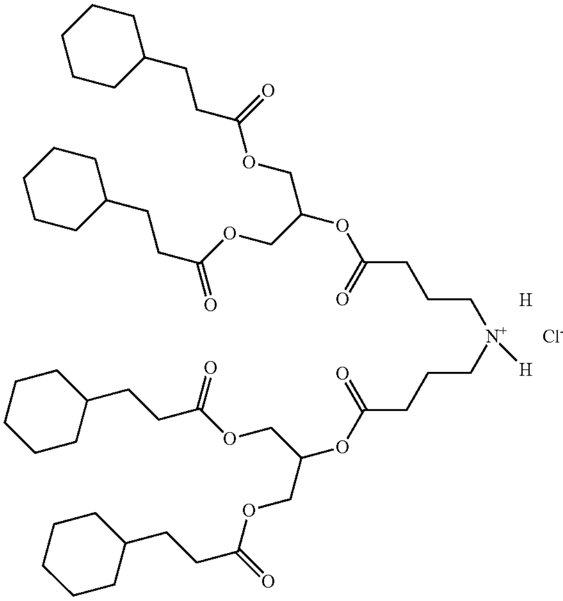

10-5

Into a 250 mL round-bottom flask purged and maintained with an inert atmosphere of nitrogen, was placed a solution of 10-4 (6.30 g, 1.00 eq) in EtOAc (20 mL) and the solution was cooled in an ice-water bath. To the cooled solution was added HCl in EtOAc (60 mL, 10 eq, 2M) dropwise at 0-10° C. The resulting solution was stirred overnight at room temperature. The resulting mixture was concentrated under vacuum. This provided in 6 g (99% yield) of 10-5 as light yellow oil. ELSD A: water/0.05% TFA: B: $CH_3CN$/0.05% TFA 95:5 to 5:95 A/B at 3 min, hold 0.7 min): RT 1.48 min, m/z 889.59 (Calcd.), (found) 890.50 (M+H).

Synthesis of LIPID 10: ((4,4'-((((3-(Dimethylamino)propyl)thio)carbonyl)azanediyl)bis(butanoyl))bis(oxy))bis(propane-2,1,3-triyl) tetrakis(3-cyclohexylpropanoate)

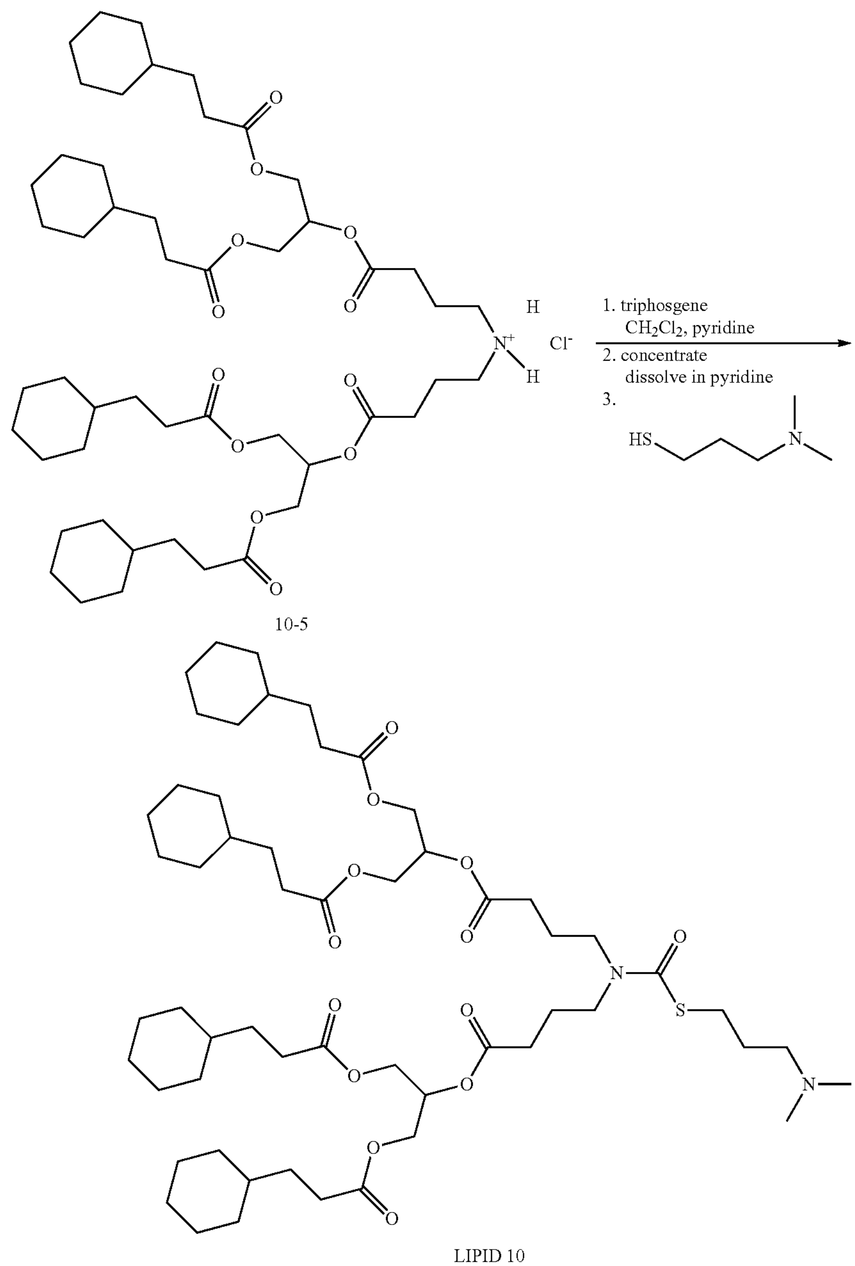

10-5

LIPID 10

Into a 250-mL 3-necked round-bottom flask purged and maintained with an inert atmosphere of nitrogen, was placed a solution of 10-5 (6.00 g, 1.00 eq) in $CH_2Cl_2$ (100 mL) and the solution was cooled in an ice-water bath under nitrogen. To the mixture was added triphosgene (1.91 g, 1.62 eq) at 0° C. This was followed by the addition of pyridine (2.56 g, 5.00 eq) dropwise with stirring at 0° C. The mixture was stirred for 4 h at r.t and then concentrated under vacuum. The residue was dissolved with pyridine (100 mL) and was cooled in an ice-water bath under nitrogen. To this solution was added 3-(dimethylamino)propane-1-thiol (0.92 g, 1.93 eq) dropwise with stirring at 0° C. over 10 min. The resulting solution was stirred overnight at room temperature. The resulting mixture was concentrated under vacuum. The residue was diluted with $CH_2Cl_2$ (500 mL) and the solution was washed with 10% aq. citric acid (2×200 mL), saturated aq. $NaHCO_3$ (2×200 mL), brine (100 mL), dried over anhydrous sodium sulfate and concentrated under vacuum to give crude LIPID 10. The residue was dissolved in $CH_2Cl_2$ (100 mL) and was adsorbed on silica gel (50 g, type: ZCX-2, 100-200 mesh) and purified on a silica gel column (250 g, type: ZCX-2, 100-200 mesh) with a $CH_2Cl_2$/MeOH gradient from 100:0 to 97:3. The fractions containing pure product were pooled and concentrated under vacuum. The product was dissolved in n-heptane (40 mL) and 0.22 g activated Charcoal powder was added. The mixture was stirred for 4 h at r.t and then filtered. The filtrate was concentrated under vacuum to yield 2 g (48% yield) of LIPID 10 as light-yellow oil. ELSD A: water/0.05% TFA: B: $CH_3CN$/0.05% TFA 95:5 to 5:95 A/B at 3 min., hold 0.7 min): RT 0.68 min, m/z 1034.65 (Calcd.), (found) 1035.65 (M+H); $^1H$ NMR (300 MHZ, $CDCl_3$): δ 5.25 (m, 2H), 4.31 (m, 4H), 4.14 (dd, J=11.9, 5.7 Hz, 4H), 3.38 (brm, 4H), 2.94 (t, J=7.3 Hz, 2H), 2.44-2.22 (20H), 1.99-1.47 (26H), 1.39-1.17 (20H), 0.95-0.79 (12H).
Example 11. Synthesis of LIPID 11: ((4,4'-(((3-(Dimethylamino)propyl)thio)carbonyl)azanediyl)bis(butanoyl))bis(oxy))bis(propane-2,1,3-triyl) tetrakis(4-cyclohexylbutanoate)
LIPID 11
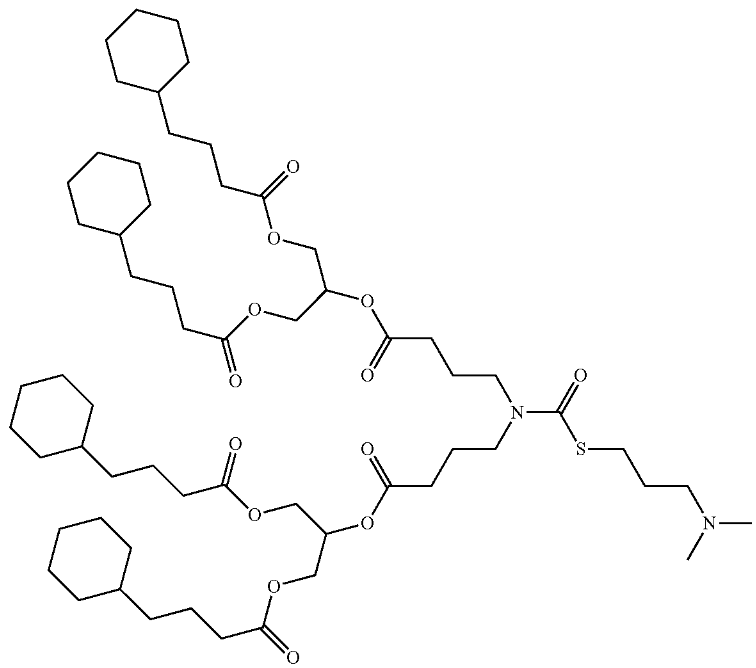
General Scheme
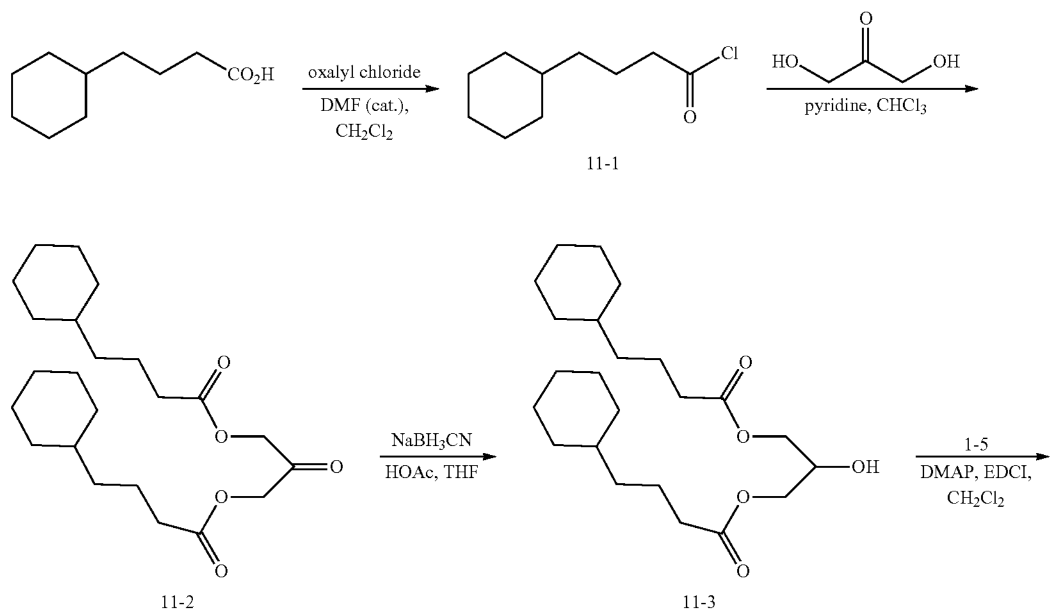

-continued
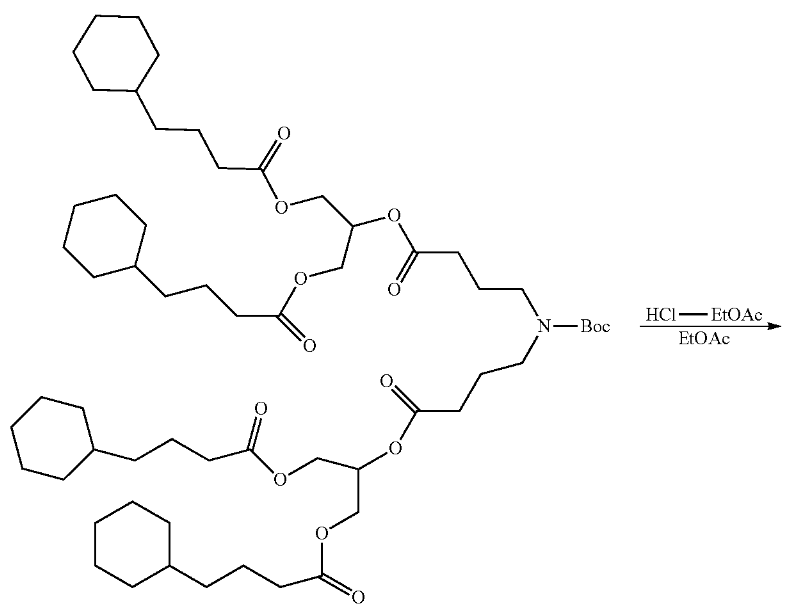
11-4
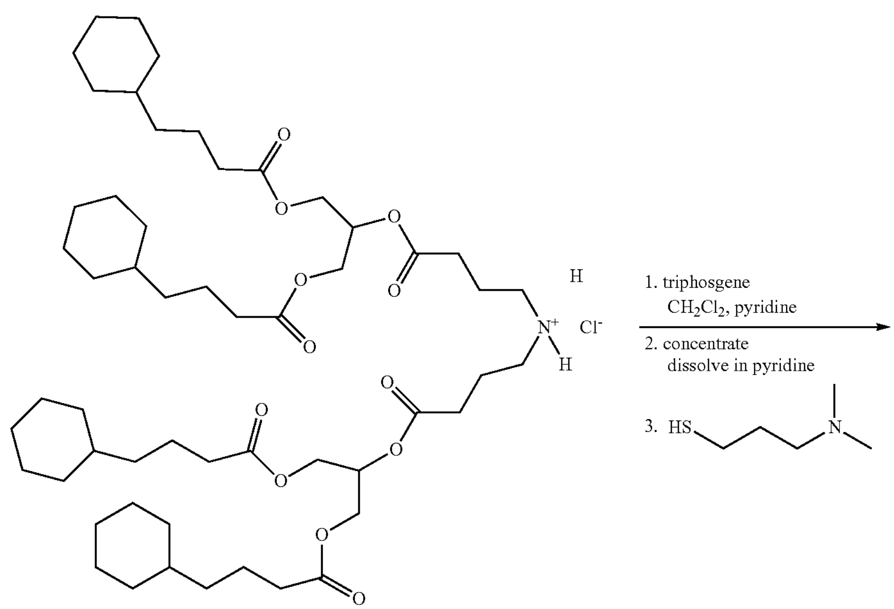
11-5

-continued

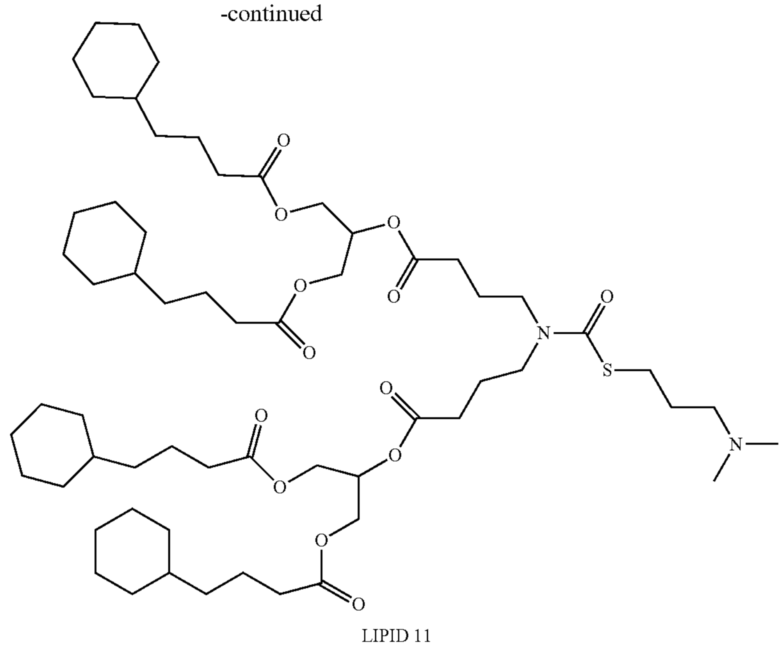

LIPID 11

Synthesis of 11-1: 4-Cyclohexylbutanoyl chloride

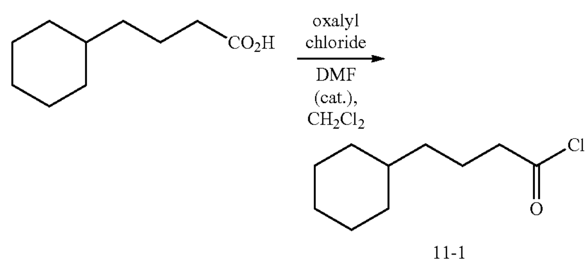

11-1

Into a 1 L 3-necked round-bottom flask purged and maintained with an inert atmosphere of nitrogen, was placed a solution of 4-cyclohexylbutanoic acid (50 g, 1.0 eq) in $CHCl_3$ (500 ml), and then, DMF (0.25 ml) was added. The solution was cooled in an ice-water bathn then oxalyl chloride (74.1 g, 2.0 eq) was added dropwise over a period of 30 minutes. The mixture was stirred at room temperature under nitrogen overnight. The mixture was concentrated under vacuum. This resulted in 55.7 g (99.9% yield) 11-1 as yellow oil that was used as such in the next step.

Synthesis of 11-2: 2-Oxopropane-1,3-diyl bis(4-cyclohexylbutanoate)

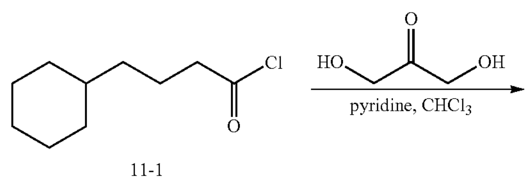

11-1

-continued

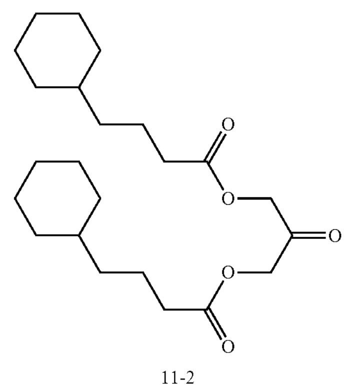

11-2

Into a 2 L 3-necked round-bottom flask purged and maintained with an inert atmosphere of nitrogen, was placed a solution of 11-1 (55.7 g, 2.5 eq), the solution was cooled in an ice-water bath and 1,3-dihydroxyacetone (10.6 g, 1.0 eq) in $CHCl_3$ (1114 mL), was then added over a period of 1 hour. Pyridine (37.3 g, 4.0 eq) was added to the mixture while maintaining temperature at 0° C. over 40 minutes. The mixture was stirred at room temperature overnight under nitrogen. The reaction mixture was quenched with water (1 L). The organic phase were separated and the aqueous layer was was extracted with $CH_2Cl_2$ (3×200 mL). The organic phases were combined and washed with 5% aqueous $NaHCO_3$ solution (300 mL), 5% aqueous HCl (300 mlL), and brine (300 mL). The solution was then dried over anhydrous $Na_2SO_4$ and the product was obtained by evaporation. This resulted in 56.4 g of crude 11-2 as yellow oil that was used as such in the next reaction.

Synthesis of 11-3: 2-hydroxypropane-1,3-diyl bis(4-cyclohexylbutanoate)

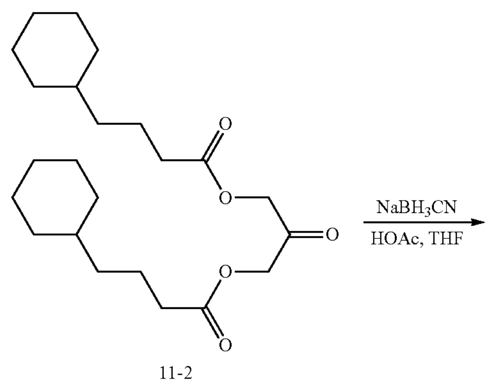

11-2

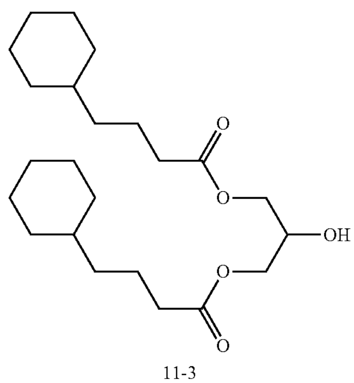

11-3

Into a 1 L 3-necked round-bottom flask purged and maintained with an inert atmosphere of nitrogen, was placed a solution of 11-2 (56.4 g, 1.0 eq) in THF (550 ml), the mixture was cooled in an ice-water bath. To the cooled solution was added HOAc (11.13 g, 1.3 eq) at 0° C. And then to the mixture was added $NaBH_3CN$ (10.79 g, 1.2 eq) at 0° C. The mixture was stirred overnight at room temperature. The reaction mixture was quenched with water (500 mL). The mixture was extracted with $CH_2Cl_2$ (3×200 ml). The organic layers were combined and washed with 5% aqueous $NaHCO_3$ solution (200 ml), 5% aqueous HCl (200 ml), and brine (200 ml). The solution was then dried over anhydrous $Na_2SO_4$ and concentrated under vacuum. The residue was dissolved in $CH_2Cl_2$ (150 mL), silica gel was added (60 g, type: ZCX-2, 100-200 mesh) and the crude product was adsorbed on the silica gel silica gel and purified on a silica gel column (240 g, type: ZCX-2, 100-200 mesh) with a petroleum ether/EtOAc gradient from 100:0 to 80:20. The fractions containing 11-3 were pooled and concentrated and dried under vacuum to get 30.3 g (65.0% overall yield in 2 steps) of 11-3 as yellow oil. ELSD A: water/0.05% TFA: B: $CH_3CN$/0.05% TFA 95:5 to 5:95 A/B at 3 min, hold 0.7 min): RT 0.76 min, m/z 396.29 (Calcd.), (found) 419.29 (M+Na).

Synthesis of 11-4: ((4,4'-((tert-butoxycarbonyl) azanediyl)bis(butanoyl))bis(oxy))bis(propane-2,1,3-triyl) tetrakis(4-cyclohexylbutanoate)

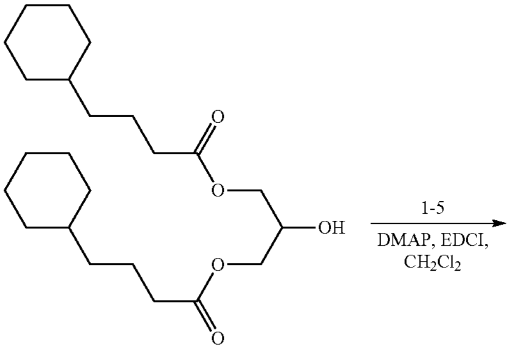

11-3

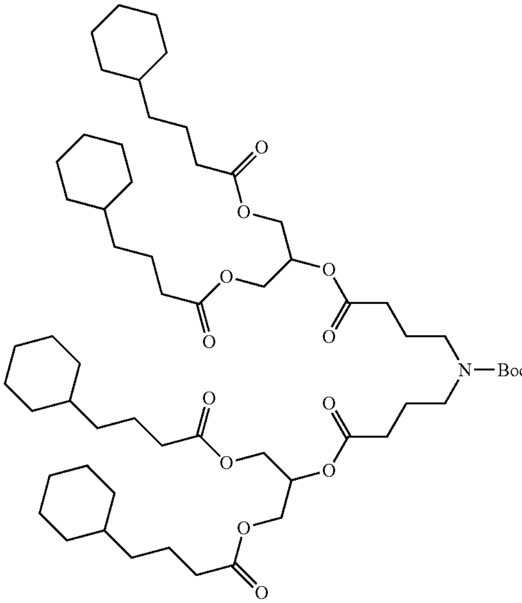

11-4

Into a 250 ml 3-necked round-bottom flask purged and maintained with an inert atmosphere of nitrogen, was added 11-3 (5.46 g, 2.0 eq) to the solution of 1-5 (2.05 g, 1.0 eq) in $CH_2Cl_2$ (100 mL), and the mixture was cooled in an ice-water bath. To the solution were added DMAP (2.3 g, 1.0 eq) followed by EDCI (14.51 g, 4.0 eq) at 0° C. The reaction mixture was stirred overnight at room temperature. The reaction was then quenched with 10% aqueous citric acid (200 mL), the organic phase was separated and washed with 10% aqueous $NaHCO_3$ (200 mL), and brine (200 mL). The mixture was dried over anhydrous sodium sulfate and concentrated under vacuum. This material was combined with another 7.05 g scale reaction (based on 11-3) and the combined material was adsorbed on silica gel (30 g, type: ZCX-2, 100-200 mesh) and purified on a silica gel column (90 g, type: ZCX-2, 100-200 mesh) with a petroleum ether/EtOAc gradient from 100:0 to 65:35. The fractions containing 11-4 were pooled and concentrated and dried under vacuum to get 14.2 g (43.0%) 11-4 as yellow oil. ELSD A: water/0.05% TFA: B: $CH_3CN$/0.05% TFA 95:5 to 5:95 A/B at 3 min, hold 0.7 min): RT 2.77 min, m/z 1045.71 (Calcd.), (found) 1068.55 (M+Na).

Synthesis of 11-5: bis(4-((1,3-bis((4-cyclohexylbutanoyl)oxy)propan-2-yl)oxy)-4-oxobutyl)ammonium chloride

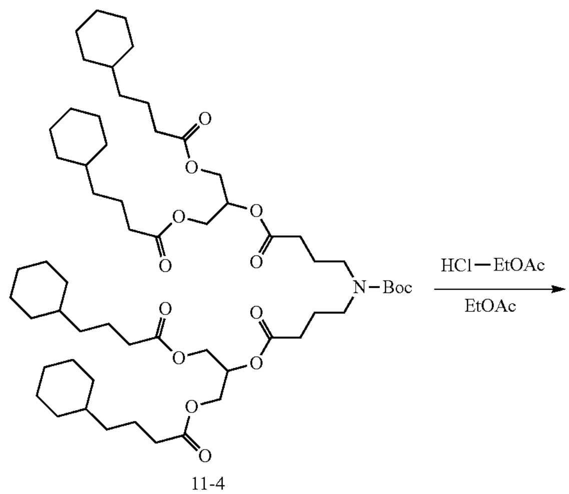

11-4

-continued

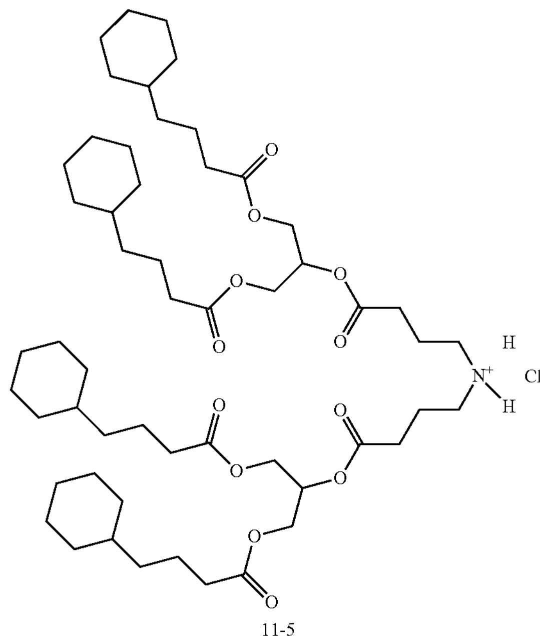

11-5

Into a 250 ml round-bottom flask purged and maintained with an inert atmosphere of nitrogen, was placed solution of 11-4 (14.17 g, 1.0 eq) in EtOAc (71 mL), and the solution was cooled in an ice-water bath. To the solution was added HCl in EtOAc (142 mL, 2 mol/L) dropwise at 0-10° C. The resulting solution was stirred overnight at room temperature. The resulting mixture was concentrated under vacuum. This provided 13.6 g (99.9% yield) 11-5 as light yellow oil. ELSD A: water/0.05% TFA: B: $CH_3CN$/0.05% TFA 95:5 to 5:95 A/B at 3 min, hold 0.7 min): RT 0.94 min, m/z 945.65 (Calcd.), (found) 946.60 (M+H).

Synthesis of LIPID 11: ((4,4'-((((3-(Dimethylamino)propyl)thio)carbonyl) azanediyl)bis(butanoyl))bis(oxy))bis(propane-2,1,3-triyl) tetrakis(4-cyclohexylbutanoate)

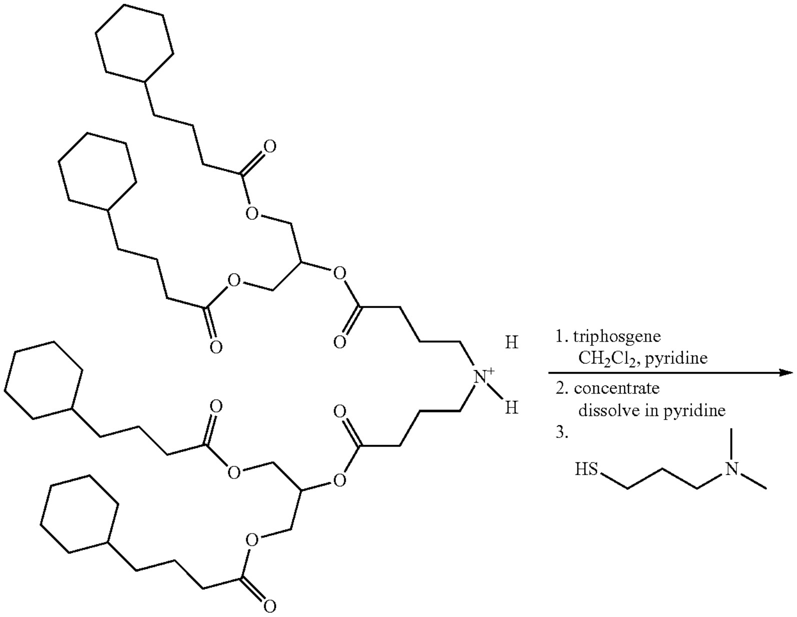

11-5

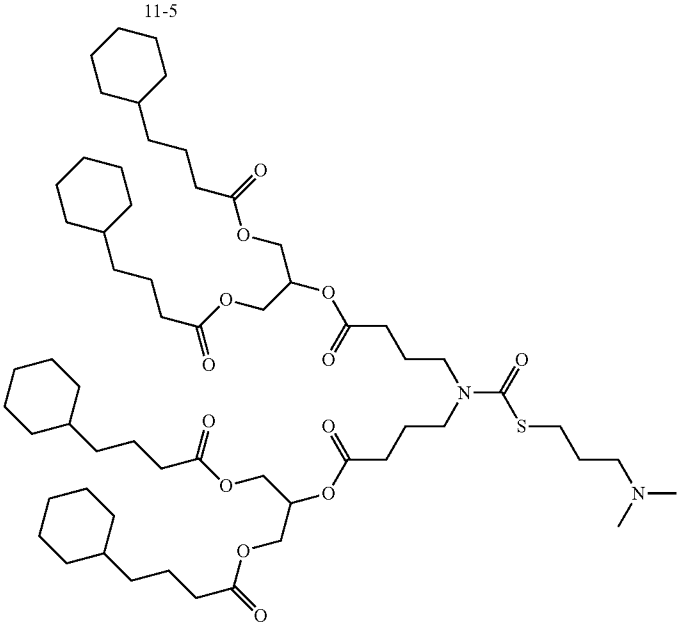

LIPID 11

Into a 1 L 3-necked round-bottom flask purged and maintained with an inert atmosphere of nitrogen, was placed a solution of 11-5 (12.0 g, 1.0 eq) in $CH_2Cl_2$ (420 mL) and the solution was cooled in an ice-water bath. To the solution was added triphosgene (5.44 g, 1.5 eq) at 0° C. This was followed by the addition of pyridine (4.82 g, 5.0 eq) dropwise with stirring at 0° C. The mixture was stirred for 4 h at room temperature and then concentrated under vacuum. The residue was dissolved in pyridine (240 mL) and the resulting solution was cooled in an ice-water bath. To this solution was added 3-(dimethylamino)propane-1-thiol (2.91 g, 2.0 eq) dropwise with stirring at 0° C. over 10 min. The resulting solution was stirred overnight at room temperature. The reaction mixture was concentrated under vacuum. The residue was diluted with DCM (200 ml). The mixture was washed with 10% aqueous $NaHCO_3$ (2×200 mL), brine (100 mL), dried over anhydrous sodium sulfate, filtered and concentrated under vacuum. The crude product was adsorbed on silica gel (20 g, type: ZCX-2, 100-200 mesh) and purified on a silica gel column (80 g, type: ZCX-2, 100-200 mesh) with an n-heptane/acetone gradient from 100:0 to 65:35. The fractions containing pure product were pooled and concentrated and dried under vacuum to get 2 g 11 that was dissolved in n-heptane (40 ml, 20 V) and activated charcoal powder (0.22 g) was added. The mixture was stirred for 4 h at room temperature and then filtered. The filtrate was concentrated under vacuum. This resulted in 2 g (14.4% yield) of 11 as light-yellow oil. ELSD A: water/0.05% TFA: B: $CH_3CN$/0.05% TFA 95:5 to 5:95 A/B at 3 min, hold 0.7 min): RT 1.00 min, m/z 1090.71 (Calcd.), (found) 1091.60 (M+H); $^1H$ NMR (300 MHz, $CDCl_3$): δ 5.24 (m, 2H), 4.32 (dd, J=11.9, 4.4 Hz, 4H), 4.15 (dd, J=11.9, 5.7 Hz, 4H), 3.39 (brm, 4H), 2.92 (t, J=7.3 Hz, 2H), 2.27-2.38 (14H), 2.05 (s, 6H), 1.85-2.00 (6H), 1.57-1.83 (29H), 1.11-1.28 (23H), 1.06-1.08 (8H).

Example 12. Synthesis of LIPID 12: ((6,6'-(((3-(Dimethylamino)propyl)thio) carbonyl) azanediyl) bis(hexanoyl))bis(oxy))bis(propane-2,1,3-triyl) tetrakis(3-cyclohexylpropanoate)

LIPID 12

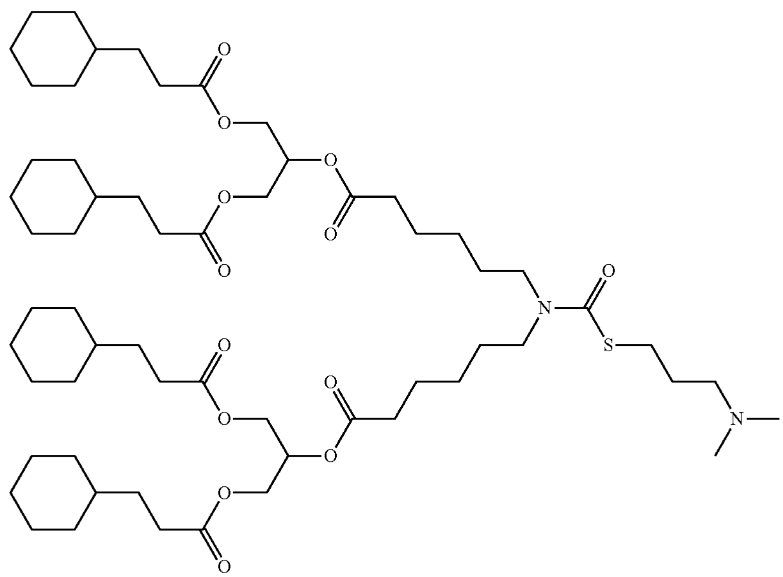

General Scheme

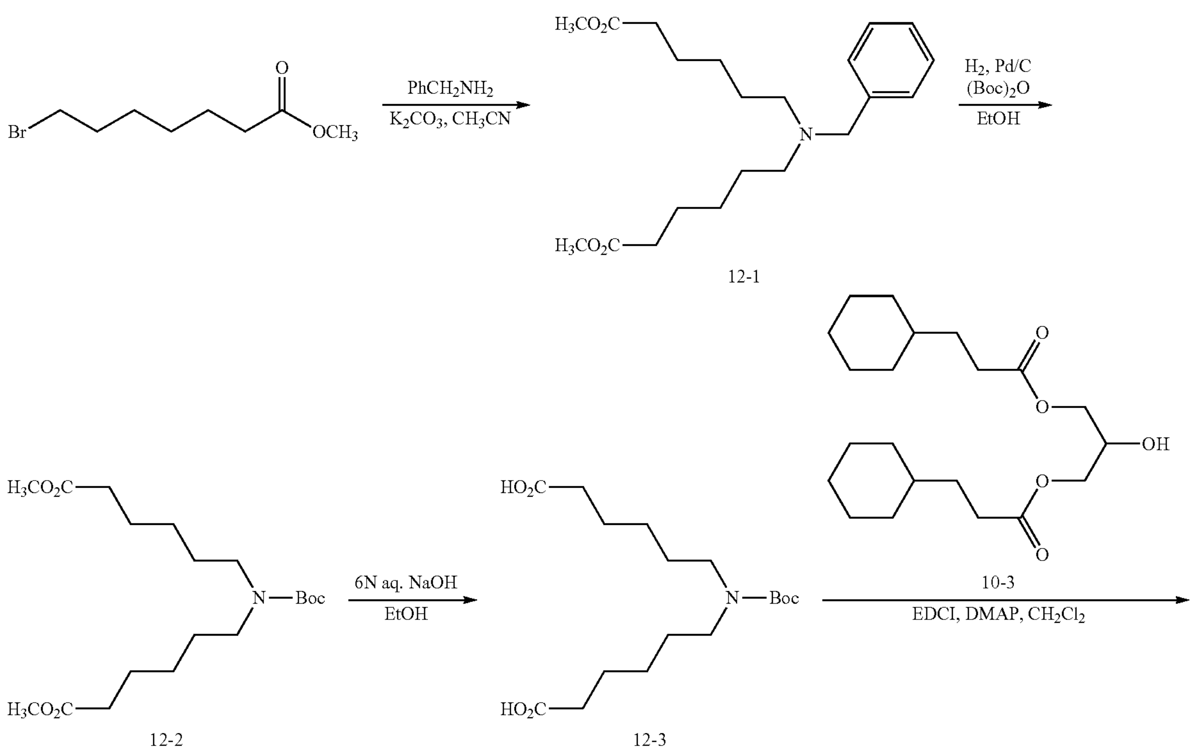

12-1

12-2

12-3

-continued
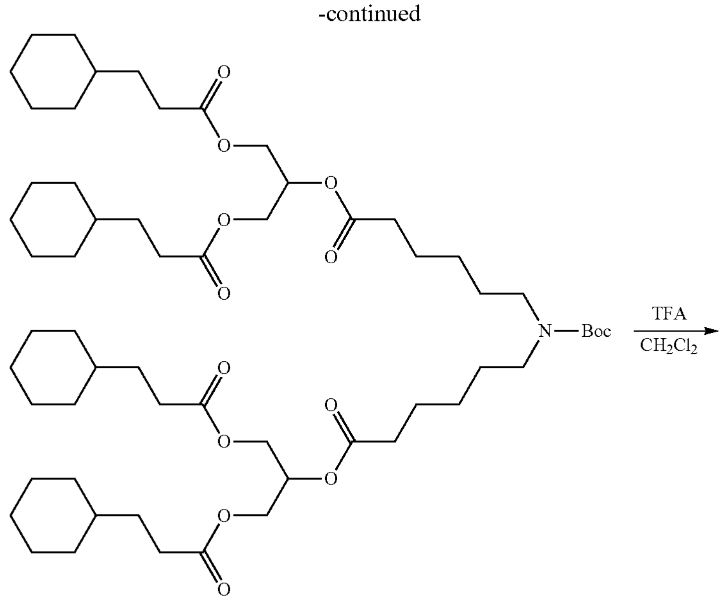
12-4
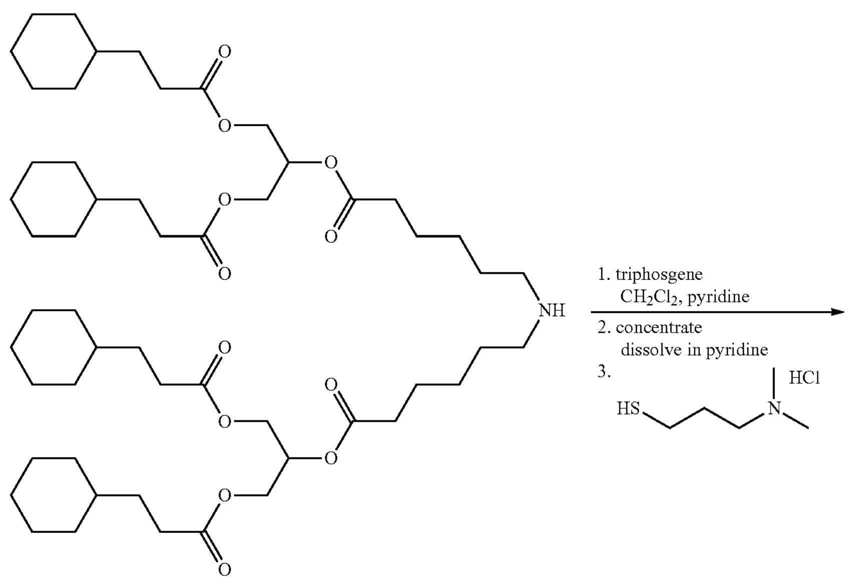
12-5

-continued

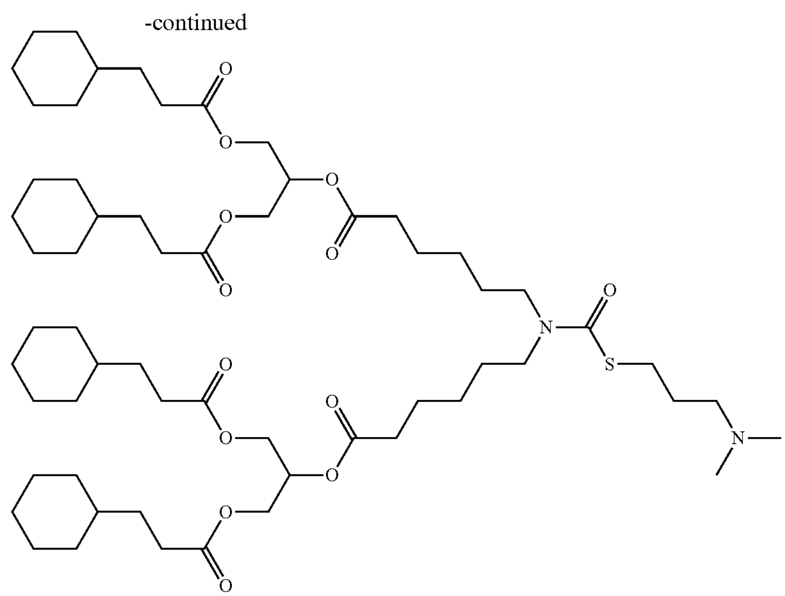

LIPID 12

Synthesis of 12-1: Dimethyl 6,6'-(benzylazanediyl)dihexanoate

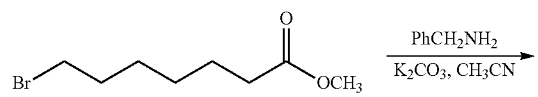

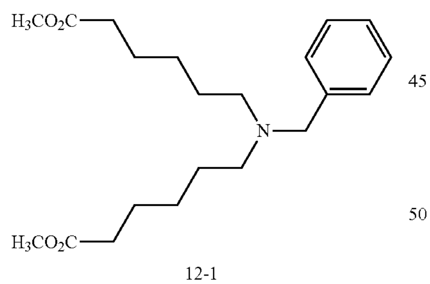

12-1

Charged $K_2CO_3$ (9.5 g, 2.3 eq), benzyl amine (3.2 g, 1.0 eq) and methyl 4-bromobutyrate (15.2 g, 2.3 eq) in $CH_3CN$ (64 mL) to a 250 ml four neck round bottle flask at 25° C. with mechanical agitation under $N_2$. The mixture was then heated (80° C.) and stirred for 15 h, The mixture was then cooled to 25° C. and the mixture was cast into water (65 mL) and the mixture was extracted with EtOAc (2×65 ml). The combined organic phases were dried ($Na_2SO_4$), filtered, and concentrated under vacuum to give crude 12-1 (10 g, crude) as yellow oil that was used as such in the next reaction.

Synthesis of 12-2: Dimethyl 6,6'-((tert-butoxycarbonyl)azanediyl)dihexanoate

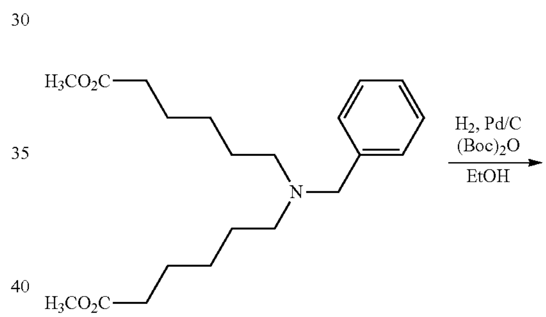

12-1

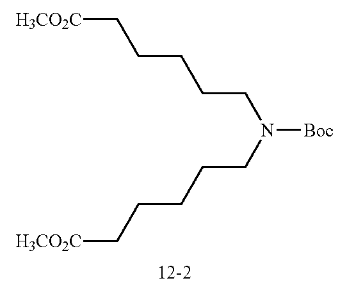

12-2

Charged 12-1 (10 g, 1.0 eq), (Boc) 20 (6.6 g, 1.1 eq) and Pd/C (1 g, 10% w/w) in EtOH (100 mL) into the 250 ml hydrogenation autoclave at ambient temperature. The mixture was stirred for 16 hrs at room temperature under 5 atm in the hydrogen atmosphere. The reaction mixture was filtered and concentrated under vacuum at 40° C. This resulted in 12-2 (11 g, crude) as light-brown oil. This was used as such in the next reaction.

Synthesis of 12-3: 6,6'-((tert-Butoxycarbonyl) azanediyl)dihexanoic Acid

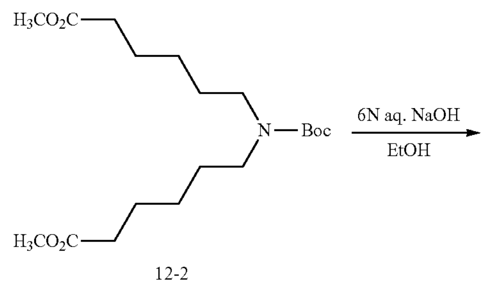

12-2

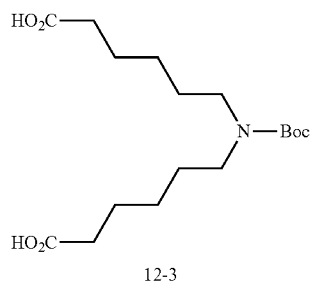

12-3

To a round bottom flask charged a solution of 12-2 (11 g, 1.0 eq) in ethanol (55 mL), at room temperature under nitrogen. 6 M aqueous NaOH (55 ml,) was added at room temperature. After the addition was complete the mixture was heated to 60° C. for 2 hours. The mixture was cooled to room temperature and was cast into brine (110 ml). The solution was extracted twice with n-BuOH/n-heptane (2:1, 110 mL) to remove the organic impurities. The aqueous phase was acidified by the addition of 3 mol/L aqueous HCl to about pH=3 and then extracted with t-BuOH:n-heptane (2:1) (110 mL, 2×). The combined organic phases were concentrated under reduced pressure to give a sticky solid. The residue was slurried with diethyl ether (22 mL) and filtered. Collected the filter cake to give 12-3 (5.6 g, 66% overall yield in three steps) as a white solid. ELSD A: water/0.05% TFA: B: $CH_3CN$/0.05% TFA 95:5 to 5:95 A/B at 3 min., hold 0.7 min): RT 1.64 min, m/z 345.22 (Calcd.), (found) 368.10 (M+Na).

Synthesis of 12-4: ((6,6'-((tert-Butoxycarbonyl) azanediyl)bis(hexanoyl))bis(oxy))bis(propane-2,1,3-triyl) tetrakis(3-cyclohexylpropanoate)

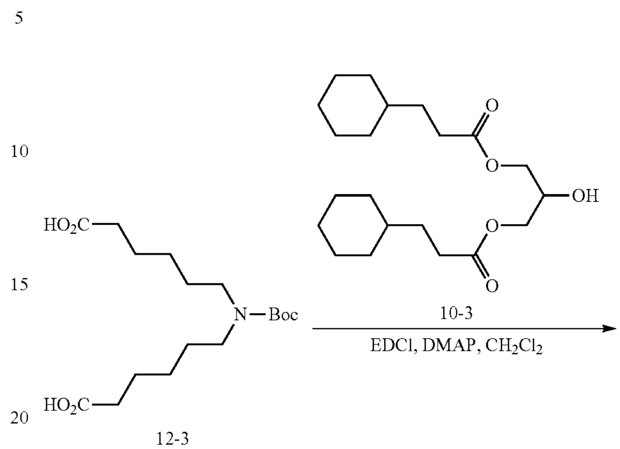

12-3

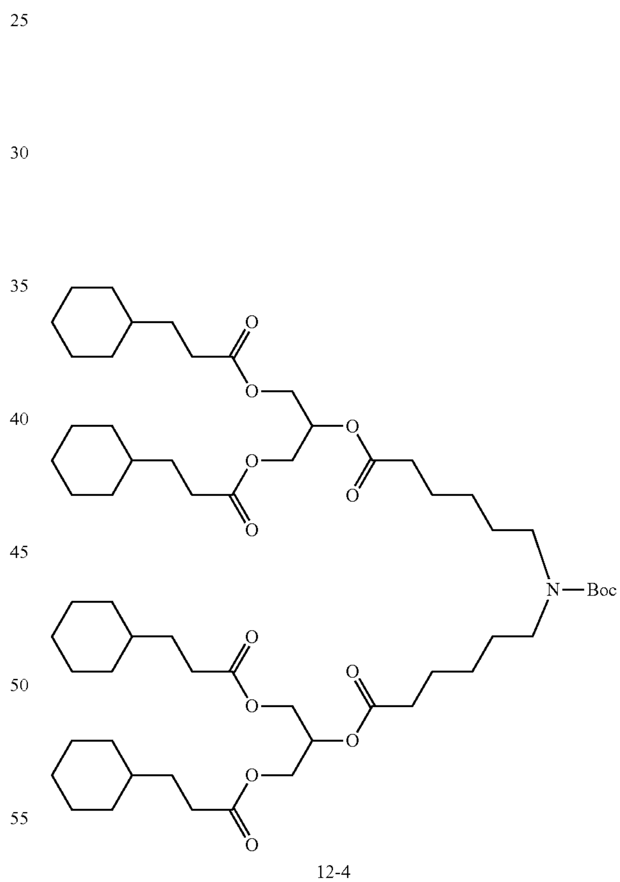

12-4

Into a 250 ml three-necked round-bottom flask, was placed 12-3 (5.6 g, 1.0 eq), 10-3 (10 g, 2.0 eq) and DMAP (1.65 g, 1.0 eq) in $CH_2Cl_2$ (85 mL), and the solution was cooled in an ice-water bath under nitrogen. EDCI (7.5 g, 2.2 eq) was added to the reaction mixture at 0° C., in portions over 15 minutes. After the addition was complete the reaction was warmed to room temperature and was stirred for 16 h at 20° C. The reaction mixture was cast into 10% aqueous citric acid (112 mL). The organic phase was separated, 10% aqueous citric acid (112 mL), brine (112 mL, dried with anhydrous $MgSO_4$ and then filtered. The solvent was removed under vacuul to give crude 12-4 which was dissolved with $CH_2Cl_2$ (65 mL) and he crude product was adsorbed on silica gel (30 g, type: ZCX-2, 100-200 mesh) and purified on a silica gel column (150 g, type: ZCX-2, 100-200 mesh) with a petroleum ether/EtOAc gradient from 100:0 to 88:12. The fractions containing pure product were pooled and concentrated and dried under vacuum to get 10.1 g (60%) of 12-4 as colorless oil. ELSD A: water/0.05% TFA: B: $CH_3CN$/0.05% TFA 95:5 to 5:95 A/B at 3 min., hold 0.7 min): RT 2.2 min, m/z 1045.71 (Calcd.), (found) 1068.65 (M+Na).

Synthesis of 12-5: ((6,6'-Azanediylbis(hexanoyl))bis(oxy))bis(propane-2,1,3-triyl) tetrakis(3-cyclohexylpropanoate)

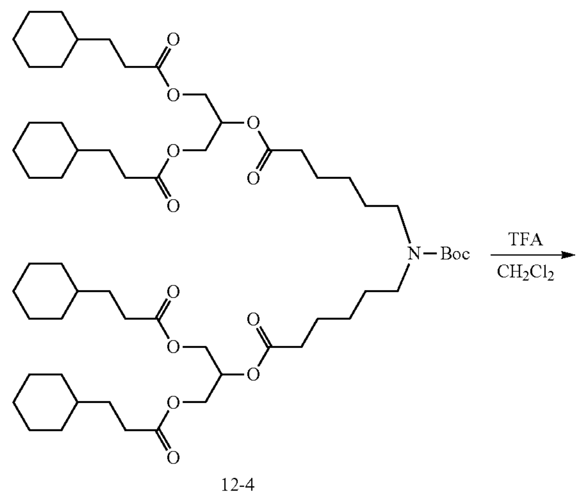

12-4

-continued

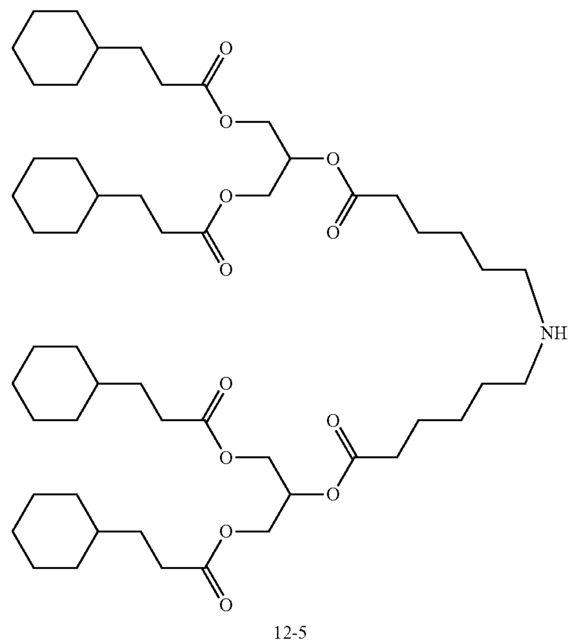

12-5

Into a 100 mL three-neck round-bottom flask, was placed 12-4 (5 g, 1.0 eq) in $CH_2Cl_2$ (50 mL) and the solution was cooled in an ice-water bath under nitrogen. Then TFA (7.5 mL) was added to reaction mixture at 0-15° C. After the addition was complete the solution was allowed to warm to room temperature and was stirred for 2 h. The mixture was concentrated under vacuum at 30° C., then n-heptane (100 mL) was added to the reaction mixture. The resulting cloudy mixture was washed with 17% aqueous sodium carbonate solution (500 mL), brine (250 mL, 3×), and dried over anhydrous $MgSO_4$. Filtration and concentration under vacuum afforded 12-5 (4.5 g, 90% yield) as yellow oil. ELSD A: water/0.05% TFA: B: $CH_3CN$/0.05% TFA 95:5 to 5:95 A/B at 3 min., hold 0.7 min): RT 0.94 min, m/z 945.65 (Calcd.), (found) 946.60 (M+H).

Synthesis of LIPID 12: ((6,6'-((((3 (dimethylamino) propyl)thio)carbonyl)azanediyl)bis(hexanoyl))bis (oxy))bis(propane-2,1,3-triyl) tetrakis(3-cyclohexyl-propanoate)

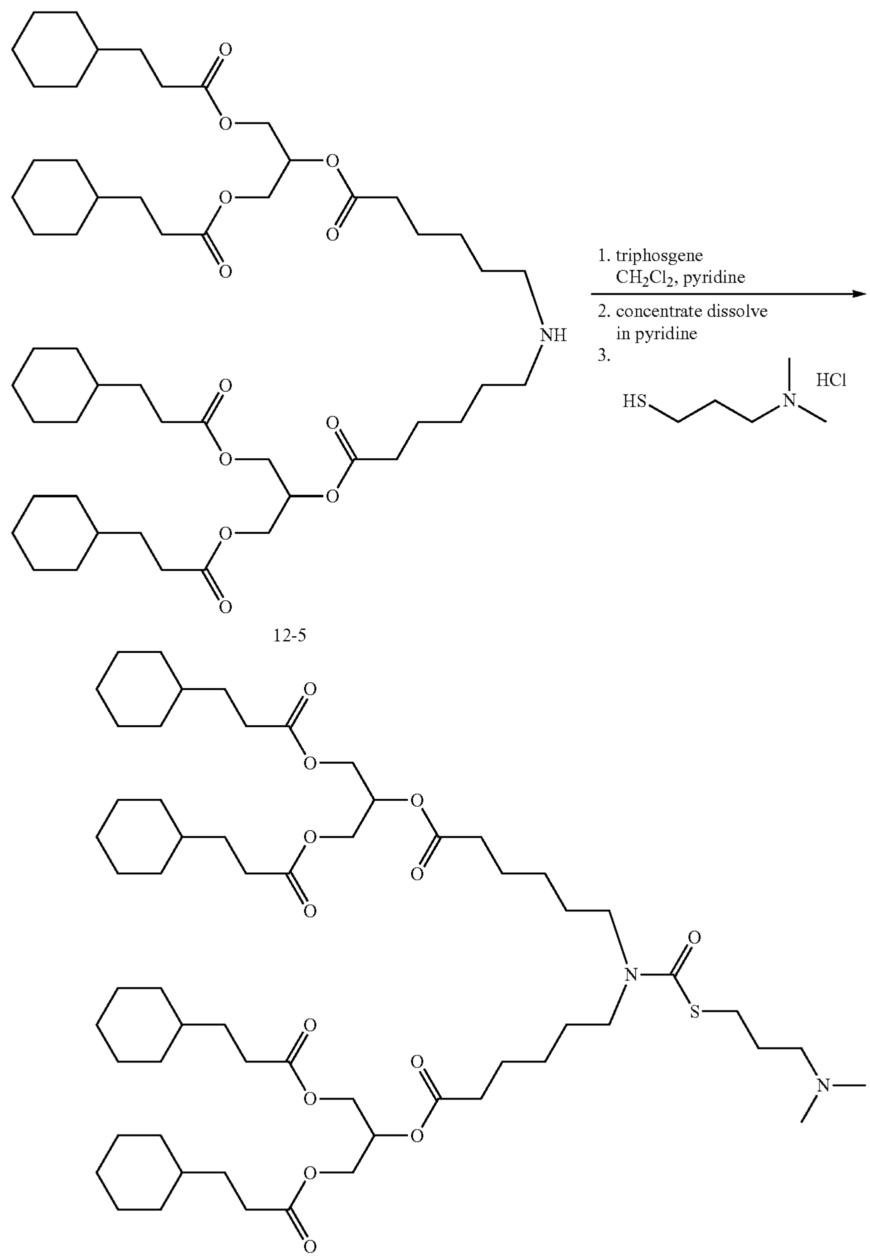

12-5

LIPID 12

Into a 250 mL three-necked round-bottom flask was added 12-5 (4.5 g, 1.0 eq) and $CH_2Cl_2$ (68 mL), and the solution was cooled in an ice-water bath under nitrogen. Then triphosgene (1.4 g, 1.0 eq) was added to the cooled solution, followed by the addition of pyridine (1.88 g, 5.0 eq) over a period of 30 minutes. After addition was complete, the reaction mixture was warmed to room temperature and then stirred for 4 hours. The solvent was removed under vacuum and the residue was dissolved in pyridine (90 mL) and the mixture was cooled in an ice-water bath under nitrogen. To this cooled solution was added 3-(dimethylamino)-1-propanethiol hydrochloride (0.57 g, 1.1 eq). After the addition was complete the reaction mixture was warmed to room temperature and was stirred for 18 hours. The mixture was concentrated under vacuum, the temperature was kept less than or equal to 20° C. to provide crude LIPID 12 which was dissolved in $CH_2Cl_2$ (90 mL) and the resulting solution was washed with 10% aqueous citric acid solution (45 mL), brine (45 mL, 3×), 10% aqueous sodium bicarbonate solution (45 mL), and brine (45 ml, 2×). The organic phase was dried over anhydrous sodium sulfate, filtered, and concentrated under reduced vacuum to give crude LIPID 12. Crude LIPID 12 was dissolved in $CH_2Cl_2$ (30 mL) and adsorbed on silica gel (15 g, type: ZCX-2, 100-200 mesh) and purified on a silica gel column (60 g, type: ZCX-2, 100-200 mesh) with a n-heptane/acetone gradient from 100:0 to 80:20. The fractions containing pure product were pooled and concentrated and dried under vacuum to get 1.5 g (29%) of LIPID 12 as a light-yellow oil. ELSD A: water/0.05% TFA: B: $CH_3CN$/0.05% TFA 95:5 to 5:95 A/B at 3 min., hold 0.7 min): RT 0.87 min, m/z 1090.71 (Calcd.), (found) 1091.60 (M+H); $^1$H NMR (300 MHz, $CDCl_3$): δ 5.27 (m, 2H), 4.30 (dd, J=11.9, 4.4 Hz, 4H), 4.1 (dd, J=11.9, 5.8 Hz, 4H), 3.27 (brm, 4H), 2.90 (t, J=7.2 Hz, 2H), 2.45-2.20 (20H), 1.81 (m, 2H), 1.71-1.63 (22H), 1.55-1.47 (12H), 1.34-1.07 (22H), 0.94-0.77 (8H).

Example 13. Synthesis of LIPID 13: Nonanoic acid 2-(3-{(3-dimethylamino-propylsulfanylcarbonyl)-[2-(2-nonanoyloxy-1-nonanoyloxymethyl-ethoxycarbonyl)-ethyl]-amino}-propionyloxy)-3-octanoyloxy-propyl ester

LIPID 13

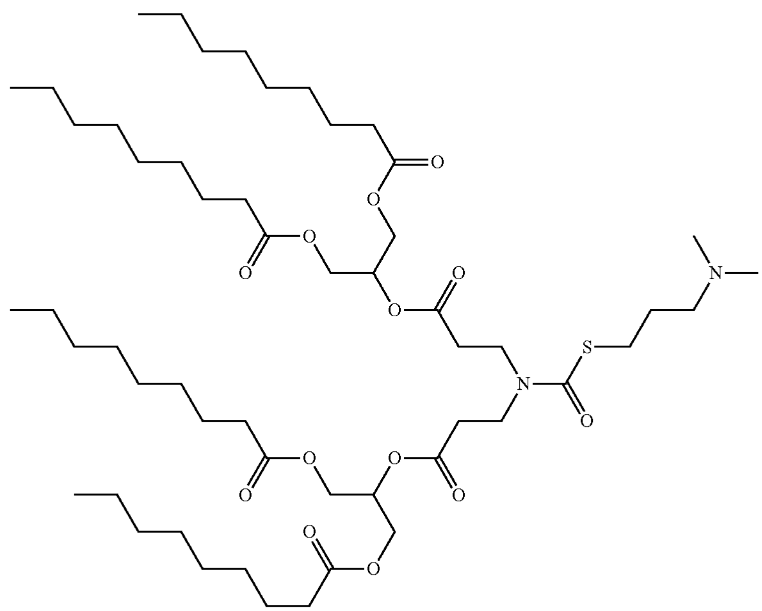

General Scheme

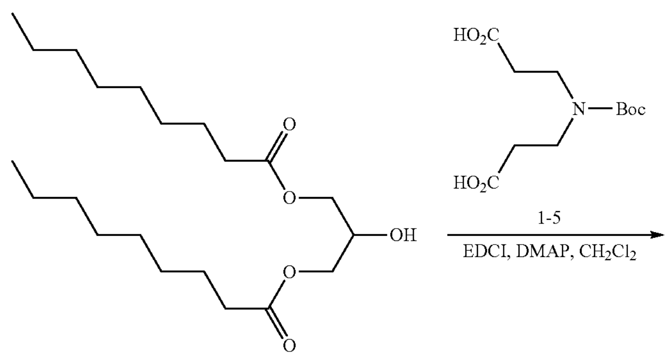

1-2

-continued
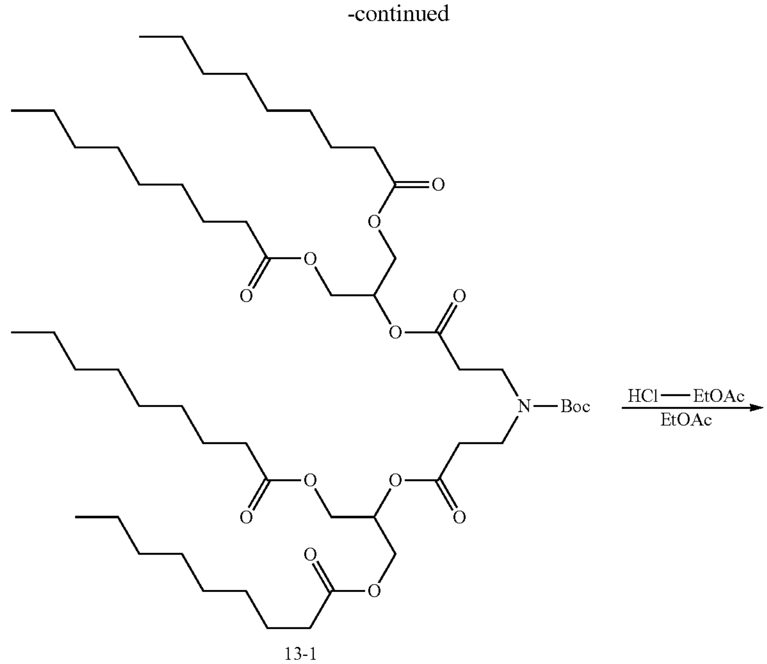
13-1
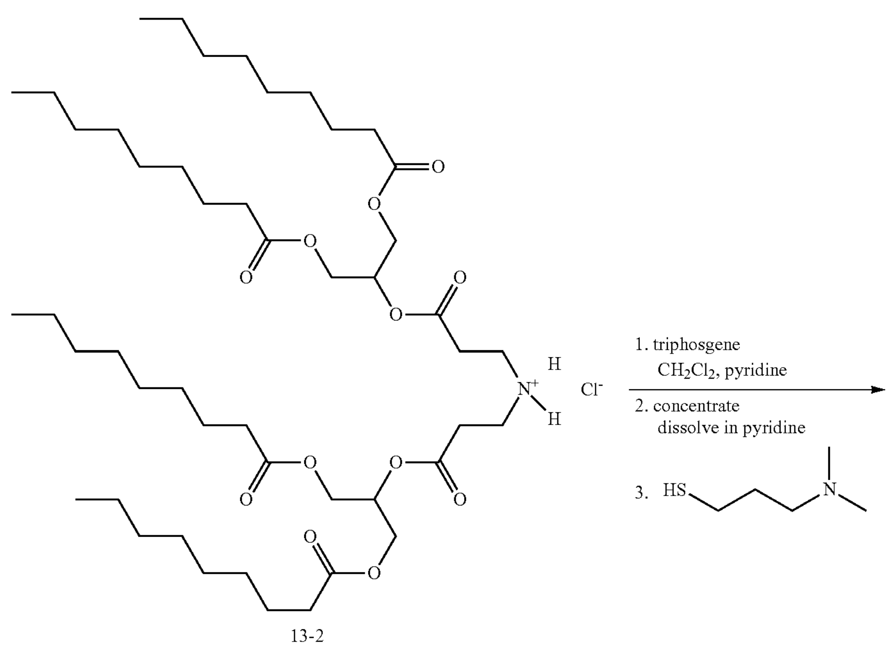
13-2

-continued
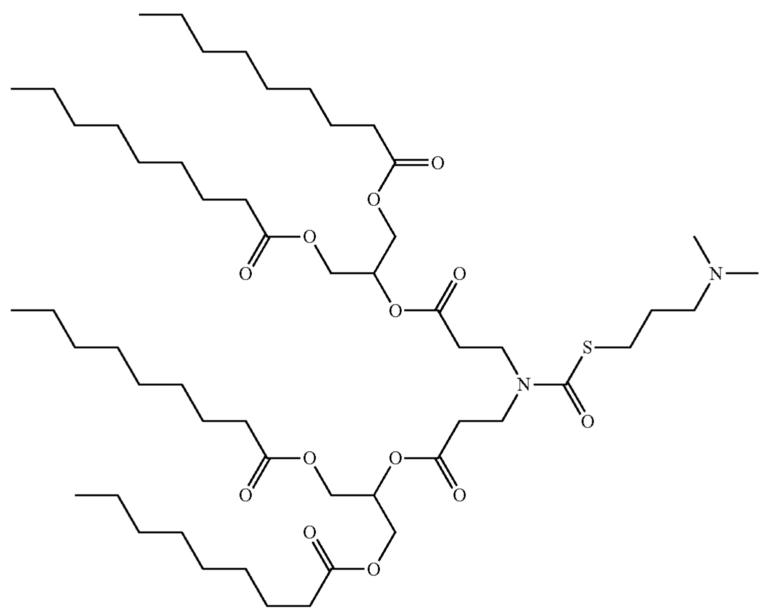
LIPID 13
Synthesis of 13-1: ((3,3'-((tert-butoxycarbonyl)azanediyl)bis(propanoyl))bis(oxy))bis(propane-2,1,3-triyl) tetranonanoate
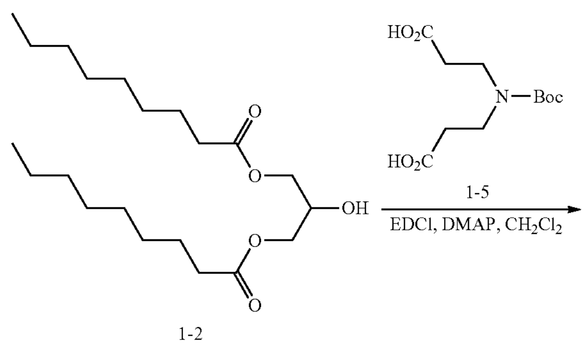
1-2
-continued
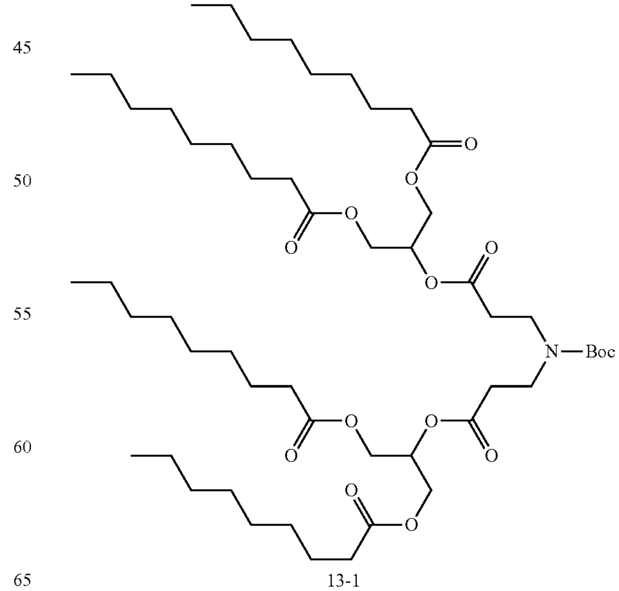
13-1

1-5 (7.3 g, 28.0 mmol) and 1-2 (18.8 g, 56.0 mmol) were dissolved in $CH_2Cl_2$ (110 mL) in a 500 mL 3-necked round bottom flask under nitrogen. The solution was cooled in an ice-water bath and DMAP (3.4 g, 28.0 mmol) and EDCI (21.5 g, 0.112 mol) were added in order. After the addition was complete, the mixture was warmed to room temperature and was allowed to stir for 16 hours. The mixture was cast into 10% aq. Citric acid (200 mL), the organic phase was separated, washed with brine (200 mL) and dried over anhydrous $Na_2SO_4$. The dessicant was removed by filtration through a sintered glass funnel and to the filtrate was added 50 g of silica gel (type: ZCX-2, 100-200 mesh). The solvent was removed in vacuo with a rotary evaporator bath temperature of 35° C. The silica gel containing adsorbed 13-1 was placed atop a column of silica gel (50 mm OD, 200 g silica gel, type: ZCX-2, 100-200 mesh. The column was eluted with a gradient of petroleum ether:EtOAc 100:0 to 97:3, 200 mL fractions. TLC analysis indicated fractions containing 13-1 which were combined and concentrated in vacuo to afford 13-1 (12.8 g, 13.2 mmol, 47%) as a pale yellow, viscous oil. $^1$H-NMR (300 mHz, DMSO-$d_6$): δ 5.18 (br m, 2H), 4.26 (m, 4H), 4.13 (m, 4), 2.29 (t, J=7.2 Hz, 8H), 1.40-1.60 (14H), 1.38 (s, 9H), 1.18-1.32 (42H), 0.86 (m, 12H).

Synthesis of 13-2: ((3,3'-Azanediylbis(propanoyl)) bis(oxy))bis(propane-2,1,3-triyl) tetranonanoate hydrochloride Salt

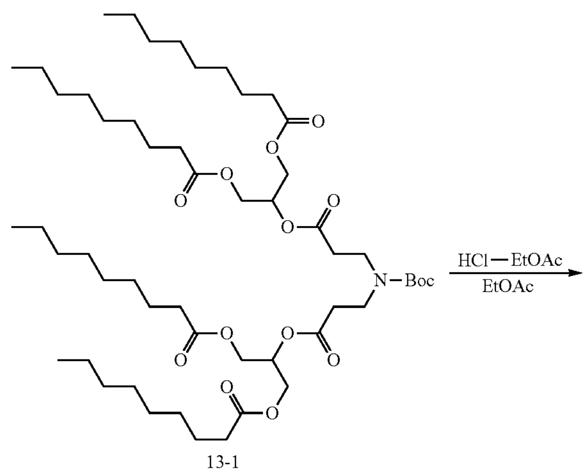

13-1

-continued

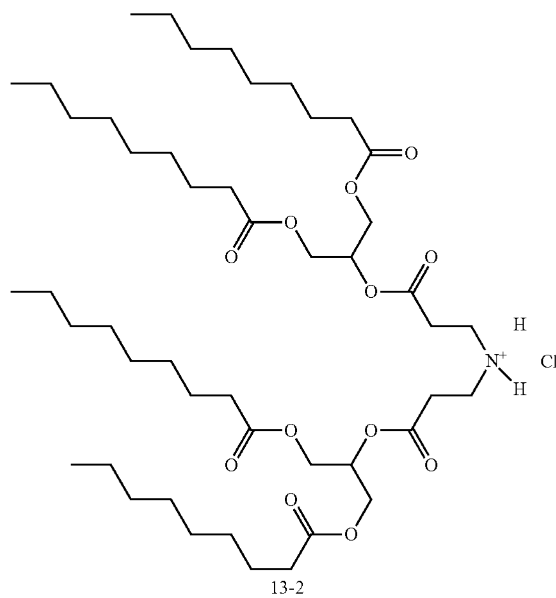

13-2

To a solution of 13-1 (12.8 g, 13.2 mmol) in EtOAc (75 mL), cooled in an ic-water bath under nitrogen, was added a solution of HCl in EtOAc (2M, 80 mL, 0.160 mol) at such a rate that the internal temperature remained between 0-10° C. After the addition was complete, the mixture was allowed to warm to room temperature and was stirred for 14 hours. Concentration in vacuo provided the HCl salt 13-2 (8.1 g, 9.37 mmol, 71%) as a light yellow, viscous oil. $^1$H-NMR (300 mHz, DMSO-$d_6$): δ 5.19 (br m, 2H), 4.25 (m, 4H), 4.14 (m, 4H), 2.73 (br t, J=6.9 Hz, 4H), 2.40 (br t, J=6.9 Hz, 4H), 2.29 (br t, J=7.2 Hz, 8H), 1.38-1.58 (8H), 1.16-1.32 (40H), 0.87 (m, 12H).

Synthesis of LIPID 13: 2-((3-((((3-(Dimethylamino)propyl)thio)carbonyl)(3-((1-(nonanoyloxy)-3-(octanoyloxy)propan-2-yl)oxy)-3-oxopropyl)amino)propanoyl)oxy)propane-1,3-diyl dinonanoate

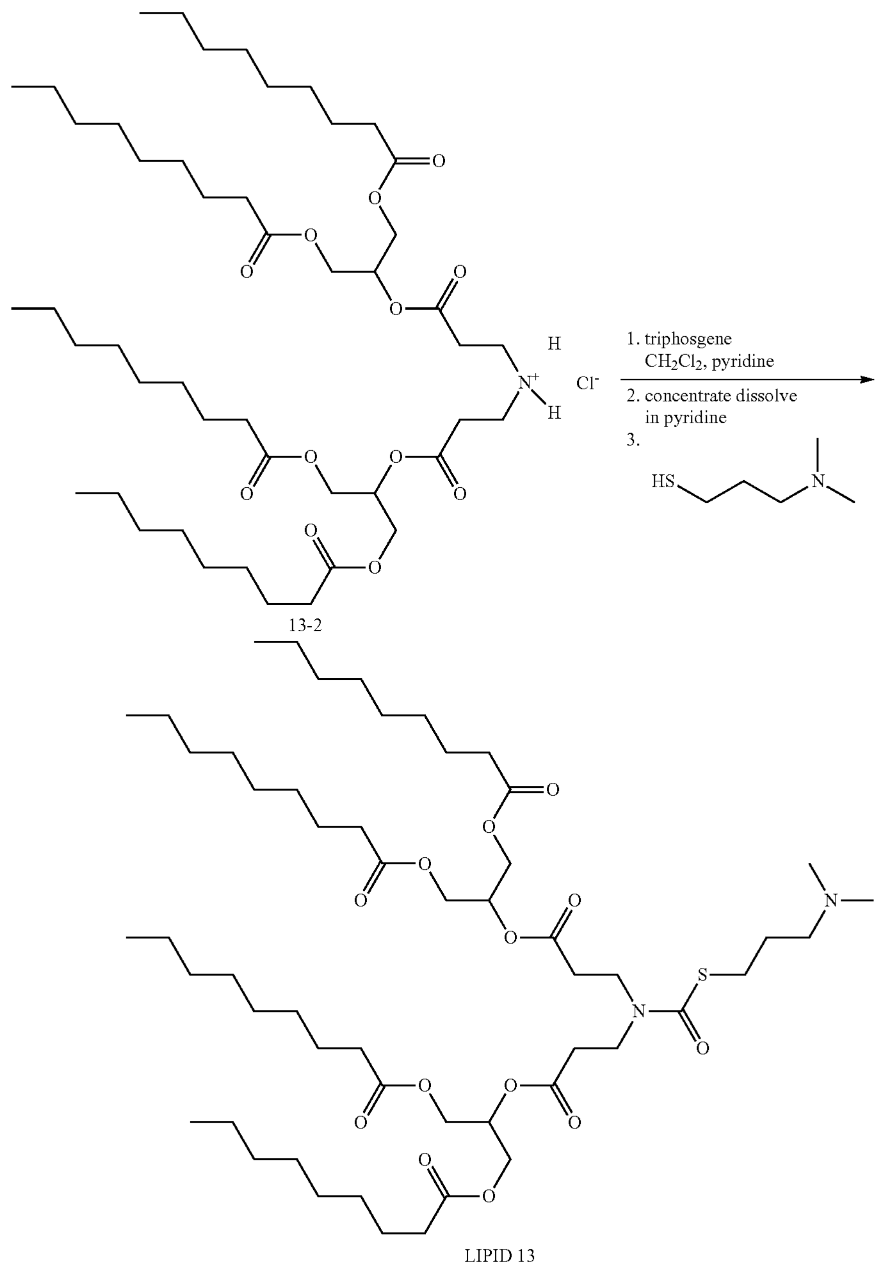

13-2

LIPID 13

To a solution of 13-2 (8.1 g, 9.37 mmol) in $CH_2Cl_2$ (280 mL), cooled in an ice-water bath under nitrogen, was added triphosgene (2.77 g, 9.33 mmol) in one portion, followed by the dropwise addition of pyridine (3.68 g, 46.52 mmol). After the addition was complete the reaction mixture was allowed to warm to room temperature and stir for 4 hours. The solvent was removed in vacuo (bath temperature 25° C.) and the residue was dissolved in pyridine (160 mL). The solution was cooled in an ice-water bath under nitrogen and 3-dimethylamino-propane-1-thiol (1.32 g, 11.1 mmol) was added dropwise over 10 minutes. After the addition was complete, the mixture was allowed to warm to room temperature and was stirred for 14 hours. The solvent was removed in vacuo and the residue was dissolved in $CH_2Cl_2$ (200 mL). The solution was washed with 10% aq. citric acid (100 mL), 5% aq. $NaHCO_3$ (100 mL), brine (100 mL), and was dried over anhydrous $Na_2SO_4$. The drying agent was removed by filtration through a sintered glass funnel and silica gel (16 g, type ZCX02, 100-200 mesh) was added to the filtrate. The solvent was removed in vacuo (bath temperature 25° C.) and the silica gelt containing adsorbed 13 was placed atop a column of silica gel (81 g silica gel type ZCX02, 100-200 mesh)—using a combi-flash. The column was eluted with a gradient of n-heptane/acetone from 100:0 to 90:10, 100 mL fractions. TLC was utilized to locate qualified fractions which were combined and concentrated in vacuo to give 13 (1.9 g) which was judged to be 90% pure by HPLC. 13 was further purified by reverse phase prep-HPLC ($C_{18}$, A: water with 0.1% formic acid, B: acetonitrile, gradient 41% B to 58% B over 8 minutes. Qualified fractions were combined and concentrated in vacuo to yield 13 (1.01 g, 1.00 mmol, 10.6%) as a clear, pale yellow, viscous oil. HPLC Purity: 99.65%; ES-MS (+ mode): Calcd. 1014.68, Found 1015.95 ($M+H^+$); $^1$H-NMR (300 mHz, $CDCl_3$): δ 5.26 (m, 2H), 4.33 (m, 4H), 4.16 (m, 4H), 3.68 (br t, J=7.2 Hz, 4H), 2.94 (t, J=7.2 Hz, 2H), 2.68 (br t, J=7.2 Hz, 4H), 2.20-2.40 (16H), 1.81 (m, 2H), 1.52-1.66 (8H), 1.16-1.38 (40H), 0.90 (m, 12H).

Example 14. Synthesis of LIPID 14

LIPID 14

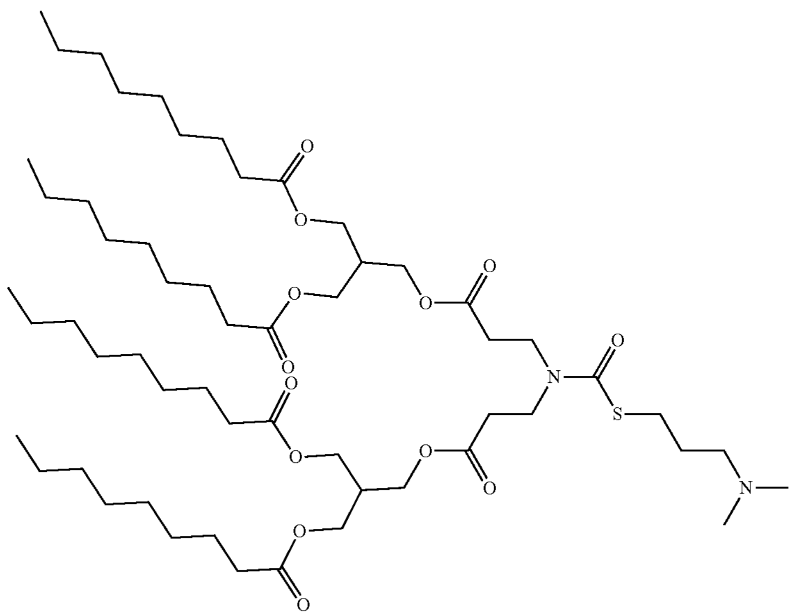

General Scheme

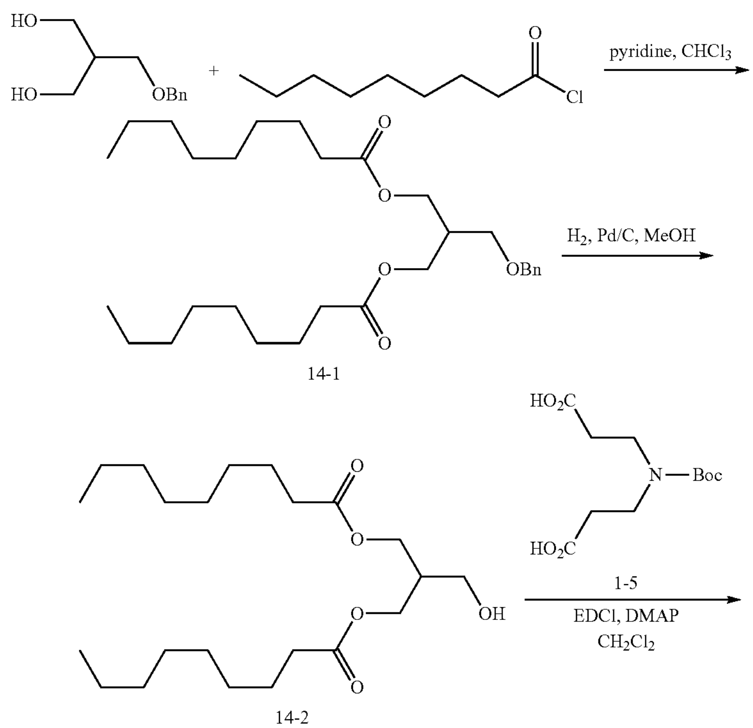

14-1

14-2

-continued
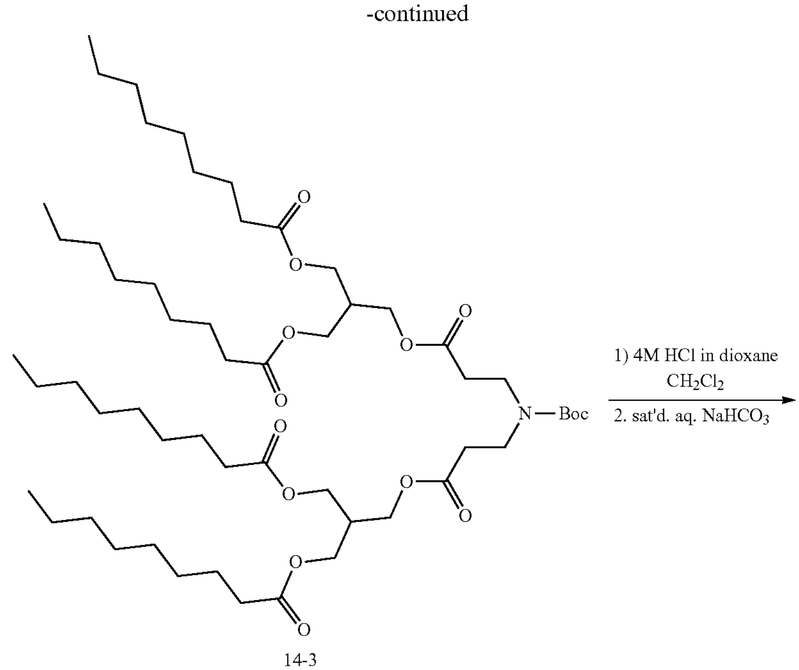
14-3
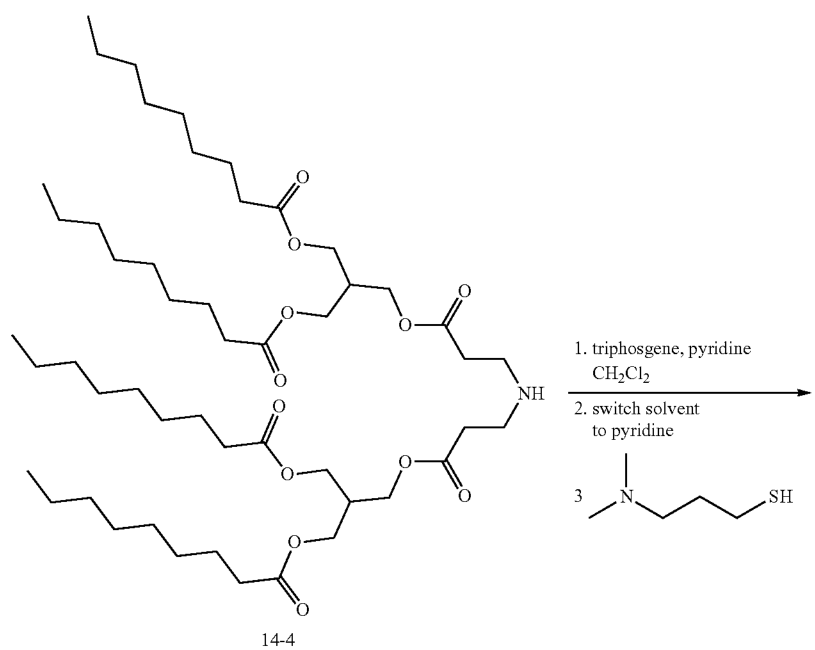
14-4

-continued

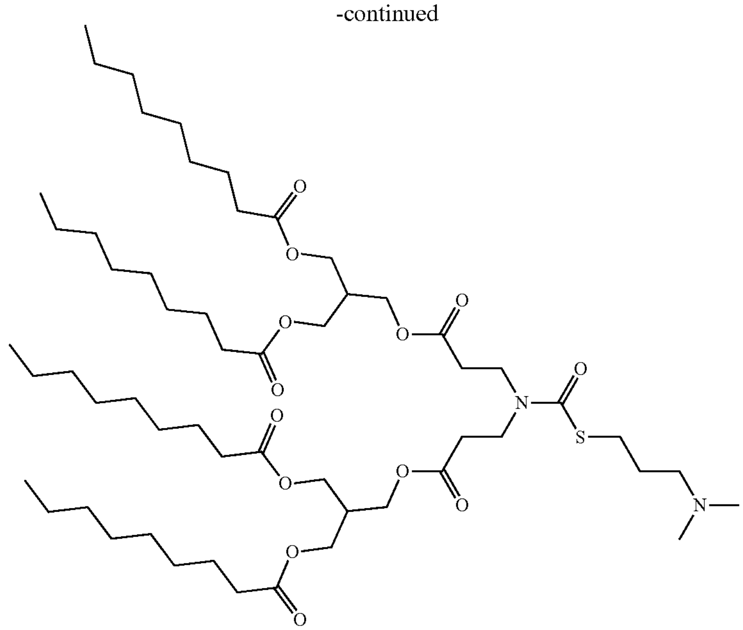

LIPID 14

Synthesis of 14-1: 2-((Benzyloxy)methyl)propane-1,3-diyl dinonanoate

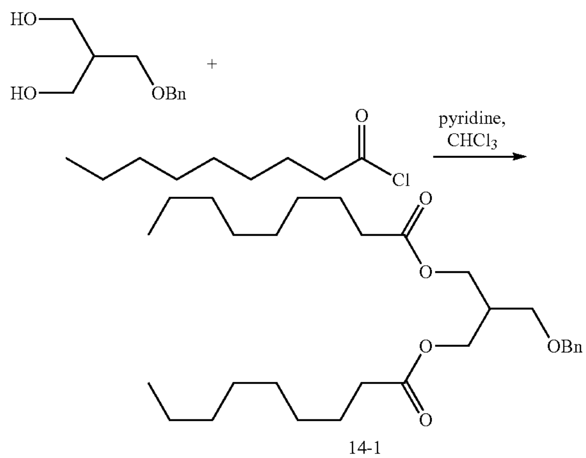

14-1

2-[(Phenylmethoxy)methyl]-1,3-propanediol (Bioorg. Med. Chem. 2017, 25, 4008-4030; 25.0 g, 0.127 mol) was dissolved in $CHCl_3$ (500 mL) and cooled in an ice water bath under nitrogen. To this solution was added nonyl chloride (56.5 g, 0.318 mol) in one portion followed by the addition of pyridine (40.0 g, 0.508 mol) dropwise over 40 minutes. The reaction mixture was allowed to warm to room temperature and then was stirred for 14 hours. The cloudy mixture was filtered through a pad of celite and the filtrate was washed with 5% aq. $NaHCO_3$ (250 mL), brine (250 mL) and dried over anhydrous $Na_2SO_4$. The drying agent was removed by filtration through a sintered glass funnel and silica gel (150 g, type: ZCX-2, 100-200 mesh) was added to the filtrate. The solvent was removed in vacuo (bath temperature <35° C.) and the silica gel with adsorbed 14-1 was added onto the top of a combi flash column (600 g, type: ZCX-2, 100-200 mesh, packed with petroleum ether:EtOAc 99:1 and eluted with petroleum ether:EtOAc 99:1 to 98:2, 1000 mL fractions). Qualified fractions were determined by TLC, combined and concentrated in vacuo to give 14-1 (60.0 g, 0.124 mol, 98%) as a colorless oil. $^1H$-NMR (300 MHz, $CDCl_3$): δ 7.28-7.40 (5H), 4.52 (s, 2H), 4.19 (m, 4H), 3.52 (d, J=5.7 Hz, 2H), 2.36 (m, 1H), 2.29 (t, J=7.5 Hz, 4H), 1.59 (m, 4H), 1.23-1.40 (18H), 0.92 (m, 6H).

Synthesis of 14-2: 2-(Hydroxymethyl)propane-1,3-diyl dinonanoate

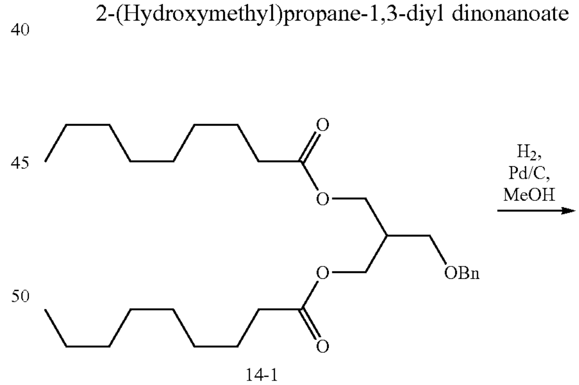

14-1

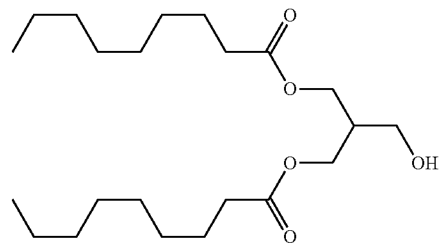

14-2 le;2.4qA solution of 14-1 (60.0 g, 0.124 mol) in MeOH (600 mL), in 11.0 L pressure vessel, was flushed with nitrogen 3×, then 10% Pd/C (18.0 g) is added to the vessel and the mixture was placed under hydrogen pressure (3 atm). The mixture was stirred under hydrogen for 14 hours, then the vessel was vented and the solution was sparged with nitrogen. The Pd/C was removed by filtration through a pad of Celite, the filter cake was rinsed with MeOH (200 mL) and the combined filtrates were concentrated in vacuo to give 14-2 (32.0 g, 82.8 mmol, 67%) as a clear, colorless oil. $^{1}$H-NMR (300 MHz, $CDCl_3$): δ 4.16 (m, 4H), 3.63 (d, J=5.7 Hz, 2H), 2.33 (t, J=7.5 Hz, 4H), 2.20 (m, 1H), 1.63 (m, 4H), 1.25-1.39 (20H), 0.90 (m, 6H).

Synthesis of 14-3: (((3,3'-((tert-butoxycarbonyl) azanediyl)bis(propanoyl))-bis(oxy))bis(methylene)) bis(propane-2,1,3-triyl) tetranonanoate

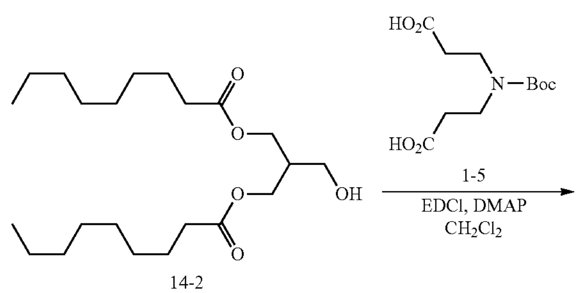

14-2

-continued

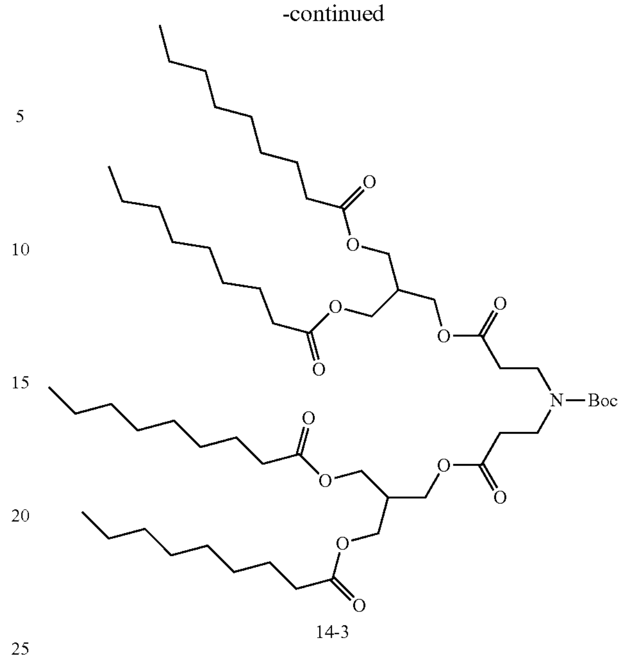

14-3

To a solution of 1-5 (5.00 g, 19.1 mmol) in $CH_2Cl_2$ (75 mL), cooled in an ice water bath under nitrogen was added in order 14-2 (14.8 g, 38.3 mmol), DMAP (2.34 g, 19.1 mmol), and EDCI (14.7 g, 76.7 mmol). The mixture was allowed to warm to room temperature and then was stirred for 14 hours. The reaction mixture was cast into 10% aq. citric acid (125 mL). The organic phase was separated, washed with brine (125 mL) and dried over anhydrous $Na_2SO_4$. Filtration through a sintered glass funnel and concentration in vacuo gave crude 14-3 (14.0 g, 14.0 mmol, 73%) which was carried forward without further purification.

Synthesis of 14-4: (((3,3'-azanediylbis(propanoyl)) bis(oxy))bis(methylene))-bis(propane-2,1,3-triyl) tetranonanoate

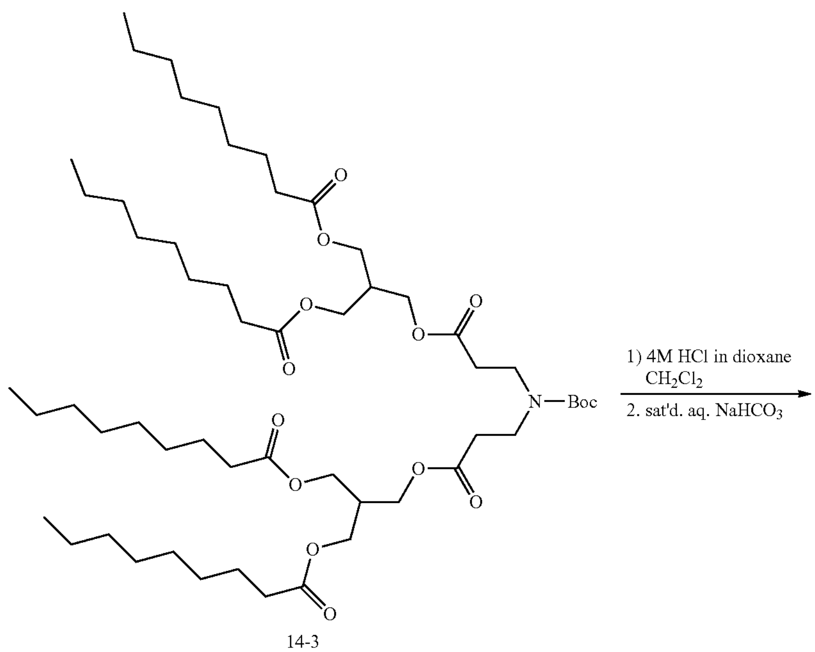

14-3

-continued

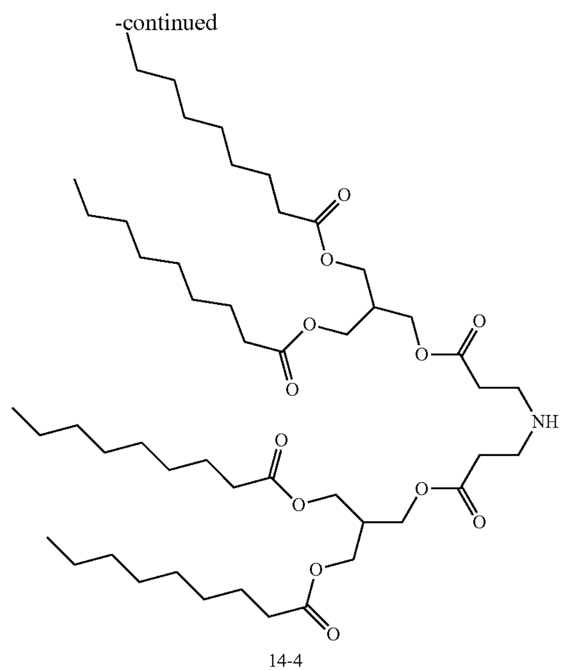

14-4

To a solution of 14-3 (14.0 g crude, assumed 14.0 mmol) in $CH_2Cl_2$ (80 mL), cooled in an ice water bath under nitrogen, was added 4.0M HCl in dioxane (35 mL, 0.140 mol) as such a rate that the internal temperature was maintained 0-10° C. The mixture was allowed to stir for 30 minutes after the addition was complete, then was allowed to warm to room temperature and stir for 16 hours. The reaction mixture was cast into saturated aq. $NaHCO_3$ (100 mL), the organic phase was separated, washed with saturated aq. $NaHCO_3$ (100 mL), brine (100 mL) and dried over anhydrous $Na_2SO_4$. Filtration and concentration in vacuo afforded crude 14-4 as a viscous yellow oil which was dissolved in $CH_2Cl_2$ (200 mL) and silica gel (20 g, type ZCX-2, 100-200 mesh) was added. Concentration in vacuo gave silica gel with adsorbed 14-4 which was placed atop a column of silica gel (100 g, type ZCX-2, 100-200 mesh), eluted with a gradient from 67:33 to 50:50 using combi-flash. Qualified fractions were located by TLC, combined, and concentrated in vacuo to give 14-4 (5.20 g, 5.79 mmol, 30% over 2 steps) as a clear, pale yellow, viscous oil. $^1$H-NMR (300 MHz, $CDCl_3$): δ 4.12-4.18 (12H), 2.93 (t, J=6.6 Hz, 4H). 2.57 (t, J=6.6 Hz, 4H), 2.42 (m, 2H), 2.33 (t, J=7.5 Hz, 8H), 1.61 (m, 8H), 1.22-1.40 (40H), 0.90 (m, 12H).

Synthesis of LIPID 14

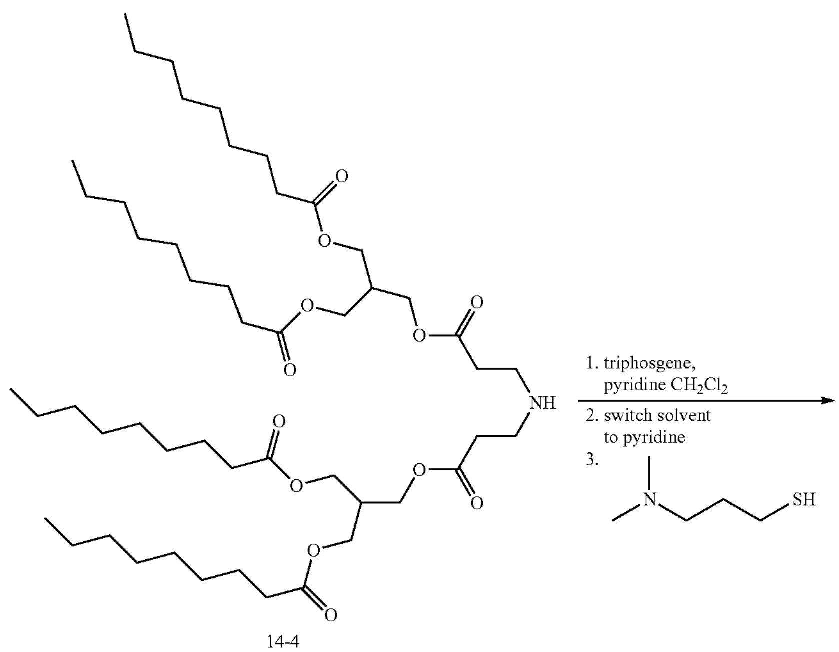

14-4

-continued

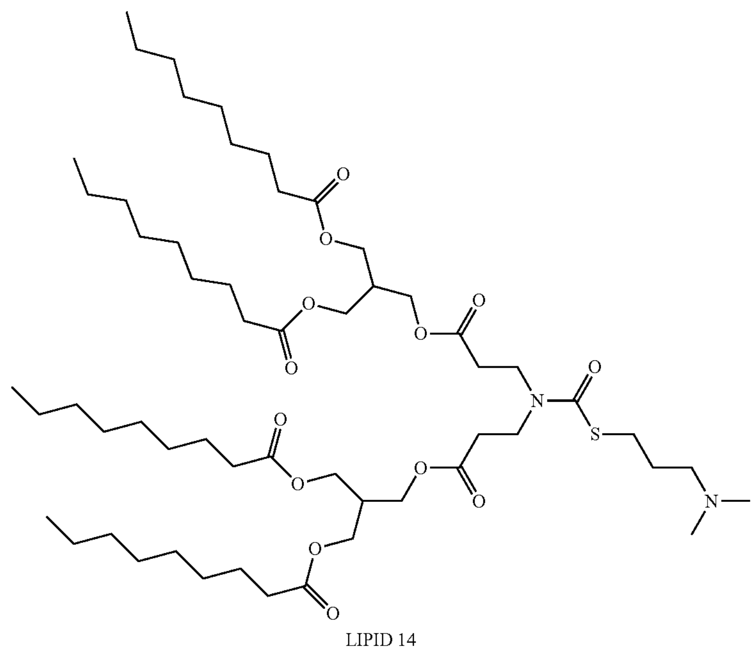

LIPID 14

To a solution of 14-4 (5.20 g, 5.79 mmol) in $CH_2Cl_2$ (175 mL), cooled in an ice-water bath under nitrogen, was added triphosgene (1.72 g, 5.75 mmol) in one portion, followed by the addition of pyridine (2.29 g, 28.9 mmol, 2.34 mL) at such a rate that the temperature remained at 0-5° C. The mixture was stirred for 30 minutes after the addition was complete, then was allowed to warm to room temperature and stir for 4 hours. The solvent was removed in vacuo and the residue was dissolved in pyridine (100 mL), and the solution was cooled in an ice water bath under nitrogen. To this stirring solution was added 3-dimethylamino-propane-1-thiol (0.82 g, 6.88 mmol) dropwise over a period of 10 minutes. The mixture was allowed to stir for 30 minutes after the addition was complete, then the mixture was warmed to room temperature and was stirred for 14 hours. The solvent was removed in vacuo and the residue was dissolved in $CH_2Cl_2$ (200 mL) and was washed with 10% aq. citric acid (2×100 mL), saturated aq. $NaHCO_3$ (2× 100 mL), brine (2×100 mL), and dried over $Na_2SO_4$. Filtration and concentration in vacuo gave crude 14 as a viscous, yellow oil which was purified by reverse phase combi-flash chromatography (A: water+0.1% $CF_3CO_2H$, B: acetonitrile; gradient 60% B to 80% B over 20 minutes then 100% for 20 minutes). Qualified fractions were combined and concentrated in vacuo to afford 14 (1.12 g, 1.07 mmol, 18.5%) as a clear, pale yellow oil. $^1$H-NMR (300 MHz, $CDCl_3$): δ 4.12-4.20 (12H), 3.65 (brt, J=7.2 Hz, 4H), 3.11 (m, 2H), 2.93 (t, J=6.9 Hz, 2H), 2.82 (s, 6H), 2.65 (brm, 4H), 2.45 (m, 4H), 2.31 (t, J=7.5 Hz, 8H), 1.61 (m, 8H), 1.18-1.35 (40H, 0.88 (m, 12H).

Example 15. Synthesis of LIPID 15: ((4,4'-(((3-(Dimethylamino)propyl)thio)carbonyl)azanediyl)bis(butanoy))bis(oxy)bis(propane-2,1,3-triyl) tetrakis(2-(4-methylcyclohexyl)acetate)
LIPID 15
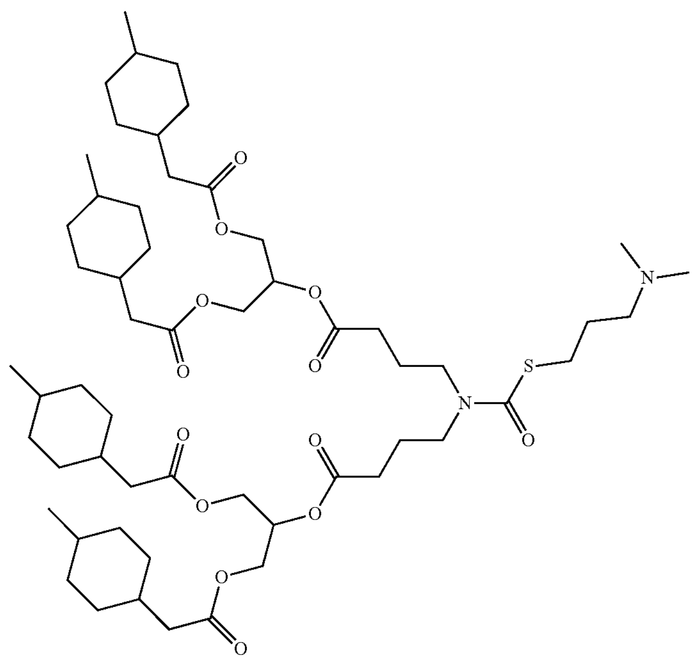
General Scheme
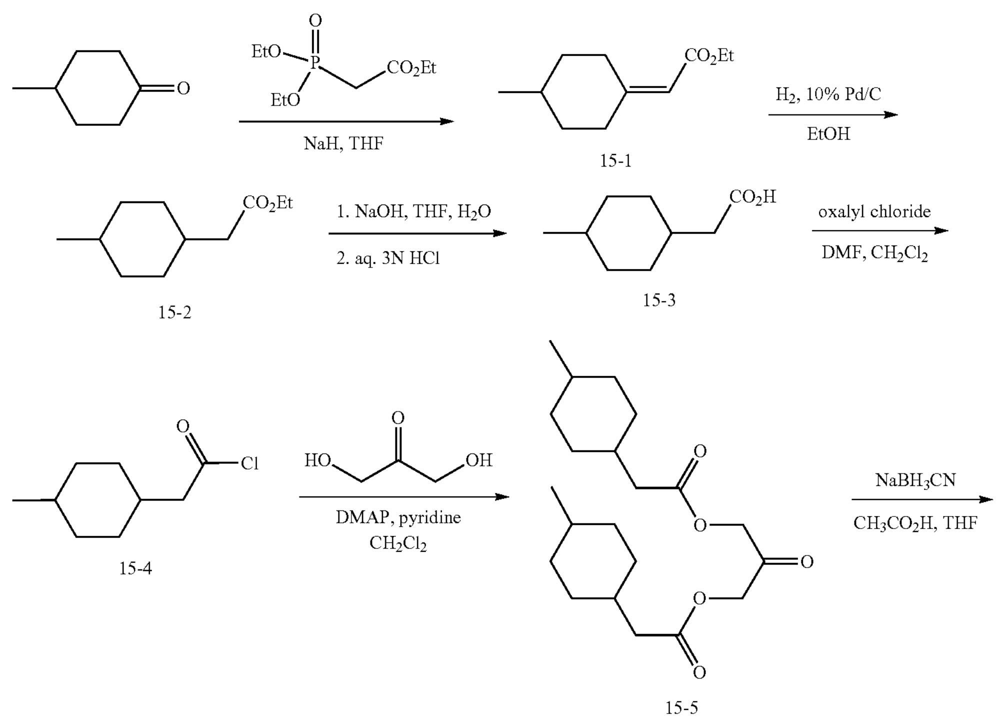
15-1
15-2
15-3
15-4
15-5

-continued
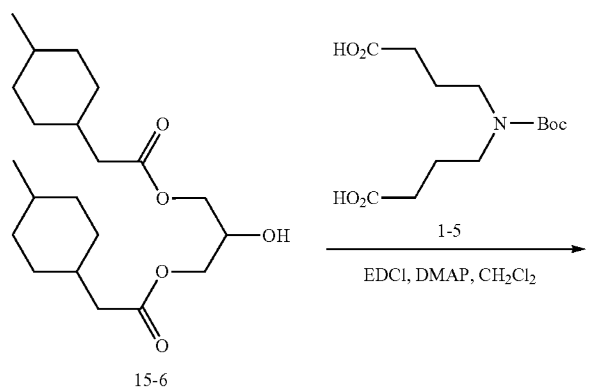
15-6
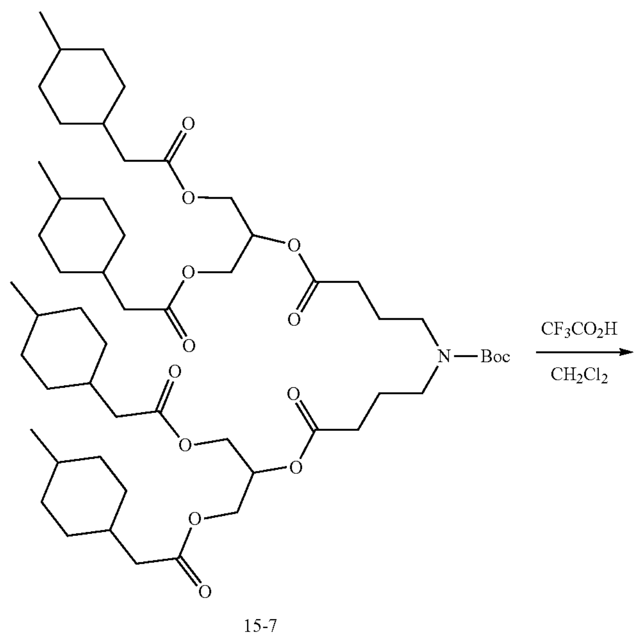
15-7
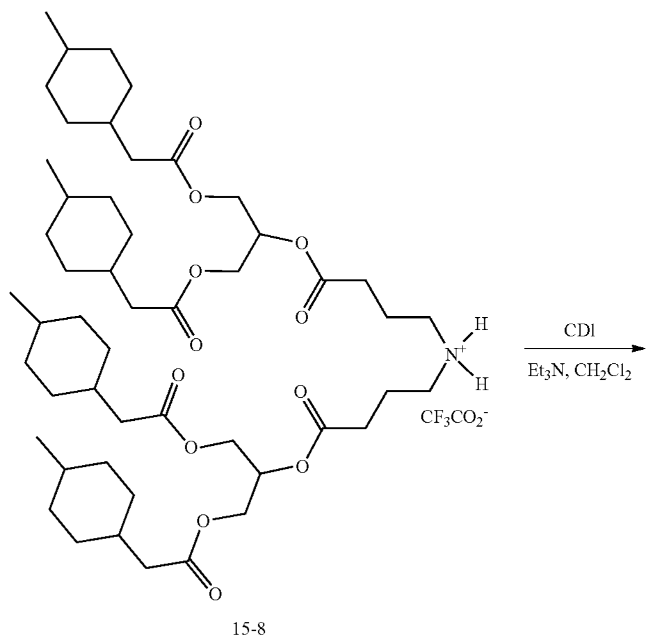
15-8

-continued

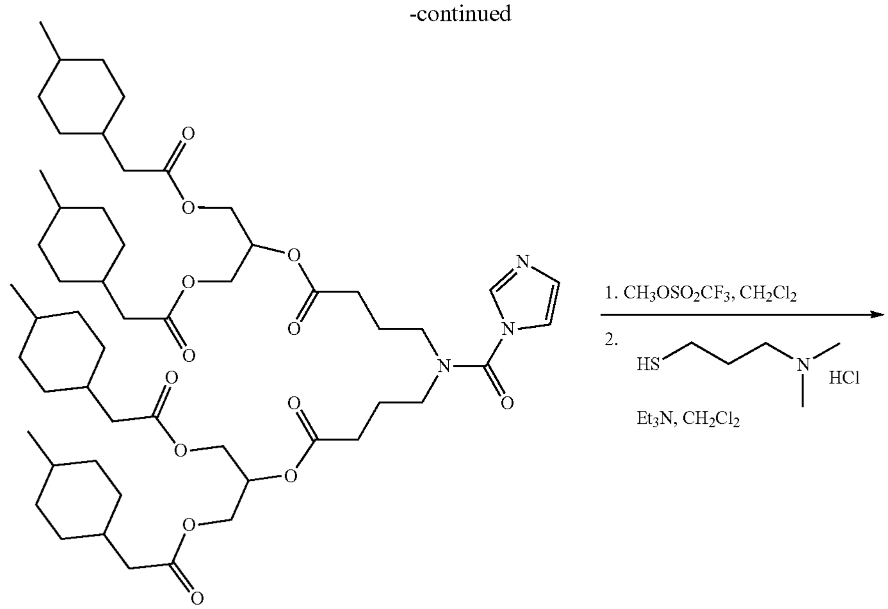

15-9

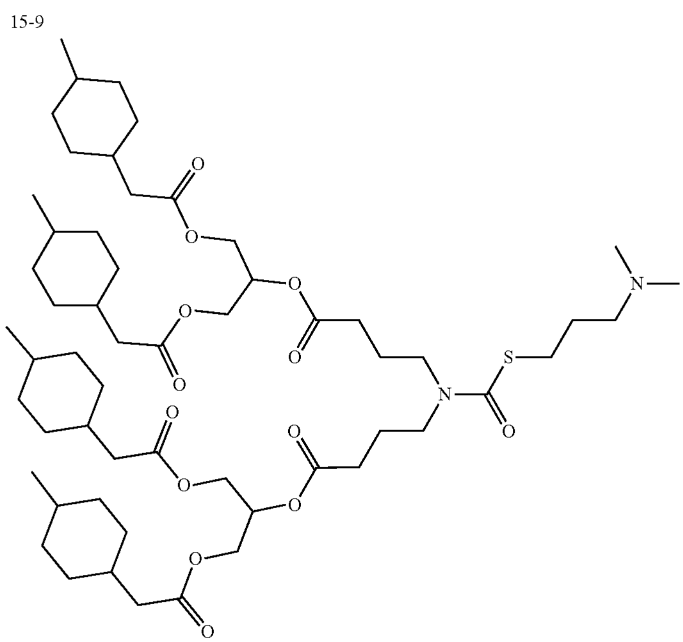

LIPID 15

Synthesis of 15-1: Ethyl 2-(4-methylcyclohexylidene)acetate

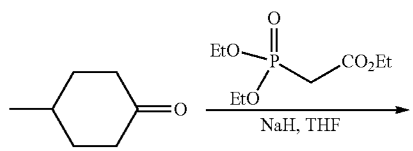

-continued

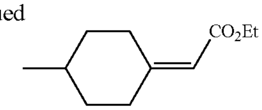

15-1

To a suspension of NaH (12.5 g, 60% in oil, washed with hexanes (2×25 mL), 0.312 mol) in anhydrous THF (600 mL), under nitrogen and cooled in an ice-water bath, was added triethyl phosphoneacetate (70.0 g, 0.312 mol) drop-wise over 30 minutes. The mixture was stirred for 2 hours in the ice water bath, then 4-methyl-cyclohexanone (35.0 g, 0.312 mol) was added over 30 minutes. The mixture was stirred for 30 minutes then was allowed to warm to room temperature and was stirred for 14 hours. The mixture was cast into water (1.2 L) and EtOAc (600 mL). The organic phase was separated and silica gel (200 g, type: ZCX-2, m100-200 mesh) was added and the solvent was then remove in vacuo (bath temperature <35° C.) to provide silica gel with adsorbed, crude 1. The silica gel is placed atop a column of silica gel (1000 g, type: ZCX-2, m100-200 mesh) eluted with a gradient to petroleum ether:EtOAc 100:0 to 95:5, collecting 1000 mL fractions using a combi-flash. Qualified fractions were located by TLC, combined and concentrated in vacuo to provide 15-1 (45.0 g, 0.247 mol, 79%) as a clear, colorless oil. LC-MS (+ mode): RT 1.804, 183.2 ($M+H^+$); $^1H$-NMR (300 MHz, $CDCl_3$): δ 5.61 (s, 1H), 4.14 (q, J=7.2 Hz, 2H), 3.75 (m, 1H), 2.14-2.30 (2H), 1.90 (m, 1H), 1.80 (m, 2H), 1.62 (m, 1H), 1.28 (t, J=7.2 Hz, 3H), 1.00-1.15 (2H), 0.82 (d, J=9.0 Hz, 3H).

Synthesis of 15-2: Ethyl 2-(4-methylcyclohexyl)acetate

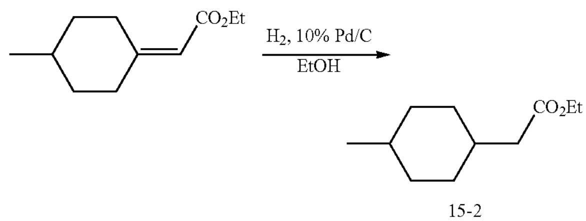

15-2

To ester 15-1 (45.0 g, 0.247 mol), dissolved in EtOH (450 mL) under nitrogen at room temperature, was added 10% Pd/C (13.5 g). Hydrogen was then bubbled through the reaction mixture for 16 hours. The solvent was then sparged with nitrogen for 1 hours, the catalyst was removed by filtration through a pad of celite and the filter cake was rinsed with EtOH (450 mL). The combined filtrates were concentrated in vacuo to yield 15-2 (35.0 g, 0.190 mol, 77%) as a pale yellow oil. $^1H$-NMR (300 MHz, $CDCl_3$): δ 4.14 (q, J=7.2 Hz, 2H), 2.25-2.40 (2H), 2.18 (m, 1H), 1.52-1.78 (3H), 1.28 (t, J=7.2 Hz, 3H), 0.78-1.03 (9H).

Synthesis of 15-3: 2-(4-Methylcyclohexyl)acetic Acid

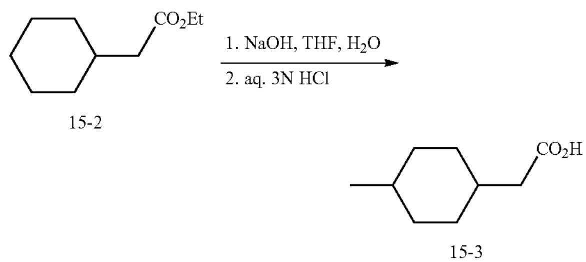

15-2

15-3

To a solution of 15-2 (35.0 g, 0.190 mol) in THF:$H_2O$ (350 mL, 50:50), at room temperature under nitrogen, was added solid NaOH (84.0 g, 2.10 mol) over a period of 30 minutes. The mixture was stirred for 16 hours, then was concentrated in vacuo to remove the THF. The aqueous solution was then adjusted to pH 3.0 through the addition of 3N aq. HCl. The reaction mixture was extracted with EtOAc (350 mL) and the organic phase was dried over $Na_2SO_4$. Filtration and concentration in vacuo provided 15-3 (25.0 g, 0.160 mol, 84%) as a white solid.

Synthesis of 15-4: 2-(4-Methylcyclohexyl)acetyl chloride

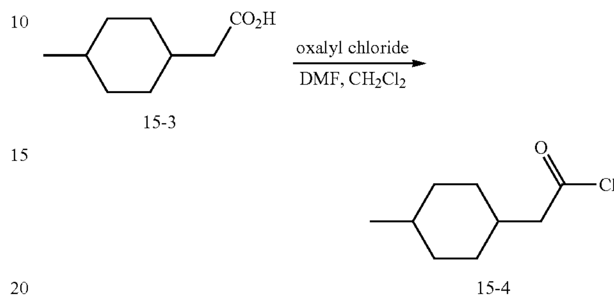

15-3

15-4

To 15-3 (25.0 g, 0.160 mol) in $CH_2Cl_2$ (250 mL), containing DMF (1.0 mL), cooled in an ice-water bath under nitrogen, was added oxalyl chloride (40.7 g, 0.321 mol), dropwise over a period of 20 minutes. The mixture was allowed to stir for 30 minutes after the addition was complete, then was warmed to room temperature ad was stirred for 14 hours. Concentration in vacuo, bath temperature <30° C., afforded 15-4 (25.2 g, 0.144 mol, 90%) ad a clear, colorless oil. $^1H$-NMR (300 MHz, $CDCl_3$): δ 2.75 (m, 2H), 1.30-1.64 (5H), 1.18-1.28 (2H), 0.80-1.05 (6H).

Synthesis of 15-5: 2-Oxopropane-1,3-diyl bis(2-(4-methylcyclohexyl)acetate)

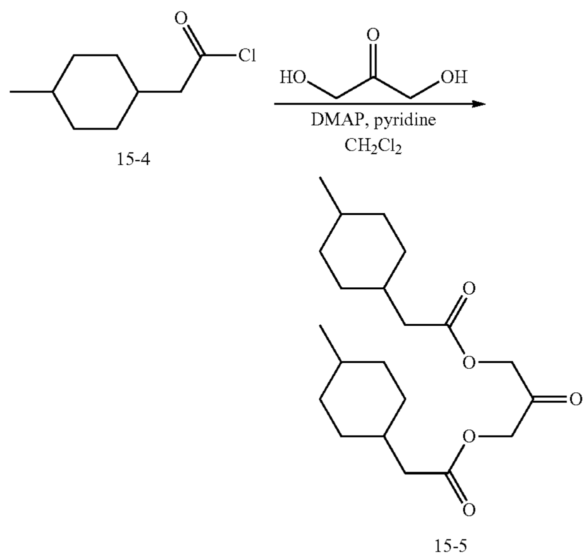

15-4

15-5

To 1.3-dihydroxyacetone (5.90 g, 65.5 mmol), in $CH_2Cl_2$ (500 mL) under nitrogen at room temperature, was added DMAP (2.40 g, 19.6 mmol) and pyridine (11.4 g, 0.144 mol), followed by the addition of 15-4 (25.2 g, 0.144 mol) dropwise over 30 minutes. The mixture was stirred for 16 hours at room temperature, then was cast into water (400 mL). The organic phase was separated, washed with water (400 mL), brine (400 mL), and dried over $Na_2SO_4$. The drying agent was removed by filtration and silica gel (60 g, type: ZCX-2, 100-200 mesh) was added to the filtrate. The solvent was removed in vacuo to give the silica gel with adsorbed, crude, 15-5. The silica gel was plated atop a column of silica gel (300 g, type: ZCX-2, 100-200 mesh), eluted with a gradient of petroleum ether:EtOAc from 100:0 to 90:10, 500 mL fractions, using a combi-flash. Qualified fractions were found using TLC, combined and concentrated in vacuo to furnish 15-5 (18.0 g, 49.1 mmol, 75%) as a clear colorless oil. LC-MS (+-mode): RT 0.36 min, 367.3 ($M+H^+$); $^1H$-NMR (300 MHz, $CDCl_3$): δ 4.76 (s, 4H), 2.40 (d, J=6.0 Hz, 1H), 2.00-2.30 (4H), 0.75-1.10 (25H).

Synthesis of 15-6: 2-Hydroxypropane-1,3-diyl bis(2-(4-methylcyclohexyl)acetate)

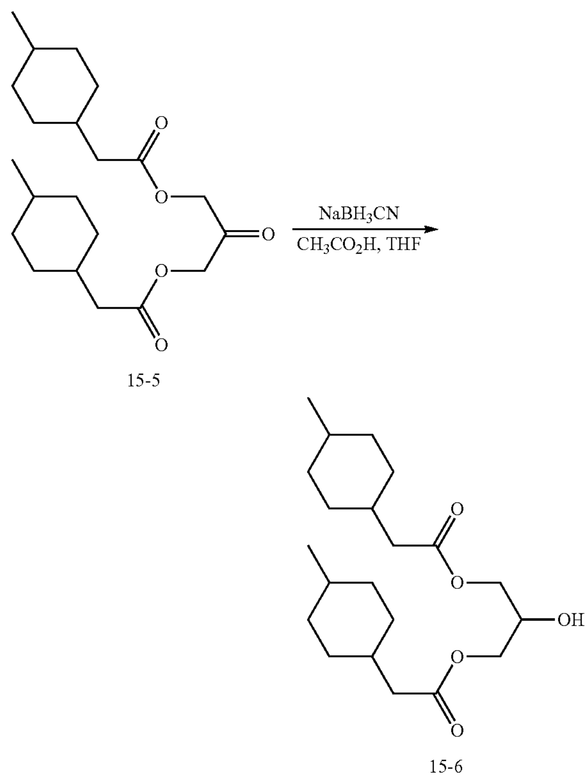

15-5

15-6

To a solution of 15-5 (18.0 g, 49.1 mmol) in THE under nitrogen, cooled in an ice-water bath, was added $CH_3CO_2H$ (25.0 g, 0.42 mol). To this stirring solution was added $NaBH_3CN$ (12.9 g, 0.205 mol) in portions over 20 minutes. The mixture was stirred for 30 minutes after the addition was complete then was warmed to room temperature and was stirred for 2 hours. The mixture was cast into water (100 mL), and was extracted with EtOAc (3×100 mL). The combined organic phases were dried over $Na_2SO_4$, the drying agent was removed by filtration and silica gel (50 g, type: ZCX-2, 100-200 mesh) was added to the filtrate. Concentration in vacuo provided silica gel containing adsorbed, crude 15-6 which was placed atop a column of silica gel (250 g, type: ZCX-2, 100-200 mesh), eluted with a gradient of petroleum ether:EtOAc from 100:0 to 92:8, 500 mL fractions were collected using a combi-flash. Qualified fractions were found using TLC, then combined and concentrated in vacuo to provide 15-6 (17.0 g, 46.1 mmol, 94%) as a clear, colorless oil. LC-MS (+-mode): RT 1.47 min, 391.2 (M+Na+); $^1H$-NMR (300 MHz, $CDCl_3$): δ 5.30 (s, 1H), 4.00-4.20 (4H), 2.30 (m, 1H), 2.18 (m, 2H), 1.90-2.05 (2H), 1.18-1.75 (14H), 0.80-1.00 (12H).

Synthesis of 15-7: ((4,4'-((tert-Butoxycarbonyl) azanediyl)bis(butanoyl))bis(oxy))bis(propane-2,1,3-triyl) tetrakis(2-(4-methylcyclohexyl)acetate)

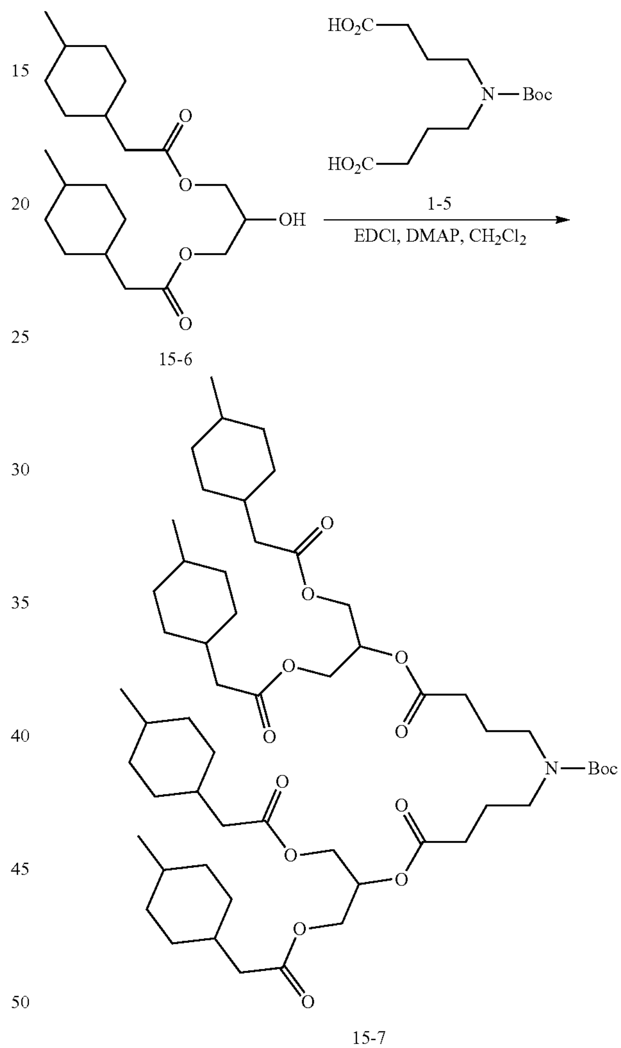

15-6

15-7

To 1-5 (6.10 g, 21.1 mmol) in $CH_2Cl_2$ (120 mL), cooled in an ice-water bath under nitrogen was added DMAP (1.00 g, 8.18 mmol) and 15-6 (17.0 g, 46.1 mmol) in one portion followed by the addition of EDCI (9.70 g, 50.6 mmol) in portions over a period of 30 minutes. The mixture was stirred for 30 minutes after the addition was complete, then was warmed to room temperature and stirred for 16 hours. The mixture was cast into brine (120 mL), the organic phase was separated and washed with brine (120 mL) and dried over $Na_2SO_4$. The drying agent was removed by filtration and silica gel (60 g, type: ZCX-2, 100-200 mesh) was added to the filtrate. Concentration in vacuo provided silica gel containing adsorbed, crude 15-7 which was placed atop a column of silica gel (300 g, type: ZCX-2, 100-200 mesh), eluted with a gradient of petroleum ether:EtOAc from 100:0 to 70:30, 500 mL fractions were collected using a combi-flash. Qualified fractions were found using TLC, then combined and concentrated in vacuo to provide 15-78 (10.0 g, 10.1 mmol, 48%) as a clear, colorless oil. LC-MS (+-mode): RT 1.654 min, 1012.9 (M+Na+); $^1$H-NMR (300 MHz, $CDCl_3$): δ 5.25 (m, 2H), 4.31 (m, 4H), 4.18 (m, 4H), 3.20 (brm, 4H), 2.31-2.40 (6H), 2.15-2.23 (5H), 2.00 (m, 1H), 1.78 (m, 4H), 1.50-1.75 (14H), 1.30-1.50 (3H), 1.35 (s, 9H), 1.18-1.30 (9H), 0.77-1.00 (26H).

Synthesis of 15-8: bis(4-((1,3-bis(2-(4-Methylcyclohexyl) acetoxy)propan-2-yl)oxy)-4-oxobutyl)ammonium trifluoroacetate

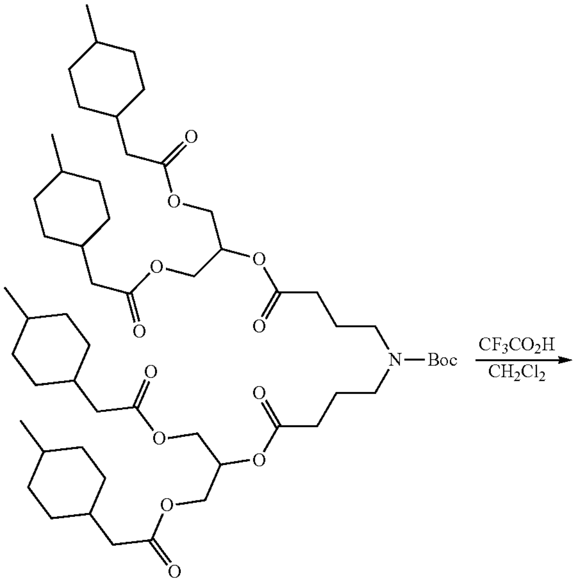

15-7

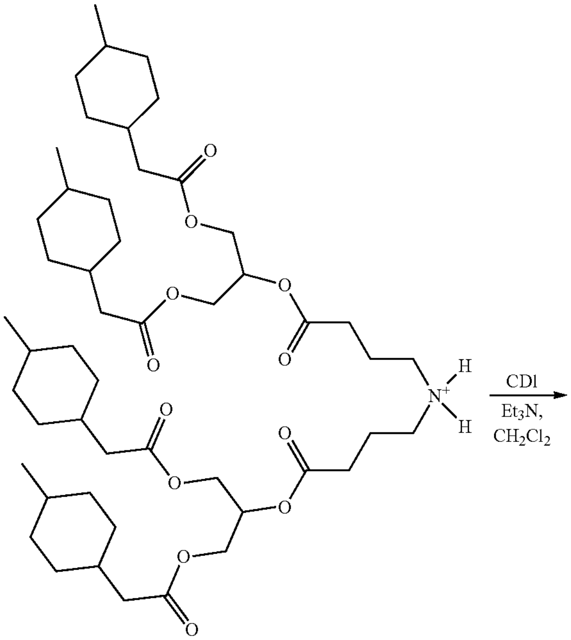

15-8

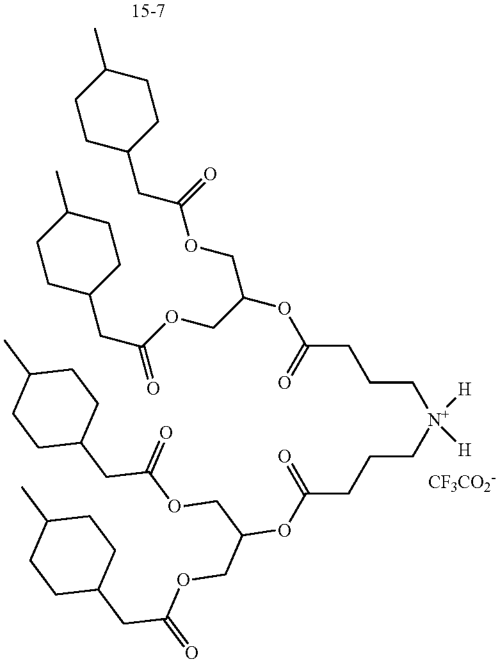

15-8

To a solution of 15-7 (10.0 g, 10.1 mmol) in $CH_2Cl_2$ (40 mL), cooled in an ice-water bath under nitrogen, was added $CF_3CO_2H$ (5.00 g, 43.9 mmol, 3.36 mL) in one portion. The mixture was stirred for 30 minutes after the addition then was warmed to room temperature and stirred for 4 hours. The mixture was concentrated in vacuo to give crude 15-8 (5.60 g, 5.58 mmol, 55%) as a colorless, viscous oil. LC-MS (+-mode): RT 0.608 min, 890.6 (M+H$^+$); $^1$H-NMR (300 MHz, $CDCl_3$): δ 11.10 (brs, 2H), 5.26 (m, 2H), 4.45 (m, 4H), 4.18 (m, 4H), 3.18 (m, 4H), 2.40 (t, J=6.5 Hz, 4H), 2.31 (t, J=7.2 Hz, 2H), 2.16-2.25 (6H), 1.82-2.08 (10H), 1.14-1.67 (22H), 0.75-1.00 (24H).

Synthesis of 15-9: ((4,4'-((1H-Imidazole-1-carbonyl)azanediyl)bis(butanoyl))-bis(oxy))bis(propane-2,1,3-triyl) tetrakis(2-(4-methylcyclohexyl)acetate)

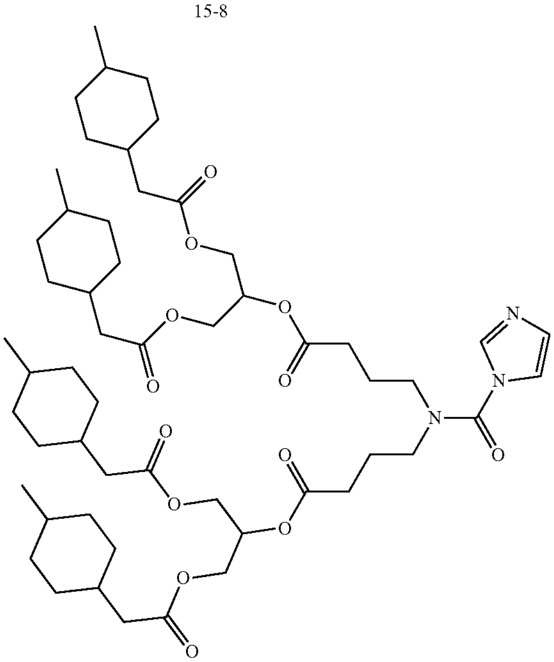

15-9

To a solution of 15-8 (5.60 g, 5.58 mmol) in $CH_2Cl_2$ (100 mL), under nitrogen, was added $Et_3N$ (1.30 g, 12.8 mmol, 1.21 mL) followed by carbonyldiimidazole (CDI, 2.00 g, 12.33 mmol). The mixture was stirred at room temperature for 14 hours then was diluted with n-heptane (100 mL). The solution was washed with water (3×100 mL), and the organic phase was dried over $Na_2SO_4$. Filtration and concentration in vacuo gave crude 15-9 (4.00 g, 4.06 mmol, 73%) as a viscous, yellow oil. LC-MS (+ mode): RT 0.645 min 984.9 ($M+H^+$); $^1$H-NMR (300 MHz, $CDCl_3$): δ 7.96 (m, 1H), 7.26 (m, 1H), 7.13 (m, 1H), 4.32 (m, 4H), 4.16 (m, 4H), 3.41 (m, 4H), 2.21-2.32 (6H), 2.08-2.16 (6H), 1.81-2.00 (6H), 1.50-1.72 (14H), 1.14-1.50 (12H), 0.75-1.00 (24H).

Synthesis of LIPID 15: ((4,4'-((((3-(dimethylamino)propyl)thio)carbonyl)-azanediyl)bis(butanoyl))bis(oxy))bis(propane-2,1,3-triyl) tetrakis(2-(4-methylcyclohexyl)acetate)

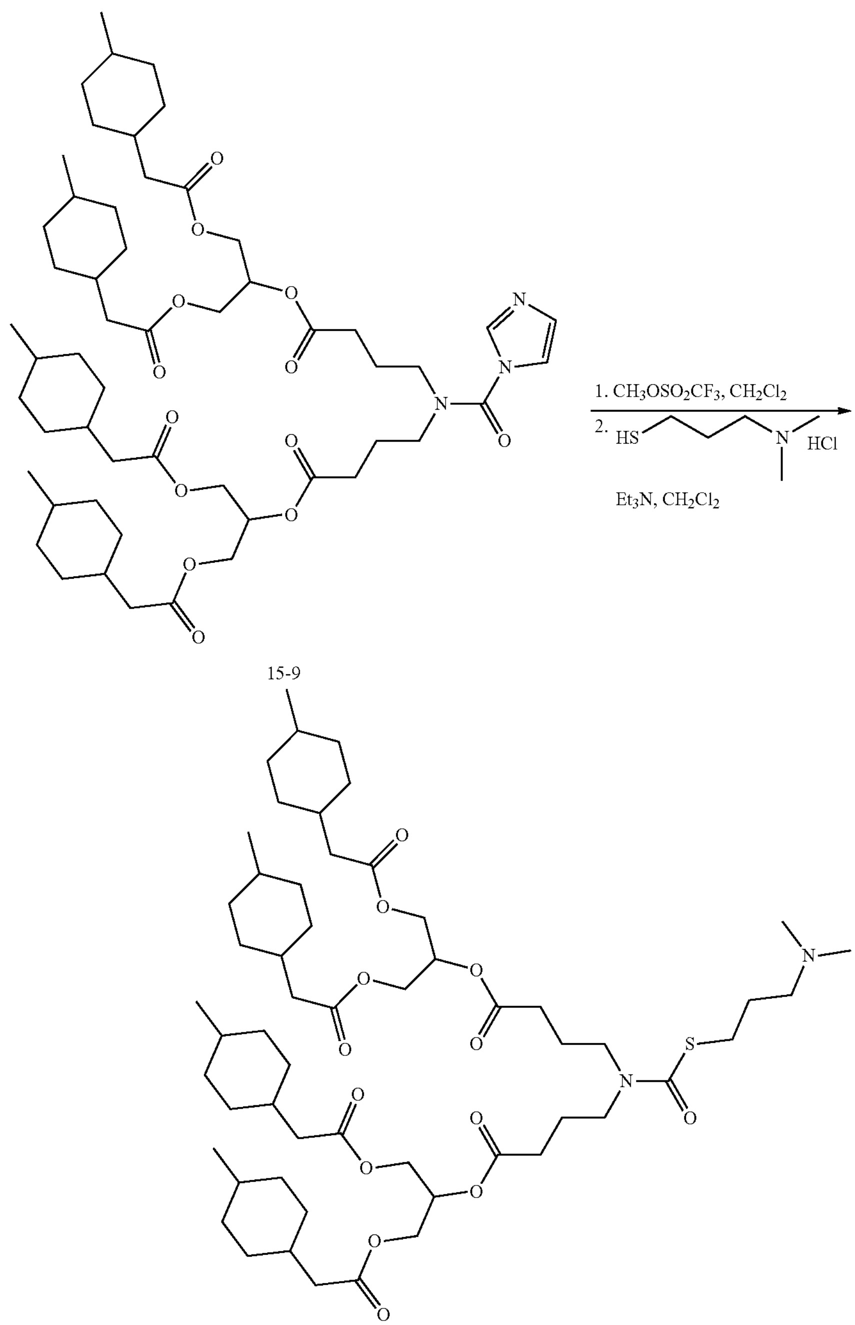

15-9

LIPID 15

To a solution of 15-9 (4.00 g, 4.06 mmol) in $CH_2Cl_2$ (80 mL), cooled in an ice-water bath under nitrogen, was added $CF_3SO_2OCH_3$ (0.70 g, 4.27 mmol) over a period of 5 minutes. The mixture was stirred for 1 hour after the addition was complete, then $Et_3N$ (0.80 g, 7.90 mmol, 1.10 mL) and 3-dimethylamino-propane-1-thiol HCl salt (0.76 g, 4.87 mmol) were added in order in one portion each. The mixture was allowed to stir for 30 minutes after the additions were complete, then the mixture was warmed to room temperature and stirred for 16 hours. Silica gel (15 g, type: ZCX-2, 100-200 mesh) was added to the solution. Concentration in vacuo provided silica gel containing adsorbed, crude 15 which was placed atop a column of silica gel (75 g, type: ZCX-2, 100-200 mesh), eluted with a gradient of $CH_2Cl_2$:MeOH from 100:0 to 96:4, 300 mL fractions were collected using a combi-flash. Qualified fractions were found using TLC, then combined and concentrated in vacuo to provide LIPID 15 (1.70 g) which was further purified by SFC (Column: Torus 2-PIC, 4.6×100 mm 5 um; mobile phase B: i-PrOH; flow rate 4 mL/min; gradient: isocratic 10% B; wave length 220 nM) to provide LIPID 15 (1.00 g, 0.965 mmol, 23.8%) as a clear, light yellow oil after concentration in vacuo. ES-MS: 1035.7 (M+H$^+$); HPLC Purity: 98.47%; $^1$H-NMR (300 MHz, $CDCl_3$): δ 5.24 (m, 2H), 4.31 (m, 4H), 4.14 (m, 4H), 3.38 (brm, 4H), 2.92 (t, J=7.3 Hz, 2H), 2.11-2.52 (18H), 1.56-2.11 (23H), 1.12-1.56 (14H), 0.75-1.11 (23H).

Example 16. Synthesis of LIPID 16: ((4,4'-((((3-(Dimethylamino)propyl)thio)carbonyl)azanediyl)bis(butanoyl))bis(oxy))bis(propane-2,1,3-triyl) tetrakis(4-ethylcyclohexane-1-carboxylate)

LIPID 16

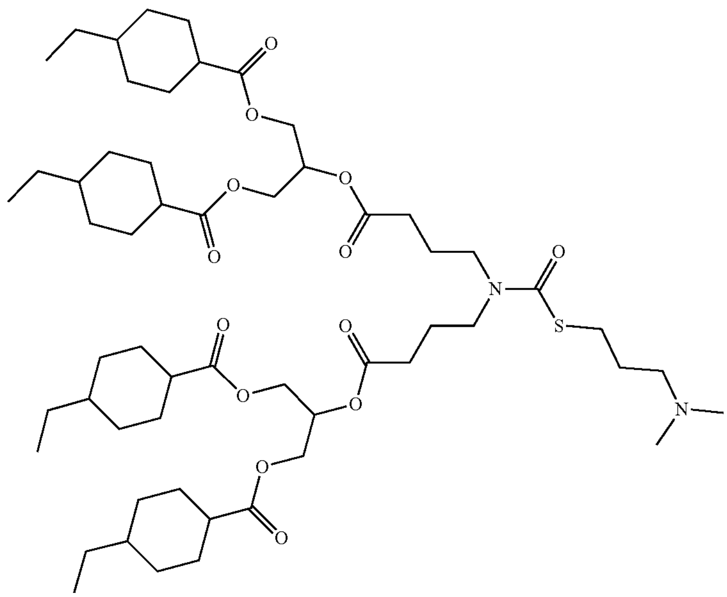

General Scheme

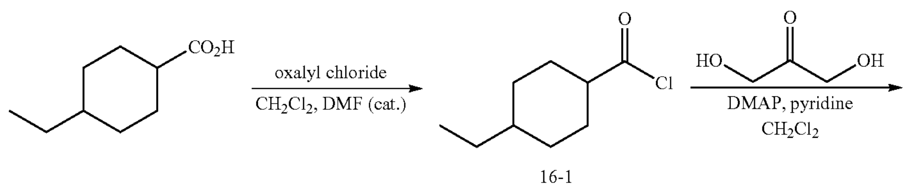

16-1

-continued
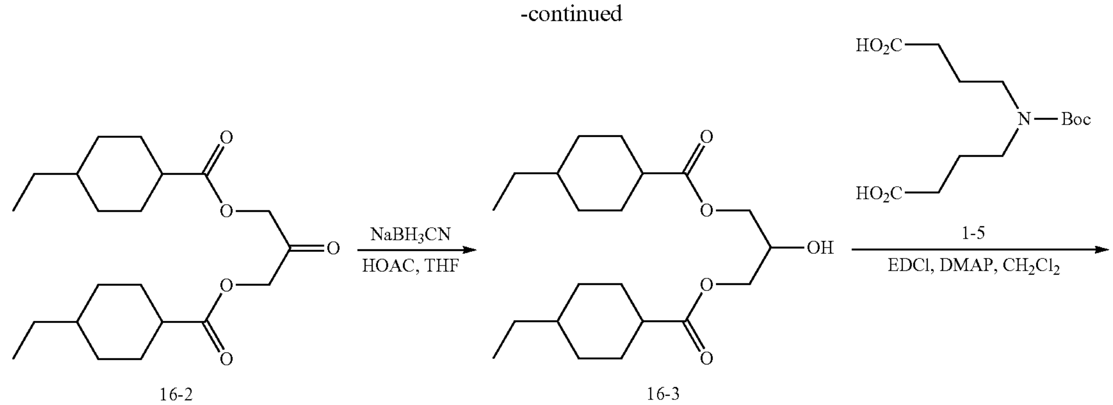
16-2
16-3
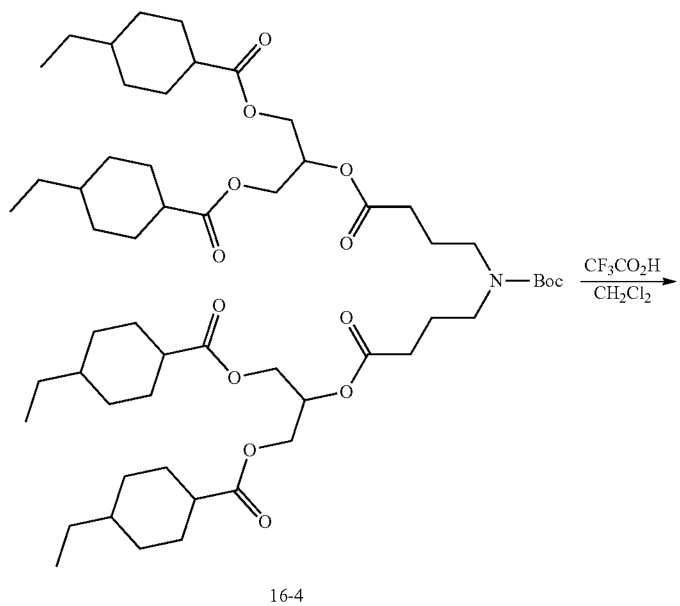
16-4
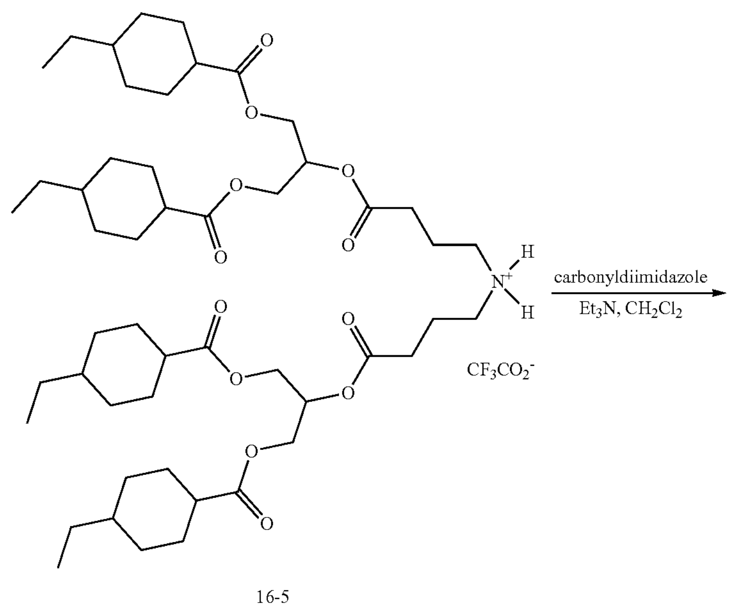
16-5

-continued

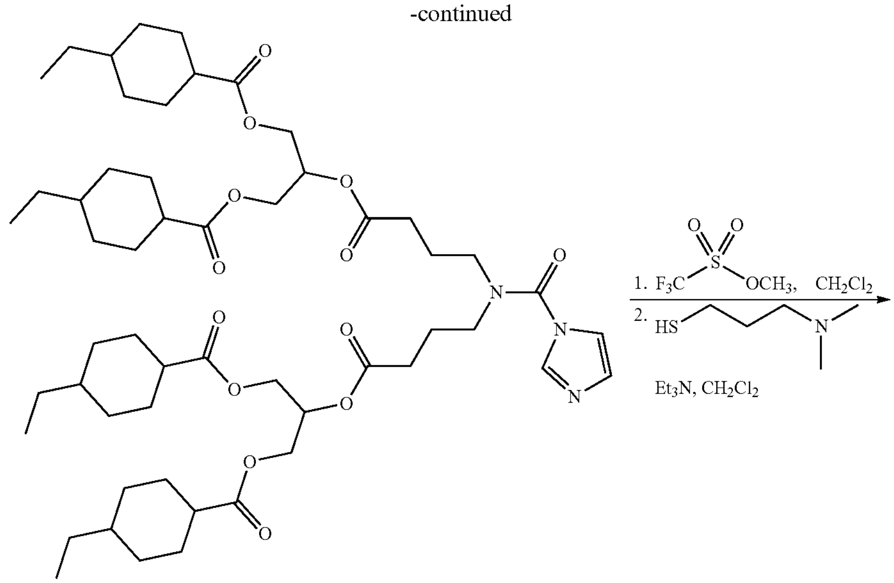

16-6

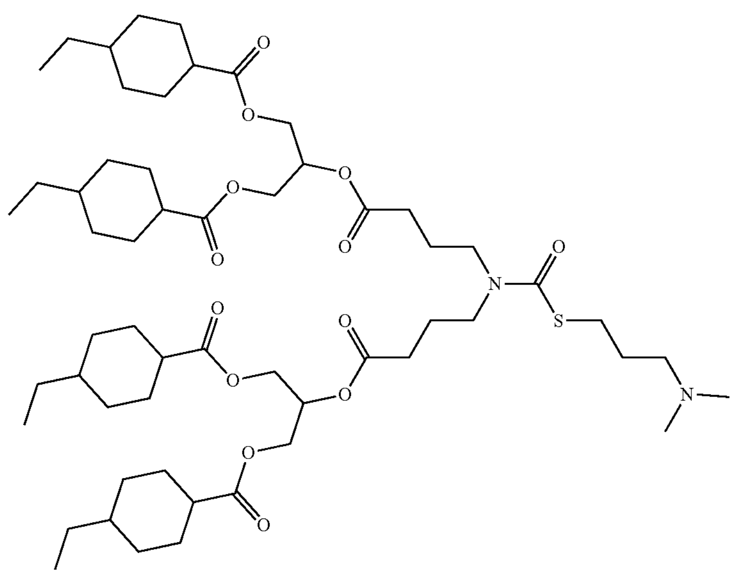

LIPID 16

Synthesis of 16-1: 4-Ethylcyclohexane-1-carbonyl chloride

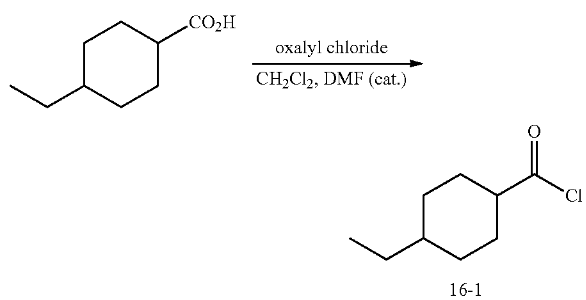

16-1

To a solution of 4-ethyl-cyclohexanecarboxylic acid (22.5 g, 0.144 mol) in $CH_2Cl_2$ (225 mL), was cooled in an ice-water bath under nitrogen, was added DMF (0.5 mL) followed by the addition of oxalyl chloride (36.6 g, 0.288 mol) over a period of 25 minutes. The mixture was allowed to stir for 30 minutes after the addition was complete, then was warmed to room temperature and was stirred for 16 hours. Concentration in vacuo afforded crude 16-1 (22.6 g, 0.129 mol, 90%) as a clear, colorless oil. $^1$H-NMR (300 MHz, $CDCl_3$): δ 2.62 (m, 1H), 2.62 (m, 2H), 1.37-1.53 (2H), 1.10-1.27 (4H), 0.80-1.00 (6H).

Synthesis of 16-2: 2-Oxopropane-1,3-diyl bis(4-ethylcyclohexane-1-carboxylate)

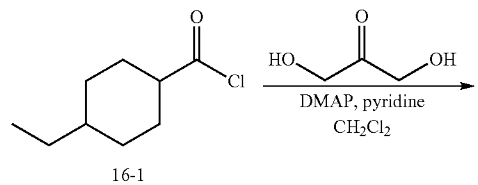

16-1

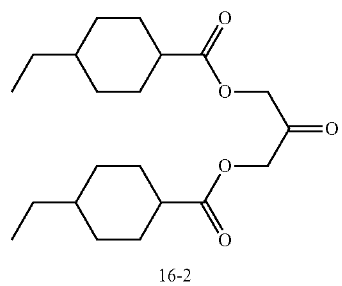

16-2

To a solution of dihydroxy-acetone (5.30 g, 58.8 mmol) in $CH_2Cl_2$ (500 mL), cooled in an ice-water bath under nitrogen was added DMAP (0.36 g, 2.94 mmol) and pyridine (10.24 g, 0.129 mol) in one portion, followed by the addition of 16-1 (22.6 g, 0.129 mol) over a period of 10 minutes. The mixture was allowed to stir for 30 minutes after the addition was complete, then was warmed to room temperature and stirred for 14 hours. The solvent was removed in vacuo and the residue was dissolved in $CH_2Cl_2$ (100 mL). Silica gel (25 g, type ZCX-2, 100-200 mesh) ws added to the solution, then the solvent was removed in vacuo to provide silica gel impregnated with adsorbed 16-2. The silica gel was placed atop a column of silica gel (250 g, type ZCX-2, 100-200 mesh) and a combi-flash was used to purify the crude 16-2 by eluting with a gradient of petroleum ether:EtOAc from 100:0 to 90:10, collecting 300 mL fractions. Qualified fractions were located by TLC, combined, and concentrated in vacuo to yield 16-2 (20.4 g, 55.6 mmol, 94%) as a clear, colorless oil. LC-MS (+ mode): RT 0.450 min, 367.3 ($M+H^+$); $^1$H-NMR (300 MHz, DMSO-$d_6$): δ 4.83 (s, 4H), 2.27 (m, 2H), 2.15 (m, 1H), 1.77-1.90 (5H), 1.48 (m, 4H), 1.00-1.33 (10H), 0.80-0.95 (8H).

Synthesis of 16-3: 2-Hydroxypropane-1,3-diyl bis(4-ethylcyclohexane-1-carboxylate)

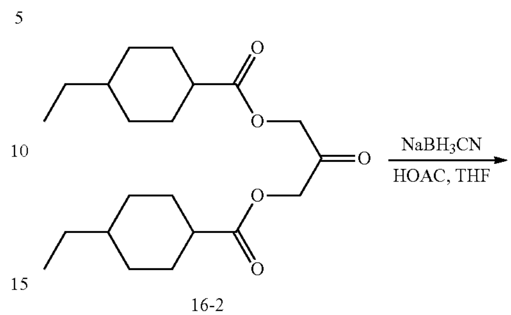

16-2

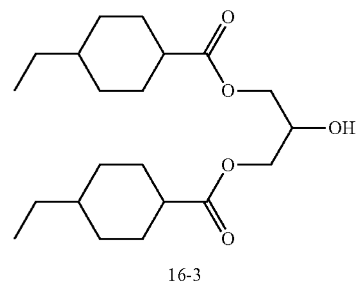

16-3

To a solution of 16-2 (20.4 g, 55.66 mmol) in THF (400 mL), cooled in an ice-water bath under nitrogen as added HOAc (33.4 g, 0.556 mol) in one portion, followed by the addition of $NaBH_3CN$ (17.5 g, 0.278 mol) in portions over a period of 30 minutes. The mixture was stirred for 30 minutes after the addition was complete, then was warmed to room temperature and was stirred for 2 hours. The mixture was cast into water (2.0 L) and the resulting solution was extracted with EtOAc (3×200 mL). The combined organic phases were dried ($Na_2SO_4$), filtered, concentrated in vacuo, and the residue was dissolved in $CH_2Cl_2$ (100 mL). To the solution of crude 16-3 was added silica gel (50 g, type ZCX-2, 100-200 mesh) and the solvent was removed in vacuo to afford silica gel containing adsorbed, crude 16-3. The silica gel was placed atop a column of silica gel (250 g, type ZCX-2, 100-200 mesh) and a combi-flash was used to purify the crude 16-3 by eluting with a gradient of petroleum ether:EtOAc from 100:0 to 92:8, collecting 300 mL fractions. Qualified fractions were located by TLC, combined, and concentrated in vacuo to yield 16-3 (16.0 g, 43.42 mmol, 78%) as a clear, colorless oil. LC-MS (+ mode): RT 1.463 min, 391.3 ($M+Na^+$); $^1$H-NMR (300 MHz, $CDCl_6$): δ 4.00-4.25 (5H), 2.32 (brs, 1H), 2.25 (m, 2H), 1.91 (m, 4H), 1.77 (m, 4H), 1.37 (m, 4H), 1.00-1.25 (8H), 0.75-0.95 (8H).

Synthesis of 16-4: ((4,4'-((tert-Butoxycarbonyl)azanediyl)bis(butanoyl))bis(oxy))bis(propane-2,1,3-triyl) tetrakis(4-ethylcyclohexane-1-carboxylate)

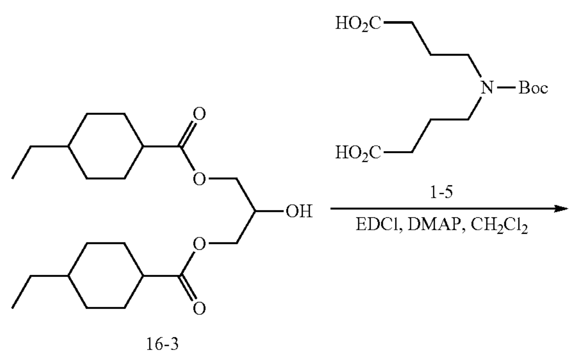

16-3

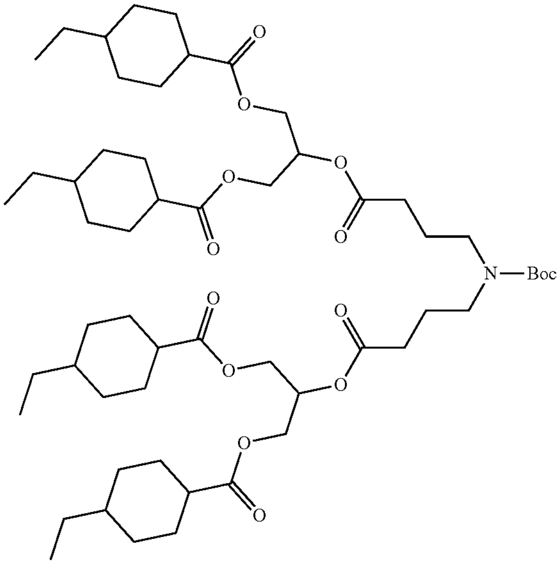

16-4

To a solution of 1-5 (5.42 g, 18.73 mmol) in $CH_2Cl_2$ (100 mL), under nitrogen, was added in order: DMAP (0.91 g, 7.49 mmol), and 16-3 (15.2 g, 41.21 mmol). The resulting solution was cooled in an ice-water bath, then EDCI (8.60 g, 44.96 mmol) was added in 5 portions over a period of 30 minutes. The mixture was stirred for 30 minutes after the addition was complete, then the solution was warmed to room temperature and was allowed to stir for 14 hours. The mixture was cast into brine (100 mL), the organic phase was separated, and dried over $Na_2SO_4$. Filtration gave a solution of crude 16-4 to which was added silica gel (15 g, type ZCX-2, 100-200 mesh) and the solvent was removed in vacuo to afford silica gel containing adsorbed, crude 16-4. The silica gel was placed atop a column of silica gel (75 g, type ZCX-2, 100-200 mesh) and a combi-flash was used to purify the crude 16-4 by eluting with a gradient of petroleum ether:EtOAc from 100:0 to 80:20, collecting 300 mL fractions. Qualified fractions were located by TLC, combined, and concentrated in vacuo to yield 16-4 (12.98 g, 13.10 mmol, 70%) as a clear, colorless oil. LC-MS (+ mode): RT 1.703 min. 890.6 (M-Boc+2H$^+$); $^1$H-NMR (300 MHz, $CDCl_3$): δ 5.50 (m, 2H), 4.32 (m, 4H), 4.21 (m, 4H), 3.20 (brm, 4H), 2.16-2.35 (7H), 1.82 (m, 8H), 1.75-1.80 (9H), 1.38 (s, 9H), 1.00-1.38 (24H), 0.75-0.90 (20H).

Synthesis of 16-5: bis(4-((1,3-bis((4-Ethylcyclohexane-1-carbonyl)oxy)propan-2-yl)oxy)-4-oxobutyl)ammonium trifluoroacetate

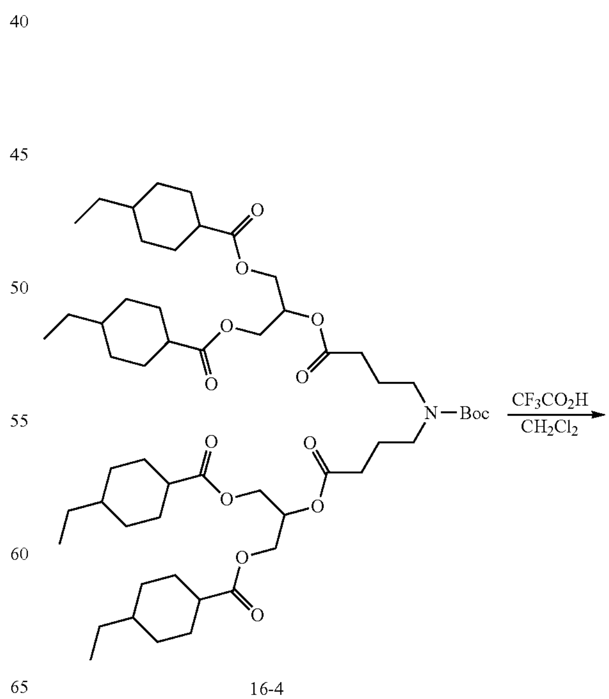

16-4

-continued

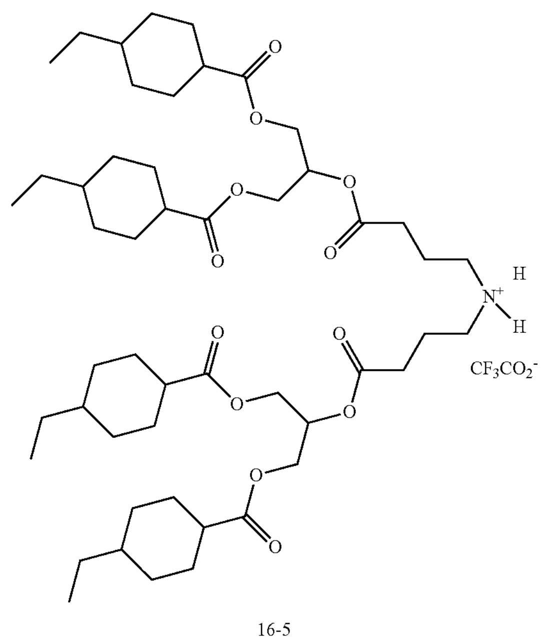

16-5

To a solution of 16-4 (12.98 g, 13.11 mmol) in $CH_2Cl_2$ (50 mL), cooled in an ice-water bath under nitrogen, was added $CF_3CO_2H$ (7.47 g, 65.54 mmol) over a period of 10 minutes. The mixture was allowed to stir for 15 minutes after the addition was complete, then it was warmed to room temperature and was stirred for 16 hours. Concentration in vacuo gave crude 16-5 (14.82 g) as a colorless oil. LC-MS (+ mode): RT 0.677 min. 890.6 ($M+H^+$); $^1$H-NMR (300 MHz, $CDCl_3$): δ 5.16 (m, 2H), 4.41 (m, 4H), 4.11 (m, 4H), 3.19 (brm, 4H), 2.42 (m, 4H), 2.25 (m, 4H), 1.75-2.20 (18H), 1.00-1.50 (22H), 0.75-0.95 (20H).

Synthesis of 16-6: ((4,4'-((1H-Imidazole-1-carbonyl)azanediyl)bis(butanoyl))bis(oxy))bis(propane-2,1,3-triyl) tetrakis(4-ethylcyclohexane-1-carboxylate)

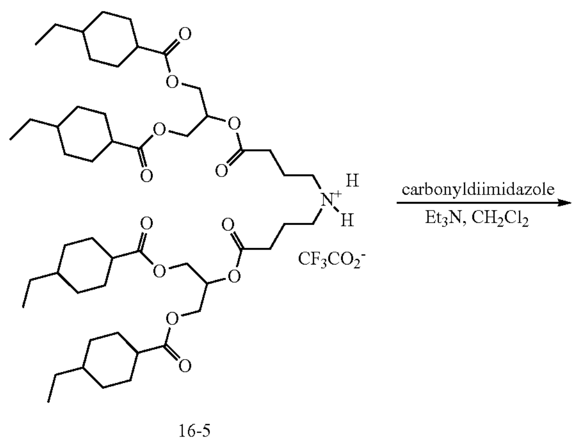

16-5

-continued

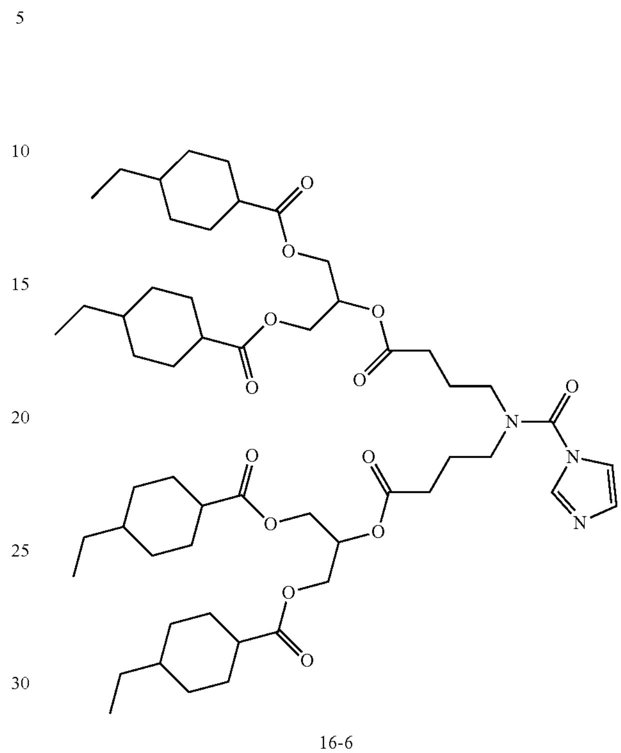

16-6

A solution of 16-5 (14.82 g, crude) was dissolved in $CH_2Cl_2$ (300 mL) and was cooled in an ice-water bath under nitrogen. To this solution was added in order $Et_3N$ (6.74 g, 66.59 mmol) and carbonyldiimidazole (5.39 g, 33.30 mmol). The mixture was stirred for 30 minutes after the additions were complete, then the solution was warmed to room temperature and was stirred for 3 hours. The solvent was removed in vacuo and the residue was dissolved in n-heptane (300 mL) and water was added to the flask. With vigorous stirring, the pH of the aqueous phase was adjusted to pH ca. 6.0 by the addition of 3% aq. citric acid solution. After the pH target was achieved, the organic phase was separated and was dried over $Na_2SO_4$. Filtration and concentration in vacuo provided crude 16-6 (13.77) which was utilized in the next step without additional purification. LC-MS (+ mode): RT 0.773 min. 984.5 ($M+H^+$); $^1$H-NMR (300 MHz, $CDCl_3$): δ 7.99 (m, 1H), 7.27 (m, 1H), 7.12 (m, 1H), 5.20 (m, 2H), 4.31 (m, 4H), 4.18 (m, 4H), 3.41 (m, 4H), 2.31 (m, 4H), 2.23 (m, 4H), 1.82-2.00 (12H), 1.79 (m, 8H), 1.00-1.40 (20H), 0.75-0.92 (20H).

Synthesis of LIPID 16: ((4,4'-((((3-(Dimethylamino)propyl)thio)carbonyl)azanediyl)bis(butanoyl))bis(oxy))bis(propane-2,1,3-triyl) tetrakis(4-ethylcyclohexane-1-carboxylate)

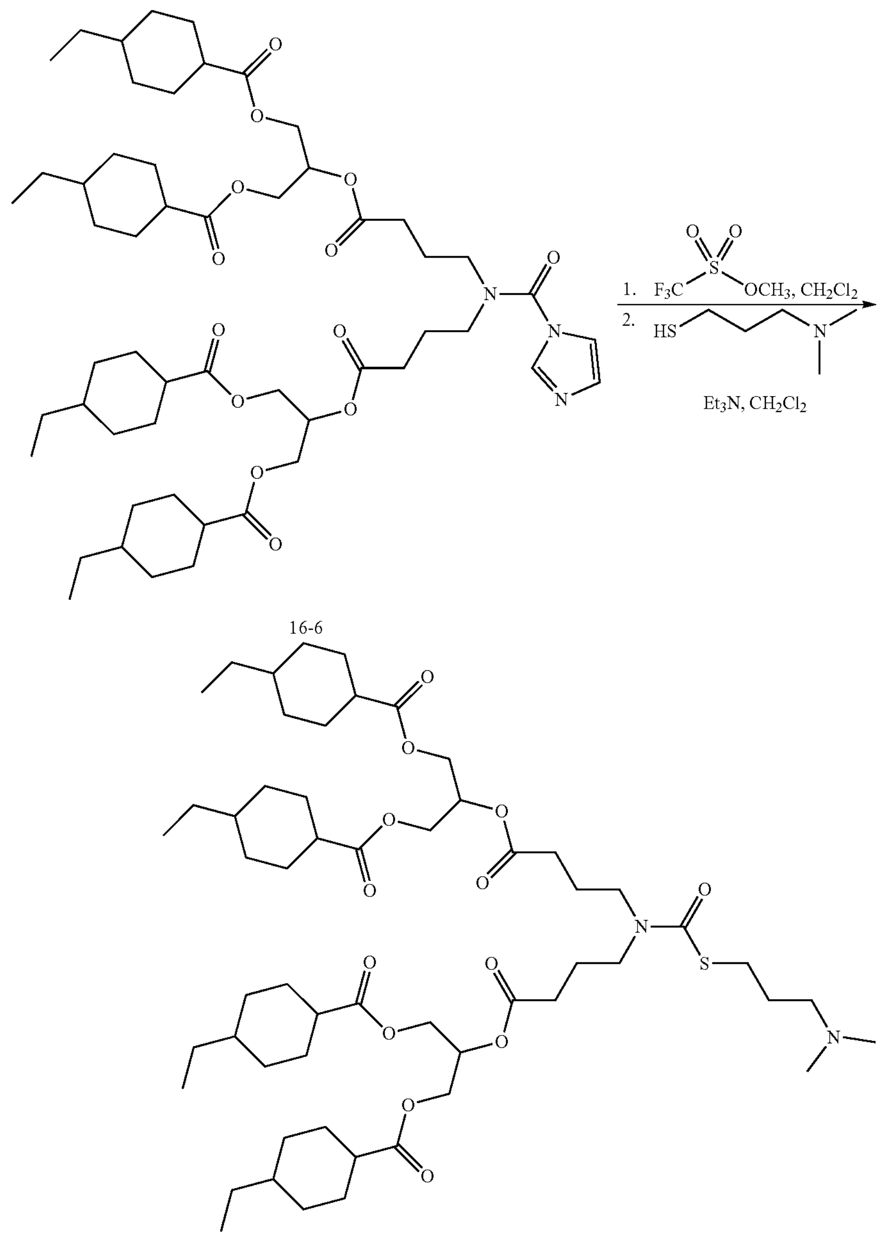

16-6

LIPID 16

A solution of 16-6 (13.77 g, crude) in $CH_2Cl_2$ (150 mL) was cooled in an ice-water bath under nitrogen. To this cooled solution was added methyl trifluoromethanesulfonate (2.52 g, 20.99 mmol) over a period of 10 minutes. The mixture was stirred for 1 hour in the ice-water bath, then $Et_3N$ (4.24 g, 41.97 mmol) was added over a period of 5 minutes followed by the addition of 3-dimethylamino-propanee-1-thiol (2.49 g, 20.99 mmol) over a period of 5 minutes. The mixture was allowed to stir for 30 minutes, then it was warmed to room temperature and was stirred for 8 hours. The mixture was concentrated in vacuo and the residue was dissolved in $CH_2Cl_2$ (100 mL) to which was added silica gel (30 g, type ZCX-2, 100-200 mesh) and the solvent was removed in vacuo to afford silica gel containing adsorbed, crude 16. The silica gel was placed atop a column of silica gel (80 g, type ZCX-2, 100-200 mesh) and a combi-flash was used to purify the crude LIPID 16 by eluting with a gradient of $CH_2Cl_2$:MeOH from 100:0 to 96:4, collecting 300 mL fractions. Qualified fractions were located by TLC, combined, and concentrated in vacuo to yield LIPID 16 (10.14 g, 9.797 mmol, 75% yield over 3 steps) as a clear, light yellow oil. ES-MS: 1036.0 (M+H$^+$); HPLC Purity 94.24%; $^1$H-NMR (300 MHz, $CDCl_3$): δ 5.24 (m, 2H), 4.30 (dd, J=11.9, 4.6 Hz, 4H), 4.14 (dd, J=11.9, 5.7 Hz, 4H), 3.38 (brm, 4H), 2.94 (t, J=7.1 Hz, 2H), 2.46 (s, 6H), 2.34 (brm, 4H), 2.20 (m, 4H), 1.72-1.91 (20H), 1.37 (m, 8H), 1.08-1.22 (16H), 0.80-0.91 (20H).
Example 17. Synthesis of LIPID 17: ((4,4'-((((3-(Dimethylamino)propyl)thio)carbonyl)azanediyl)bis(butanoyl)bis(oxy))bis(propane-2,1,3-triyl) tetrakis(3-cyclohexyl-2-methylpropanoate)
LIPID 17
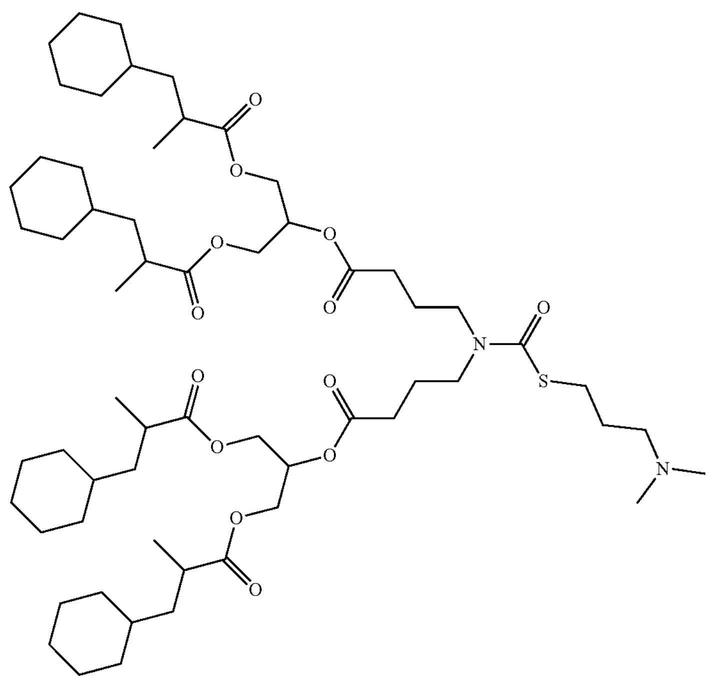
General Scheme
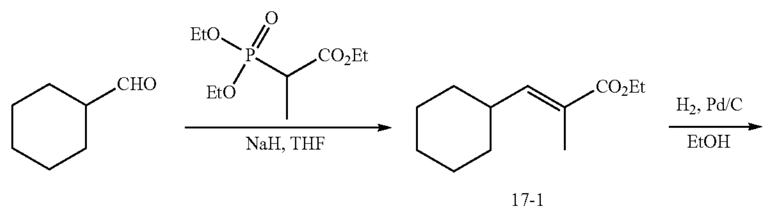
17-1
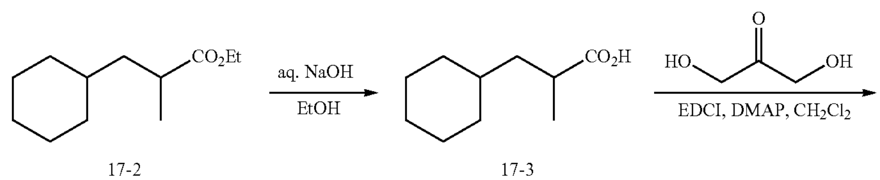
17-2
17-3

-continued
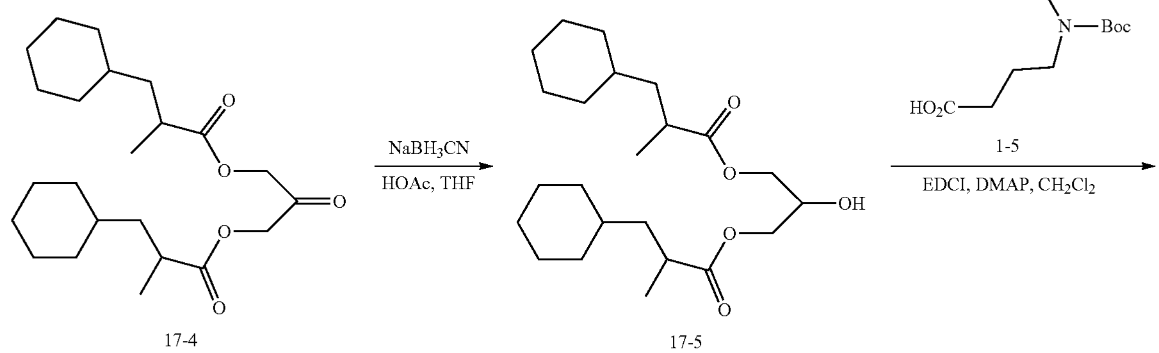
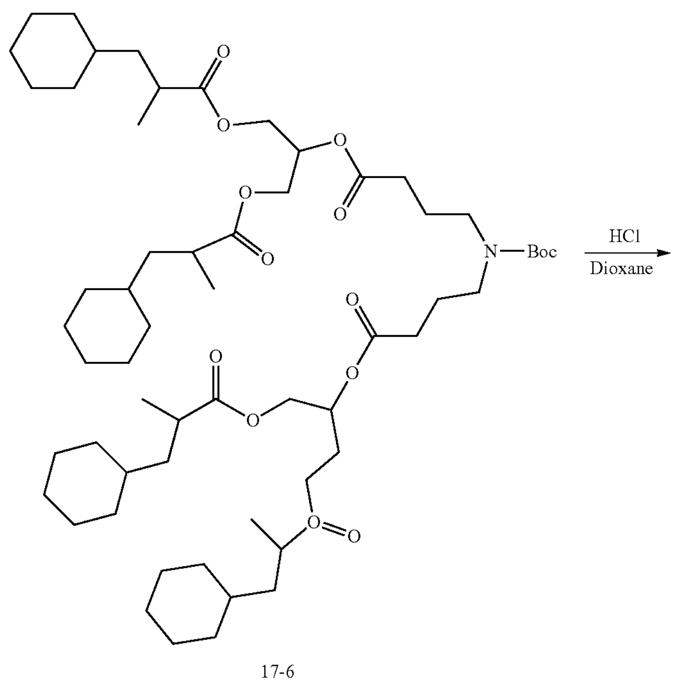

-continued
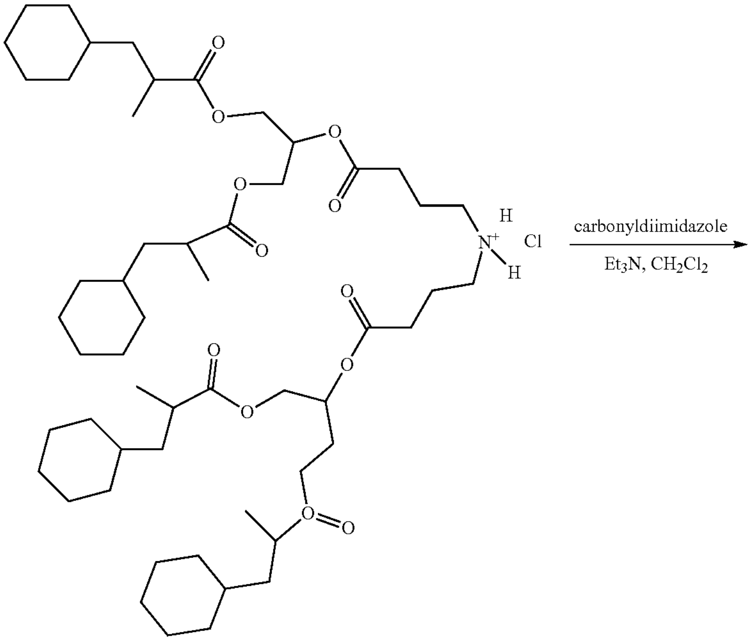
17-7
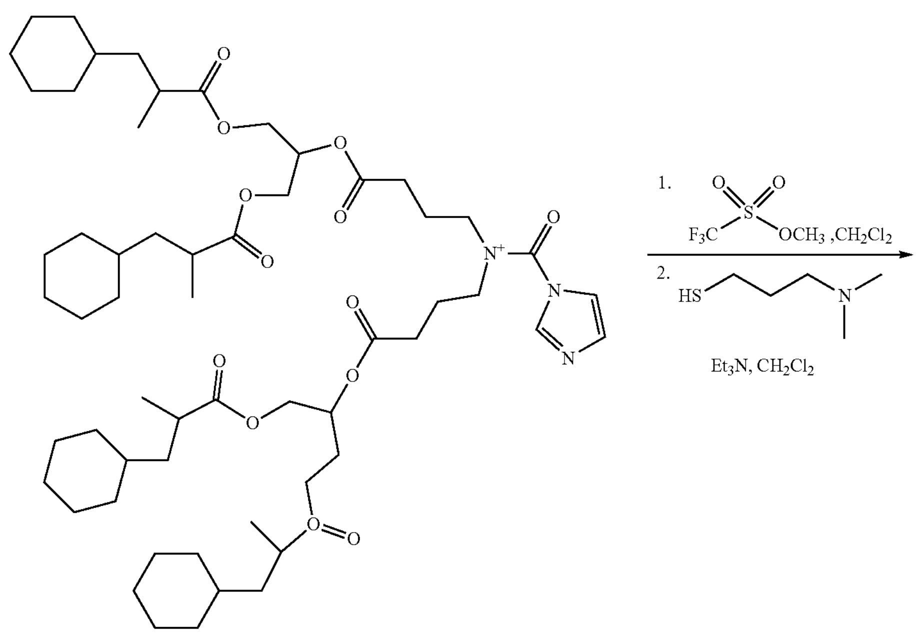
17-8

-continued

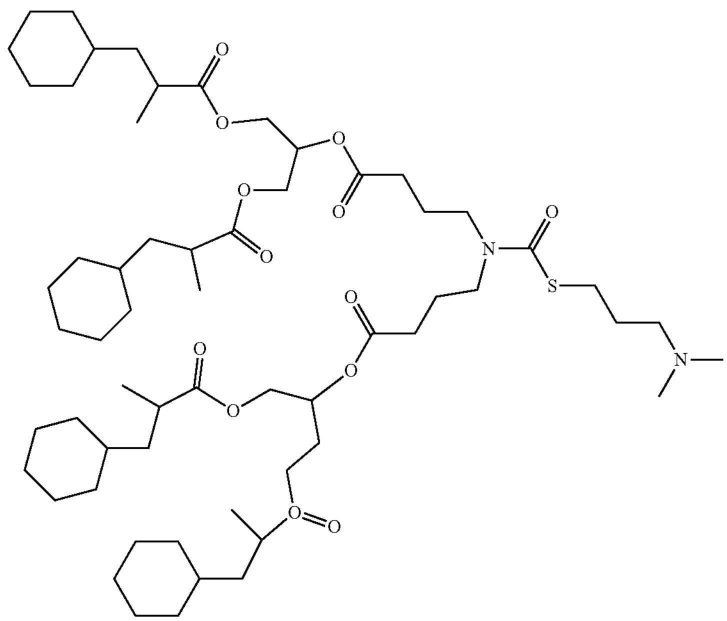

LIPID 17

Synthesis of 17-1: Ethyl (E)-3-cyclohexyl-2-methylacrylate

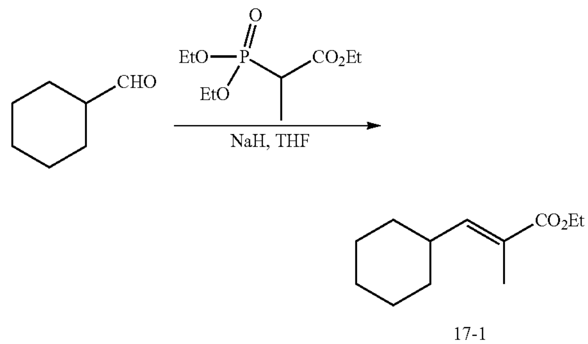

17-1

Into a 2 L 4-necked round-bottom flask purged and maintained with an inert atmosphere of nitrogen, was charged NaH (60%, 21.42 g, 0.534 mol, 1.0 equiv) and THF (822 mL). Then, ethyl 2-(diethoxyphosphoryl)propanoate (127.2 g, 0.536 mol, 1.0 equiv) was added dropwise over 30 min at room temperature and the mixture was stirred for 1.5 h after the addition was complete. Cyclohexane carboxaldehyde (60.0 g, 0.536 mol, 1.0 equiv) in THF (318 mL) was added dropwise over 30 min and the mixture was stirred for 2 h at room temperature. The reaction was quenched with saturated aqueous $NH_4Cl$ (1.5 L) and extracted with MTBE (2×0.75 L). The combined organic layers were washed with $H_2O$ (0.75 L), brine (0.75 L, 12.5 V), dried with anhydrous $Na_2SO_4$, filtered and concentrated under vacuum. This resulted in 105 g 17-1 (crude) as a yellow oil that was used in the next step without further purification.

Synthesis of 17-2: Ethyl 3-cyclohexyl-2-methylpropanoate

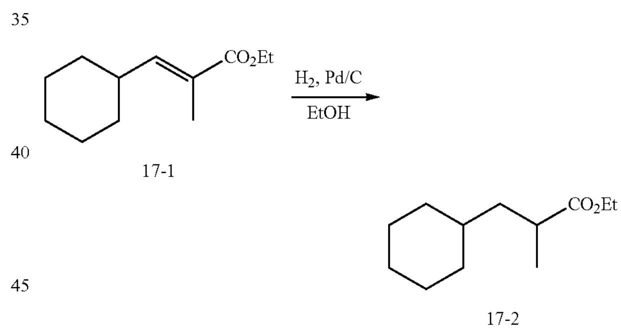

17-1

17-2

Into a 2 L round-bottom flask, flushed with nitrogen, was charged 17-1 (120.0 g, 1.0 equiv) in EtOH (1.2 L). Then, 10% wt Pd/C (36.0 g, 30% w./w.) was added in one portion. Then the mixture was stirred under $H_2$ atmosphere for 4 h at room temperature. Filtered and the filter cake was washed with $CH_2Cl_2$ (1.2 L). The filtrate was concentrated under vacuum to give crude 17-2. Crude 17-2 was dissolved in $CH_2Cl_2$ (1 L) and added 200 g of silica gel (type: ZCX-2, 100-200 mesh, 1.67 w./w.), the solvent was then removed under vacuum while maintaining the temperature below 35° C. Charged 1 kg of silica gel (type: ZCX-2, 100-200 mesh, 8.33 w./w.) to the column, followed by the last step prepared dry silica gel which absorbed the reaction mixture. A combi-flash was utilized to purify the product eluting with a petroleum ether/EtOAc gradient from 100:0 to 95:5, collecting 1000 mL fractions. Took samples for TLC analysis and combined qualified products. This resulted in 94 g (76% yield) of 17-2 as yellow oil.

Synthesis of 17-3:3-Cyclohexyl-2-methylpropanoic Acid

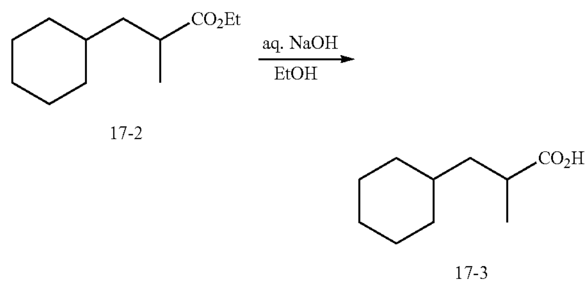

17-2

17-3

Into a 2 L 3-necked round-bottom flask purged and maintained with an inert atmosphere of nitrogen, was placed 17-2 (57.0 g, 0.288 mol, 1.0 equiv) in EtOH (285 mL) at room temperature. Then, NaOH (17.3 g, 0.433 mol, 1.5 equiv) in $H_2O$ (285 mL) was added in one portion. The resulting solution was then warmed to 70° C. and was stirred for 3 h. The reaction was cooled to room temperature and extracted with n-heptane (2×200 mL). The $H_2O$ layer was adjusted to pH=2 with aqueous HCl (12 mol/L), then extracted with MTBE (2× 300 mL). The combined organic layers were washed with $H_2O$ (2×150 mL), dried with anhydrous $Na_2SO_4$, filtered and concentrated under vacuum. This resulted in 47 g (0.276 mol, 96% yield) 17-3 as colorless oil. ELSD A: water/5 mM $NH_4^+HCO_3^-$: B: $CH_3CN$ 90:10 to 10:9 A/B at 2 min., hold 1 min): RT 0.56 min, m/z 170.1 (Calcd.), (found) 169.13 (M−H).

Synthesis of 17-4: 2-Oxopropane-1,3-diyl bis(3-cyclohexyl-2-methylpropanoate)

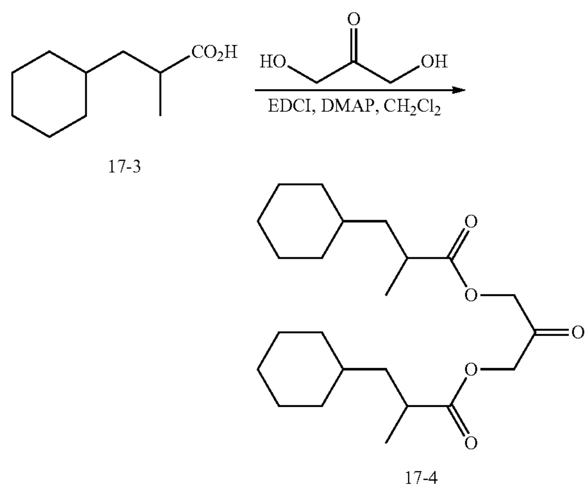

17-3

17-4

Into a 1 L 3-necked round-bottom flask purged and maintained with an inert atmosphere of nitrogen, was added 1,3-dihydroxyacetone (17.5 g, 0.194 mol, 1.0 equiv) and 17-3 (66.0 g, 0.388 mol, 2.0 equiv) in $CH_2Cl_2$ (350 mL). The temperature was reduced to 0° C. in an ice/water bath. To the cooled solution was added DMAP (12.0 g, 0.098 mol, 0.5 equiv) and EDCI (112 g, 0.583 mol, 3.0 equiv) at 0° C. The ice/water bath was removed, and the temperature was raised gradually. The reaction mixture was stirred overnight at room temperature. Directly, to the reaction mixture, was added 200 g of silica gel (type: ZCX-2, 100-200 mesh, 11.4 w./w.), and the solvent was removed under vacuum while maintaining the temperature below 35° C. Charged 1 kg of silica gel (type: ZCX-2, 100-200 mesh, 57.1 w./w.) to the column, followed by the last step prepared dry silica gel which absorbed the reaction mixture. Using combi-flash to purify the product, eluting with a petroleum ether/EtOAc gradient from 100:0 to 90:10, collecting 1000 fractions. Took sample for TLC analysis and combined qualified products. This resulted in 73 g (0.184 mol, 95% yield) of 17-4 as light-yellow oil. Product has no MS signal and used as such in the next step.

Synthesis of 17-5: 2-Hydroxypropane-1,3-diyl bis(3-cyclohexyl-2-methylpropanoate)

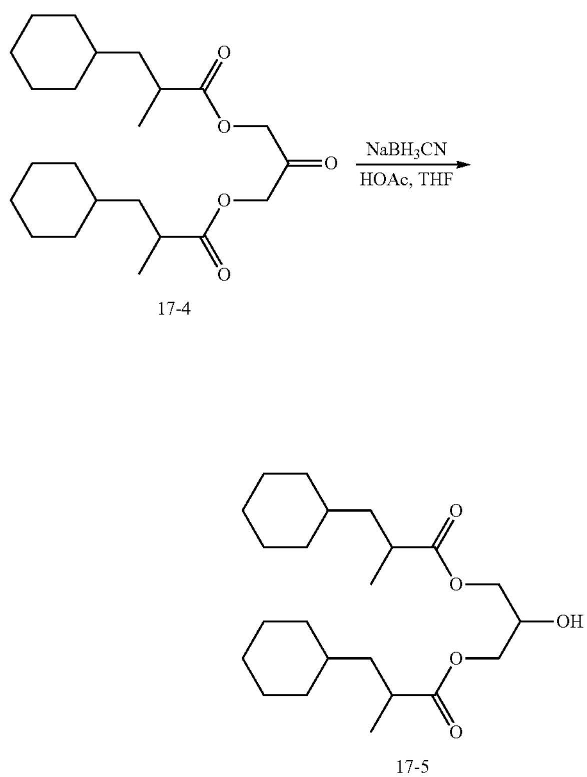

17-4

17-5

Into a 1 L 3-necked round-bottom flask purged and maintained with an inert atmosphere of nitrogen, was placed a solution of 17-4 (56.0 g, 0.142 mol, 1.0 equiv) in THF (560 mL). The temperature was reduced to 0° C. in an ice/water bath. To the solution was added HOAc (12.8 g, 0.213 mol, 1.5 equiv) at 0° C., and then to the mixture was added $NaBH_3CN$ (12.5 g, 0.199 mol, 1.4 equiv) at 0° C. The ice/water bath was removed, and the temperature was raised gradually. The reaction mixture was stirred for 8 h at room temperature. The reaction mixture was quenched with $H_2O$ (1.1 L) and extracted with $CH_2Cl_2$ (1.6 L). The organic layer was washed with aqueous $NaHCO_3$ (560 mL), $H_2O$ (2×280 mL), dried with anhydrous $Na_2SO_4$ and filtered. The filtrate was used for next step directly.

Synthesis of 17-6: ((4,4'-((tert-Butoxycarbonyl) azanediyl)bis(butanoyl))bis(oxy))bis(propane-2,1,3-triyl) tetrakis(3-cyclohexyl-2-methylpropanoate)

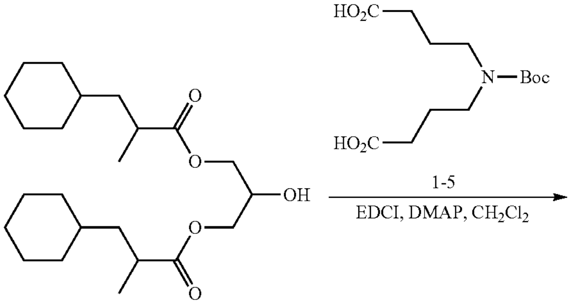

17-5

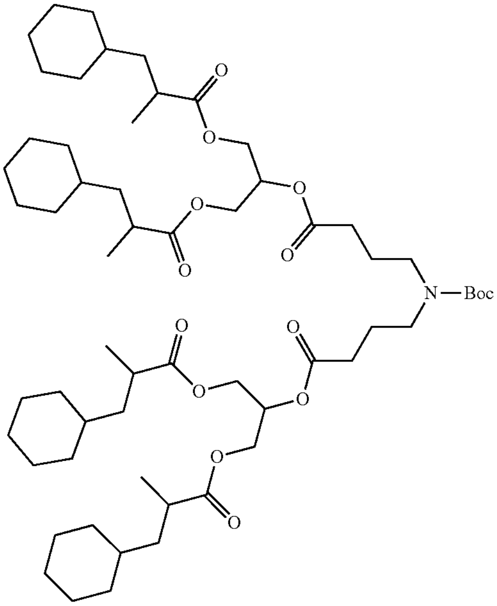

17-6

Into a 2 L 3-necked round-bottom flask purged and maintained with an inert atmosphere of nitrogen, was added 1-5 (20.0 g, 0.069 mol, 1.0 equiv) and 17-5 (solution from above, 0.138 mol, 2.0 equiv). The temperature was reduced to 0° C. in an ice/water bath. To the solution was added DMAP (8.4 g, 0.069 mol, 1.0 equiv) and EDCI (53 g, 0.277 mol, 4.0 equiv) at 0° C. The ice/water bath was removed, and the temperature was raised gradually. The reaction mixture was stirred overnight at room temperature. Directly to the reaction mixture was added 200 g of silica gel (type: ZCX-2, 100-200 mesh, 10.0 w./w.), the mixture was then concentrated under vacuum while maintaining the temperature below 35° C. Charged 1.5 kg of silica gel (type: ZCX-2, 100-200 mesh, 75.0 w./w.) to the column, followed by the last step prepared dry silica gel which absorbed the reaction mixture. Using combi-flash to purify the product, eluting with a petroleum ether/EtOAc gradient from 100:0 to 90:10, collecting 500 mL fractions. Took sample for TLC analysis and combined qualified products. This resulted in 30.8 g (59.6 mmol, 42% for 2 steps) of 17-6 as light-yellow oil. ELSD A: water/0.05% TFA: B: $CH_3CN$/0.05% TFA 95:5 to 5:95 A/B at 3 min., hold 1.0 min): RT 2.08 min, m/z (Calcd.) 1045.7, (found) 946.6 (M-Boc+H).

Synthesis of 17-7: bis(4-((1,3-bis((3-Cyclohexyl-2-methylpropanoyl)oxy)propan-2-yl)oxy)-4-oxobutyl) ammonium chloride

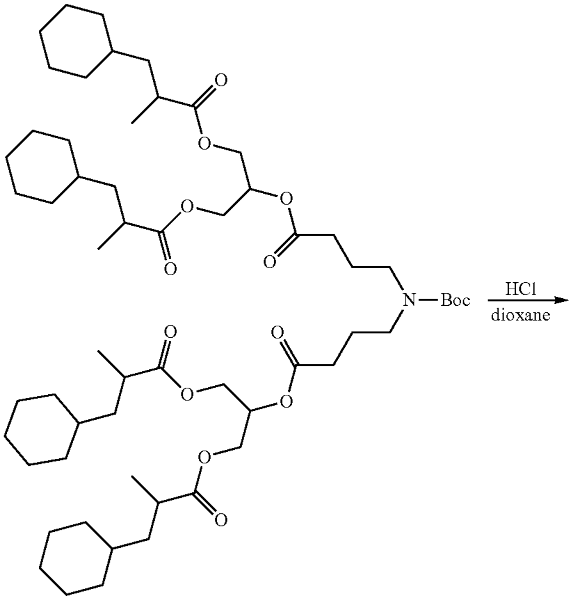

17-6

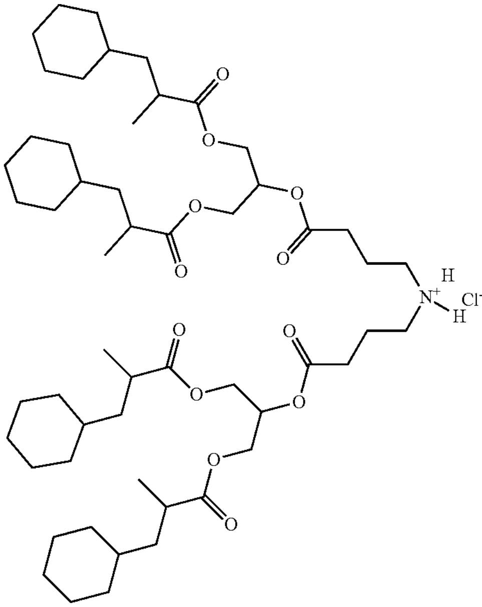

17-7

Into a 1 L round-bottom flask purged and maintained with an inert atmosphere of nitrogen, was placed a solution of 17-6 (48.0 g, 0.046 mol, 1.0 equiv) in 1,4-dioxane (240 mL) and the solution was cooled in an ice-water bath. To the solution was added 4M HCl in 1,4-dioxane (240 mL) dropwise at 0-10° C. over 10 min. The resulting solution was stirred overnight at room temperature. The mixture was concentrated under vacuum. This provided 48 g (crude) of 17-7 as yellow oil. ELSD A: water/0.05% TFA: B: $CH_3CN$/0.05% TFA 95:5 to 5:95 A/B at 3 min., hold 1.0 min): RT 0.92 min, m/z (Calcd.) 945.6, (found) 946.6 (M+H).

Synthesis of 17-8: ((4,4'-((1H-Imidazole-1-carbonyl)azanediyl)bis(butanoyl))-bis(oxy))bis(propane-2,1,3-triyl) tetrakis(3-cyclohexyl-2-methylpropanoate)

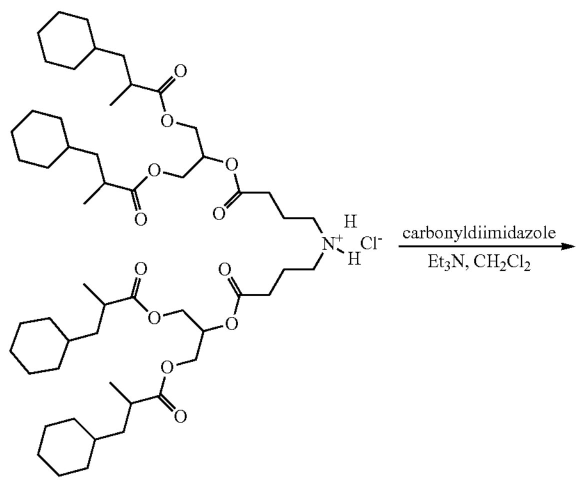

17-7

-continued

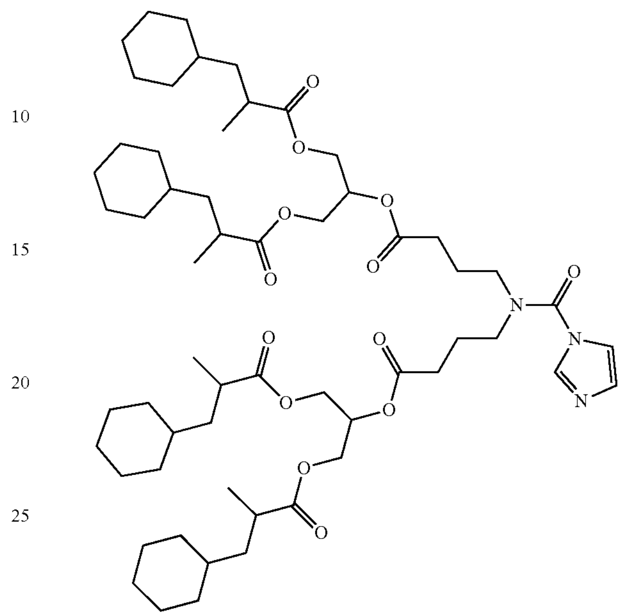

17-8

Under nitrogen atmosphere, charged 17-7 (48.0 g, 0.046 mol, 1.0 equiv) in $CH_2Cl_2$ (1.06 L) into a 2 L 3-necked round-bottom bottle. Then, carbonyldiimidazole (15.9 g, 0.098 mol, 2.1 equiv) was added followed by pyridine (15.4 g, 0.196 mol, 4.26 equiv) and the mixture was stirred overnight at room temperature. The resulting solution was washed with 3% aqueous citric acid (2×500 mL), $H_2O$ (3×500 mL) and brine (500 mL), dried with anhydrous $Na_2SO_4$, and concentrated at 35° C. under vacuum. The crude mixture was dissolved in $CH_2Cl_2$ (800 mL) and 100 g of silica gel (type: ZCX-2, 100-200 mesh, 2.08 w./w.) was added and the solvent was removed under vacuum while maintaining the temperature below 35° C. Charged 300 g of silica gel (type: ZCX-2, 100-200 mesh, 6.25 w./w.) to the column, followed by the last step prepared dry silica gel which absorbed the reaction mixture. Using a combi-flash to purify the produce, eluting with a petroleum ether/EtOAc gradient from 100:0 to 70:30, collecting 400 mL fractions. Took samples for TLC analysis and combined qualified products. This resulted in 39 g (37.5 mmol, 81% yield) 17-8 as an oil. ELSD A: water/0.05% TFA: B: $CH_3CN$/0.05% TFA 95:5 to 5:95 A/B at 2 min, hold 0.6 min): RT 1.0 min, m/z (Calcd.) 1039.6, (found) 1040.6 (M+H).

Synthesis of LIPID 17: ((4,4'-((((3-(Dimethylamino)propyl)thio)carbonyl)-azanediyl)bis(butanoyl))bis(oxy))bis(propane-2,1,3-triyl) tetrakis(3-cyclohexyl-2-methylpropanoate)

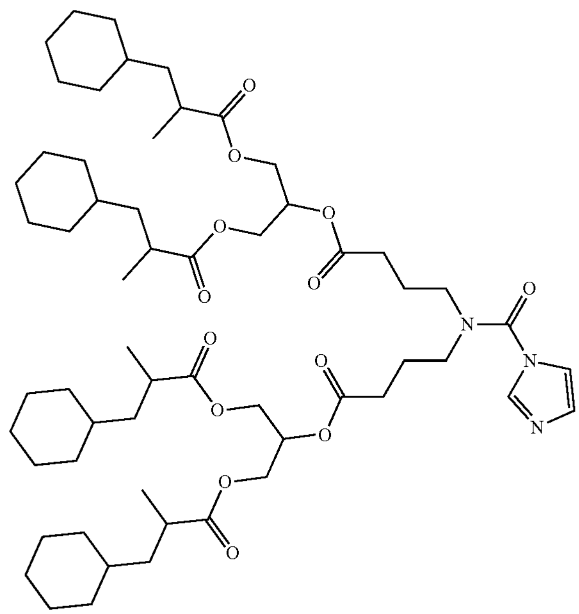

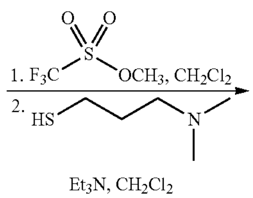

17-8

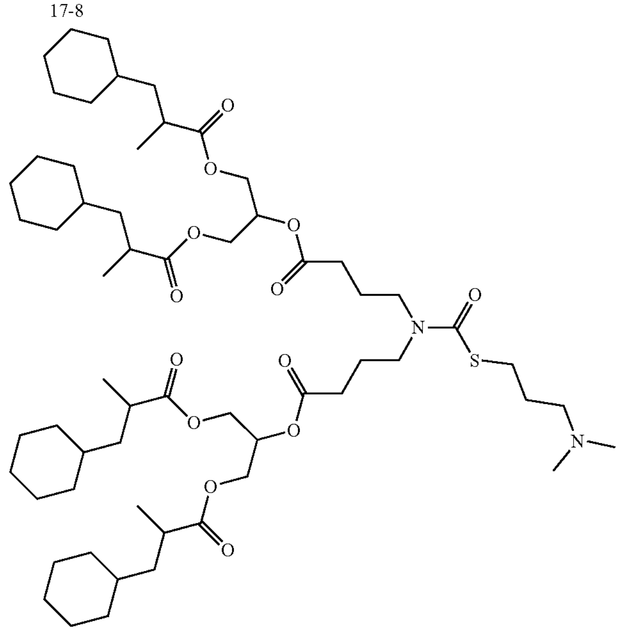

LIPID 17

Into a 500 mL 3-necked round-bottom flask purged and maintained with an inert atmosphere of nitrogen, was placed a solution of 17-8 (20.0 g, 0.019 mol, 1.0 equiv) in $CH_2Cl_2$ (200 mL). The reaction temperature was reduced to 0° C. in an ice/water batch. To the mixture was added methyl trifluoromethansulfonate (3.3 g, 0.020 mol, 1.05 equiv) at 0° C. After addition, continue stirring the reaction for 3 hours at 0° C. Charged the trimethylamine 2.0 M in THF (28.9 mL, 0.058 mol, 3.0 equiv) into the reactor at 0° C. After addition, continue stirring the reaction for 0.5-1 hours at 0° C. Charged 3-(dimethylamino)propane-1-thiol (3.0 g, 0.025 mol, 1.3 equiv) into the reactor at 0° C. After addition, the reaction was allowed to come to room temperature and then continued to stir for 5.0 hours. Charged sodium chloride aqueous solution (10.0 wt. %, 200 mL) and 10% aqueous citric acid solution (10.0 wt %, 200 mL) into the reactor. Stirred for 15 minutes and then let reactor stand for 15 minutes to allow for phase separation at room temperature. Collected the organic layer. This operation was repeated one additional time. Charged sodium chloride aqueous solution (10.0 wt. %, 200 mL) and charge sodium bicarbonate aqueous solution (5.0 wt. %, 200 mL) into the reactor. Stirred for 15 minutes and then let reactor stand for 15 minutes to allow for phase separation at room temperature. Collect the organic layer. This operation was repeated one additional time. Charged sodium chloride aqueous solution (10.0 wt. %, 400 mL) into the reactor. Stirred for at least 15 minutes and then let reactor stand for at least 15 minutes to allow for phase separation at room temperature. Collected the organic layer. Charged the n-heptane (250 mL) into the reactor. Concentrated the solution to about 300 mL under vacuum while maintaining the temperature at 20-40° C. Charged 10.0 wt. % citric acid methanol/water (10:1, 200 mL) solution into the reactor. After addition, stirred for 15 minutes and then let reactor stand for 15 minutes to allow phase separation at 36±5° C. Collected the MeOH/$H_2O$ layer. Charged n-heptane (250 mL) into the reactor to wash the MeOH/$H_2O$ phase. Repeat this n-heptane washing operation eight times. Charged n-heptane (500 mL), 15.0 wt. % sodium carbonate solution (250 mL) and 10.0 wt. % sodium chloride solution (250 mL) into the reactor. Stirred for 15 minutes and then let reactor stand for 15 minutes to allow for phase separation at room temperature. Collected the organic layer. Charged 5.0 wt. % sodium bicarbonate solution (400 mL) into the reactor. Stirred for 15 minutes and then let reactor stand for 15 minutes to allow for phase separation at room temperature. Collected the organic layer and dried over anhydrous sodium sulfate and concentrated under vacuum. To the residue in $CH_2Cl_2$ (300 ml) was added 30 g of silica gel (type: ZCX-2, 100-200 mesh, 1.5 w./w.), the mixture was then concentrated under vacuum while maintaining the temperature below 35° C. Charged 200 g of silica gel (type: ZCX-2, 100-200 mesh, 10.0 w./w.) to the column, followed by the last step prepared dry silica gel which absorbed the reaction mixture. Using combi-flash to purify the product, eluting with a $CH_2Cl_2$/MeOH gradient from 100:0 to 90:10, collecting 400 mL fractions. Took samples for TLC analysis and combined qualified products. This resulted in 11.5 g (55% yield) of LIPID 17 as yellow oil. ELSD A: water/0.05% TFA: B: $CH_3CN$/0.05% TFA 80:20 to 20:80 A/B at 3 min., hold 1 min): RT 0.97 min, m/z (Calcd.) 1090.7, (found) 1091.7 (M+H). $^1$H-NMR (300 MHz, $CDCl_3$): δ 5.25 (m, 2H), 4.34 (dt, J=11.9, 4.0 Hz, 4H), 4.15 (m, 4H), 3.38 (brm, 4H), 2.92 (t, J=7.3 Hz, 2H), 2.67-2.49 (4H), 2.48-2.22 (12H), 1.89-1.84 (6H), 1.78-1.51 (24H), 1.35-1.07 (32H), 0.99-0.76 (8H).

Example 18. Synthesis of LIPID 18: ((4,4'-(((3-(Dimethylamino)propyl)thio)carbonyl)azanediyl)bis(butanoyl))bis(oxy)bis(propane-2,1,3-triyl) tetrakis(2-methyloctanoate)

LIPID 18

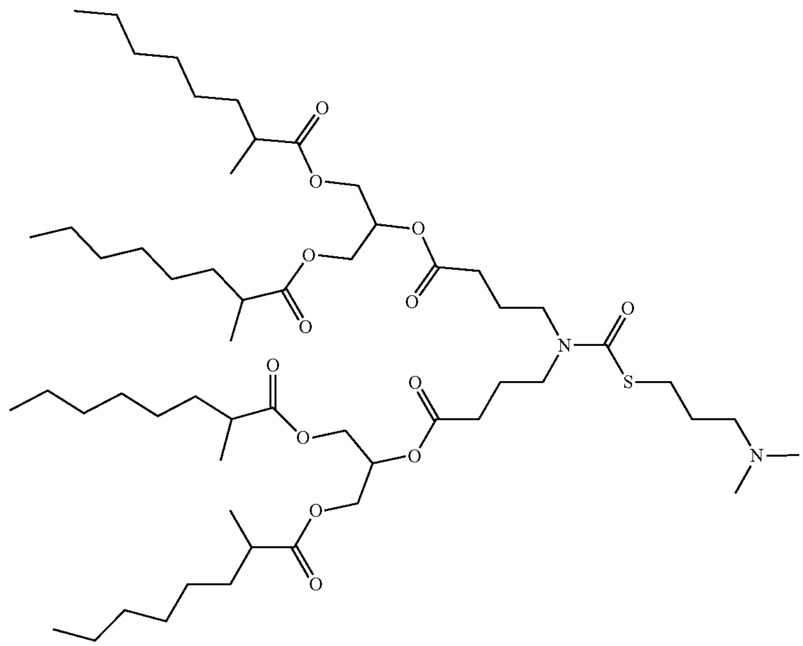

General Scheme

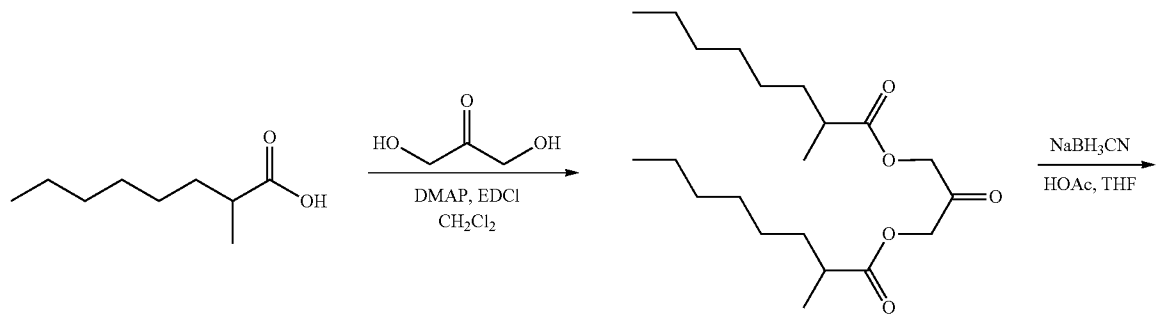

18-1

-continued
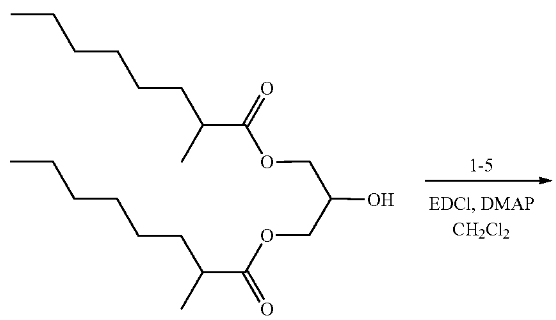
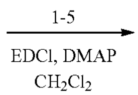
18-2
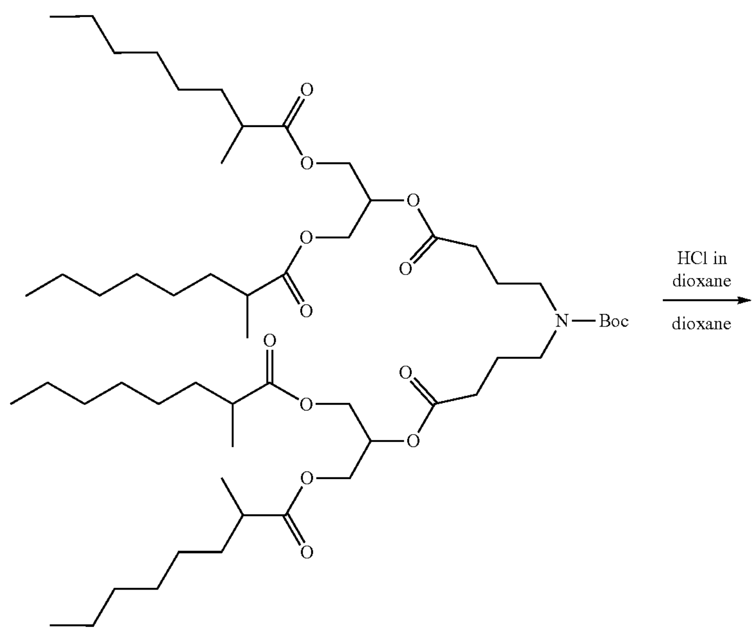
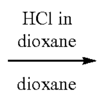
18-3
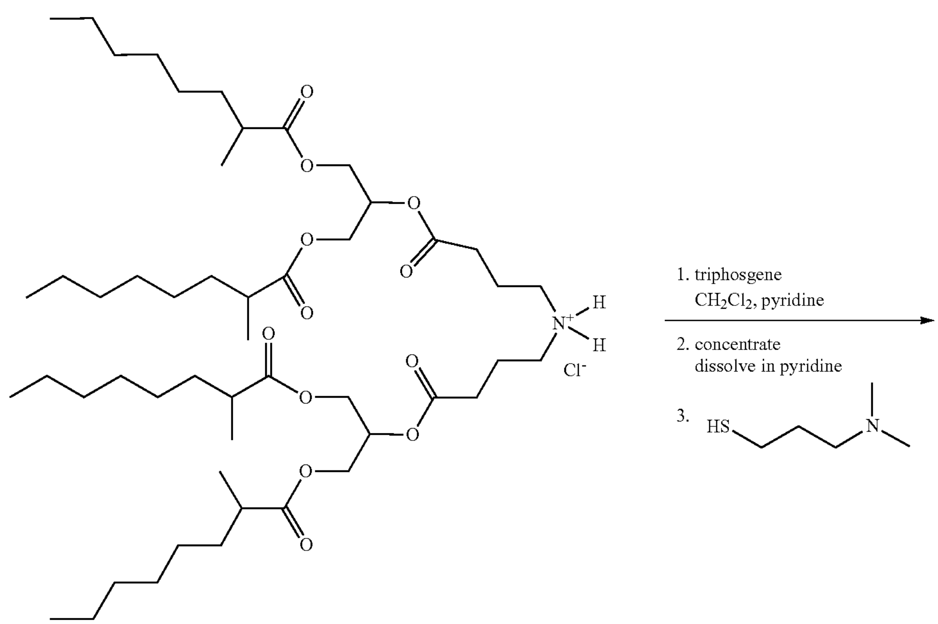
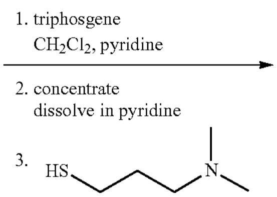
18-4

-continued

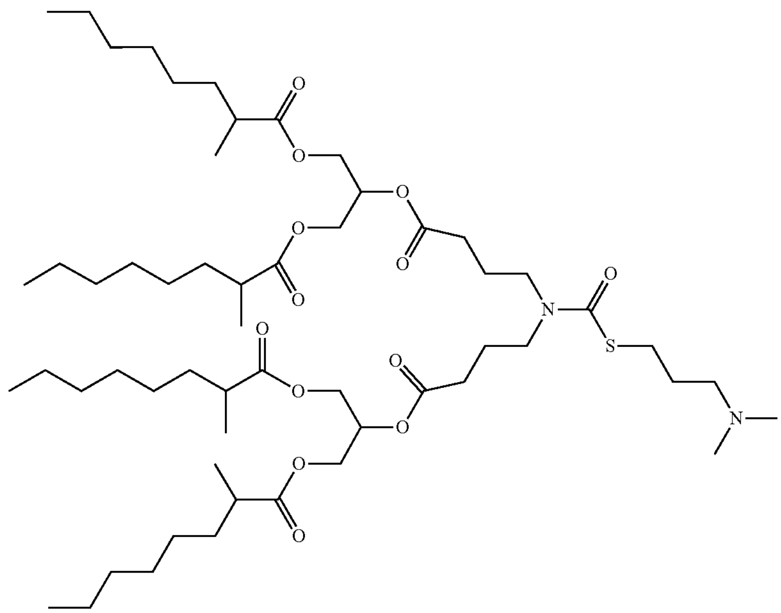

LIPID 18

Synthesis of 18-1:2-Oxopropane-1,3-diyl bis(2-methyloctanoate)

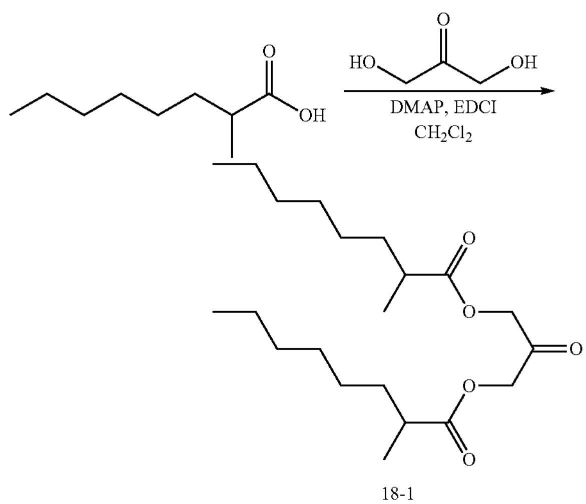

18-1

Into a 50 ml 3-necked round-bottom flask purged and maintained with an inert atmosphere of nitrogen, was added 1,3-dihydroxyacetone (1.42 g, 1.0 equiv) and 2-methyloctanoic acid (5.0 g, 2.0 equiv, Org. Biomol. Chem. 2014, 12, 3649-3663) in $CH_2Cl_2$ (30 mL). The solution was cooled in an ice-water bath, then was added DMAP (0.96 g, 0.5 equiv) and EDCI (12.1 g, 4.0 equiv) at 0° C. The reaction mixture was brought to room temperature and stirred overnight. To the mixture was added 20 g of silica gel (type: ZCX-2, 100-200 mesh, 15.5 w./w.), the solvent was removed under vacuum while maintaining the temperature below 35° C. Charged 100 g of silica gel (type: ZCX-2, 100-200 mesh, 77.5 w/w) to the column, followed by the last step prepared dry silica gel which absorbed the reaction mixture. The crude product was purified using a Combi Flash purification system, eluting with a petroleum ether/EtOAc gradient from 100:0 to 90:10 collected every 200±50 mL). Took sample for TLC analysis and qualified fractions were combined and concentrated under vacuum. This resulted in 4.9 g (85% yield) of 18-1 as light-yellow oil. ELSD A: water/0.05% TFA: B: $CH_3CN$/0.05% TFA 95:5 to 5:95 A/B at 2 min., hold 1.3 min): RT 1.6 min, m/z (Calcd.) 370.3, (found) 371.3 (M+H).

Synthesis of 18-2: 2-Hydroxypropane-1,3-diyl bis(2-methyloctanoate)

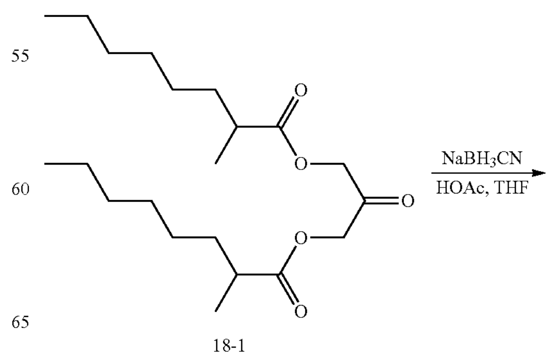

18-1

-continued

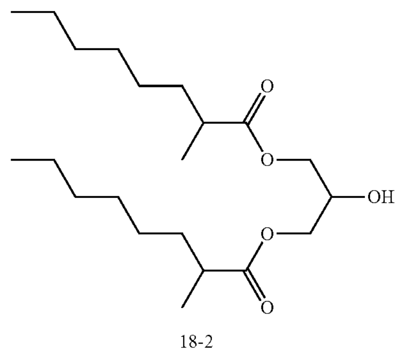

18-2

Into a 100 mL 3-necked round-bottom flask purged and maintained with an inert atmosphere of nitrogen, was placed a solution of 18-1 (4.9 g, 1.0 equiv) in THF (50 mL) and the solution was cooled in an ice-water bath. To the solution was added HOAc (1.03 g, 1.3 equiv) at 0° C., followed by the addition $NaBH_3CN$ (1.0 g, 1.2 equiv) at 0° C. The ice water bath was removed after adding all reagents. The reaction mixture was stirred overnight at room temperature. The reaction mixture was quenched with $H_2O$ (100 mL) and extracted with $CH_2Cl_2$ (150 mL). The organic layer was washed with 5% aqueous $NaHCO_3$ (50 mL), $H_2O$ (2×50 mL), dried with anhydrous $Na_2SO_4$ and filtered. The filtrate, containing 18-2, was used for next step directly.

Synthesis of 18-3: ((4,4'-((tert-butoxycarbonyl) azanediyl)bis(butanoyl))bis(oxy))bis(propane-2,1,3-triyl) tetrakis(2-methyloctanoate)

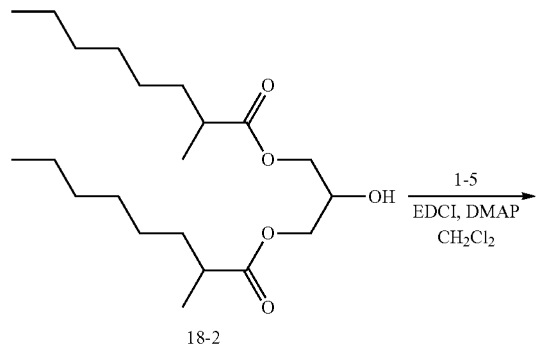

18-2

-continued

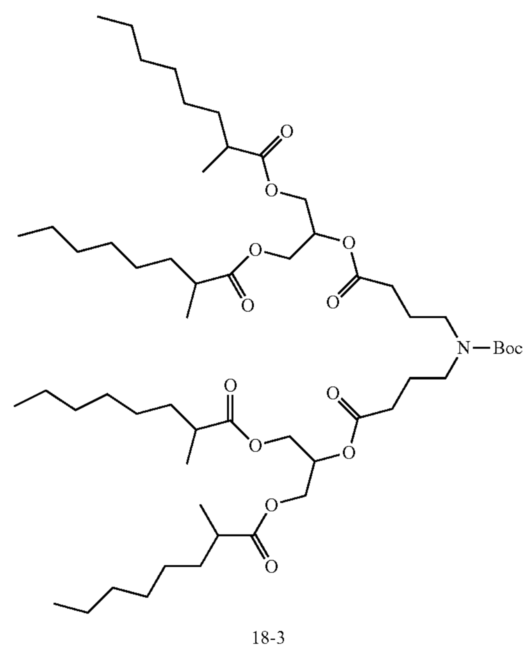

18-3

Into a 100 mL 3-necked round-bottom flask purged and maintained with an inert atmosphere of nitrogen, was added 18-2 (8.8 g, 2.3 equiv) and 1-5 (3.0 g, 1.0 equiv) in $CH_2Cl_2$ (60 mL) and the mixture was cooled in an ice-water bath. To the solution was added DMAP (1.26 g, 1.0 equiv) and EDCI (7.96 g, 4.0 equiv) at 0° C. The ice water bath was removed after adding all reagents. The reaction mixture was stirred overnight at room temperature. To the mixture was added 20 g of silica gel (type: ZCX-2, 100-200 mesh, 6.7 w./w.), and the solvent was removed under vacuum while maintaining the temperature below 35° C. Charged 120 g of silica gel (type: ZCX-2, 100-200 mesh, 40.0 w/w) to the column, followed by the last step prepared dry silica gel which absorbed the reaction mixture. A combi-flash was utilized to purify the product, eluting with a petroleum ether/EtOAc gradient from 100:0 to 90:10, collecting 200 mL fractions. Took sample for TLC analysis and combined qualified products. This resulted in 4.3 g (42% yield) of 18-3 as light-yellow oil. ELSD A: water/0.05% TFA: B: $CH_3CN$/ 0.05% TFA 80:20 to 20:80 A/B at 3 min., hold 1 min): RT 1.97 min, m/z (Calcd.) 997.7, (found) 1020.6 (M+Na).

Synthesis of 18-4: bis(4-((1,3-bis((2-methyloctanoyl)oxy)propan-2-yl)oxy)-4-oxobutyl)ammonium chloride

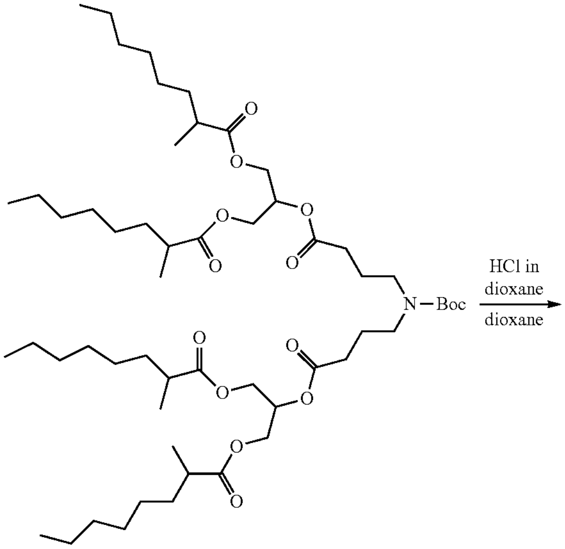

18-3

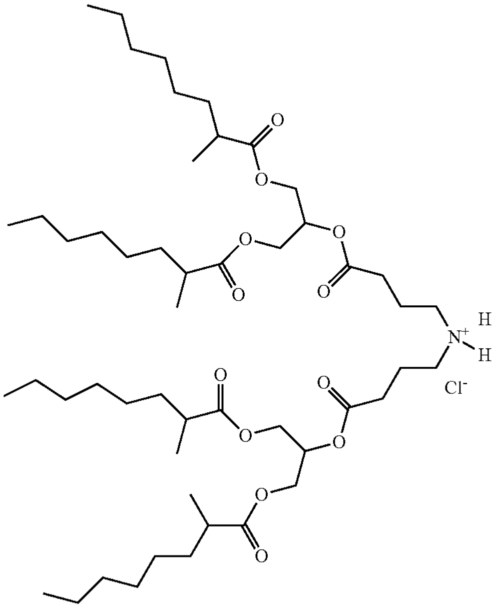

18-4

Into a 100 mL round-bottom flask purged and maintained with an inert atmosphere of nitrogen, was placed a solution of 18-3 (4.3 g, 1.0 equiv) in 1,4-dioxane (21 mL) and the solution was cooled in an ice-water bath. To the cooled solution was added 4M HCl in 1,4-dioxane (21 mL) dropwise at 0-10° C. over 10 min. The resulting solution was stirred overnight at room temperature. The reaction mixture was concentrated under vacuum. This resulted in 4 g (crude) of 18-4 as yellow oil. ELSD A: water/0.05% TFA: B: $CH_3CN$/0.05% TFA 95:5 to 5:95 A/B at 2 min., hold 1.3 min): RT 1.6 min, m/z (Calcd.) 897.6, (found) 898.6 (M+H).

Synthesis of LIPID 18: ((4,4'-((((3-(Dimethylamino)propyl)thio)carbonyl)-azanediyl)bis(butanoyl))bis(oxy))bis(propane-2,1,3-triyl) tetrakis(2-methyloctanoate)

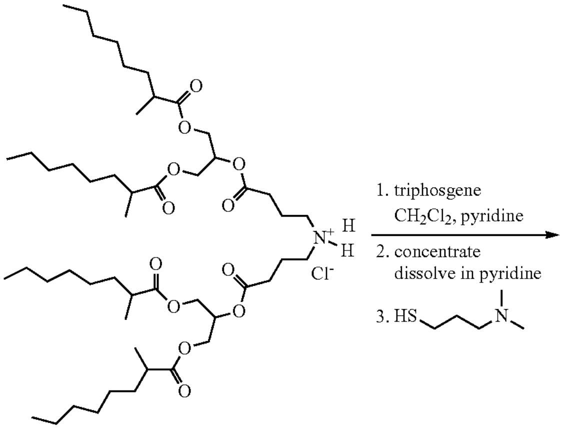

18-4

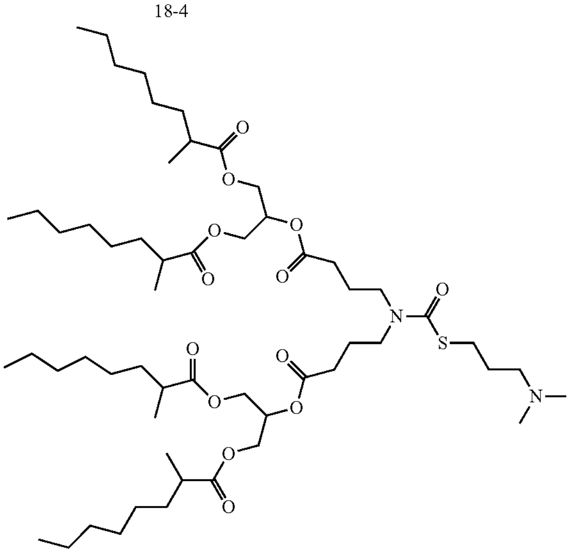

LIPID 18

Into a 250 mL 3-necked round-bottom flask purged and maintained with an inert atmosphere of nitrogen, was placed a solution of 18-4 (3.8 g, 1.0 equiv) in $CH_2Cl_2$ (80 mL) and the solution was cooled in an ice-water bath. To the mixture was added triphosgene (1.26 g, 1.0 equiv) at 0° C., followed by the addition of pyridine (1.67 g, 5.0 equiv) dropwise with stirring at 0° C. The ice water bath was removed after adding all reagents. The mixture was stirred for 4 h at room temperature and then concentrated under vacuum (temperature <30° C.). The residue was dissolved with pyridine (80 mL), cooled in an ice-water bath under nitrogen, then 3-(dimethylamino)propane-1-thiol (1.0 g, 2.0 equiv) was added dropwise with stirring at 0° C. in 10 min. The resulting solution was stirred for overnight at room temperature. The reaction mixture was concentrated under vacuum and the residue was diluted with $CH_2Cl_2$ (80 mL). The solution was washed with 10% aq. citric acid (40 mL), $H_2O$ (40 mL), saturated $NaHCO_3$ (2×40 mL) and brine (40 mL, 10 V). The organic layer was dried over anhydrous sodium sulfate and concentrated under vacuum. To the residue, dissolved in $CH_2Cl_2$ (60 mL), was added 8 g of silica gel (type: ZCX-2, 100-200 mesh, 2.11 w./w.), and the solvent was removed under vacuum while maintaining the temperature below 35° C. Charged 100 g of silica gel (type: ZCX-2, 100-200 mesh, 26.3 w/w) to the column, followed by the last step prepared dry silica gel which absorbed the reaction mixture. Using a combi-flash to purify the product, eluting with a $CH_2Cl_2$/MeOH gradient from 100:0 to 90:10, collecting 100 mL fractions. Took samples for TLC analysis and combined qualified products. This resulted in 1.3 g (29% yield for 2 steps) of LIPID 18 as yellow oil. ELSD A: water/0.05% TFA: B: $CH_3CN$/0.05% TFA 80:20 to 20:80 A/B at 3 min., hold 2.1 min): RT 1.1 min, m/z (Calcd.) 1042.7, (found) 1043.6 (M+H). $^1$H-NMR (300 MHz, $CDCl_3$): δ 5.25 (m, 2H), 4.34 (m, 4H), 4.16 (m, 4H), 3.38 (brm, 4H), 2.92 (m, 4H), 2.66 (s, 6H), 2.46 (m, 4H), 2.35 (brs, 4H), 2.09 (m, 2H), 1.90 (brs, 4H), 1.64 (m, 4H), 1.47-1.20 (38H), 1.15-1.13 (12H), 0.95-0.81 (12H).

Example 19. Synthesis of LIPID 19: ((4,4-(((3-(Dimethylamino)propyl)thio)carbonyl)azanediyl)bis(butanoyl))bis(oxy))bis(propane-2,1,3-triyl) tetrakis(2,2-dimethylheptanoate)

LIPID 19

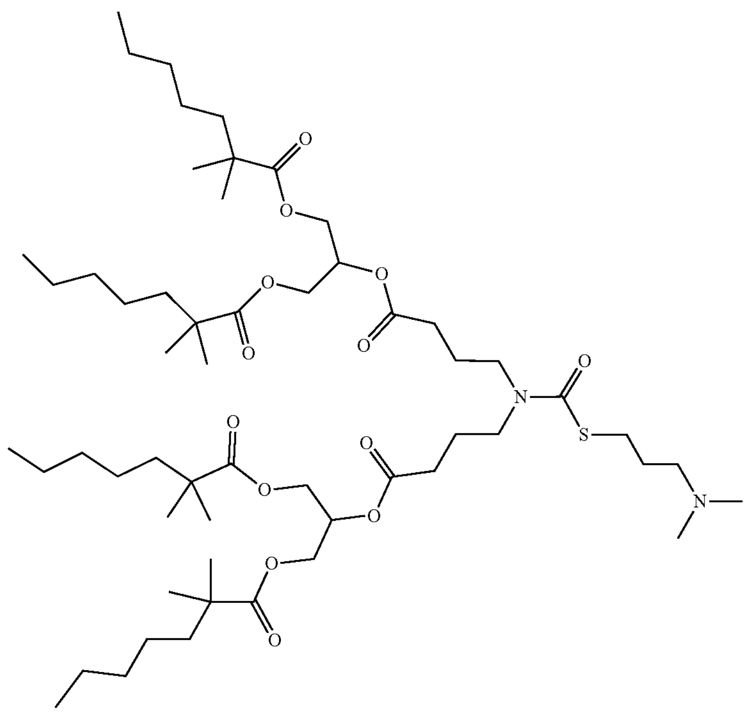

General Scheme

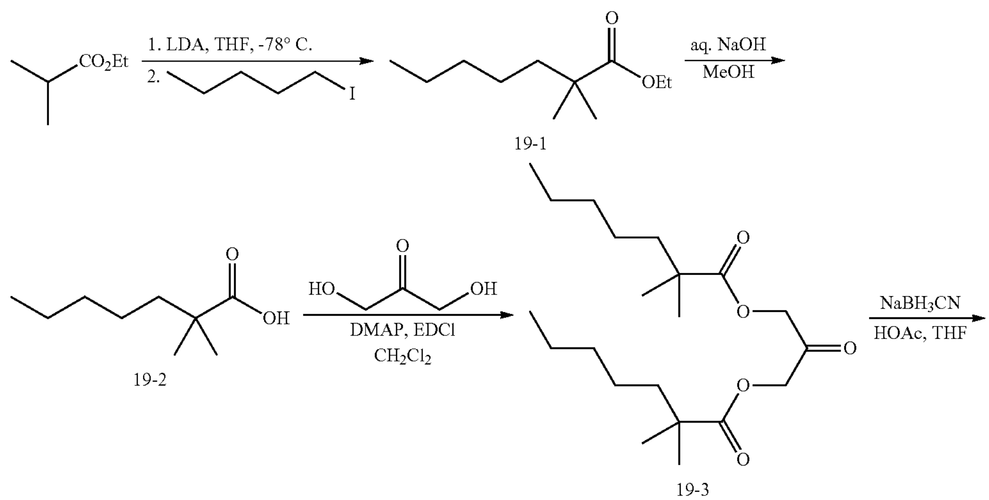

19-1

19-2

19-3

-continued
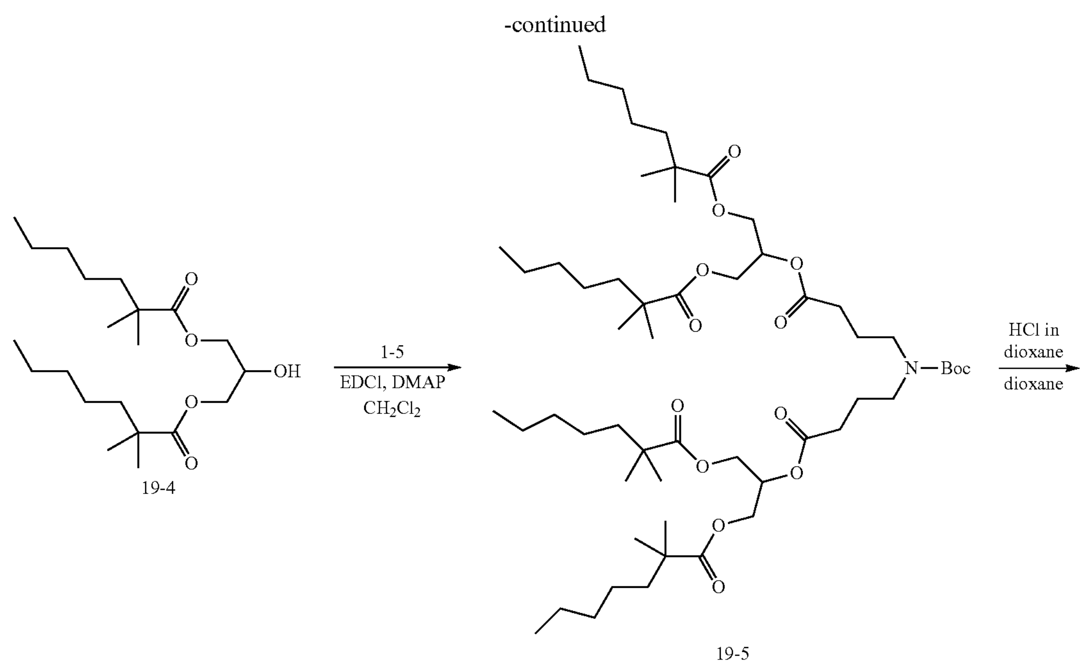
19-4
19-5
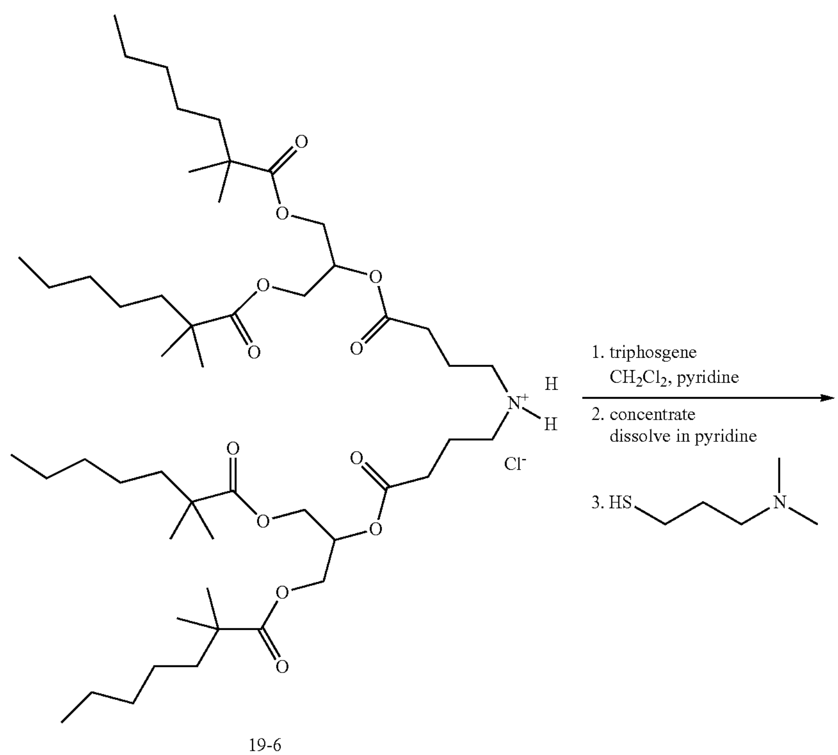
19-6

-continued

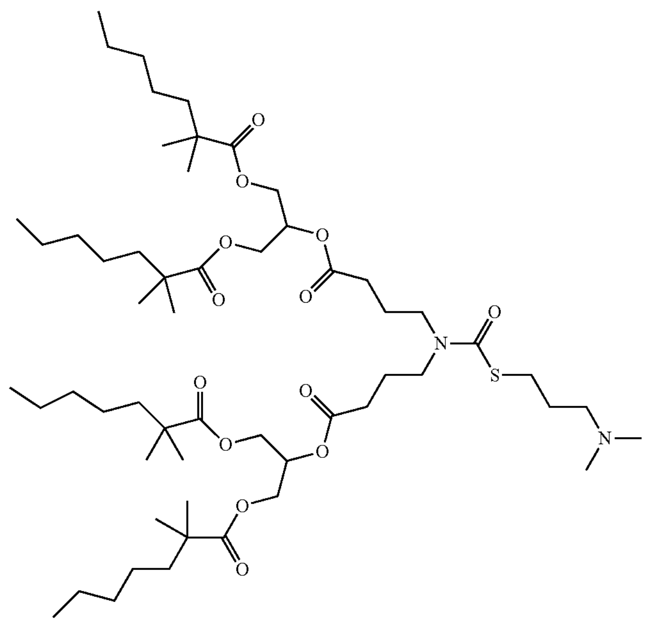

LIPID 19

Synthesis of 19-1: Ethyl 2,2-dimethylheptanoate

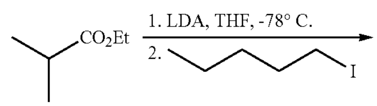

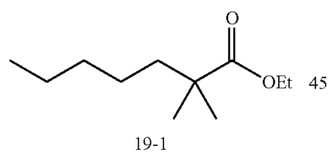

19-1

Into a 500 ml 3-necked round-bottom flask purged and maintained with an inert atmosphere of nitrogen, was placed ethyl isobutyrate (40.0 g, 1.0 equiv) in THF (400 mL). The resulting solution was cooled to −78° C., then LDA (205.6 ml, in hexane, 1.05 equiv) was added dropwise, and the resulting solution was stirred for 1 h at −78° C. Then, 1-iodopentane (92.8 g, 1.2 equiv) was added dropwise, and the resulting solution was stirred for 5 h at −78° C. The cooling bath was removed, and the solution was stirred overnight at room temperature. The pH value of the solution was adjusted to 6 with aqueous HCl solution (1 mol/L). The resulting solution was extracted with ethyl acetate (2×300 mL) and the organic layers were combined. The resulting mixture was washed with brine (500 mL), dried over anhydrous sodium sulfate and concentrated under vacuum. This resulted in 51 g (75.6%) of 19-1 as yellow oil that was used in the next step without further purification.

Synthesis of 19-2: 2,2-Dimethyl heptanoic Acid

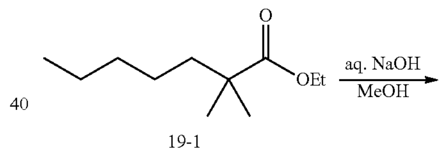

19-1

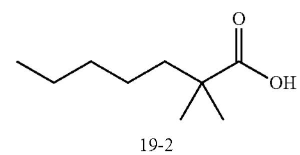

19-2

Into a 2-L 3-necked round-bottom flask purged and maintained with an inert atmosphere of nitrogen, was placed 19-1 (70.0 g, 1.0 equiv) in MeOH (700 mL). A solution of NaOH (49.0 g, 3.0 equiv) in $H_2O$ (350 mL) was added dropwise to the solution at room temperature. The resulting solution was warmed and stirred for 4 h at 60° C. The resulting mixture was concentrated under vacuum after cooling to room temperature. The residue was dissolved in $H_2O$ (200 mL), extracted with MTBE (200 mL) and the aqueous layer was separated. The pH value of the aq. layer was adjusted to 5 with aqueous HCl solution (1 mol/L). The resulting solution was extracted with ethyl acetate (2×100 mL) and the organic layers combined. The resulting mixture was washed with brine (200 mL), dried over anhydrous sodium sulfate, filtered, and concentrated under vacuum. This resulted in 32 g (68%) of 19-2 as yellow oil which was used without purification.

Synthesis of 19-3: 2-Oxopropane-1,3-diyl bis(2,2-dimethylheptanoate)

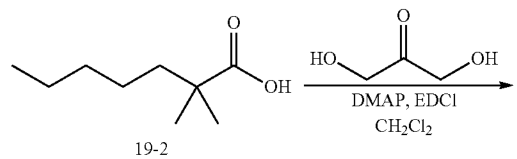

19-2

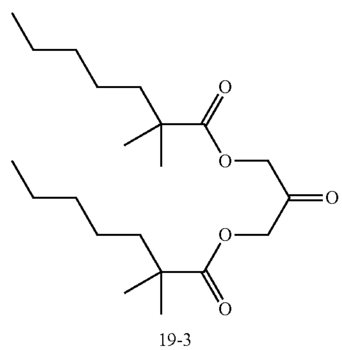

19-3

Into a 500 mL 3-necked round-bottom flask purged and maintained with an inert atmosphere of nitrogen, was added 1,3-dihydroxyacetone (12.0 g, 1.0 equiv) in $CH_2Cl_2$ (240 mL). The solution was cooled to 0° C. in an ice/water bath. To the solution were added 19-2 (44.0 g, 2.1 equiv), DMAP (16.3 g, 1.0 equiv) followed by EDCI (76.7 g, 3.0 equiv) at 0° C. The ice/water bath was removed and the reaction mixture was stirred overnight at room temperature. To the reaction solution was added 25 g of silica gel (type: ZCX-2, 100-200 mesh, 2.08 w./w.), the mixture was then concentrated under vacuum while maintaining the temperature below 35° C. Charged 500 g of silica gel (type: ZCX-2, 100-200 mesh, 41.7 w./w.) to the column, followed by the last step prepared dry silica gel which absorbed the reaction mixture. Using a combi-flash to purify the product, eluting with a petroleum ether/EtOAc gradient from 95:5 to 90:10, collecting 1000 fractions. Took samples for TLC analysis and combined qualified products. Concentration under vacuum resulted in 40.6 g (75.8%) 19-3 as colorless oil. ELSD A: water/0.05% TFA: B: $CH_3CN$/0.05% TFA 95:5 to 5:95 A/B at 2 min., hold 1.3 min): RT 1.8 min, m/z (Calcd.) 370.2, (found) 393.2 (M+Na).

Synthesis of 19-4: 2-Hydroxypropane-1,3-diyl bis(2,2-dimethylheptanoate)

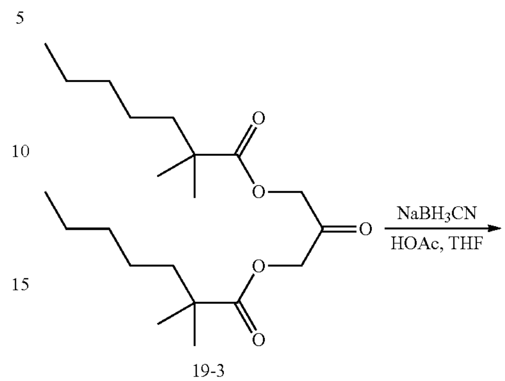

19-3

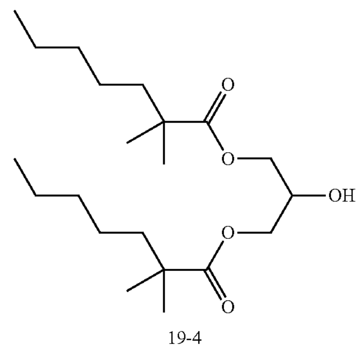

19-4

Into a 500 mL 3-necked round-bottom flask purged and maintained with an inert atmosphere of nitrogen, was placed 19-3 (15.5 g, 1.0 equiv) in THF (155 mL). The solution was cooled to 0° C. in an ice/water bath. To the solution was added HOAc (3.26 g, 1.3 equiv) at 0° C., and then, to the mixture was added $NaBH_3CN$ (3.16 g, 1.2 equiv) in one batch at 0° C. The ice/water bath was removed, and the mixture was stirred for 16 h at room temperature. The reaction was quenched with water (200 mL). The mixture was extracted with $CH_2Cl_2$ (3×200 mL). The combined organic phases were washed with brine (500 mL), then dried with $Na_2SO_4$. Filtration and concentration under vacuum gave crude 19-4 which was dissolved in $CH_2Cl_2$ (75 mL) and 30 g of silica gel (type: ZCX-2, 100-200 mesh, 1.94 w./w.) was added to the solution, the mixture was concentrated under vacuum while maintaining the temperature below 35° C. Charged 200 g of silica gel (type: ZCX-2, 100-200 mesh, 12.9 w./w.) to the column, followed by the last step prepared dry silica gel which absorbed the reaction mixture. Using a combi-flash to purify the product, eluting with a petroleum ether/EtOAc gradient from 90:10 to 85:15, collecting 400 mL fractions. Took samples for TLC analysis and combined qualified products. Concentration under vacuum gave in 12.3 g (79.3% yield) 19-4 as yellow oil. ELSD A: water/0.05% TFA: B: $CH_3CN$/0.05% TFA 95:5 to 5:95 A/B at 2 min, hold 1.2 min): RT 1.5 min, m/z (Calcd.) 372.2, (found) 395.2 (M+Na).

Synthesis of 19-5: ((4,4'-((tert-Butoxycarbonyl) azanediyl)bis(butanoyl))bis(oxy))bis(propane-2,1,3-triyl) tetrakis(2,2-dimethylheptanoate)

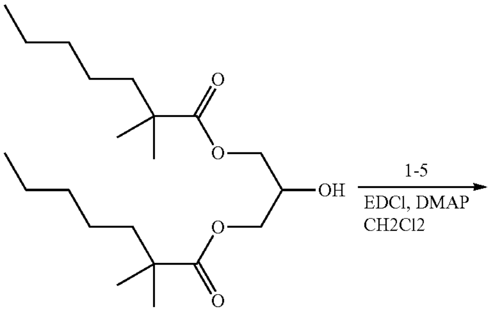

19-4

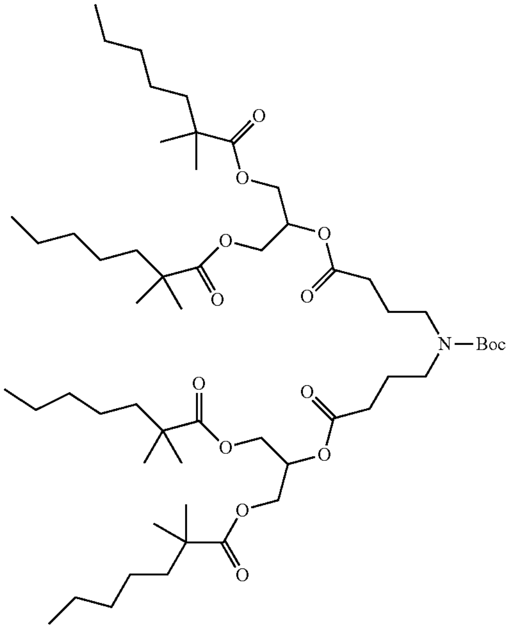

19-5

Into a 250 mL 3-necked round-bottom flask purged and maintained with an inert atmosphere of nitrogen, was placed 1-5 (4.77 g, 1.0 equiv) in $CH_2Cl_2$ (80 mL). The solution was cooled to 0° C. in an ice/water bath, then 19-4 (12.3 g, 2.0 equiv), DMAP (2.0 g, 1.0 equiv) were added in order, followed by EDCI (9.5 g, 3.0 equiv) at 0° C. The ice/water bath was removed and the resulting solution was stirred for 16 h at room temperature. To the reaction solution was added 15 g of silica gel (type: ZCX-2, 100-200 mesh, 3.14 w./w.), the mixture was concentrated under vacuum while maintaining the temperature below 35° C. Charged 200 g of silica gel (type: ZCX-2, 100-200 mesh, 41.9 w./w.) to the column, followed by the last step prepared dry silica gel which absorbed the reaction mixture. Using a combi-flash to purify the product, eluting with a petroleum ether/EtOAc gradient from 90:10 to 86:14, collecting 400 mL fractions. Took samples for TLC analysis and then combined qualified products. This resulted in 15.8 g (96.3%) of 19-5 as yellow oil.

Synthesis of 19-6: bis(4-((1,3-bis((2,2-dimethylheptanoyl)oxy)propan-2-yl)oxy)-4-oxobutyl)ammonium chloride

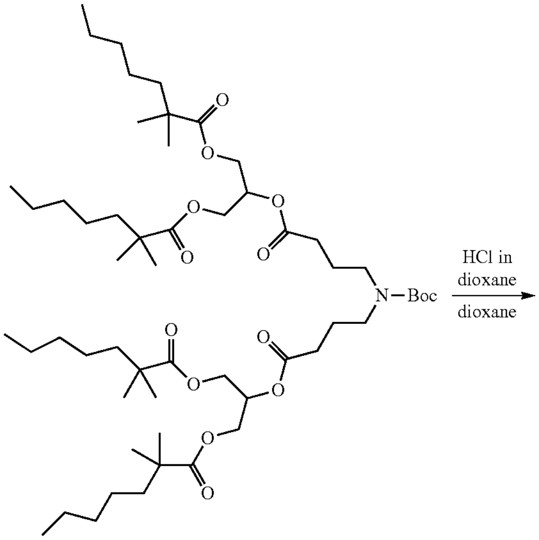

19-5

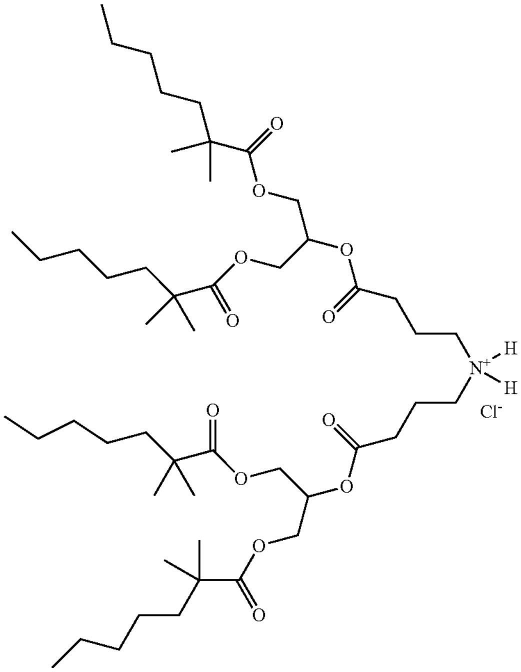

19-6

Into a 250 mL round-bottom flask purged and maintained with an inert atmosphere of nitrogen, was placed a solution of 19-5 (6.0 g, 1.0 equiv) in $CH_2Cl_2$ (30 mL). The solution was cooled to 0° C. in an ice/water bath. To the solution was added HCl in dioxane (60 mL, 4 mol/L) dropwise at 0-10° C. The ice/water bath was removed and the resulting solution was stirred overnight at room temperature. The reaction mixture was concentrated under vacuum resulting in 6.2 g (crude) of 19-6 as light-yellow oil. ELSD A: water/0.05% TFA: B: $CH_3CN$/0.05% TFA 95:5 to 5:95 A/B at 2 min., hold 1.2 min): RT 1.5 min, m/z (Calcd.) 897.6, (found) 898.5 (M+H).

Synthesis of LIPID 19: ((4,4'-((((3-(Dimethylamino)propyl)thio)carbonyl)-azanediyl)bis(butanoyl))bis(oxy))bis(propane-2,1,3-triyl) tetrakis(2,2-dimethylheptanoate)

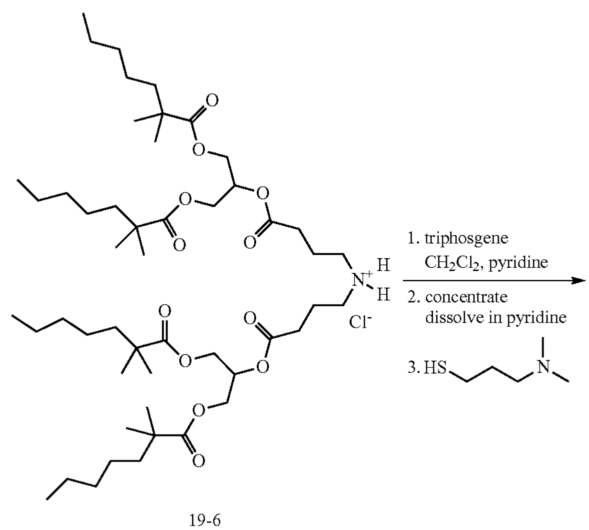

19-6

-continued

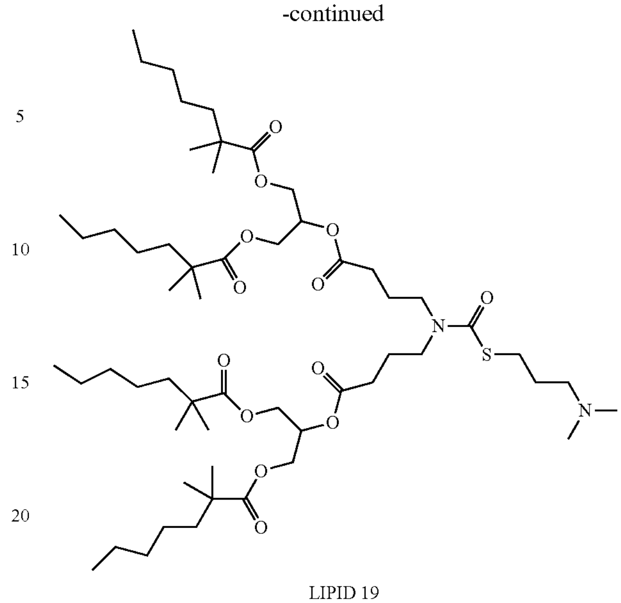

LIPID 19

Into a 500 ml 3-necked round-bottom flask purged and maintained with an inert atmosphere of nitrogen, was placed a solution of 19-6 (6.0 g, 1.0 equiv) in $CH_2Cl_2$ (210 mL). The solution was cooled to 0° C. in an ice/water bath. To the mixture was added triphosgene (2.69 g, 1.5 equiv) at 0° C. This was followed by the addition of pyridine (2.53 g, 5.0 equiv) dropwise with stirring at 0° C. The ice/water batch was removed and the mixture was stirred for 4 h at room temperature and then concentrated under vacuum (temperature <30° C.). The residue was dissolved with pyridine (120 mL, 20 V) and the solution was cooled to 0° C. in an ice/water bath. To this solution was added 3-(dimethylamino)propane-1-thiol (1.53 g, 2.0 equiv) dropwise with stirring at 0° C. in 10 min. The ice/water batch was removed and the resulting solution was stirred overnight at room temperature. The reaction mixture was concentrated under vacuum and crude 19 was dissolved in $CH_2Cl_2$ (100 mL) and 12 g of silica gel (type: ZCX-2, 100-200 mesh), was added and the mixture was concentrated vacuum while maintaining the temperature below 35° C. Charged 100 g of silica gel (type: ZCX-2, 100-200 mesh) to the column, followed by the last step prepared dry silica gel which absorbed the reaction mixture. Using a combi-flash to purify the product, eluting with a $CH_2Cl_2$/acetone gradient from 75/25 to 70/30, collecting 200 mL fractions. Took samples for TLC analysis and combined qualified products. This resulted in 1.0 g (13.8% yield) 19 as yellow oil. ELSD A: water/0.05% TFA: B: $CH_3CN$/0.05% TFA 95:5 to 5:95 A/B at 2 min., hold 1.2 min): RT 1.5 min, m/z (Calcd.) 1042.7, (found) 1043.9 (M+H). $^1$H-NMR (300 MHz, $CDCl_3$): δ 5.28 (m, 2H), 4.32 (dd, J=11.9, 4.4 Hz, 4H), 4.11 (dd, J=11.9, 5.7 Hz, 4H), 3.38 (brm, 4H), 2.91 (m, 2H), 2.18-2.33 (6H), 2.23 (s, 6H), 1.78 (brm, 4H), 1.55-1.42 (8H), 1.35-1.10 (50H), 0.87 (t, J=6.9 Hz, 12H).

Example 20. Synthesis of LIPID 20: ((3,3'-((((3-(Dimethylamino)propyl)thio)carbonyl)azanediyl)bis(propanoyl))bis(oxy))bis(methylene))bis(2-methyl-propane-2,1,3-triyl) tetrakis(3-(4-methylcyclohexyl)propanoate)
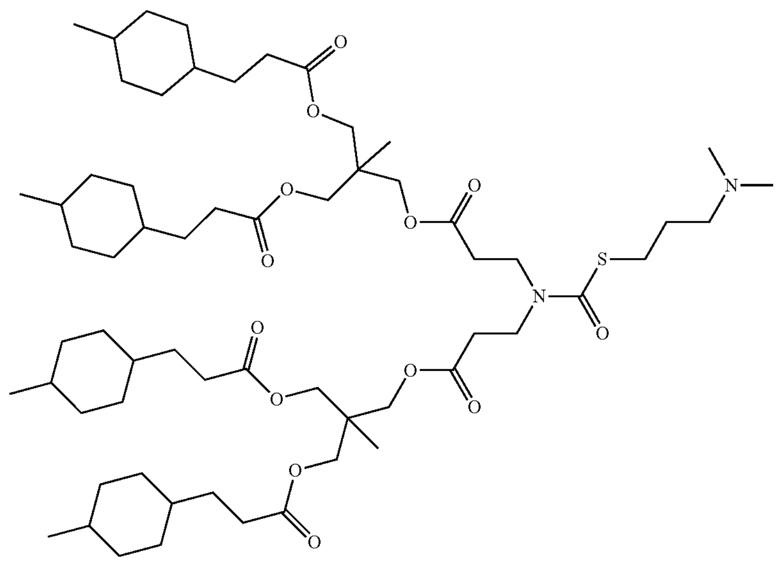
30
LIPID 20
General scheme
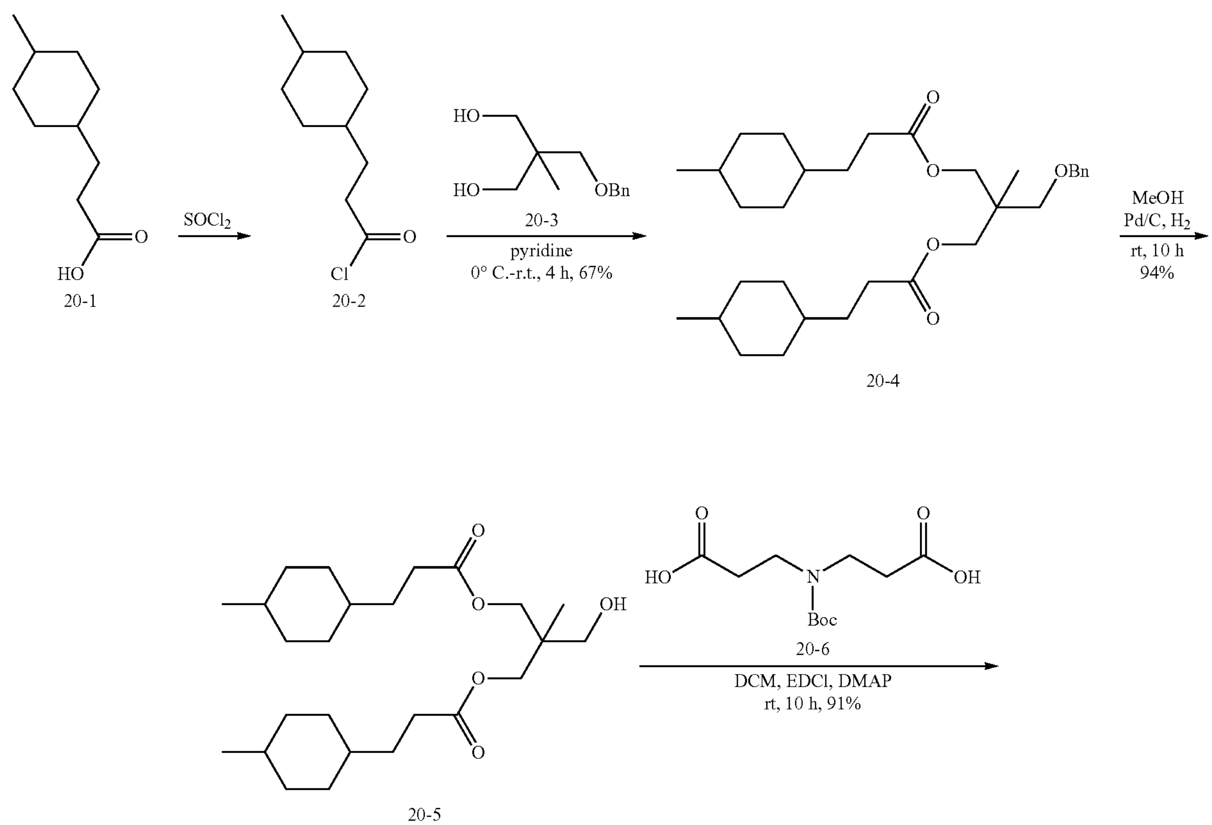

-continued
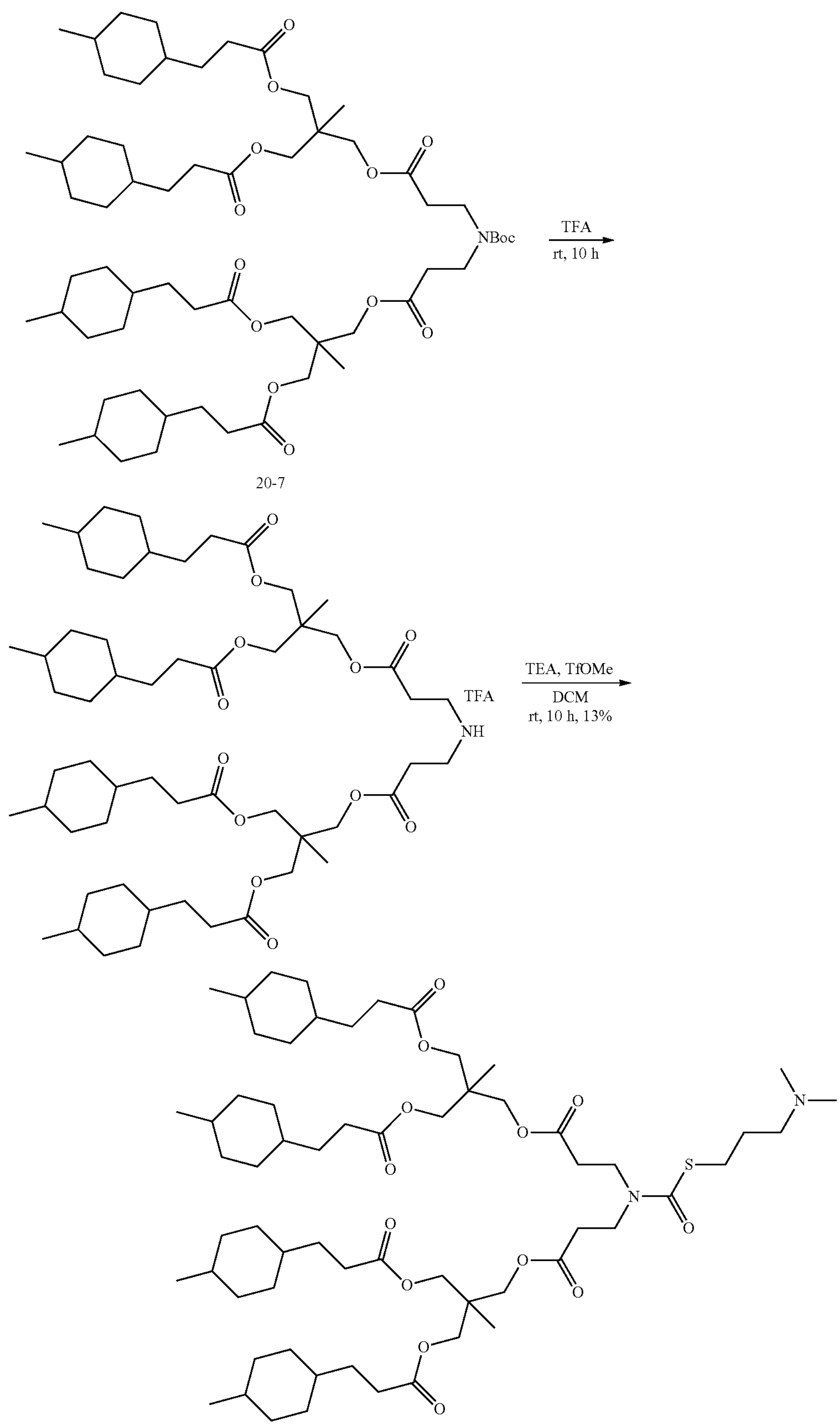
20-7
Lipid 20

Synthesis of 20-2: 3-(4-methylcyclohexyl)propanoyl chloride

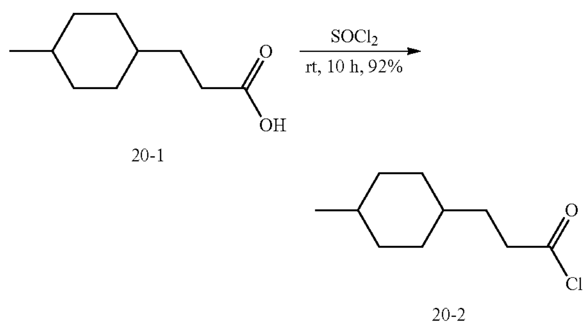

20-1

20-2

Into a 25 mL 3-necked round-bottom flask were added $SOCl_2$ (100 mL, 1378.615 mmol, 4.69 equiv.) and commercially available 3-(4-methylcyclohexyl)propanoic acid (50 g, 293.682 mmol, 1 equiv.) at room temperature. The resulting mixture was stirred for 10 h at room temperature and concentrated under reduced pressure to afford 3-(4-methylcyclohexyl)propanoyl chloride (51 g, 92.03%) as a yellow oil which was used as such without further purification or characterization.

Synthesis of 20-4: 2-((benzyloxy)methyl)-2-methylpropane-1,3-diyl bis(3-(4-methylcyclohexyl)-propanoate)

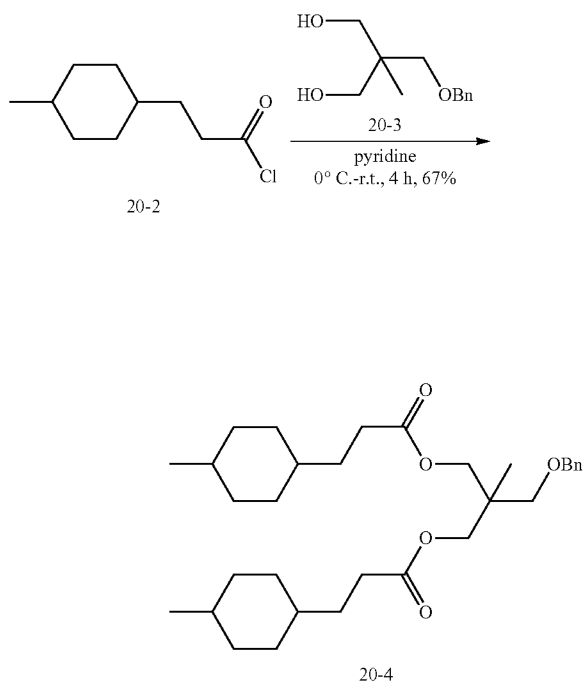

20-2

20-4

Into a 1 L 3-necked round-bottom flask were added commercially available 2-[(benzyloxy)methyl]-2-methylpropane-1,3-diol (20-3, 27.1 g, 128.7 mmol, 1.00 equiv.), pyridine (25.45 g, 321.7 mmol, 2.5 equiv.) and $CH_2Cl_2$ (500 mL, 20V) at room temperature. The mixture was allowed to cool down to 0° C. To the above mixture was added 20-2 (51.00 g, 270.2 mmol, 2.1 equiv.) dropwise at 0° C. The resulting mixture was stirred for additional 4 h at rt. The reaction was quenched by the addition of Water (1 L) at 0° C. The resulting mixture was extracted with $CH_2Cl_2$ (3×500 mL). Combined organic layer was dried over anhydrous $Na_2SO_4$, filtered, and the filtrate was concentrated under reduced pressure. The residue was adsorbed on 540 g of silica gel (type: ZCX-2, 100-200 mesh, 2.00 w./w.) and purified on a 2700 g of silica gel column, using combi-flash purification system. Product was eluted with PE/EA (gradient from 100:0 to 70:30, collected every 500±10 mL). After TLC analysis (EA:PE=1:10) qualified fractions were and combined, concentrated and dried under vacuum to afford (45 g, 67.9%) 20-4 as colorless oil. ELSD A: water/0.05% TFA: B: $CH_3CN$ 95:5 to 5:95 A/B at 2 min., hold 1.2 min): RT 1.48 min, m/z (Calcd.) 514.4, (found) 537.5 (M+Na).

Synthesis of 20-5:2-(hydroxymethyl)-2-methylpropane-1,3-diyl bis(3-(4-methylcyclohexyl)-propanoate)

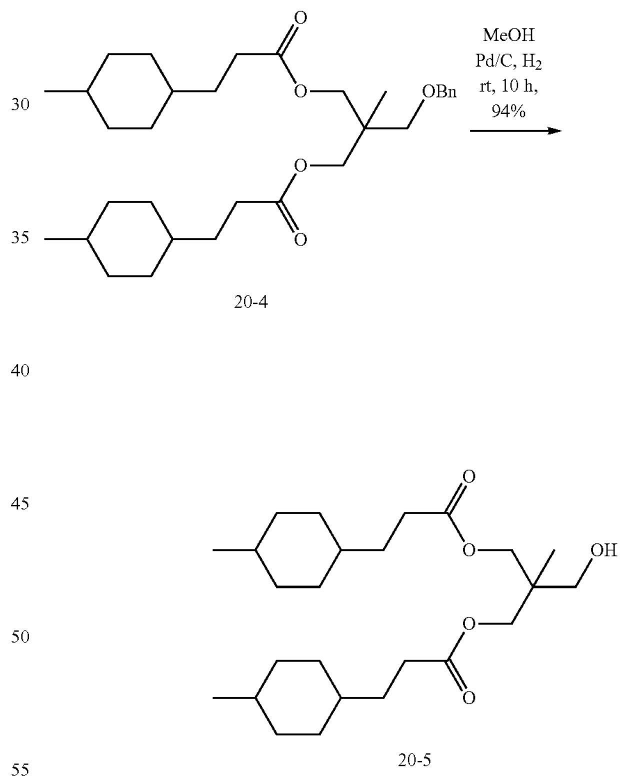

20-4

20-5

To a solution of 20-4 (45 g, 87.4 mmol, 1 equiv.) in MeOH (500 mL, 11V) was added Pd/C (10%, 4.5 g) under nitrogen atmosphere in a 1 L 3-necked round-bottom flask. The mixture was hydrogenated at room temperature for 10 h under hydrogen atmosphere using a hydrogen balloon. Reaction was filtered through a Celite pad and concentrated under reduced pressure to afford 20-5 (35 g, 94.3%) as a colorless oil. ELSD A: water/0.05% TFA: B: $CH_3CN$ 95:5 to 5:95 A/B at 2 min., hold 1.2 min): RT 1.29 min, m/z (Calcd.) 424.3, (found) 447.4 (M+Na).

Synthesis of 20-7: (((3,3'-((tert-butoxycarbonyl) azanediyl)bis(propanoyl))bis(oxy))bis(methylene)) bis(2-methylpropane-2,1,3-triyl) tetrakis(3-(4-methylcyclohexyl)propanoate)

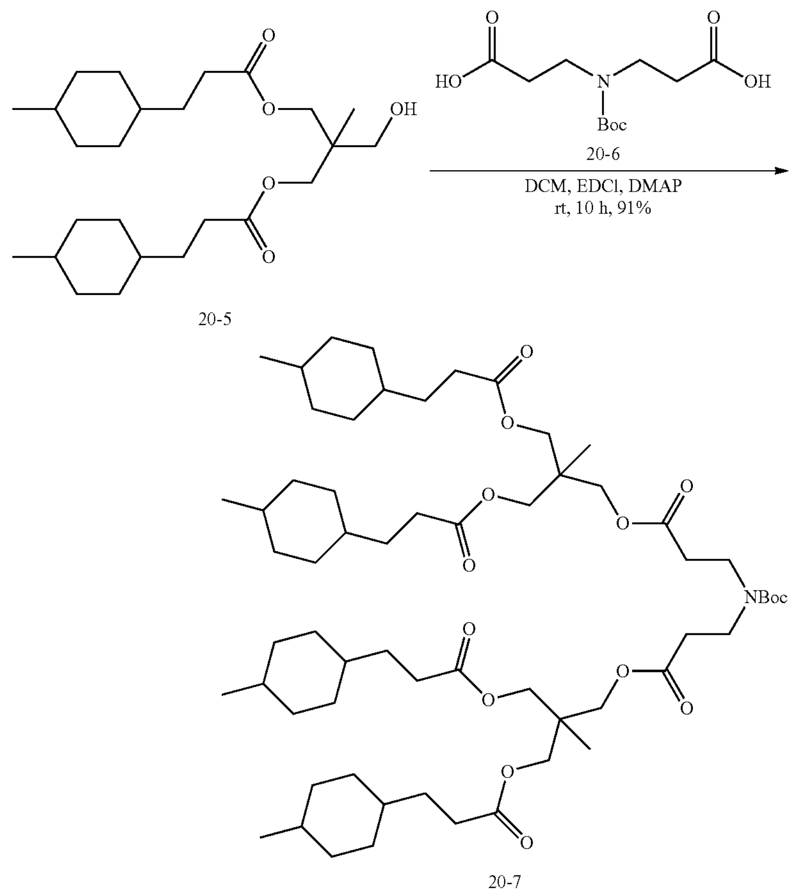

20-5

20-6

20-7

Into a 1 L 3-necked round-bottom flask were added 20-5 (35.04 g, 82.5 mmol, 2.2 equiv.), 3-[(tert-butoxycarbonyl)(2-carboxyethyl)amino]propanoic acid (20-6, 9.8 g, 37.5 mmol, 1.00 equiv.), EDCI (14.38 g, 75.0 mmol, 2 equiv.), DCM (700 mL, 20V) and DMAP (4.58 g, 37.48 mmol, 1.00 equiv.) at room temperature. The resulting mixture was stirred for 10 h at room temperature and diluted with water (500 mL). The resulting mixture was extracted with $CH_2Cl_2$ (3×500 mL), and the combined organic layer was dried over anhydrous $Na_2SO_4$. After filtration, the filtrate was concentrated under reduced pressure. The residue was adsorbed on 540 g of silica gel (type: ZCX-2, 100-200 mesh, 2.00 w./w.) and purified on a 2.7 Kg of silica gel column, using combi-flash purification system. Product was eluted with PE/EA (gradient from 100:0 to 50:50, collected every 500±10 mL). After TLC analysis (EA:PE=1:10) qualified fractions were and combined, concentrated, and dried under vacuum to afford (37 g, 91.8%) 20-7 as colorless oil which was used in the next step, based on purity and structure by $^1$H NMR.

Synthesis of 20-8: (((3,3'-azanediylbis(propanoyl)) bis(oxy))bis(methylene))bis(2-methylpropane-2,1,3-triyl) tetrakis(3-(4-methylcyclohexyl)propanoate) Trfluoroacetic Acid Salt

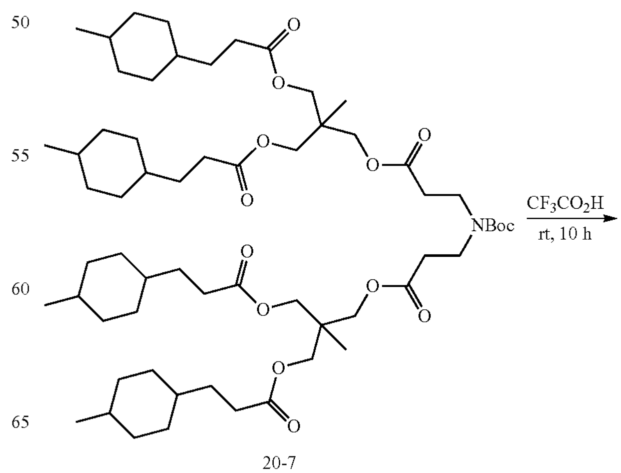

20-7

-continued

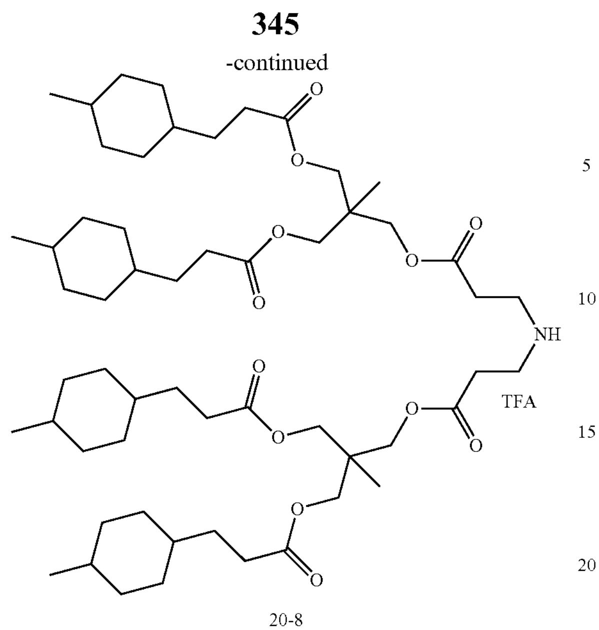

20-8

Into a 500 mL 3-necked round-bottom flask were added 20-7 (37 g, 34.4 mmol, 1 equiv.), DCM (370 mL) and trifluoroacetic acid (150 mL) at room temperature. The resulting mixture was stirred for 10 h at room temperature. The resulting mixture was concentrated under reduced pressure to afford 20-8 as a colorless oil (40 g, crude). Both $^1$H NMR and HPLC indicated ~94% pure product. It was used as such in the next reaction after drying under vacuum.

Synthesis of LIPID 20: ((3,3'-((((3-(Dimethylamino)propyl)thio)carbonyl) azanediyl)bis(propanoyl))bis(oxy))bis(methylene))bis(2-methylpropane-2,1,3-triyl) tetrakis(3-(4-methylcyclohexyl) propanoate)

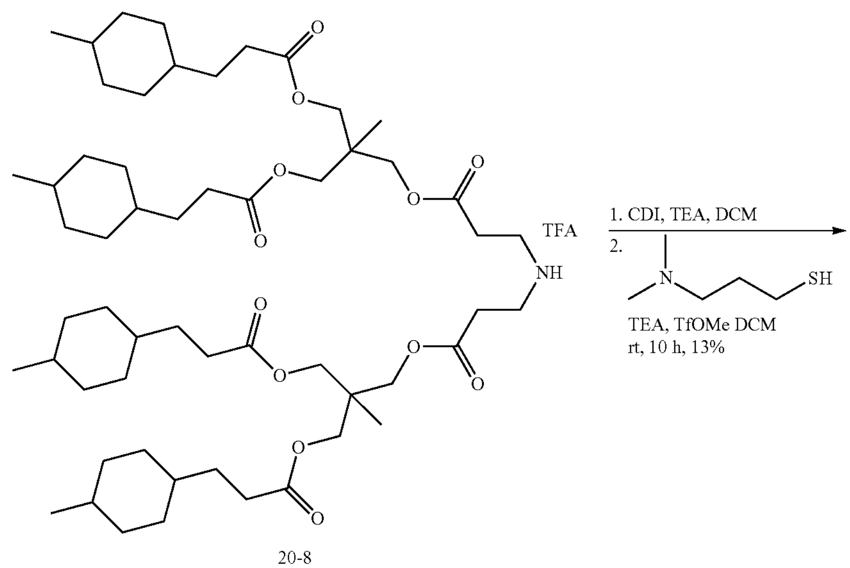

20-8

-continued

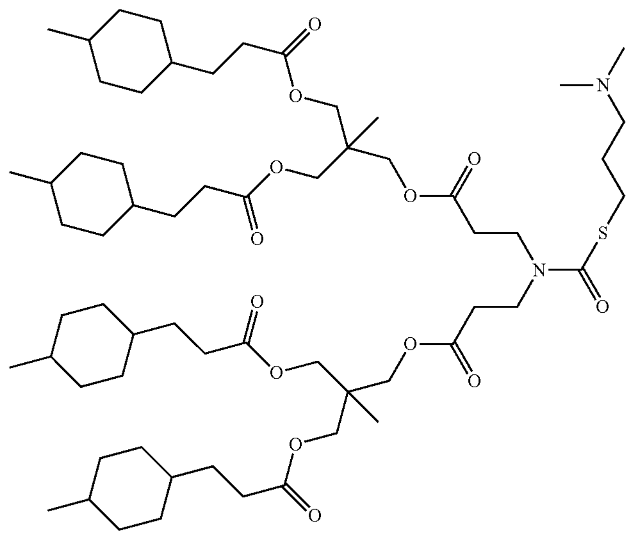

Lipid 20

Into a 1 L 3-neck round-bottom flask were added 20-8 (37 g, 34 mmol, 1 equiv.), TEA (10.32 g, 102 mmol, 3 equiv.), CDI (6.06 g, 37.4 mmol, 1.1 equiv.) and DCM (1.48 L, 40V) at room temperature. The resulting mixture was stirred for 10 h at room temperature. The mixture was allowed to cool down to 0° C. To the above mixture was added methyl trifluoromethane sulfonate (6.14 g, 37.4 mmol, 1.1 equiv.) dropwise at 0° C. The resulting mixture was stirred for 1 h at 0° C. and to the mixture was added 3-(dimethylamino) propane-1-thiol (4.46 g, 37.4 mmol, 1.1 equiv.) dropwise at 0° C. The resulting mixture was stirred for additional 10 h at room temperature, diluted with water (300 mL) and extracted with $CH_2Cl_2$ (3×300 mL). Combined organic layer was dried over anhydrous $Na_2SO_4$, filtered, and evaporated. The residue was adsorbed on 74 g of silica gel (type: ZCX-2, 100-200 mesh, 2.00 w./w.) and purified on a 370 g of silica gel column, using combi-flash purification system. Product was eluted with PE/EA (gradient from 100:0 to 90:10, collected every 500±10 mL). After TLC analysis (EA:PE=1: 10) qualified fractions were and combined, concentrated, and dried under vacuum to afford LIPID 20 (5.1 g, 13.3%) as yellow oil. ELSD A: water/0.05% TFA: B: $CH_3CN$/ 0.05% TFA 95:5 to 5:95 A/B at 25 min.): RT 10.3 min, m/z (Calcd.) 1118.8, (found) 1119.9 (M+H). $^1H$ NMR (300 MHz, Chloroform-d) δ 4.005 (d, J=6.6 Hz, 12H), 3.654 (t, J=7.2 Hz, 4H), 2.956 (t, J=7.0 Hz, 2H), 2.755-2.598 (m, 6H), 2.519 (s, 6H), 2.373-2.248 (m, 8H), 2.023-1.899 (m, 2H), 1.769-1.092 (m, 46H), 1.044-0.995 (m, 6H), 0.941-0.830 (m, 16H).

Example 21. Synthesis of LIPID 21: ((3,3'-((((3-(Dimethylamino)propyl)thio)carbonyl)azanediyl)bis (propanoyl))bis(oxy))bis(methylene))bis(2-methyl-propane-2,1,3-triyl) tetrakis(2-(4-methylcyclohexyl) acetate)

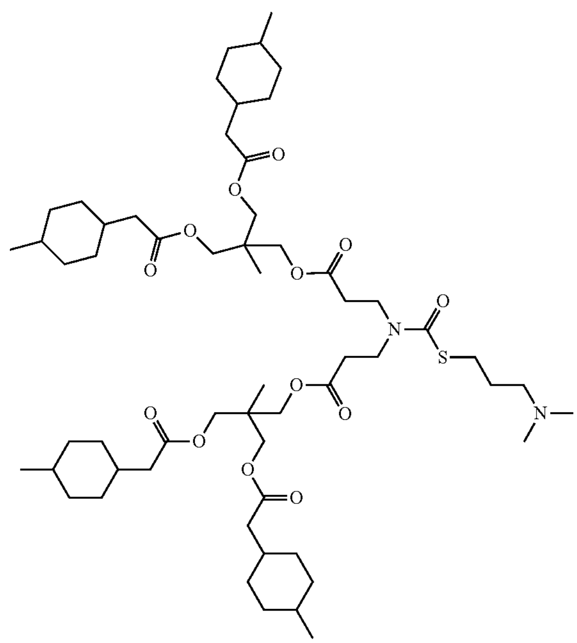

LIPID 21
General scheme
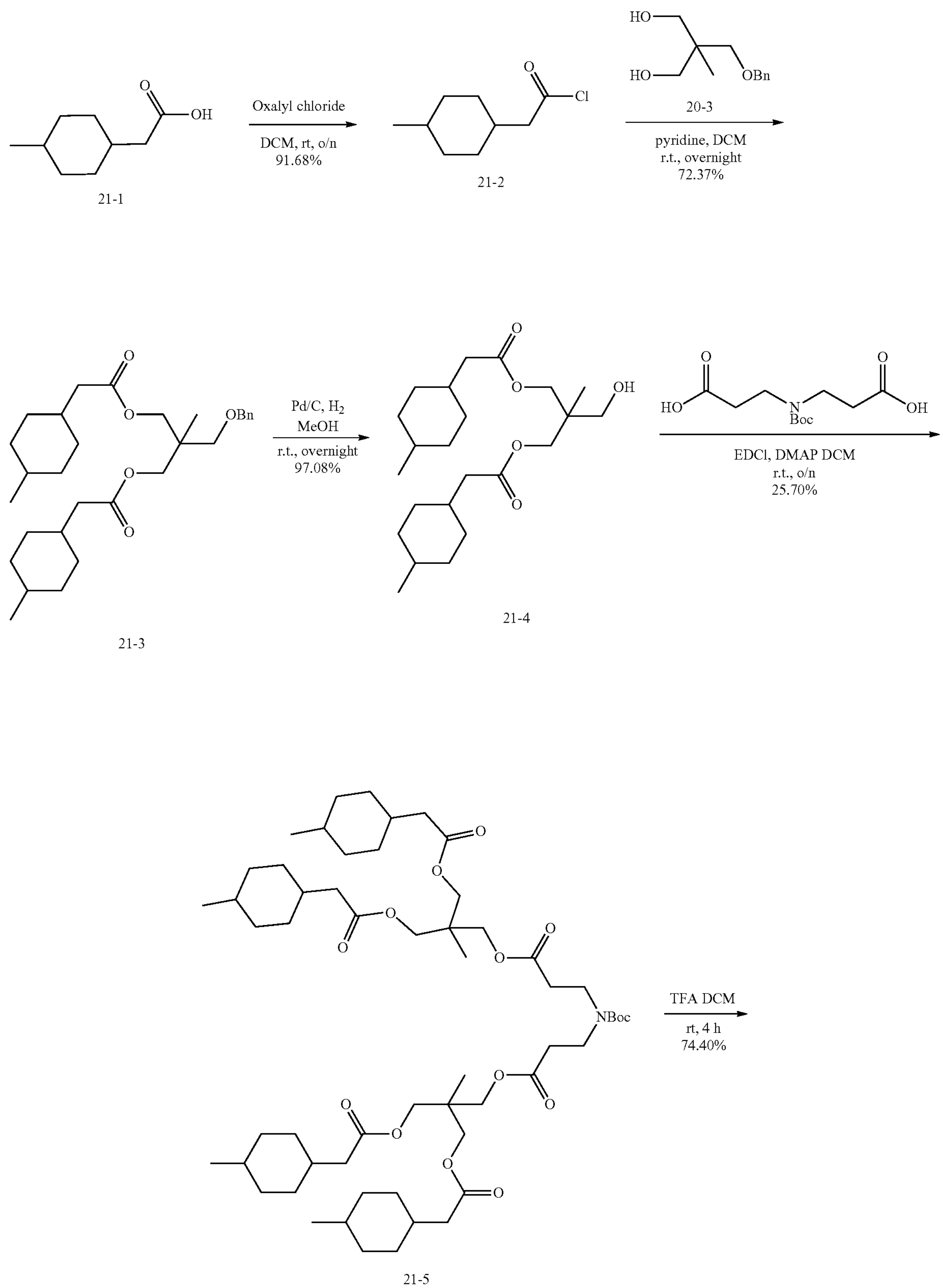
21-1 21-2 21-3 21-4 21-5

-continued
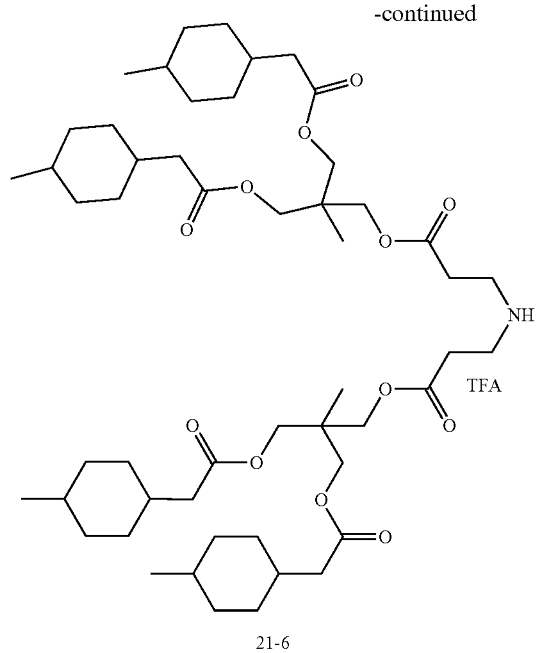
21-6
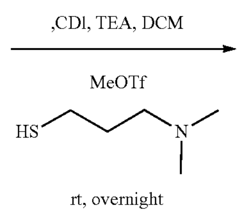
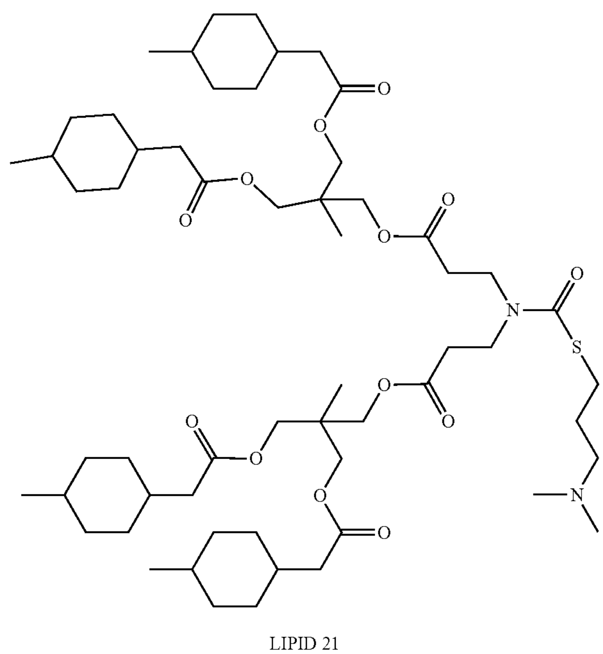
LIPID 21
Synthesis of 21-2: 2-(4-methylcyclohexyl)acetyl chloride
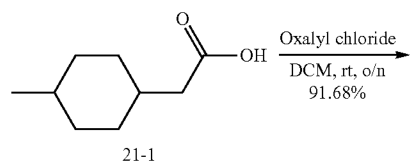
21-1
-continued
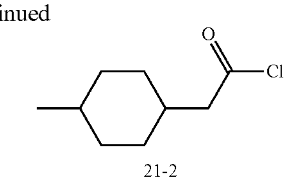
21-2
Into a 2 L three-necked round-bottle flask under nitrogen was added 21-1 (80 g, 512.0 mmol, 1.00 equiv.) in DCM (800 mL, 10 V). The solution was cooled to 0° C. is an ice/water bath and oxalyl chloride (130 g, 1024.2 mmol, 2.00 equiv.) was added dropwise at 0° C. The ice/water bath was removed, and the reaction was stirred overnight at room temperature. The reaction mixture was concentrated under vacuum to get 21-2 (82 g, 91.7%) as colorless oil that was used in the next reaction as such.

Synthesis of 21-3: 2-((benzyloxy)methyl)-2-methylpropane-1,3-diyl bis(2-(4-methylcyclohexyl)acetate)

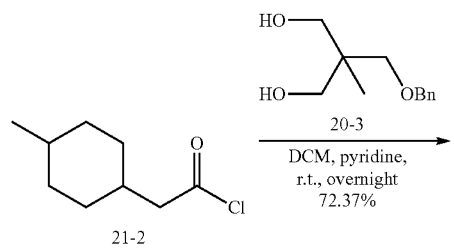

21-2

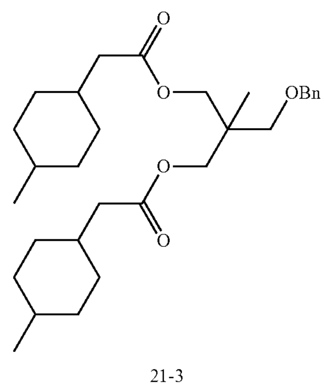

21-3

A solution of 20-3 (40 g, 190.2 mmol, 1.00 equiv.) in DCM (800 mL) was treated with pyridine (60.19 g, 760.9 mmol, 4.00 equiv.) and DMAP (6.97 g, 57.0 mmol, 0.30 equiv.) at 0° C. under nitrogen atmosphere followed by the addition of 21-2 (83.1 g, 475.6 mmol, 2.50 equiv.) dropwise at 0° C. The mixture was stirred for 16 h at room temperature. The resulting mixture was diluted with water (500 mL) and acidified to pH 6 with HCl (aq.). The aqueous layer was extracted with DCM (2×200 mL). Combined organic layer was washed with of brine (1×300 mL), dried over anhydrous $Na_2SO_4$, filtered and the filtrate was concentrated under reduced pressure to afford 21-3 (67 g, 72.4%) as a colorless oil. ELSD A: water/0.05% TFA: B: $CH_3CN$ 95:5 to 5:95 A/B at 3 min.): RT 2.49 min, m/z (Calcd.) 486.3, (found) 509.4 (M+Na).

Synthesis of 21-4: 2-(hydroxymethyl)-2-methylpropane-1,3-diyl bis(2-(4-methylcyclohexyl)acetate)

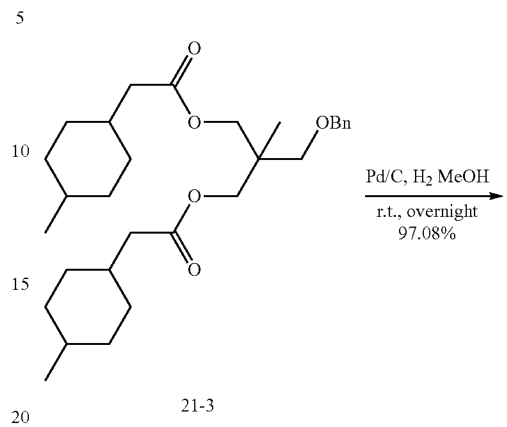

21-3

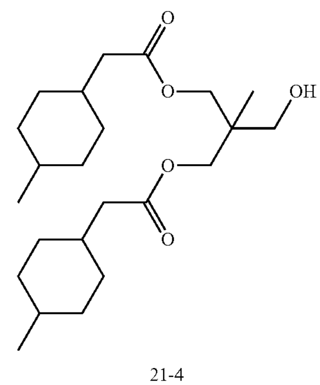

21-4

Into a 2 L 4-necked round-bottom flask was charged a solution of 21-3 (67 g, 137.66 mmol, 1.00 equiv.) in MeOH (670 mL 10V) was added Pd/C (20.1 g, 18.9 mmol, 0.14 equiv., 10% wt) in one portion and the resulting mixture was stirred for 16 h at room temperature under $H_2$. The reaction mixture was filtered, and the filter cake was washed with MeOH (1×300 mL). The filtrate was concentrated under vacuum to get 21-4 (53 g, 97.1%) as colorless oil. ELSD A: water/0.05% TFA: B: $CH_3CN$ 95:5 to 5:95 A/B at 3 min.): RT 2.11 min, m/z (Calcd.) 396.3, (found) 397.2 (M+H).

Synthesis of 21-5: (((3,3'-((tert-butoxycarbonyl) azanediyl)bis(propanoyl))bis(oxy))bis(methylene)) bis(2-methylpropane-2,1,3-triyl) tetrakis(2-(4-methylcyclohexyl)acetate)

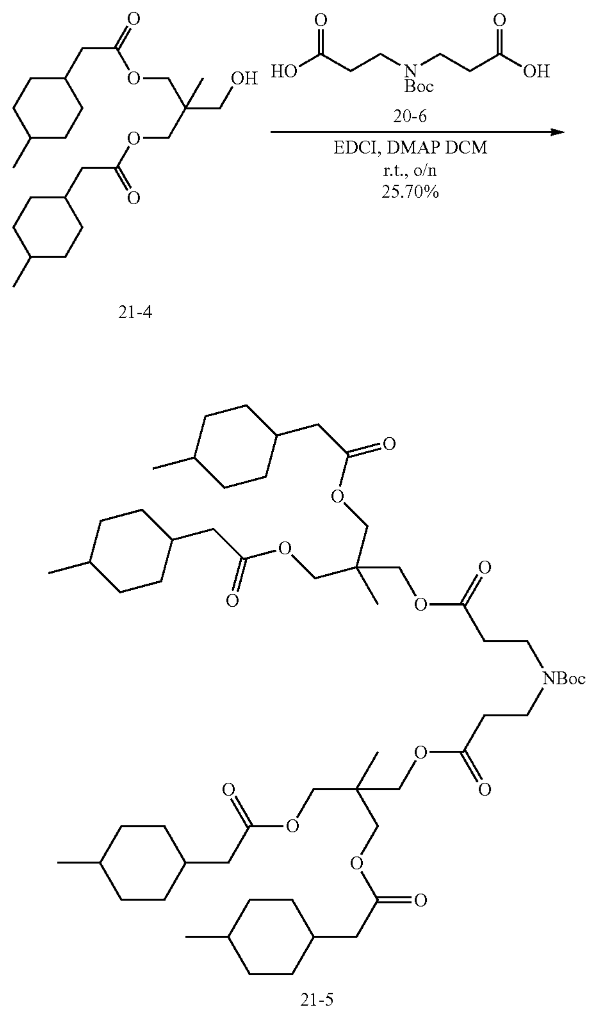

21-4

21-5

To a 2 L 4-necked round-bottle flask under nitrogen was added 21-4 (50 g, 126.1 mmol, 1.00 equiv.), followed by DMAP (15.40 g, 126.1 mmol, 1.00 equiv.) and 20-6 (72.47 g, 277.4 mmol, 2.20 equiv.) in DCM (1000 mL, 20V). The solution was cooled to 0° C. in an ice/water bath and to this was added EDCI (96.68 g, 504.3 mmol, 4.00 equiv.). The ice/water batch was removed, and the mixture was stirred for 16 h at room temperature. The mixture was washed with brine (1×1 L, 20 V) and the organic layer was dried over $Na_2SO_4$, filtered, and evaporated. The crude product was adsorbed on 300 g of silica gel (type: ZCX-2, 100-200 mesh, 2.00 w./w.) and purified on a 900 g of silica gel column, using combi-flash purification system. Product was eluted with PE/EA (gradient from 100:0 to 70:30, collected every 500±10 mL). After TLC analysis (EA:PE 1:8) qualified fractions were and combined, concentrated, and dried under vacuum to afford 21-5 (33 g, 25.7%) as colorless oil. After verifying purity and identity ($^1$H NMR) the material was used in the next reaction.

Synthesis of 21-6: (((3,3'-azanediylbis(propanoyl)) bis(oxy))bis(methylene))bis(2-methylpropane-2,1,3-triyl) tetrakis(2-(4-methylcyclohexyl)acetate) Trifluoroacetic Acid Salt

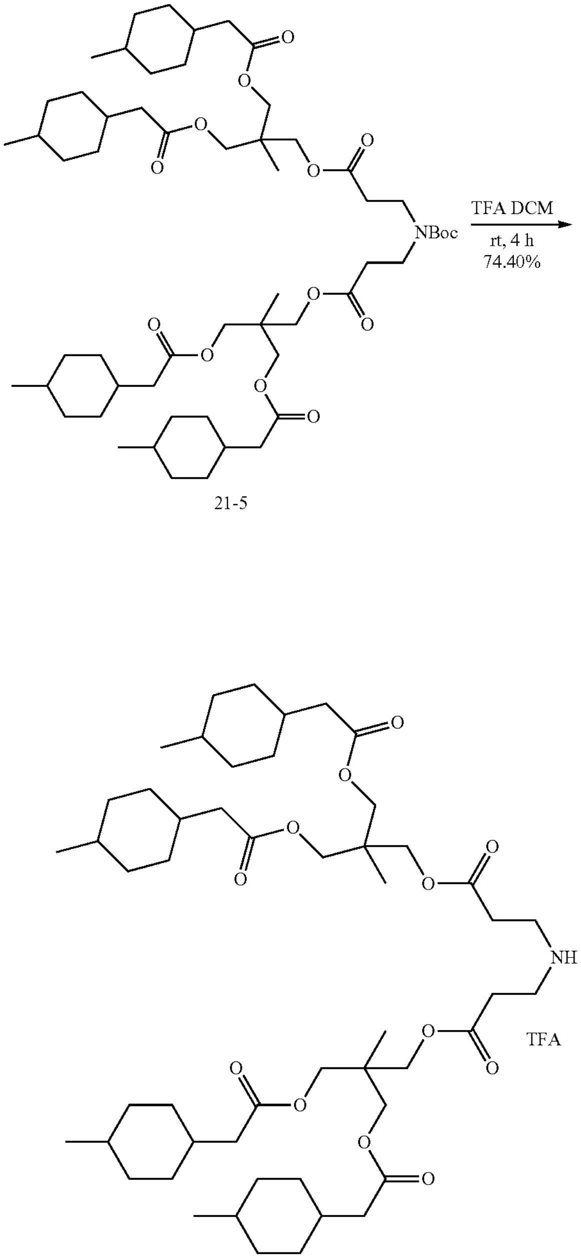

21-5

21-6

To a 250 mL three-necked round-bottle flask under nitrogen was added 21-5 (33 g, 32.4 mmol, 1.00 equiv.) in DCM (150 mL, 5V). The solution was cooled to 0° C. in an ice/water bath. To this was added trifluoroacetic acid (15.88 g, 162.0 mmol, 5.00 equiv.). The ice/water bath was removed, and the mixture was stirred for 4 h at room temperature. The reaction was concentrated under vacuum to get 21-6 (24.5 g, 74.4%) as colorless oil that was used as such in the next reaction.

Synthesis of LIPID 21: ((3,3'-((((3-(Dimethylamino)propyl)thio)carbonyl)azanediyl)bis(propanoyl))bis(oxy))bis(methylene))bis(2-methylpropane-2,1,3-triyl) tetrakis(2-(4-methylcyclohexyl) acetate)

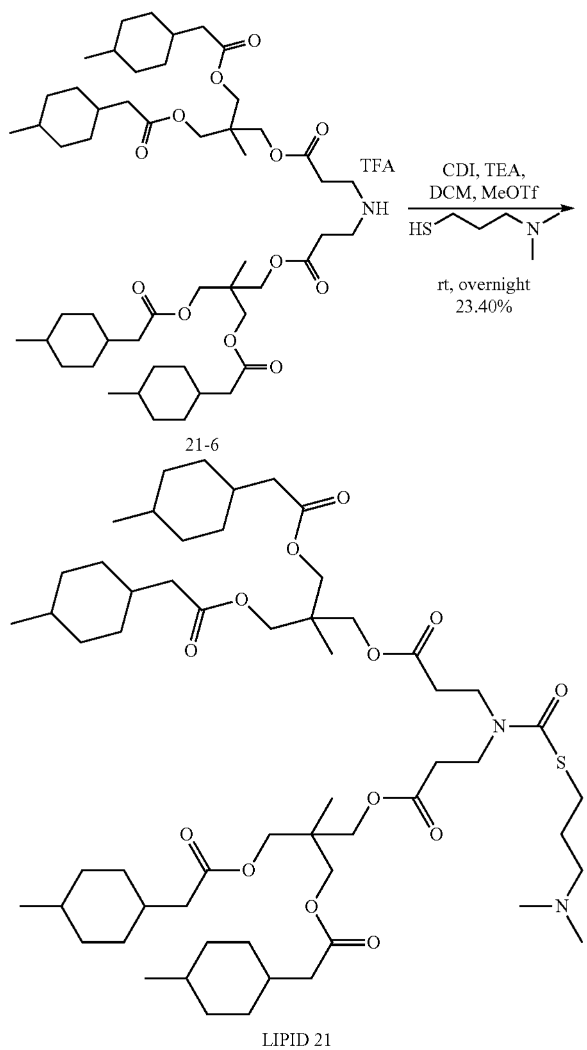

21-6

LIPID 21

Into a 1 L 3-necked round-bottom flask purged and maintained with an inert atmosphere of nitrogen was placed a solution of 21-6 (24.5 g, 24.1 mmol, 1.00 equiv.) in DCM (500 mL, 20 V). To this was added the TEA (9.76 g, 96.4 mmol, 4.00 equiv.), followed by the addition of CDI (7.82 g, 48.21 mmol, 2.00 equiv.). The mixture was stirred overnight at room temperature. The solution was cooled to 0° C. in an ice/water bath.

Then, methyltrifluoromethane sulfonate (4.35 g, 26.5 mmol, 1.10 equiv.) was added and the mixture was stirred at 0° C. for 1 hour. Then, 3-(dimethylamino)propane-1-thiol (3.45 g, 28.9 mmol, 1.20 equiv.) were added to the solution, ice/water bath was removed and the mixture was stirred overnight at room temperature. Crude compound was adsorbed on 50 g of silica gel (type: ZCX-2, 100-200 mesh, 3.75 w./w.) and purified on a 200 g of silica gel (type: ZCX-2, 300-400 mesh, 18.8 w./w.) using Combiflash system. Product was eluted with DCM/MeOH gradient from 100:0 to 96:4, collected every 300±50 mL). Fractions were analyzed (TLC, DCM:MeOH=10:1, Rf-0.5), and qualified fractions were combined and concentrated to get LIPID 21 (6 g, 23.4%) as light yellow oil. ELSD A: water/0.05% TFA: B: $CH_3CN$/0.05 TFA 75:25 to 25:75 A/B at 25 min.): RT 10.9 min, m/z (Calcd.) 1062.7, (found) 1063.8 (M+H). $^1$H-NMR-LIPID 21: (400 MHZ, $CDCl_3$, ppm): δ 4.02 (d, J=8.2 Hz, 12H), 3.67 (t, J=7.3 Hz, 4H), 2.95 (t, J=7.2 Hz, 2H), 2.67 (t, J=7.2 Hz, 4H), 2.53 (s, 2H), 2.45-2.28 (m, 8H), 2.24-2.16 (m, 6H), 2.01 (d, J=3.4 Hz, 1H), 1.90 (t, J=7.3 Hz, 2H), 1.71 (dd, J=5.8, 3.1 Hz, 14H), 1.56-1.46 (m, 5H), 1.44-1.20 (m, 9H), 1.05-0.84 (m, 30H).

Example 22. Synthesis of LIPID 22: ((3,3'-((((3-(Dimethylamino)propyl)thio)carbonyl)azanediyl)bis(propanoyl))bis(oxy))bis(methylene)bis(2-methylpropane-2,1,3-triyl) tetrakis(2-(4-ethylcyclohexyl) acetate)

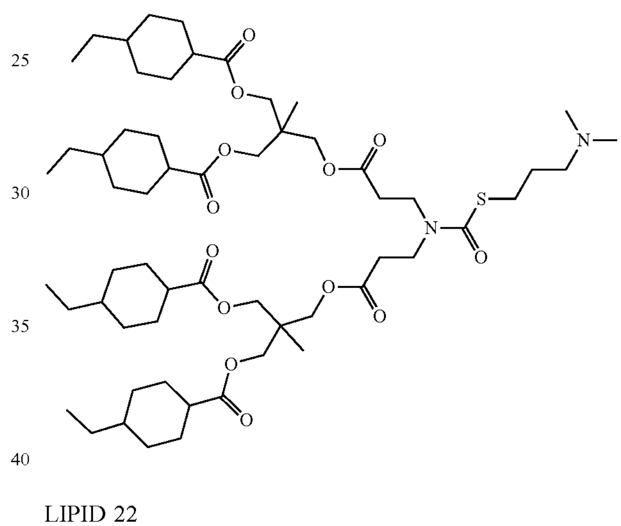

LIPID 22

General scheme

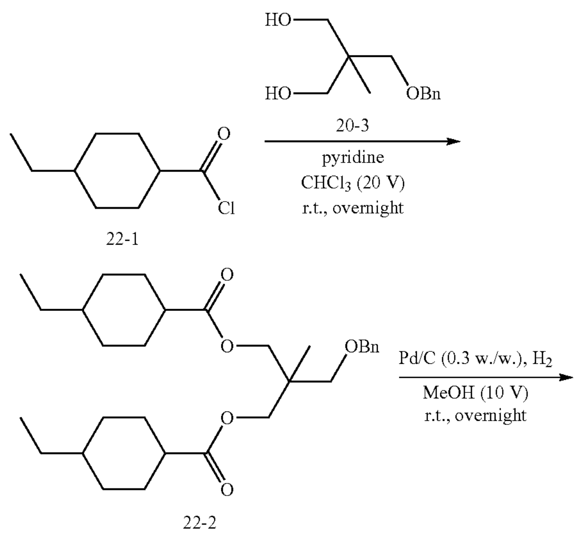

22-1

22-2

-continued

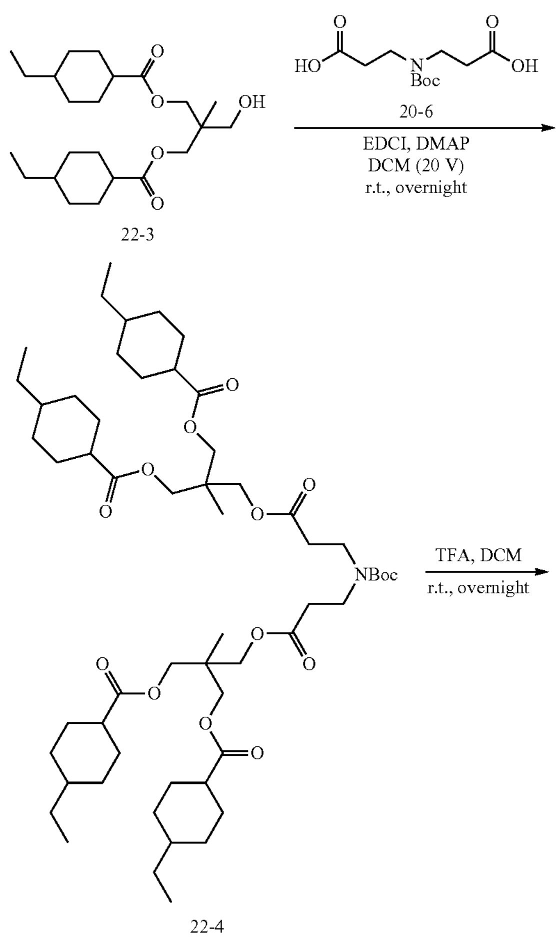

22-3

22-4

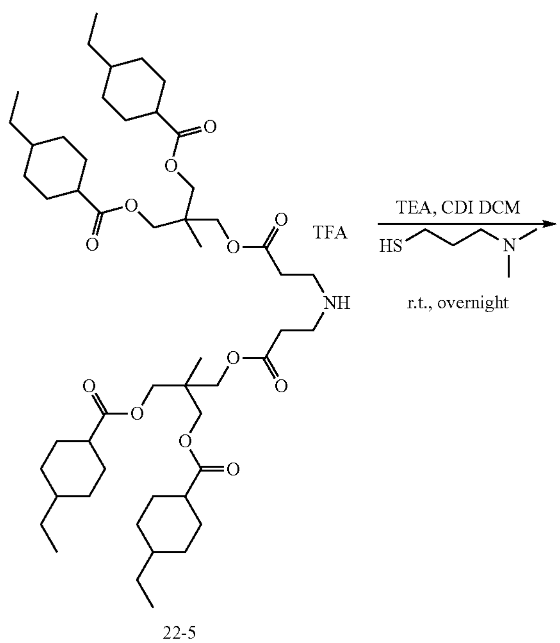

22-5

-continued

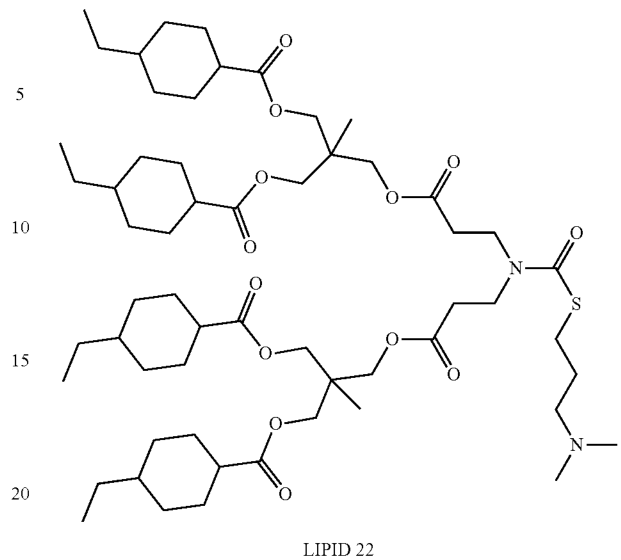

LIPID 22

Synthesis of 22-2: 2-((benzyloxy)methyl)-2-methylpropane-1,3-diyl bis(4-ethylcyclohexane-1-carboxylate)

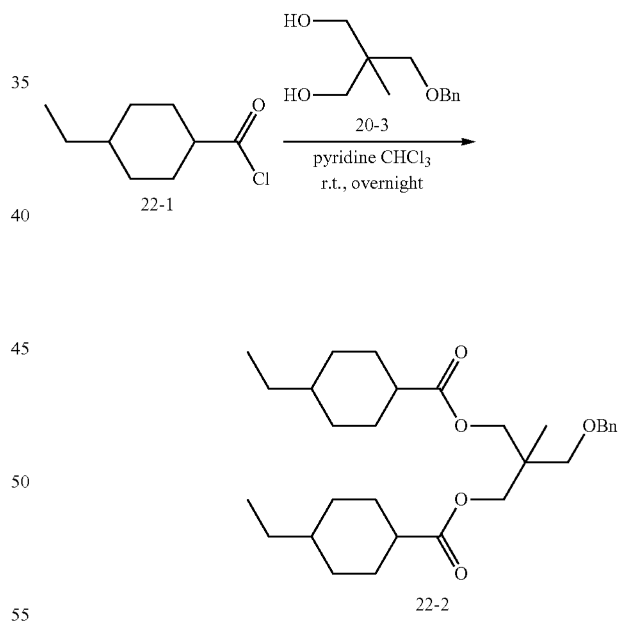

22-1

22-2

Into a 3 L three-necked round-bottom flask was added 20-3 (70.0 g, 0.33 mol, 1.00 equiv.), $CHCl_3$ (1400 mL, 20 V) and pyridine (105.0 g 4.0 equiv.) at room temperature under the $N_2$ atmosphere. Followed by the addition of 22-1 (127.0 g, 0.73 mol, 2.20 equiv.) dropwise at 0° C. The resulting mixture was stirred for additional overnight at room temperature. The reaction was quenched with water (700 mL, 10 V) at room temperature and the organic layers was washed with saturated $NaHCO_3$ aqueous solution (1000 mL, 15 V), HCl (1000 mL, 15 V, 1 mol/L) and brine (1000 mL, 15 V).

The organic phase was dried with anhydrous $Na_2SO_4$ and then filtered. After filtration, the filtrate was concentrated under vacuum. This resulted in (120 g, 0.25 mol, 74.0% yield) 22-2 as yellow oil. ELSD A: water/0.05% TFA: B: $CH_3CN$ 95:5 to 5:95 A/B at 2 min.): RT 1.8 min, m/z (Calcd.) 486.3, (found) 509.5 (M+Na).

Synthesis of 22-3: 2-(hydroxymethyl)-2-methylpropane-1,3-diylbis(4-ethylcyclohexane-1-carboxylate)

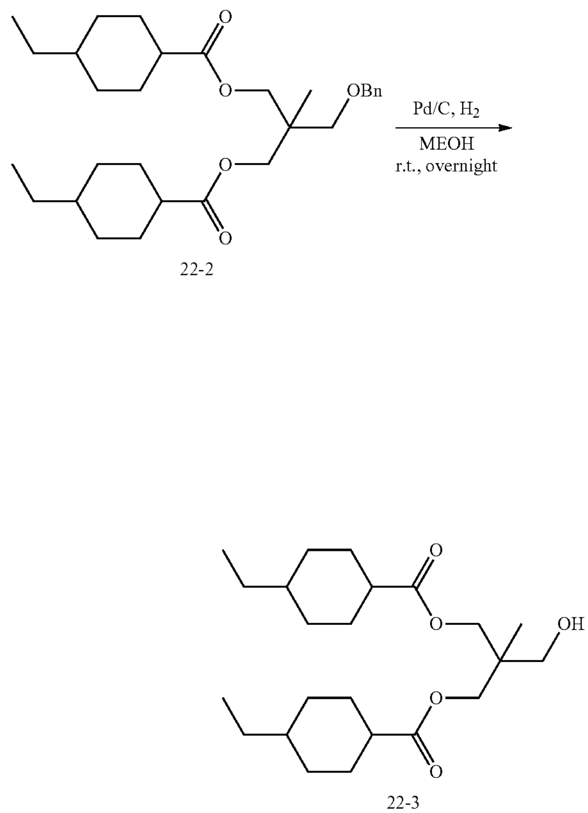

22-2

22-3

Into a 3 L three-necked round-bottom flask was added Pd/C (36.0 g, 0.3 w./w.) in MeOH (1.2 L, 10 V) at room temperature. Then, 22-2 (120.0 g, 0.25 mol, 1.00 equiv.) was added to the reaction mixture at room temperature. Replaced the reaction system with $H_2$ for three times. The resulting solution was stirred for overnight at room temperature under $H_2$ atmosphere. LCMS indicated completed consumption of 22-2. The resulting mixture was filtered, the filter cake was washed with MeOH (2×1000 mL, 8 V). The filtrate was concentrated and dried under vacuum. This resulted in (90 g, 0.23 mol, 92.0% yield) 22-3 as yellow oil that was used without further purification. ELSD A: water/0.05% TFA: B: $CH_3CN$ 95:5 to 5:95 A/B at 2 min.): RT 1.5 min, m/z (Calcd.) 396.3, (found) 397.3 (M+H).

Synthesis of 22-4: (((3,3'-((tert-butoxycarbonyl)azanediyl)bis(propanoyl))bis(oxy))bis(methylene))bis(2-methylpropane-2,1,3-triyl) tetrakis(4-ethylcyclohexane-1-carboxylate)

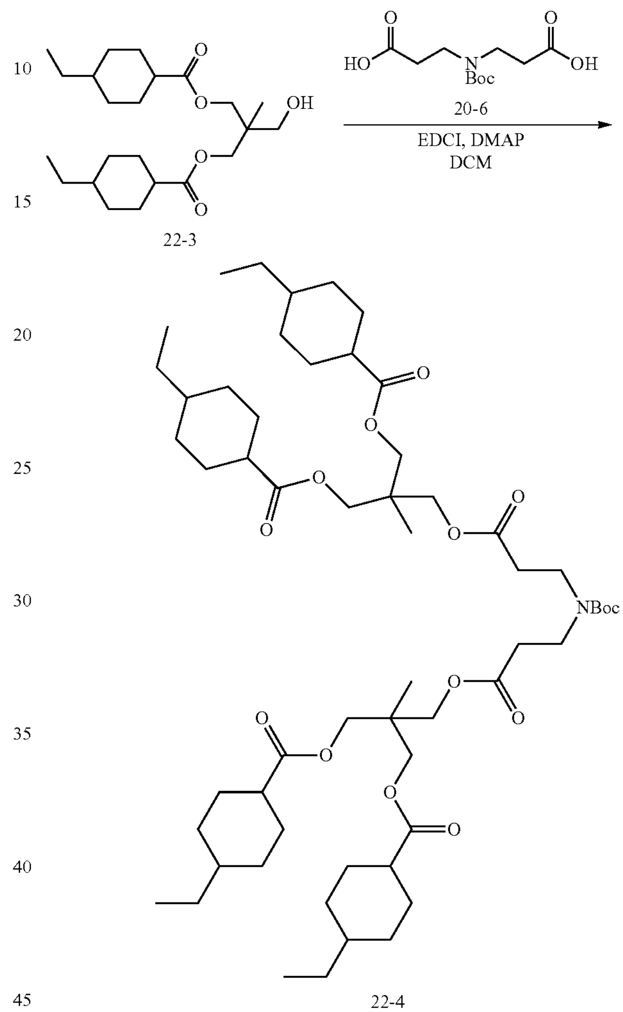

22-3

22-4

Into a 5 L four-neck round-bottom flask was added 22-3 (90 g, 0.22 mol, 2.20 equiv.), DCM (1.8 L, 20 V) and 20-6 (26.96 g, 0.10 mol, 1.00 equiv.) at room temperature under the $N_2$ atmosphere. Then, DMAP (12.61 g, 0.10 mol, 1.0 equiv.) and EDCI (79.12 g, 0.41 mol, 4.0 equiv.) was added to the reaction mixture at 0° C. The resulting mixture was stirred for additional overnight at room temperature. The reaction system was quenched with water (1000 mL, 11 V). The organic phase was washed with brine (1000 mL, 11 V). The organic phase was dried with anhydrous $Na_2SO_4$ and then filtered. Crude product was adsorbed on 120 g of silica gel (type: ZCX-2, 100-200 mesh, 1.40 w./w.) and purified on a silica gel column (800 g of silica gel type: ZCX-2, 100-200 mesh, 10.00 w./w.) using PE/THF (v/v) gradient from 100:0 to 95:5). Fractions were analyzed (TLC, THF:PE=1:5), combined, concentrated and dried under vacuum to afford (70 g, 0.07 mol, 43.90% yield) 22-4 as yellow oil. ELSD A: water/0.05% TFA: B: $CH_3CN$ 100:0 to 0:100 A/B at 3 min.): RT 1.0 min, m/z (Calcd.) 1017.7, (found) 1040.6 (M+Na).

Synthesis of 22-5: (((3,3'-azanediylbis(propanoyl)) bis(oxy))bis(methylene))bis(2-methylpropane-2,1,3-triyl) tetrakis(4-ethylcyclohexane-1-carboxylate) Trifluoroacetic Acid Salt

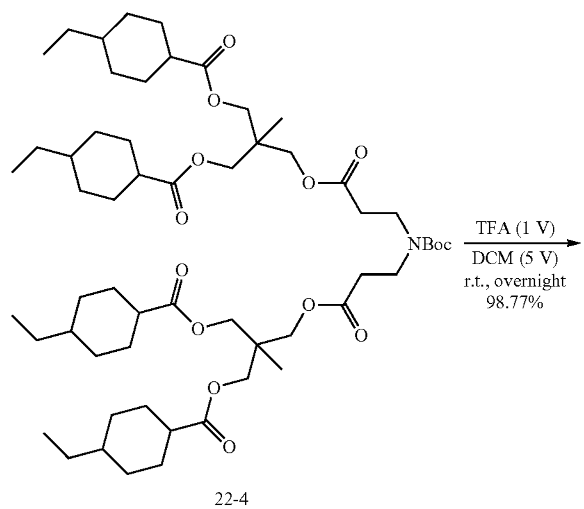

22-4

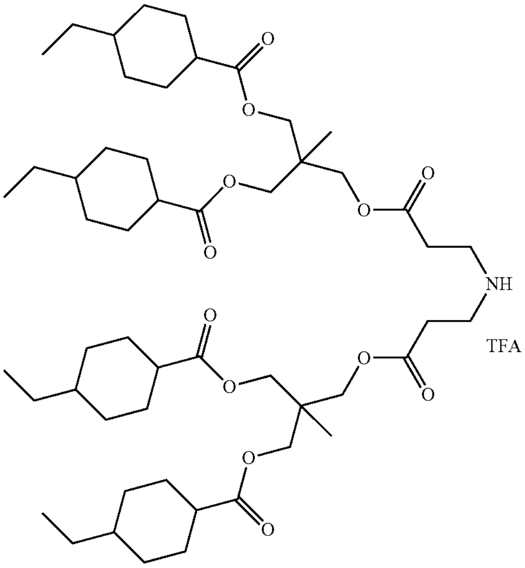

22-5

Into a 1 L three-necked flask was added 22-4 (70 g, 0.68 mol, 1.00 equiv.) in DCM (350 mL, 5 V) and TFA (70 mL, 1 V) at room temperature under the $N_2$ atmosphere. The resulting solution was stirred for overnight at room temperature. The resulting mixture was concentrated under vacuum. This resulted in (69 g, 0.06 mol, 98.8% yield) 22-5 (trifluoroacetic acid salt) as a yellow oil. ELSD A: water/0.05% TFA: B: $CH_3CN$ 95:5 to 5:95 A/B at 3 min.): RT 2.2 min, m/z (Calcd.) 917.6, (found) 918.5 (M+H).

Synthesis of LIPID 22: ((3,3'-((((3-(Dimethylamino)propyl)thio)carbonyl) azanediyl)bis(propanoyl))bis(oxy))bis(methylene))bis(2-methylpropane-2,1,3-triyl) tetrakis(2-(4-ethylcyclohexyl) acetate)

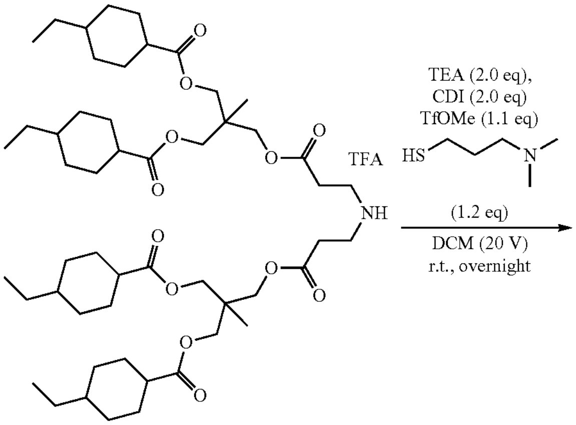

22-5

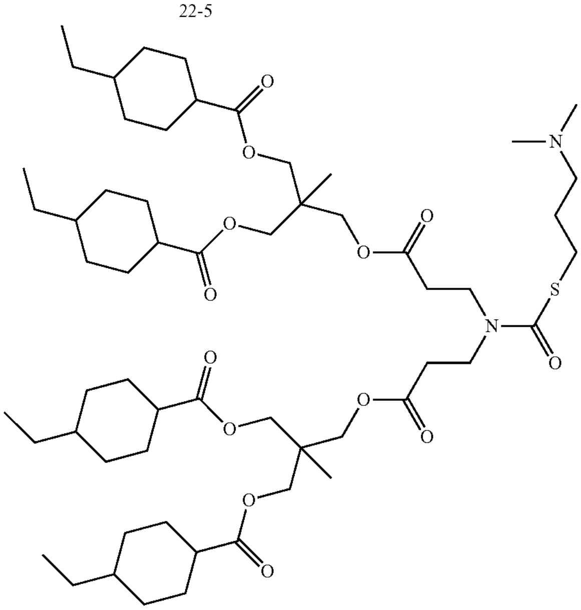

LIPID 22

Into a 3 L three-necked flask was added 22-5 (69.0 g, 0.06 mol, 1.00 equiv.) in DCM (1.38 L, 20 V) and TEA (13.74 g, 0.14 mol, 2.0 equiv.) followed by CDI (22.02 g, 0.14 mol, 2.0 equiv.) at room temperature under nitrogen atmosphere. The resulting mixture was stirred for additional 3 h at room temperature. Then into the reaction was added TfOMe (12.26 g, 0.07 mol, 1.10 equiv.) at 0° C. and stirred for 1 h at 0° C. under nitrogen atmosphere. To the above mixture was added 3-(dimethylamino)propane-1-thiol (9.71 g, 81.5 mmol, 1.20 equiv.) at 0° C. and stirred overnight at room temperature. The reaction system was quenched with water (1 L, 15 V) and organic phase was washed with brine (1 L, 15 V), dried with anhydrous $Na_2SO_4$, and filtered. Crude product was adsorbed on 90 g of silica gel (type: ZCX-2, 100-200 mesh, 1.40 w./w.) and purified on a silica gel column (800 g of silica gel type: ZCX-2, 100-200 mesh, 10.00 w./w.) using heptane/ethyl acetate (v/v) gradient from 100:0 to 70:30). Fractions were analyzed (TLC, THF:PE=1:5), combined, concentrated, and dried under vacuum to afford 5.5 g of LIPID 22 as yellow oil. ELSD A: water/0.05% TFA: B: $CH_3CN$ 95:5 to 5:95 A/B at 3 min.): RT 2.2 min, m/z (Calcd.) 1062.6, (found) 1063.8 (M+H). $^1H$ NMR-LIPID 22: (400 MHZ, $CDCl_3$, ppm) δ 4.01 (d, J=12.8 Hz, 12H), 3.67 (t, J=7.2 Hz, 4H), 2.95 (t, J=7.2 Hz, 2H), 2.67 (t, J=7.3 Hz, 4H), 2.36-2.18 (m, 10H), 2.01-1.91 (m, 8H), 1.894-1.76 (m, 10H), 1.41 (qd, J=13.0, 3.4 Hz, 8H), 1.30-1.08 (m, 13H), 1.03 (s, 6H), 0.98-0.83 (m, 20H).

Example 23. Synthesis of LIPID 23: ((3,3'-((((3-(Dimethylamino)propyl)thio)carbonyl)azanediyl)bis(propanoyl))bis(oxy))bis(methylene))bis(2-methylpropane-2,1,3-triyl) tetrakis(3,3-dimethylheptanoate)

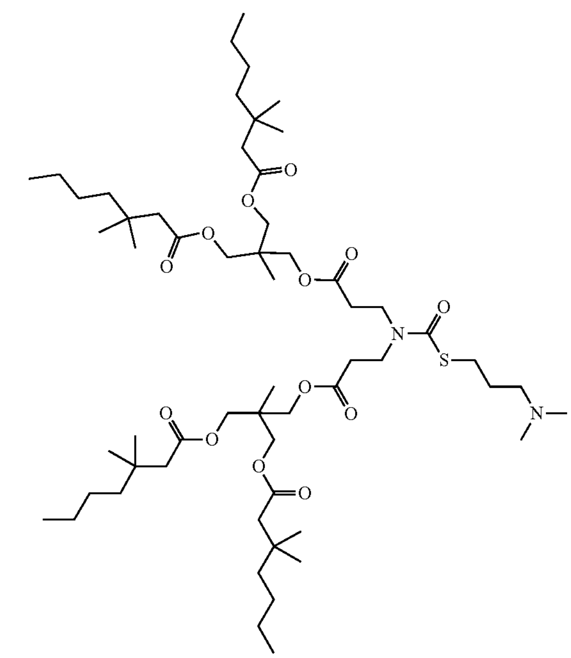 [SMILES: CCCCC(C)(C)CC(=O)OCC(C)(COC(=O)CCN(CCC(=O)OCC(C)(COC(=O)CC(C)(C)CCCC)COC(=O)CC(C)(C)CCCC)C(=O)SCCCN(C)C)COC(=O)CC(C)(C)CCCC]

LIPID 23

General scheme

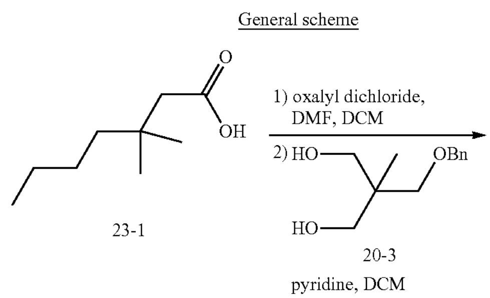

23-1

20-3

-continued

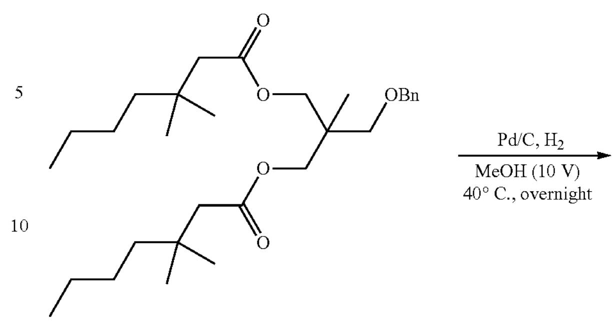

23-2

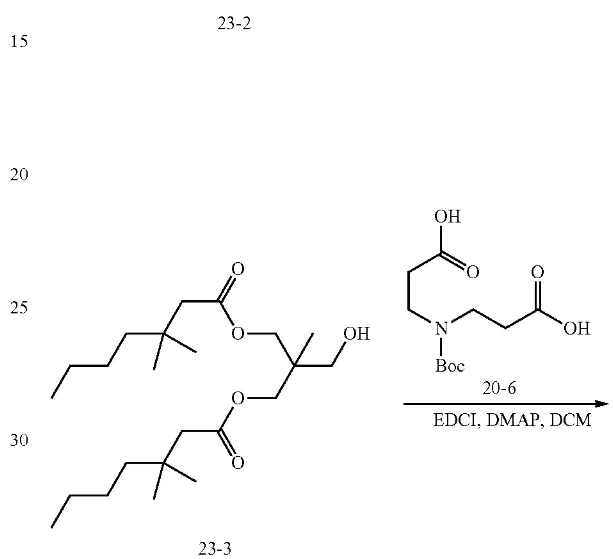

20-6

23-3

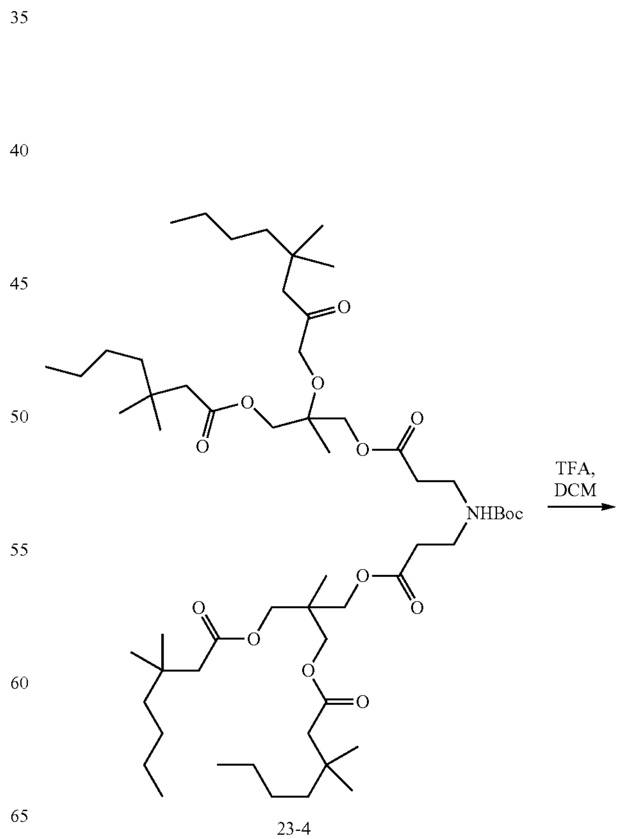

23-4

-continued

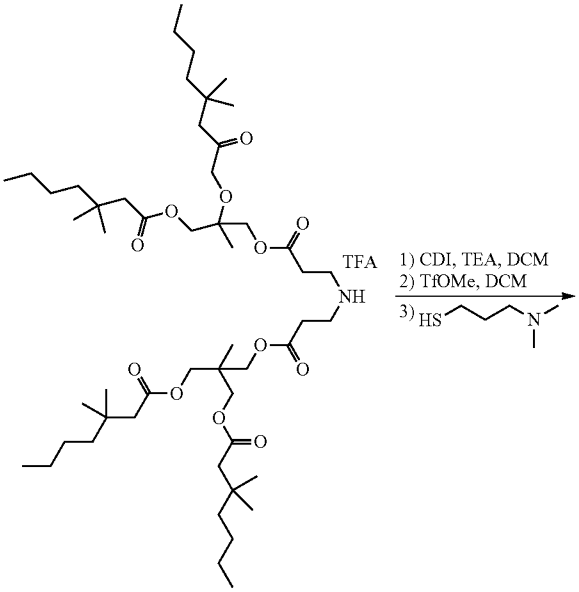

23-5

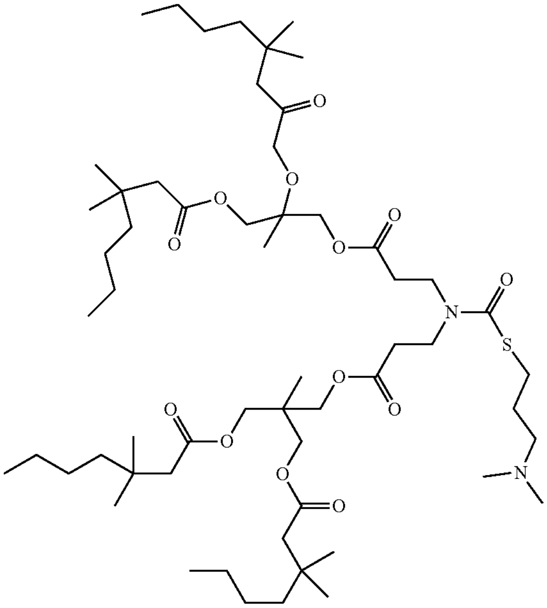

LIPID 23

Synthesis of 23-2: 2-((benzyloxy)methyl)-2-methylpropane-1,3-diyl bis(3,3-dimethylheptanoate)

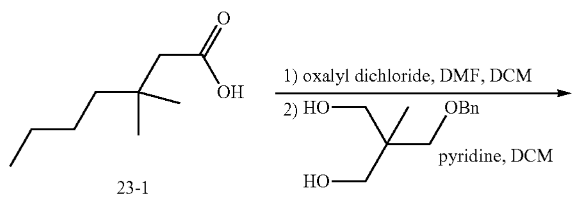

23-1

-continued

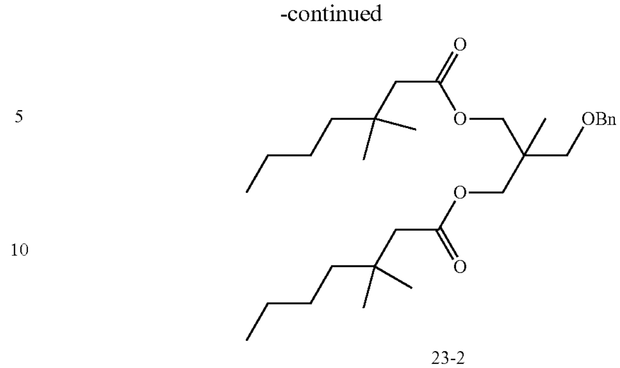

23-2

Into a stirred solution of 23-1 (84.66 g, 535.0 mmol, 2.50 equiv.) and DMF (1.56 g, 21.40 mmol, 0.10 equiv.) in DCM (1 L) was added oxalyl chloride (65.19 g, 513.61 mmol, 2.40 equiv.) dropwise at 0° C. under air atmosphere. The resulting mixture was stirred for 2 h at room temperature under air atmosphere. The resulting mixture was concentrated under vacuum and the residue was dissolved in DCM (200 mL). The above mixture was added dropwise to a stirred solution of 20-3 (45 g, 214.00 mmol, 1.00 equiv.) and pyridine (67.71 g, 856.0 mmol, 4.00 equiv.) in DCM (800 mL) at 0° C. under air atmosphere. The resulting mixture was stirred for 2 h at 0° C. under air atmosphere. The reaction was quenched by the addition of saturated aqueous $NH_4Cl$ (1 L) at 0° C. The resulting mixture was extracted with $CH_2Cl_2$ (2× 500 mL). The combined organic layers were dried over anhydrous $Na_2SO_4$. After filtration, the filtrate was concentrated under reduced pressure. Crude product was adsorbed on 200 g of silica gel (type: ZCX-2, 100-200 mesh, 1.40 w./w.) and purified on a silica gel column (1.5 Kg of silica gel type: ZCX-2, 100-200 mesh, 10.00 w./w.) using petroleum ether/ethyl acetate (v/v) gradient from 100:0 to 95:5). Fractions were analyzed (TLC, PE:EA=20:1), combined, concentrated, and dried under vacuum to 23-2 (81 g, 77.13%) as a colorless oil. ELSD A: water/0.05% TFA: B: $CH_3CN$ 95:5 to 5:95 A/B at 3 min.): RT 2.6 min, m/z (Calcd.) 490.4, (found) 491.5 (M+H).

Synthesis of 23-3:2-(hydroxymethyl)-2-methylpropane-1,3-diyl bis(3,3-dimethylheptanoate)

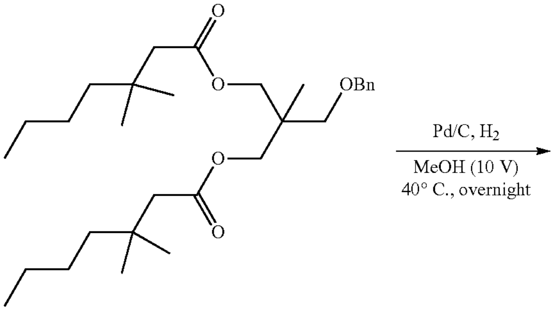

23-2

-continued

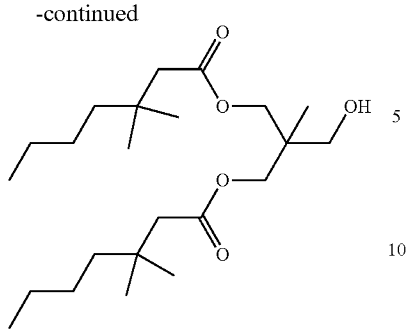

23-3

A solution of 23-2 (91 g, 185.4 mmol, 1.00 equiv.) and Pd/C (9.87 g, 92.7 mmol, 0.50 equiv.) in MeOH (2 L) was stirred for overnight at 40° C. under hydrogen (5 atm) atmosphere. The resulting mixture was filtered, the filter cake was washed with MeOH (2×100 mL). The filtrate was concentrated under reduced pressure. Crude product was adsorbed on 200 g of silica gel (type: ZCX-2, 100-200 mesh, 1.40 w./w.) and purified on a silica gel column (1 Kg of silica gel type: ZCX-2, 100-200 mesh, 10.00 w./w.) using petroleum ether/ethyl acetate (v/v) gradient from 100:0 to 90:10). Fractions were analyzed (TLC, PE:EA=10:1), combined, concentrated, and dried under vacuum to 23-3 (68 g, 91.4%) as a colorless oil. ELSD A: water/0.05% TFA: B: $CH_3CN$ 95:5 to 5:95 A/B at 3 min.): RT 2.2 min, m/z (Calcd.) 400.3, (found) 401.4 (M+H).

Synthesis of 23-4: (((3,3'-((tert-butoxycarbonyl) azanediyl)bis(propanoyl))bis(oxy))bis(methylene)) bis(2-methylpropane-2,1,3-triyl) tetrakis(3,3-dimethylheptanoate)

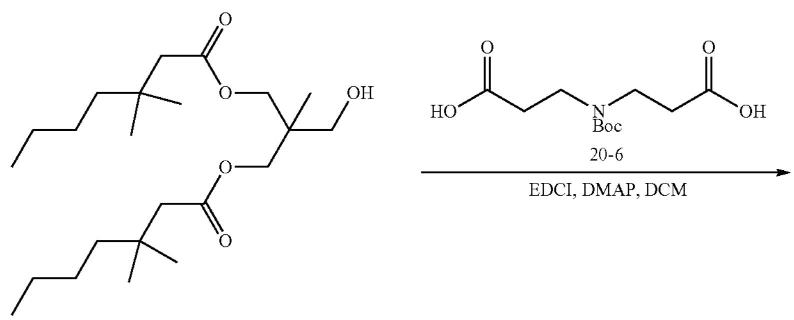

23-3

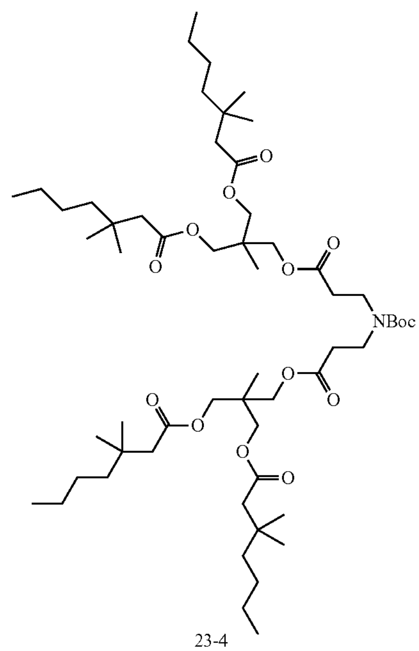

23-4

To a stirred solution of 20-6 (14.8 g, 56.64 mmol, 1.00 equiv.) and 23-3 (49.92 g, 124.62 mmol, 2.20 equiv.) in DCM (1 L) was added EDCI (27.15 g, 141.61 mmol, 2.50 equiv.) and DMAP (3.46 g, 28.32 mmol, 0.50 equiv.) at room temperature under air atmosphere. The resulting mixture was stirred for overnight at room temperature under air atmosphere. The reaction was quenched by the addition of ice/salt mixture (1 L) at room temperature. The resulting mixture was extracted with $CH_2Cl_2$ (2×500 mL). The combined organic layers were dried over anhydrous $Na_2SO_4$. After filtration, the filtrate was concentrated under reduced pressure. Crude product was adsorbed on 150 g of silica gel (type: ZCX-2, 100-200 mesh, 1.40 w./w.) and purified on a silica gel column (1 Kg of silica gel type: ZCX-2, 100-200 mesh, 10.00 w./w.) using petroleum ether/ethyl acetate (v/v) gradient from 100:0 to 75:25). Fractions were analyzed (TLC, PE:EA=4:1), combined, concentrated, and dried under vacuum to 23-4 (41 g, 70.5%) as a colorless oil. Material was used in the next reaction after verifying identity and purity by NMR.

Synthesis of 23-5: (((3,3'-azanediylbis(propanoyl)) bis(oxy))bis(methylene))bis(2-methylpropane-2,1,3-triyl) tetrakis(3,3-dimethylheptanoate) Trifluoroacetic acid salt -continued

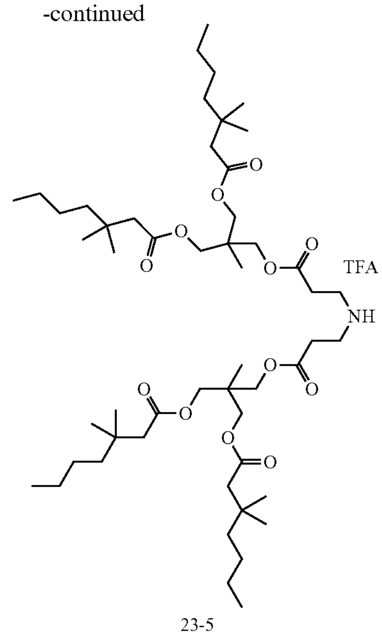

23-5

To a stirred solution of 23-4 (41 g, 39.94 mmol, 1.00 equiv.) in DCM (600 mL) was added TFA (60 mL) dropwise at room temperature under air atmosphere. The resulting mixture was stirred for overnight at room temperature. The resulting mixture was concentrated under reduced pressure and dried under vacuum. This resulted in 23-5 as its trifluoracetic acid salt (42 g, 102.6%) as a light brown oil that was used as such. ELSD A: water/0.05% TFA: B: $CH_3CN$ 95:5 to 5:95 A/B at 2 min.): RT 1.6 min, m/z (Calcd.) 925.7, (found) 949. (M+H+Na).

Synthesis of LIPID 23: ((3,3'-((((3-(Dimethylamino)propyl)thio)carbonyl) azanediyl)bis(propanoyl))bis(oxy))bis(methylene))bis(2-methylpropane-2,1,3-triyl) tetrakis(3,3-dimethylheptanoate)

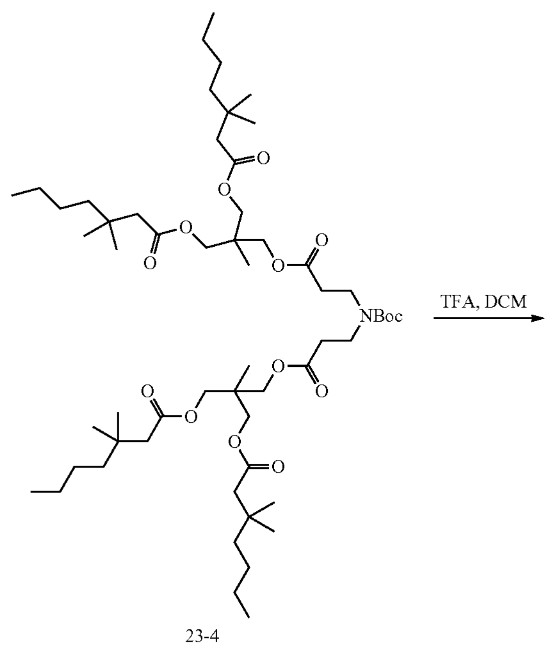

23-4

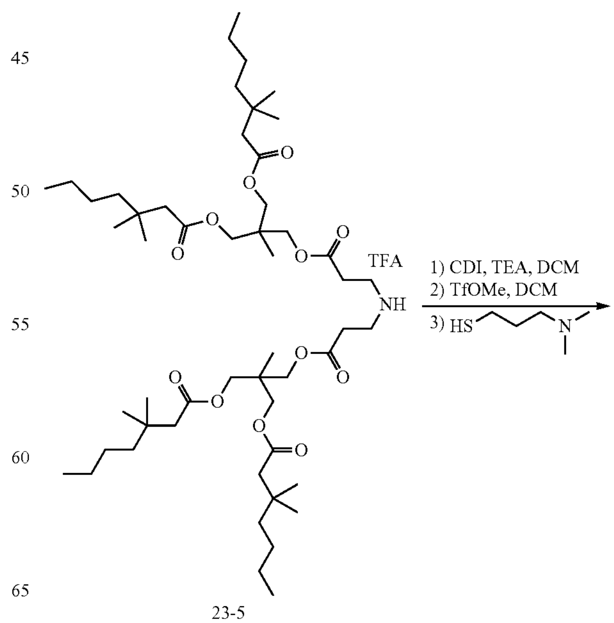

23-5

-continued

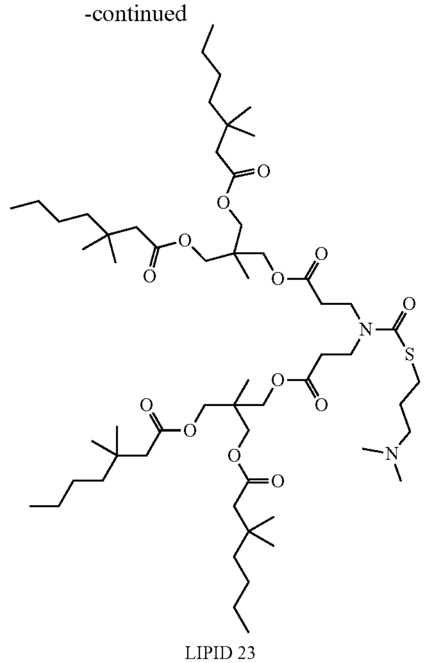

LIPID 23

To a stirred solution of 23-5 (41 g, 40.0 mmol, 1.00 equiv.) and TEA (8.10 g, 80.0 mmol, 2.00 equiv.) in DCM (1 L) was added CDI (12.98 g, 80.0 mmol, 2 equiv.) at room temperature under air atmosphere. The resulting mixture was stirred for overnight at room temperature and quenched by the addition of water (1 L) at room temperature. The resulting mixture was extracted with $CH_2Cl_2$ (2×500 mL).

The combined organic layer was dried over anhydrous $Na_2SO_4$. After filtration, the filtrate was concentrated under reduced pressure and the residue was dissolved in DCM (1 L). To the above mixture was added methyl triflate (7.22 g, 44.0 mmol, 1.10 equiv.) dropwise over 1 h at 0° C. The resulting mixture was stirred for additional 2 h at 0° C. To the above mixture was added TEA (8.10 g, 80.0 mmol, 2.00 equiv.) and 3-(dimethylamino)propane-1-thiol (5.73 g, 48.0 mmol, 1.20 equiv.) at 0° C. and stirred overnight at room temperature. The resulting mixture was concentrated under reduced pressure. Crude product was adsorbed on 60 g of silica gel (type: ZCX-2, 100-200 mesh, 1.40 w./w.) and purified on a silica gel column (600 g of silica gel type: ZCX-2, 100-200 mesh, 10.00 w./w.) using petroleum ether/ethyl acetate (v/v) gradient from 100:0 to 50:50). Fractions were analyzed (TLC, PE:EA=1:1), combined, concentrated, and dried under vacuum to LIPID 23 ((5.0327 g, 11.80%)) as a colorless oil. ELSD A: water/0.05% TFA: B: $CH_3CN$/0.05 TFA 95:5 to 5:95 A/B at 5 min.): RT 3.9 min, m/z (Calcd.) 1070.7, (found) 1071.8 (M+H); $^1$H-NMR-LIPID 23: (400 MHZ, $CDCl_3$, ppm) δ 4.03 (s, 4H), 3.98 (s, 8H), 3.66 (t, J=7.3 Hz, 4H), 2.94 (t, J=7.3 Hz, 2H), 2.67 (t, J=7.2 Hz, 4H), 2.39 (d, J=13.2 Hz, 2H), 2.28 (s, 6H), 2.22 (s, 8H), 1.84 (p, J=7.4 Hz, 2H), 1.38-1.18 (m, 24H), 1.04 (s, 6H), 0.98 (s, 24H), 0.96-0.87 (m, 12H).

Example 24. Synthesis of LIPID 24: ((3,3'-((((3-(Dimethylamino)propyl)thio)carbonyl)azanediyl)bis(propanoyl))bis(oxy))bis(methylene))bis(2-methyl-propane-2,1,3-triyl) tetrakis(octanoate)

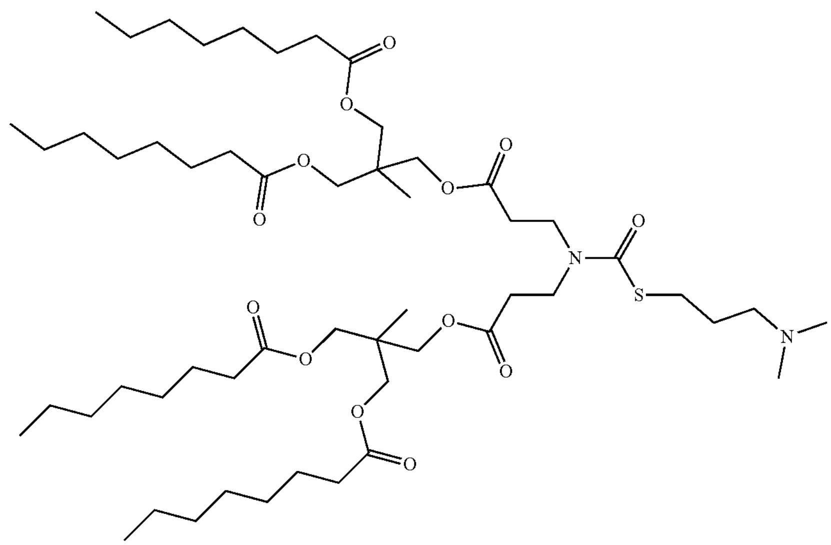 [SMILES: CCCCCCCC(=O)OCC(C)(COC(=O)CCCCCCC)COC(=O)CCN(CCC(=O)OCC(C)(COC(=O)CCCCCCC)COC(=O)CCCCCCC)C(=O)SCCCN(C)C]

LIPID 24
General scheme
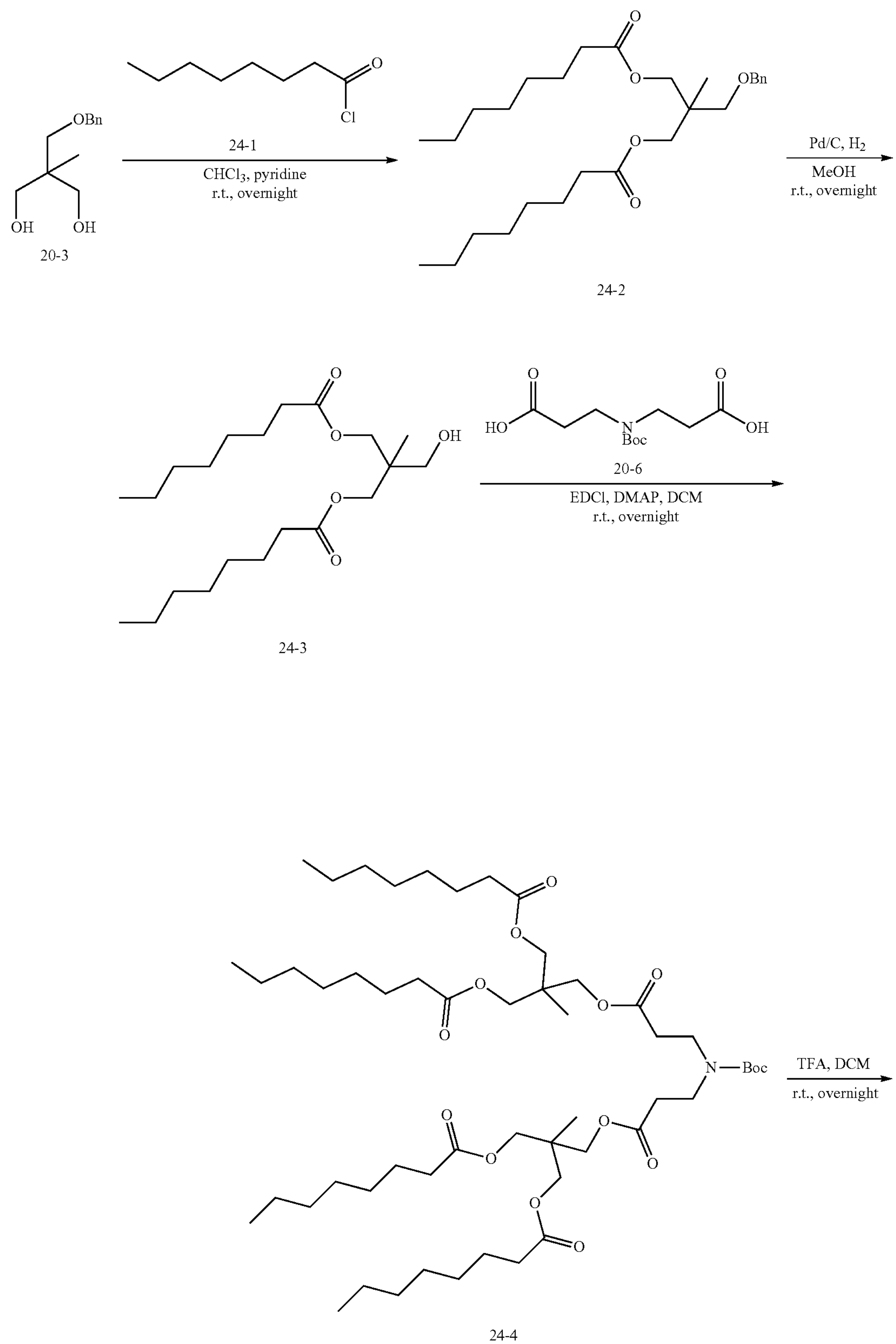

-continued
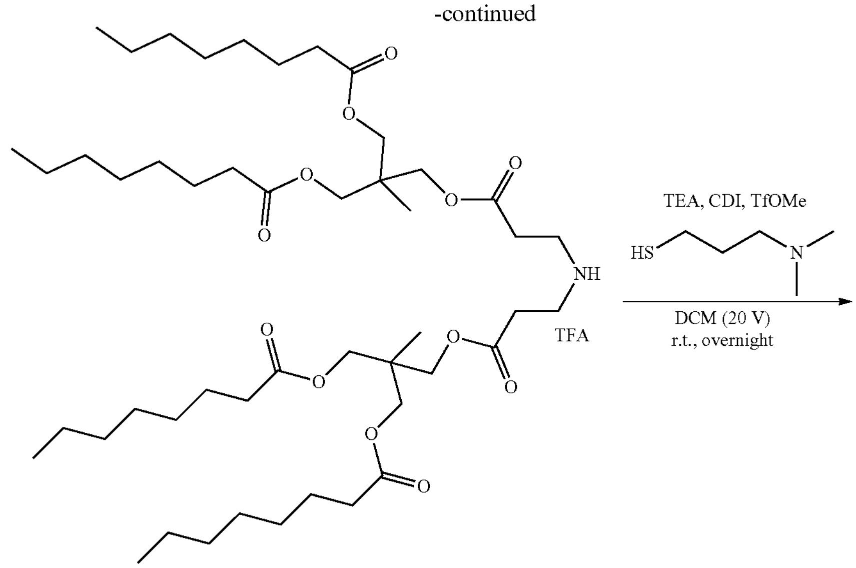
24-5
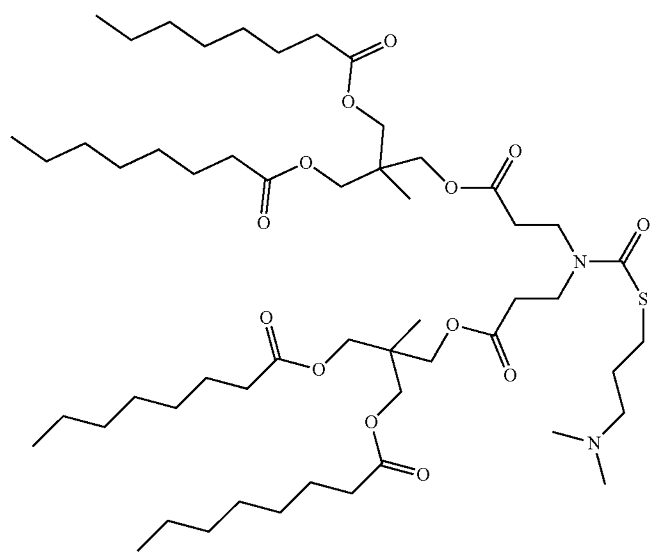
LIPID 24
Synthesis of 24-2: 2-((benzyloxy)methyl)-2-methylpropane-1,3-diyl dioctanoate
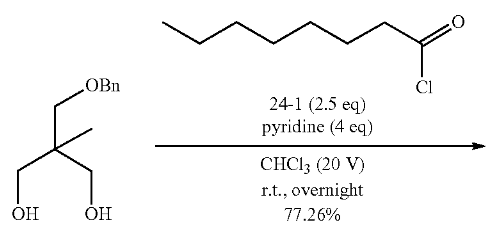
20-3
-continued
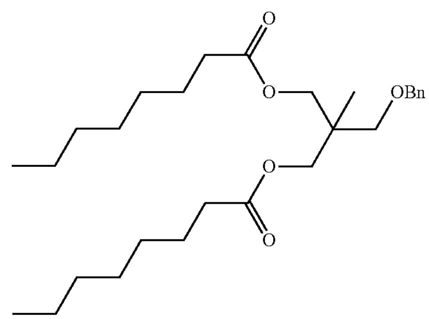
24-2

Into a 3 L three-necked round-bottom flask was added 20-3 (70.0 g, 0.33 mol, 1.00 equiv.), $CHCl_3$ (1.40 L, 20 V) and pyridine (105.3 g, 1.33 mol, 4.00 equiv.) at room temperature under the $N_2$ atmosphere, followed by addition a solution of 24-1 (119 g, 0.73 mol, 2.20 equiv.) in $CHCl_3$ (120 mL, 1V) dropwise at 0° C. The resulting mixture was stirred for additional overnight at room temperature. The reaction was quenched with water (700 mL, 10 V) at room temperature. The organic layer was washed with saturated $NaHCO_3$ aqueous solution (1000 mL, 15 V), HCl (1000 mL, 15 V, 1 mol/L) and brine (1000 mL, 15 V). The organic phase was dried with anhydrous $Na_2SO_4$ and then filtered. After filtration, the filtrate was concentrated and dried under vacuum. This was resulted in (119 g, 0.25 mol, 74.06%) 24-2 as yellow oil. ELSD A: water/0.05% TFA: B: $CH_3CN$ 95:5 to 5:95 A/B at 2 min.): RT 1.7 min, m/z (Calcd.) 462.3, (found) 485.5 (M+Na).

Synthesis of 24-3:2-(hydroxymethyl)-2-methylpropane-1,3-diyl dioctanoate

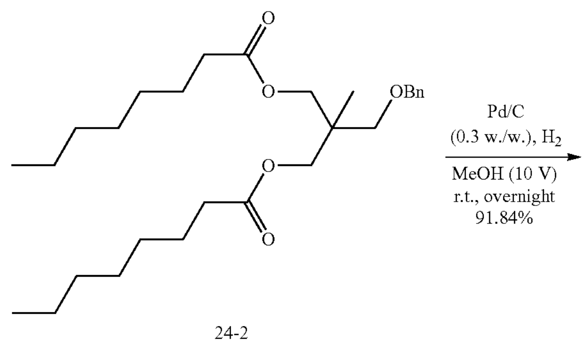

24-2

-continued

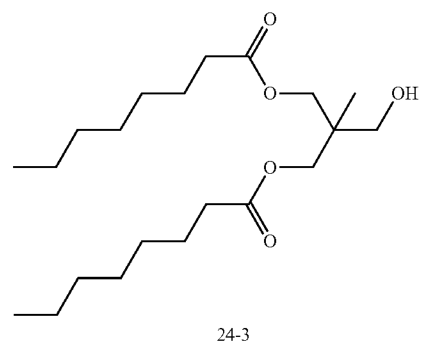

24-3

Into a 3 L three-necked round-bottom flask was added Pd/C (36.0 g, 0.3 w/w) and MeOH (1.2 L, 10 V) at room temperature. Then, 24-2 (119.0 g, 0.25 mol, 1.00 equiv.) was added to the reaction mixture at room temperature. Replaced the reaction system with $H_2$ for three times. The resulting solution was stirred for overnight at room temperature under $H_2$ atmosphere. LCMS indicated completed consumption of 24-2. The resulting mixture was filtered, the filter cake was washed with MeOH (2×1000 mL, 8V) and the filtrate was concentrated under reduced pressure. This resulted in (88 g, 0.23 mol, 91.8%) 24-3 as yellow oil. ELSD A: water/0.05% TFA: B: $CH_3CN$ 95:5 to 5:95 A/B at 2 min.): RT 1.5 min, m/z (Calcd.) 372.3, (found) 373.3 (M+H).

Synthesis of 24-4: (((3,3'-((tert-butoxycarbonyl) azanediyl)bis(propanoyl))bis(oxy))bis(methylene)) bis(2-methylpropane-2,1,3-triyl)tetraoctanoate

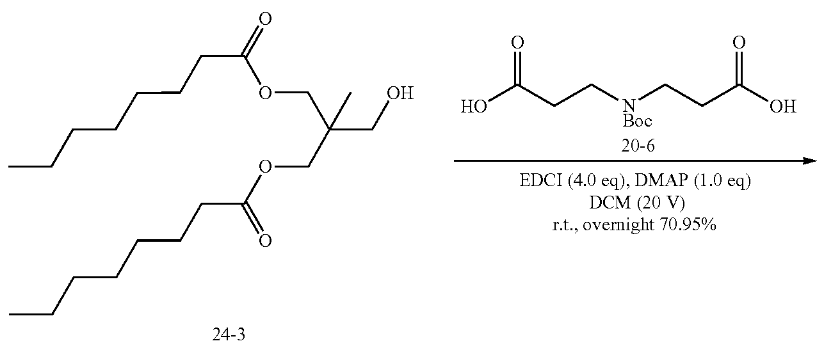

24-3

-continued

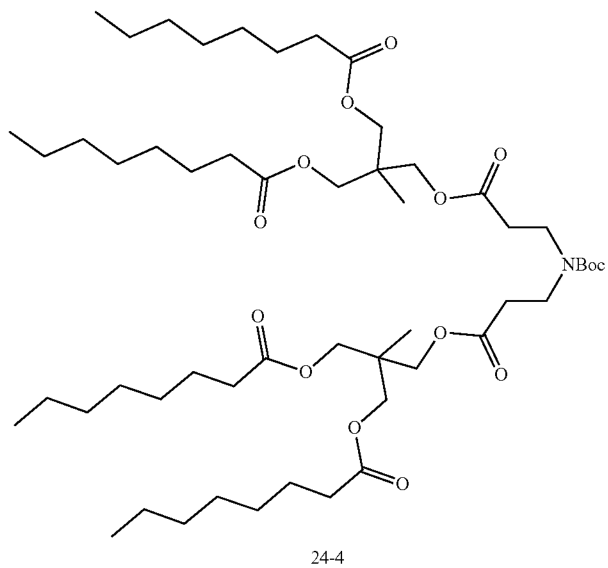

24-4

Into a 5 L four-necked flask was added 24-3 (75 g, 0.20 mol, 2.20 equiv.), DCM (1.5 L, 20 V) and 20-6 (23.91 g, 0.09 mol, 1.00 equiv.) at room temperature under the $N_2$ atmosphere. Then, DMAP (11.2 g, 0.09 mol, 1.00 equiv.) and EDCI (70.1 g, 0.36 mol, 4.00 equiv.) were added to the reaction mixture at 0° C. and stirred for additional overnight at room temperature. The reaction was quenched with water (900 mL, 12 V). The organic phase was washed with brine (900 mL, 12 V), dried with anhydrous $Na_2SO_4$, and filtered. Crude product was adsorbed on 130 g of silica gel (type: ZCX-2, 100-200 mesh, 1.40 w./w.) and purified on a silica gel column (900 g of silica gel type: ZCX-2, 100-200 mesh, 10.00 w./w.) using petroleum ether/THF (v/v) gradient from 100:0 to 95:5). Fractions were analyzed (TLC, PE:THF=1:6), combined, concentrated, and dried under vacuum to get 24-4 (63 g, 0.06 mol, 70.9% yield) as a colorless oil. ELSD A: water/0.05% TFA: B: $CH_3CN$/100:0 to 0:100 A/B at 3 min.): RT 0.78 min, m/z (Calcd.) 969.6, (found) 992.6 (M+Na).

Synthesis of 24-5: (((3,3'-azanediylbis(propanoyl)) bis(oxy))bis(methylene))bis(2-methylpropane-2,1,3-triyl)tetraoctanoate trifluoroacedtic Acid Salt

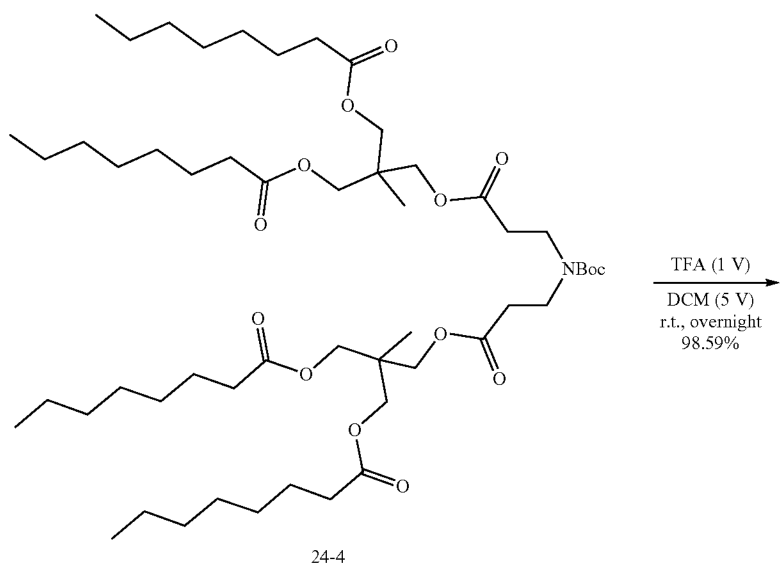

24-4

-continued

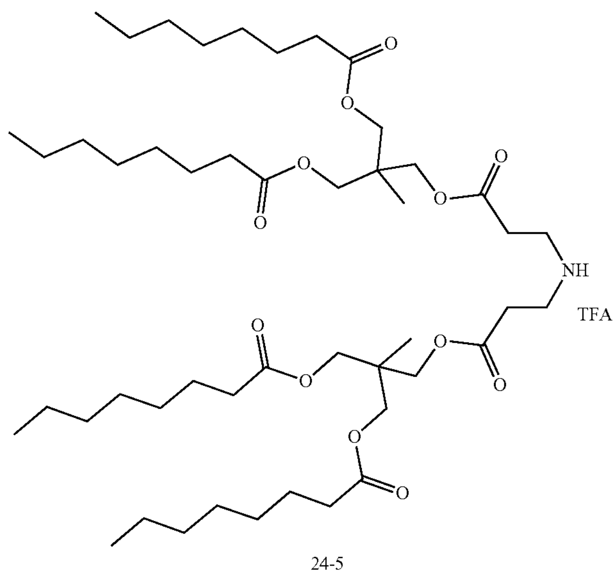

24-5

Into a 1 L three-necked flask was added 24-4 (63 g, 0.06 mol, 1.00 equiv.), DCM (315 mL, 5 V) and TFA (63 mL, 1V) at room temperature under the $N_2$ atmosphere. The resulting solution was stirred for overnight at room temperature. The mixture was concentrated and dried under vacuum. This resulted in (61.98 g, 0.06 mol, 98.6% yield) 24-5 as its trifluoroacetic acid salt as a yellow oil. ELSD A: water/0.05% TFA: B: $CH_3CN$/100:0 to 0:100 A/B at 3 min.): RT 0.53 min, m/z (Calcd.) 869.6, (found) 870.5 (M+H).

Synthesis of LIPID 24: ((3,3'-((((3-(Dimethylamino)propyl)thio)carbonyl) azanediyl)bis(propanoyl))bis(oxy))bis(methylene))bis(2-methylpropane-2,1,3-triyl) tetrakis(octanoate)

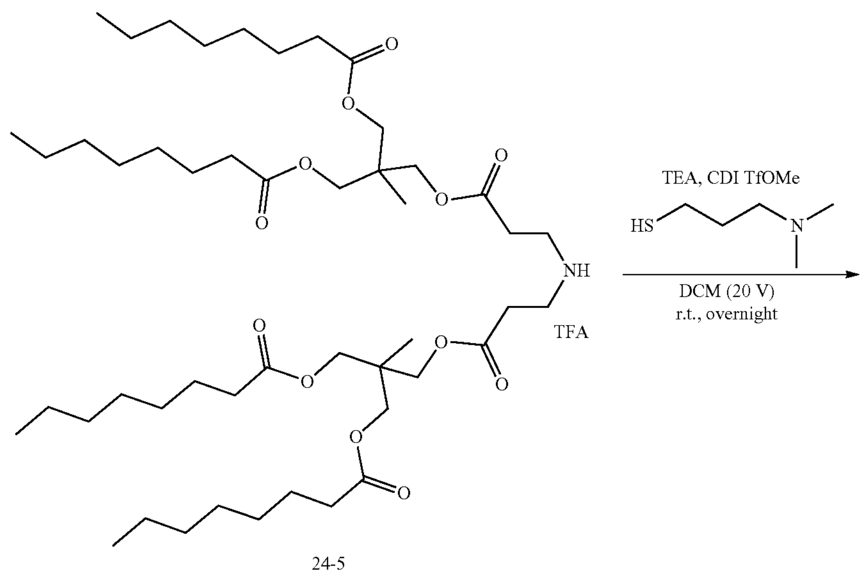

24-5

-continued

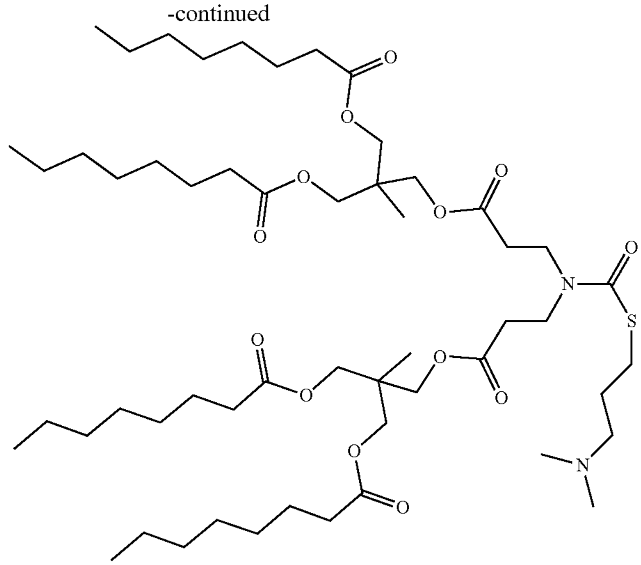

LIPID 24

Into a 3 L three-necked flask was added 24-5 (61.98 g, 0.06 mol, 1.00 equiv.), DCM (1.24 L, 20 V) and TEA (12.95 g, 0.12 mol, 2.00 equiv.) followed by the addition of CDI (20.76 g, 0.12 mol, 2.00 equiv.) at room temperature under nitrogen atmosphere. The resulting mixture was stirred for 3 h at room temperature. Then, into the reaction were added methyl triflate (17.69 g, 0.07 mol, 1.10 equiv.) at 0° C. and stirred for 1 h at 0° C. under nitrogen atmosphere. To the above mixture was added 3-(dimethylamino)propane-1-thiol (9.16 g, 0.07 mol, 1.20 equiv.) at 0° C. and stirred overnight at room temperature. The reaction system was quenched with water (1000 mL, 16 V). The organic phase was washed with brine (1000 mL, 16 V), dried with anhydrous $Na_2SO_4$, and then filtered. Crude product was adsorbed on 90 g of silica gel (type: ZCX-2, 100-200 mesh, 1.40 w./w.) and purified on a silica gel column (650 g of silica gel type: ZCX-2, 100-200 mesh, 10.00 w./w.) using heptane/ethyl acetate (v/v) gradient from 100:0 to 30:70). Fractions were analyzed (TLC, heptane:EA=1:10), combined, concentrated, and dried under vacuum to get LIPID 24 (5.3 g, 8% yield) as a colorless oil. ELSD A: water/0.05% TFA: B: $CH_3CN$/100:0 to 0:100 A/B at 5 min.): RT 3.46 min, m/z (Calcd.) 1014.8, (found) 1015.8 (M+H). $^1$H-NMR-LIPID 24: (400 MHz, DMSO-$d_6$, ppm) δ 4.00 (d, J=9.3 Hz, 12H), 3.65 (t, J=7.2 Hz, 4H), 2.93 (t, J=7.2 Hz, 2H), 2.65 (t, J=7.3 Hz, 4H), 2.46 (s, 2H), 2.31 (t, J=7.5 Hz, 14H), 1.91-1.80 (m, 2H), 1.61 (dt, J=8.7, 4.8 Hz, 8H), 1.34-1.22 (m, 32H), 1.01 (s, 6H), 0.93-0.82 (m, 12H).

Example 25. Synthesis of LIPID 25: ((4,4'-((((3-(Dimethylamino)propyl)thio)carbonyl)azanediyl)bis(butanoyl))bis(oxy))bis(methylene))bis(propane-2,1,3-triyl) tetranonanoate

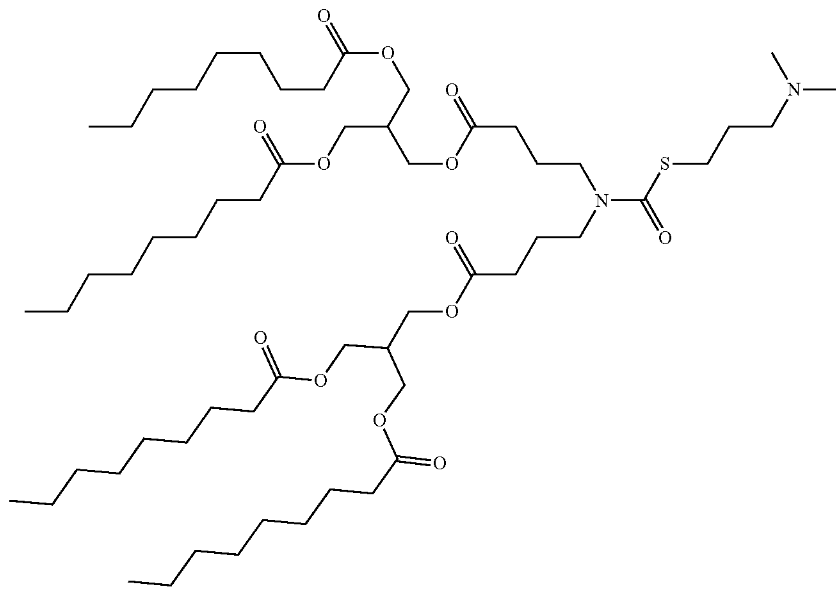 [SMILES: CCCCCCCCC(=O)OCC(COC(=O)CCCCCCCC)COC(=O)CCCN(CCCC(=O)OCC(COC(=O)CCCCCCCC)COC(=O)CCCCCCCC)C(=O)SCCCN(C)C]

LIPID 25
General scheme
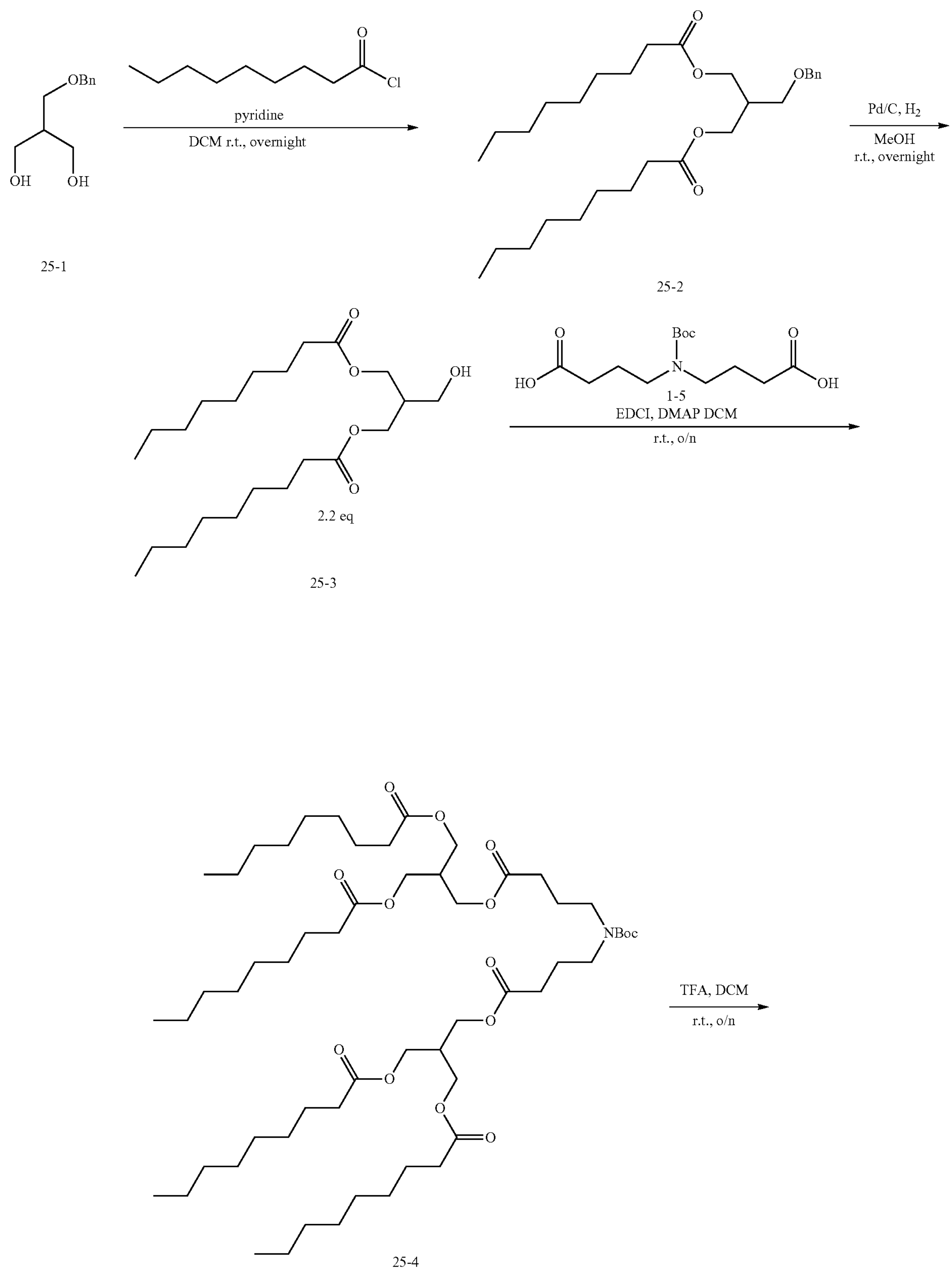
25-1
25-2
25-3
25-4

-continued
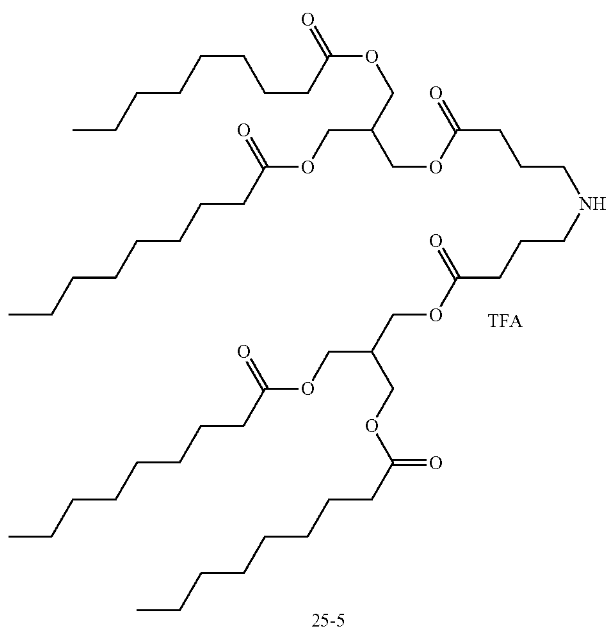
25-5
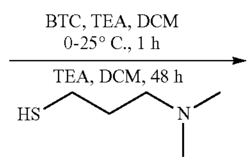
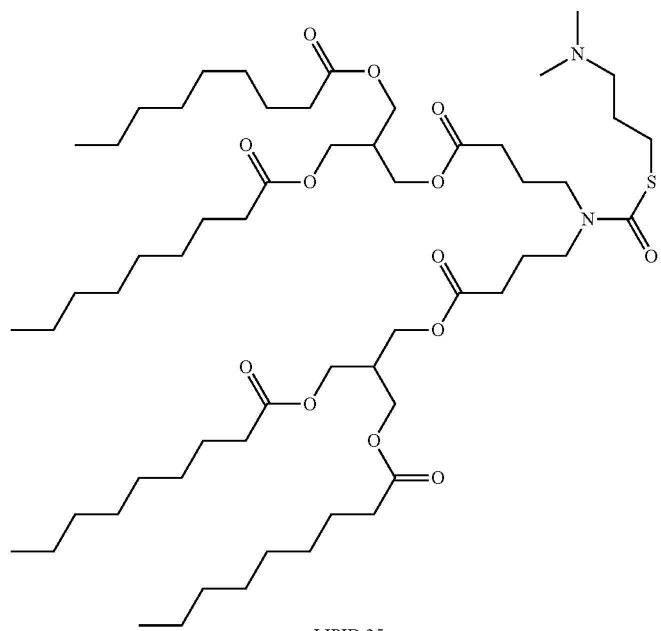
LIPID 25

Synthesis of 25-2: ((benzyloxy)methyl)propane-1,3-diyl dinonanoate

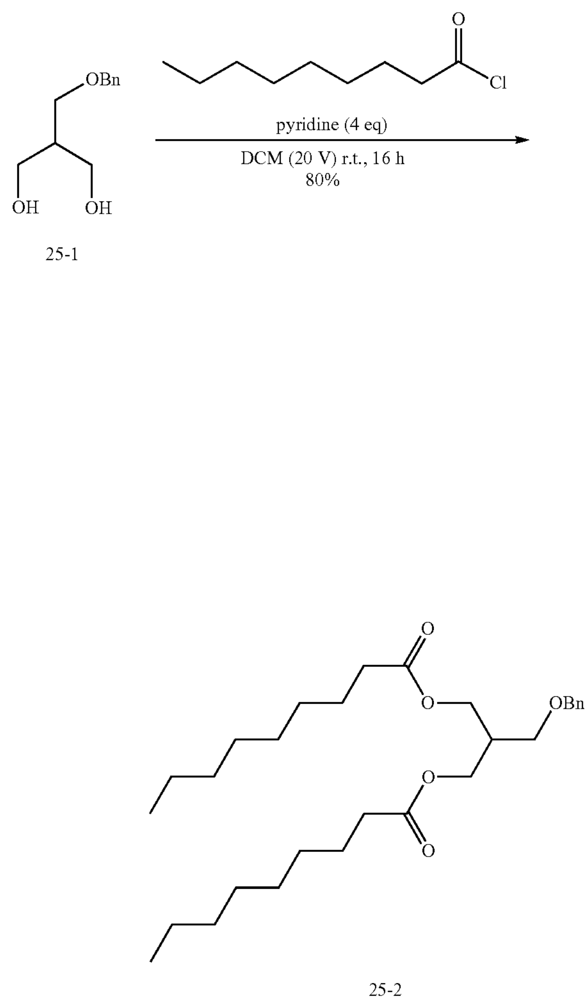

25-1

25-2

Into a 5 L 4-necked round-bottle flask purged and maintained with an inert atmosphere of nitrogen were added 25-1 (100 g, 0.51 mol, 1.00 equiv.), pyridine (161.2 g, 2.04 mol, 4.00 equiv.) in DCM (2.0 L, 20 V). To the solution was added nonanoyl chloride (224.5 g, 1.27 mol, 2.50 equiv.) dropwise at 20° C. for 30 min and stirred for 16 h at room temperature. The reaction was washed with water (1×1.0 L, 10 V) and brine (1×1.0 L mL, 10 V), organic layer was separated, dried, and evaporated. Crude product was adsorbed on 500 g of silica gel (type: ZCX-2, 100-200 mesh, 1.40 w./w.) and purified on a silica gel column (3 Kg of silica gel type: ZCX-2, 100-200 mesh, 10.00 w./w.) using Pet. ether/ethyl acetate (v/v) gradient from 100:0 to 90:10). Fractions were analyzed (TLC, PE:EA=6:1), combined, concentrated, and dried under vacuum to get 25-2 (194 g, 0.41 mol, 80.0% yield) as light yellow oil. ELSD A: water/0.05% TFA: B: $CH_3CN$/95:5 to 5:95 A/B at 3 min.): RT 2.5 min, m/z (Calcd.) 476.4, (found) 499.3 (M+Na).

Synthesis of 25-3: 2-(hydroxymethyl)propane-1,3-diyl dinonanoate

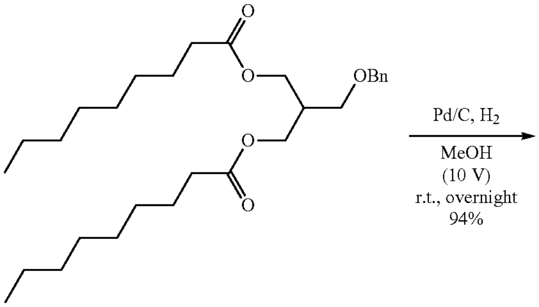

25-2

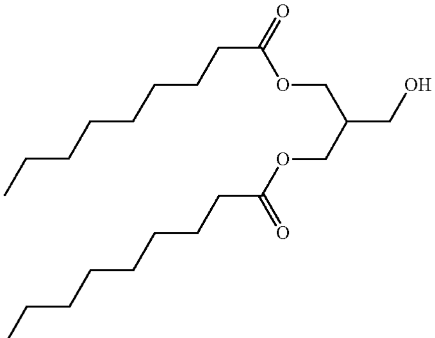

25-3

Into a 3 L 4-necked round-bottom flask was charged a solution of 25-2 (194.0 g, 0.41 mol, 1.00 equiv.) in MeOH (1.94 L, 10 V). Pd/C (38.8 g, 10% wt, 20% w/w) was added in one portion and hydrogenated for 16 h at room temperature. The reaction mixture was filtered, and the filter cake was washed with MeOH (0.97 L, 5 V). The filtrate was concentrated under vacuum to get 25-3 (148.0 g, 0.28 mol, 94.0% yield) as light-yellow oil. ELSD A: water/0.05% TFA: B: $CH_3CN$/95:5 to 5:95 A/B at 3 min.): RT 2.2 min, m/z (Calcd.) 386.3, (found) 387.3 (M+H).

Synthesis of 25-4: (((4,4'-((tert-butoxycarbonyl) azanediyl)bis(butanoyl))bis(oxy))bis(methylene))bis (propane-2,1,3-triyl) tetranonanoate

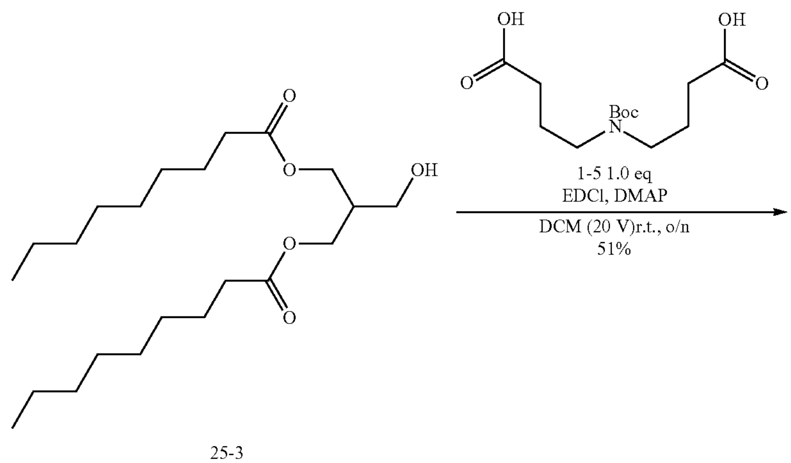

25-3

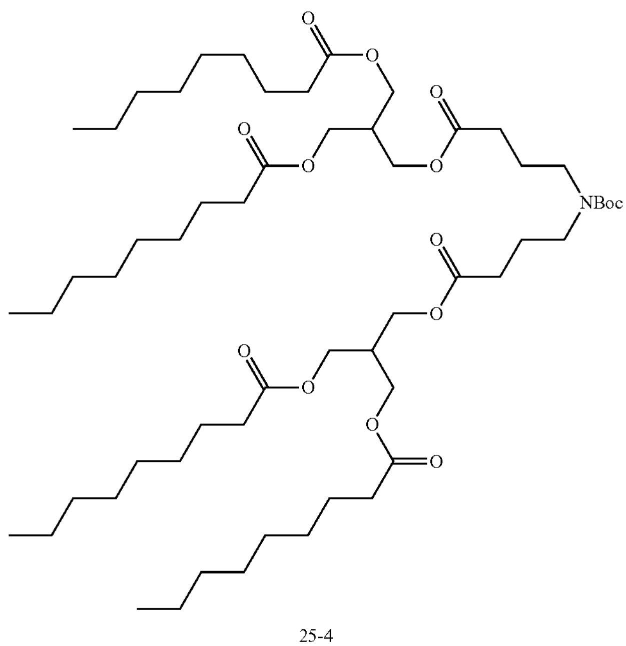

25-4

Into a 1000 mL 3-neck round-bottom flask purged and maintained with an inert atmosphere of nitrogen, was added 25-3 (76.4 g, 0.19 mol, 2.00 equiv.) and 1-5 (26.0 g, 0.09 mol, 1.00 equiv.) in DCM (3 L, 20 V) followed by DMAP (11.0 g, 0.09 mol, 0.50 equiv.) and EDCI (41.4 g, 0.21 mol, 2.40 equiv.) at 0° C. Ice water bath was removed and the reaction mixture was stirred for overnight at room temperature. The reaction was quenched with ice water (0.52 L, 20 V) and extracted with DCM (2×0.52 L, 20 V), washed with brine (1×0.52 L, 20 V), and the organic phase was dried with anhydrous $Na_2SO_4$ and filtered. Crude product was adsorbed on 150 g of silica gel (type: ZCX-2, 100-200 mesh, 1.40 w./w.) and purified on a silica gel column (900 g of silica gel type: ZCX-2, 100-200 mesh, 10.00 w./w.) using petroleum ether/ethyl acetate (v/v) gradient from 100:0 to 70:30). Fractions were analyzed (TLC, PE:EA=3:1), combined, concentrated, and dried under vacuum to get 25-4 (47 g, 46 mol, 80.0% yield) as light yellow oil. ELSD A: water/0.05% TFA: B: $CH_3CN$/100:0 to 0:100 A/B at 3 min.): RT 1.3 min, m/z (Calcd.) 1025.7, (found) 1048.0 (M+Na).

Synthesis of (((4,4'-azanediylbis(butanoyl))bis(oxy)) bis(methylene))bis(propane-2,1,3-triyl) tetranonanoate triufluoroacetic Acid Salt

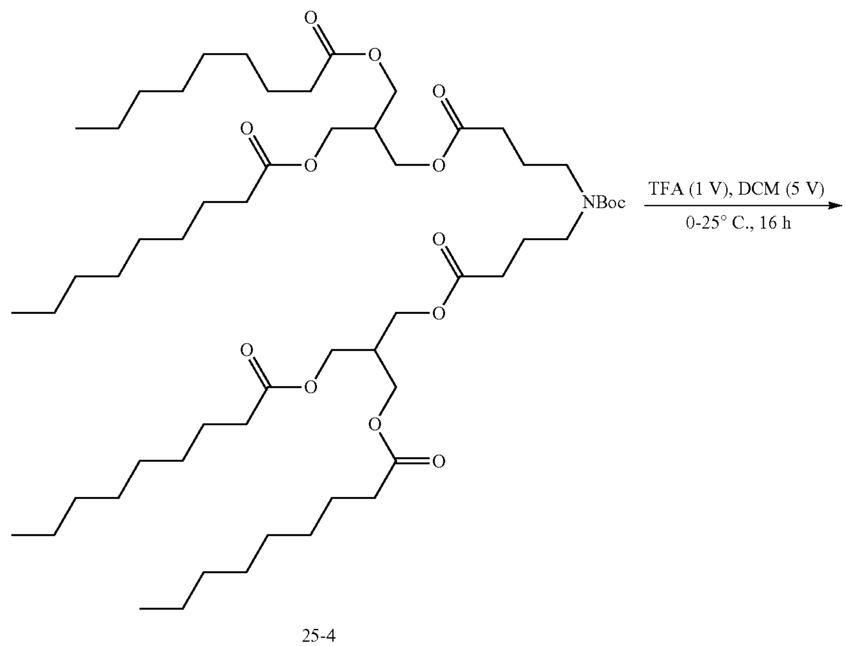

25-4

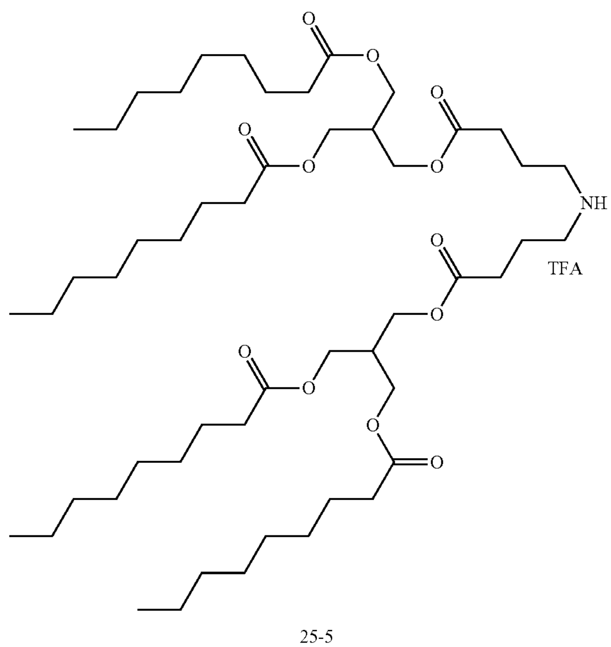

25-5

Into a 500 mL 3-necked round-bottom flask purged and maintained with an inert atmosphere of nitrogen, was placed a solution of 25-4 (47 g, 0.45 mol, 1.00 equiv.) in DCM (235 mL, 5V). To the solution was added TFA (47 mL, 1.0 V) dropwise at 0-5° C. for 20 min. The resulting solution was warmed to room temperature and stirred for 16 h at room temperature. The resulting mixture was concentrated under vacuum to get (49 g, 0.047 mol, crude) of 25-5 its trifluoroacetic acid salt as a yellow oil. ELSD A: water/0.05% TFA: B: $CH_3CN$/95:5 to 5:95 A/B at 3 min.): RT 2.3 min, m/z (Calcd.) 925.7, (found) 926.7 (M+H).

Synthesis of LIPID 25: ((4,4'-((((3-(Dimethylamino)propyl)thio)carbonyl) azanediyl)bis(butanoyl))bis(oxy))bis(methylene))bis(propane-2,1,3-triyl) tetranonanoate

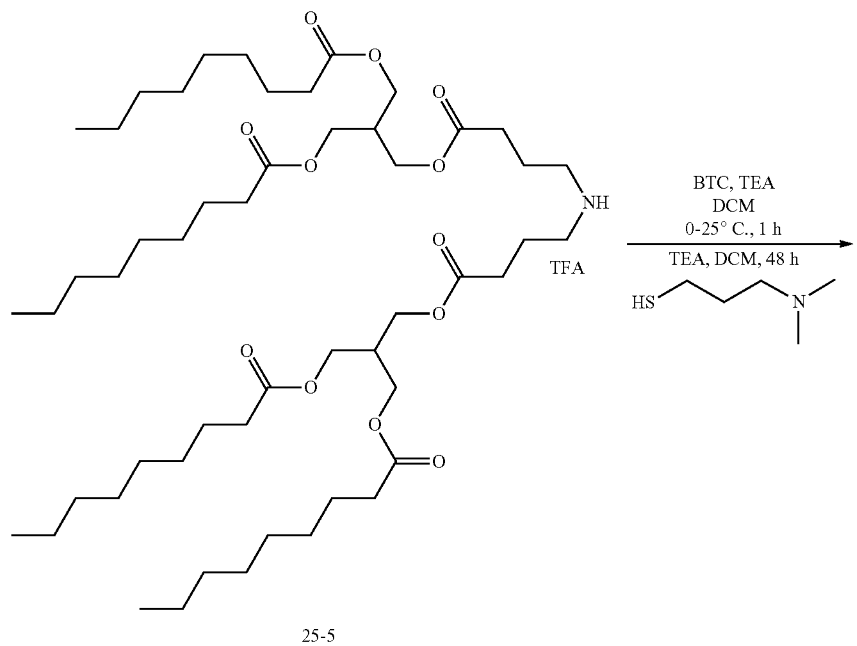

25-5

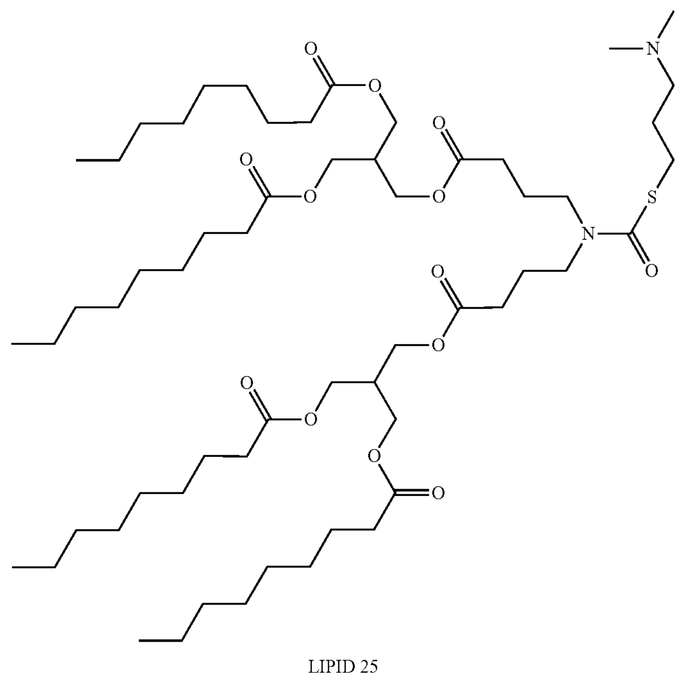

LIPID 25

Into a 1 L 4-necked round-bottom flask purged and maintained with an inert atmosphere of nitrogen, was placed a solution of 25-5 (30 g, 0.02 mol, 1.00 equiv.) in DCM (0.6 L, 20 V). To the mixture was added TEA (5.92 g, 0.05 mol, 2.00 equiv.) at 0-5° C., followed by triphosgene (BTC, 0.5 equiv.) in batches at 0-5° C. The ice water bath was removed, and the reaction mixture was stirred for 1 h at room temperature. After concentrating the reaction system it was dissolved in DCM (0.6 L, 20 V), TEA (8.86 g, 0.08 mol, 3.00 equiv.) and 3-(dimethylamino)propane-1-thiol (3.83 g, 0.03 mol, 1.10 equiv.) were added at 0° C. The resulting solution was warmed to r.t and stirred for 48 h at room temperature. The reaction system was quenched with ice water (0.6 L, 20 V) and extracted with DCM (2×0.6 L, 20 V), washed with brine (2×0.6 L, 20 V). The organic phase was dried with anhydrous $Na_2SO_4$, filtered, and concentrated under reduced pressure. Crude product was adsorbed on 60 g of silica gel (type: ZCX-2, 100-200 mesh, 1.40 w./w.) and purified on a silica gel column (900 g of silica gel type: ZCX-2, 100-200 mesh, 10.00 w./w.) using heptane/ethyl acetate (v/v) gradient from 100:0 to 70:30). Fractions were analyzed (TLC, Heptane:EA=6:1), combined, concentrated, and dried under vacuum to get LIPID 25 (5.5 g, 17.5%) as light yellow oil. ELSD A: water/0.05% TFA: B: $CH_3CN$/100:0 to 0:100 A/B at 3 min.): RT 2.2 min, m/z (Calcd.) 1070.7, (found) 1072.0 (M+H). $^1$HNMR-LIPID 25: (300 MHz, $CDCl_3$, ppm): δ 4.15 (dd, J=6.0, 3.1 Hz, 12H), 3.39 (s, 4H), 2.93 (t, J=7.2 Hz, 2H), 2.48-2.21 (m, 22H), 2.01-1.76 (m, 6H), 1.71-1.53 (m, 8H), 1.29 (q, J=4.3, 3.6 Hz, 40H), 0.98-0.81 (m, 12H).

Example 26. LIPID 26: ((3,3'-((((2-(Dimethylamino)ethyl)thio)carbonyl)azanediyl)bis(propanoyl))bis(oxy))bis(methylene))bis(propane-2,1,3-triyl) tetranonanoate

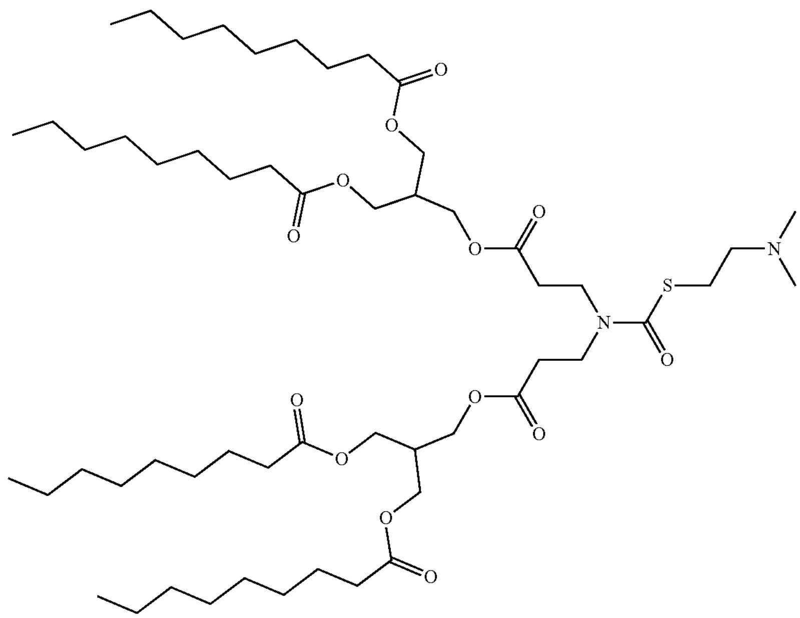 [SMILES: CCCCCCCCC(=O)OCC(COC(=O)CCCCCCCC)COC(=O)CCN(CCC(=O)OCC(COC(=O)CCCCCCCC)COC(=O)CCCCCCCC)C(=O)SCCN(C)C]

LIPID 26

General scheme

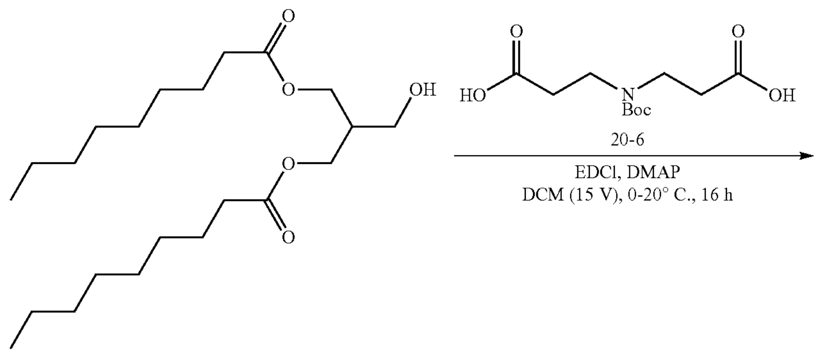

-continued
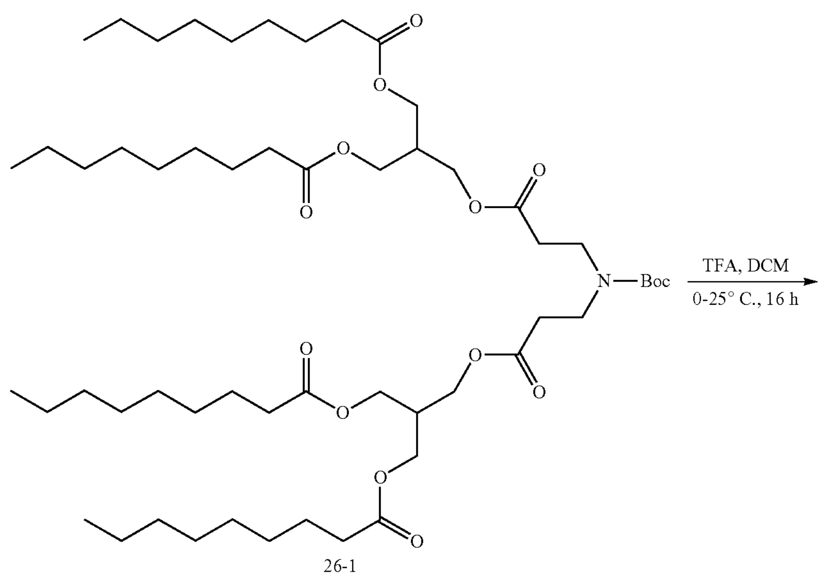
26-1
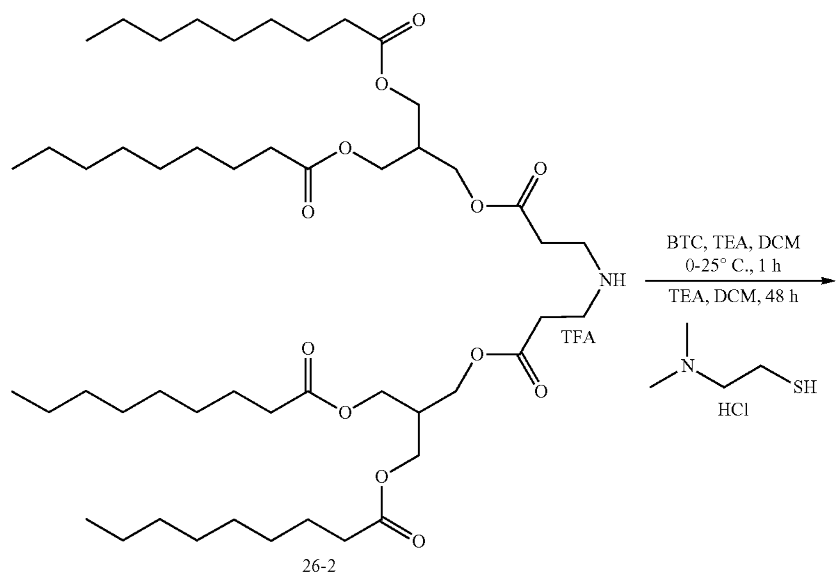
26-2

-continued
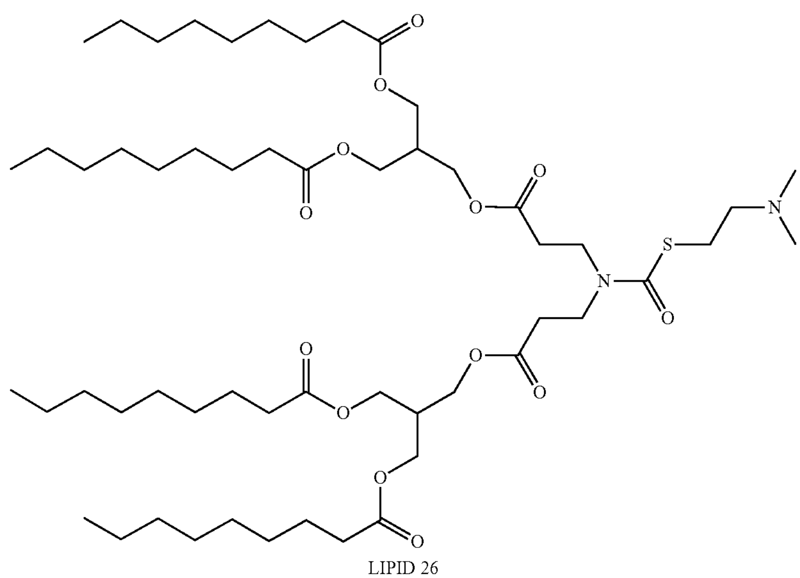
LIPID 26
Synthesis of 26-1: (((3,3'-((tert-butoxycarbonyl) azanediyl)bis(propanoyl))bis(oxy))bis(methylene)) bis(propane-2,1,3-triyl) tetranonanoate
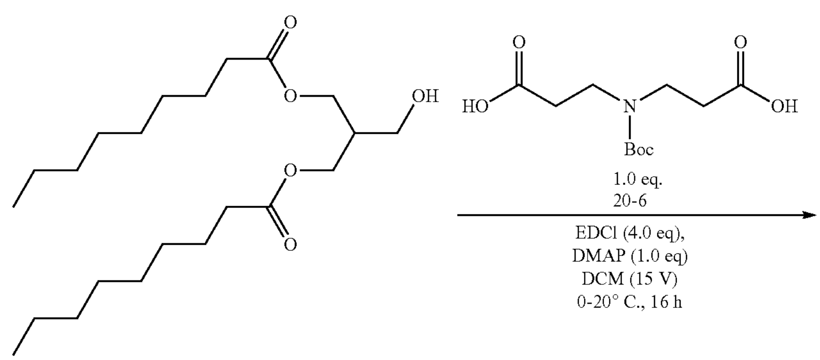
25-3

-continued

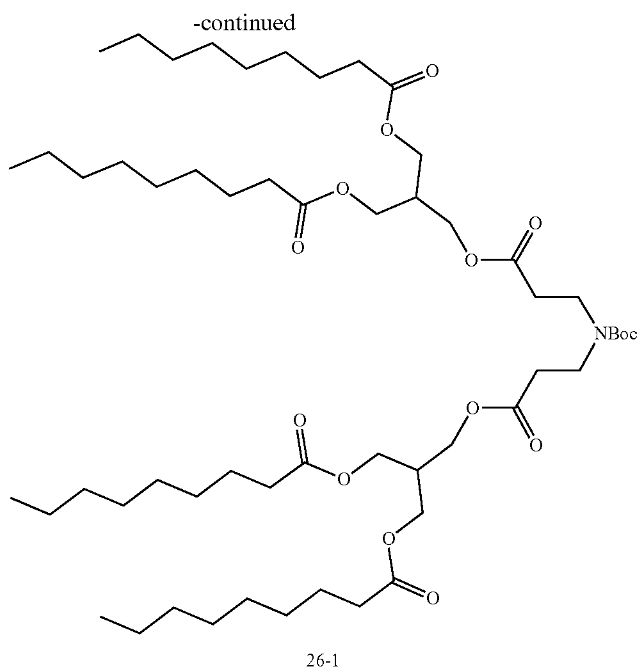

26-1

Into a 1000 mL 3-necked round-bottom flask purged and maintained with an inert atmosphere of nitrogen, was added 25-3 (84.6 g, 0.21 mol, 2.20 equiv.) and 20-6 (26.0 g, 0.099 mol, 1.00 equiv.) in DCM (520 mL, 20 V) followed by DMAP (12.1 g, 0.1 mol, 1.00 equiv.) and EDCI (45.9 g, 0.23 mol, 2.40 equiv.) at 0° C. The reaction mixture was stirred for overnight at room temperature. The reaction was quenched with ice water (0.52 L, 20 V), extracted with DCM (2×0.52 L, 20 V), and washed with brine (1×0.52 L, 20 V). The organic phase was dried with anhydrous $Na_2SO_4$ and filtered. Crude product was adsorbed on 150 g of silica gel (type: ZCX-2, 100-200 mesh, 1.40 w./w.) and purified on a silica gel column (900 g of silica gel type: ZCX-2, 100-200 mesh, 10.00 w./w.) using petroleum ether/ethyl acetate (v/v) gradient from 100:0 to 70:30). Fractions were analyzed (TLC, PE:EA=3:1), combined, concentrated, and dried under vacuum to get 26-1 (49.6 g, 48.9%) as light yellow oil. ELSD A: water/0.05% TFA: B: $CH_3CN$/100:0 to 0:100 A/B at 3 min.): RT 0.99 min, m/z (Calcd.) 997.7, (found) 1020.8 (M+Na).

Synthesis of 26-2: (((3,3'-azanediylbis(propanoyl)) bis(oxy))bis(methylene))bis(propane-2,1,3-triyl) tetranonanoate trifluroacetic Acid Salt

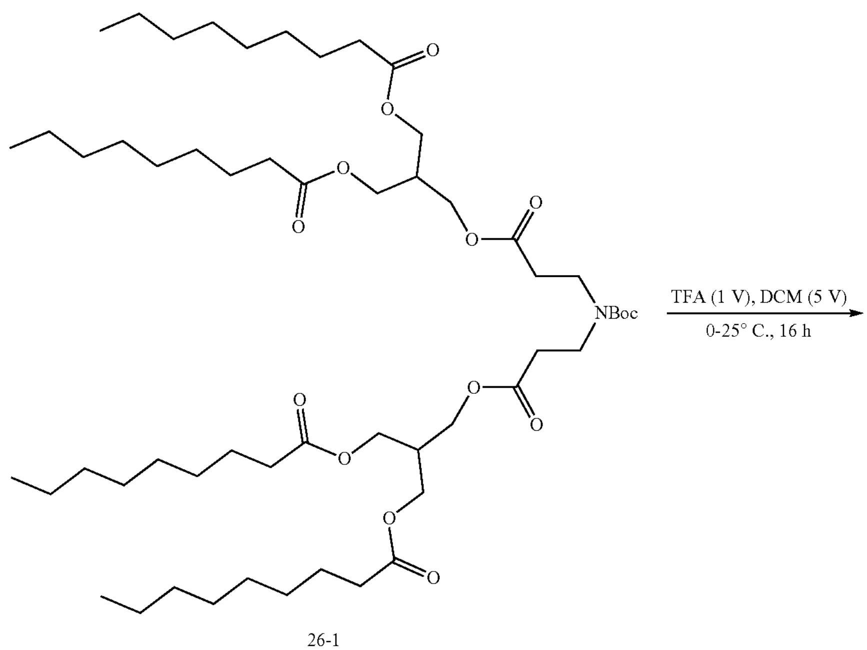

26-1

-continued

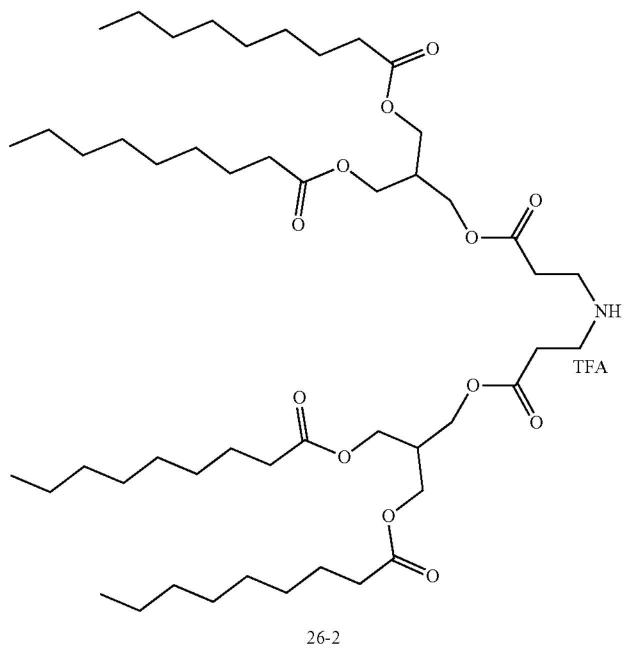

26-2

Into a 500 mL 3-necked round-bottom flask purged and maintained with an inert atmosphere of nitrogen, was placed a solution of 26-1 (48.6 g, 0.45 mol, 1.00 equiv.) in DCM (243 mL, 5V). To the solution was added TFA (48.6 mL, 1.0 V) dropwise at 0-5° C. for 20 min. The resulting solution was warmed to room temperature and stirred for 16 h at room temperature. The resulting mixture was concentrated under vacuum to get 50.5 g, (0.050 mol, crude) of 26-2 as its trifluoracetic acid salt as a yellow oil. ELSD A: water/0.05% TFA: B: $CH_3CN$/95:0 to 5:95 A/B at 3 min.): RT 2.3 min, m/z (Calcd.) 897.6, (found) 898.7 (M+H).

Synthesis of LIPID 26: ((3,3'-((((2-(Dimethylamino)ethyl)thio)carbonyl)azanediyl)bis(propanoyl))bis(oxy))bis(methylene))bis(propane-2,1,3-triyl) tetranonanoate

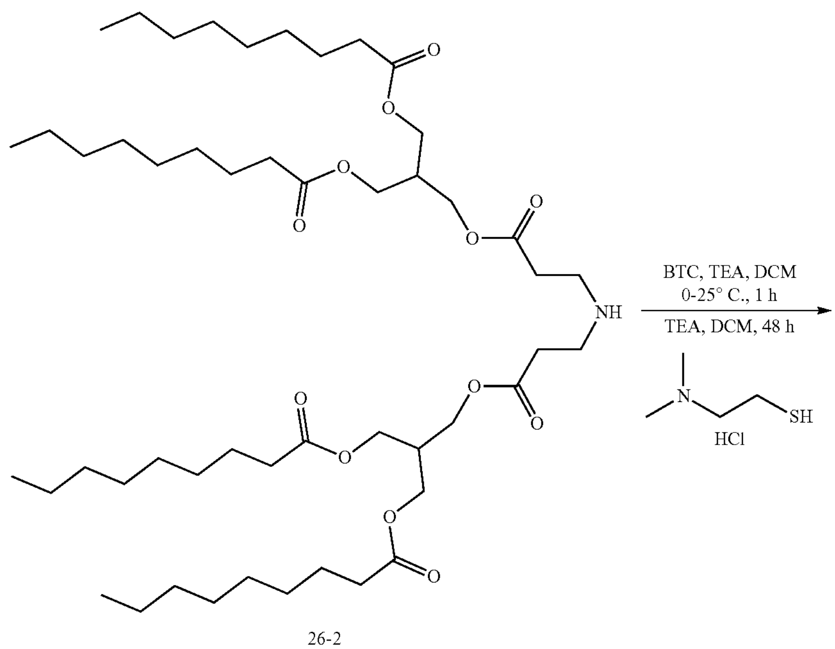

26-2

-continued

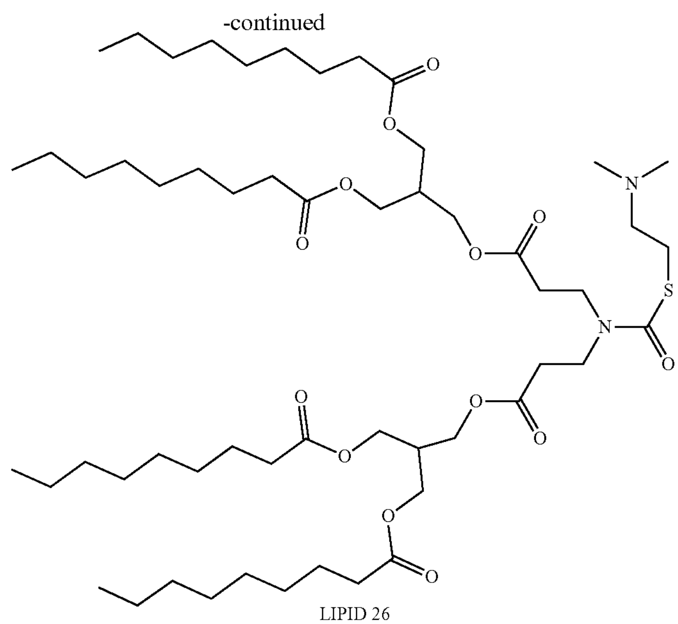

LIPID 26

Into a 1 L 4-necked round-bottom flask purged and maintained with an inert atmosphere of nitrogen, was placed a solution of 26-2 (30 g, 0.03 mol, 1.00 equiv., crude) in DCM (0.6 L, 20 V). To the mixture was added TEA (6.08 g, 0.06 mol, 2.00 equiv.) into the reactor at 0-5° C., then added BTC (4.47 g, 0.015 mol, 0.5 equiv.) in batches at 0-5° C. The ice water bath was removed the reaction mixture was stirred for 1 h at room temperature. After concentrating the reaction system it was dissolved in DCM (0.6 L, 20 V), TEA (12.16 g, 0.12 mol, 4.00 equiv.) and 2-(dimethylamino) ethane-1-thiol hydrochloride (4.67 g, 0.03 mol, 1.10 equiv.) were added at 0° C. The resulting solution was warmed to room temperature and stirred for 48 h. The reaction was quenched with ice water (0.6 L, 20 V) and extracted with DCM (2×0.6 L, 20 V), washed with brine (2×0.6 L, 20 V), dried with anhydrous $Na_2SO_4$, and filtered. Crude product was adsorbed on 60 g of silica gel (type: ZCX-2, 100-200 mesh, 1.40 w./w.) and purified on a silica gel column (900 g of silica gel type: ZCX-2, 100-200 mesh, 10.00 w./w.) using heptane/ethyl acetate (v/v) gradient from 100:0 to 70:30). Fractions were analyzed (TLC, heptane:THF=7:1), combined, concentrated, and dried under vacuum to get LIPID 26 (5.4 g, 17.5%) as light yellow oil. ELSD A: water/0.05% TFA: B: $CH_3CN$/100:0 to 0:100 A/B at 3 min.): RT 2.2 min, m/z (Calcd.) 1028.7, (found) 1030.0 (M+H). $^1$HNMR-LIPID 26: (300 MHz, $CDCl_3$, ppm): δ 4.15 (t, J=5.5 Hz, 12H), 3.68 (t, J=7.2 Hz, 4H), 3.07 (t, J=7.0 Hz, 2H), 2.67 (t, J=7.2 Hz, 4H), 2.59 (t, J=7.0 Hz, 2H), 2.49-2.25 (m, 16H), 1.64 (q, J=7.3 Hz, 8H), 1.30 (dd, J=5.9, 3.0 Hz, 40H), 0.95-0.84 (m, 12H).

Example 27. LIPID 27: ((3,3'-((((3-(Dimethylamino)propyl)thio)carbonyl) azanediyl)bis(propanoyl))bis(oxy))bis(methylene))bis(propane-2,1,3-triyl) tetrakis(3-(4-methylcyclohexyl)propanoate)

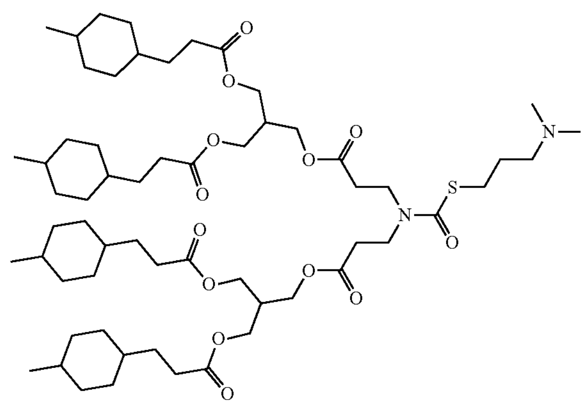

LIPID 27

General scheme

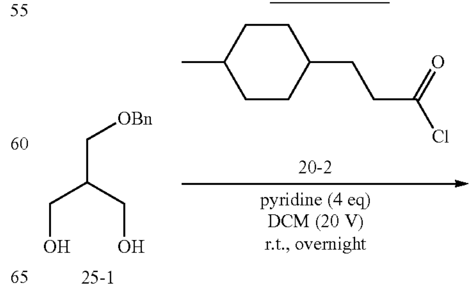

-continued

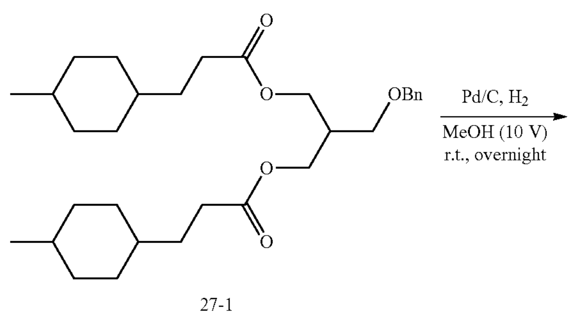

27-1

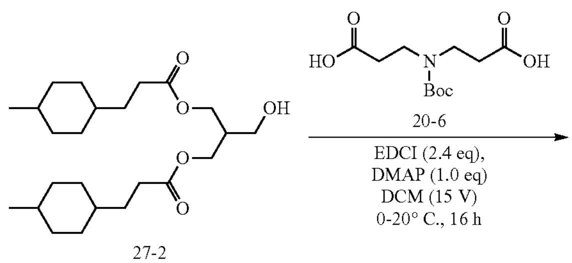

27-2

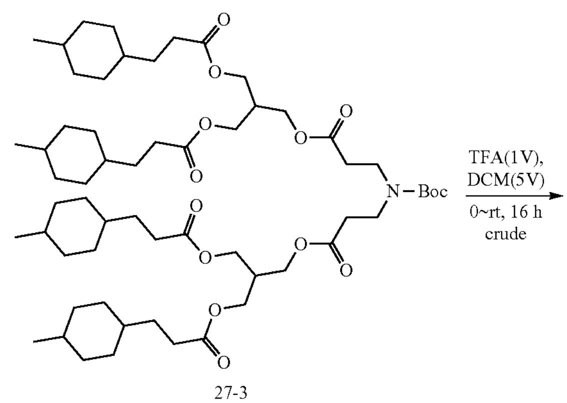

27-3

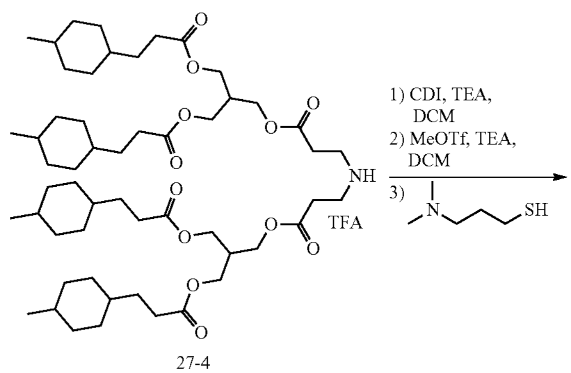

27-4

-continued

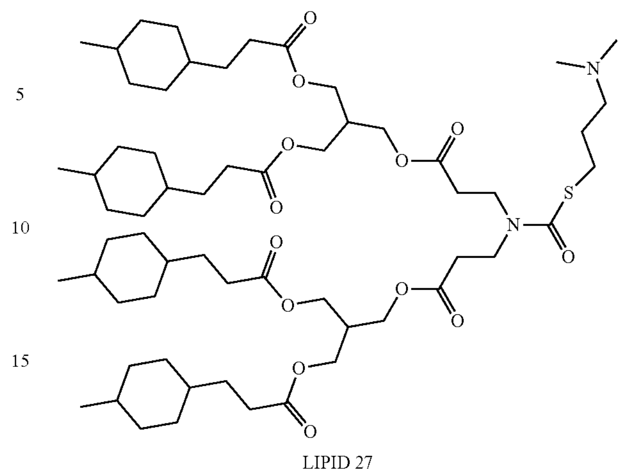

LIPID 27

Synthesis of 27-1: 2-((benzyloxy)methyl)propane-1, 3-diyl bis(3-(4-methylcyclohexyl)propanoate)

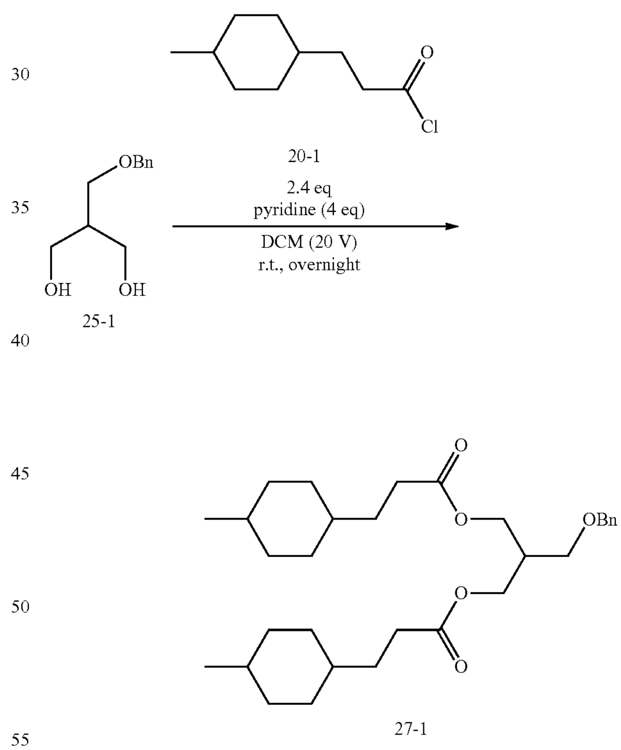

25-1

27-1

Into a 5 L 4-necked round-bottle flask purged and maintained with an inert atmosphere of nitrogen were added 25-1 (30 g, 0.15 mol, 1.00 equiv.), pyridine (48.3 g, 0.61 mol, 4.00 equiv.) in DCM (0.6 L, 20 V). To the solution was added 20-1 (69.0 g, 0.36 mol, 2.40 equiv.) dropwise at 0° C. for 30 min, then the resulting solution was stirred for overnight at room temperature. The reaction was washed with water (1×0.6 L, 10 V), brine (1×0.6 L, 10 V), dried ($Na_2SO_4$) and concentrated under reduced pressure. Crude product was adsorbed on 180 g of silica gel (type: ZCX-2, 100-200 mesh, 1.40 w./w.) and purified on a silica gel column (1 Kg of silica gel type: ZCX-2, 100-200 mesh, 10.00 w./w.) using petroleum ether/ethyl acetate (v/v) gradient from 100:0 to 90:10). Fractions were analyzed (TLC, PE:EA=6:1), combined, concentrated, and dried under vacuum to get 27-1 (60 g, 75%) as light yellow oil. ELSD A: water/0.05% TFA: B: $CH_3CN$/95:0 to 5:95 A/B at 3 min.): RT 2.5 min, m/z (Calcd.) 500.3, (found) 523.3 (M+Na).

Synthesis of 27-2:2-(hydroxymethyl)propane-1,3-diyl bis(3-(4-methylcyclohexyl)propanoate)

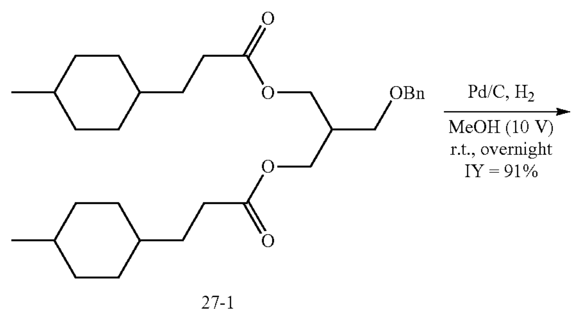

27-1

-continued

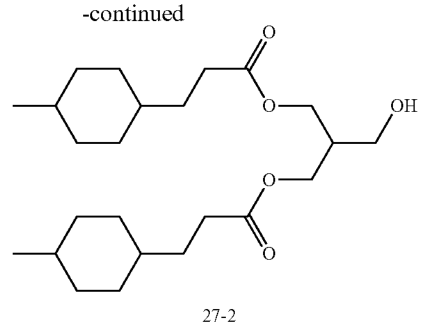

27-2

Into a 3 L 4-necked round-bottom flask was charged a solution of 27-1 (60.0 g, 0.12 mol, 1.00 equiv.) in MeOH (1.94 L, 10 V) and 10% wt Pd/C (12.0 g, 20% w./w.) was added in one portion. The reaction mixture was hydrogenated under hydrogen gas at room temperature. The reaction mixture was filtered, and the filter cake was washed with MeOH (300 mL, 5 V). The filtrate was concentrated under vacuum to get 27-2 (46.0 g, 0.12 mol, 91.0% yield) as light-yellow oil. ELSD A: water/0.05% TFA: B: $CH_3CN$/95:0 to 5:95 A/B at 3 min.): RT 2.2 min, m/z (Calcd.) 410.3, (found) 411.3 (M+H).

Synthesis of 27-3: (((3,3'-((tert-butoxycarbonyl)azanediyl)bis(propanoyl))bis(oxy))bis(methylene))bis(propane-2,1,3-triyl) tetrakis(3-(4-methylcyclohexyl)propanoate)

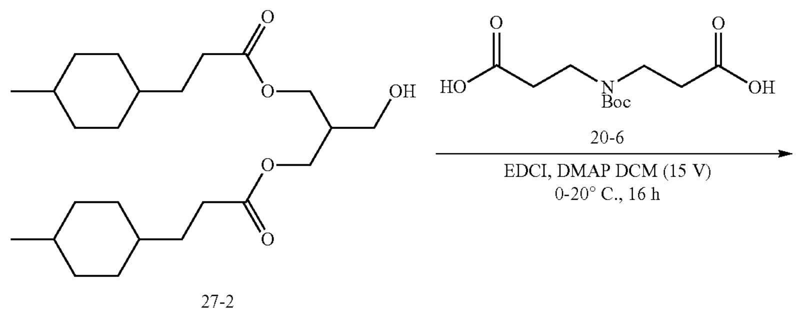

27-2

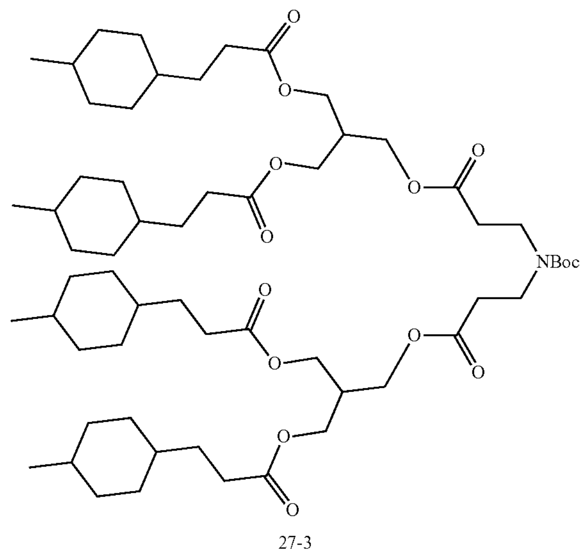

27-3

Into a 1000 mL 3-necked round-bottom flask purged and maintained with an inert atmosphere of nitrogen, was added 27-2 (103.6 g, 0.25 mol, 2.20 equiv.) and 20-6 (30.0 g, 0.11 mol, 1.00 equiv.) in DCM (600 mL, 20 V). To the solution was added DMAP (14.0 g, 0.11 mol, 1.00 equiv.) and EDCI (53.0 g, 0.27 mol, 2.40 equiv.) at 0° C. The ice water bath was removed after adding all reagents. The reaction mixture was stirred for overnight at room temperature. The reaction system was quenched with ice water (0.60 L, 20 V). The system was extracted with DCM (2×0.60 L, 20 V) and washed with brine (1×0.60 L, 20 V). The organic phase was dried with anhydrous $Na_2SO_4$ and then filtered. Crude product was adsorbed on 260 g of silica gel (type: ZCX-2, 100-200 mesh, 1.40 w./w.) and purified on a silica gel column (1.3 Kg of silica gel type: ZCX-2, 100-200 mesh, 10.00 w./w.) using petroleum ether/ethyl acetate (v/v) gradient from 100:0 to 70:30). Fractions were analyzed (TLC, PE:EA=3:1), combined, concentrated, and dried under vacuum to get 27-3 (38.2 g, 36.5 mmol, 31.8%) as light yellow oil. ELSD A: water/0.05% TFA: B: $CH_3CN$/100:0 to 0:100 A/B at 3 min): RT 1.2 min, m/z (Calcd.) 1045.7, (found) 1068.6 (M+Na).

Synthesis of (((3,3'-azanediylbis(propanoyl))bis(oxy))bis(methylene))bis(propane-2,1,3-triyl) tetrakis(3-(4-methylcyclohexyl)propanoate) trifluroacetic Acid Salt

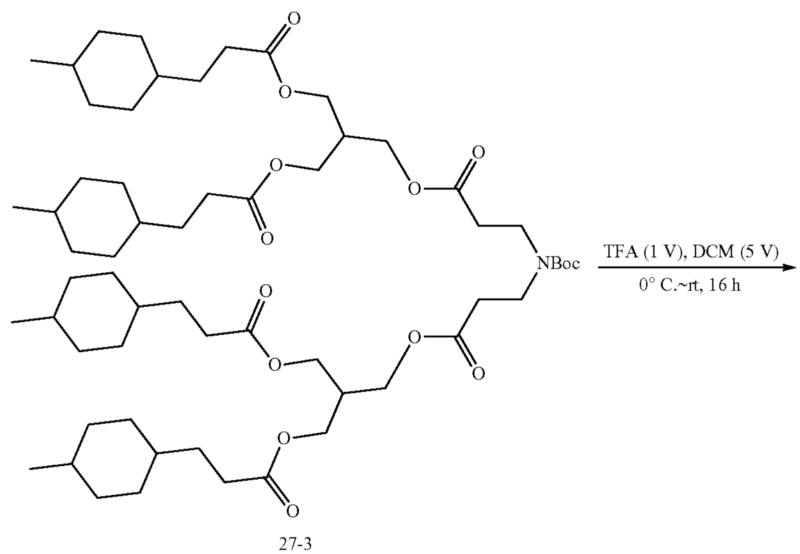

27-3

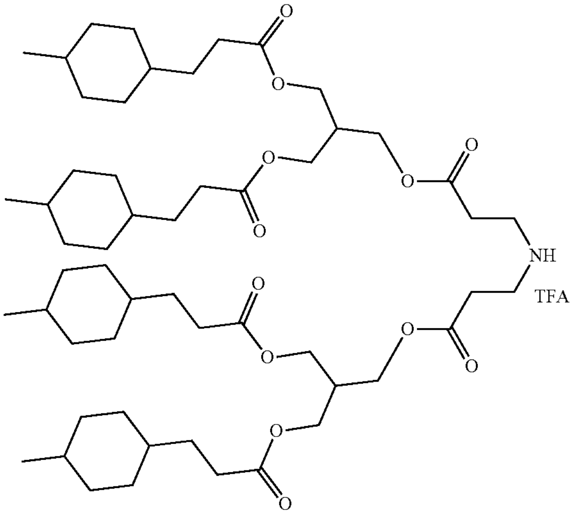

27-4

Into a 500 mL 3-necked round-bottom flask purged and maintained with an inert atmosphere of nitrogen, was placed a solution of 27-3 (38.2 g, 0.036 mol, 1.00 equiv.) in DCM (191 mL, 5V). To the solution was added TFA (38.2 mL, 1.0 V) dropwise at 0-5° C. for 20 min and stirred for 16 h at room temperature. The resulting mixture was concentrated and dried under vacuum to get (38.0 g, 0.036 mol, crude) of 27-4 as its trifluoroacetic acid salt as a yellow oil. ELSD A: water/0.05% TFA: B: $CH_3CN$/95:5 to 5:95 A/B at 3 min): RT 2.3 min, m/z (Calcd.) 945.6, (found) 946.6 (M+H).

Synthesis of LIPID 27: ((3,3'-((((3-(Dimethylamino)propyl)thio)carbonyl) azanediyl)bis(propanoyl))bis(oxy))bis(methylene))bis(propane-2,1,3-triyl) tetrakis(3-(4-methylcyclohexyl)propanoate)

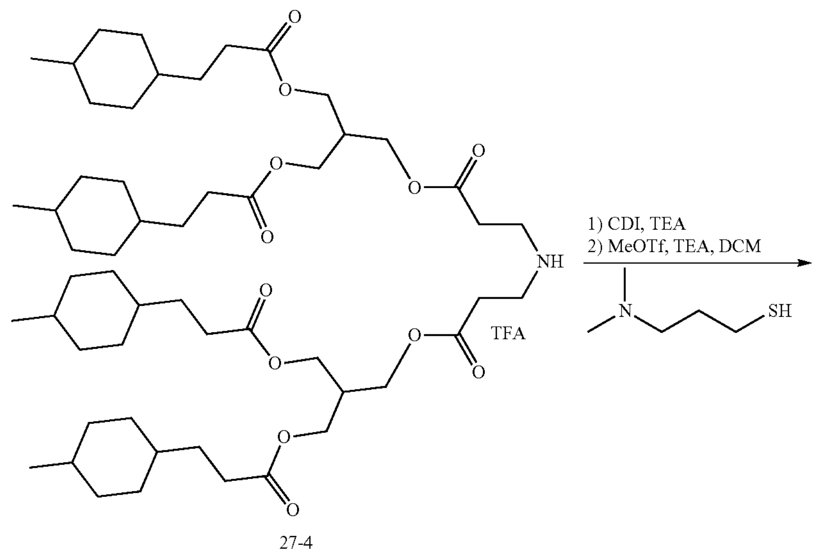

27-4

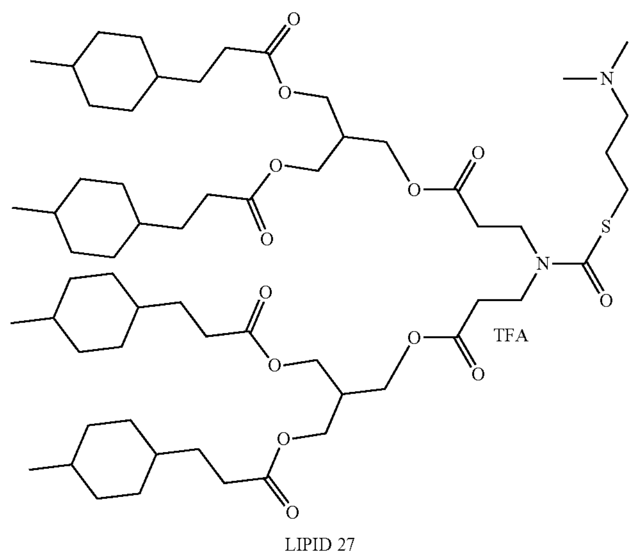

LIPID 27

Into a 1000 mL 3-necked round-bottom flask purged and maintained with an inert atmosphere of nitrogen, was placed a solution of 27-4 (29.0 g, 0.02 mol, 1.00 equiv.) in DCM (580 mL, 20 V). To this was added TEA (4.2 g, 0.03 mol, 1.50 equiv.), followed by CDI (4.95 g, 0.02 mol, 1.10 equiv.). The mixture was stirred overnight at room temperature, LCMS showed the reaction was completed. Then, TfOMe (5.01 g, 0.02 mol, 1.10 equiv.) was added and the mixture was stirred at 0° C. for 1 hour. Then, TEA (4.2 g, 0.03 mol, 1.50 equiv.) and 3-(dimethylamino)propane-1-thiol (3.64 g, 0.03 mol, 1.10 equiv.) were added to the solution. The ice/water bath was removed, and the mixture was stirred overnight at room temperature. The reaction system was quenched with ice water (580 mL, 20 V). The system was extracted with DCM (2×580 mL, 20 V) and washed with brine (2×580 mL, 20 V). The organic phase was dried with anhydrous $Na_2SO_4$ and then filtered. Crude product was adsorbed on 58 g of silica gel (type: ZCX-2, 100-200 mesh, 1.40 w./w.) and purified on a silica gel column (350 g of silica gel type: ZCX-2, 100-200 mesh, 10.00 w./w.) using heptane/ethyl acetate (v/v) gradient from 100:0 to 70:30). Fractions were analyzed (TLC, heptane:EA=7:1), combined, concentrated, and dried under vacuum to get LIPID 27 (5.4 g, 4.9 mmol, 17.8%) as light yellow oil. ELSD A: water/0.05% TFA: B: $CH_3CN$/0.05% TFA 100:0 to 0:100 A/B at 25 min.): RT 11.7 min, m/z (Calcd.) 1090.7, (found) 1091.8 (M+H). $^1$HNMR-LIPID 27: (300 MHz, $CDCl_3$, ppm): δ 4.24-4.08 (m, 12H), 3.67 (t, J=7.2 Hz, 4H), 2.94 (t, J=7.3 Hz, 2H), 2.67 (t, J=7.2 Hz, 4H), 2.51-2.29 (m, 12H), 1.82 (p, J=7.3 Hz, 2H), 1.76-1.58 (m, 13H), 1.58-1.20 (m, 30H), 1.16 (tq, J=10.9, 3.3 Hz, 1H), 0.90 (dd, J=14.8, 6.7 Hz, 16H).

Example 28. LIPID 28: ((4,4'-((((3-(Dimethylamino)propyl)thio)carbonyl)azanediyl)bis(butanoyl))bis(oxy)bis(propane-2,1,3-triyl) tetrakis(octahydro-1H-indene)
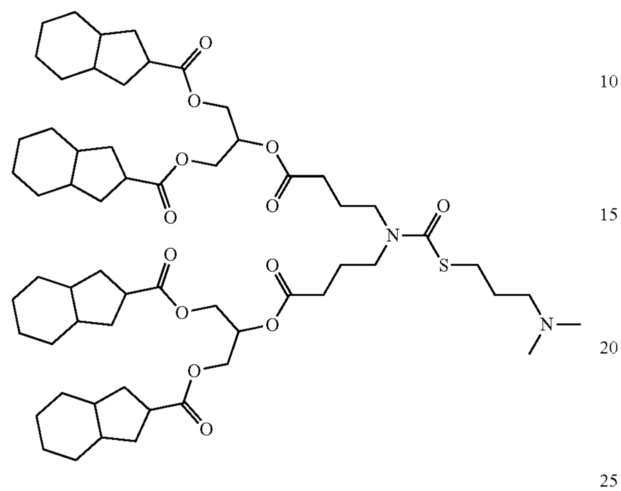
LIPID 28
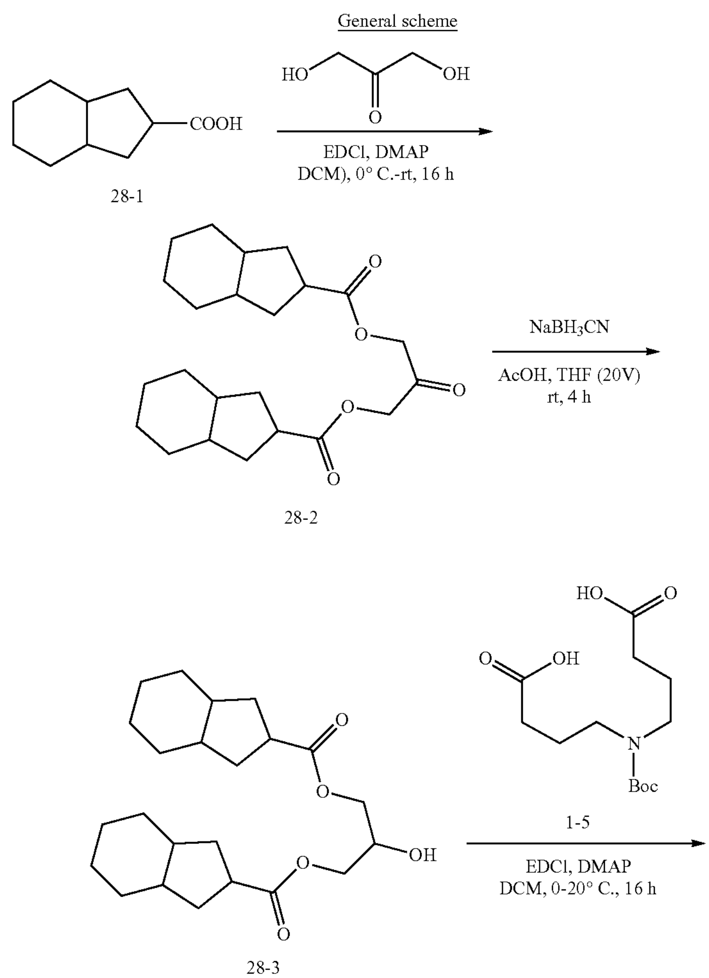

-continued
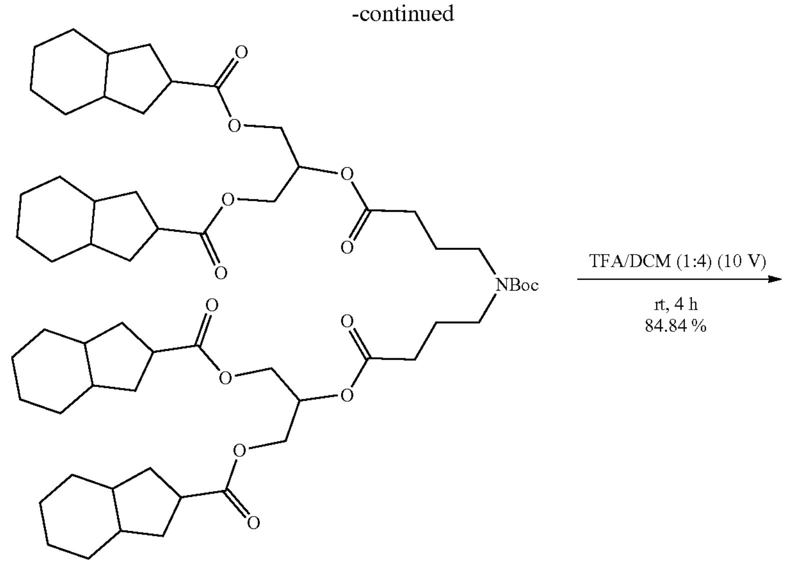
28-4
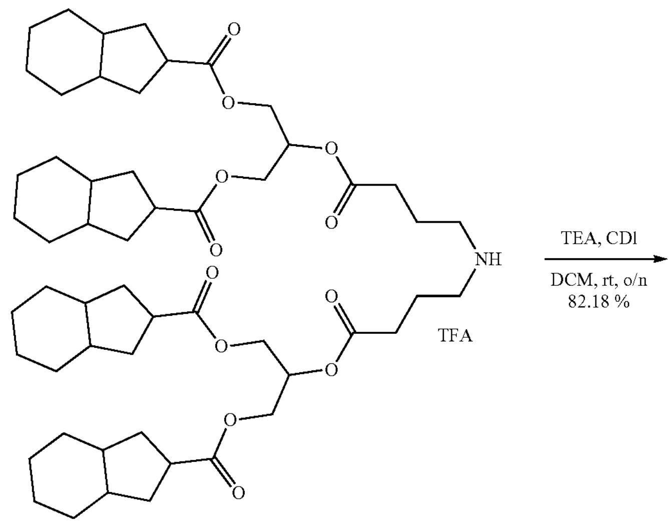
28-5
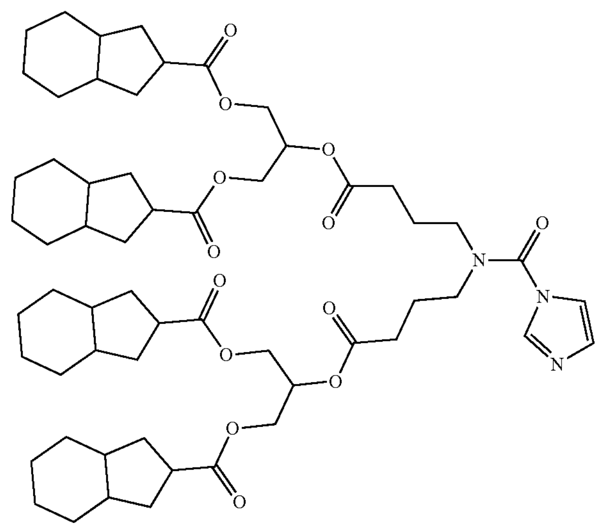
28-6

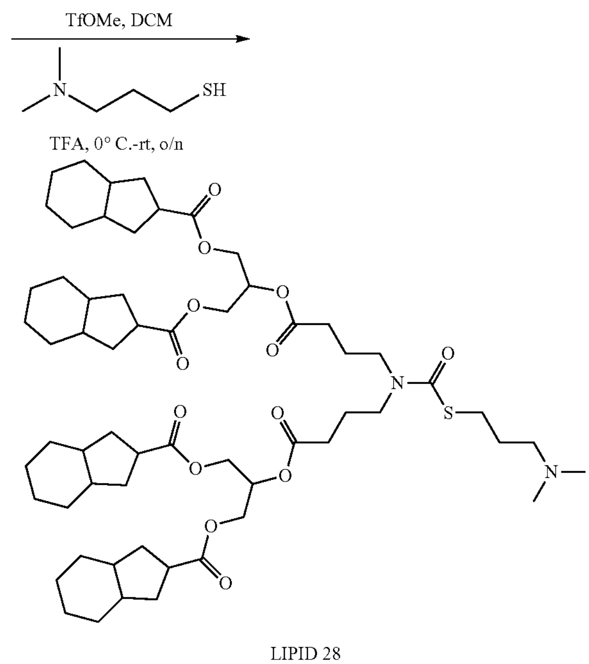

LIPID 28

Synthesis of 28-2:2-oxopropane-1,3-diyl bis(octahydro-1H-indene-2-carboxylate)

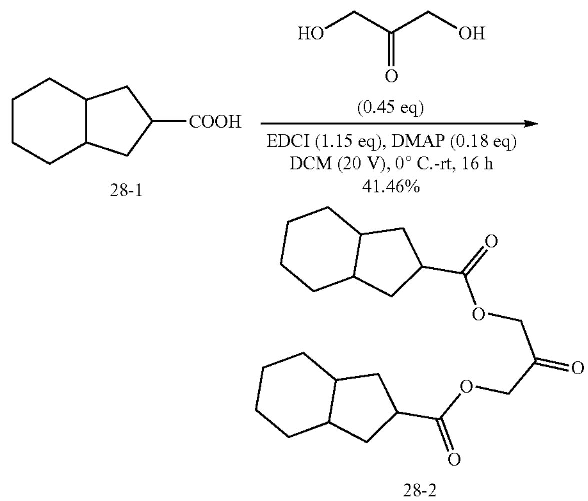

28-1

28-2

To 1.6 L (20V) of DCM in a 3 L 3-necked round-bottle flask was added 28-1 (80.00 g, 475.5 mmol, 1.00 equiv.), dihydroxyacetone (19.28 g, 214.0 mmol, 0.45 equiv.), DMAP (10.46 g, 85.6 mmol, 0.18 equiv.) and EDCI (84.90 g, 546.8 mmol, 1.15 equiv.) at 0° C. The reaction mixture was stirred for 16 h at room temperature. The resulting mixture was diluted with brine (1.6 L, 20 V). The organic solvent was removed under reduced pressure. The residual solution was extracted with ethyl acetate (2×1.6 L, 40 V). The combined organic layers were washed with brine (1.6 L, 20 V), dried over anhydrous $Na_2SO_4$, and then filtered. Crude product was adsorbed on 160 g of silica gel (type: ZCX-2, 100-200 mesh, 1.40 w./w.) and purified on a silica gel column (1.6 Kg of silica gel type: ZCX-2, 100-200 mesh, 10.00 w./w.) using petroleum ether/ethyl acetate (v/v) gradient from 100:0 to 90:10). Fractions were analyzed (TLC, heptane:EA=7:1), combined, concentrated, and dried under vacuum to get 28-2 (77 g, 0.197 mmol, 41.5%) as light yellow oil that was used in the next reaction.

Synthesis of 28-3:2-hydroxypropane-1,3-diyl bis(octahydro-1H-indene-2-carboxylate)

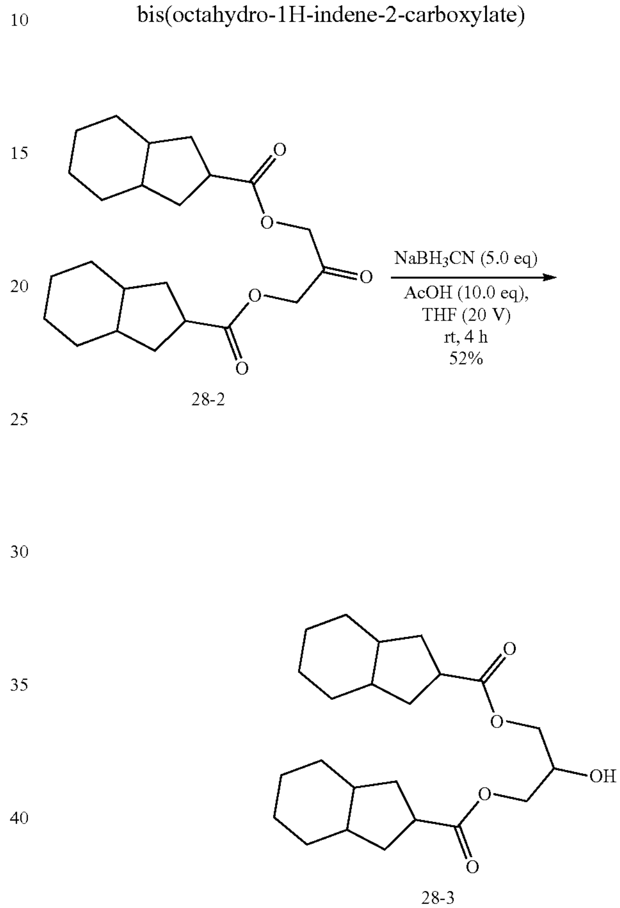

28-2

28-3

To a 3 L three-necked round-bottom flask were added 28-2 (75 g, 0.19 mol, 1.00 equiv.), THF (1.50 L, 20 V) and AcOH (115.3 g, 1.92 mmol, 10.0 equiv.) at room temperature. Then, $NaBH_3CN$ (60.34 g, 0.96 mol, 5.0 equiv.) was added to the above mixture at 0° C. in several portions. The reaction mixture was stirred for 4 h at room temperature. The reaction system was quenched with the addition of water (1.50 L, 20 V) at room temperature. The mixture was extracted with ethyl acetate (2×1.50 L, 40 V). The combined organic layers were washed with brine (1.5 L, 20 V), dried with anhydrous $Na_2SO_4$, and then filtered. Crude product was adsorbed on 150 g of silica gel (type: ZCX-2, 100-200 mesh, 1.40 w./w.) and purified on a silica gel column (1.2 Kg of silica gel type: ZCX-2, 100-200 mesh, 10.00 w./w.) using petroleum ether/ethyl acetate (v/v) gradient from 100:0 to 87:13). Fractions were analyzed (TLC, PE:EA=5:1), combined, concentrated, and dried under vacuum to get 28-3 (55 g, 0.14 mmol, 52%) as light yellow oil that was used in the next reaction. ELSD A: water/0.05% ammonia: B: $CH_3CN$ 95:5 to 5:95 A/B at 3 min.): RT 2.2 min, m/z (Calcd.) 392.3, (found) 375.2 (M-OH).

Synthesis of 28-4: ((4,4'-((tert-butoxycarbonyl)azanediyl)bis(butanoyl))bis(oxy))bis(propane-2,1,3-triyl) tetrakis(octahydro-1H-indene-2-carboxylate)

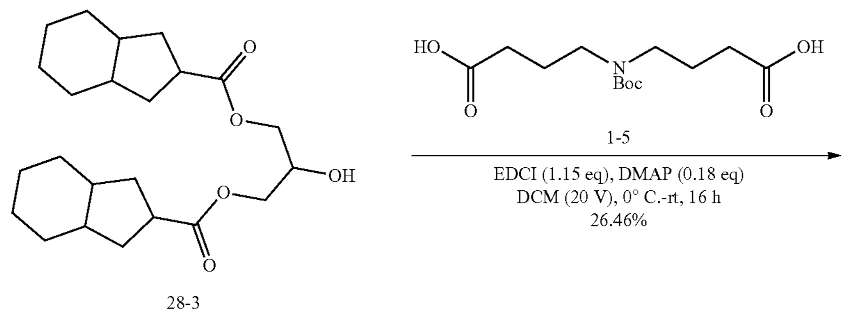

28-3

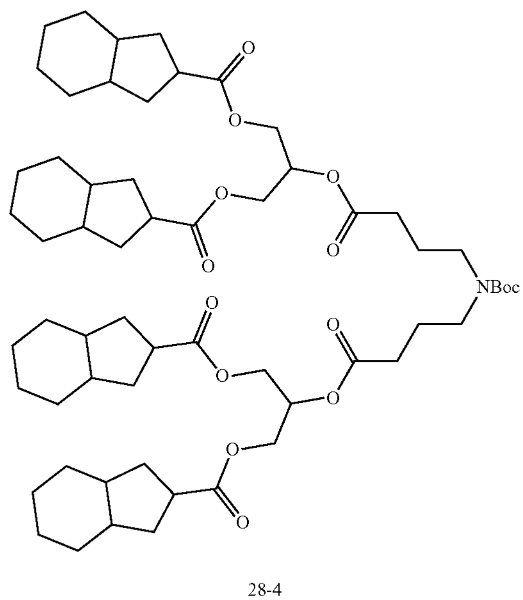

28-4

To a 2 L three-necked round-bottle flask was added 28-3 (40 g, 101.9 mmol, 1.00 equiv.), 28-5 (13.27 g, 45.85 mmol, 0.45 equiv.), DCM (0.8 L, 20 V), DMAP (2.24 g, 18.34 mmol, 0.18 equiv.). Then, EDCI (18.19 g, 117.2 mmol, 1.15 equiv.) was added to the above mixture at 0° C. in several portions. The reaction mixture was stirred for 16 h at room temperature. The reaction was monitored by LCMS. The resulting mixture was diluted with brine (0.8 L, 20 V). The mixture was extracted with ethyl acetate (2×0.8 L, 40V). The combined organic layers were washed with brine (0.8 L, 20V). The organic phase was dried with anhydrous $Na_2SO_4$ and then filtered. Crude product was adsorbed on 80 g of silica gel (type: ZCX-2, 100-200 mesh, 1.40 w./w.) and purified on a silica gel column (800 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=5:1), combined, concentrated, and dried under vacuum to get 28-4 (28 g, 0.027 mmol, 26.5%) as light yellow oil that was used in the next reaction.

Synthesis of 28-5: ((4,4'-azanediylbis(butanoyl))bis(oxy))bis(propane-2,1,3-triyl) tetrakis(octahydro-1H-indene-2-carboxylate) trifluoroacetic acid salt

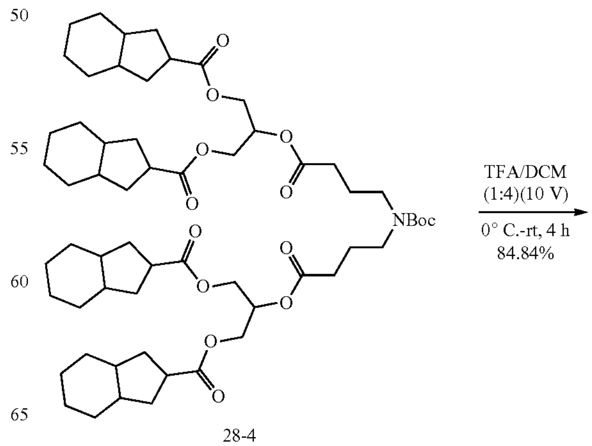

28-4

-continued

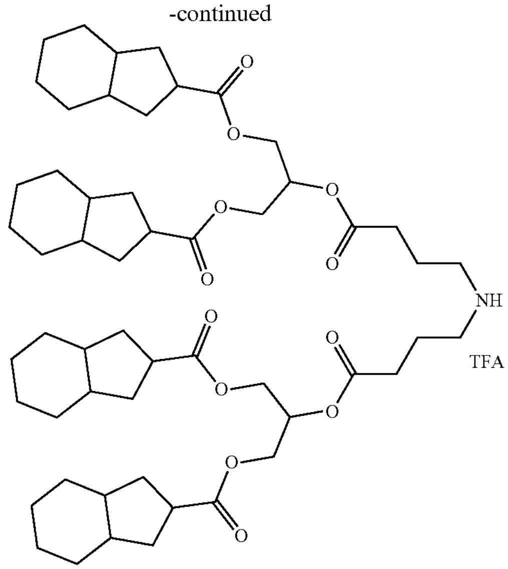

28-5

To a 500 mL round-bottle flask was added 28-4 (27 g, 26.00 mmol, 1.00 equiv.) in DCM (108 mL, 4 V) at room temperature. The solution was cooled to 0° C. in an ice/water bath. To this solution was added TFA (13.5 g, 0.5 V) at 0° C. The ice/water bath was removed, and the mixture was stirred for 4 h at room temperature. The reaction was monitored by LCMS. The reaction was concentrated and dried under vacuum to get 28-5 as its trifluoroacetic acid salt (22 g, 0.021 mmol, 84.8%) as a light brown oil that was used without further purification. ELSD A: water/0.05% TFA: B: $CH_3CN$ 95:5 to 5:95 A/B at 3 min.): RT 2.0 min, m/z (Calcd.) 937.7, (found) 938.8 (M+H).

Synthesis of 28-6: ((4,4'-((1H-imidazole-1-carbonyl)azanediyl)bis(butanoyl))bis(oxy))bis(propane-2,1,3-triyl) tetrakis(octahydro-1H-indene-2-carboxylate)

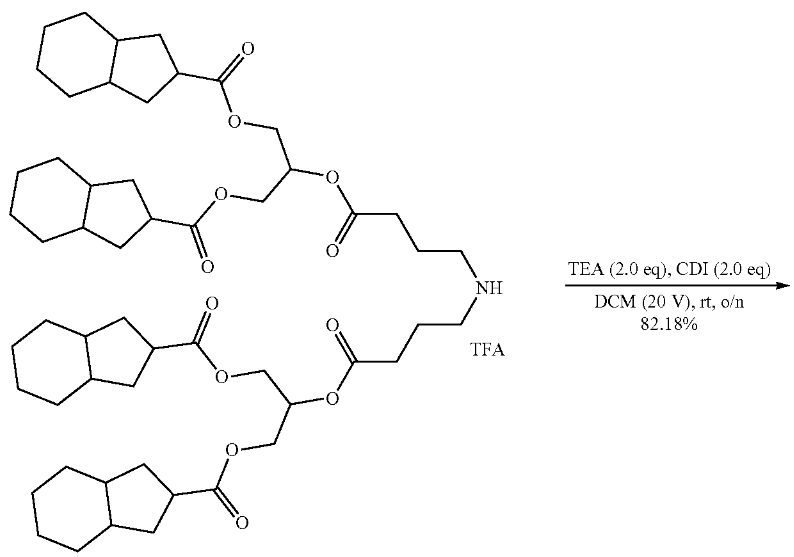

28-5

-continued

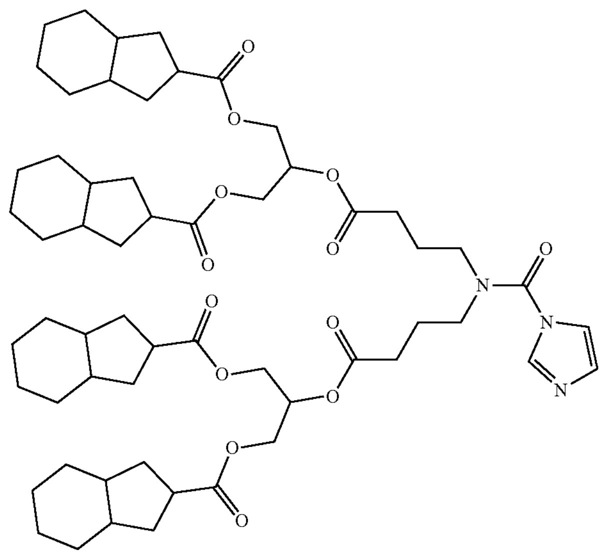

28-6

Into a 2 L 3-necked round-bottom flask purged and maintained with an inert atmosphere of nitrogen, was placed a solution of 28-5 (22 g, 21.23 mmol, 1.00 equiv.) in DCM (440 mL). To this solution was added the TEA (4.30 g, 42.46 mmol, 2.00 equiv.) followed by CDI (6.88 g, 42.46 mmol, 2.00 equiv.) at room temperature. The mixture was stirred overnight at room temperature, LCMS showed the reaction was completed. The resulting mixture was diluted with water (400 mL). The mixture was extracted with $CH_2Cl_2$ (2×200 mL). The combined organic layers were washed with brine (400 mL), dried over anhydrous $Na_2SO_4$. After filtration, the filtrate was concentrated under reduced pressure. This resulted in 28-6 (18 g, 0.017 mmol, 82.18%) as a brown oil which was used in the next step as such. ELSD A: water/0.05% TFA: B: $CH_3CN$ 95:5 to 5:95 A/B at 3 min.): RT 2.2 min, m/z (Calcd.) 1031.7, (found) 1032.8 (M+H).

Synthesis of LIPID 28: ((4,4'-((((3-(Dimethylamino)propyl)thio)carbonyl) azanediyl)bis(butanoyl))bis(oxy)bis(propane-2,1,3-triyl) tetrakis(octahydro-1H-indene)

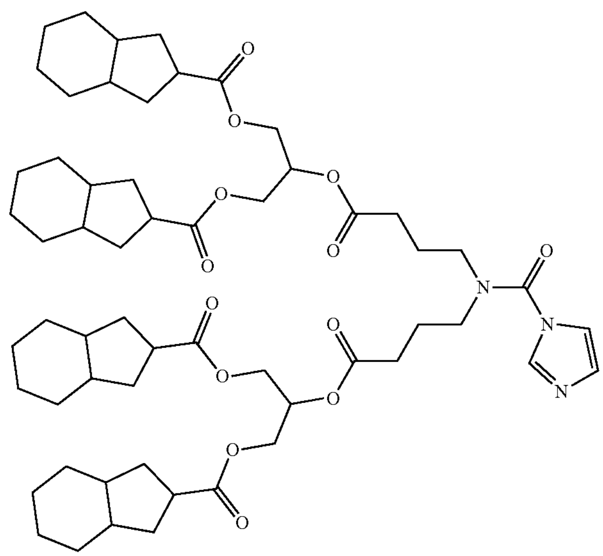

28-6

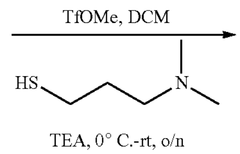

-continued

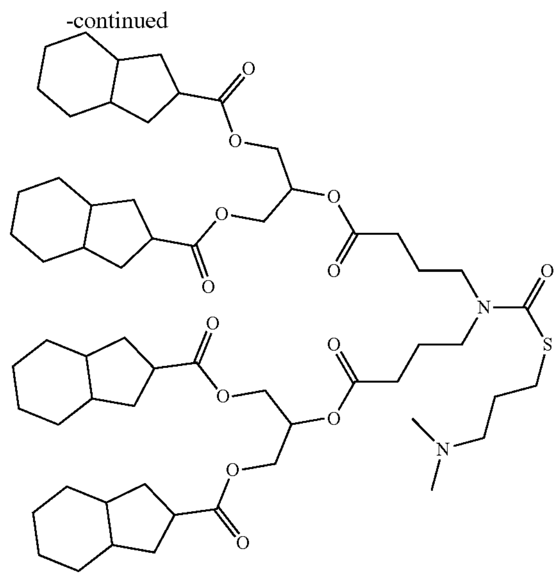

LIPID 28

Into a 1 L 3-necked round-bottom flask purged and maintained with an inert atmosphere of nitrogen, was placed a solution of 28-6 (15 g, 14.53 mmol, 1.00 equiv.) in DCM (300 mL, 20V). The solution was cooled to 0° C. in an ice/water bath. Then, TfOMe (2.62 g, 15.98 mmol, 1.10 equiv.) was added and the mixture was stirred at 0° C. for 1 hour. LCMS showed complete consumption of 28-6. Then, TEA (2.94 g, 29.06 mmol, 2.00 equiv.) and 3-(dimethylamino)propane-1-thiol (2.08 g, 17.43 mmol, 1.20 equiv.) were added to the solution. The ice/water bath was removed, and the mixture was stirred overnight at room temperature. The reaction was monitored by LCMS. The resulting mixture was concentrated under reduced pressure. The residue was diluted with water (300 mL, 20 V) and extracted with ethyl acetate (2×300 mL, 40 V). The combined organic layers were washed with brine (300 mL), dried over anhydrous $Na_2SO_4$. After filtration, the filtrate was concentrated under reduced pressure. The residue was purified by reverse flash chromatography with the following conditions: Welch Ultimate XB-Phenyl 50 mm*250 mm 10 um; mobile phase, (0.1% FA) water and $CH_3CN$; 50-90% in 15 min and hold 8 min; flow rate: 90 ml/min; UV 220 nm This resulted in LIPID 28 (3.2302 g, 20.52%) as a light-yellow oil. ELSD A: water/0.05% TFA: B: $CH_3CN$ 95:5 to 5:95 A/B at 25 min.): RT 10.0 min, m/z (Calcd.) 1082.6, (found) 1083.7 (M+H). 1H-NMR-LIPID 28: (400 MHZ, $CDCl_3$, ppm): δ 5.29-5.26 (m, 2H), 4.34-4.29 (m, 4H), 4.18-4.13 (m, 5H), 3.69-3.67 (m, 1H), 3.38 (s, 4H), 2.97-2.82 (m, 7H), 2.38-2.34 (m, 6H), 2.24 (s, 6H), 2.11-1.99 (m, 4H), 1.97-1.84 (m, 18H), 1.83-1.75 (m, 12H), 1.56-1.15 (m, 34H), 1.09-0.91 (m, 1H).

Example 29. LIPID 30: ((4,4'-((((3-(dimethylamino)propyl)thio)carbonyl)azanediyl)bis(butanoyl))bis(oxy))bis(propane-2,1,3-triyl) tetrakis(octahydro-1H-indene-5-carboxylate)

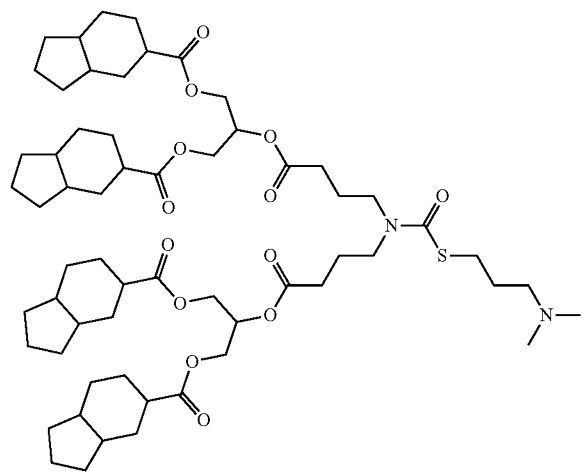 [SMILES: CN(C)CCCSC(=O)N(CCCC(=O)OC(COC(=O)C1CCC2CCCC2C1)COC(=O)C1CCC2CCCC2C1)CCCC(=O)OC(COC(=O)C1CCC2CCCC2C1)COC(=O)C1CCC2CCCC2C1]

LIPID 30

General Scheme

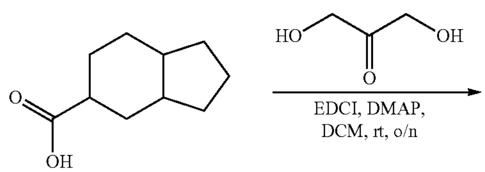

30-1

-continued
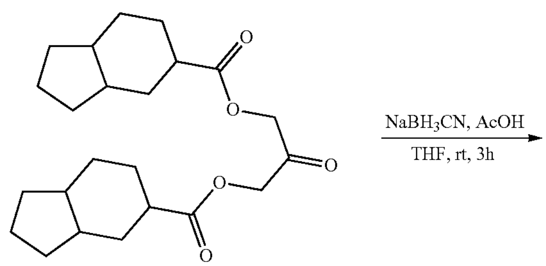
30-2
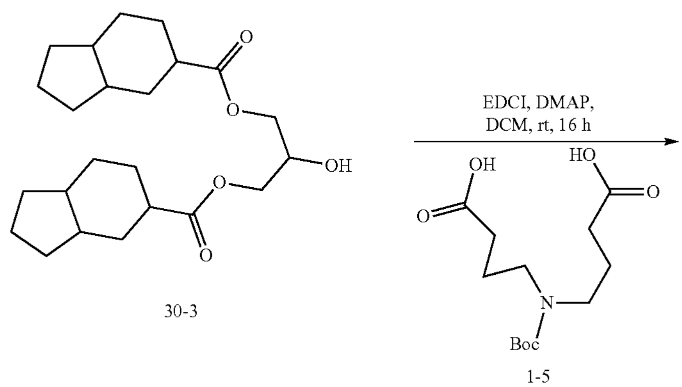
30-3
1-5
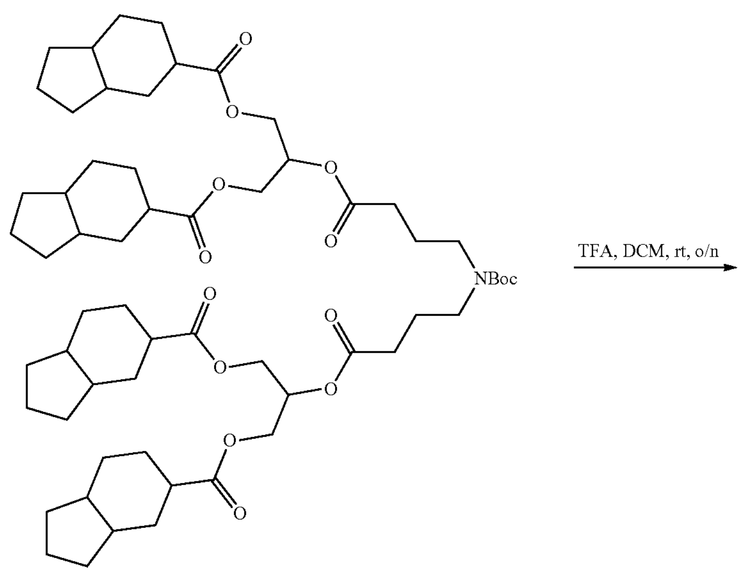
30-4

-continued
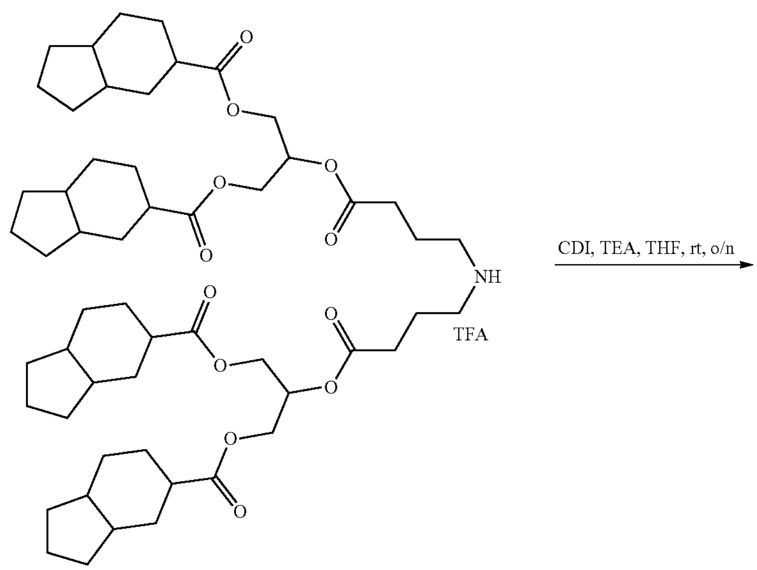
30-5
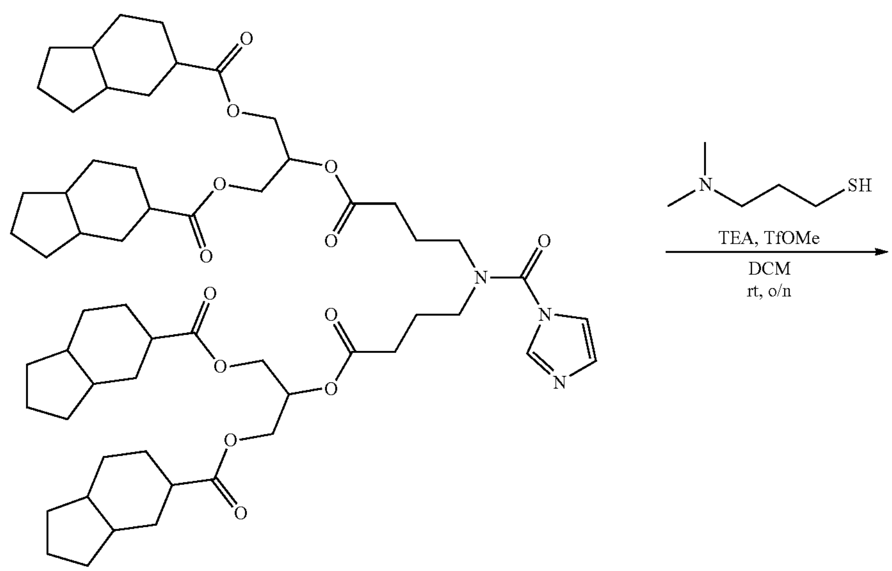
30-6

-continued

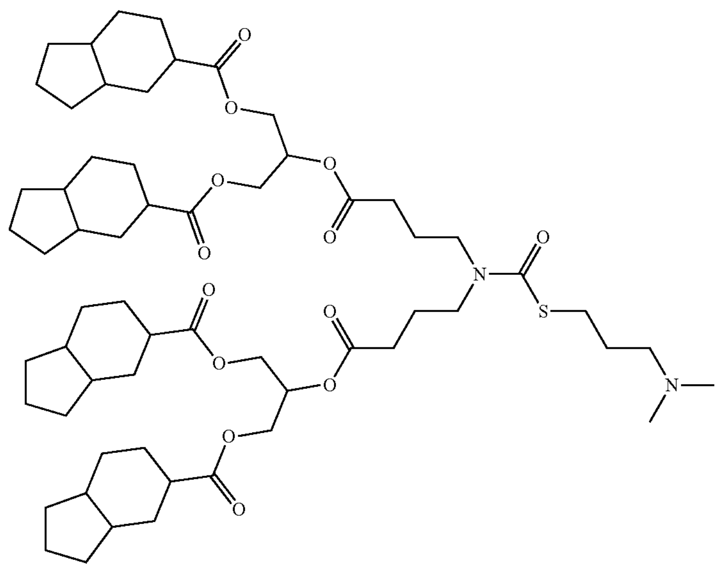

LIPID 30

Synthesis of 30-2:2-oxopropane-1,3-diyl bis(octahydro-1H-indene-5-carboxylate)

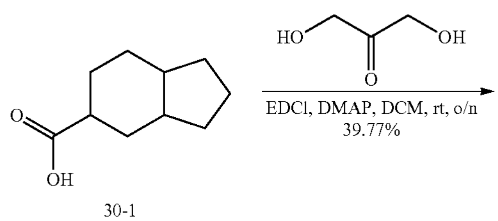

30-1

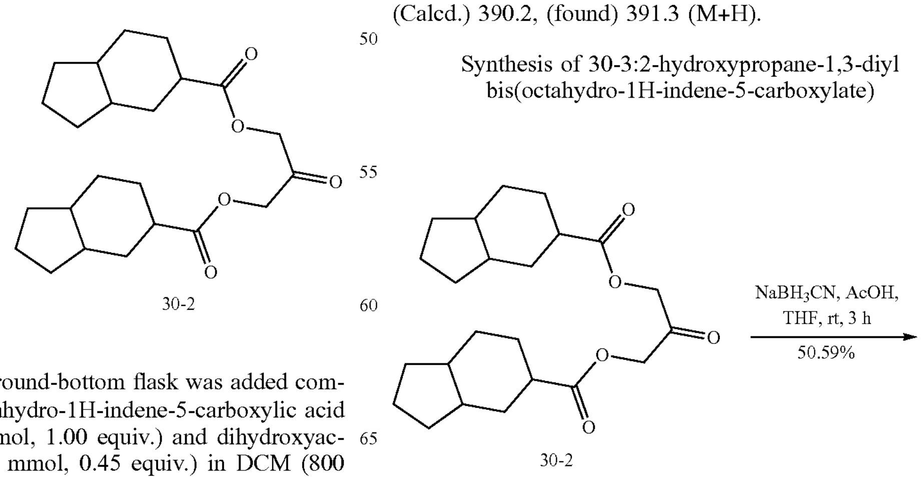

30-2

Into a 2 L 4-necked round-bottom flask was added commercially available octahydro-1H-indene-5-carboxylic acid (30-1, 65 g, 386.36 mmol, 1.00 equiv.) and dihydroxyacetone (15.66 g, 173.86 mmol, 0.45 equiv.) in DCM (800 mL). DMAP (9.44 g, 77.27 mmol, 0.20 equiv.) and EDC·HCl (88.88 g, 463.63 mmol, 1.20 equiv.) were added in portions at room temperature. The resulting mixture was stirred for overnight at room temperature and concentrated under vacuum. Crude product was adsorbed on 120 g of silica gel (type: ZCX-2, 100-200 mesh, 1.40 w./w.) and purified on a silica gel column (600 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=20:1), combined, concentrated, and dried under vacuum to get 30-2 (60 g, 0.15 mmol, 40%) as a colorless oil. ELSD A: water/0.05% TFA: B: $CH_3CN$ 95:5 to 5:95 A/B at 3 min.): RT 2.2 min, m/z (Calcd.) 390.2, (found) 391.3 (M+H).

Synthesis of 30-3:2-hydroxypropane-1,3-diyl bis(octahydro-1H-indene-5-carboxylate)

30-2

-continued

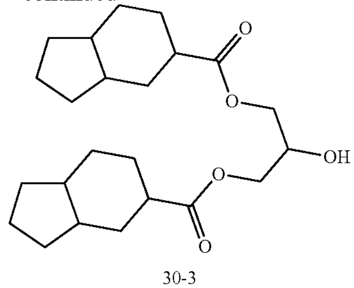

30-3

Into a 1000 mL 3-necked round-bottom flask was added 30-2 (59 g, 151.08 mmol, 1.00 equiv.) and AcOH (90.73 g, 1510.81 mmol, 10 equiv.) in THF (600 mL). $NaBH_3CN$ (47.47 g, 755.40 mmol, 5.00 equiv.) was added in portions at room temperature and the mixture was stirred for 3 h. pH of the mixture was brought to 9 with saturated $NaHCO_3$ (aq.). The resulting mixture was extracted with EtOAc (2×500 mL). The combined organic layers were collected and dried over anhydrous $Na_2SO_4$. After filtration, the filtrate was concentrated under reduced pressure. Crude product was adsorbed on 120 g of silica gel (type: ZCX-2, 100-200 mesh, 1.40 w./w.) and purified on a silica gel column (600 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=20:1), combined, concentrated, and dried under vacuum to get 30-3 (30 g, 0.076 mmol, 50.6%) as a colorless oil. ELSD A: water/0.02% TFA: B: $CH_3CN$ 95:5 to 5:95 A/B at 3 min.): RT 2.1 min, m/z (Calcd.) 392.2, (found) 375.3 (M-OH).

Synthesis of 30-4: ((4,4'-((tert-butoxycarbonyl) azanediyl)bis(butanoyl))bis(oxy))bis(propane-2,1,3-triyl) tetrakis(octahydro-1H-indene-5-carboxylate)

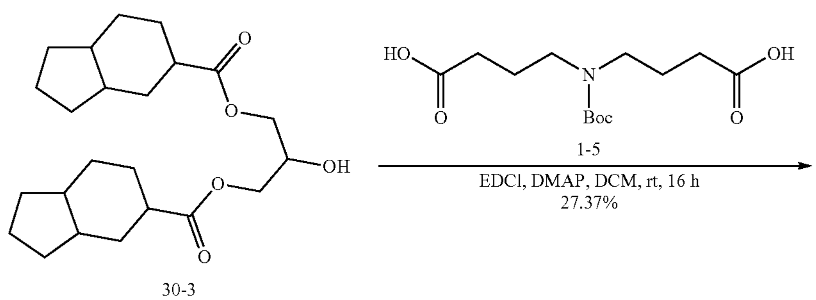

30-3

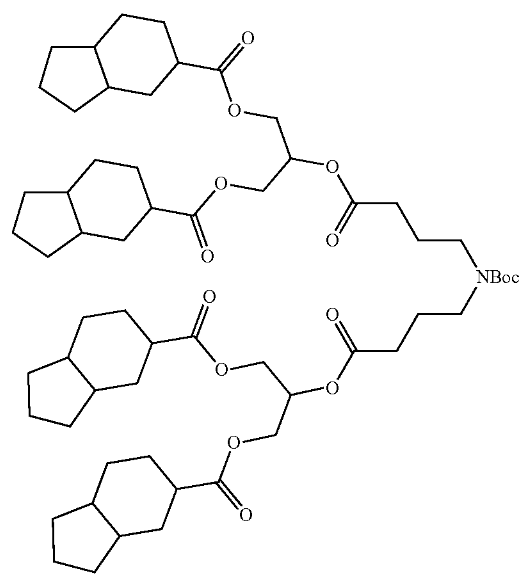

30-4

To a 1000 mL three-necked round-bottle flask was added 30-3 (29 g, 73.87 mmol, 1.00 equiv.) and 1-5 (9.62 g, 33.24 mmol, 0.45 equiv.) in DCM (600 mL). DMAP (1.81 g, 14.77 mmol, 0.20 equiv.) and EDC·HCl (13.76 g, 88.65 mmol, 1.20 equiv.) were added in portions at room temperature. The resulting mixture was stirred for 16 h at room temperature. The resulting mixture was concentrated under vacuum. Crude product was adsorbed on 60 g of silica gel (type: ZCX-2, 100-200 mesh, 1.40 w/w) and purified on a silica gel column (400 g of silica gel type: ZCX-2, 100-200 mesh, 10.00 w/w) using petroleum ether/ethyl acetate (v/v) gradient from 100:0 to 90:10). Fractions were analyzed (TLC, PE:EA=20:1), combined, concentrated, and dried under vacuum to get 30-4 (21 g, 0.02 mmol, 27.4%) as a colorless oil which was directly used in the next step.

Synthesis of ((4,4'-azanediylbis(butanoyl))bis(oxy))bis(propane-2,1,3-triyl) tetrakis(octahydro-1H-indene-5-carboxylate) trifluoroacetic Acid Salt

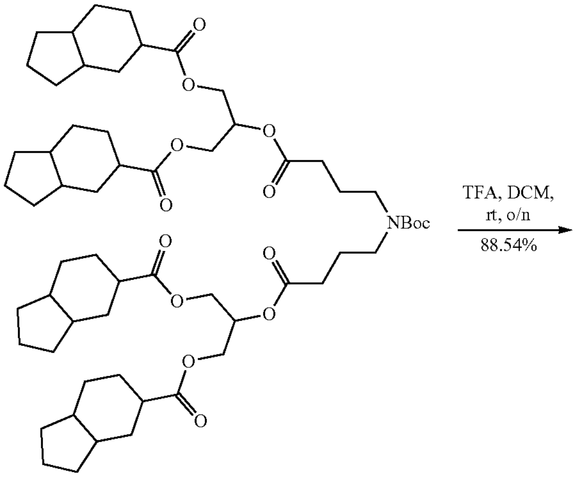

30-4

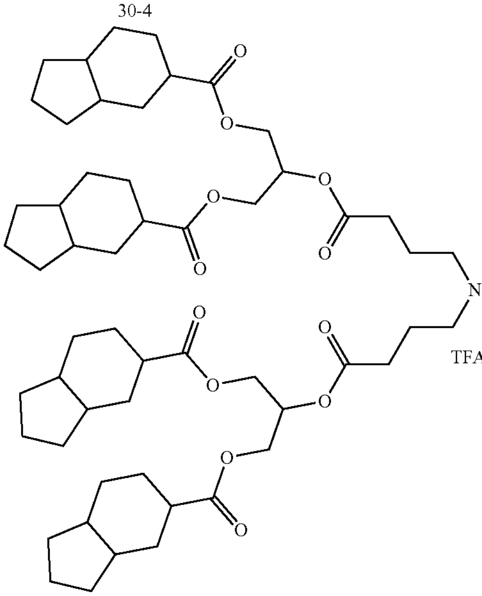

30-5

To a 1 L three-necked round-bottle flask was added 30-4 (20 g, 19.26 mmol, 1.00 equiv.) in DCM (80 mL) followed by TFA (10 mL, 134.63 mmol, 6.99 equiv.) drop-wise at room temperature. The resulting mixture was stirred overnight at room temperature and concentrated and dried under reduced pressure. This resulted in 30-5 as its trifluoroacetic acid salt (16 g, 0.015 mmol, 88.5%) as a light-yellow oil. ELSD A: water/0.02% TFA: B: $CH_3CN$ 95:5 to 5:95 A/B at 3 min.): RT 2.0 min, m/z (Calcd.) 937.6, (found) 938.7 (M+H).

Synthesis of ((4,4'-((1H-imidazole-1-carbonyl)azanediyl)bis(butanoyl))bis(oxy))bis(propane-2,1,3-triyl) tetrakis(octahydro-1H-indene-5-carboxylate)

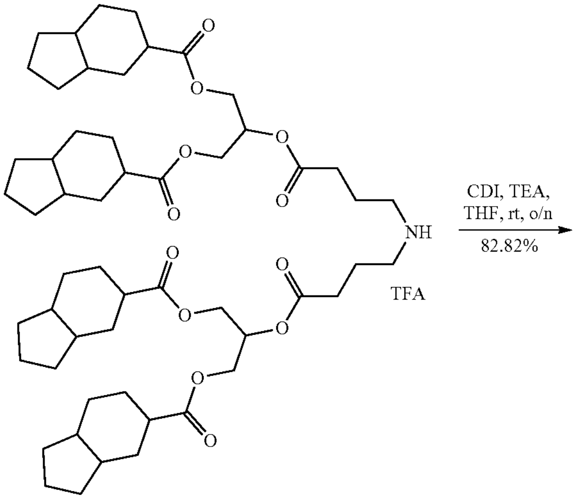

30-5

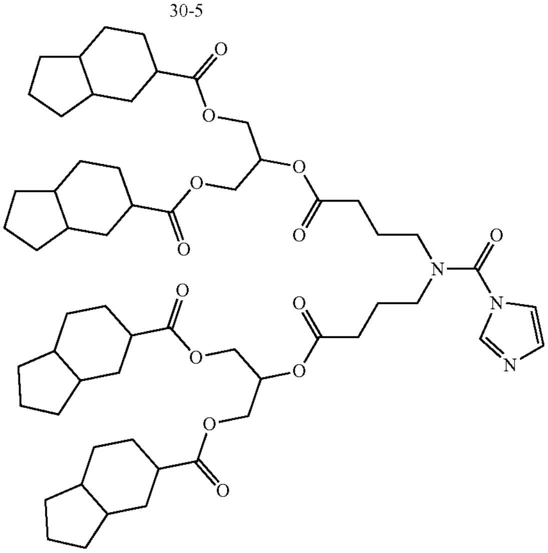

30-6

To a 500 mL three-necked round-bottle flask was added 30-5 (16 g, 17.05 mmol, 1.00 equiv.) and CDI (2.96 g, 18.24 mmol, 1.20 equiv.), TEA (3.08 g, 30.43 mmol, 2.00 equiv.) in THF (320 mL). The resulting mixture was stirred overnight at room temperature and concentrated under vacuum. To this was added water (500 mL), extracted with EtOAc (2×500 mL), combined organic layer was dried over anhydrous $Na_2SO_4$ and filtered. The filtrate was concentrated under reduced pressure to afford 30-6 (13 g, 0.012 mmol, 82.82%) as a light-yellow oil which was immediately used in the next step. ELSD A: water/0.02% TFA: B: $CH_3CN$ 95:5 to 5:95 A/B at 3 min.): RT 2.1 min, m/z (Calcd.) 1031.6, (found) 1032.7 (M+H).

Synthesis of LIPID 30: ((4,4'-((((3-(dimethylamino)propyl)thio)carbonyl) azanediyl)bis(butanoyl))bis(oxy))bis(propane-2,1,3-triyl) tetrakis(octahydro-1H-indene-5-carboxylate)

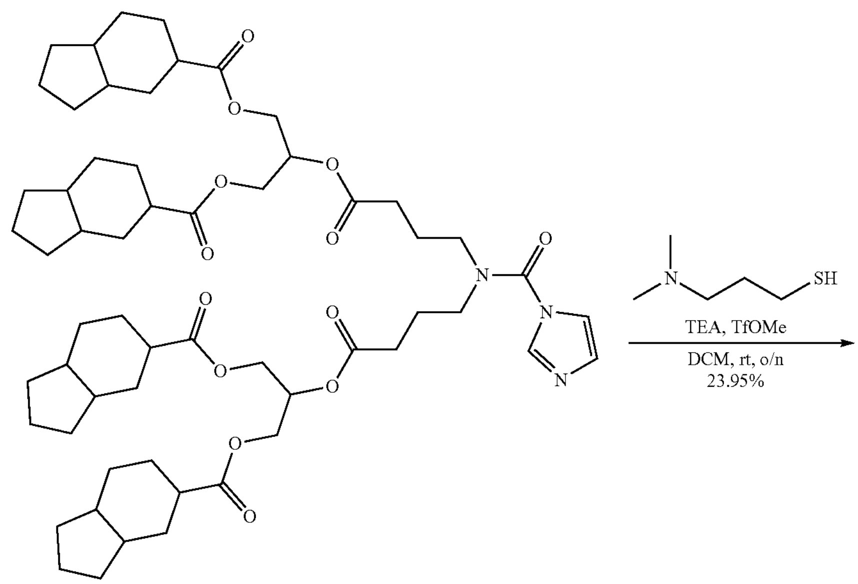

30-6

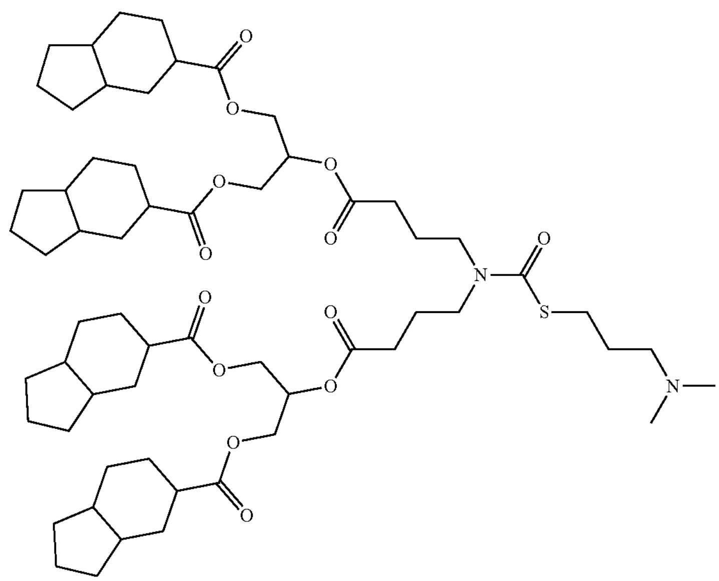

LIPID 30

To a 250 mL three-necked round-bottle flask was added 30-6 (13 g, 12.59 mmol, 1.00 equiv.) in DCM (320 mL). Methyl trifluoromethanesulfonate (2.27 g, 13.85 mmol, 1.10 equiv.) was added dropwise in portions at 0° C., after 1 h, TEA (2.55 g, 25.18 mmol, 2.00 equiv.) was added drop-wise followed by 3-(dimethylamino)propane-1-thiol (1.65 g, 13.85 mmol, 1.10 equiv.). The resulting mixture was stirred for overnight at room temperature and concentrated under vacuum. The residue was purified by reverse flash chromatography with the following conditions: column, C18 silica gel; mobile phase, acetonitrile in Water (0.1% TFA), 50% to 90% gradient in 20 min; detector, UV 224 nm. This resulted in LIPID 30 (3.2678 g, 24%) as a light-yellow oil. ELSD A: water/0.02% TFA: B: $CH_3CN$ 95:5 to 5:95 A/B at 25 min.): RT 10.2 min, m/z (Calcd.) 1082.6, (found) 1083.8 (M+H).

$^1H$ NMR (400 MHz, $CDCl_3$, ppm): δ 5.27 (p, J=5.3 Hz, 2H), 4.41-4.12 (m Hz, 4H), 4.24-4.06 (m, 5H), 3.44 (d, J=36.6 Hz, 4H), 2.93 (t, J=7.3 Hz, 2H), 2.61-2.18 (m, 17H), 2.16-1.80 (m, 20H), 1.80-1.4 (m, 39H), 1.42-1.40 (m, 6H), 1.31-1.0 (m, 6H).

Example 30. Synthesis of LIPID 32: ((4,4'-(((3-(dimethylamino) propoxy)carbonyl)azanediyl)bis(butanoyl))bis(oxy))bis(propane-2,1,3-triyl) tetranonanoate
LIPID 32
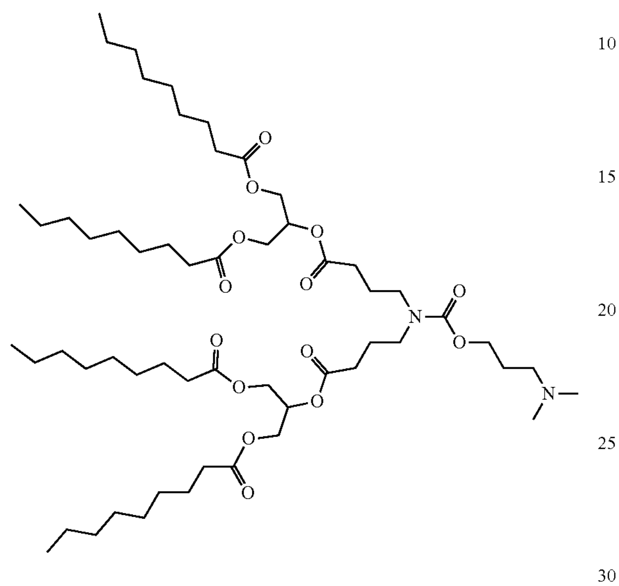
The following method is contemplated.
General Scheme
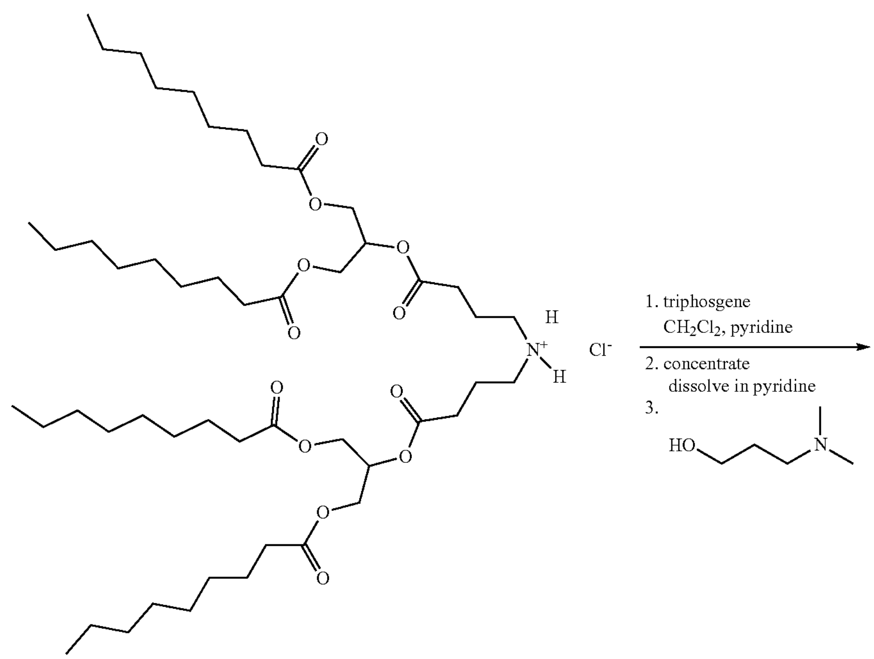
1-7

-continued

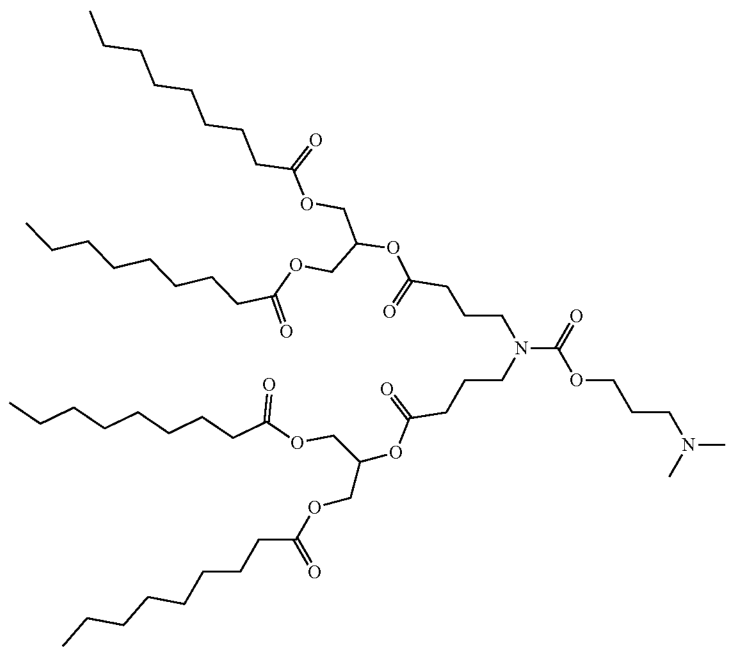

LIPID 32

Ammonium salt 1-7 (taken from the synthesis of LIPID 1) will be dissolved in $CH_2Cl_2$, cooled in an ice-water bath under nitrogen, and triphosgene will be added. After the addition of the triphosgene, pyridine will be added and the mixture will be stirred for 4 hours, then the solvent will be removed in vacuo and the residue will be dissolved in pyridine and cooled in an ice-water bath under nitrogen. To this cooled solution 3-dimethylamino-1-propanol will be added and the solution should be stirred for 30 minutes after the addition is made and then will be warmed to room temperature and will be allowed to stir for 14 hours. The mixture will then be concentrated in vacuo and the residue will be dissolved in $CH_2Cl_2$, adsorbed on silica gel, and purified by chromatography using a Combi-flash apparatus. Fractions containing the desired carbamate product will be concentrated in vacuo dissolved in n-heptane, treated with activated charcoal, filtered, washed with a mixture of methanol and water, dried, and concentrated in vacuo to afford the target LIPID 32, ((4,4'-(((3-(dimethylamino) propoxy)carbonyl)azanediyl)bis(butanoyl))bis(oxy))bis(propane-2,1,3-triyl) tetranonanoate.

Example 31. Synthesis of LIPID 33: ((4,4'-((3-(dimethylamino)propyl) carbamoyl)azanediyl)bis(butanoyl))bis(oxy))bis(propane-2,1,3-triyl) tetranonanoate

LIPID 33

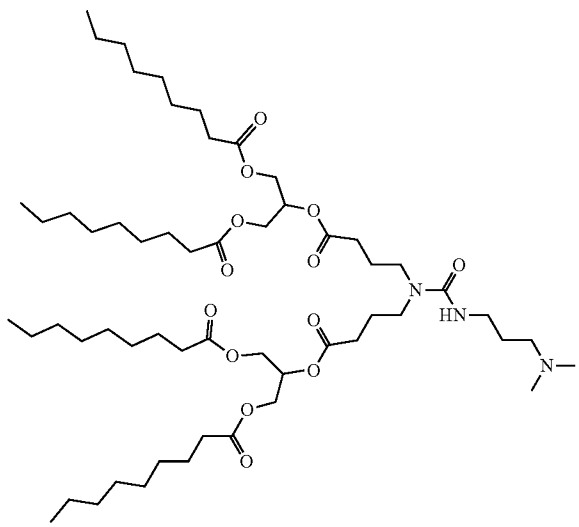

The following method is contemplated.
General Scheme
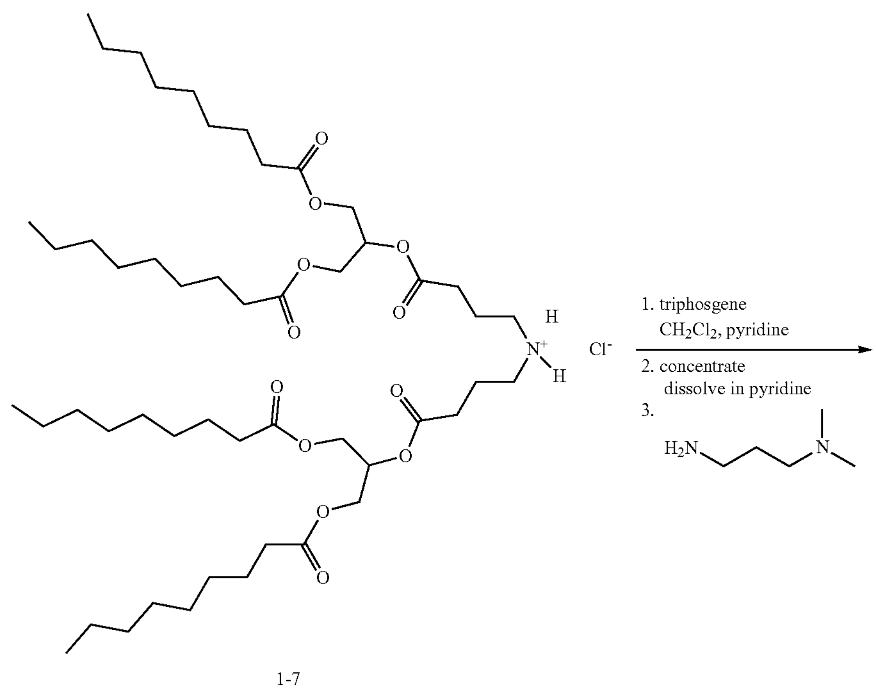
1-7
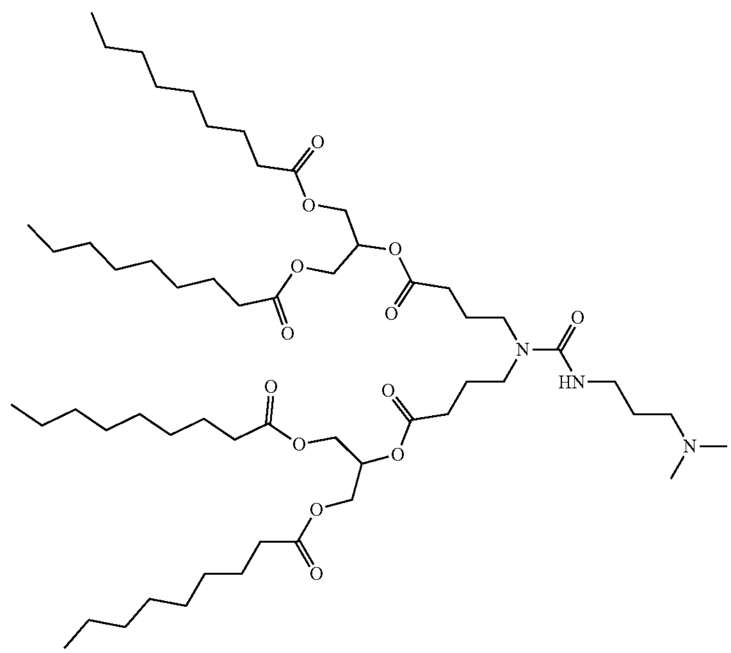
LIPID 33

Ammonium salt 1-7 (taken from the synthesis of LIPID 1) will be dissolved in $CH_2Cl_2$, cooled in an ice-water bath under nitrogen, and triphosgene will be added. After the addition of the triphosgene, pyridine will be added and the mixture will be stirred for 4 hours, then the solvent will be removed under in vacuo and the residue will be dissolved in pyridine and cooled in an ice-water bath under nitrogen. To this cooled solution 3-dimethylamino-1-aminopropane will be added and the solution will be stirred for 30 minutes after the addition is made and then will be warmed to room temperature and will be allowed to stir for 14 hours. The mixture will then be concentrated in vacuo and the residue will be dissolved in $CH_2Cl_2$, adsorbed on silica gel, and purified by chromatography using a Combi-flash apparatus. Fractions containing the desired urea product will be concentrated in vacuo dissolved in n-heptane, treated with activated charcoal, filtered, washed with a mixture of methanol and water, dried, and concentrated in vacuo to afford the target LIPID 33, ((4,4'-(((3-(dimethylamino)propyl) carbamoyl)azanediyl)bis(butanoyl))bis(oxy))bis(propane-2,1,3-triyl) tetranonanoate.

Example 32. Synthesis of LIPID 34: ((4,4'-((((3-(dimethylamino)propyl)thio)carbonyl)azanediyl)bis(butanoyl))bis(oxy))bis(propane-2,1,3-triyl) tetrakis(2-(p-tolyl)acetate)

LIPID 34

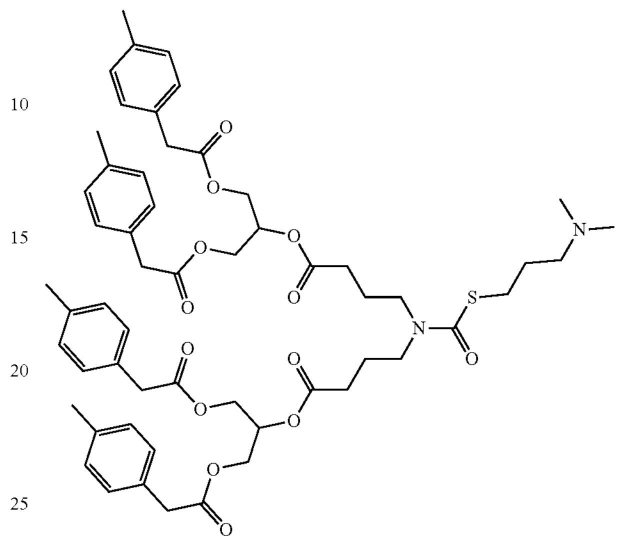

The following method is contemplated.

General Scheme

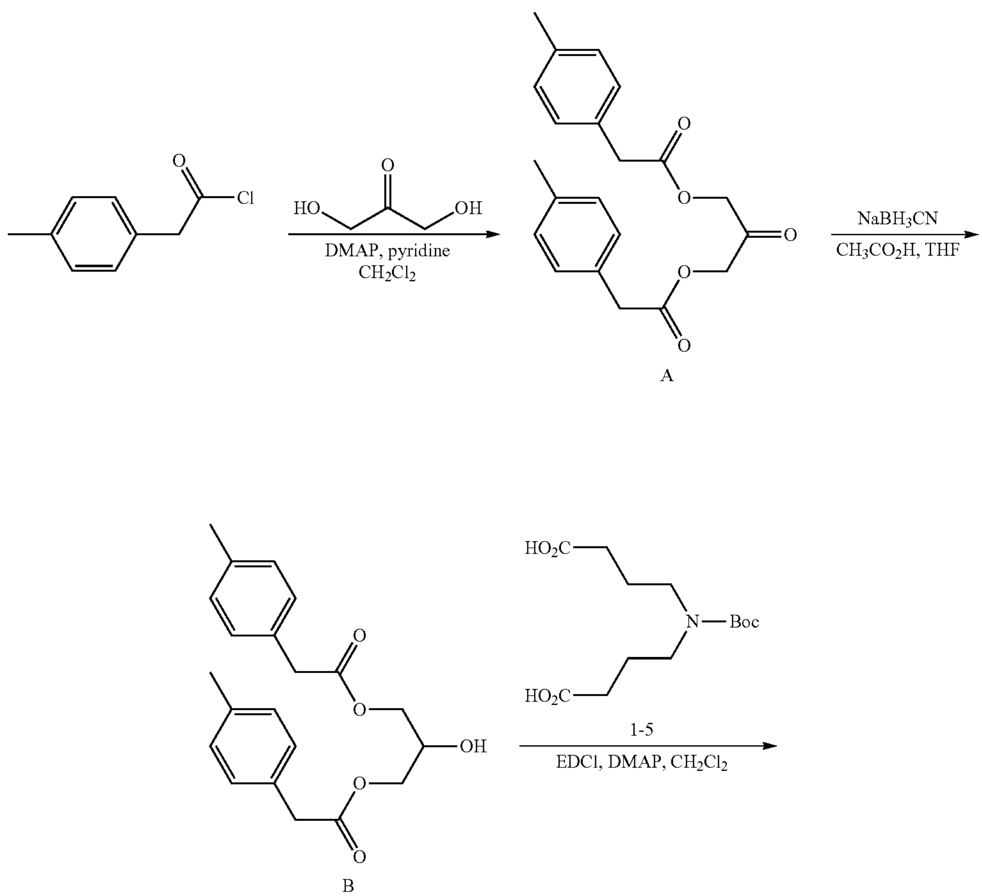

-continued
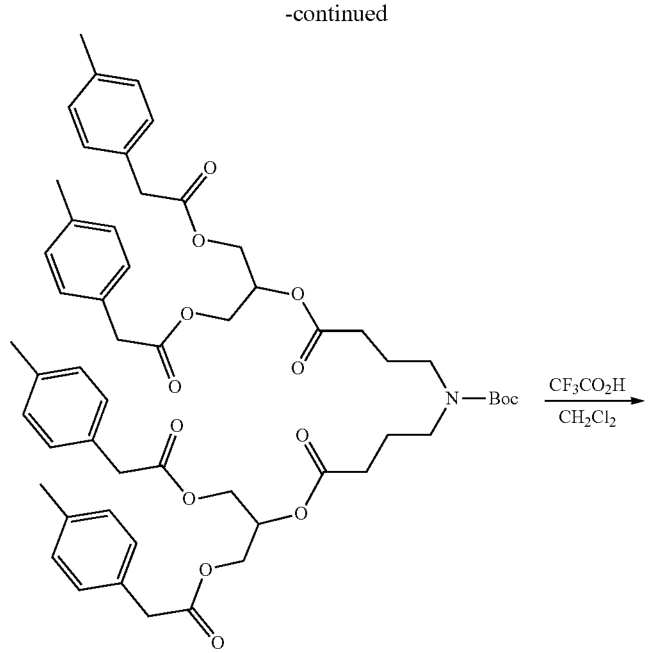
C
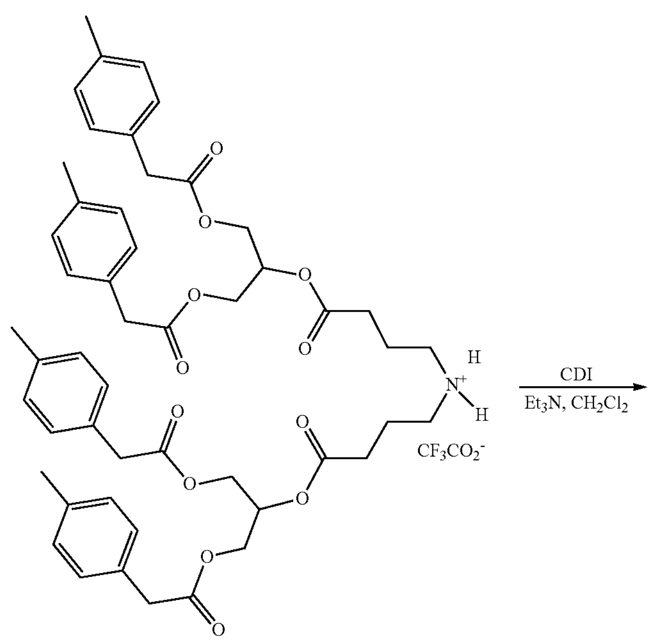
D

-continued
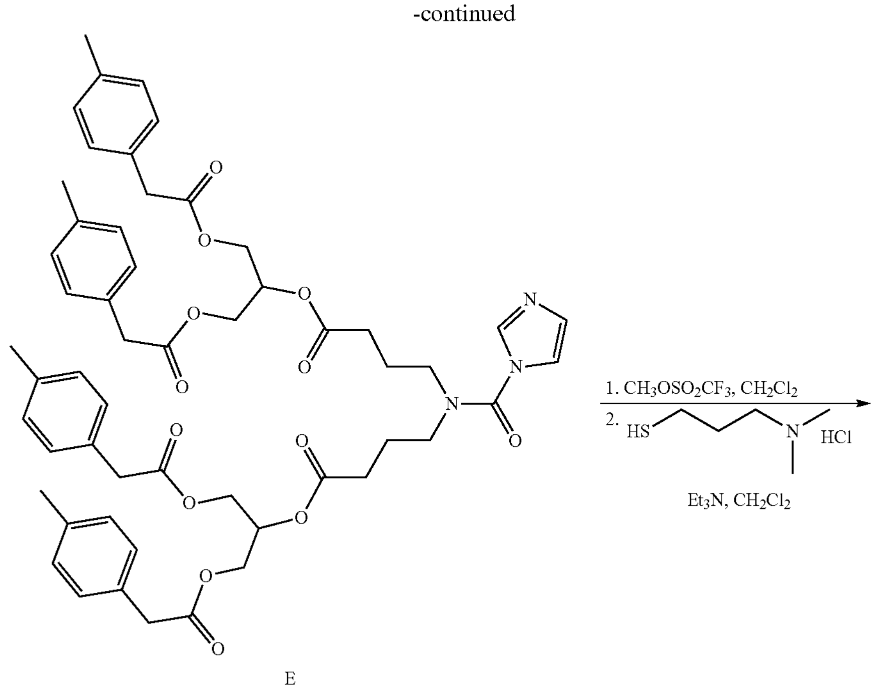
E
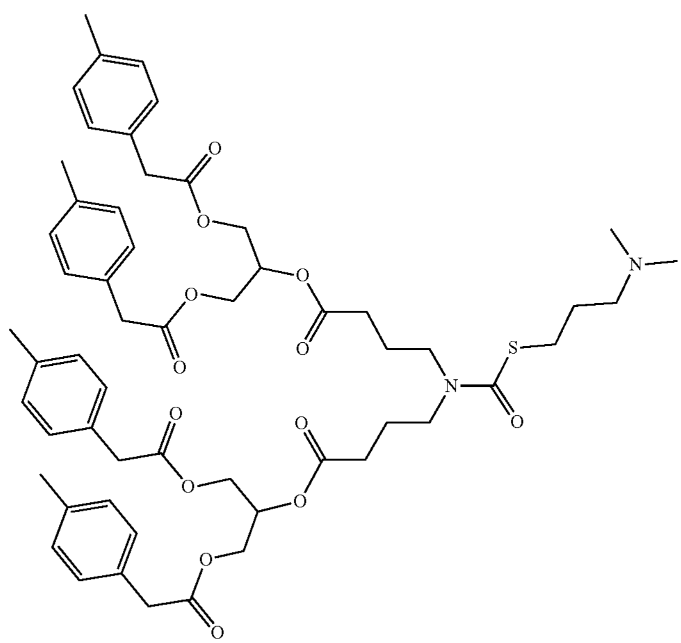
LIPID 34
*J. Am. Chem. Soc.* 2020, *142*, 8910-8917

2-(p-Tolyl) acetyl chloride will be prepared from commercially available 2-(p-tolyl) acetic acid by the method of *J. Am. Chem. Soc.* 2020, 142, 8910-8917, and the acid chloride will be dissolved in $CH_2Cl_2$, 1,3-dihydroxyacetone will be added, followed by DMAP and pyridine. The mixture will be stirred at room temperature under nitrogen, then will be concentrated in vacuo to give crude 2-oxopropane-1,3-diyl bis(2-(p-tolyl)acetate) A.

Crude A will be dissolved in THF and will be cooled in an ice-water bath under nitrogen, then HOAc will be added followed by $NaBH_3CN$. The mixture will be warmed to room temperature and will stir for 14 hours. The mixture will be cast into water, extracted with EtOAc, and the combined organic phases will be dried, filtered, and concentrated in vacuo to give crude 2-hydroxypropane-1,3-diyl bis(2-(p-tolyl)acetate) B. Crude B will be adsorbed on silica gel and will be purified by Combi-flash chromatography to provide 2-hydroxypropane-1,3-diyl bis(2-(p-tolyl)acetate) B.

2-Hydroxypropane-1,3-diyl bis(2-(p-tolyl)acetate) B will be dissolved in $CH_2C_{12}$, cooled in an ice-water bath under nitrogen and 1-5 (from the synthesis of LIPID 1) will be added. To the cooled mixture will be added DMAP and EDCI. The mixture will be warmed to room temperature, will be allowed to stir for 14 hours, then will be washed with brine and will be dried. The solution will be filtered, concentrated in vacuo, the resulting crude ((4,4'-((tert-butoxycarbonyl)azanediyl)bis(butanoyl))bis(oxy))bis(propane-2,1,3-triyl) tetrakis(2-(p-tolyl)acetate) C will then be adsorbed onto silica gel and will be purified using a Combi-flash to give ((4,4'-((tert-butoxycarbonyl)azanediyl)bis(butanoyl))bis(oxy))bis(propane-2,1,3-triyl) tetrakis(2-(p-tolyl) acetate) C.

((4,4'-((tert-Butoxycarbonyl)azanediyl)bis(butanoyl))bis (oxy))bis(propane-2,1,3-triyl) tetrakis(2-(p-tolyl)acetate) C will be dissolved in in $CH_2Cl_2$, cooled in an ice-water bath under nitrogen, and trifluoroacetic acid will be added. The mixture will be warmed to room temperature and will stir for 4 hours. The solvent will be removed in vacuo and this will gave crude bis(4-((1,3-bis(2-(p-tolyl) acetoxy)propan-2-yl) oxy)-4-oxobutyl)ammonium trifluoroacetate D.

Crude bis(4-((1,3-bis(2-(p-tolyl) acetoxy)propan-2-yl) oxy)-4-oxobutyl)ammonium trifluoroacetate D will be dissolved in $CH_2Cl_2$, under nitrogen, and $Et_3N$ and carbonyldiimidazole will be added, then the mixture will be allowed to stir for 12 hours. The mixture will then be diluted with n-heptane, washed with water, and dried. Filtration and concentration in vacuo will give crude ((4,4'-((1H-imidazole-1-carbonyl)azanediyl)bis(butanoyl))bis(oxy))bis(propane-2,1,3-triyl) tetrakis(2-(p-tolyl)acetate) E.

Crude ((4,4'-((1H-imidazole-1-carbonyl)azanediyl)bis (butanoyl))bis(oxy))bis(propane-2,1,3-triyl) tetrakis(2-(p-tolyl)acetate) E will be dissolved in $CH_2Cl_2$, under nitrogen and cooled in an ice-water bath, then methyl triflate will be added, this will be followed by the addition of $Et_3N$ and 3-dimethylamino-propane-1-thiol HCl salt. The mixture will be warmed to room temperature and will be allowed to stir, then will be concentrated in vacuo to give the crude lipid ((4,4'-((((3-(dimethylamino)propyl)thio)carbonyl) azanediyl)bis(butanoyl))bis(oxy))bis(propane-2,1,3-triyl) tetrakis(2-(p-tolyl)acetate). The crude lipid will be adsorbed on silica gel and purified using a Combi-flash. The lipid will then be dissolved in n-heptane and washed with a methanol/water mixture which will give purified LIPID 34 ((4,4'-((((3-(dimethylamino)propyl) thio)carbonyl)azanediyl)bis(butanoyl))bis(oxy))bis(propane-2,1,3-triyl) tetrakis(2-(p-tolyl) acetate).

Example 33. Synthesis of LIPID 35: [2-[4-[3-(dimethylamino) propoxycarbonyl-[4-[2-(2-methyloctanoyloxy)-1-(2-methyloctanoyloxymethyl)ethoxy]-4-oxo-butyl]amino]butanoyloxy]-3-(2-methyloctanoyloxy)propyl] 2-methyloctanoate

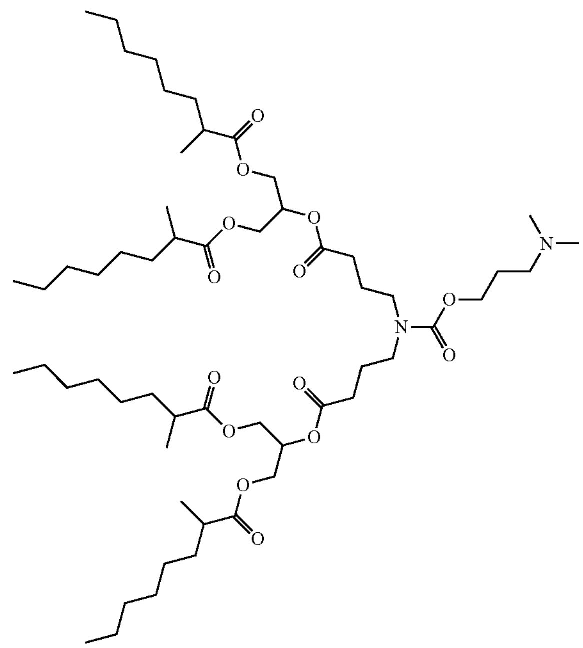 [SMILES: CCCCCCC(C)C(=O)OCC(COC(=O)C(C)CCCCCC)OC(=O)CCCN(CCCC(=O)OC(COC(=O)C(C)CCCCCC)COC(=O)C(C)CCCCCC)C(=O)OCCCN(C)C]

LIPID 35

General scheme

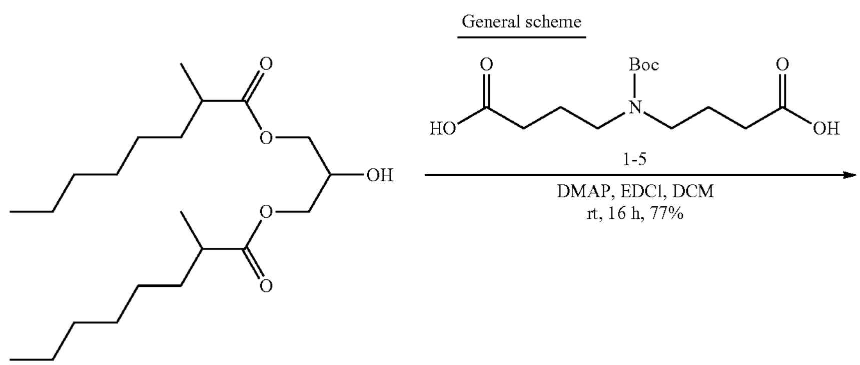

18-2

-continued
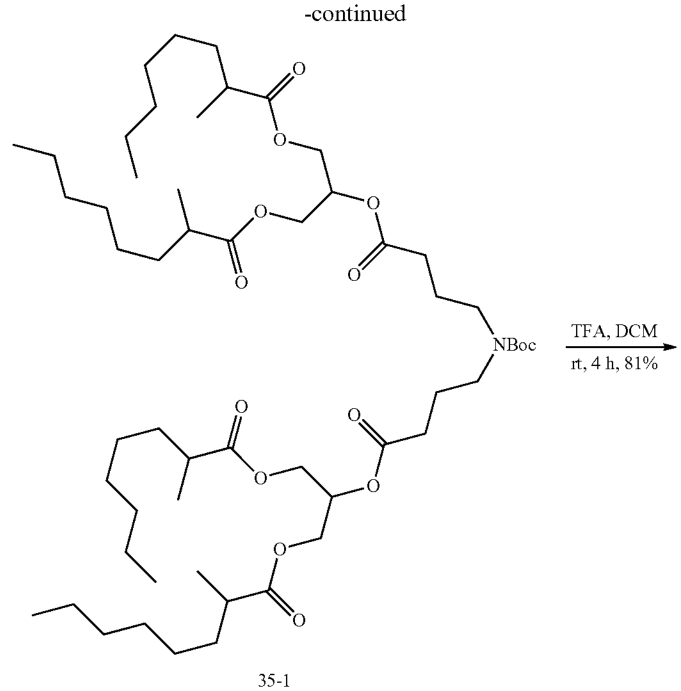
35-1
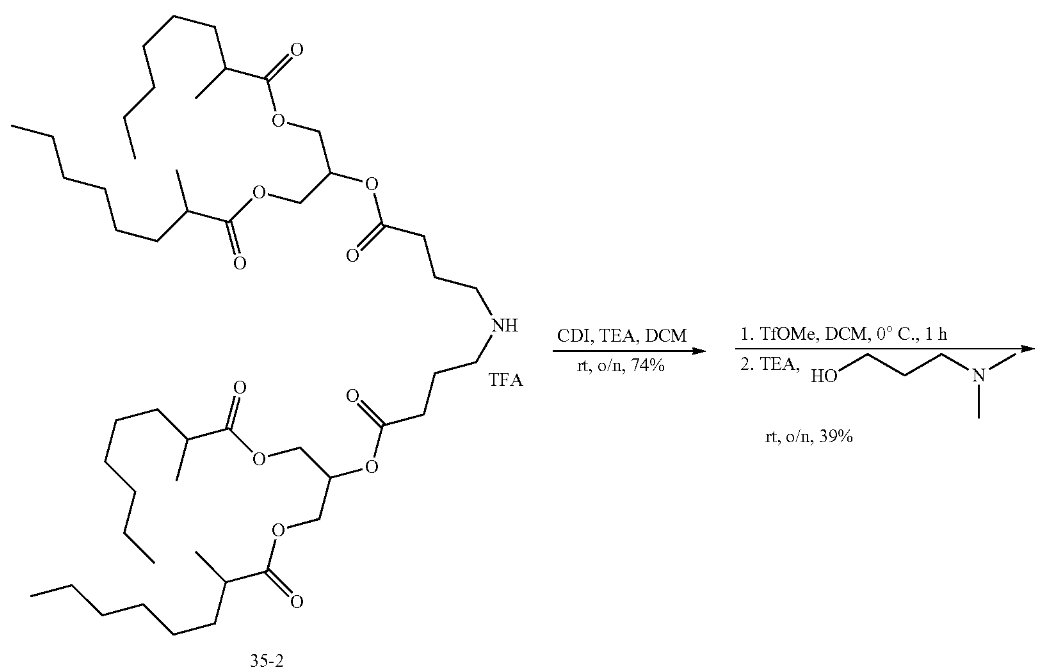
35-2

-continued
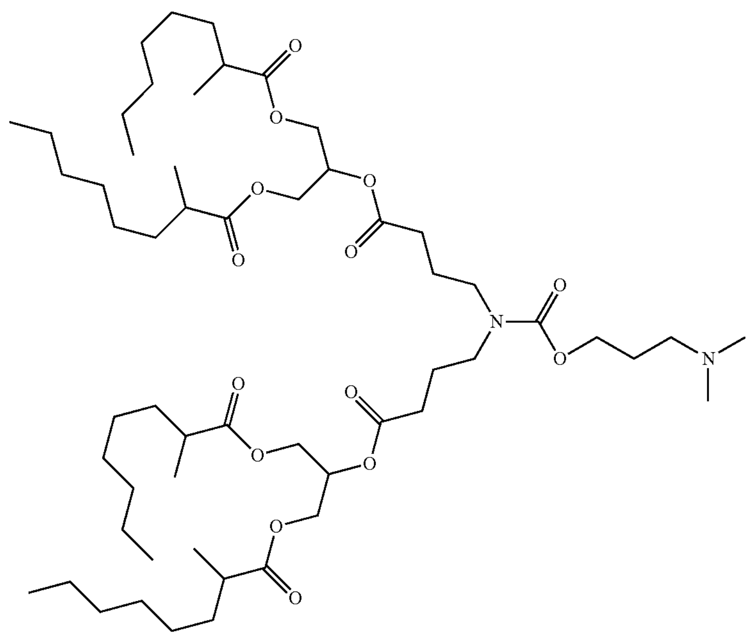
LIPID 35
Lipid 35
Synthesis of 35-1: [2-[4-[tert-butoxycarbonyl-[4-[2-(2-methyloctanoyloxy)-1-(2-methyloctanoyloxymethyl)ethoxy]-4-oxo-butyl]amino]butanoyloxy]-3-(2-methyloctanoyloxy)propyl]2-methyloctanoate
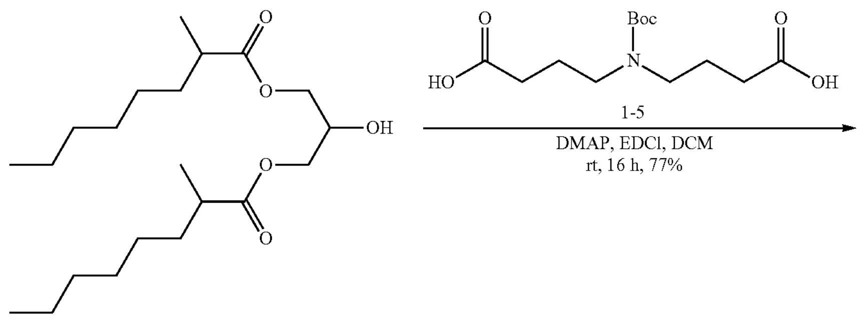
18-2

-continued

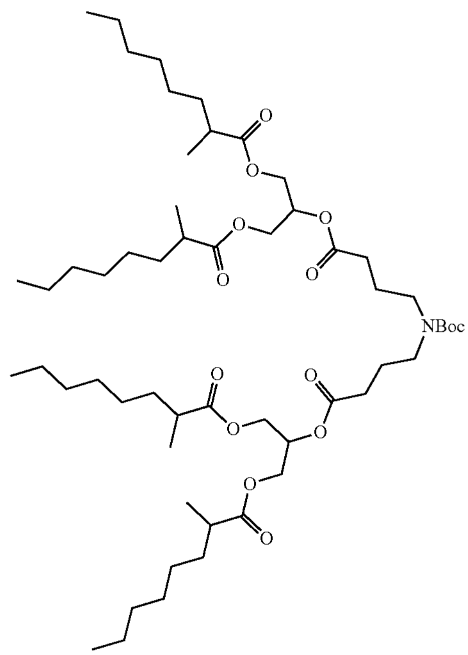

35-1

To a 2 L 3-necked round-bottom flask were added 18-2 (26 g, 69.84 mmol, 1.00 equiv.), 1-5 (9.09 g, 31.43 mmol, 0.45 equiv.), DCM (520 mL, 20 V) and DMAP (4.30 g, 34.92 mmol, 0.5 equiv.). The mixture was cooled to 0° C. and EDCI (12.99 g, 83.81 mmol, 1.2 equiv.) was added in several portions. The mixture was stirred for 15 min at 0° C., and for additional 16 h at 25° C. The resulting mixture was washed with water (2×260 mL) and brine (1×260 mL). The organic phase was collected and dried over anhydrous $Na_2SO_4$ and then filtered. Crude product was adsorbed on 50 g of silica gel (type: ZCX-2, 100-200 mesh, 1.40 w./w.) and purified on a silica gel column (400 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=100:1), combined, concentrated, and dried under vacuum to get 35-1 (24 g, 77%) as a light-yellow oil. This material was used as such in the next reaction after confirming the identity by $^1$H NMR. ELSD A: water/0.02% TFA: B: $CH_3CN$ 95:5 to 5:95 A/B at 3 min.): RT 2.6 min, m/z (Calcd.) 997.7, (found) 1020.8 (M+Na).

Synthesis of 35-2: [3-(2-methyloctanoyloxy)-2-[4-[[4-[2-(2-methyloctanoyloxy)-1-(2-methyloctanoyloxymethyl) ethoxy]-4-oxo-butyl]amino]butanoyloxy]propyl] 2-methyloctanoate trifluoroacetic Acid Salt

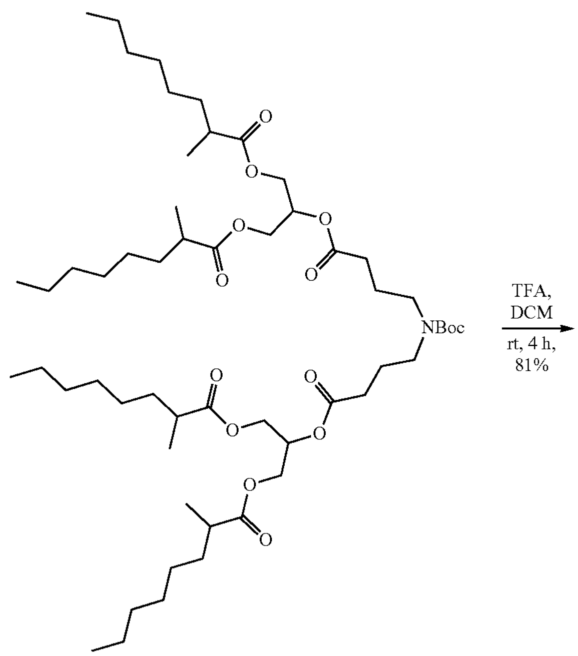

35-1

-continued

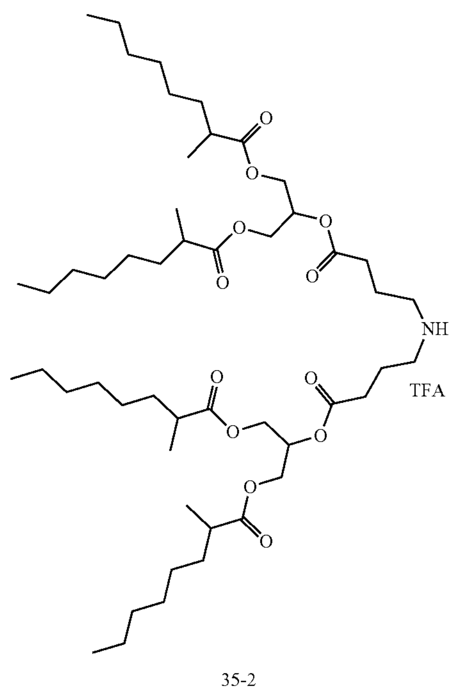

35-2

To a 250 mL round-bottle flask, a solution of 35-1 (24 g, 24.06 mmol, 1 equiv.) in DCM (96 mL, 4 V) was charged. The solution was cooled to 0° C. in an ice-water bath, and TFA (24 mL, 1 V) was added. The ice/water bath was removed, and the mixture was stirred for 4 h at room temperature. The reaction was concentrated under vacuum and diluted with n-heptane (168 mL) at 0±5° C. While maintaining the temperature at 5±5° C., the resulting solution was washed with a solution of $K_2HPO_4$ (24.14 g, 6.0 equiv.) in deionized water (192 mL). The organic phase was concentrated and dried under vacuum to afford 35-2 (19.5 g, 81%) as a light-yellow oil. This crude product was used as such in the next reaction.

Synthesis of 35-3: [2-[4-[imidazole-1-carbonyl-[4-[2-(2-methyloctanoyloxy)-1-(2-methyl octanoyloxymethyl) ethoxy]-4-oxo-butyl]amino]butanoyloxy]-3-(2-methyloctanoyl oxy)propyl] 2-methyloctanoate

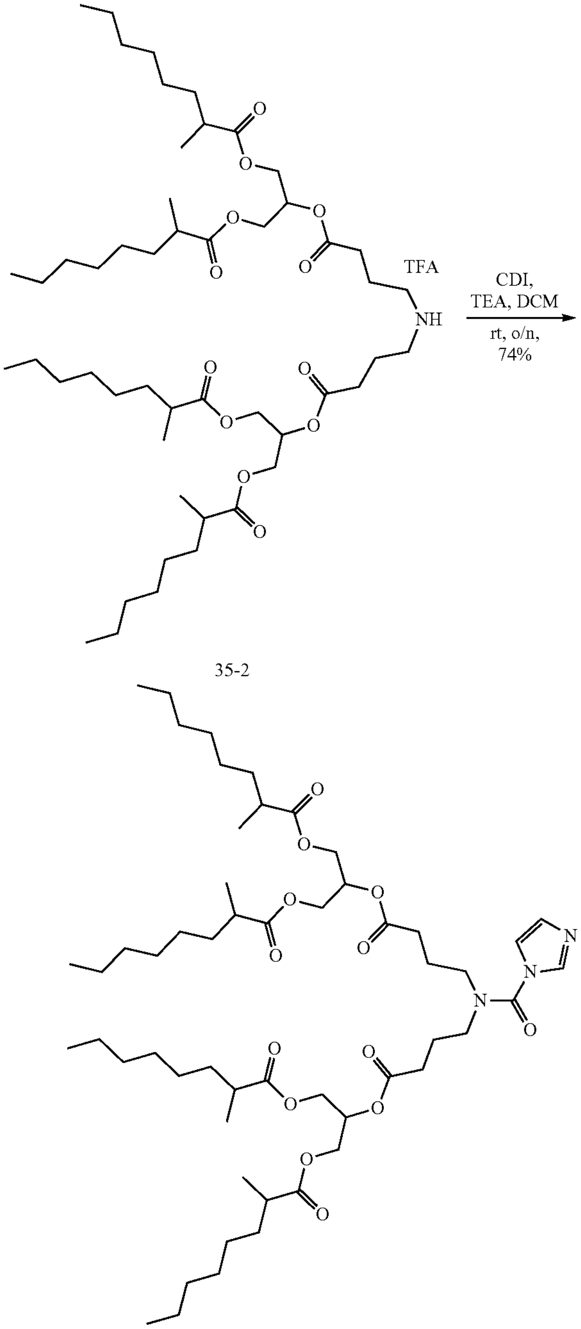

35-2

35-3

To a 1 L 3-necked round-bottom flask, purged and inserted with nitrogen, a solution of 35-2 (12 g, 12.05 mmol, 1 equiv.) in DCM (240 mL) was charged. To this solution, TEA (2.44 g, 24.1 mmol, 2.0 equiv.) and CDI (8.79 g, 54.24 mmol, 4.5 equiv.) were added at room temperature and the reaction mixture was stirred overnight. The resulting mixture was washed with 0.8 M HCl (1×120 mL). The organic layer was washed with 10% brine (120 mL), dried over anhydrous $Na_2SO_4$, and filtered. The filtrate was concentrated under reduced pressure. The residue was dissolved in n-heptane (240 mL), the resulting solution was washed with MeOH/$H_2O$ (5:1) (2× 240 mL). The heptane layer was dried over anhydrous $Na_2SO_4$ and filtered. The filtrate was concentrated under reduced pressure to obtain 35-3 (8.9 g, 74%) as a light-brown oil, that was used as such in the next reaction.

Synthesis of LIPID 35: [2-[4-[3-(dimethylamino) propoxycarbonyl-[4-[2-(2-methyloctanoyl oxy)-1-(2-methyloctanoyloxymethyl) ethoxy]-4-oxo-butyl] amino]butanoyloxy]-3-(2-methyloctanoyloxy)propyl] 2-methyloctanoate

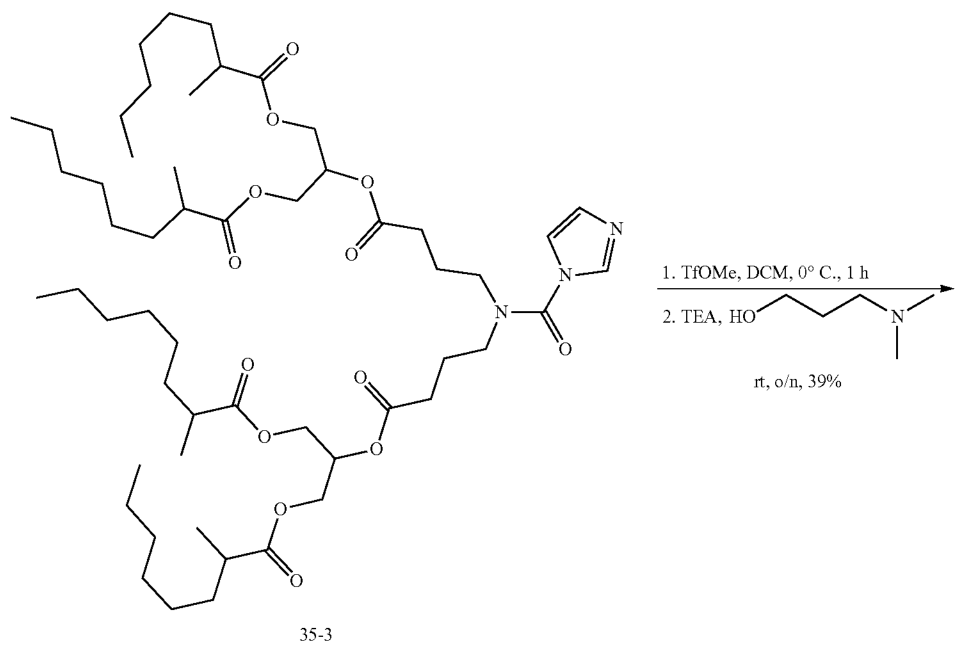

35-3

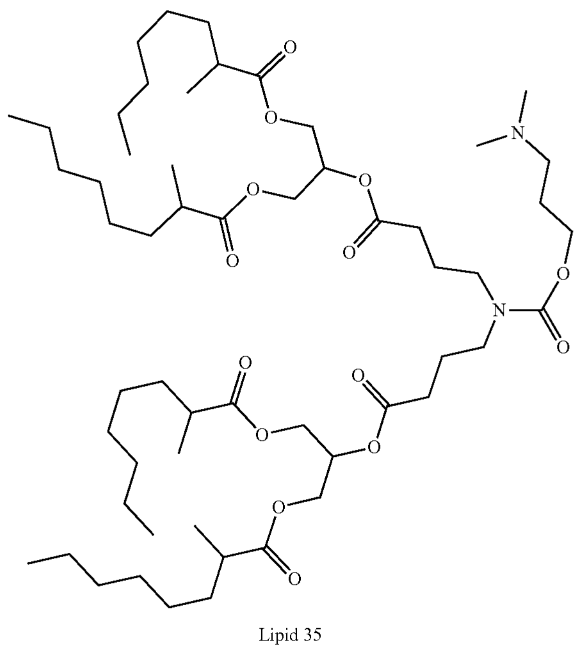

Lipid 35

To a 250 mL 3-necked round-bottom flask, purged and inerted with nitrogen, a solution of 35-3 (3.0 g, 3.02 mmol, 1 equiv.) in DCM (60 mL, 20V) was charged. The solution was cooled to 0° C. in an ice-water bath, and TfOMe (0.55 g, 3.33 mmol, 1.10 equiv.) was added. After stirring at 0° C. for 1 h, TEA (0.61 g, 6.05 mmol, 2.00 equiv.) and 3-(dimethylamino)propan-1-ol (0.37 g, 3.63 mmol, 1.20 equiv.) were added to the solution at cold. The reaction mixture was warmed to room temperature and stirred overnight. The mixture was diluted with DCM (100 mL) and washed subsequently with $H_2O$ (2×100 mL) and brine (1×100 mL). The organic phase was dried over anhydrous $Na_2SO_4$ and filtered. Crude product was adsorbed on 20 g of silica gel (type: ZCX-2, 100-200 mesh, 2.00 w./w.) and purified on a 120 g of silica gel column using a combi-flash purification system. The column was eluted with heptane/EA (gradient from 100:0 to 60:40) and the eluent was collected in fractions. After TLC analysis (heptane:EA=3:1), high-purity product fractions were combined and concentrated in vacuo to afford LIPID 35 (1.6 g) as a yellow oil in 89.0% purity by HPLC-CAD. The LIPID 35 (1.6 g) thus obtained, was purified by prep-achiral-SFC (Column: GreenSep Basic, 3*25 cm, 5 μm; A: $CO_2$, B: IPA:ACN=1:1; 80 mL/min; isocratic 45% B; 35° C.; 220 nm). The enantio-rich product fractions were combined and concentrated to obtain LIPID 35 (1.22 g, 39%) as a light-yellow oil. ELSD A: water/0.02% TFA: B: $CH_3CN$ 95:5 to 5:95 A/B at 25 min.): RT 12.6 min, m/z (Calcd.) 1026.7, (found) 1027.7 [M+H]. $^1H$ NMR (300 MHz, Chloroform-d) δ 5.264-5.231 (m, 2H), 4.363-4.283 (m, 4H), 4.186-4.099 (m, 6H), 3.256 (d, J=8.1 Hz, 4H), 2.570-2.297 (m, 16H), 1.939-1.801 (m, 6H), 1.678-1.606 (m, 4H), 1.457-1.408 (m, 4H), 1.330-1.250 (m, 32H), 1.149 (d, J=6.9 Hz, 12H), 0.899-0.855 (m, 12H).

Example 34. Synthesis of LIPID 36: [2-[4-[3-(dimethylamino)propylcarbamoyl-[4-[2-(2-methyloctanoyl oxy)-1-(2-methyloctanoyloxymethyl)ethoxy]-4-oxo-butyl]amino]butanoyloxy]-3-(2-methyl octanoyloxy)propyl] 2-methyloctanoate

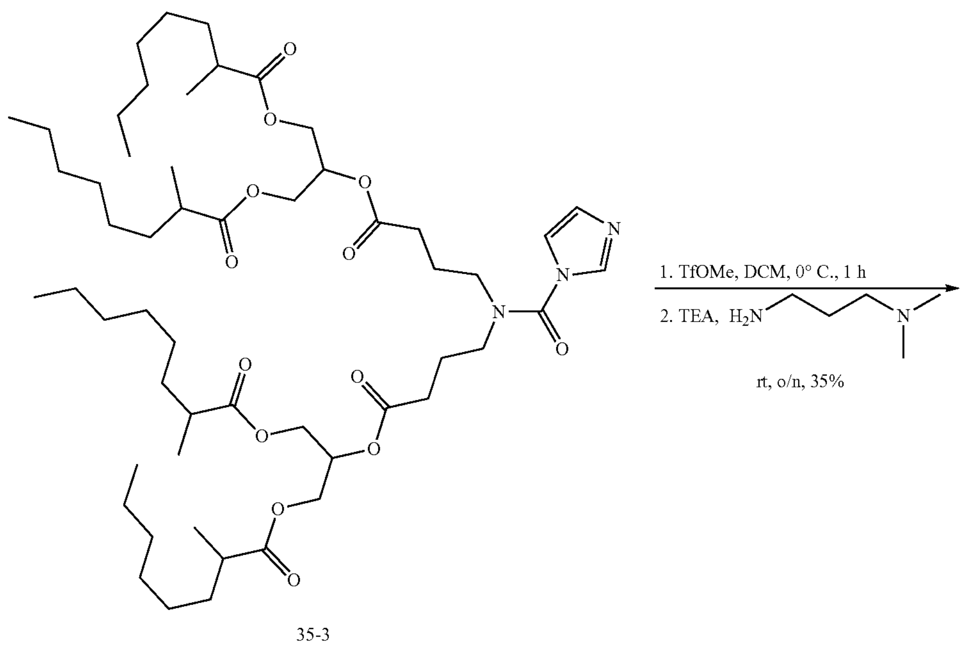

35-3

-continued

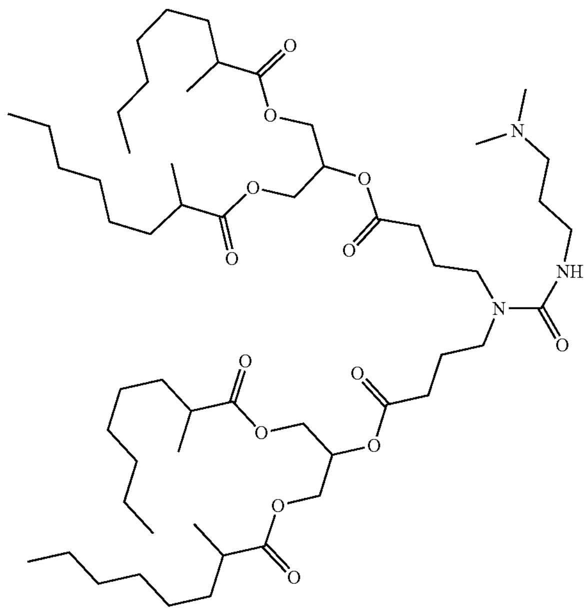

Lipid 36

To a 250 mL 3-necked round-bottom flask, purged and inserted with nitrogen, 35-3 (3 g, 3.02 mmol, 1 equiv.) and DCM (60 mL, 20V) were added. To the mixture, methyl trifluoromethanesulfonate (0.55 g, 3.33 mmol, 1.10 equiv) was added dropwise at 0° C. After stirring at 0° C. for 1 h, TEA (0.61 g, 6.05 mmol, 2.00 equiv.) and 3-(dimethylamino)propylamine (0.37 g, 3.63 mmol, 1.20 equiv.) were added. The reaction mixture was warmed to room temperature and stirred overnight. The mixture was diluted with DCM (200 mL) and washed with brine (1×100 mL). The organic layer was concentrated under vacuum, the residue was purified by reverse phase flash chromatography on a C18 silica gel column. The column was eluted with water/MeCN (gradient from 50:50 to 20:80 in 20 min) with monitoring by UV at 205 nm, the eluent was collected in fractions. High-purity product fractions were combined and concentrated in vacuo to afford LIPID 36 (2.5 g) as a light-yellow oil in 93.03% purity by HPLC-CAD. The LIPID 36 (2.5 g) thus obtained, was purified by prep-achiral-SFC (Column: GreenSep Basic, 3*25 cm, 5 μm; A: $CO_2$, B: IPA:ACN=1:1; 80 mL/min; isocratic 45% B; 35° C.; 220 nm). The enantio-rich product fractions were combined and concentrated to obtain LIPID 36 (1.09 g, 35%) as a light-yellow oil. ELSD A: water/0.02% TFA: B: $CH_3CN$ 95:5 to 5:95 A/B at 3 min.): RT 2.2 min, m/z (Calcd.) 1025.8, (found) 1026.7 [M+H]. $^1H$ NMR (300 MHz, $CDCl_3$, ppm): δ 6.227 (t, J=6.0 Hz, 1H), 5.258-5.225 (m, 2H), 4.363-4.297 (m, 4H), 4.189-4.111 (m, 4H), 3.365-3.346 (m, 2H), 3.247 (t, J=7.5 Hz, 4H), 3.001 (s, 2H), 2.710 (s, 6H), 2.483-2.328 (m, 8H), 2.008-1.978 (m, 2H), 1.868-1.818 (m, 4H), 1.677-1.606 (m, 4H), 1.431-1.345 (m, 4H), 1.266 (s, 32H), 1.149-1.126 (m, 12H), 0.877 (t, J=6.3 Hz, 12H).

Example 35. Synthesis of LIPID 37: [2-[4-[[3-(dimethylamino)propyl-methyl-carbamoyl]-[4-[2-(2-methyloctanoyloxy)-1-(2-methyloctanoyloxymethyl) ethoxy]-4-oxo-butyl]amino]butanoyloxy]-3-(2-methyloctanoyloxy)propyl] 2-methyloctanoate

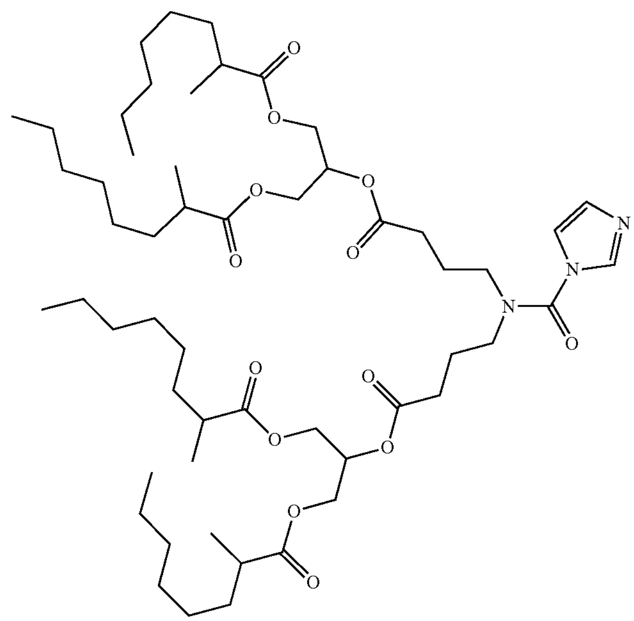

35-3

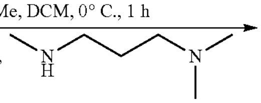

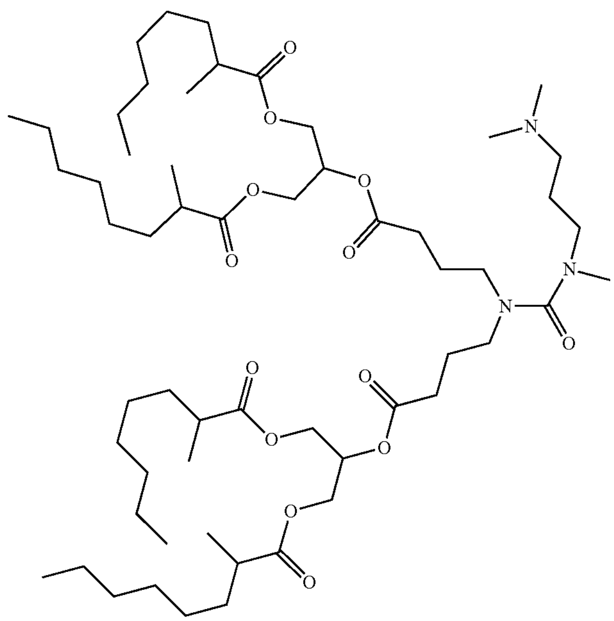

Lipid 37

To a 250 mL 3-necked round-bottom flask, purged and inserted with nitrogen, 35-3 (3 g, 3.02 mmol, 1 equiv.) and DCM (60 mL, 20V) were added. To the mixture, methyl trifluoromethanesulfonate (0.55 g, 3.33 mmol, 1.10 equiv.) was added dropwise at 0° C. After stirring at 0° C. for 1 h, TEA (0.61 g, 6.05 mmol, 2.00 equiv.) and [3-(dimethylamino)propyl] (methyl)amine (0.42 g, 3.63 mmol, 1.20 equiv.) were added. The reaction mixture was stirred for 1 h at 0° C. and then warmed to room temperature and stirred overnight. The mixture was diluted with DCM (200 mL) and washed with brine (1×100 mL). The organic layer was concentrated under vacuum, the residue was purified by reverse phase flash chromatography on a C18 silica gel column. The column was eluted with water/MeCN (gradient from 50:50 to 20:80 in 20 min) with monitoring by UV at 205 nm, the eluent was collected in fractions. High-purity product fractions were combined and concentrated in vacuo to afford LIPID 37 (2.7 g) as a light-yellow oil in 91.42% purity by HPLC-CAD. The LIPID 37 (2.7 g) thus obtained, was purified by prep-achiral-SFC (Column: GreenSep Basic, 3*25 cm, 5 μm; A: $CO_2$, B: IPA:ACN=1:1; 80 mL/min; isocratic 45% B; 35° C.; 220 nm). The enantio-rich product fractions were combined and concentrated to obtain LIPID 37 (1.13 g, 36%) as a light-yellow oil. ELSD A:

water/0.02% TFA: B: $CH_3CN$ 95:5 to 5:95 A/B at 25 min.): RT 13.2 min, m/z (Calcd.) 1039.7, (found) 1041.2 [M+H]. $^1H$ NMR (300 MHZ, $CDCl_3$, ppm): δ 5.249-5.216 (m, 2H), 4.368-4.301 (m, 4H), 4.181-4.093 (m, 4H), 3.267-3.221 (m, 2H), 3.148 (t, J=7.5 Hz, 4H), 2.858 (s, 3H), 2.821-2.702 (m, 2H), 2.595 (s, 6H), 2.480-2.281 (m, 8H), 1.970 (s, 2H), 1.877-1.805 (m, 4H), 1.676-1.604 (m, 4H), 1.430-1.362 (m, 4H), 1.266 (s, 32H), 1.148-1.125 (m, 12H), 0.878 (t, J=6.3 Hz, 12H).
Example 36: Synthesis of LIPID 38: [2-[4-[5-(dimethylamino) pentanoyl-4-[2-(2-methyl octanoyloxy)-1-(2-methyloctanoyloxymethyl) ethoxyl-4-oxo-butyl]amino]butanoyloxy]-3-(2-methyloctanoyloxy) propyl] 2-methyloctanoate
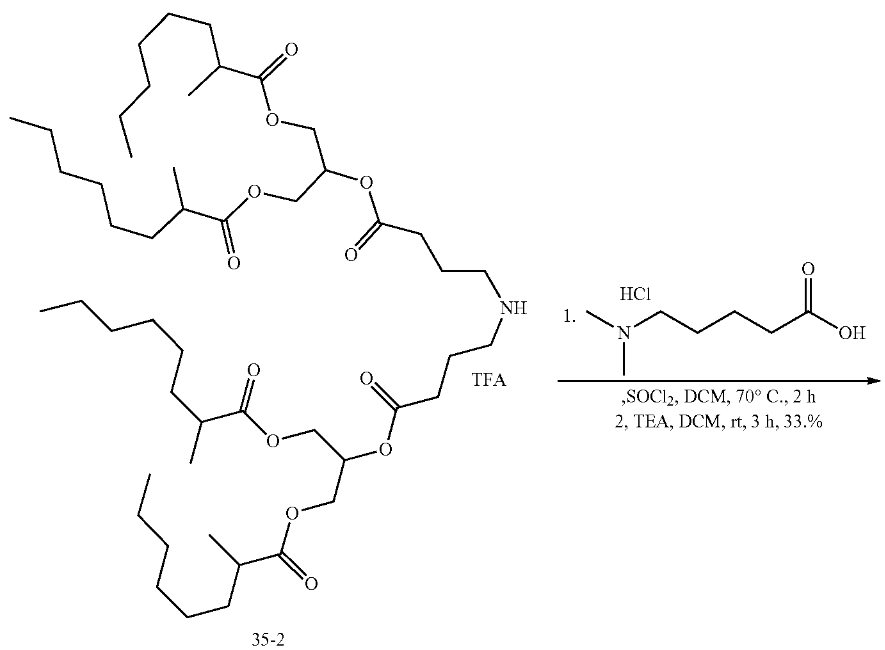
35-2
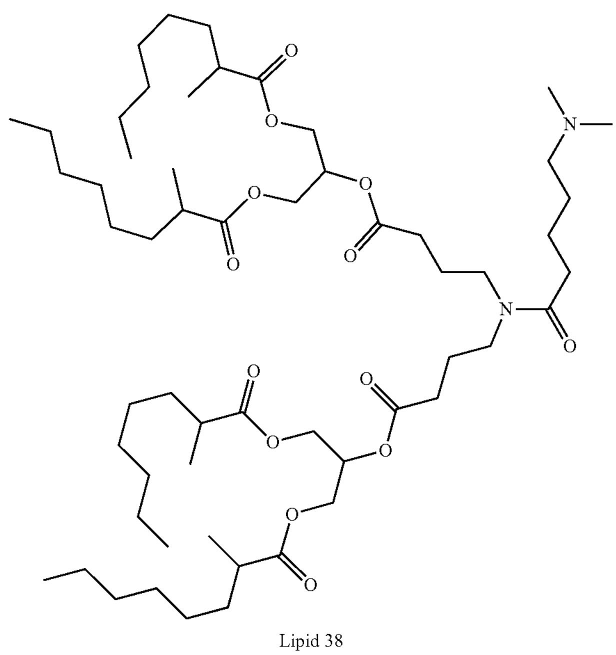
Lipid 38

To a 100 mL 3-necked round-bottom flask, purged and inserted with nitrogen, a solution of the hydrochloride salt of 5-(dimethylamino) pentanoic acid (1.86 g, 1.57 mmol, 3 equiv.) in DCM (15 mL) was charged. After adding $SOCl_2$ (0.93 g, 7.83 mmol, 3 equiv.), the solution was heated to 70° C. and stirred for 2 h. The mixture was concentrated under reduced pressure, the residue was dissolved in DCM (52 mL). The solution was cooled to 0° C., TEA (0.79 g, 7.83 mmol, 3.00 equiv.) and 35-2 (2.60 g, 2.61 mmol, 1.00 equiv.) were added at cold. The mixture was warmed to room temperature and stirred for 3 hours. The mixture was diluted with DCM (90 mL) and washed with water (2×50 mL) and brine (1×50 mL). The organic phase was dried over anhydrous $Na_2SO_4$ and filtered. Crude product was adsorbed on 20 g of silica gel (type: ZCX-2, 100-200 mesh, 2.00 w./w.), and was purified on a 120 g of silica gel column using a combi-flash purification system. The column was eluted with heptane/EA (gradient from 100:0 to 60:40) and the eluent was collected in fractions. After TLC analysis (heptane:EA=5:1), high-purity product fractions were combined and concentrated in vacuo to afford LIPID 38 (1.6 g) as a yellow oil in 84.4% purity by HPLC-CAD. The LIPID 38 (1.6 g) thus obtained, was purified by prep-achiral-SFC (Column: GreenSep Basic, 3*25 cm, 5 μm; A: $CO_2$, B: IPA:ACN=1:1; 80 mL/min; isocratic 45% B; 35° C.; 220 nm). The enantio-rich product fractions were combined and concentrated to obtain LIPID 38 (0.89 g, 33%) as a yellow oil. ELSD A: water/0.02% TFA: B: $CH_3CN$ 95:5 to 5:95 A/B at 25 min.): RT 14.0 min, m/z (Calcd.) 1024.7, (found) 1025.8 [M+H]. $^1H$ NMR (300 MHz, Chloroform-d) δ 5.246 (s, 2H), 4.384-4.279 (m, 4H), 4.180-4.094 (m, 4H), 3.379-3.273 (m, 4H), 2.481-2.299 (m, 18H), 1.860-1.812 (m, 4H), 1.693 (t, J=12 Hz, 8H), 1.427-1.390 (m, 4H), 1.266 (s, 32H), 1.151-1.124 (m, 12H), 0.898-0.854 (m, 12H).

Example 37: Synthesis of LIPID 39: [2-[4-[5-(dimethylamino) pentyl-4-[2-(2-methyl octanoyloxy)-1-(2-methyloctanoyloxymethyl) ethoxyl-4-oxo-butyl] amino]butanoyloxy]-3-(2-methyloctanoyloxy) propyl] 2-methyloctanoate

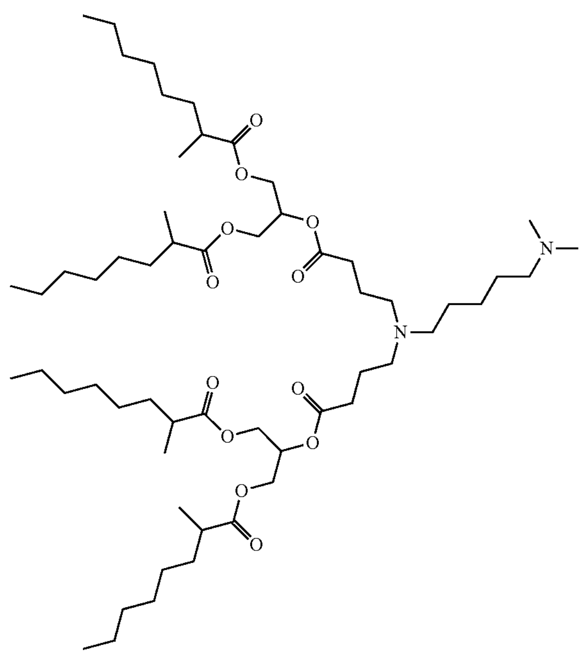 [SMILES: CCCCCCC(C)C(=O)OCC(COC(=O)C(C)CCCCCC)OC(=O)CCCN(CCCCCN(C)C)CCCC(=O)OC(COC(=O)C(C)CCCCCC)COC(=O)C(C)CCCCCC]

LIPID 39

General scheme

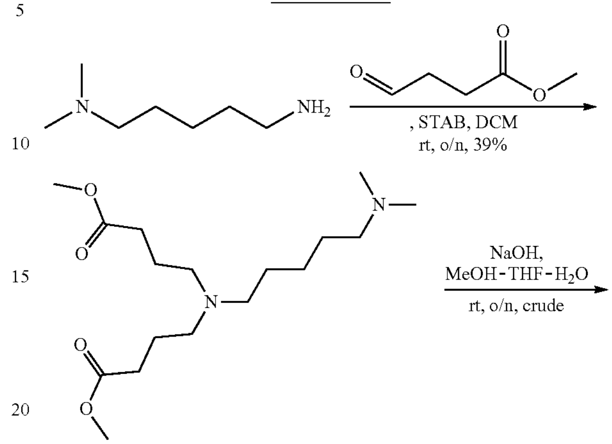

39-1

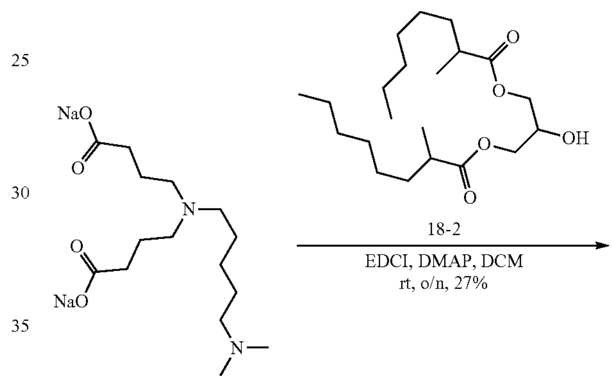

18-2

39-2

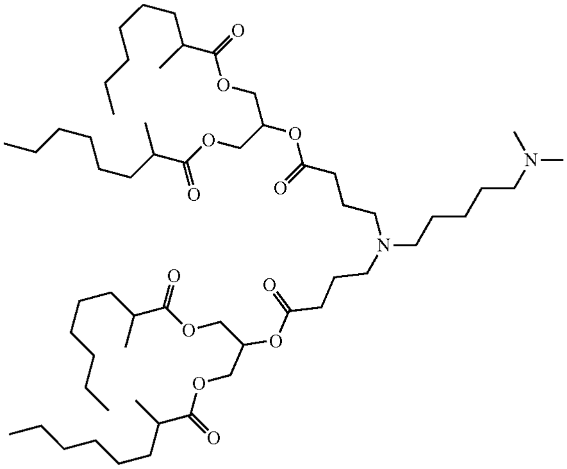

Lipid 39

Synthesis of 39-1: methyl 4-[5-(dimethylamino) pentyl-(4-methoxy-4-oxo-butyl)amino]butanoate

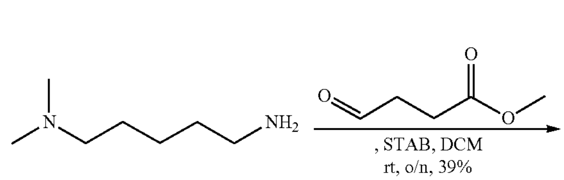

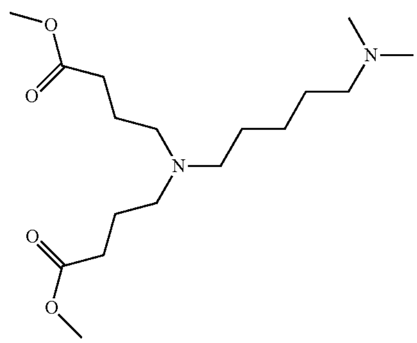

39-1

A mixture of 5-(dimethylamino) amylamine (3.10 g, 23.80 mmol, 1 equiv.) and methyl 4-oxobutanoate (8.29 g, 71.41 mmol, 3.0 equiv.) in DCM (60 mL, 20V) was stirred for 30 min at room temperature. To the above mixture, sodium triacetoxyborohydride (STAB, 25.22 g, 119.02 mmol, 5.0 equiv.) was added in portions at room temperature. The mixture was stirred overnight at room temperature. The reaction was quenched by the addition of sat. aqueous $Na_2CO_3$ solution (60 mL) at room temperature. The resulting mixture was extracted with DCM (2×60 mL), the combined organics were washed with brine (120 mL), dried over anhydrous $Na_2SO_4$, and filtered. To the filtrate, 6 g silica gel (type: ZCX-2, 100-200 mesh, 2.00 w./w.) was added, after concentration to dryness, the residue was purified on a 30 g of silica gel column, using a combi-flash purification system. The column was eluted with DCM/MeOH (95:5) and the eluent was collected in fractions. After TLC analysis (DCM:MeOH=8:1), pure product fractions were combined and concentrated in vacuo to afford 39-1 (3.1 g, 39%) as light-yellow oil. ELSD A: water/0.05% TFA: B: $CH_3CN$/0.05% TFA, 95:5 to 5:95 A/B, RT 0.49 min), m/z (Calcd.) 330.3, (found) 331.5 [M+H].

Synthesis of 39-2:4-[3-carboxypropyl-[5-(dimethylamino) pentyl]amino]butanoic Acid Disodium Salt

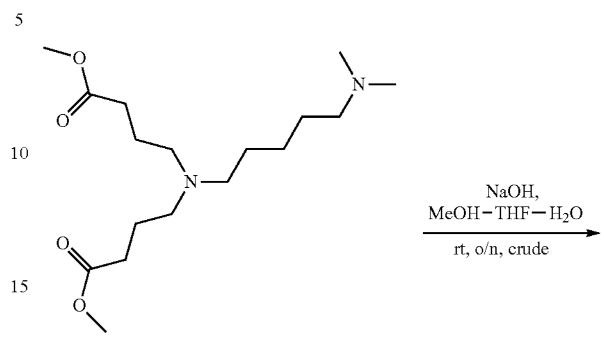

39-1

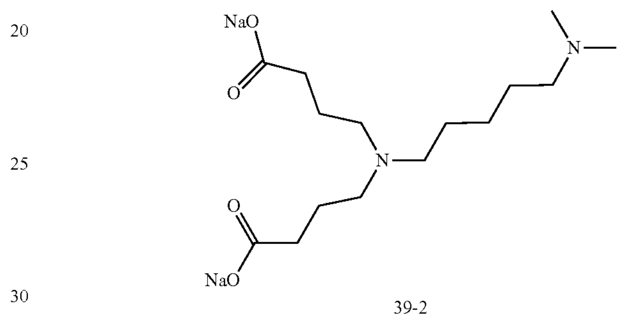

39-2

To a solution of 39-1 (3.0 g, 9.08 mmol, 1 equiv.) in MeOH (6.0 mL, 2V) and THF (6.0 mL, 2V), an aqueous solution of NaOH (1.09 g, 27.23 mmol, 3.0 equiv.) in $H_2O$ (3.0 mL, 1V) was added with stirring at room temperature. The resulting mixture was stirred overnight at room temperature and concentrated under reduced pressure. Crude 39-2 (4.1 g), obtained as a light-yellow solid was used in the next step, without further purification. ELSD A: water/0.05% TFA: B: $CH_3CN$/0.05% TFA, 95:5 to 5:95 A/B, RT 0.25 min), m/z (Calcd.) 302.2, (found) 303.4 [M+H].

Synthesis of LIPID 39. [2-[4-[5-(dimethylamino) pentyl-[4-[2-(2-methyloctanoyloxy)-1-(2-methyloctanoyloxymethyl)ethoxy]-4-oxo-butyl]amino]butanoyloxy]-3-(2-methyloctanoyl oxy)propyl] 2-methyloctanoate

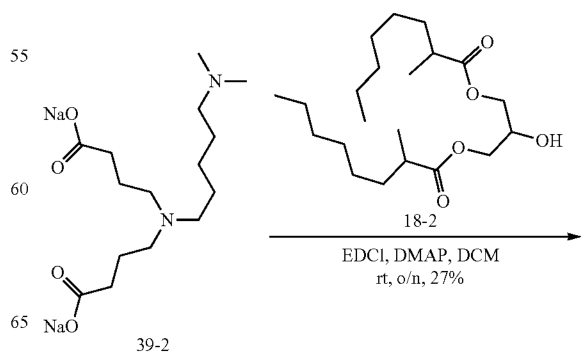

39-2

-continued

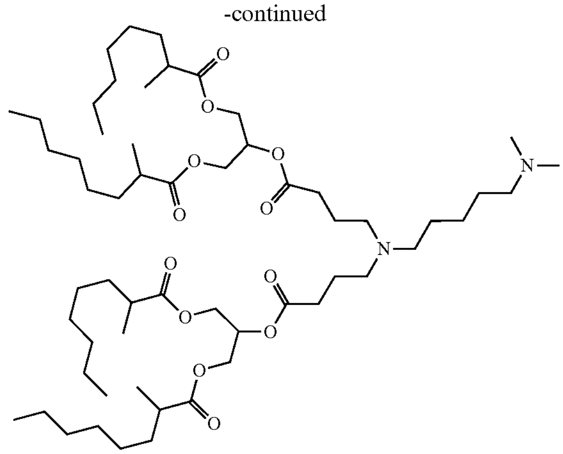

Lipid 39

To a solution of 39-2 (1.28 g, 3.70 mmol, 1 equiv.) and 18-2 (2.75 g, 7.39 mmol, 2.0 equiv.) in DCM (25 mL, 20V), DMAP (0.45 g, 3.70 mmol, 1.0 equiv.) and EDCI (4.25 g, 22.17 mmol, 6.0 equiv.) were added with stirring at room temperature, the reaction mixture was stirred overnight at room temperature. The resulting mixture was quenched with 10% acetic acid (50 mL) and extracted with DCM (2×50 mL). The combined organic layers were washed with aqueous 10% $Na_2CO_3$ (2×50 mL), dried over anhydrous $Na_2SO_4$ and filtered. Crude product was adsorbed on 6.4 g of silica gel (type: ZCX-2, 100-200 mesh, 5.00 w./w.) and was purified on 32 g of silica gel using combi-flash purification system. The column was eluted with DCM/MeOH (gradient from 100:0 to 90:10, and the eluent was collected in fractions. After TLC analysis, product fractions were combined and concentrated in vacuo to afford LIPID 39 (1.70 g) in 90.1% purity by HPLC-CAD as a yellow oil. The LIPID 39 (1.70 g) obtained was repurified by reverse-phase flash chromatography (Column: Ultimate XB-phenyl 50×250 mm, 10 μm, A: water (0.1% TFA), B: 90% MeCN in water, 90 mL/min, 50% to 90% B in 15 min, ELSD detection) and the product fractions were combined and concentrated under reduced pressure. The residue was dissolved in n-heptane (50 mL), the solution was washed with saturated aqueous $Na_2CO_3$ (50 mL) and then with MeOH/$H_2O$ (4:1) (2× 50 mL). The heptane phase was dried over anhydrous $Na_2SO_4$ and filtered. The filtrate was concentrated under reduced pressure to afford LIPID 39 (1.01 g, 27%) as a yellow oil. ELSD A: water/0.05% TFA: B: $CH_3CN$/0.05% TFA, 95:5 to 5:95 A/B, 25 min, RT 13.2 min. m/z (Calcd.) 1010.8, (found) 1011.8 [M+H]. $^1H$ NMR (400 MHz, Chloroform-d) δ 5.289-5.253 (m, 2H), 4.340-4.280 (m, 4H), 4.169-4.102 (m, 4H), 2.470-2.409 (m, 10H), 2.363-2.307 (m, 4H), 2.283-2.233 (m, 8H), 1.738-1.618 (m, 8H), 1.516-1.373 (m, 8H), 1.267 (s, 34H), 1.139 (d, J=6.8 Hz, 12H), 0.894-0.860 (m, 12H).

Example 38: Synthesis of LIPID 40: bis[2-(2-methyloctanoyloxy)-1-(2-methyloctanoyl oxymethyl) ethyl] 5-[4-(dimethylamino)butanoyloxy]nonanedioate

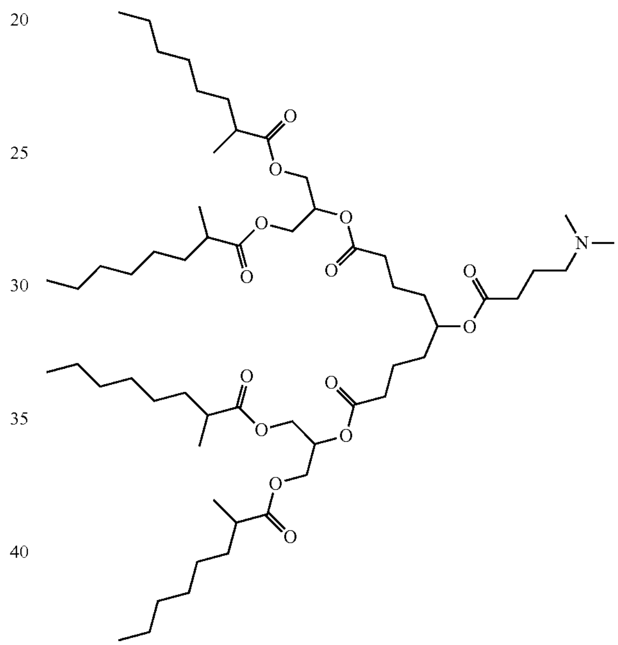

LIPID 40

General Scheme:

General Scheme

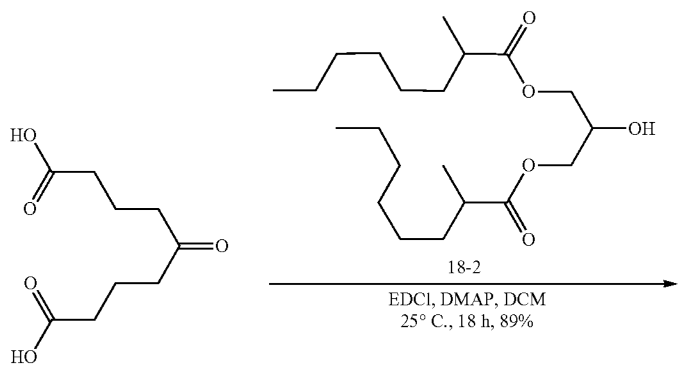

-continued
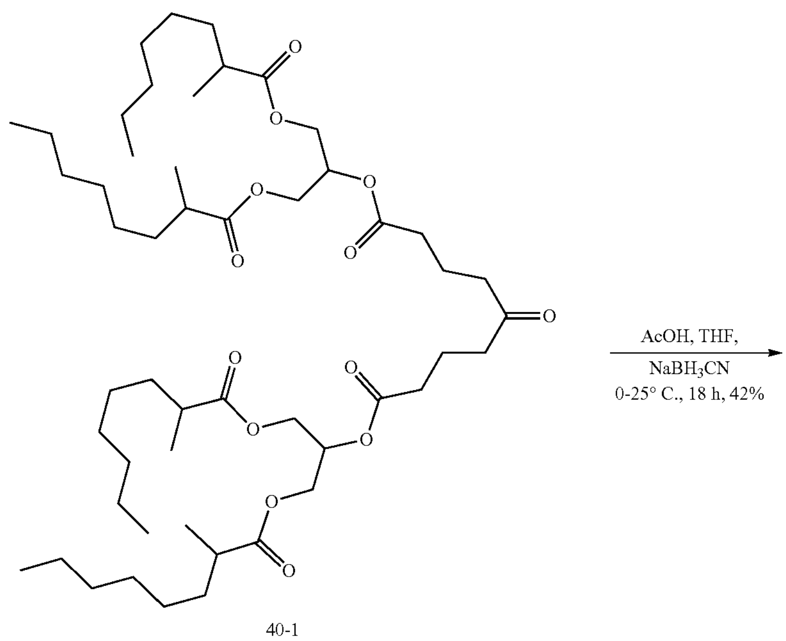
40-1
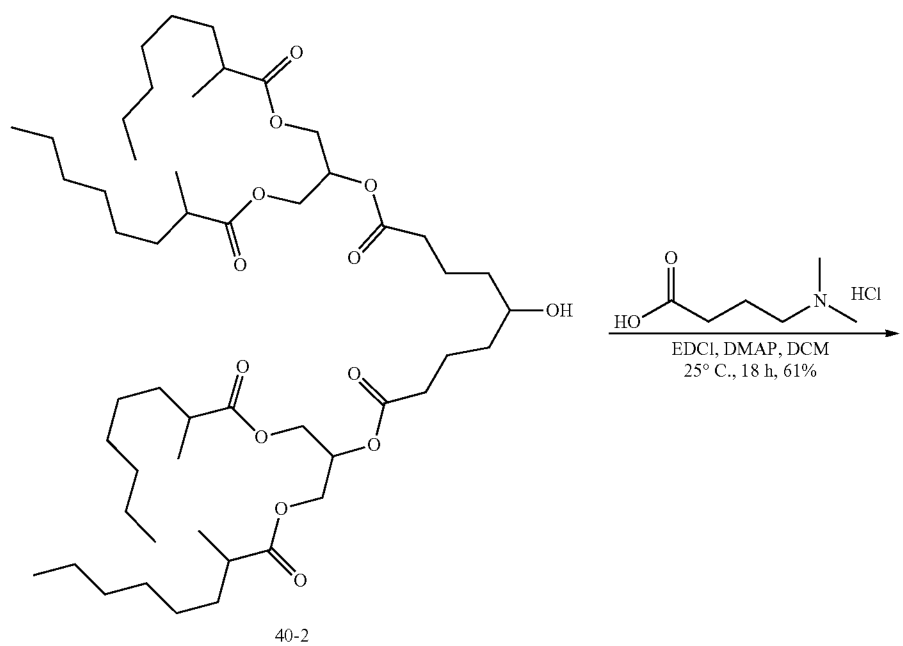
40-2

-continued
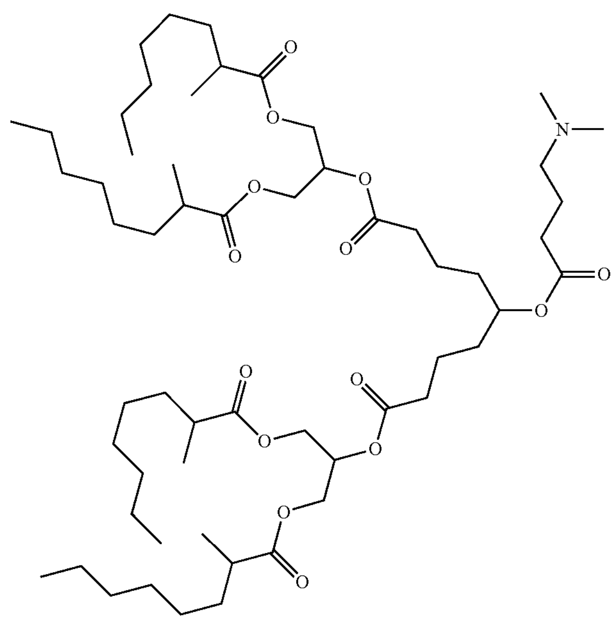
Lipid 40
Synthesis of 40-1: bis[2-(2-methyloctanoyloxy)-1-(2-methyloctanoyloxymethyl)ethyl] 5-oxo nonanedioate
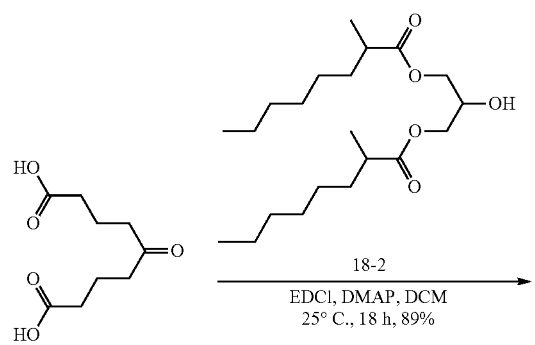
-continued
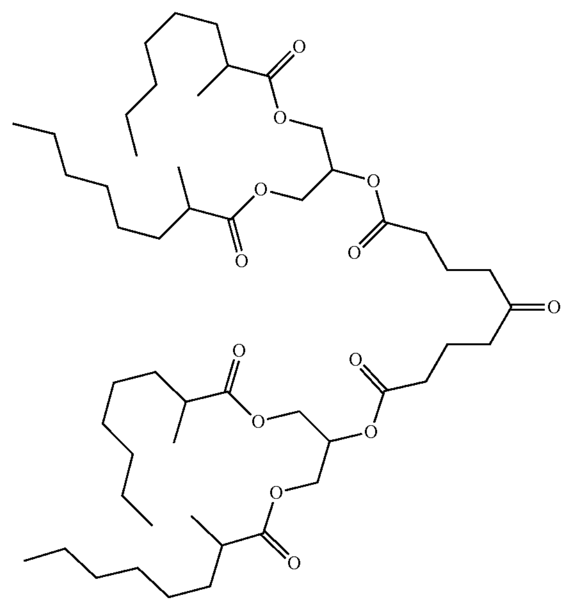
40-1

To a 250 mL round-bottom flask, 5-oxoazelaic acid (1.00 g, 4.95 mmol, 1.0 equiv.), 18-2 (3.87 g, 10.39 mmol, 2.1 equiv.) and DCM (80 mL) were added at 25° C. DMAP (0.60 g, 4.95 mmol, 1.0 equiv.) and EDCI (2.09 g, 10.88 mmol, 2.2 equiv.) were added and the resulting mixture was stirred for 18 h at 25° C. The reaction mixture was diluted with DCM (100 mL), washed with brine (2× 40 mL), dried over anhydrous $Na_2SO_4$ and filtered. To the filtrate, 6 g of silica gel (type: ZCX-2, 100-200 mesh, 5.00 w./w.) was added, after concentration to dryness, the residue was purified on an 80 g silica gel column, using combi-flash to purification system. The column was eluted with heptane/EA. (gradient from 5:1 to 1:1) and the eluent was collected in fractions. After TLC analysis (heptane/EA=2:1), the product fractions were combined and concentrated in vacuo to afford 40-1 (4.0 g, 89%) as a colorless oil. ELSD (A: water/0.05% TFA: B: $CH_3CN$/0.05% TFA, 95:5 to 5:95 A/B, RT 1.9 min), m/z (Calcd.) 910.6, (found) 933.9 [M+Na].

Synthesis of 40-2: bis[2-(2-methyloctanoyloxy)-1-(2-methyloctanoyloxymethyl)ethyl] 5-hydroxy nonanedioate

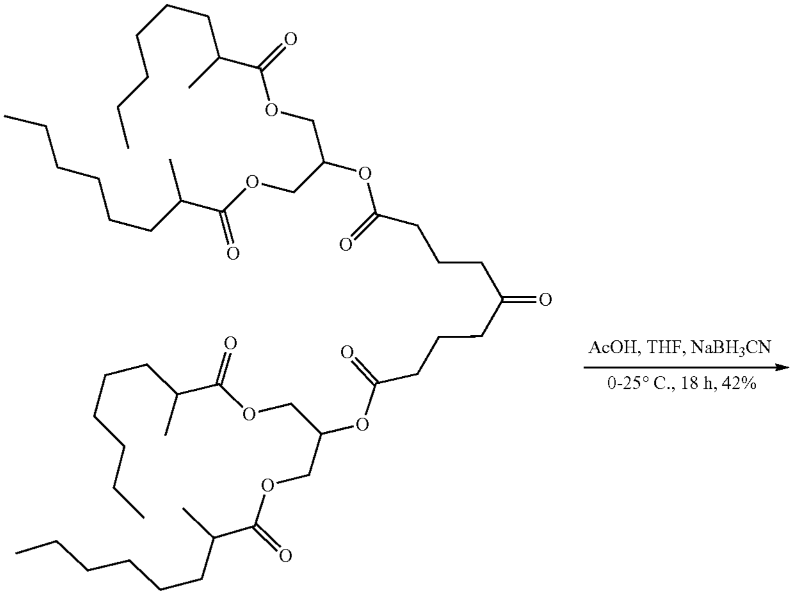

40-1

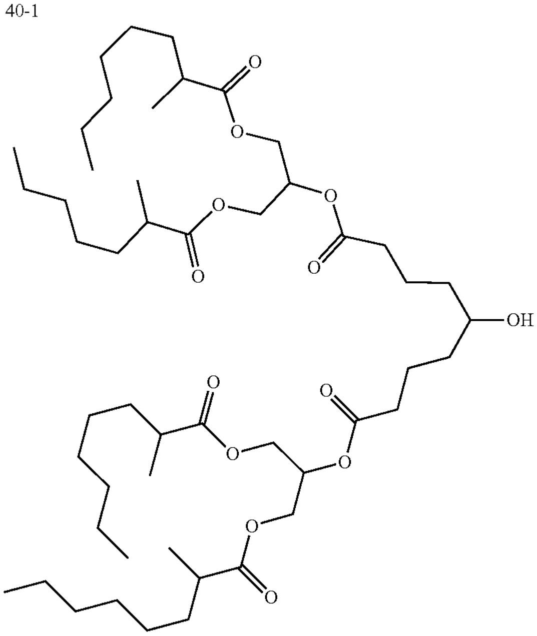

40-2

To a 250 mL round-bottom flask 40-1 (3.6 g, 3.95 mmol, 1 equiv.) and tetrahydrofuran (80 mL) were added at 25° C. The mixture was cooled to 0° C., acetic acid (0.47 g, 7.90 mmol, 2 equiv.) was added, and stirring was continued for 10 min at cold. To the above mixture, $NaBH_3CN$ (1.99 g, 31.61 mmol, 8 equiv.) was added in portions at 0° C. The resulting mixture was stirred for an additional 1 h at 0° C. and then for 18 h at 25° C. After quenching the reaction with water at 0° C., the resulting mixture was extracted with DCM (2×50 mL). The combined organic layers were washed with 5% aqueous $NaHCO_3$ (2×50 mL) and $H_2O$ (1×50 mL), and then dried over anhydrous $Na_2SO_4$. The organic phase was filtered, to the filtrate 6 g of silica gel (type: ZCX-2, 100-200 mesh, 5.00 w./w.) was added, after concentration to dryness, the residue was purified on an 80 g of silica gel column using combi-flash purification system. The column was eluted with heptane/EA. (gradient from 5:1 to 1:1) and the eluent was collected in fractions. After TLC analysis (heptane/EA=2:1), the pure product fractions were combined and concentrated in vacuo to afford 40-2 (1.5 g, 42%) as a colorless oil. The material was used after confirming identity by $^1H$ NMR.

Synthesis of LIPID 40: bis[2-(2-methyloctanoyloxy)-1-(2-methyloctanoyl oxymethyl)ethyl] 5-[4-(dimethylamino)butanoyloxy]nonanedioate

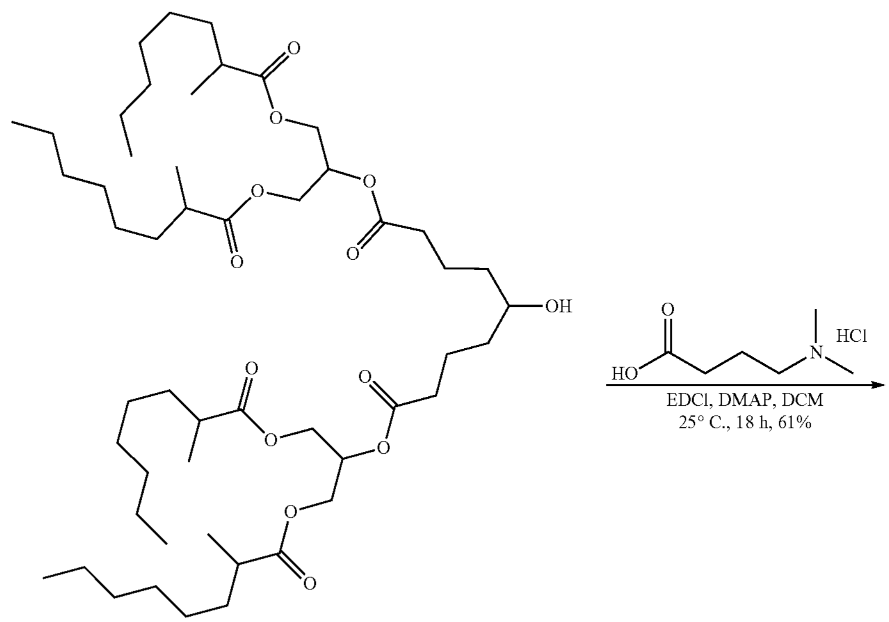

40-2

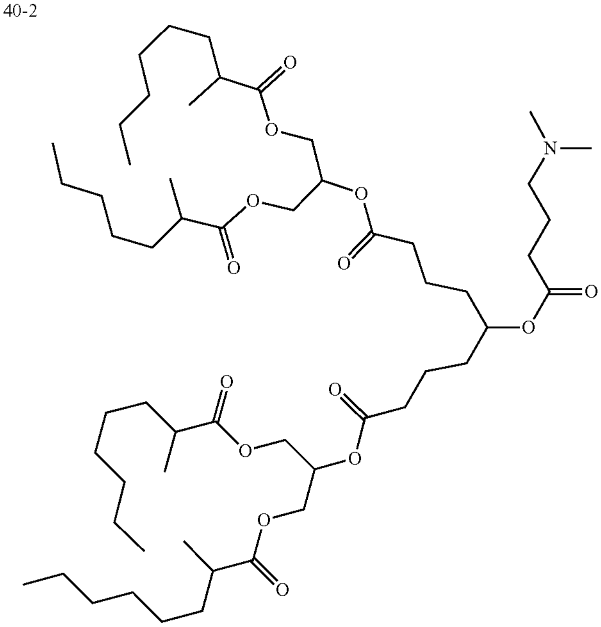

Lipid 40

To a 100 mL round-bottom flask, 40-2 (1.4 g, 1.53 mmol, 1 equiv.) and 4-(dimethylamino)butanoic acid hydrochloride (0.31 g, 1.84 mmol, 1.2 equiv.) in DCM (50 mL) were added at 25° C. DMAP (37.46 mg, 0.31 mmol, 0.2 equiv.) and EDCI (0.38 g, 1.993 mmol, 1.3 equiv.) were added and the resulting mixture was stirred for 18 h at 25° C. The reaction mixture was diluted with DCM (100 mL), washed with brine (2×50 mL), dried over anhydrous $Na_2SO_4$, and filtered. To the filtrate, 6 g of silica gel (type: ZCX-2, 100-200 mesh, 5.00 w./w.) was added, after concentration to dryness, the residue was purified on an 80 g silica gel column, using combi-flash to purification system. The column was eluted with heptane/EA. (gradient from 15:1 to 3:1) and the eluent was collected in fractions. After TLC analysis (heptane/EA=3:1), the pure product fractions were combined and concentrated in vacuo to afford LIPID 40 (1.2 g) as a colorless oil in 91.2% purity by HPLC-CAD. The LIPID 40 (1.2 g) thus obtained, was purified by prep-achiral-SFC (Column: GreenSep Basic, 3*25 cm, 5 μm; A: $CO_2$, B: IPA: ACN=1:1; 80 mL/min; isocratic 45% B; 35° C.; 220 nm). The enantio-rich product containing fractions were combined and concentrated to obtain LIPID 40 (0.95 g, 61%) as a colorless oil. ELSD (A: water/0.05% TFA: B: $CH_3CN$/0.05% TFA, 95:5 to 5:95 A/B, 25 min. RT 12.8 min), m/z (Calcd.) 1025.7, (found) 1026.9 [M+H]. $^1H$ NMR (400 MHz, Chloroform-d, ppm) δ 5.303-5.215 (m, 2H), 4.945-4.838 (m, 1H), 4.391-4.263 (m, 4H), 4.201-4.072 (m, 4H), 2.504-2.402 (m, 4H), 2.376-2.268 (m, 8H), 2.225 (s, 6H), 1.855-1.746 (m, 2H), 1.720-1.531 (m, 12H), 1.469-1.347 (m, 4H), 1.340-1.205 (m, 34H), 1.185-1.098 (m, 12H), 0.912-0.843 (m, 12H).

Example 39. LIPID 41: ((4,4'-((((3-(dimethylamino)propyl)thio)carbonyl)azanediyl)bis(butanoyl))bis(oxy))bis(propane-2,1,3-triyl) tetrakis(2-methyl-4-(p-tolyl)butanoate)

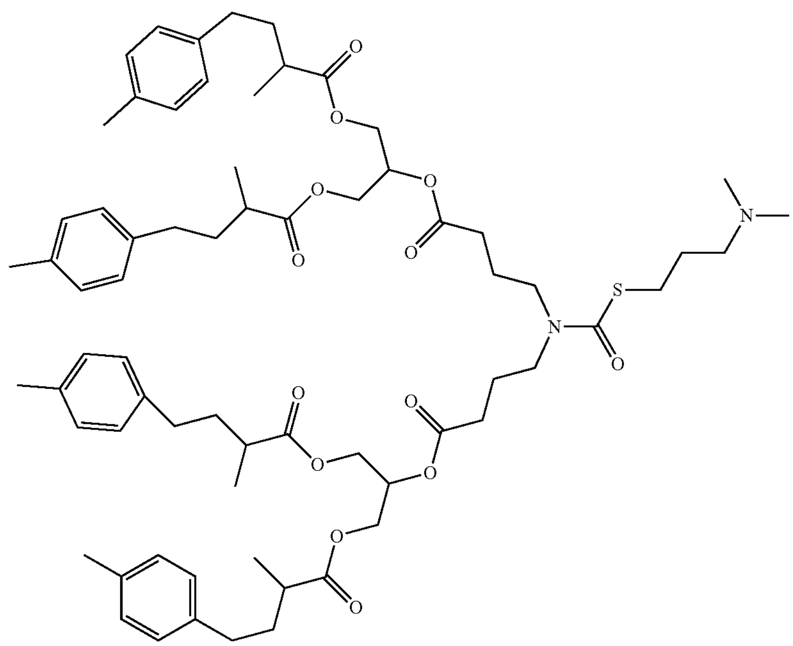

LIPID 41

General scheme

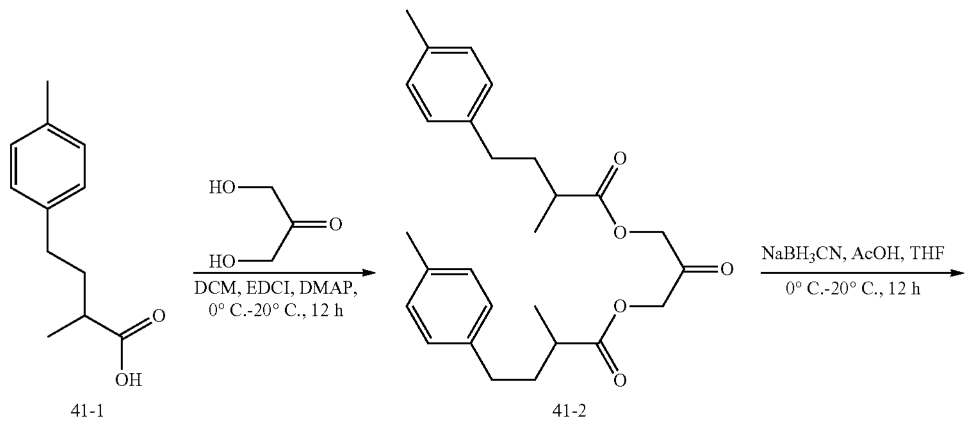

-continued
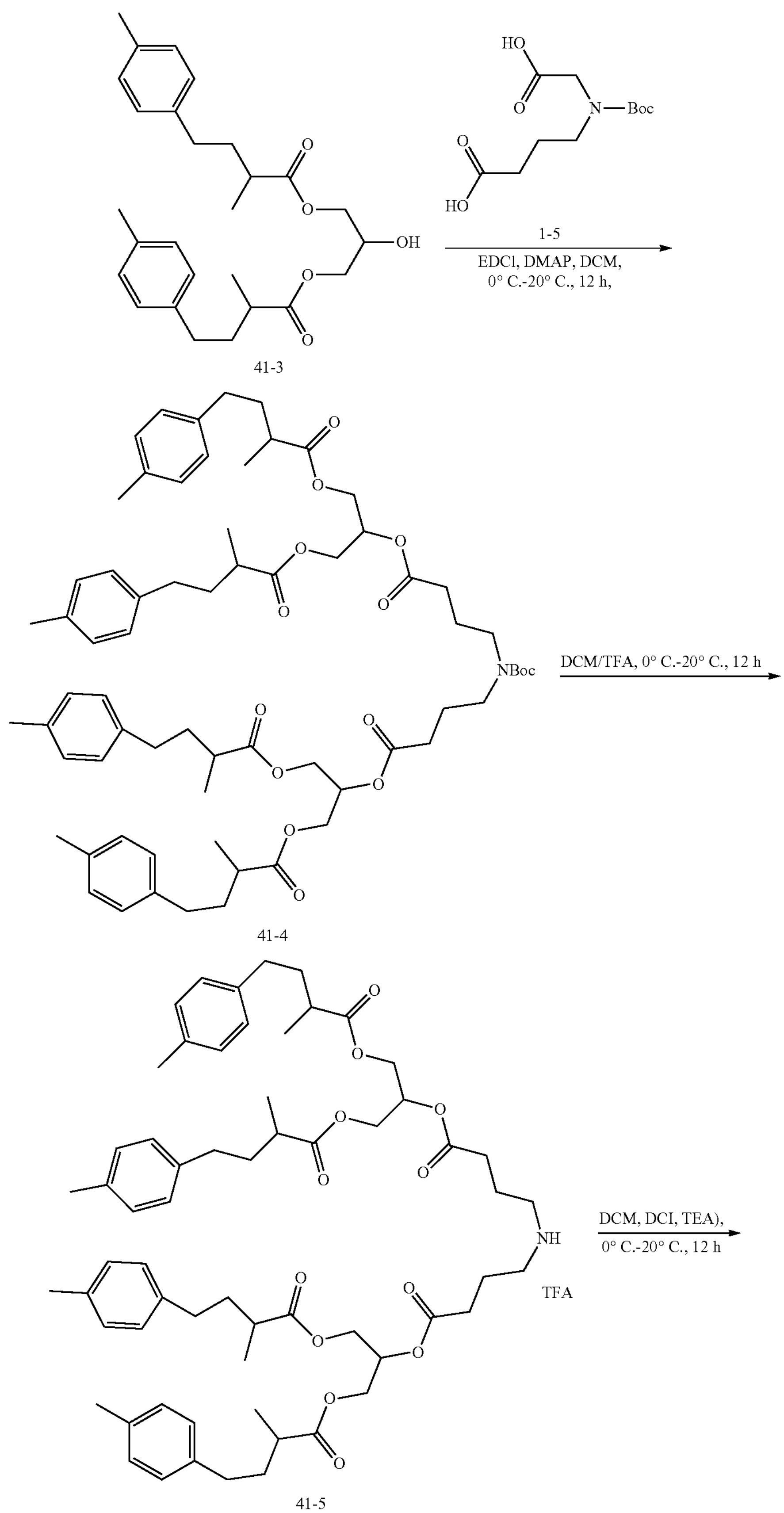
41-3
41-4
41-5

-continued
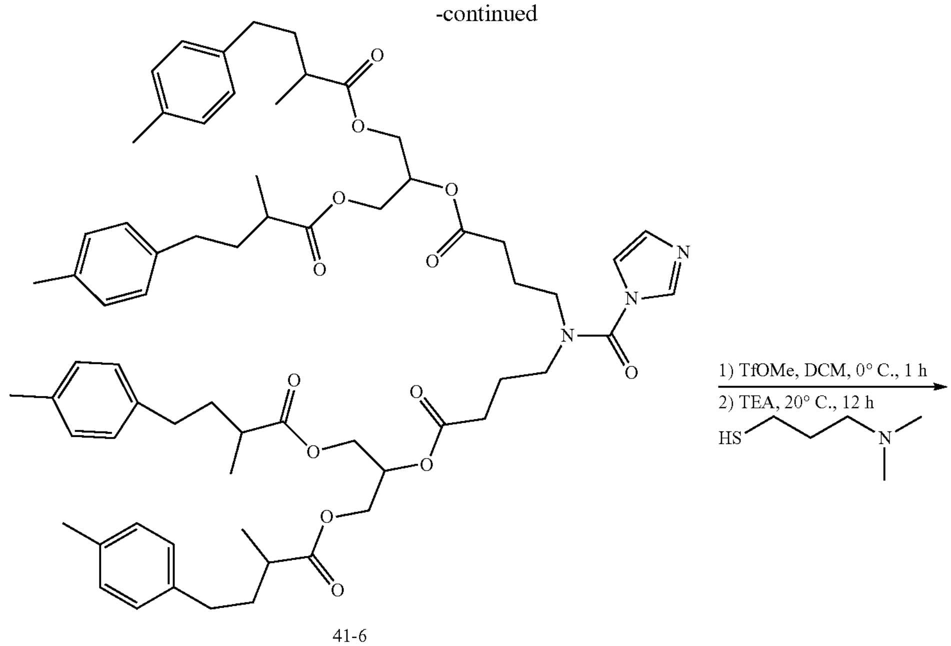
41-6
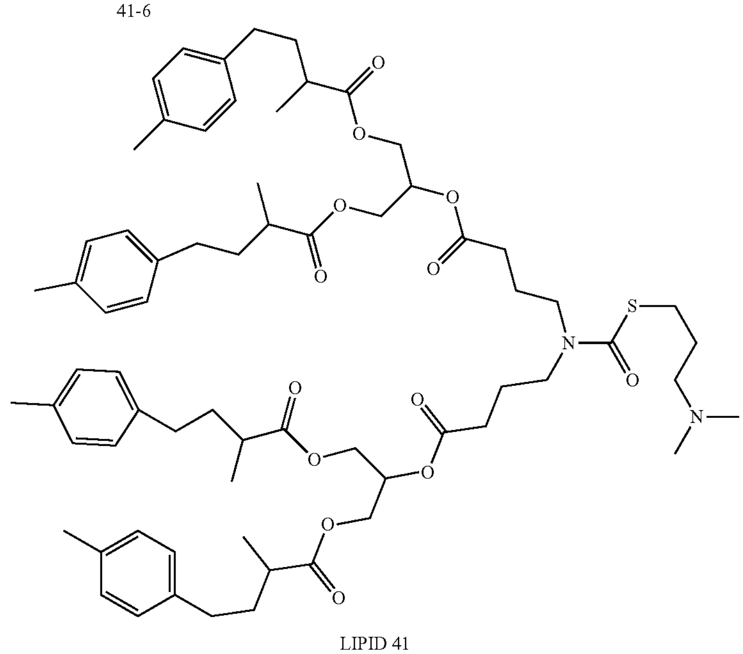
LIPID 41
Synthesis of 41-2: 2-oxopropane-1,3-diyl bis(2-methyl-4-(p-tolyl)butanoate)
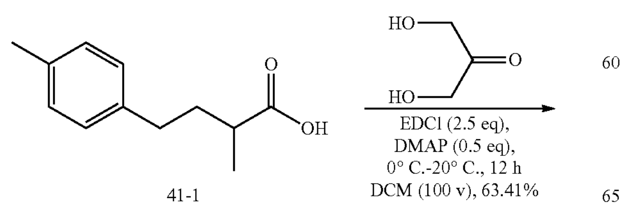
41-1

-continued

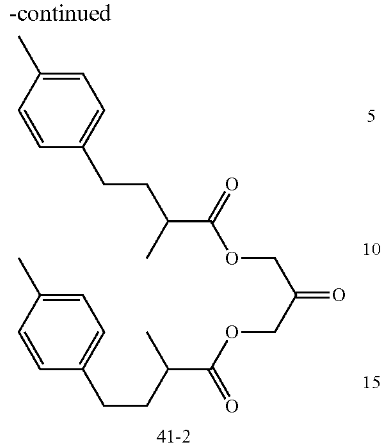

41-2

Into a 500 mL round-bottom flask, was placed dihydroxyacetone (2.5 g, 27.75 mmol, 1.00 equiv.), DCM (250 mL, 100 V), 2-methyl-4-(4-methylphenyl)butanoic acid (41-1, 12.27 g, 63.83 mmol, 2.3 equiv.), DMAP (1.70 g, 13.88 mmol, 0.5 equiv.). EDCI (13.30 g, 69.38 mmol, 2.5 equiv.) was added at 0° C. Then the reaction was stirred at 20° C. for 12 h. The reaction mixture was diluted with DCM (500 mL, 200 V). The organic layer was washed with (500 mL, 200 V) of water, brine (250 mL, 100 V), dried with anhydrous $Na_2SO_4$, filtered, and concentrated under vacuum. Crude product was adsorbed on 25 g of silica gel (type: ZCX-2, 100-200 mesh, 1.40 w./w.) and purified on a silica gel column (200 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=20:1), combined, concentrated, and dried under vacuum to get 41-2 (8.1 g, 18.49 mmol, 63.4%) as a colorless oil which was directly used in the next step. ELSD A: water/0.02% TFA: B: $CH_3CN$ 95:5 to 5:95 A/B at 3 min.): RT 2.4 min, m/z (Calcd.) 438.2, (found) 456.2 ($M+H_2O$).

Synthesis of 41-3: 2-hydroxypropane-1,3-diyl bis(2-methyl-4-(p-tolyl)butanoate)

-continued

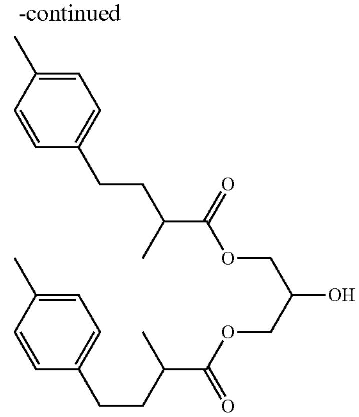

41-3

Into a 250 mL round-bottom flask, was placed 41-2 (8 g, 18.24 mmol, 1 equiv.), THF (80 mL), AcOH (10.95 g, 182.34 mmol, 10 equiv.), and $NaBH_3CN$ (5.73 g, 91.18 mmol, 5.0 equiv.) was added at 0° C. Then the reaction was stirred at 20° C. for 12 h. The reaction mixture was diluted with DCM (400 mL, 50 V). The organic layer was washed with (200 mL, 25 V) of water, brine (200 mL, 20 V), dried with anhydrous $Na_2SO_4$, filtered, and the filtrate was concentrated under vacuum. Crude product was adsorbed on 40 g of silica gel (type: ZCX-2, 100-200 mesh, 1.40 w./w.) and purified on a silica gel column (160 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=20:1), combined, concentrated, and dried under vacuum to get 41-3 (6.6 g, 15.000 mmol, 85.7%) as a light-yellow oil. ELSD A: water/0.02% TFA: B: $CH_3CN$ 95:5 to 5:95 A/B at 3 min.): RT 1.9 min, m/z (Calcd.) 440.2, (found) 463.2 (M+Na).

Synthesis of 41-4: ((4,4'-((tert-butoxycarbonyl)azanediyl)bis(butanoyl))bis(oxy))bis(propane-2,1,3-triyl) tetrakis(2-methyl-4-(p-tolyl)butanoate)

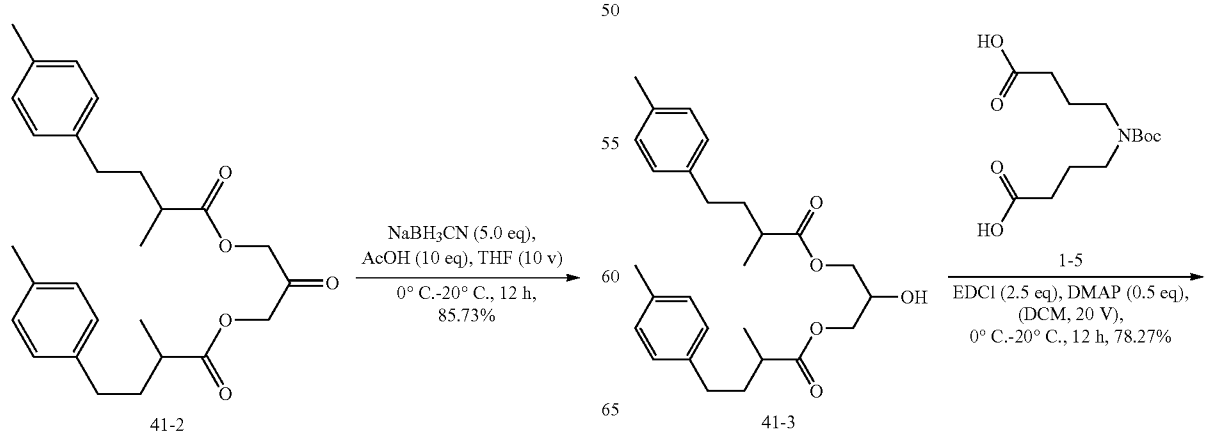

41-2

41-3

-continued

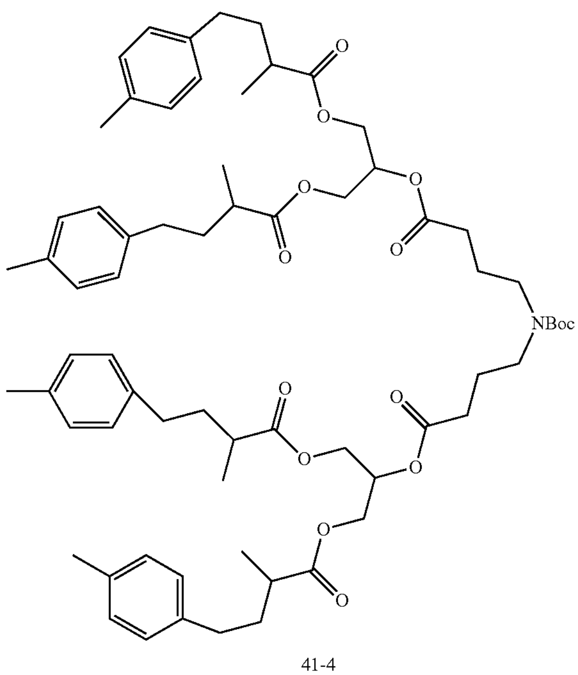

41-4

Into a 100 mL round-bottom flask, was placed 1-5 (2 g, 6.91 mmol, 1 equiv.) in DCM (40 mL, 20 V) followed by 41-3 (6.40 g, 14.52 mmol, 2.1 equiv.), DMAP (0.42 g, 3.46 mmol, 0.5 equiv.), and EDCI (3.31 g, 17.28 mmol, 2.5 equiv.) at 0° C. Then the reaction was stirred at 20° C. for 12 h. The resulting mixture was diluted with DCM (200 mL, 100 V). The organic layer was washed with (100 mL, 50 V) of water, brine (100 mL, 50 V), dried with anhydrous $Na_2SO_4$, filtered, and the filtrate was concentrated under vacuum. Crude product was adsorbed on 20 g of silica gel (type: ZCX-2, 100-200 mesh, 1.40 w./w.) and purified on a silica gel column (100 g of silica gel type: ZCX-2, 100-200 mesh, 10.00 w./w.) using petroleum ether/ethyl acetate (v/v) gradient from 100:0 to 90:10). Fractions were analyzed (TLC, PE:EA=100:1), combined, concentrated, and dried under vacuum to get 41-4 (6.3 g, 5.6 mmol, 78.2%) as a colorless oil. ELSD A: water/0.02% TFA: B: $CH_3CN$ 95:5 to 5:95 A/B at 3 min.): RT 2.5 min, m/z (Calcd.) 1134.6, (found) 1033.6 (M-Boc).

Synthesis of 41-5: ((4,4'-azanediylbis(butanoyl))bis(oxy))bis(propane-2,1,3-triyl) tetrakis(2-methyl-4-(p-tolyl)butanoate)trifluoroacetic Acid Salt

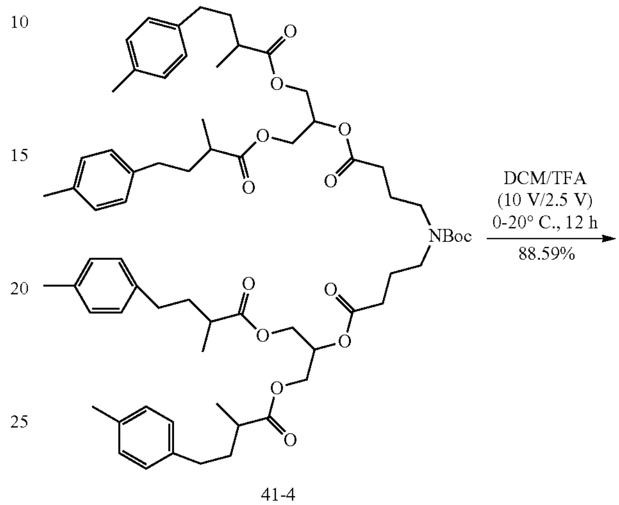

41-4

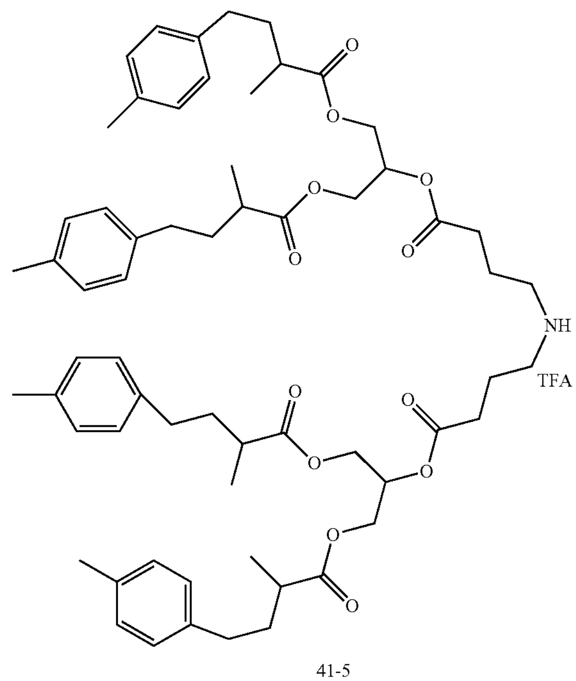

41-5

Into a 250 mL round-bottom flask, was placed 41-4 (6.0 g, 5.29 mmol, 1 equiv.), DCM (60 mL, 10 V), and TFA (15 mL, 2.5 V) was added at 0° C. The reaction mixture was stirred at 20° C. for 12 h. The resulting mixture was concentrated and dried under reduced pressure to get crude 41-5 as its trifluoroacetic acid salt (5.3 g, 4.68 mmol, 88.5%) as a yellow oil that was used without further purification. ELSD A: water/0.02% TFA: B: $CH_3CN$ 95:5 to 5:95 A/B at 3 min.): RT 1.9 min, m/z (Calcd.) 1033.6, (found) 1034.6 (M+H).

Synthesis of 41-6: ((4,4'-((1H-imidazole-1-carbonyl)azanediyl)bis(butanoyl))bis(oxy))bis(propane-2,1,3-triyl) tetrakis(2-methyl-4-(p-tolyl)butanoate)

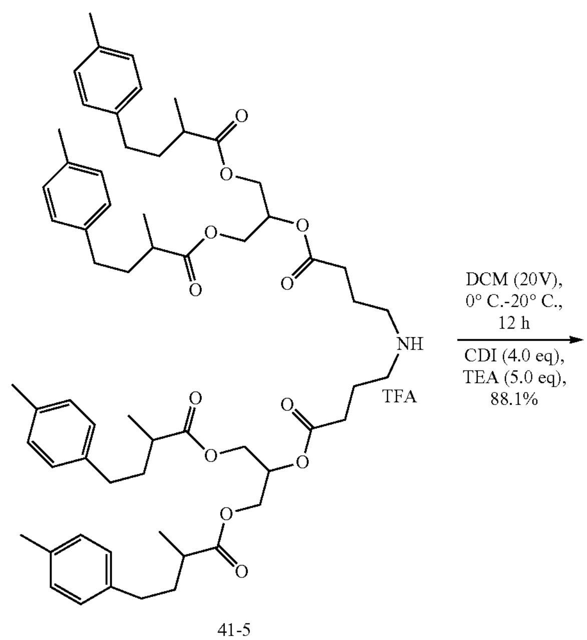

41-5

-continued

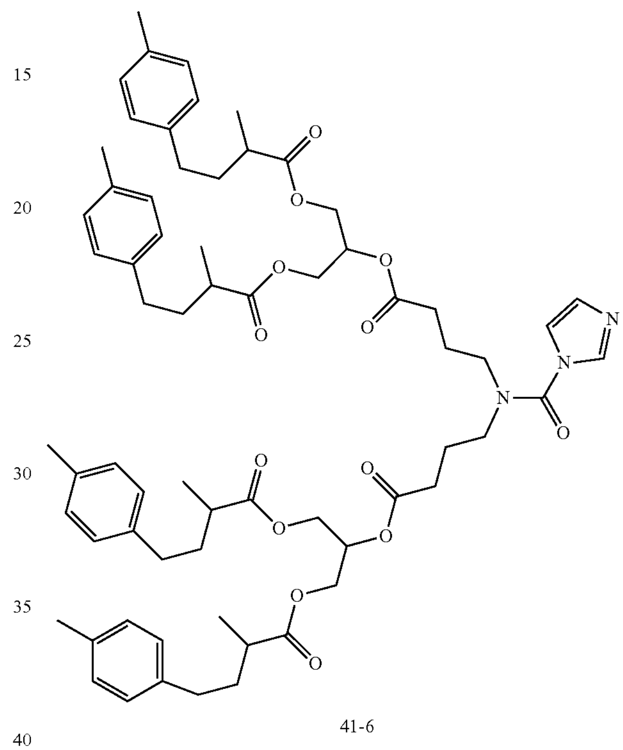

41-6

Into a 500 mL round-bottom flask 41-5 (5.0 g, 4.42 mmol, 1 equiv.) in DCM (100 mL, 20 V) was added followed by CDI (2.86 g, 17.64 mmol, 4 equiv.) and TEA (2.23 g, 22.04 mmol, 5.0 equiv.) at 0° C. The reaction mixture was stirred at 20° C. for 12 h. The resulting mixture was diluted with DCM (200 mL, 40 V), washed with water (100 mL, 20 V), brine (100 mL, 20 V), dried over anhydrous $Na_2SO_4$, filtered, and concentrated under reduced pressure to get 41-6 (4.5 g, 3.99 mmol, 88.1%) as a yellow oil that was used directly in the next reaction without purification. ELSD A: water/0.02% TFA: B: $CH_3CN$ 95:5 to 5:95 A/B at 3 min.): RT 2.2 min, m/z (Calcd.) 1127.6, (found) 1128.6 (M+H).

Synthesis of LIPID 41: ((4,4'-((((3-(dimethylamino)propyl)thio)carbonyl) azanediyl)bis(butanoyl))bis(oxy))bis(propane-2,1,3-triyl) tetrakis(2-methyl-4-(p-tolyl)butanoate)
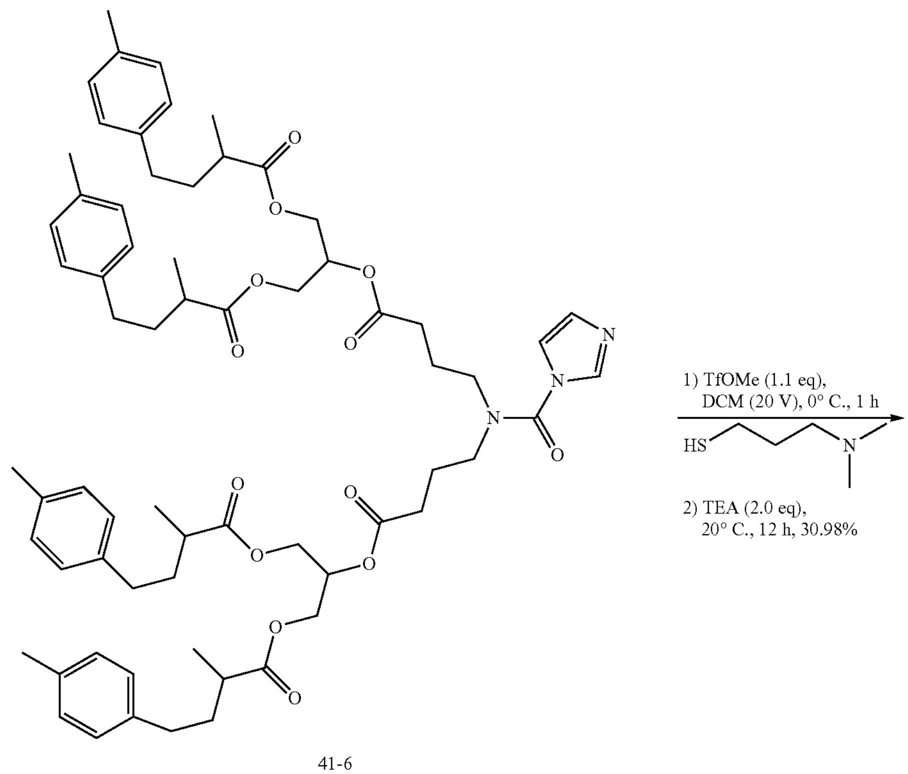
41-6
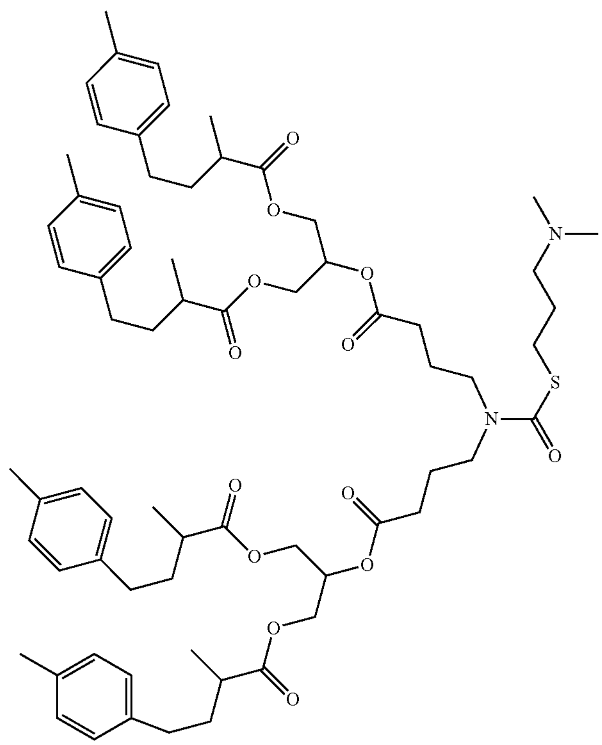
LIPID 41

Into a 250 mL round-bottom flask was taken 41-6 (4.0 g, 3.55 mmol, 1 equiv.) in DCM (80 mL, 20 V). To this was added the methyl triflate (0.64 g, 3.90 mmol, 1.1 equiv.) at 0° C. The reaction mixture was stirred at 0° C. for 1 h. Then TEA (0.72 g, 7.12 mmol, 2.0 equiv.) and 3-(dimethylamino) propane-1-thiol (0.63 g, 5.28 mmol, 1.5 equiv.) were added at 0° C. The reaction mixture was stirred at 20° C. for 12 h. The mixture was washed with $H_2O$ (40 mL, 10 V) three times and brine (40 mL, 10 V), dried over $Na_2SO_4$, filtered and the crude product was adsorbed on 40 g of silica gel (type: ZCX-2, 100-200 mesh, 1.40 w./w.) and purified on a silica gel column (200 g of silica gel type: ZCX-2, 100-200 mesh, 10.00 w./w.) using heptane/ethyl acetate (v/v) gradient from 100:0 to 40:60). Fractions were analyzed (TLC, Heptane:EA=5:1), combined, concentrated, and dried under vacuum to get 3.1 g (89%) of LIPID 41 which was further purified on Prep-Achiral-SFC (IntelFlash-1, Column: C18 silica gel; mobile phase A: IPA, phase B: Acetonitrile; 0% to 40% gradient in 25 min, 40% in 5 min; Detector, UV 220 nm/254 nm.). Qualified fractions were combined and concentrated to get pure LIPID 41 (1.2 g, 1.0 mmol, 31%) as a colorless semi-solid. ELSD A: water/0.05% TFA: B: $CH_3CN$/0.05% TFA 95:5 to 5:95 A/B at 3 min.): RT 2.1 min, m/z (Calcd.) 1178.6, (found) 1179.8 (M+H). $^1$H-NMR-LIPID 41: (300 MHz, Chloroform-d, ppm) δ 7.122-7.056 (m, 16H), 5.318-5.286 (m, 2H), 4.404-4.343 (m, 4H), 4.217-4.141 (m, 4H), 3.314 (brs, 4H), 2.913 (t, J=7.2 Hz, 2H), 2.614-2.453 (m, 14H), 2.350-2.297 (m, 22H), 2.060-1.939 (m, 4H), 1.931-1.793 (m, 6H), 1.788-1.632 (m, 4H), 1.201 (d, J=7.0 Hz, 12H).

Example 40. Biological Data of the Compounds of the Present Disclosure

A variety of assays were conducted to assess the efficacy of lipids of the present disclosure. A description of these assays follows.

Protocol for Factor VII Knock Down Evaluation

Lipid formulations comprising a FVII siRNA further described below were evaluated for their knockdown activity using the protocol of this example. In the FVII evaluation, seven to eight week-old, female Balb/C mice were purchased from Charles River Laboratories (Hollister, CA). The mice were held in a pathogen-free environment and all procedures involving the mice were performed in accordance with guidelines established by the Institutional Animal Care and Use Committee (IACUC). Lipid nanoparticles containing factor VII siRNA were administered intravenously at a dosing volume of 10 mL/kg and two dose levels (0.03 and 0.01 mg/kg). After 48 h, the mice were anesthetized with isoflurane and blood was collected retro-orbitally into Microtainer® tubes coated with 0.109 M sodium citrate buffer (BD Biosciences, San Diego, CA) and processed to plasma. Plasma specimens were tested for factor VII levels immediately or stored at −80° C. for later analysis. Measurement of FVII protein in plasma was determined using the colorimetric Biophen VII assay kit (Aniara Diagnostica, USA). Absorbance was measured at 405 nm and a calibration curve was generated using the serially diluted control plasma to determine levels of factor VII in plasma from treated animals, relative to the saline-treated control animals.

Protocol for hEPO mRNA Expression Evaluation

Lipid formulations comprising a hEPO mRNA below were evaluated for their ability to express hEPO in vivo according to the protocol of this example. All animal experiments were conducted using institutionally-approved protocols (IACUC). In this protocol, female Balb/c mice at least 6-8 weeks of age were purchased from Charles River Laboratory. The mice were intravenously injected with hEPO-LNPs via the tail vein with one of two dose levels of hEPO (0.1 and 0.03 mg/kg). After 6 hr, blood was collected with serum separation tubes, and the serum was isolated by centrifugation. Serum hEPO levels were then measured using an ELISA assay (Human Erythropoietin Quantikine IVD ELISA Kit, R&D Systems, Minneapolis, MD).

Mouse Plasma Stability

Lipid stock solution was prepared by dissolution of the lipid in isopropanol at the concentration of 5 mg/mL. A requisite volume of the lipid-isopropanol solution was then diluted to 100 μM concentration at a total volume of 1.0 mL with in 50:50 (v/v) ethanol/water. Ten microliters of this 100 μM solution was spiked into 1.0 mL of mouse plasma (BioIVT, Cat. No.: MSE00PLNHUNN, CD-1 mouse, anticoagulant: sodium heparin, not filtered) that was prewarmed to 37° C. and and was stirred at 50 rpm with a magnetic stir bar. The starting concentration of lipids in plasma was thus 1 μM. At time points 0, 15, 30, 45, 60 and 120 min, 0.1 mL of the plasma was withdrawn from the reaction mixture and the protein was precipitated by adding 0.9 mL of ice-cold 4:1 (v/v) acetonitrile/methanol with 1 μg/mL of a selected internal standard lipid added. After filtration through a 0.45 micron 96-well filtering plate, the filtrates were analyzed by LC-MS (Thermo Fisher's Vanquish UHPLC-LTQ XL linear ion trap Mass Spectrometer); Waters XBridge BEH Shield RP18 2.5 micron (2.1×100 mm) column with its matching guard column. Mobile phase A was 0.1% formic acid in water, and mobile phase B was 0.1% formic acid in 1:1 (v/v) acetonitrile/methanol. Flow rate was 0.5 ml/min. Elution gradient was: Time 0-1 min: 10% B; 1-6 min: 10%-95% B; 6-8.5 min: 95% B; 8.5-9 min: 95%-10% B; 9-10 min: 10% B. Mass spectrometry was in positive scanning mode from 600-1100 m/z. The peak of the molecular ion of the lipids was integrated in the extracted ion chromatography (XIC) using Xcalibur software (Thermo Fisher). The relative peak area compared to T=0, after normalization by the peak area of the internal standard, was used as the percentage of the lipid remaining at each time point. $T_{1/2}$ values were calculated using the first-order decay model.

In Vivo Biodegradability Assay

In vivo biodegradability assay was performed to assess the biodegradability of lipids in the LNP. Briefly, mice were injected with either 0.1 or 0.03 mg/Kg dose and after 24 or 48 hours mice livers were collected. To measure the concentration of lipids in the mouse liver, liver samples were homogenized in appropriate buffer in 1-10 dilution and mixed with the same amount of stabilized plasma. The samples were then mixed with organic solvents spiked with internal standard to precipitate proteins. After centrifugation, supernatant was diluted further with organic solvent before sample analysis by LC-MS. In LC-MS analysis, positive electrospray ionization was used, and multiple reaction monitoring (MRM) parameters were set up to specifically target the lipid analyte and internal standard. Calibration standards were prepared in stabilized plasma and mixed with same amount of homogenization buffer before protein precipitation. Quality control samples with known amounts of lipid was prepared in blank liver homogenate to monitor the precision and accuracy of the assay.

Example 41. Log D and pKa Data of the Compounds of the Present Disclosure

Calculated Log D (c Log D) and calculated pKa (cpKa) values for lipid compounds were determined using ACD Labs Version B and ACD Labs Structure Designer version 12.0, respectively. Measured pKa values were determined based on the pH measured in the indicated formulation (i.e., EPO or FVII formulation). The data are summarized in Table 1 and Table 2.

TABLE 1

Biological Assays, Half-Life, Degradability, and cpKa and cLogD Data

| LIPID/ Attri-butes | FVII KD % 0.03 mpk | FVII KD % 0.01 mpk | EPO exprssn (ng/mL) 0.03 mpk | EPO exprssn (ng/mL) 0.1 mpk | Plasma half life % remain-ing after 2 h | In vivo degrad-ability (ng/tissue) at 48 h 0.03 mpk | In vivo degrad-ability (ng tissue) at 48 h 0.1 mpk | c-pka (pKa: EPO/ FVII) | cLogD |
|---|---|---|---|---|---|---|---|---|---|
| 1 | 100 | 84 | 432 | 1413 | 14 | BLOQ | BLOQ | 9.34 (6.4/ 6.64) | 13.9 |
| 2 | ND | ND | ND | ND | ND | ND | ND | 9.36 | 11.9 |
| 3 | 87 | 51 | 191 | 471 | 15 | BLOQ | BLOQ | 9.36 (6.41/ 6.49) | 13.95 |
| 4 | 33 | 71 | 392 | 1108 | 13 | BLOQ | BLOQ | 9.31 (6.22/ ND) | 12.58 |
| 5 | 62 | 90 | 87 | 533 | 40 | BLOQ | BLOQ | 9.36 (6.37/ 6.54) | 13.09 |
| 6 | 64 | 87 | 46 | 324 | 6 | BLOQ | BLOQ | 9.34 (7.12/ 7.02) | 13.9 |
| 7 | ND | ND | ND | ND | ND | ND | ND | 9.31 (ND) | ND |
| 8 | ND | ND | 169 | 701 | 81 | BLOQ | BLOQ | 9.29 (6.50/ ND) | 13.23 |
| 9 | ND | ND | ND | ND | ND | ND | ND | 9.30 ND | ND |
| 10 | 83 | 92 | 387 | 1179 | 36 | BLOQ | BLOQ | 9.35 (6.46/ 6.67) | 11.59 |
| 11 | 22 | 84 | 169 | 548 | 40 | BLOQ | BLOQ | 9.35 (6.6/ 6.68) | 13.63 |
| 12 | 69 | 91 | 286 | 768 | 57 | BLOQ | BLOQ | 9.35 (6.46/ 6.61) | 13.08 |
| 13 | 87 | 60 | ND | ND | 74 | <340 | <340 | 9.34 (6.40/ 6.61) | 13.29 |
| 14 | 90 | 65 | ND | ND | 116 | <340 | <340 | 9.34 (7.19/ 6.86) | 13.63 |
| 15 | ND | ND | ND | ND | 256 | <340 | <340 | 9.34 (6.57/ 6.45) | 12.72 |
| 16 | 88 | 58 | 2088 | 6358 | 40 | <340 | <340 | 9.34 (6.50/ 6.45) | 12.72 |
| 17 | 81 | 55 | 1082 | 1555 | ND | BLOQ | BLOQ | 9.34 (6.35/ 6.35) | 13.01 |
| 18 | 88 | 60 | ND | 1081 | 100 | <340 | 639 | 9.34 (6.44/ 6.49) | 13.27 |
| 19 | ND | ND | ND | ND | ND | <340 | 847 | 9.34 (6.27/ ND) | 14.92 |
| 20 | ND | ND | ND | ND | ND | ND | ND | 9.34 (ND) | 14.29 |
| 21 | ND | ND | ND | ND | ND | ND | ND | 9.34 (ND) | 12.26 |
| 22 | ND | ND | ND | ND | ND | ND | ND | 9.34 | 12.26 |
| 23 | ND | ND | ND | ND | ND | ND | ND | 9.34 | 13.43 |
| 24 | ND | ND | ND | ND | ND | ND | ND | 9.34 | 12.41 |
| 25 | ND | ND | ND | ND | ND | ND | ND | 9.34 | 14.23 |
| 26 | ND | ND | ND | ND | ND | ND | ND | 8.66 | 13.95 |
| 27 | ND | ND | ND | ND | ND | ND | ND | 9.34 | 13.47 |
| 28 | ND | ND | ND | ND | ND | ND | ND | 9.34 | 12.02 |

TABLE 1-continued

| Biological Assays, Half-Life, Degradability, and cpKa and cLogD Data | | | | | | | | | |
|---|---|---|---|---|---|---|---|---|---|
| LIPID/ Attri- butes | FVII KD % 0.03 mpk | FVII KD % 0.01 mpk | EPO exprssn (ng/mL) 0.03 mpk | EPO exprssn (ng/mL) 0.1 mpk | Plasma half life % remain- ing after 2 h | In vivo degrad- ability (ng/tissue) at 48 h 0.03 mpk | In vivo degrad- ability (ng tissue) at 48 h 0.1 mpk | c-pka (pKa: EPO/ FVII) | cLogD |
| 29 | ND | ND | ND | ND | ND | ND | ND | 9.34 | 9.91 |
| 30 | ND | ND | ND | ND | ND | ND | ND | 9.34 | 12.02 |
| 31 | ND | ND | ND | ND | ND | ND | ND | 9.34 | 14.13 |
| 32 | ND | ND | ND | ND | ND | ND | ND | ND | ND |
| 33 | ND | ND | ND | ND | ND | ND | ND | ND | ND |
| 34 | ND | ND | ND | ND | ND | ND | ND | ND | ND |

ND: not determined

BLOQ: below level of quantification

TABLE 2

| Biological Assays, Half-Life, Degradability, and cpKa and cLogD Data | | | | | | | | | |
|---|---|---|---|---|---|---|---|---|---|
| LIPID/ Attri- butes | FVII KD % 0.03 mpk | FVII KD % 0.01 mpk | EPO exprssn (ng/mL) 0.03 mpk | EPO exprssn (ng/mL) 0.1 mpk | Plasma half life % remain- ing after 2 h | In vivo degrad- ability (ng/tissue) at 48 h 0.03 mpk | In vivo degrad- ability (ng/tissue) at 48 h 0.1 mpk | c-pKa (pKa: EPO/ FVII) | cLogD |
| 1 | 100 | 84 | 432 | 1413 | 14 | BLOQ | BLOQ | 9.34 (6.4/ 6.64) | 13.9 |
| 2 | ND | ND | ND | ND | ND | ND | ND | 9.36 | 11.9 |
| 3 | 87 | 51 | 191 | 471 | 15 | BLOQ | BLOQ | 9.36 (6.41/ 6.49) | 13.95 |
| 4 | 33 | 71 | 392 | 1108 | 13 | BLOQ | BLOQ | 9.3 (6.22/ ND) | 12.58 |
| 5 | 62 | 90 | 87 | 533 | 40 | BLOQ | BLOQ | 9.36 (6.37/ 6.54) | 13.09 |
| 6 | 64 | 87 | 46 | 324 | 6 | BLOQ | BLOQ | 9.34 (7.12/ 7.02) | 13.9 |
| 7 | ND | ND | ND | ND | ND | ND | ND | 9.31 (ND) | ND |
| 8 | ND | ND | 169 | 701 | 81 | BLOQ | BLOQ | 9.29 (6.50/ ND) | 13.23 |
| 9 | ND | ND | ND | ND | ND | ND | ND | 9.30 ND | ND |
| 10 | 83 | 92 | 387 | 1179 | 36 | BLOQ | BLOQ | 9.35 (6.46/ 6.67) | 11.59 |
| 11 | 22 | 84 | 169 | 548 | 40 | BLOQ | BLOQ | 9.35 (6.6/ 6.68) | 13.63 |
| 12 | 69 | 91 | 286 | 768 | 57 | BLOQ | BLOQ | 9.35 (6.46/ 6.61) | 13.08 |
| 13 | 87 | 60 | ND | 1488.1 | 74 | <340 | <340 | 9.34 (6.40/ 6.61) | 13.29 |
| 14 | 90 | 65 | ND | 1152 | 100 | <340 | <340 | 9.34 (7.19/ 6.86) | 13.63 |

TABLE 2-continued

Biological Assays, Half-Life, Degradability, and cpKa and cLogD Data

| LIPID/ Attri- butes | FVII KD % 0.03 mpk | FVII KD % 0.01 mpk | EPO exprssn (ng/mL) 0.03 mpk | EPO exprssn (ng/mL) 0.1 mpk | Plasma half life % remain- ing after 2 h | In vivo degrad- ability (ng/tissue) at 48 h 0.03 mpk | In vivo degrad- ability (ng/tissue) at 48 h 0.1 mpk | c-pKa (pKa: EPO/ FVII) | cLogD |
|---|---|---|---|---|---|---|---|---|---|
| 15 | 89.7 | 66.8 | ND | 1899 | 100 | <340 | <340 | 9.34 (6.57/ 6.45) | 12.72 |
| 16 | 88 | 58 | ND | 2088 | 40 | <340 | <340 | 9.34 (6.50/ 6.45) | 12.72 |
| 17 | 81 | 55 | ND | 1082 | 100 | BLOQ | BLOQ | 9.34 (6.35/ 6.35) | 13.01 |
| 18 | 88 | 60 | ND | 1081 | 100 | <340 | 639 | 9.34 (6.44/ 6.49) | 13.27 |
| 19 | ND | ND | ND | 958 | 100 | <340 | 847 | 9.34 (6.27/ ND) | 14.92 |
| 20 | 74 | 36 | ND | 1148 | 100 | <340 | <340 | 9.34 (ND) | 14.29 |
| 21 | 90 | 57 | ND | 1028 | 100 | <340 | <340 | 9.34 (ND) | 12.26 |
| 22 | 87 | 56 | ND | 1104 | 100 | <340 | <340 | 9.34 (ND) | 12.26 |
| 23 | 61.7 | 17 | ND | 730 | 100 | <340 | <340 | 9.34 (ND) | 13.43 |
| 24 | 87.4 | 60.5 | ND | 1420 | 100 | BLOQ | BLOQ | 9.34 | 12.41 |
| 25 | 95 | 63 | ND | 2945 | 100 | BLOQ | BLOQ | 9.34 | 14.23 |
| 26 | 50 | 8 | ND | 70 | 100 | BLOQ | BLOQ | 8.66 | 13.95 |
| 27 | 84.9 | 48.1 | ND | 69 | 100 | BLOQ | BLOQ | 9.34 | 13.47 |
| 28 | 75.3 | 26 | ND | 216 | 100 | BLOQ | BLOQ | 9.34 | 12.02 |
| 29 | ND | ND | ND | ND | ND | ND | ND | 9.34 | 9.91 |
| 30 | 62.1 | 3.2 | ND | 95 | 100 | BLOQ | BLOQ | 9.34 | 12.02 |
| 31 | ND | ND | ND | ND | ND | ND | ND | 9.34 | 14.13 |
| 32 | ND | ND | ND | ND | ND | ND | ND | ND | ND |
| 33 | ND | ND | ND | ND | ND | ND | ND | ND | ND |
| 34 | ND | ND | ND | ND | ND | ND | ND | ND | ND |
| 35 | 84 | 68.5 | ND | 678 | ND | ND | ND | 9.27 | 13.03 |
| 36 | 0 | 0 | ND | 0 | ND | ND | ND | 9.58 | 11.82 |
| 37 | ND | ND | ND | ND | ND | ND | ND | 9.58 | 12.7 |
| 38 | ND | ND | ND | ND | ND | ND | ND | 9.68 | 12.28 |
| 39 | ND | ND | ND | ND | ND | ND | ND | ND | 11.83 |
| 40 | ND | ND | ND | ND | ND | ND | ND | 9.36 | 13.31 |
| 41 | 76 | 56 | ND | 1209 | ND | ND | ND | ND | ND |

ND: not determined

BLOQ: below level of quantification

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula I, or a pharmaceutically acceptable salt thereof:

(I)

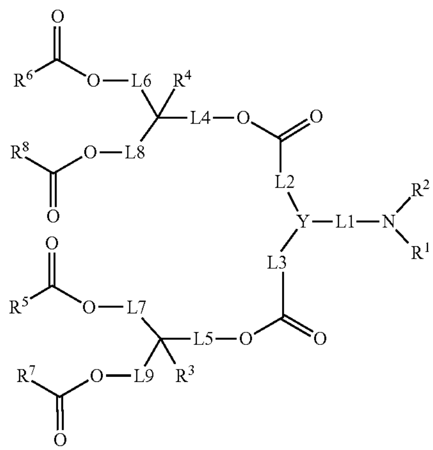

wherein:

$R^1$ and $R^2$ are each independently H or $C_{1-6}$ alkyl; or $R^1$ and $R^2$ are joined to form a saturated heterocyclic ring, wherein:

$R^1$ is a linear $C_{1-4}$ alkylene; and $R^2$ is $—(CH_2)_m(X)_n—$, wherein

X is O, S, or $NR^9$, wherein $R^9$ is H or $C_{1-6}$ alkyl;

m is 1, 2, 3 or 4, and n is 0 or 1;

L1 is a linear $C_{1-6}$ alkylene optionally substituted with one to three methyl groups;

Y is selected from the group consisting of:

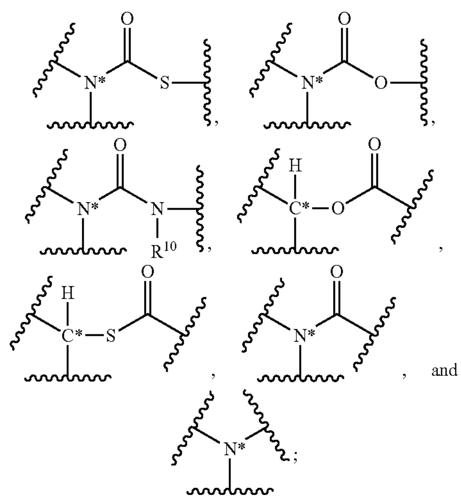

wherein:

each asterisk (*) indicates the atom attached to L2 and L3; and $R^{10}$ is H or $C_{1-6}$ alkyl;

L2 and L3 are each independently a linear $C_{1-8}$ alkylene;

L4, L5, L6, L7, L8 and L9 are each independently absent or $—CH_2—$, provided that:

at least two of L4, L6 and L8 are $—CH_2—$; and at least two of L5, L7 and L9 are $—CH_2—$;

$R^3$ and $R^4$ are each independently H, methyl or ethyl; and $R^5$, $R^6$, $R^7$ and $R^8$ are each independently selected from the group consisting of:

(a) linear $C_{1-20}$ alkyl, wherein each said linear $C_{1-20}$ alkyl is optionally substituted with one or more substituents selected from the group consisting of:

(i) $C_{1-6}$ alkyl, $C_{1-6}$ alkoxy and —F, wherein each said $C_{1-6}$ alkyl substituent is optionally substituted with one or more groups selected from the group consisting of $C_{1-3}$ alkoxy and —F;

(ii) $C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

(iii) $C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and (iv) $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F;

(b) $C_{3-8}$ monocycloalkyl, wherein each said $C_{3-8}$ monocycloalkyl is optionally substituted with one or more substituents selected from the group consisting of $C_{1-6}$ alkyl, $C_{1-6}$ alkoxy and —F;

(c) $C_{7-12}$ bicycloalkyl, wherein each said $C_{7-12}$ bicycloalkyl is optionally substituted with one or more substituents selected from the group consisting of $C_{1-6}$ alkyl, $C_{1-6}$ alkoxy and —F; and (d) $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-6}$ alkoxy and —F.

2. The compound of claim 1, wherein Y is selected from the group consisting of:

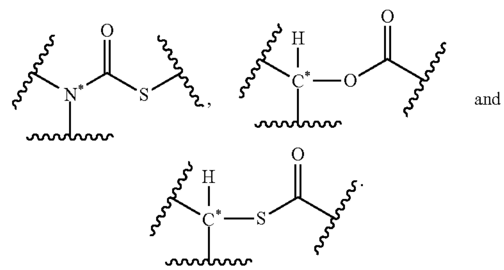

3. The compound of claim 1, wherein $R^1$ and $R^2$ are each independently $C_{1-6}$ alkyl.

4. The compound of claim 1, wherein $R^5$, $R^6$, $R^7$ and $R^8$ are each independently selected from the group consisting of:

(a) linear $C_{1-8}$ alkyl, wherein each said linear $C_{1-8}$ alkyl is optionally substituted with one or more substituents selected from the group consisting of:

(i) $C_{1-3}$ alkyl, $C_{1-3}$ alkoxy and —F, wherein each said $C_{1-3}$ alkyl substituent is optionally substituted with one or more groups selected from the group consisting of $C_{1-3}$ alkoxy and —F;

(ii) saturated $C_{3-6}$ monocycloalkyl, wherein each said saturated $C_{3-6}$ monocycloalkyl is optionally substituted with one or more substituents selected from the group consisting of $C_{1-6}$ alkyl, $C_{1-3}$ alkoxy and —F;

(iii) saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F; and (iv) $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-3}$ alkoxy and —F;

(b) saturated $C_{3-6}$ monocycloalkyl, wherein each said $C_{3-6}$ monocycloalkyl is optionally substituted with one or more substituents selected from the group consisting of $C_{1-6}$ alkyl, $C_{1-3}$ alkoxy and —F;

(c) saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F; and (d) $C_{6-10}$ aryl, wherein each said $C_{6-10}$ aryl is a monocyclic or bicyclic aromatic hydrocarbon optionally substituted with one or more substituents selected from the group consisting of $C_{1-6}$ alkyl, $C_{1-3}$ alkoxy and —F.

5. The compound of claim 4, wherein $R^5$, $R^6$, $R^7$ and $R^8$ are each independently linear $C_{1-8}$ alkyl, wherein each said linear $C_{1-8}$ alkyl is optionally substituted with one or more substituents selected from the group consisting of $C_{1-3}$ alkyl, $C_{1-3}$ alkoxy and —F, wherein each said $C_{1-3}$ alkyl substituent is optionally substituted with one or more groups selected from the group consisting of $C_{1-3}$ alkoxy and —F.

6. The compound of claim 4, wherein $R^5$, $R^6$, $R^7$ and $R^8$ are each independently linear $C_{1-8}$ alkyl optionally substituted with saturated $C_{3-6}$ monocycloalkyl, wherein each said saturated $C_{3-6}$ monocycloalkyl is optionally substituted with one or more substituents selected from the group consisting of $C_{1-6}$ alkyl, $C_{1-3}$ alkoxy and —F.

7. The compound of claim 6, wherein each said saturated $C_{3-6}$ monocycloalkyl is optionally substituted with one or more $C_{1-3}$ alkyl.

8. The compound of claim 4, wherein $R^5$, $R^6$, $R^7$ and $R^8$ are each independently linear $C_{1-8}$ alkyl optionally substituted with saturated $C_{7-12}$ bicycloalkyl, wherein each said saturated $C_{7-12}$ bicycloalkyl is optionally substituted with one or more substituents selected from the group consisting of $C_{1-6}$ alkyl, $C_{1-3}$ alkoxy and —F.

9. The compound of claim 4, wherein $R^5$, $R^6$, $R^7$ and $R^8$ are each independently saturated $C_{3-6}$ monocycloalkyl, wherein each said $C_{3-6}$ monocycloalkyl is optionally substituted with one or more substituents selected from the group consisting of $C_{1-6}$ alkyl, $C_{1-3}$ alkoxy and —F.

10. The compound of claim 4, wherein $R^5$, $R^6$, $R^7$ and $R^8$ are each independently monocycloalkyl selected from the group consisting of:

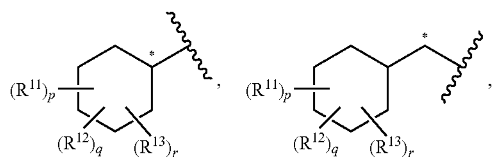

-continued

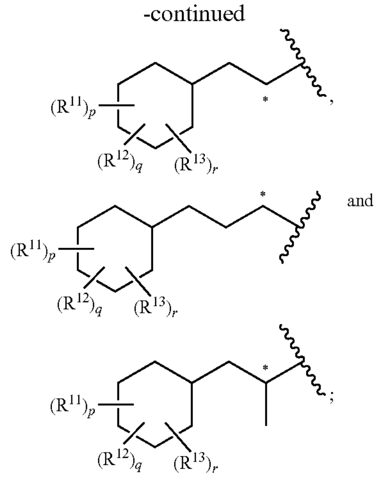

wherein:

each asterisk (*) indicates the atom attached to the carbonyl carbon;

each $R^{11}$ is independently $C_{1-6}$ alkyl;

each $R^{12}$ is independently $C_{1-3}$ alkoxy;

each $R^{13}$ is —F;

each p is independently 0 to 11;

each q is independently 0 to 11; and each r is independently 0 to 11;

wherein the sum of p, q and r is no greater than 11.

11. The compound of claim 4, wherein $R^5$, $R^6$, $R^7$ and $R^8$ are each independently selected from the group consisting of:

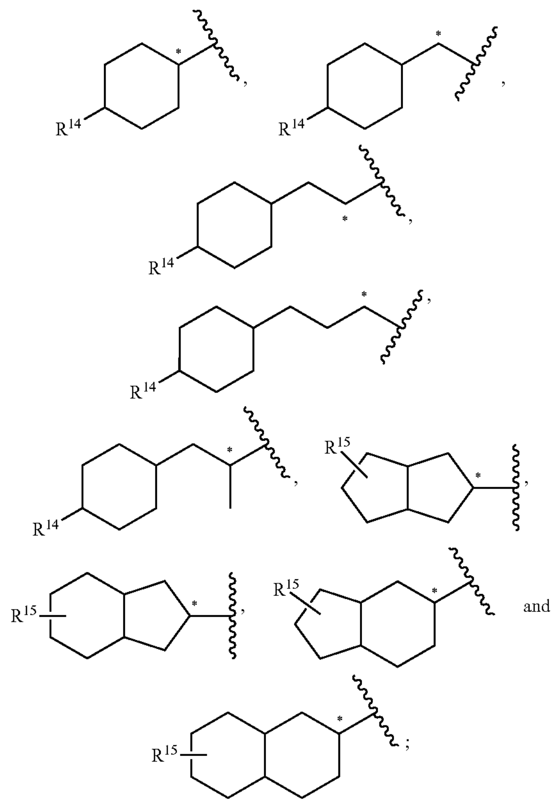

wherein:

each asterisk (*) indicates the atom attached to the carbonyl carbon;

each $R^{14}$ is independently H or $C_{1-6}$ alkyl; and each $R^{15}$ is independently H or $C_{1-6}$ alkyl.

12. The compound of claim 1, wherein L1 is linear unsubstituted alkylene.

13. The compound of claim 1, wherein L2 and L3 are each independently linear $C_{1-5}$ alkylene.

14. The compound of claim 1, wherein L6, L7, L8 and L9 are each —$CH_2$—; and L4 and L5 are absent.

15. The compound of claim 1 selected from the group consisting of:

LIPID 1

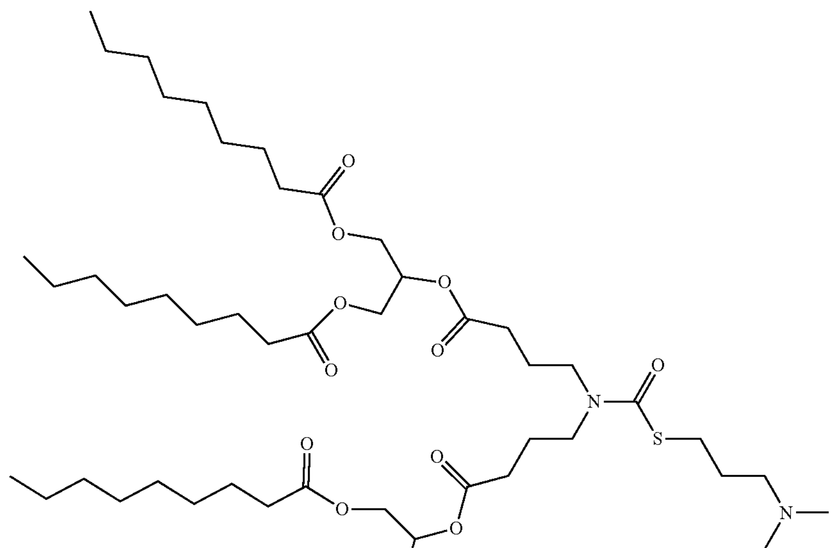

;

LIPID 2

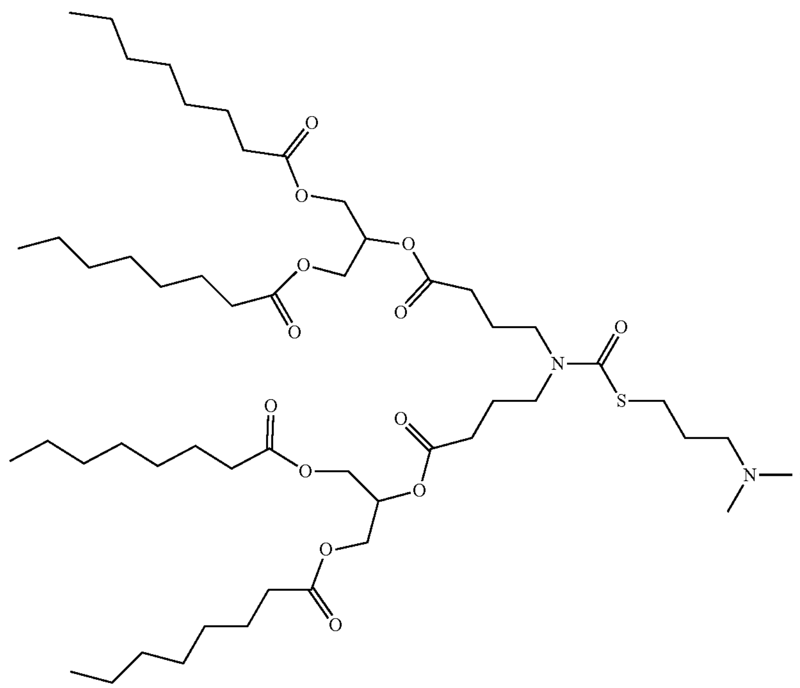

;

-continued
LIPID 3
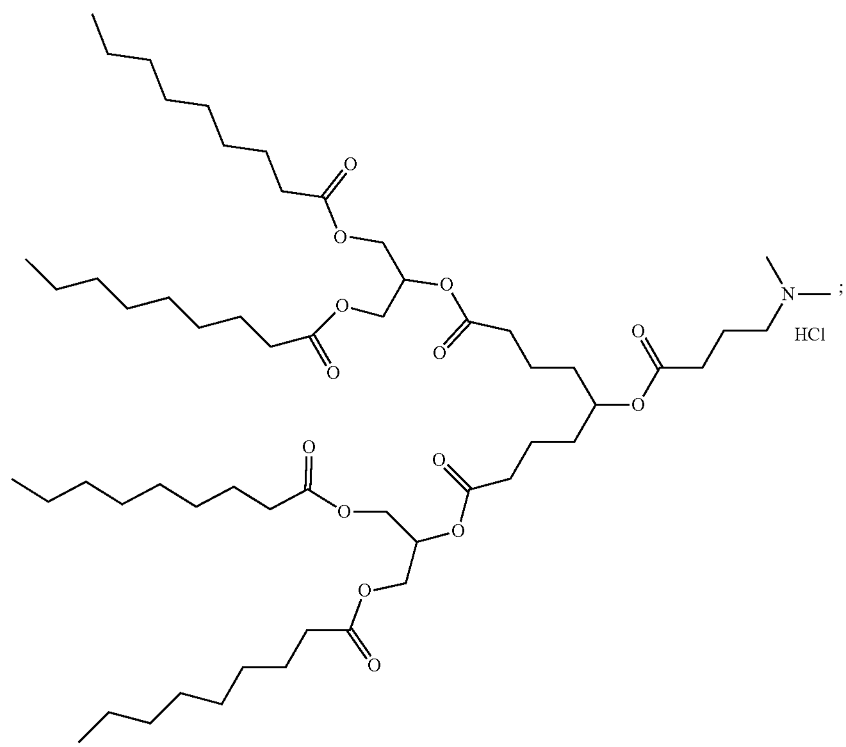
LIPID 4
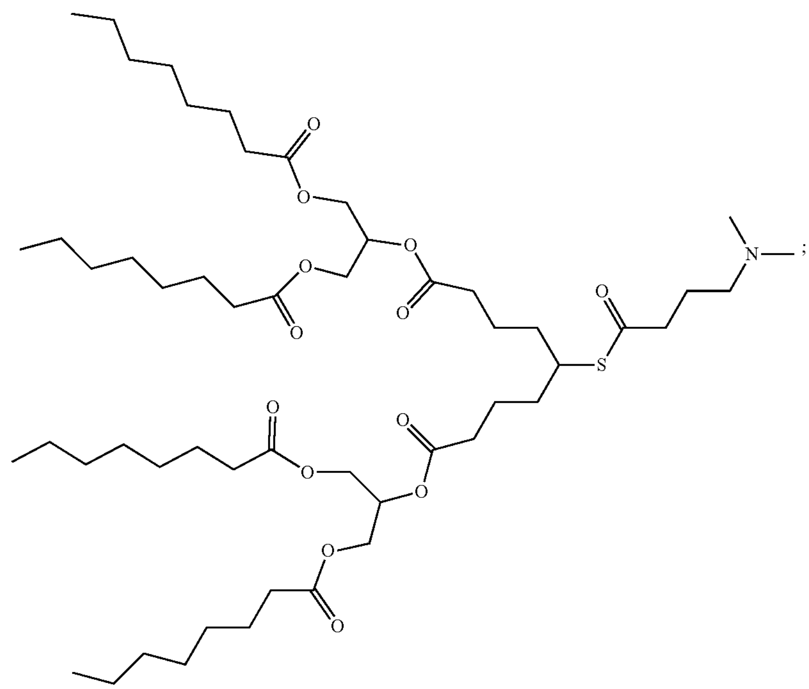

-continued
LIPID 5
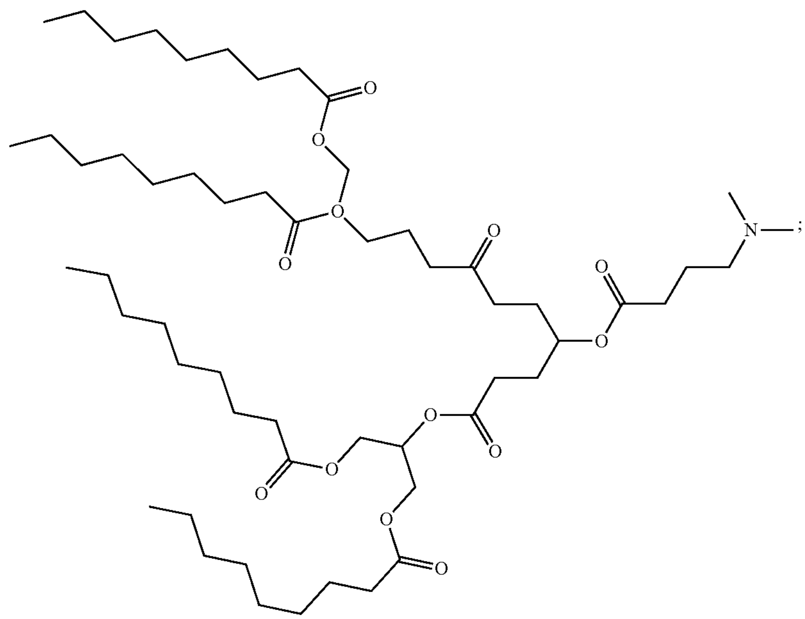
LIPID 6
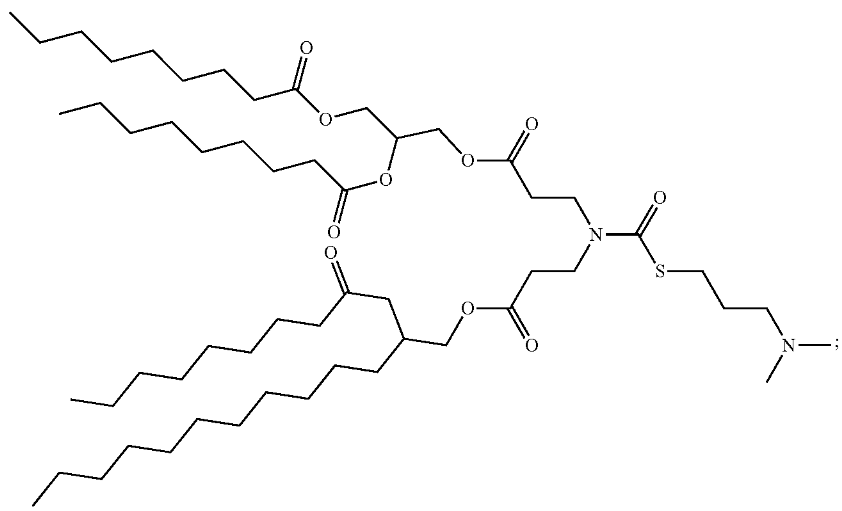
LIPID 6a
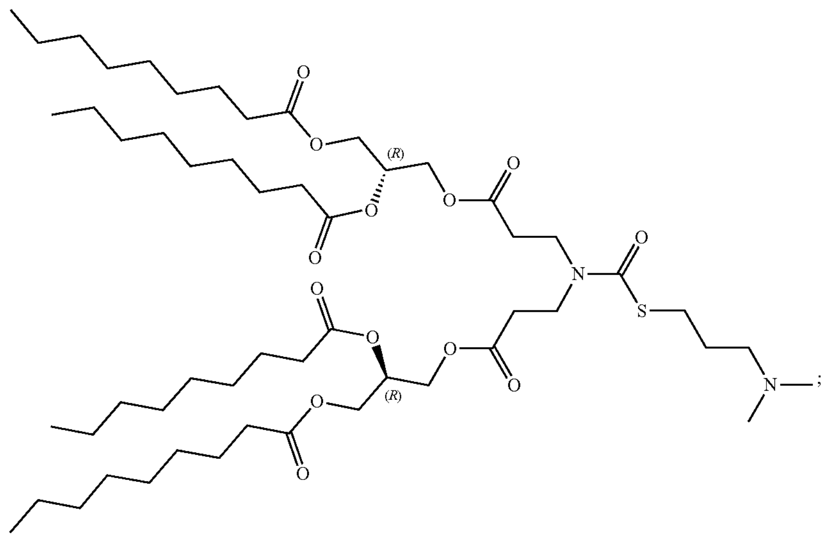

-continued
LIPID 7
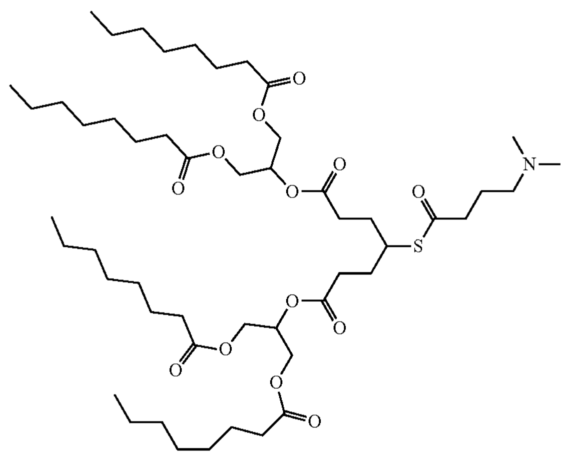
;
LIPID 8
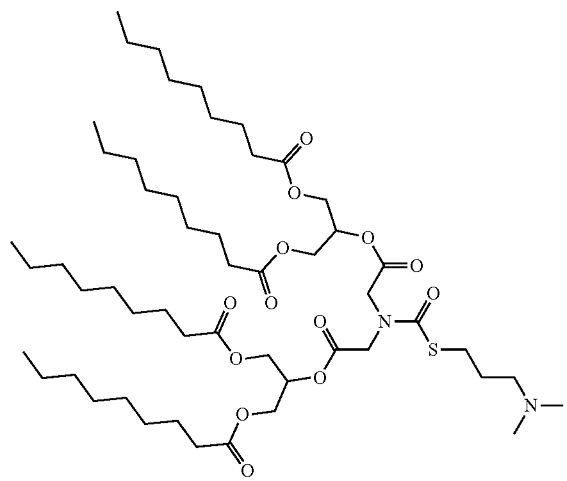
;
LIPID 9
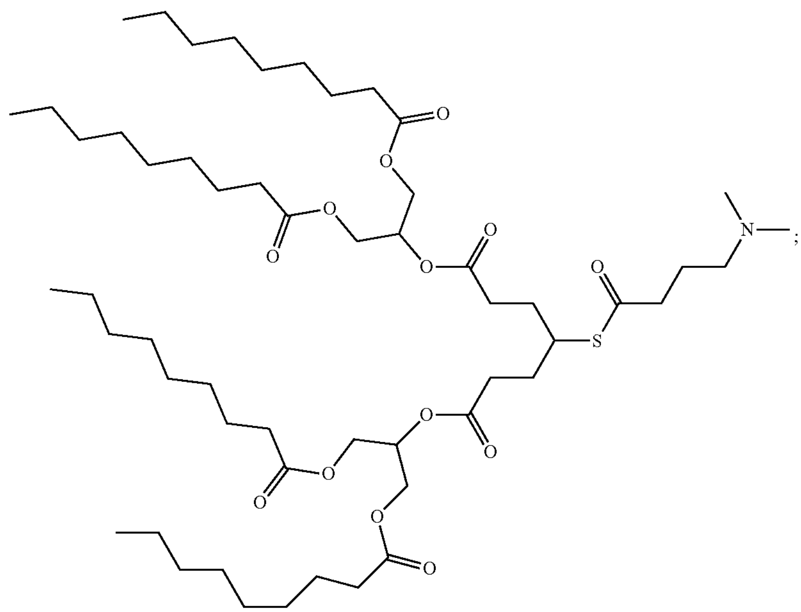
;
LIPID 10
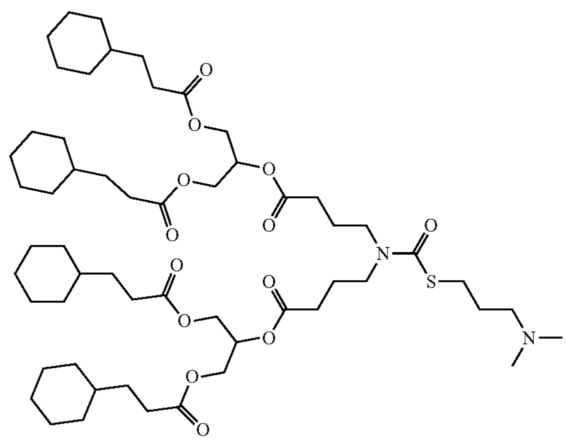
;
LIPID 11
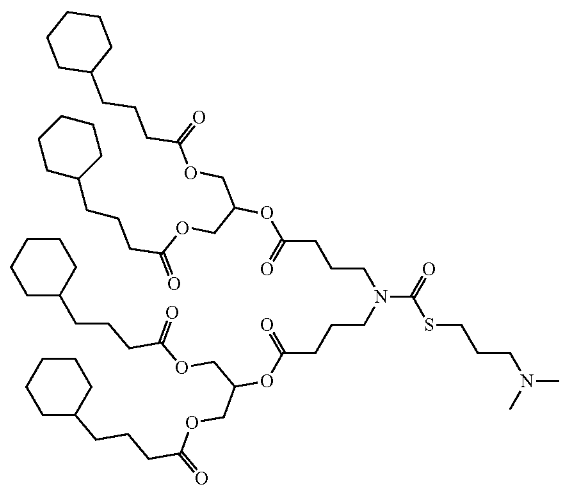
;

-continued
LIPID 12
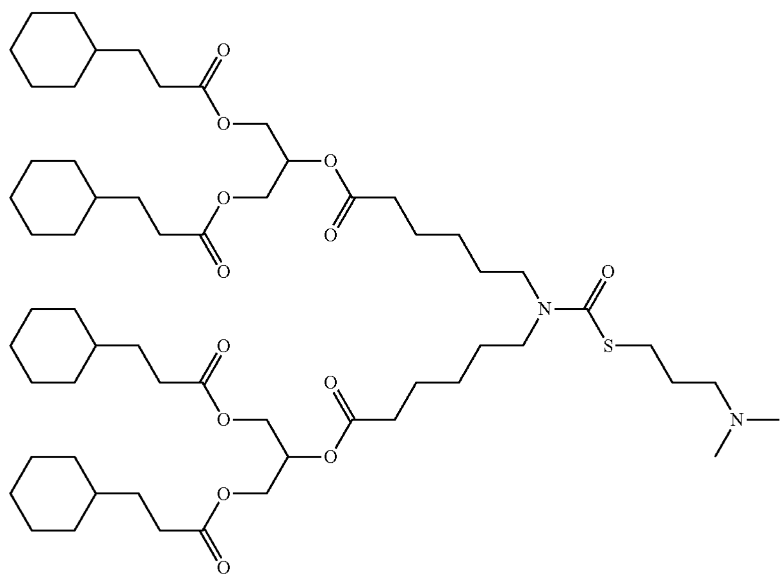
;
LIPID 13
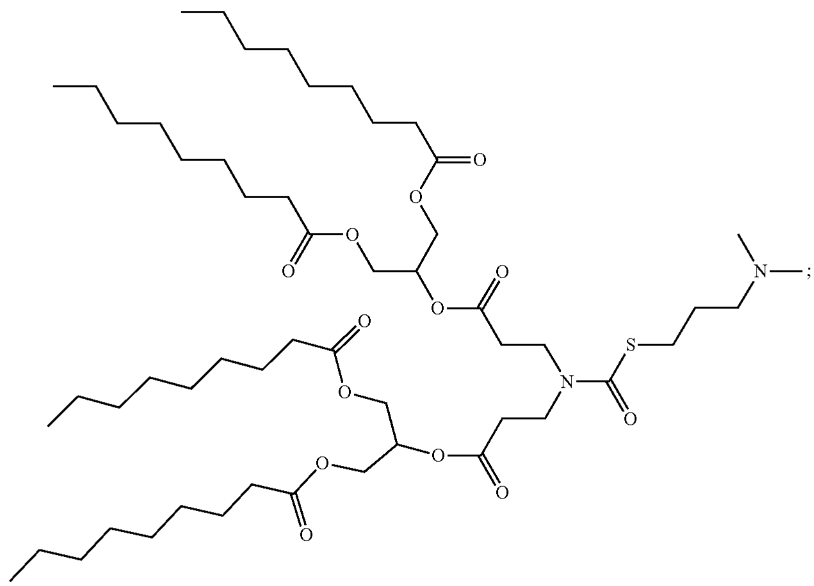
;

-continued
LIPID 14
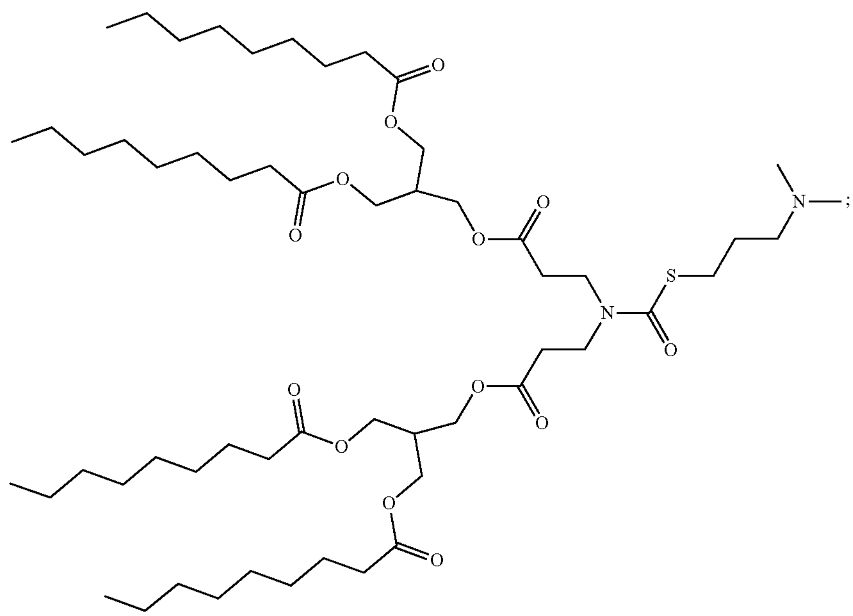
;
LIPID 15
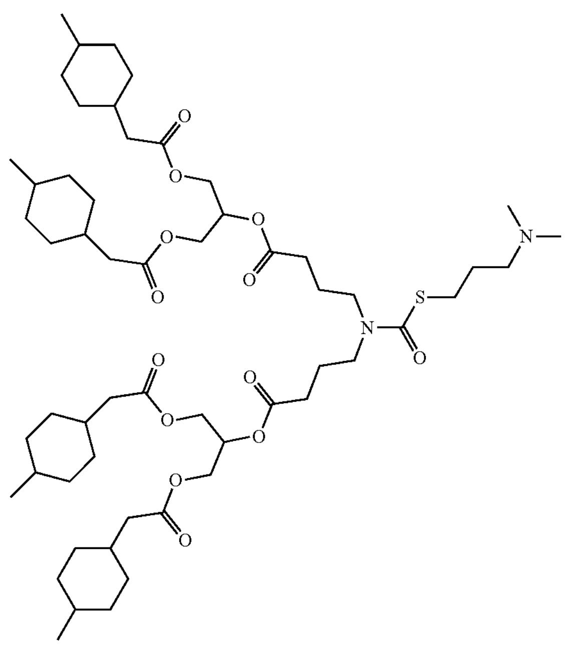
;
LIPID 16
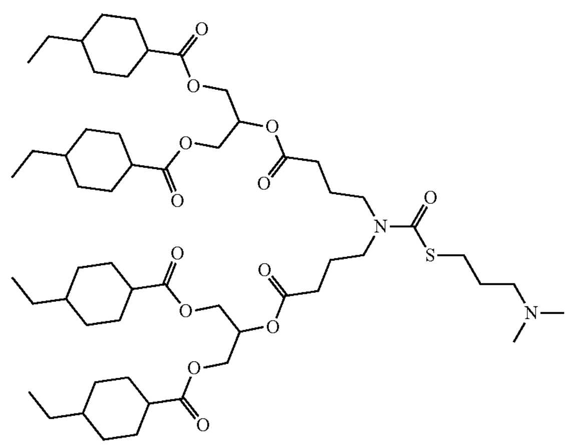
;

-continued
LIPID 17
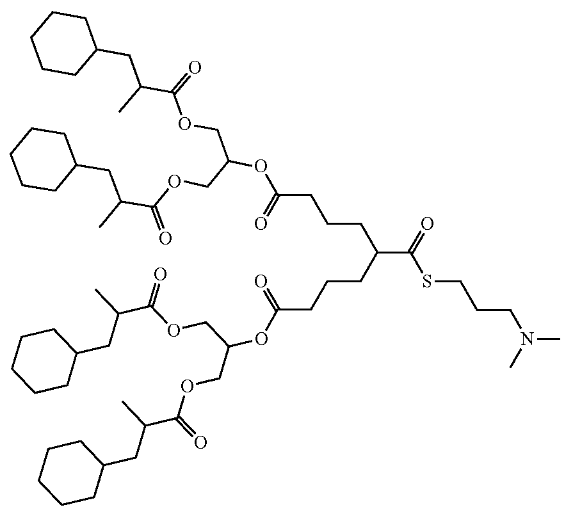
;
LIPID 18
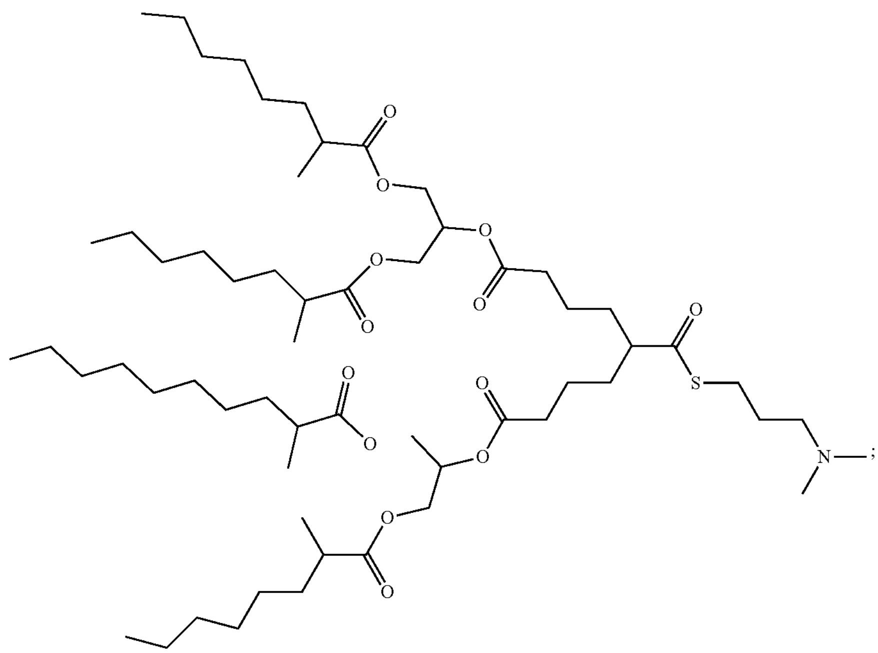
LIPID 19
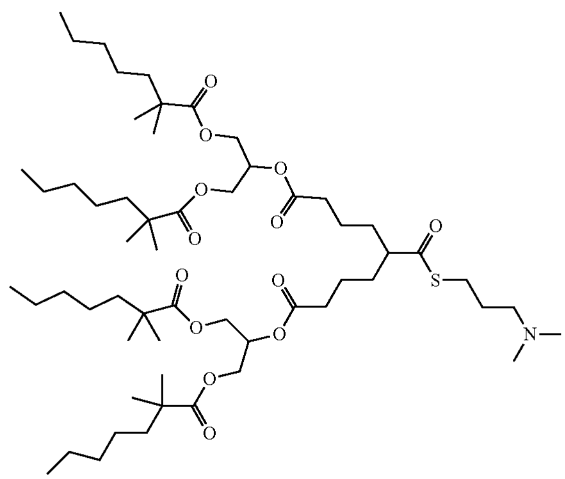
;
LIPID 20
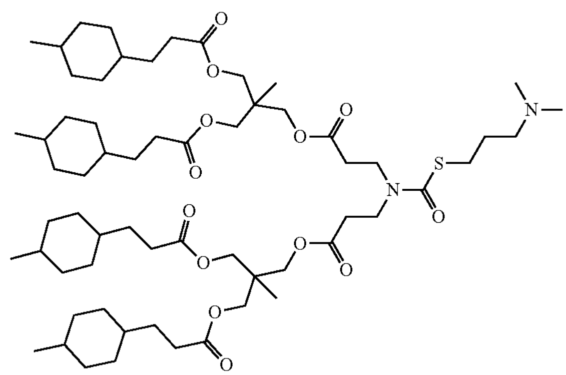
;

-continued
LIPID 21
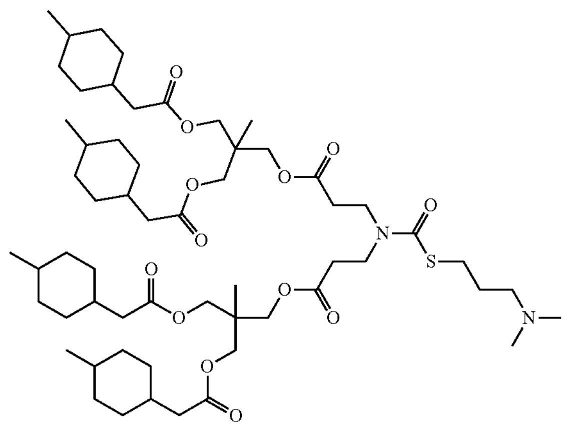
;
LIPID 22
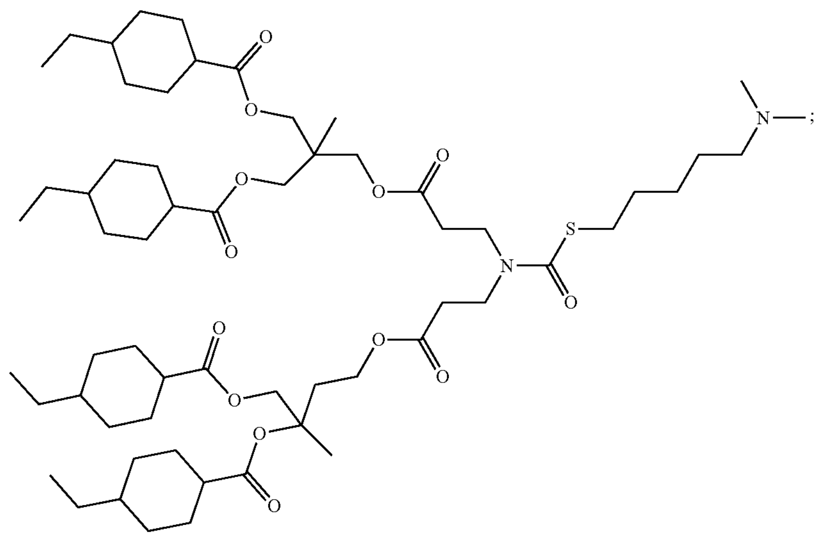
;
LIPID 23
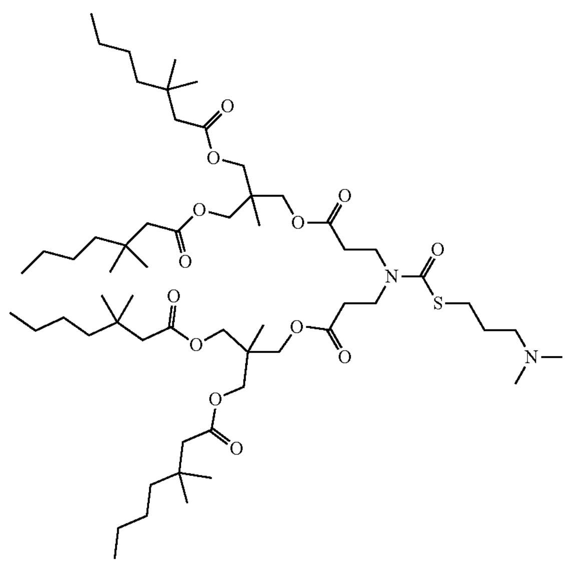
;
LIPID 24
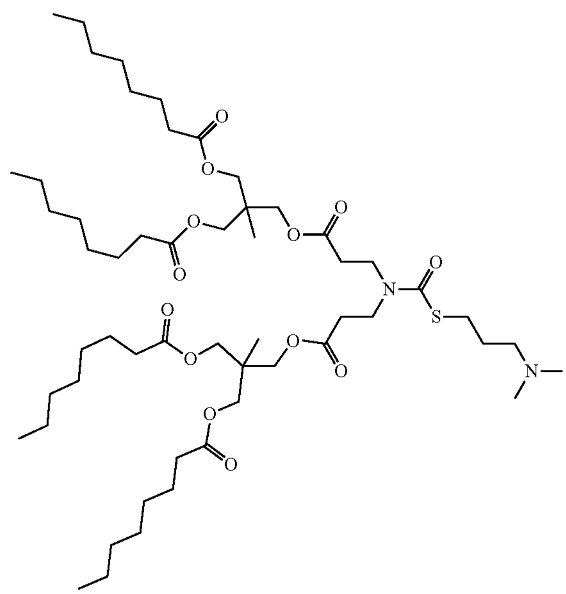
;

-continued
LIPID 25
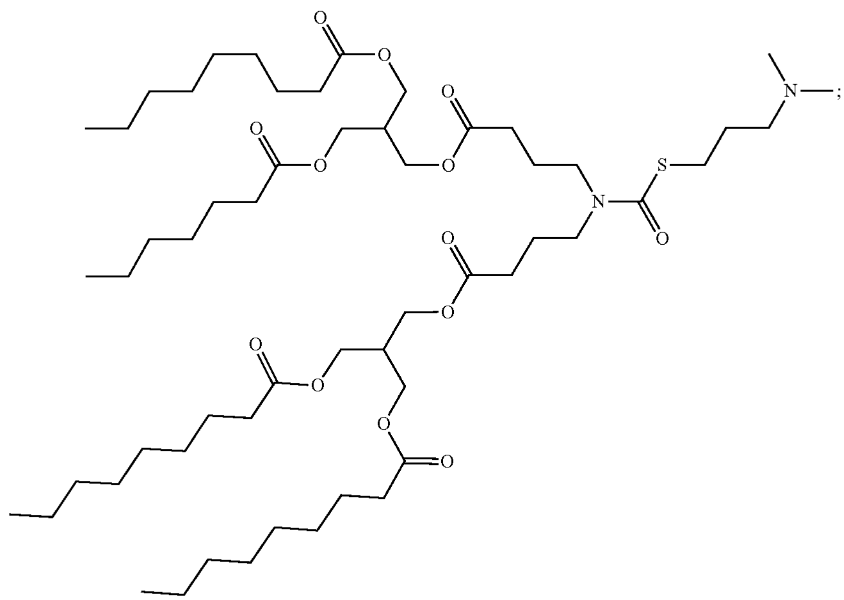
LIPID 26
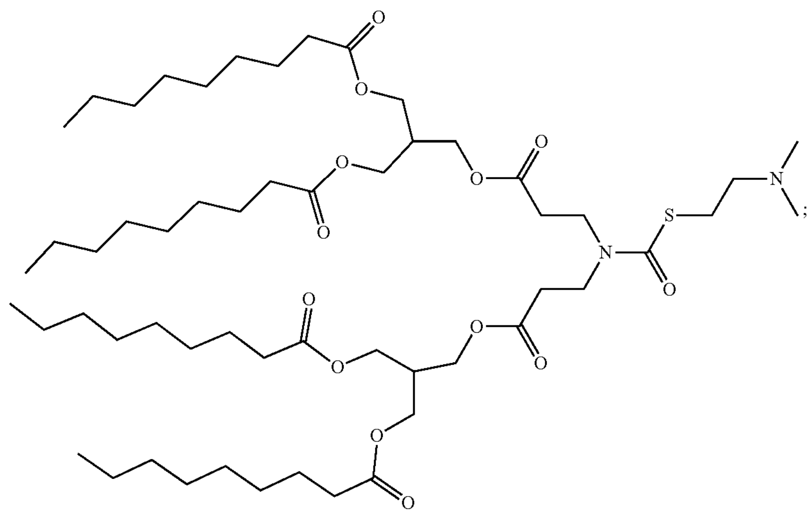
LIPID 27
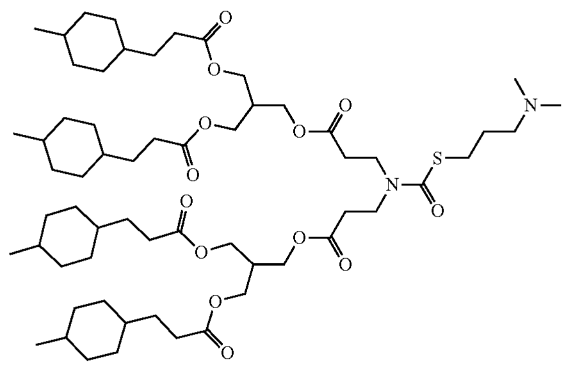
;
LIPID 28
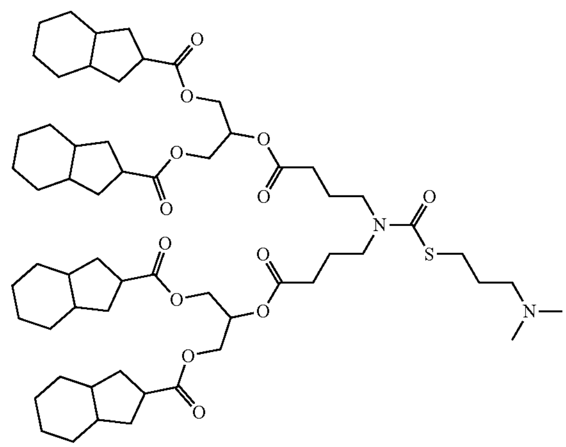
;

-continued
LIPID 29
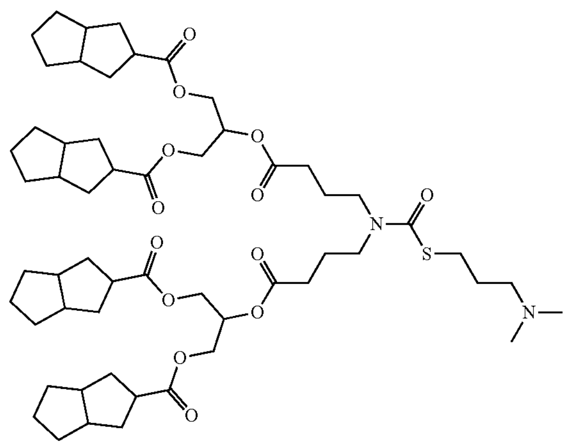
;
LIPID 30
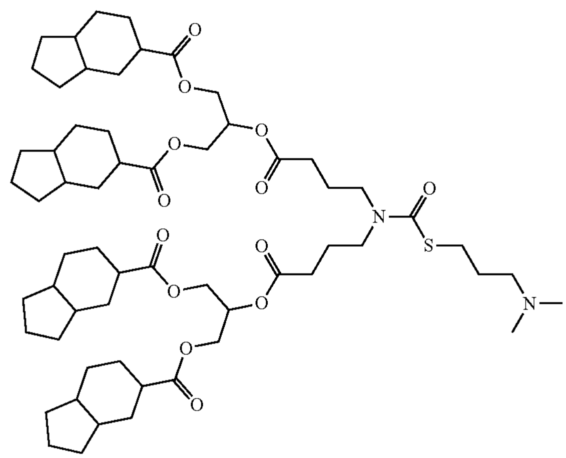
;
LIPID 31
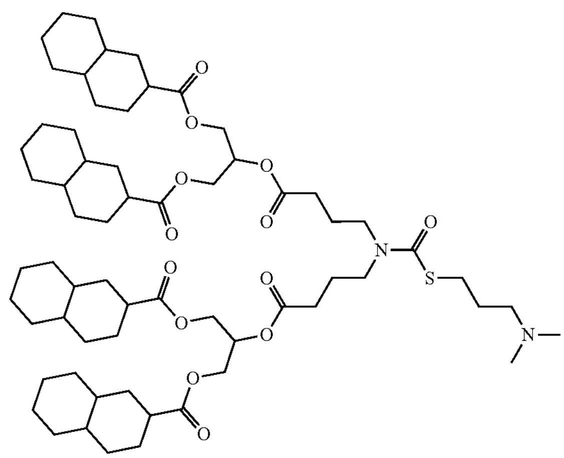
;
LIPID 32
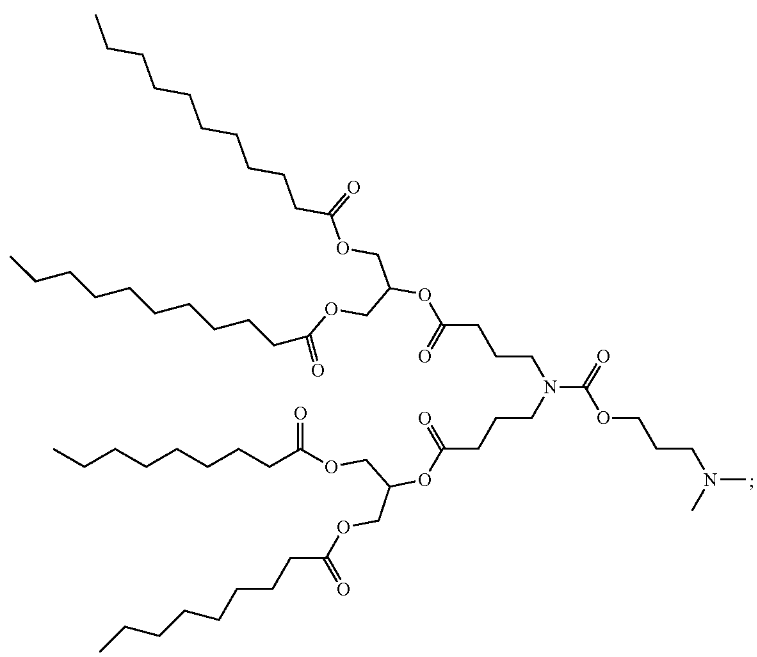
;

-continued
LIPID 33
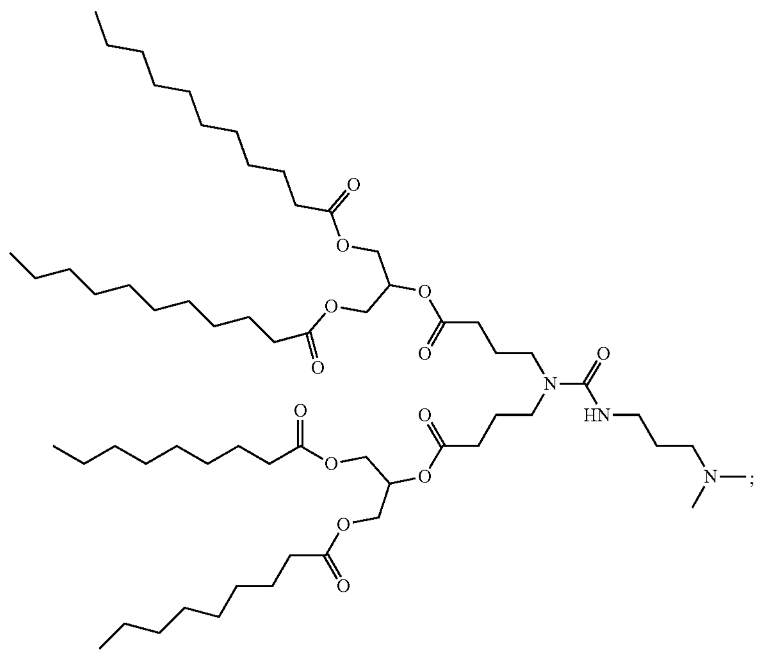
LIPID 34
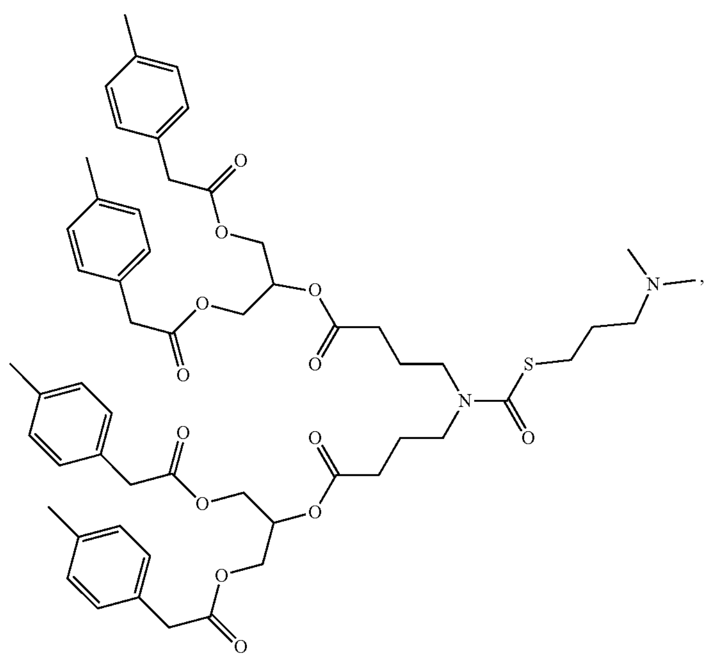

-continued
LIPID 35
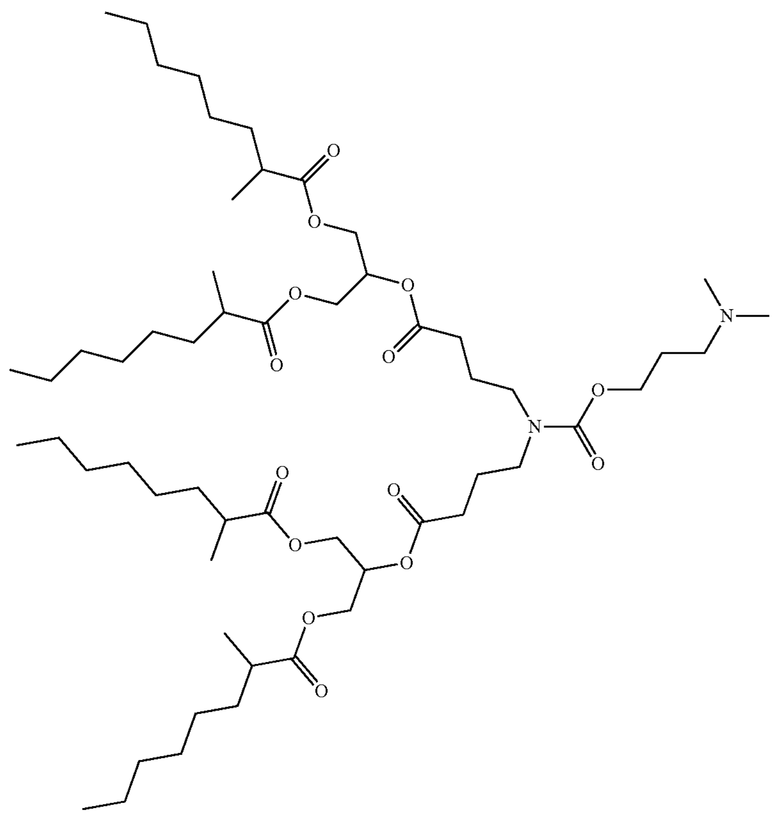
LIPID 36
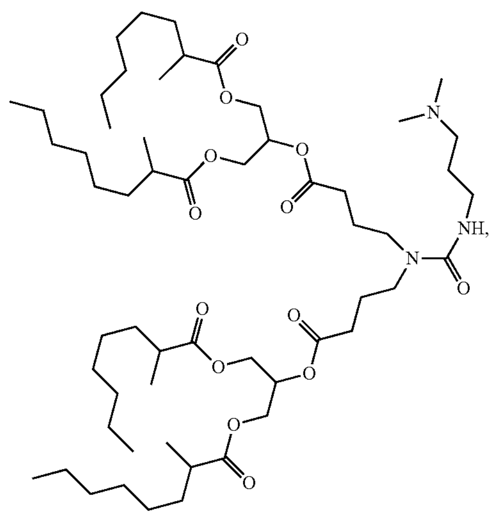
LIPID 37
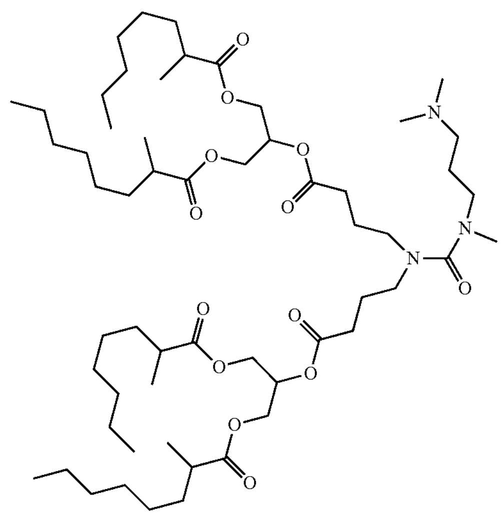

-continued
LIPID 38
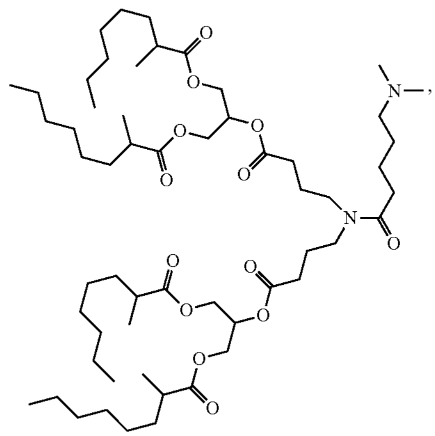
LIPID 39
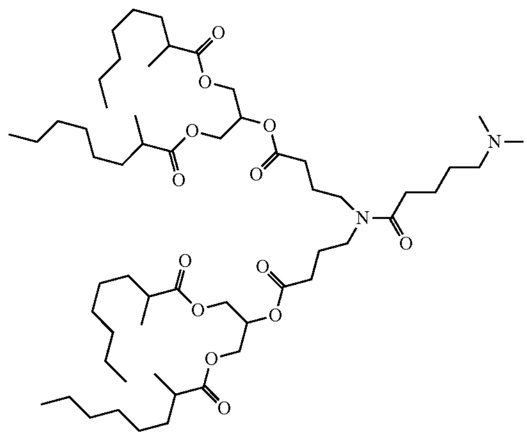
LIPID 40
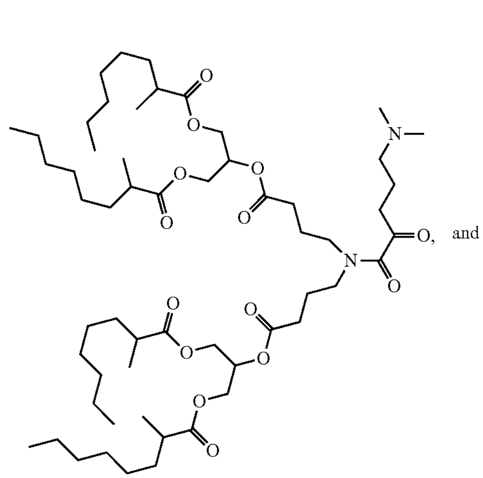
and
LIPID 41
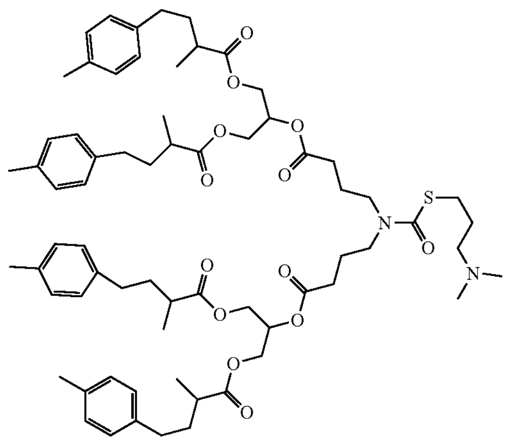
or pharmaceutically acceptable salts thereof.

16. The compound of claim 15, wherein the compound is:

LIPID 1

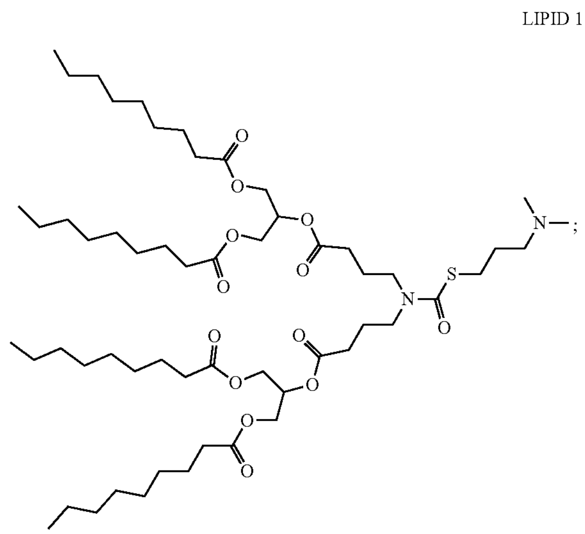 [SMILES: CCCCCCCCC(=O)OCC(COC(=O)CCCCCCCC)OC(=O)CCCN(CCCC(=O)OC(COC(=O)CCCCCCCC)COC(=O)CCCCCCCC)C(=O)SCCCN(C)C]

or a pharmaceutically acceptable salt thereof.

17. The compound of claim 15, wherein the compound is:

LIPID 10

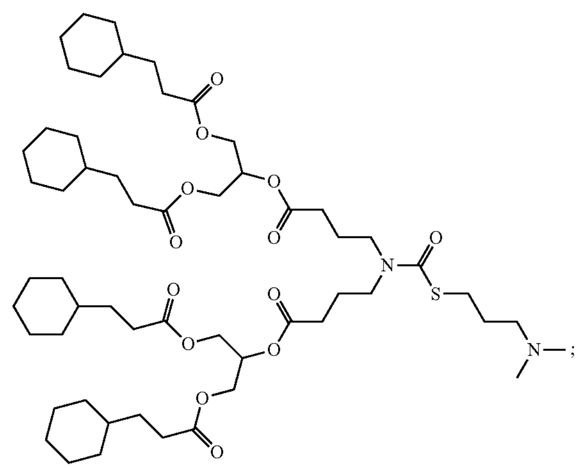

or a pharmaceutically acceptable salt thereof.

18. The compound of claim 15, wherein the compound is:

LIPID 11

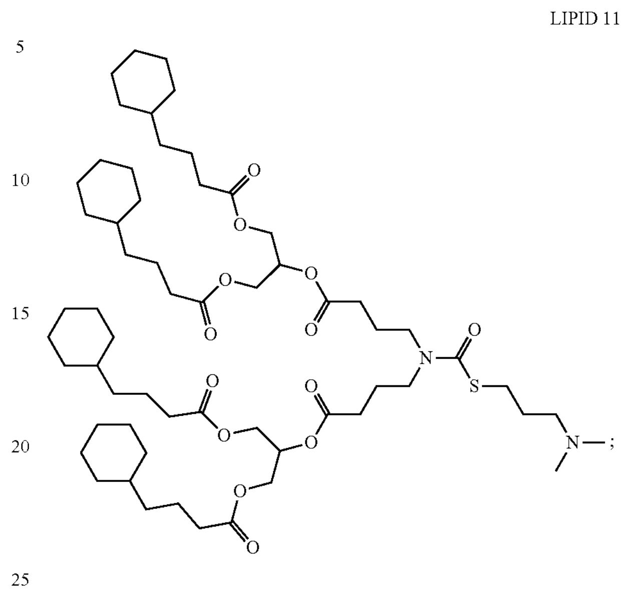

or a pharmaceutically acceptable salt thereof.

19. The compound of claim 15, wherein the compound is:

LIPID 15

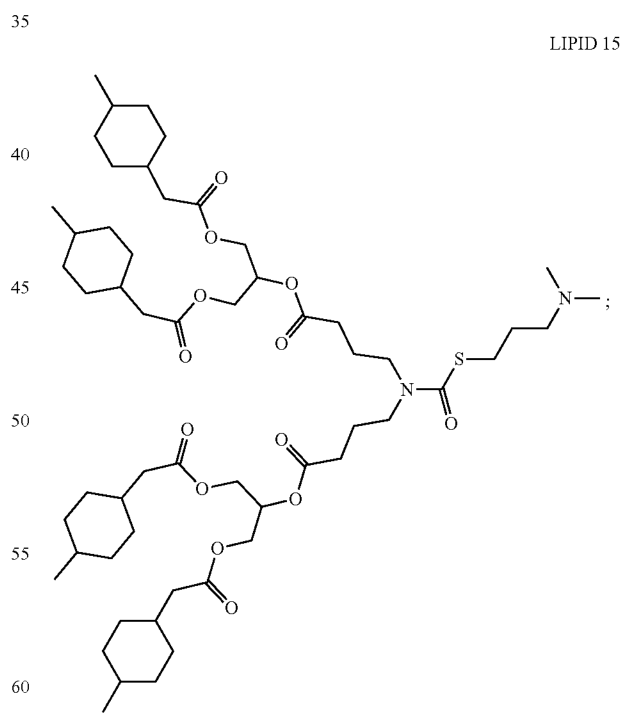

or a pharmaceutically acceptable salt thereof.

20. The compound of claim 15, wherein the compound is:

LIPID 16

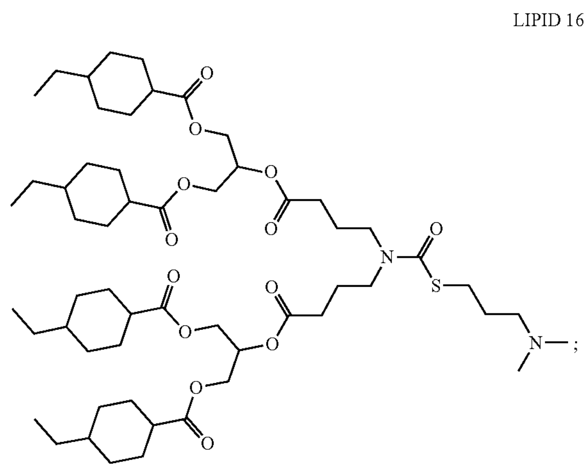 [SMILES: CCC1CCC(C(=O)OCC(COC(=O)C2CCC(CC)CC2)OC(=O)CCCN(CCCC(=O)OC(COC(=O)C2CCC(CC)CC2)COC(=O)C2CCC(CC)CC2)C(=O)SCCCN(C)C)CC1]

or a pharmaceutically acceptable salt thereof.

21. The compound of claim 15, wherein the compound is:

LIPID 17

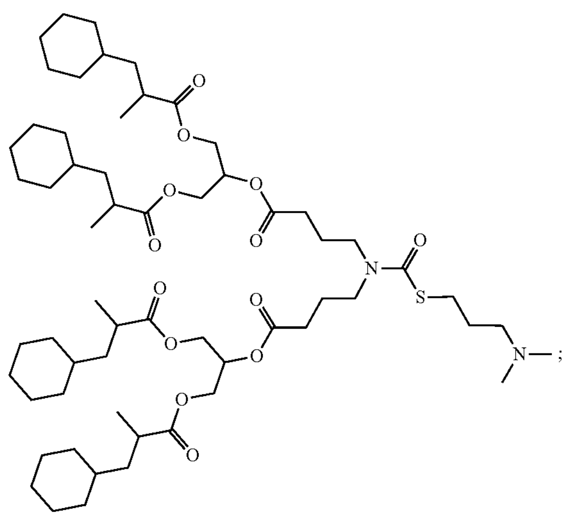

or a pharmaceutically acceptable salt thereof.

22. The compound of claim 15, wherein the compound is:

LIPID 18

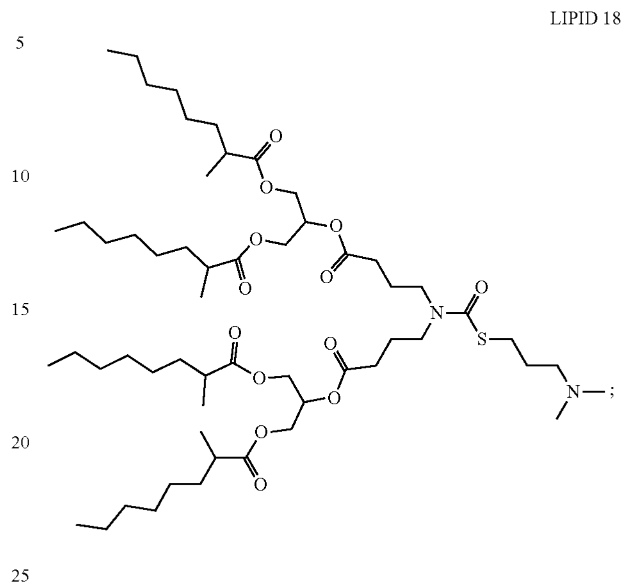

or a pharmaceutically acceptable salt thereof.

23. The compound of claim 15, wherein the compound is:

LIPID 19

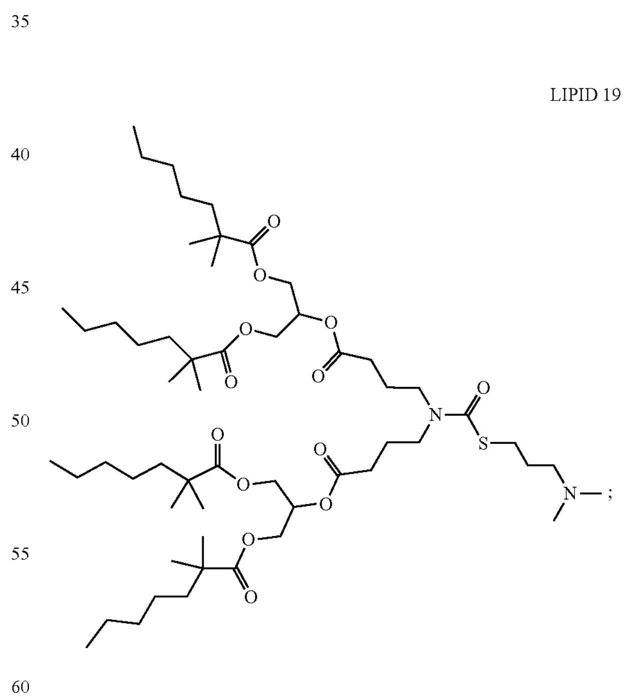

or a pharmaceutically acceptable salt thereof.

24. The compound of claim 15, wherein the compound is:

LIPID 22

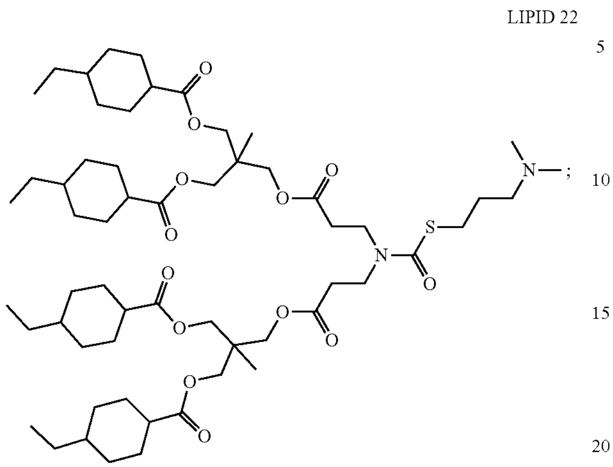

or a pharmaceutically acceptable salt thereof.

25. The compound of claim 15, wherein the compound is:

LIPID 23

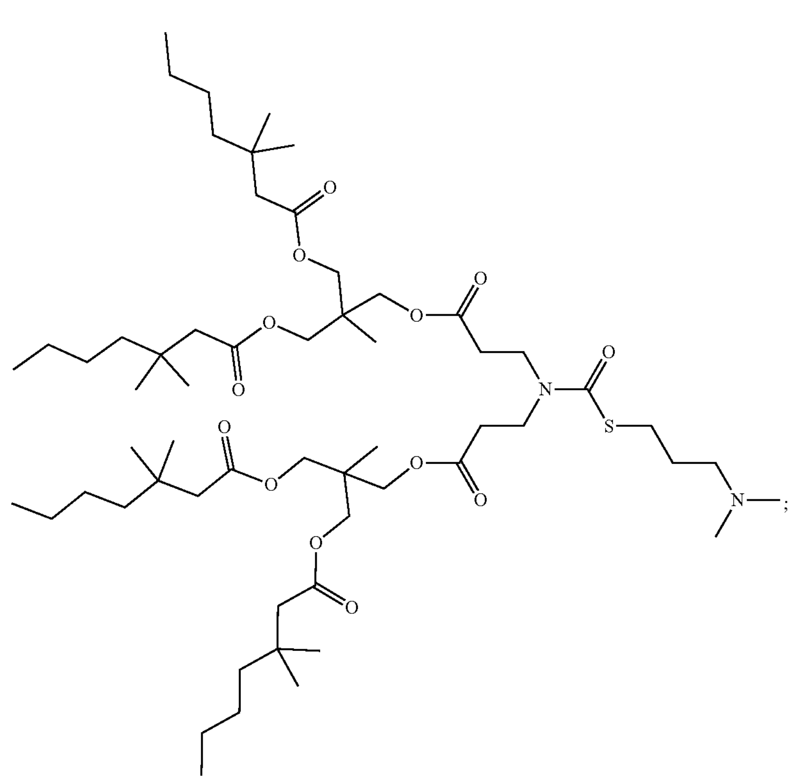

or a pharmaceutically acceptable salt thereof.

26. A lipid composition comprising a nucleic acid and a compound of claim 1.

27. The lipid composition of claim 26, wherein the nucleic acid is selected from an siRNA, an mRNA, a self-replicating RNA, a DNA plasmid, and an antisense oligonucleotide, wherein the mRNA or the self-replicating RNA comprises a coding region that encodes a therapeutic protein of interest.

28. The lipid composition of claim 27, wherein the therapeutic protein of interest is an enzyme, and antibody, an antigen, a receptor, or a transporter.

29. The lipid composition of claim 26, wherein the lipid composition comprises liposomes, lipoplexes, or lipid nanoparticles.

30. A lipid nanoparticle comprising a plurality of ligands, wherein each ligand is independently a compound of claim 1, wherein the plurality of ligands self-assembles to form the lipid nanoparticle comprising an interior and an exterior.

31. A pharmaceutical composition comprising the lipid nanoparticle of claim 26 and a pharmaceutically acceptable excipient.

32. The pharmaceutical composition of claim 31, wherein the pharmaceutical is a lyophilized composition.

* * * * *